(12) United States Patent
Lange et al.

(10) Patent No.: US 11,426,364 B2
(45) Date of Patent: Aug. 30, 2022

(54) IMMUNOMODULATOR COMPOUNDS

(71) Applicant: CHEMOCENTRYX, INC., Mountain View, CA (US)

(72) Inventors: Christopher Lange, El Cerrito, CA (US); Viengkham Malathong, Mountain View, CA (US); Darren J. McMurtrie, Sunnyvale, CA (US); Sreenivas Punna, Sunnyvale, CA (US); Rajinder Singh, Belmont, CA (US); Ju Yang, Palo Alto, CA (US); Penglie Zhang, Foster City, CA (US)

(73) Assignee: ChemoCentryx, Inc., San Carlos, CA (US)

( * ) Notice: Subject to any disclaimer, the term of this patent is extended or adjusted under 35 U.S.C. 154(b) by 0 days.

(21) Appl. No.: 16/751,019

(22) Filed: Jan. 23, 2020

(65) Prior Publication Data
US 2021/0052514 A1 Feb. 25, 2021

Related U.S. Application Data

(62) Division of application No. 15/633,569, filed on Jun. 26, 2017, now Pat. No. 10,639,284.

(Continued)

(51) Int. Cl.
| | |
|---|---|
| *A61P 31/00* | (2006.01) |
| *A61K 31/085* | (2006.01) |
| *C07D 211/40* | (2006.01) |
| *A61P 35/00* | (2006.01) |
| *C07C 215/12* | (2006.01) |
| *C07F 5/02* | (2006.01) |
| *C07D 401/14* | (2006.01) |
| *C07D 213/30* | (2006.01) |
| *C07D 405/12* | (2006.01) |
| *C07C 229/22* | (2006.01) |
| *C07D 319/18* | (2006.01) |

(Continued)

(52) U.S. Cl.
CPC .......... *A61K 31/085* (2013.01); *A61K 31/015* (2013.01); *A61K 31/03* (2013.01); *A61K 31/277* (2013.01); *A61K 38/00* (2013.01); *A61K 45/06* (2013.01); *A61P 29/00* (2018.01); *A61P 31/00* (2018.01); *A61P 35/00* (2018.01); *C07C 43/168* (2013.01); *C07C 215/12* (2013.01); *C07C 229/22* (2013.01); *C07C 235/20* (2013.01); *C07C 235/42* (2013.01); *C07C 255/54* (2013.01); *C07C 317/22* (2013.01); *C07D 205/04* (2013.01); *C07D 211/40* (2013.01); *C07D 213/30* (2013.01); *C07D 213/61* (2013.01); *C07D 213/80* (2013.01); *C07D 213/85* (2013.01); *C07D 237/08* (2013.01); *C07D 239/30* (2013.01); *C07D 239/42* (2013.01); *C07D 319/18* (2013.01); *C07D 401/04* (2013.01); *C07D 401/12* (2013.01); *C07D 401/14* (2013.01); *C07D 405/12* (2013.01); *C07D 405/14* (2013.01); *C07D 409/12* (2013.01); *C07D 413/12* (2013.01); *C07D 417/12* (2013.01); *C07F 5/025* (2013.01); *C07F 9/58* (2013.01); *A61K 31/36* (2013.01); *A61K 31/44* (2013.01); *A61K 31/505* (2013.01); *A61K 47/34* (2013.01);

(Continued)

(58) Field of Classification Search
CPC .......... A61K 31/44; A61P 31/00; A61P 35/00; C07C 215/12; C07D 211/40; C07D 213/30; C07D 213/61; C07D 213/80; C07D 213/85

See application file for complete search history.

(56) References Cited

U.S. PATENT DOCUMENTS

| | | |
|---|---|---|
| 10,392,405 B2 | 8/2019 | Malathong et al. |
| 10,568,874 B2 | 2/2020 | Lange et al. |

(Continued)

FOREIGN PATENT DOCUMENTS

| | | | |
|---|---|---|---|
| CN | 108395443 A | 8/2018 | |
| CN | 108863963 A | 11/2018 | |

(Continued)

OTHER PUBLICATIONS

Wells et al., "The dormancy, etc.," Cancer Res.,3811-3816. (Year: 2013).*

(Continued)

*Primary Examiner* — D Margaret M Seaman
(74) *Attorney, Agent, or Firm* — Mintz Levin Cohn Ferris Glovsky and Popeo PC

(57) ABSTRACT

Compounds are provided that are useful as immunomodulators. The compounds have the following Formula (II):

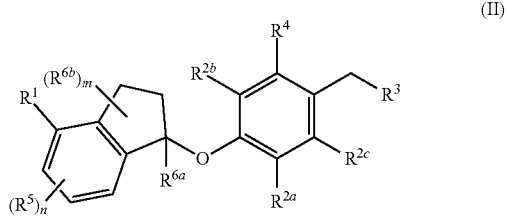

(II)

including stereoisomers and pharmaceutically acceptable salts thereof, wherein $R^1$, $R^{2a}$, $R^{2b}$, $R^{2c}$, $R^3$, $R^4$, $R^5$, $R^{6a}$, $R^{6b}$, m and n are as defined herein. Methods associated with preparation and use of such compounds, as well as pharmaceutical compositions comprising such compounds, are also disclosed.

6 Claims, No Drawings

Related U.S. Application Data

(60) Provisional application No. 62/355,119, filed on Jun. 27, 2016, provisional application No. 62/440,100, filed on Dec. 29, 2016.

(51) Int. Cl.

| | | |
|---|---|---|
| *C07D 417/12* | (2006.01) |
| *A61K 45/06* | (2006.01) |
| *C07C 235/42* | (2006.01) |
| *C07C 235/20* | (2006.01) |
| *C07D 239/42* | (2006.01) |
| *C07C 255/54* | (2006.01) |
| *C07D 213/61* | (2006.01) |
| *C07D 413/12* | (2006.01) |
| *C07D 205/04* | (2006.01) |
| *C07D 237/08* | (2006.01) |
| *C07D 401/12* | (2006.01) |
| *C07D 213/85* | (2006.01) |
| *C07D 239/30* | (2006.01) |
| *C07D 405/14* | (2006.01) |
| *C07D 401/04* | (2006.01) |
| *C07D 409/12* | (2006.01) |
| *C07D 213/80* | (2006.01) |
| *A61P 29/00* | (2006.01) |
| *C07C 317/22* | (2006.01) |
| *C07F 9/58* | (2006.01) |
| *A61K 31/015* | (2006.01) |
| *A61K 31/03* | (2006.01) |
| *A61K 31/277* | (2006.01) |
| *A61K 38/00* | (2006.01) |
| *C07C 43/168* | (2006.01) |
| *A61K 31/36* | (2006.01) |
| *A61K 31/44* | (2006.01) |
| *A61K 31/505* | (2006.01) |
| *A61K 47/34* | (2017.01) |

(52) U.S. Cl.
CPC ...... *C07C 2601/02* (2017.05); *C07C 2602/08* (2017.05); *Y02A 50/30* (2018.01)

(56) References Cited

U.S. PATENT DOCUMENTS

| | | | |
|---|---|---|---|
| 10,639,284 B2 | 5/2020 | Lange et al. | |
| 10,654,815 B2 | 5/2020 | Yang et al. | |
| 10,815,208 B2 | 10/2020 | Feng et al. | |
| 10,882,833 B2 | 1/2021 | Feng et al. | |
| 10,919,852 B2* | 2/2021 | Lange | C07D 405/12 |
| 10,941,129 B2 | 3/2021 | Feng et al. | |
| 10,975,049 B2 | 4/2021 | Feng et al. | |
| 11,059,834 B2 | 7/2021 | Malathong et al. | |
| 11,135,210 B2 | 10/2021 | Lange et al. | |
| 2003/0220349 A1 | 11/2003 | MacLean et al. | |
| 2008/0194557 A1 | 8/2008 | Barbosa et al. | |
| 2010/0292227 A1 | 11/2010 | Yoakim et al. | |
| 2017/0107216 A1 | 4/2017 | Wu et al. | |
| 2017/0145025 A1 | 5/2017 | Li et al. | |
| 2017/0174679 A1 | 6/2017 | Lajkiewicz et al. | |
| 2019/0308957 A1 | 10/2019 | Wang et al. | |
| 2020/0392083 A1 | 12/2020 | Jiang et al. | |
| 2021/0008049 A1 | 1/2021 | Malathong et al. | |
| 2021/0032270 A1 | 2/2021 | Yang et al. | |
| 2021/0147356 A1 | 5/2021 | Lange et al. | |
| 2021/0236476 A1 | 8/2021 | Li et al. | |

FOREIGN PATENT DOCUMENTS

| | | |
|---|---|---|
| CN | 109336857 A | 2/2019 |
| CN | 109438263 A | 3/2019 |
| CN | 109503546 A | 3/2019 |
| CN | 109665968 A | 4/2019 |
| CN | 109721527 A | 5/2019 |
| CN | 109776377 A | 5/2019 |
| CN | 109776445 A | 5/2019 |
| CN | 110 092 745 A | 8/2019 |
| CN | 110128415 A | 8/2019 |
| CN | 110200959 A | 9/2019 |
| EP | 3 733 659 A1 | 11/2020 |
| WO | 2007/126957 A2 | 11/2007 |
| WO | 2007/126957 A3 | 11/2007 |
| WO | 2008/008059 A1 | 1/2008 |
| WO | 2015/033299 A1 | 3/2015 |
| WO | 2015/033301 A1 | 3/2015 |
| WO | 2015/034820 A1 | 3/2015 |
| WO | 2015/160641 A2 | 10/2015 |
| WO | 2015/160641 A3 | 10/2015 |
| WO | 2017/066227 A1 | 4/2017 |
| WO | 2017/070089 A1 | 4/2017 |
| WO | 2017/106634 A1 | 6/2017 |
| WO | 2017/112730 A1 | 6/2017 |
| WO | 2017/118762 A1 | 7/2017 |
| WO | 2017/176965 A1 | 10/2017 |
| WO | 2017/192961 A1 | 11/2017 |
| WO | 2017/202273 A1 | 11/2017 |
| WO | 2017/202274 A1 | 11/2017 |
| WO | 2017/202275 A1 | 11/2017 |
| WO | 2017/202276 A1 | 11/2017 |
| WO | 2017/205464 A1 | 11/2017 |
| WO | 2017/222976 A1 | 12/2017 |
| WO | 2018/006795 A1 | 1/2018 |
| WO | 2018/009505 A1 | 1/2018 |
| WO | 2018/013789 A1 | 1/2018 |
| WO | 2018/044783 A1 | 3/2018 |
| WO | 2018/044963 A1 | 3/2018 |
| WO | 2018/045142 A1 | 3/2018 |
| WO | 2018/118848 A1 | 6/2018 |
| WO | 2018/119221 A1 | 6/2018 |
| WO | 2018/119224 A1 | 6/2018 |
| WO | 2018/119236 A1 | 6/2018 |
| WO | 2018/119263 A1 | 6/2018 |
| WO | 2018/119266 A1 | 6/2018 |
| WO | 2018/119286 A1 | 6/2018 |
| WO | 2018/121560 A1 | 7/2018 |
| WO | 2018/183171 A1 | 10/2018 |
| WO | 2018/195321 A1 | 10/2018 |
| WO | 2018/196768 A1 | 11/2018 |
| WO | 2019/023575 A1 | 1/2019 |
| WO | 2019/034172 A1 | 2/2019 |
| WO | 2019/070643 A1 | 4/2019 |
| WO | 2019/076343 A1 | 4/2019 |
| WO | 2019/087214 A1 | 5/2019 |
| WO | 2019/120297 A1 | 6/2019 |
| WO | 2019/128918 A1 | 7/2019 |
| WO | 2019/147662 A1 | 8/2019 |
| WO | 2019/149183 A1 | 8/2019 |
| WO | 2019/160882 A1 | 8/2019 |
| WO | 2019/169123 A1 | 9/2019 |
| WO | 2019/174533 A1 | 9/2019 |
| WO | 2019/175897 A1 | 9/2019 |
| WO | 2019/191707 A1 | 10/2019 |
| WO | 2019/192506 A1 | 10/2019 |
| WO | 2019/204609 A1 | 10/2019 |
| WO | 2019/217821 A1 | 11/2019 |
| WO | 2020/011209 A1 | 1/2020 |
| WO | 2020/011243 A1 | 1/2020 |
| WO | 2020/014643 A1 | 1/2020 |
| WO | 2020/015716 A1 | 1/2020 |
| WO | 2020/015717 A1 | 1/2020 |
| WO | 2020/025030 A1 | 2/2020 |

OTHER PUBLICATIONS

Chambers et al, "Dissemination and Growth, etc.," Nature Reviews, vol. 2, pp. 663-672, (Year: 2002).*
Vieira et al., "Response to anti-PD1, etc.," Oxford Medical Case Reports, 21-24 (Year: 2020).*
Saerens et al., "Immune checkpoint, etc.," European Journal of Cancer, 152, 165-188. (Year: 2021).*

(56) References Cited

OTHER PUBLICATIONS

Simone, Oncology: Introduction, Cecil Textbook of Medicine, ed Bennett et al. W.B. Saunders CO 20th ed, vol. 1, pp. 1004-1010 (Year: 1996).*
Gura, Systems for Identifying New Drugs Are Often Faulty, Cancer Models, Science, 278(5340), pp. 1041-1042. (Year: 1997).*
Johnson et al., Relationships between drug activity in NCI in vitro and in vivo and early clinical trials, British Journal of Cancer 64(10): 1424-1431. (Year: 2001).*
Golub et al., "Molecular Classification, etc.," Science, 286, 531-537. (Year: 1999).*
Pearce et al., "Failure modes, etc.," Cancer Drug Design and Discovery, ed. Stephen Neidle, Chapter 18, pp. 424-435. (Year: 2008).*
Zhang, Frontiers in Pharmacology, May 2020, vol. 11, article 722, pp. 1-15. (Year: 2020).*
International Search Report dated Sep. 15, 2017 corresponding to PCT/US2017/039313 filed Jun. 26, 2017 (3 pages).
Written Opinion completed Aug. 23, 2017 corresponding to PCT/US2017/039313 filed Jun. 26, 2017 (6 pages).
Extended European Search Report dated Jan. 20, 2018 corresponding to EP 17821019.1 filed Jun. 26, 2017 (8 pages).
International Search Report and Written Opinion dated Oct. 23, 2018 corresponding to PCT/US2018/045553 filed Aug. 7, 2018(11 pages).
International Search Report and Written Opinion dated Oct. 10, 2018 corresponding to PCT/US2018/044088 filed Jul. 27, 2018(11 pages).
International Search Report dated Apr. 16, 2019 corresponding PCT/US2019/018919 filed Feb. 21, 2019; 19 pages.
International Search Report and Written Opinion dated Dec. 27, 2019 corresponding to PCT/US2019/048466 filed Aug. 28, 2019; 19 pages.
International Search Report dated Oct. 8, 2020 corresponding to PCT/US2020/041316 filed Jul. 9, 2020; 8 pages.
Extended European Search Report dated Oct. 23, 2020 corresponding to EP 18837877.2 filed Jul. 27, 2018 (8 pages).
Extended European Search Report dated Mar. 4, 2021 corresponding to EP 18844749.4 filed Aug. 7, 2018; 5 pages.
Extended European Search Report dated Oct. 13, 2021 corresponding to EP 19757004.7 filed Feb. 21, 2019; 7 pages.
Twomey, Julianne D. et al., "Cancer Immunotherpay Update: FDA-Approved Checkpoint Inhibitors and Companion Diagnostics," *The APPS Journal* (published online Mar. 7, 2021) 23: 39, 11 pages.

* cited by examiner

IMMUNOMODULATOR COMPOUNDS

CROSS-REFERENCES TO RELATED APPLICATIONS

This application is a divisional of U.S. patent application Ser. No. 15/633,569 filed Jun. 26, 2017, now U.S. Pat. No. 10,639,284, which is an application claiming benefit of priority under 35 U.S.C. § 119(e) to U.S. Provisional Patent Application Ser. No. 62/440,100 filed on Dec. 29, 2016 and to U.S. Provisional Patent Application Ser. No. 62/355,119 filed on Jun. 27, 2016, the contents of each are incorporated herein by reference in their entirety.

STATEMENT AS TO RIGHTS TO INVENTIONS MADE UNDER FEDERALLY SPONSORED RESEARCH AND DEVELOPMENT

Not applicable

REFERENCE TO A "SEQUENCE LISTING," A TABLE, OR A COMPUTER PROGRAM LISTING APPENDIX SUBMITTED ON A COMPACT DISK

Not applicable

BACKGROUND OF THE DISCLOSURE

Programmed cell death-1 (PD-1) is a member of the CD28 superfamily that delivers negative signals upon interaction with its two ligands, PD-L1 or PD-L2. PD-1 and its ligands are broadly expressed and exert a wide range of immunoregulatory roles in T cells activation and tolerance. PD-1 and its ligands are involved in attenuating infectious immunity and tumor immunity, and facilitating chronic infection and tumor progression.

Modulation of the PD-1 pathway has therapeutic potential in various human diseases (Hyun-Tak Jin et al., Curr Top Microbiol Immunol. (2011); 350:17-37). Blockade of the PD-1 pathway has become an attractive target in cancer therapy. Therapeutic antibodies that block the programmed cell death protein-1 (PD-1) immune checkpoint pathway prevent T-cell down regulation and promote immune responses against cancer. Several PD-1 pathway inhibitors have shown robust activity in various phases of clinical trials (R D Harvey, Clinical Pharmacology and Therapeutics (2014); 96(2), 214-223).

Accordingly, agents that block the interaction of PD-L1 with either PD-1 or CD80 are desired. Some antibodies have been developed and commercialized. However there is still a need for alternative compounds such as small molecules which may have advantageous characteristics in term of oral administration, stability, bioavailability, therapeutic index, and toxicity. A few patent applications disclosing non-peptidic small molecules have been published (WO 2015/160641, WO 2015/034820, and WO 2017/066227 from BMS; WO 2015/033299 and WO 2015/033301 from Aurigene; WO 2017/070089, US 2017/0145025 and WO 2017/106634 from Incyte) However, there remains a need for alternative small molecules useful as inhibitors of the PD-1 pathway.

BRIEF SUMMARY OF THE DISCLOSURE

In one aspect, provided herein are compounds having the formula (II):

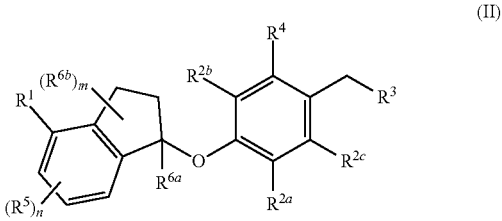

or a pharmaceutically acceptable salt thereof, wherein $R^1$, $R^{2a}$, $R^{2b}$, $R^{2c}$, $R^3$, $R^4$, $R^5$, $R^{6a}$, $R^{6b}$, m and n are as defined herein.

In addition to the compounds provided herein, the present disclosure further provides pharmaceutical compositions containing one or more of these compounds, as well as methods associated with preparation and use of such compounds. In some embodiments, the compounds are used in therapeutic methods to treat diseases associated with the PD-1/PD-L1 pathway.

BRIEF DESCRIPTION OF THE DRAWINGS

Not applicable

DETAILED DESCRIPTION OF THE DISCLOSURE

Abbreviation and Definitions

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkyl" in its broadest sense is also meant to include those unsaturated groups such as alkenyl and alkynyl groups. The term "alkenyl" refers to an unsaturated alkyl group having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., $C_{3-6}$cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc. The bicyclic or polycyclic rings may be fused, bridged, spiro or a combination thereof. The term "heterocycloalkyl" or "heterocyclyl" refers to a cycloalkyl group that contain from one to five heteroatoms selected from N, O, and S, wherein the nitrogen and sulfur atoms are optionally oxidized, and the nitrogen atom(s) are optionally quaternized. The heterocycloalkyl may be a monocyclic, a bicyclic or a polycyclic ring system. The bicyclic or polycyclic rings may be fused, bridged, spiro or a combination thereof. It is understood that the recitation for $C_{4-12}$ heterocyclyl, refers to a heterocycloalkyl moiety having from 5 to 12 ring members where at least one of the ring members is a heteroatom. Non limiting examples of heterocycloalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S, S-oxide, piperazine, pyran, pyridone, 3-pyrroline, thiopyran, pyrone, tetrahydrofuran, tetrhydrothiophene, quinuclidine, and the like. A heterocycloalkyl group can be attached to the remainder of the molecule through a ring carbon or a heteroatom.

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present disclosure. A "lower alkyl" or "lower alkylene" is a shorter chain alkyl or alkylene group, generally having four or fewer carbon atoms. Similarly, "alkenylene" and "alkynylene" refer to the unsaturated forms of "alkylene" having double or triple bonds, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$,—S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. Up to two heteroatoms may be consecutive, such as, for example, —$CH_2$—NH—O$CH_3$ and —$CH_2$—O—Si($CH_3$)$_3$. Similarly, the terms "heteroalkenyl" and "heteroalkynyl" by itself or in combination with another term, means, unless otherwise stated, an alkenyl group or alkynyl group, respectively, that contains the stated number of carbons and having from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group.

The term "heteroalkylene" by itself or as part of another substituent means a divalent radical, saturated or unsaturated or polyunsaturated, derived from heteroalkyl, as exemplified by —$CH_2$—$CH_2$—S—$CH_2CH_2$— and —$CH_2$—S—$CH_2$—$CH_2$—NH—$CH_2$—, —O—$CH_2$—CH=CH—, —$CH_2$—CH=C(H)$CH_2$—O—$CH_2$— and —S—$CH_2$—C≡C—. For heteroalkylene groups, heteroatoms can also occupy either or both of the chain termini (e.g., alkyleneoxy, alkylenedioxy, alkyleneamino, alkylenediamino, and the like).

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as —$NR^aR^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "hydroxyalkyl" or "alkyl-OH" refers to an alkyl group, as defined above, where at least one of the hydrogen atoms is replaced with a hydroxy group. As for the alkyl group, hydroxyalkyl groups can have any suitable number of carbon atoms, such as $C_{1-6}$. Exemplary alkylhydroxy groups include, but are not limited to, hydroxy-methyl, hydroxyethyl (where the hydroxy is in the 1- or 2-position), hydroxypropyl (where the hydroxy is in the 1-, 2- or 3-position), etc.

The term "$C_{1-3}$ alkyl-guanidinyl" refers to a $C_{1-3}$ alkyl group, as defined above, where at least one of the hydrogen atoms is replaced with a guanidinyl group (—NC(NH)NH$_2$). In some embodiments, $C_{1-3}$ alkyl-guanidinyl refers a $C_{1-3}$ alkyl group where one of the hydrogen atoms is replaced with a guanidinyl.

The term "aryl" means, unless otherwise stated, a polyunsaturated, typically aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. It is understood that the recitation for $C_{5-10}$ heteroaryl, refers to a heteroaryl moiety having from 5 to 10 ring members where at least one of the ring members is a heteroatom. Non-limiting examples of aryl groups include phenyl, naphthyl and biphenyl, while non-limiting examples of heteroaryl groups include pyridyl, pyridazinyl, pyrazinyl, pyrimidinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems are selected from the group of acceptable substituents described below.

The term "carbocyclic ring" or "carbocyclyl" refers to cyclic moieties with only carbon atoms as ring vertices. Carbocyclic ring moieties are saturated or unsaturated and can be aromatic. Generally, carbocyclic moieties have from 3 to 10 ring members. Carbocyclic moieties with multiple ring structure (e.g. bicyclic) can include a cycloalkyl ring fused to a aromatic ring (e.g. 1,2,3,4-tetrahydronaphthalene). Thus, carboclicic rings include cyclopentyl, cyclohexenyl, naphthyl, and 1,2,3,4-tetrahydronaphthyl. The term "heterocyclic ring" refers to both "heterocycloalkyl" and "heteroaryl" moieties. Thus, heterocyclic rings are saturated or unsaturated and can be aromatic. Generally, heterocyclic rings are 4 to 10 ring members and include piperidiyl, tetrazinyl, pyrazolo, and indolyl.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like).

The above terms (e.g., "alkyl," "aryl" and "heteroaryl"), in some embodiments, will include both substituted and unsubstituted forms of the indicated radical. Preferred substituents for each type of radical are provided below. For brevity, the terms aryl and heteroaryl will refer to substituted or unsubstituted versions as provided below, while the term "alkyl" and related aliphatic radicals is meant to refer to unsubstituted version, unless indicated to be substituted.

Substituents for the alkyl radicals (including those groups often referred to as alkylene, alkenyl, alkynyl and cycloalkyl) can be a variety of groups selected from: -halogen, —OR', —NR'R", —SR', —SiR'R"R'", —OC(O)R', —C(O)R', —CO$_2$R", —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN and —NO$_2$ in a number ranging from zero to (2 m'+1), where m' is the total number of carbon atoms in such radical. R', R" and R'" each independently refer to hydrogen, unsubstituted $C_{1-8}$ alkyl, unsubstituted heteroalkyl, unsubstituted aryl, aryl substituted with 1-3 halogens, unsubstituted $C_{1-8}$ alkyl, $C_{1-8}$ alkoxy or $C_{1-8}$ thioalkoxy groups, or unsubstituted aryl-$C_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl. The term "acyl" as used by itself or as part of another group refers to an alkyl radical wherein two substituents on the carbon that is closest to the point of attachment for the radical is replaced with the substitutent =O (e.g., —C(O)CH$_3$, —C(O)CH$_2$CH$_2$OR' and the like).

Similarly, substituents for the aryl and heteroaryl groups are varied and are generally selected from: -halogen, —OR', —OC(O)R', —NR'R", —SR', —R', —CN, —NO$_2$, —CO$_2$R", —CONR'R", —C(O)R', —OC(O)NR"R'", —NR"C(O)R', —NR"C(O)$_2$R', —NR'—C(O)NR"R'", —NH—C(NH$_2$)=NH, —NR'C(NH$_2$)=NH, —NH—C (NH$_2$)=NR', —S(O)R', —S(O)$_2$R', —S(O)$_2$NR'R", —NR'S (O)$_2$R", —N$_3$, perfluoro($C_1$-$C_4$)alkoxy, and perfluoro($C_1$-$C_4$)alkyl, in a number ranging from zero to the total number of open valences on the aromatic ring system; and where R', R" and R'" are independently selected from hydrogen, $C_{1-8}$ alkyl, $C_{3-6}$ cycloalkyl, $C_{2-8}$ alkenyl, $C_{2-8}$ alkynyl, unsubstituted aryl and heteroaryl, (unsubstituted aryl)-$C_{1-4}$ alkyl, and unsubstituted aryloxy-$C_{1-4}$ alkyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted $C_{1-6}$ alkyl.

As used herein, the term "heteroatom" is meant to include oxygen (O), nitrogen (N), sulfur (S) and silicon (Si).

The term "ionic liquid" refers to any liquid that contains mostly ions. Preferably, in the present disclosure, "ionic liquid" refers to the salts whose melting point is relatively low (e.g., below 250° C.). Examples of ionic liquids include but are not limited to 1-butyl-3-methylimidazolium tetrafluoroborate, 1-hexyl-3-methylimidazolium tetrafluoroborate, 1-octyl-3-methylimidazolium tetrafluoroborate, 1-nonyl-3-methylimidazolium tetrafluoroborate, 1-decyl-3-methylimidazolium tetrafluoroborate, 1-hexyl-3-methylimidazolium hexafluorophosphate and 1-hexyl-3-methylimidazolium bromide, and the like.

The terms "patient" and "subject" include primates (especially humans), domesticated companion animals (such as dogs, cats, horses, and the like) and livestock (such as cattle, pigs, sheep, and the like).

As used herein, the term "treating" or "treatment" encompasses both disease-modifying treatment and symptomatic treatment, either of which may be prophylactic (i.e., before the onset of symptoms, in order to prevent, delay or reduce the severity of symptoms) or therapeutic (i.e., after the onset of symptoms, in order to reduce the severity and/or duration of symptoms).

The term "pharmaceutically acceptable salts" is meant to include salts of the active compounds which are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occuring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

Certain compounds of the present disclosure can exist in unsolvated forms as well as solvated forms, including hydrated forms. In general, the solvated forms are equivalent to unsolvated forms and are intended to be encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

Certain compounds of the present disclosure possess asymmetric carbon atoms (optical centers) or double bonds; the racemates, diastereomers, geometric isomers, regioisomers and individual isomers (e.g., separate enantiomers) are all intended to be encompassed within the scope of the present disclosure. The compounds of the present disclosure may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present disclosure, whether radioactive or not, are intended to be encompassed within the scope of the present disclosure. For example, the compounds may be prepared such that any number of hydrogen atoms are replaced with a deuterium ($^2$H) isotope. The compounds of the present disclosure may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3$H), iodine-125 ($^{125}$I) or carbon-14 ($^{14}$C), or non-radioactive isotopes, such as deuterium ($^2$H) or carbon-13 ($^{13}$C). Such isotopic variations can provide additional utilities to those described elsewhere within this application. For instance, isotopic variants of the compounds of the disclosure may find additional utility, including but not limited to, as diagnostic and/or imaging reagents, or as cytotoxic/radiotoxic therapeutic agents. Additionally, isotopic variants of the compounds of the disclosure can have altered pharmacokinetic and pharmacodynamic characteristics which can contribute to enhanced safety, tolerability or efficacy during treatment. All isotopic variations of the compounds of the present disclosure, whether radioactive or not, are intended to be encompassed within the scope of the present disclosure.

Compounds

In one aspect, the present disclosure provides compounds having the formula (II)

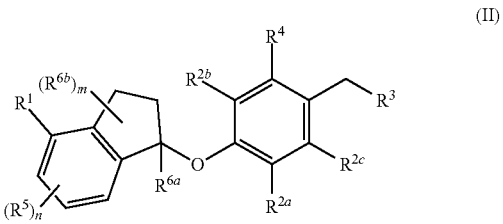

(II)

or a pharmaceutically acceptable salt thereof; wherein:

$R^1$ is selected from the group consisting of halogen, $C_{5-8}$ cycloalkyl, $C_{6-10}$ aryl and thienyl, wherein the $C_{6-10}$ aryl and thienyl are optionally substituted with 1 to 5 $R^x$ substituents;

each $R^x$ is independently selected from the group consisting of halogen, —CN, —$R^c$, —$CO_2R^a$, —$CONR^aR^b$, —C(O)$R^a$, —OC(O)$NR^aR^b$, —$NR^bC(O)R^a$, —$NR^bC(O)_2R^a$, —$NR^a$—C(O)$NR^aR^b$, —$NR^aR^b$, —$OR^a$, —O—$X^1$—$OR^a$, —O—$X^1$—$CO_2R^a$, —O—$X^1$—$CONR^aR^b$, —$X^1$—$OR^a$, —X—$NR^aR^b$, —$X^1$—$CO_2R^a$, —$X^1$—$CONR^aR^b$, —$SF_5$, and —$S(O)_2NR^aR^b$, wherein each $X^1$ is a $C_{1-4}$ alkylene; each $R^a$ and $R^b$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, wherein the five or six-membered ring is optionally substituted with oxo; each $R^c$ is independently selected from the group consisting of $C_{1-8}$ alkyl, $C_{2-8}$ alkenyl, $C_{2-8}$ alkynyl and $C_{1-8}$ haloalkyl; and optionally when two $R^x$ substituents are on adjacent atoms, they are combined to form a fused five, six or seven-membered carbocyclic or heterocyclic ring optionally substituted with from 1 to 3 substituents independently selected from halo, oxo, $C_{1-8}$ haloalkyl and $C_{1-8}$ alkyl;

each $R^{2a}$, $R^{2b}$ and $R^{2c}$ is independently selected from the group consisting of H, halogen, —CN, —$R^d$, —$CO_2R^e$, —$CONR^eR^f$, —$C(O)R^e$, —$OC(O)NR^eR^f$, —$NR^fC(O)R^e$, —$NR^fC(O)_2R^d$, —$NR^e$—$C(O)NR^eR^f$, —$NR^eR^f$, —$OR^e$, —O—$X^2$—$OR^e$, —O—$X^2$—$NR^eR^f$, —O—$X^2$—$CO_2R^e$, —O—$X^2$—$CONR^eR^f$, —$X^2$—$OR^e$, —$X^2$—$NR^eR^f$, —$X^2$—$CO_2R^e$, —$X^2$—$CONR^eR^f$, —$SF_5$, —$S(O)_2NR^eR^f$, $C_{6-10}$ aryl and $C_{5-10}$ heteroaryl, wherein each $X^2$ is a $C_{1-4}$ alkylene; each $R^e$ and $R^f$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O and S, and optionally substituted with oxo; each $R^d$ is independently selected from the group consisting of $C_{1-8}$ alkyl, $C_{2-8}$ alkenyl, and $C_{1-8}$ haloalkyl;

$R^3$ is selected from the group consisting of —$NR^gR^h$ and $C_{4-12}$ heterocyclyl, wherein the $C_{4-12}$ heterocyclyl is optionally substituted with 1 to 6 $R^y$;

each $R^y$ is independently selected from the group consisting of halogen, —CN, —$R^i$, —$CO_2R^j$, —$CONR^jR^k$, —$CONHC_{1-6}$ alkyl-OH, —$C(O)R^j$, —$OC(O)NR^jR^k$, —$NR^jC(O)R^k$, —$NR^jC(O)_2R^k$, CONOH, $PO_3H_2$, —$NR^j$—$C_{1-6}$ alkyl-$C(O)_2R^k$, —$NR^jC(O)NR^jR^k$, —$NR^jR^k$, —$OR^j$, —$S(O)_2NR^jR^k$, —O—$C_{1-6}$alkyl-$OR^j$, —O—$C_{1-6}$ alkyl-$NR^jR^k$, —O—$C_{1-6}$ alkyl-$CO_2R^j$, —O—$C_{1-6}$ alkyl-$CONR^jR^k$, —$C_{1-6}$ alkyl-$OR^j$, —$C_{1-6}$ alkyl-$NR^jR^k$, —$C_{1-6}$ alkyl-$CO_2R^j$, —$C_{1-6}$ alkyl-$CONR^jR^k$, and $SF_5$, wherein the $C_{1-6}$ alkyl portion of $R^y$ is optionally further substituted with OH, $S_2NH_2$, $CONH_2$, CONOH, $PO_3H_2$, COO—$C_{1-8}$alkyl or $CO_2H$, wherein each $R^j$ and $R^k$ is independently selected from hydrogen, $C_{1-8}$ alkyl optionally substituted with 1 to 2 substituents selected from OH, $SO_2NH_2$, $CONH_2$, CONOH, $PO_3H_2$, COO—$C_{1-8}$alkyl or $CO_2H$, and $C_{1-8}$ haloalkyl optionally substituted with 1 to 2 substituents selected from OH, $S_2NH_2$, $CONH_2$, CONOH, $PO_3H_2$, COO—$C_{1-8}$alkyl or $CO_2H$, or when attached to the same nitrogen atom $R^j$ and $R^k$ can be combined with the nitrogen atom to form a five or six-membered ring having from 0 to 2 additional heteroatoms as ring members selected from N, O or S, and optionally substituted with oxo; each $R^i$ is independently selected from the group consisting of —OH, $C_{1-8}$ alkyl, $C_{2-8}$ alkenyl, and $C_{1-8}$ haloalkyl each of which may be optionally substituted with OH, $SO_2NH_2$, $CONH_2$, CONOH, $PO_3H_2$, COO—$C_{1-8}$alkyl or $CO_2H$;

$R^g$ is selected from the group consisting of H, $C_{1-8}$ haloalkyl and $C_{1-8}$ alkyl;

$R^h$ is selected from —$C_{1-8}$alkyl, $C_{1-8}$ haloalkyl, $C_{1-8}$ alkyl-COOH, $C_{1-8}$ alkyl-OH, $C_{1-8}$ alkyl-$CONH_2$, $C_{1-8}$ alkyl-$SO_2NH_2$, $C_{1-8}$ alkyl-$PO_3H_2$, $C_{1-8}$ alkyl-CONOH, $C_{1-8}$ alkyl-$NR^{h1}R^{h2}$, —C(O)—$C_{1-8}$alkyl, —C(O)—$C_{1-8}$alkyl-OH, —C(O)—$C_{1-8}$alkyl-COOH, $C_{3-10}$ cycloalkyl, —$C_{3-10}$ cycloalkyl-COOH, —$C_{3-10}$ cycloalkyl-OH, $C_{4-8}$ heterocyclyl, —$C_{4-8}$ heterocyclyl-COOH, —$C_{4-8}$ heterocyclyl-OH, —$C_{1-8}$ alkyl-$C_{4-8}$ heterocyclyl, —$C_{1-8}$ alkyl-$C_{3-10}$ cycloalkyl, $C_{5-10}$ heteroaryl, —$C_{1-8}$alkyl-$C_{5-10}$ heteroaryl, $C_{10}$ carbocyclyl, —$C_{1-8}$ alkyl-$C_{6-10}$ aryl, —$C_{1-8}$ alkyl-(C═O)—$C_{6-10}$ aryl, —$C_{1-8}$ alkyl-NH(C═O)—$C_{1-8}$ alkenyl, —$C_{1-8}$ alkyl-NH(C═O)—$C_{1-8}$ alkyl, —$C_{1-8}$ alkyl-NH(C═O)—$C_{1-8}$ alkynyl, —$C_{1-8}$ alkyl-(C═O)—NH—$C_{1-8}$ alkyl-COOH, and —$C_{1-8}$ alkyl-(C═O)—NH—$C_{1-8}$ alkyl-OH optionally substituted with $CO_2H$; or $R^h$ combined with the N to which it is attached is a mono-, di- or tri-peptide comprising 1-3 natural amino acids and 0-2 non-natural amino acids, wherein the non-natural aminoacids have an alpha carbon substituent selected from the group consisting of $C_{2-4}$ hydroxyalkyl, $C_{1-3}$ alkyl-guanidinyl, and $C_{1-4}$ alkyl-heteroaryl, the alpha carbon of each natural or non-natural amino acids are optionally further substituted with a methyl group, and the terminal moiety of the mono-, di-, or tri-peptide is selected from the group consisting of C(O)OH, C(O)O—$C_{1-6}$ alkyl, and $PO_3H_2$, wherein $R^{h1}$ and $R^{h2}$ are each independently selected from the group consisting of H, $C_{1-6}$ alkyl, and $C_{1-4}$ hydroxyalkyl;

the $C_{1-8}$ alkyl portions of $R^h$ are optionally further substituted with from 1 to 3 substituents independently selected from OH, COOH, $SO_2NH_2$, $CONH_2$, CONOH, COO—$C_{1-8}$ alkyl, $PO_3H_2$ and $C_{5-6}$ heteroaryl optionally substituted with 1 to 2 $C_{1-3}$ alkyl substituents, the $C_{10}$ carbocyclyl, $C_{5-10}$ heteroaryl and the $C_{6-10}$ aryl portions of $R^h$ are optionally substituted with 1 to 3 substituents independently selected from OH, $B(OH)_2$, COOH, $SO_2NH_2$, $CONH_2$, CONOH, $PO_3H_2$, COO—$C_{1-8}$alkyl, $C_{1-4}$alkyl, $C_{1-4}$alkyl-OH, $C_{1-4}$alkyl-$SO_2NH_2$, $C_{1-4}$alkyl $CONH_2$, $C_{1-4}$alkyl-CONOH, $C_{1-4}$alkyl-$PO_3H_2$, $C_{1-4}$alkyl-COOH, and phenyl and the $C_{4-8}$ heterocyclyl and $C_{3-10}$ cycloalkyl portions of $R^h$ are optionally substituted with 1 to 4 $R^w$ substituents;

each $R^w$ substituent is independently selected from $C_{1-4}$ alkyl, $C_{1-4}$ alkyl-OH, $C_{1-4}$ alkyl-COOH, $C_{1-4}$ alkyl-$SO_2NH_2$, $C_{1-4}$ alkyl $CONH_2$, $C_{1-4}$ alkyl-CONOH, $C_{1-4}$ alkyl-$PO_3H$, OH, COO—$C_{1-8}$ alkyl, COOH, $SO_2NH_2$, $CONH_2$, CONOH, $PO_3H_2$ and oxo;

$R^4$ is selected from the group consisting of O—$C_{1-8}$ alkyl, O—$C_{1-8}$ haloalkyl, O—$C_{1-8}$ alkyl-$R^z$, $C_{6-10}$ aryl, $C_{5-10}$ heteroaryl, —O—$C_{1-4}$ alkyl-$C_{6-10}$aryl and —O—$C_{1-4}$ alkyl-$C_{5-10}$ heteroaryl, wherein the $C_{6-10}$ aryl and the $C_{5-10}$ heteroaryl are optionally substituted with 1 to 5 $R^z$;

each $R^z$ is independently selected from the group consisting of halogen, —CN, —$R^m$, —$CO_2R^n$, —$CONR''R^p$, —$C(O)R''$, —$OC(O)NR''R^p$, —$NR''C(O)R^p$, —$NR''C(O)_2R^m$, —$NR''$—$C(O)NR''R^p$, —$NR''R^p$, —$OR''$, —O—$X^3$—$OR''$, —O—$X^3$—$NR''R^p$, —O—$X^3$—$CO_2R''$, —O—$X^3$—$CONR''R^p$, —$X^3$—$OR''$, —$X^3$—$NR''R^p$, —$X^3$—$CO_2R''$, —$X^3$—$CONR''R^p$, —$SF_5$, —$S(O)_2R''R^p$, —$S(O)_2NR''R^p$, and three to seven-membered carbocyclic or four to seven-membered heterocyclic ring wherein the three to seven-membered carbocyclic or four to seven-membered heterocyclic ring is optionally substituted with 1 to 5 $R^t$, wherein each $R^t$ is independently selected from the group consisting of $C_{1-8}$ alkyl, $C_{1-8}$haloalkyl, —$CO_2R''$, —$CONR''R^p$, —$C(O)R''$, —$OC(O)NR''R^p$, —$NR''C(O)R^p$, —$NR''C(O)_2R^m$, —$NR''$—$C(O)NR''R^p$, —$NR''R^p$, —$OR''$, —O—$X^3$—$OR''$, —O—$X^3$—$NR''R^p$, —O—$X^3$—$CO_2R''$, —O—$X^3$—$CONR''R^p$, —$X^3$—$OR''$, —$X^3$—$NR''R^p$, —$X^3$—$CO_2R''$, —$X^3$—$CONR''R^p$, —$SF_5$, and —$S(O)_2NR''R^p$;

wherein each $X^3$ is a $C_{1-4}$ alkylene; each $R''$ and $R^p$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, and optionally substituted with oxo; each $R^m$ is independently selected from the group consisting of $C_{1-8}$alkyl, $C_{2-8}$ alkenyl, and $C_{1-8}$ haloalkyl; and optionally when two $R^z$ substituents are on adjacent atoms, they are combined to form a fused five or six-membered carbocyclic or heterocyclic ring optionally substituted with oxo;

n is 0, 1, 2 or 3;

each $R^5$ is independently selected from the group consisting of halogen, —CN, —$R^q$, —$CO_2R^r$, —$CONR^rR^s$, —C(O)$R^r$, —OC(O)$NR^rR^s$, —$NR^rC(O)R^s$, —$NR^rC(O)_2R^q$, —$NR^r$—C(O)$NR^rR^s$, —$NR^rR^s$, —$OR^r$, —O—$X^4$—$OR^r$, —O—$X^4$—$NR^rR^s$, —O—$X^4$—$CO_2R^r$, —O—$X^4$—$CONR^rR^s$, —$X^4$—$OR^r$, —$X^4$—$NR^rR^s$, —$X^4$—$CO_2R^r$, —$X^4$—$CONR^rR^s$, —$SF_5$, —$S(O)_2NR^rR^s$, wherein each $X^4$ is a $C_{1-4}$ alkylene; each $R^r$ and $R^s$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, and optionally substituted with oxo; each $R^q$ is independently selected from the group consisting of $C_{1-8}$ alkyl, and $C_{1-8}$ haloalkyl;

$R^{6a}$ is selected from the group consisting of H, $C_{1-4}$ alkyl and $C_{1-4}$ haloalkyl;

each $R^{6b}$ is independently selected from the group consisting of F, $C_{1-4}$ alkyl, O—$R^u$, $C_{1-4}$ haloalkyl, $NR^uR^v$, wherein each $R^u$ and $R^v$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, and optionally substituted with oxo; and m is 0, 1, 2, 3 or 4

In some embodiments, the present disclosure provides compounds having the formula (II)

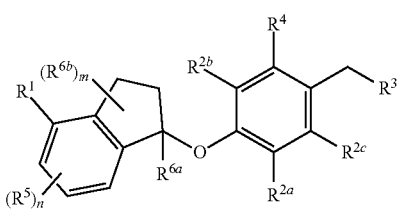

(II)

or a pharmaceutically acceptable salt thereof; wherein:

$R^1$ is selected from the group consisting of $C_{6-10}$ aryl and thienyl, wherein the $C_{6-10}$ aryl and thienyl are optionally substituted with 1 to 5 $R^x$ substituents;

each $R^x$ is independently selected from the group consisting of halogen, —CN, —$R^c$, —$CO_2R^a$, —$CONR^aR^b$, —C(O)$R^a$, —OC(O)$NR^aR^b$, —$NR^bC(O)R^a$, —$NR^bC(O)_2R^c$, —$NR^a$—C(O)$NR^aR^b$, —$NR^aR^b$, —$OR^a$, —O—$X^1$—$OR^a$, —O—$X^1$—$CO_2R^a$, —O—$X^1$—$CONR^aR^b$, —$X^1$—$OR^a$, —$X^1$—$NR^aR^b$, —$X^1$—$CO_2R^a$, —$X^1$—$CONR^aR^b$, —$SF_5$, —$S(O)_2NR^aR^b$, wherein each $X^1$ is a $C_{1-4}$ alkylene; each $R^a$ and $R^b$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, wherein the five or six-membered ring is optionally substituted with oxo; each $R^c$ is independently selected from the group consisting of $C_{1-8}$ alkyl, $C_{2-8}$ alkenyl, $C_{2-8}$ alkynyl and $C_{1-8}$ haloalkyl; and optionally when two $R^x$ substituents are on adjacent atoms, they are combined to form a fused five, six or seven-membered carbocyclic or heterocyclic ring optionally substituted with from 1 to 3 substituents independently selected from oxo, $C_{1-8}$ haloalkyl and $C_{1-8}$ alkyl;

each $R^{2a}$, $R^{2b}$ and $R^{2c}$ is independently selected from the group consisting of H, halogen, —CN, —$R^d$, —$CO_2R^e$, —$CONR^eR^f$, —C(O)$R^e$, —OC(O)$NR^eR^f$, —$NR^fC(O)R^e$, —$NR^fC(O)_2R^d$, —$NR^e$—C(O)$NR^eR^f$, —$NR^eR^f$, —$OR^e$, —O—$X^2$—$OR^e$, —O—$X^2$—$NR^eR^f$, —O—$X^2$—$CO_2R^e$, —O—$X^2$—$CONR^eR^f$, —$X^2$—$OR^e$, —$X^2$—$NR^eR^f$, —$X^2$—$CO_2R^e$, —$X^2$—$CONR^eR^f$, —$SF_5$, —$S(O)_2NR^eR^f$, wherein each $X^2$ is a $C_{1-4}$ alkylene; each $R^e$ and $R^f$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, and optionally substituted with oxo; each $R^d$ is independently selected from the group consisting of $C_{1-8}$ alkyl, $C_{2-8}$ alkenyl, and $C_{1-8}$ haloalkyl;

$R^3$ is selected from the group consisting of $NR^gR^h$ and $C_{4-12}$ heterocyclyl wherein the $C_{4-12}$ heterocyclyl is optionally substituted with 1 to 6 $R^y$;

each $R^y$ is independently selected from the group consisting of halogen, —CN, —$R^i$, —$C_2R^j$, —$CONR^jR^k$, —$CONHC_{1-6}$ alkyl-OH, —C(O)$R^j$, —OC(O)$NR^jR^k$, —$NR^jC(O)R^k$, —$NR^jC(O)_2R^k$, —CONOH, —$PO_3H_2$, —$NR^j$—$C_{1-6}$ alkyl-C(O)$_2R^k$, —$NR^jC(O)NR^jR^k$, —$NR^jR^k$, —$OR^j$, —$S(O)_2NR^jR^k$, —O—$C_{1-6}$alkyl-$OR^j$, —O—$C_{1-6}$ alkyl-$NR^jR^k$, —O—$C_{1-6}$ alkyl-$CO_2R^j$, —O—$C_{1-6}$ alkyl-$CONR^jR^k$, —$C_{1-6}$ alkyl-$OR^j$, —$C_{1-6}$ alkyl-$NR^jR^k$, —$C_{1-6}$ alkyl-$CO_2R^j$, —$C_{1-6}$ alkyl-$CONR^jR^k$, and $SF_5$, wherein the $C_{1-6}$ alkyl is optionally substituted with OH, $SO_2NH_2$, $CONH_2$, CONOH, $PO_3H_2$, COO—$C_{1-8}$alkyl or $CO_2H$, wherein each $R^j$ and $R^k$ is independently selected from hydrogen, $C_{1-8}$ alkyl optionally substituted with OH, $SO_2NH_2$, $CONH_2$, CONOH, $PO_3H_2$, COO—$C_{1-8}$alkyl or $CO_2H$, and $C_{1-8}$ haloalkyl optionally substituted with OH, $SO_2NH_2$, $CONH_2$, CONOH, $PO_3H_2$, COO—$C_{1-8}$alkyl or $CO_2H$, or when attached to the same nitrogen atom $R^j$ and $R^k$ can be combined with the nitrogen atom to form a five or six-membered ring having from 0 to 2 additional heteroatoms as ring members selected from N, O or S, and optionally substituted with oxo; each $R^i$ is independently selected from the group consisting of $C_{1-8}$ alkyl, $C_{2-8}$ alkenyl, and $C_{1-8}$ haloalkyl each of which may be optionally substituted with OH, $SO_2NH_2$, $CONH_2$, CONOH, $PO_3H_2$, COO—$C_{1-8}$alkyl or $CO_2H$;

$R^g$ is selected from the group consisting of H, $C_{1-8}$ haloalkyl and $C_{1-8}$ alkyl;

$R^h$ is selected from —$C_{1-8}$ alkyl, —$C_{1-8}$ alkyl-N(C=O)—$C_{1-8}$ alkenyl, —$C_{1-8}$alkyl-N(C=O)—$C_{1-8}$alkyl, —$C_{1-8}$alkyl-N(C=O)—$C_{1-8}$ alkynyl, —$C_{1-8}$alkyl-(C=O)—N—$C_{1-8}$ alkyl-OH optionally substituted with $CO_2H$, —$C_{1-8}$ alkyl-(C=O)—N—$C_{1-8}$ alkyl-COOH, $C_{3-10}$ cycloalkyl, —$C_{3-10}$ cycloalkyl-COOH, $C_{4-8}$ heterocyclyl, —$C_{4-8}$ heterocyclyl-COOH, —$C_{4-8}$heterocyclyl-OH, —$C_{3-10}$ cycloalkyl-OH, —C(O)—$C_{1-8}$alkyl, —C(O)—$C_{1-8}$alkyl-OH, —C(O)—$C_{1-8}$alkyl-COOH, $C_{1-8}$ haloalkyl, —$C_{1-8}$ alkyl-$C_{4-8}$ heterocyclyl, —$C_{1-8}$ alkyl-$C_{3-10}$ cycloalkyl, —$C_{1-8}$alkyl-$C_{5-10}$ heteroaryl, —$C_{1-8}$ alkyl-$C_{6-10}$ aryl, $C_{1-8}$ alkyl-OH, $C_{1-8}$ alkyl-$CONH_2$, $C_{1-8}$alkyl-$SO_2NH_2$, $C_{1-8}$ alkyl-$PO_3H_2$, $C_{1-8}$ alkyl-CONOH, $C_{3-10}$ cycloalkyl, and $C_{1-8}$ alkyl-COOH, wherein the $C_{1-8}$alkyl is optionally substituted with from 1 to 3 substituents independently selected from OH, COOH, $SO_2NH_2$, $CONH_2$, CONOH, COO—$C_{1-8}$alkyl and $PO_3H_2$, wherein the $C_{5-10}$ heteroaryl and the $C_{6-10}$ aryl are optionally substituted with 1 to 3 substituents independently selected from OH, $B(OH)_2$, COOH, $SO_2NH_2$, $CONH_2$, CONOH, $PO_3H_2$, COO—$C_{1-8}$alkyl, $C_{1-4}$alkyl, $C_{1-4}$alkyl-OH, $C_{1-4}$alkyl-$SO_2NH_2$, $C_{1-4}$alkyl $CONH_2$, $C_{1-4}$alkyl-CONOH, $C_{1-4}$alkyl-PO$_3$H$_2$, and C$_{1-4}$alkyl-COOH, and wherein the C$_{4-8}$ heterocyclyl and C$_{3-10}$ cycloalkyl are optionally substituted with 1 to 3 R$^w$ substituents;

each R$^w$ substituent is independently selected from C$_{1-4}$ alkyl, C$_{1-4}$ alkyl-OH, C$_{1-4}$ alkyl-COOH, C$_{1-4}$ alkyl-SO$_2$NH$_2$, C$_{1-4}$ alkyl CONH$_2$, C$_{1-4}$ alkyl-CONOH, C$_{1-4}$ alkyl-PO$_3$H, OH, COO—C$_{1-8}$alkyl, COOH, SO$_2$NH$_2$, CONH$_2$, CONOH, PO$_3$H$_2$ and oxo;

R$^4$ is selected from the group consisting of O—C$_{1-8}$ alkyl, O—C$_{1-8}$ haloalkyl, O—C$_{1-8}$ alkyl-R$^z$, C$_{6-10}$ aryl, C$_{5-10}$ heteroaryl, —O—C$_{1-4}$ alkyl-C$_{6-10}$aryl and —O—C$_{1-4}$ alkyl-C$_{5-10}$ heteroaryl, wherein the C$_{6-10}$ aryl and the C$_{5-10}$ heteroaryl are optionally substituted with 1 to 5 R$^z$;

each R$^z$ is independently selected from the group consisting of halogen, —CN, —R$^m$, —CO$_2$R$^n$, —CONR"R$^p$, —C(O)R$^n$, —OC(O)NR"R$^p$, —NR"C(O)R$^p$, —NR"C(O)$_2$ R$^m$, —NR"—C(O)NR"R$^p$, —NR"R$^p$, —OR$^n$, —O—X$^3$—OR$^n$, —O—X$^3$—NR"R$^p$, —O—X$^3$—CO$_2$R$^n$, —O—X$^3$—CONR"R$^p$, —X$^3$—OR$^n$, —X$^3$—NR"R$^p$, —X$^3$—CO$_2$R$^n$, —X$^3$—CONR"R$^p$, —SF$_5$, —S(O)$_2$NR"R$^p$, and three to seven-membered carbocyclic or four to seven-membered heterocyclic ring wherein the three to seven-membered carbocyclic or four to seven-membered heterocyclic ring is optionally substituted with 1 to 5 R$^t$, wherein each R$^t$ is independently selected from the group consisting of C$_{1-8}$alkyl, C$_{1-8}$haloalkyl, —CO$_2$R$^n$, —CONR"R$^p$, —C(O)R$^n$, —OC(O)NR"R$^p$, —NR"C(O)R$^p$, —NR"C(O)$_2$R$^m$, —NR"—C(O)NR"R$^p$, —NR"R$^p$, —OR$^n$, —O—X$^3$—OR$^n$, —O—X$^3$—NR"R$^p$, —O—X$^3$—CO$_2$R$^n$, —O—X$^3$—CONR"R$^p$, —X$^3$—OR$^n$, —X$^3$—NR"R$^p$, —X$^3$—CO$_2$R$^n$, —X$^3$—CONR"R$^p$, —SF$_5$, and —S(O)$_2$NR"R$^p$;

wherein each X$^3$ is a C$_{1-4}$ alkylene; each R$^n$ and R$^p$ is independently selected from hydrogen, C$_{1-8}$ alkyl, and C$_{1-8}$ haloalkyl, or when attached to the same nitrogen atom can be combined with the nitrogen atom to form a five or six-membered ring having from 0 to 2 additional heteroatoms as ring members selected from N, O or S, and optionally substituted with oxo; each R$^m$ is independently selected from the group consisting of C$_{1-8}$ alkyl, C$_{2-8}$ alkenyl, and C$_{1-8}$ haloalkyl; and optionally when two R$^z$ substituents are on adjacent atoms, they are combined to form a fused five or six-membered carbocyclic or heterocyclic ring optionally substituted with oxo;

the subscript n is 0, 1, 2 or 3;

each R$^5$ is independently selected from the group consisting of halogen, —CN, —R$^q$, —C$_2$R$^r$, —CONR'R$^s$, —C(O)R$^r$, —OC(O)NR'R$^s$, —NR'C(O)R$^s$, —NR'C(O)$_2$R$^q$, —NR'—C(O)NR'R$^s$, —NR'R$^s$, —OR$^r$, —O—X$^4$—OR$^r$, —O—X$^4$—NR'R$^s$, —O—X$^4$—CO$_2$R$^r$, —O—X$^4$—CONR'R$^s$, —X$^4$—OR$^r$, —X$^4$—NR'R$^s$, —X$^4$—CO$_2$R$^r$, —X$^4$—CONR'R$^s$, —SF$_5$, —S(O)$_2$NR'R$^s$, wherein each X$^4$ is a C$_{1-4}$ alkylene; each R$^r$ and R$^s$ is independently selected from hydrogen, C$_{1-8}$ alkyl, and C$_{1-8}$ haloalkyl, or when attached to the same nitrogen atom can be combined with the nitrogen atom to form a five or six-membered ring having from 0 to 2 additional heteroatoms as ring members selected from N, O or S, and optionally substituted with oxo; each R$^q$ is independently selected from the group consisting of C$_{1-8}$ alkyl, and C$_{1-8}$ haloalkyl;

R$^{6a}$ is selected from the group consisting of H, C$_{1-4}$ alkyl and C$_{1-4}$ haloalkyl;

each R$^{6b}$ is independently selected from the group consisting of F, C$_{1-4}$ alkyl, O—R$^u$, C$_{1-4}$ haloalkyl, NR"R$^v$, wherein each R$^u$ and R$^v$ is independently selected from hydrogen, C$_{1-8}$ alkyl, and C$_{1-8}$ haloalkyl, or when attached to the same nitrogen atom can be combined with the nitrogen atom to form a five or six-membered ring having from 0 to 2 additional heteroatoms as ring members selected from N, O or S, and optionally substituted with oxo; and the subscript m is 0, 1, 2, 3 or 4.

In some embodiments, the compound, or a pharmaceutically acceptable salt thereof has the formula (IIa)

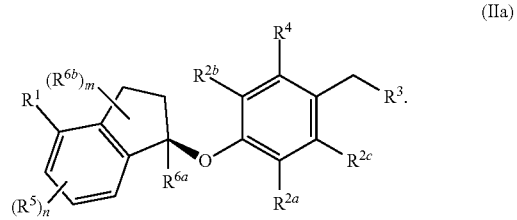

In some embodiments, the compound, or a pharmaceutically acceptable salt thereof having the formula (IIb)

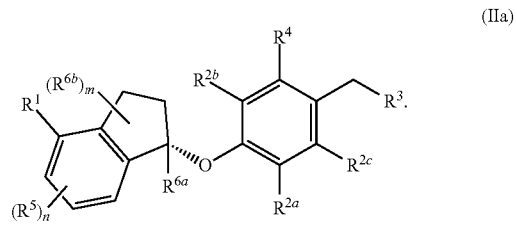

In some embodiments, R$^1$ is selected from the group consisting of phenyl and thienyl, wherein the phenyl and thienyl are optionally substituted with 1 to 5 R$^x$ substituents. In some embodiments, R$^1$ is phenyl optionally substituted with 1 or 2 R$^x$ wherein each R$^x$ is independently selected from halogen, C$_{1-8}$ alkyl, O—C$_{1-8}$ alkyl, O—C$_{1-8}$ haloalkyl, —NR$^a$R$^b$, and CN, and optionally when two R$^x$ substituents are on adjacent atoms, they are combined to form a fused six-membered heterocyclic ring optionally substituted with from 1 to 3 substituents independently selected from oxo, C$_{1-8}$ haloalkyl and C$_{1-8}$ alkyl. In some embodiments, R$^1$ is phenyl optionally substituted with F. In some embodiments, R$^1$ is selected from the group consisting of:

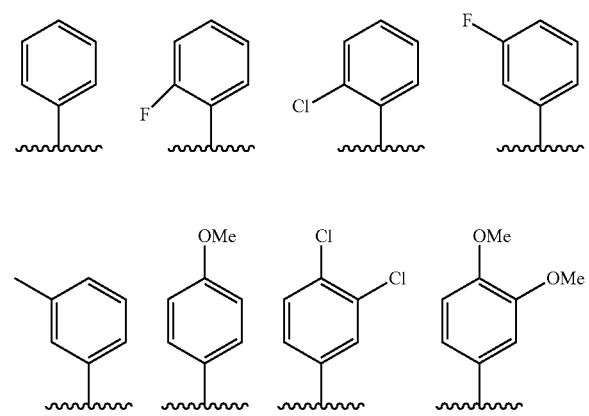

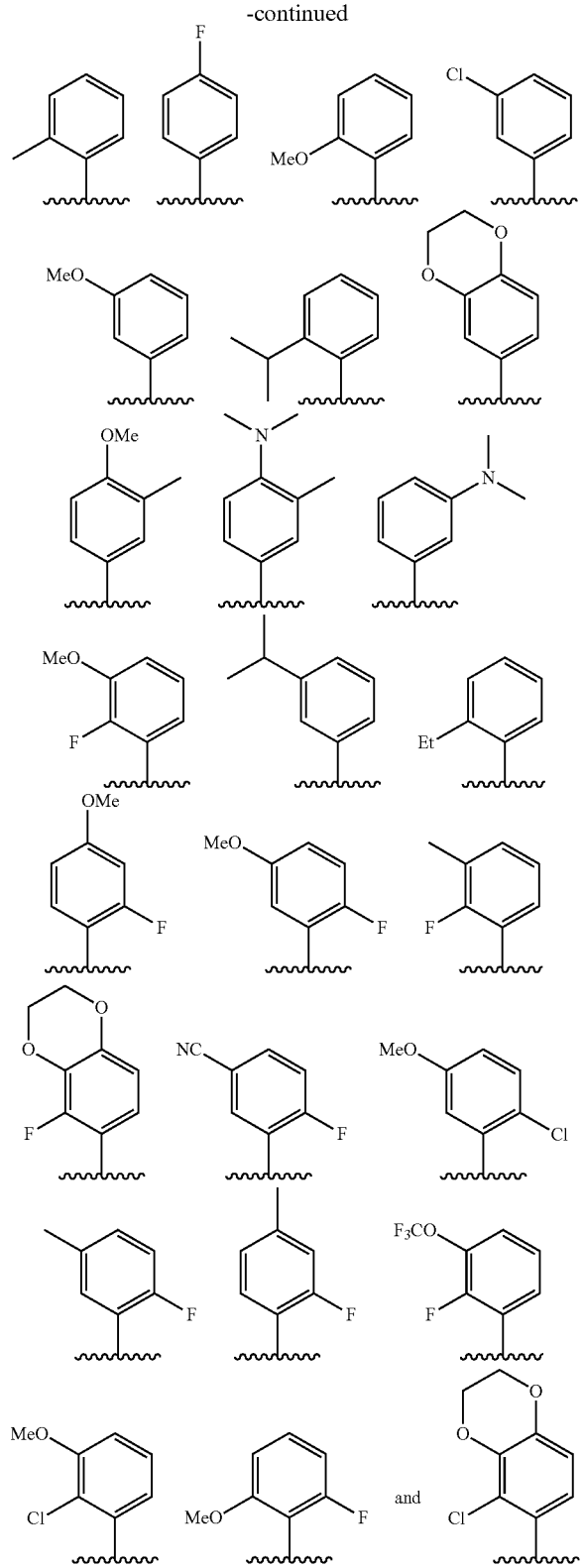

In some embodiments, each $R^{2a}$, $R^{2b}$ and $R^{2c}$ is independently selected from the group consisting of H, halogen, —CN, —$R^d$, —$NR^eR^f$, —$OR^e$, —$X^2$—$OR^e$, —$X^2$—$NR^eR^f$, wherein $X^2$ is $C_{1-4}$ alkylene; each $R^e$ and $R^f$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, and optionally substituted with oxo; each $R^d$ is independently selected from the group consisting of $C_{1-8}$ alkyl, $C_{2-8}$ alkenyl, and $C_{1-8}$ haloalkyl. In some embodiments, $R^{2b}$ and $R^{2c}$ are both H and $R^{2a}$ is selected from the group consisting of halogen, $C_{1-4}$ alkyl, $C_{2-4}$ alkenyl, $C_{1-3}$ haloalkyl, —CN, —OMe and OEt. In some embodiments, $R^{2b}$ and $R^{2c}$ are both H and $R^{2a}$ is halogen. In some embodiments, $R^{2b}$ and $R^{2c}$ are both H and $R^{2a}$ is Cl.

In some embodiments, n is 0, 1 or 2 and each $R^5$ is independently selected from the group consisting of halogen, —CN, —$R^q$, —$NR^rR^s$, and —$OR^r$, wherein each $R^r$ and $R^s$ is independently selected from hydrogen, $C_{1-8}$ alkyl and $C_{1-8}$ haloalkyl and each $R^q$ is independently selected from the group consisting of $C_{1-8}$ alkyl and $C_{1-8}$ haloalkyl. In some embodiments, n is 0.

In some embodiments, $R^{6a}$ is H. In some embodiments, m is 0. In some embodiments, m is 1 and $R^b$ is selected from the group consisting of F, $C_{1-4}$ alkyl, O—$R^u$, $C_{1-4}$ haloalkyl and $NR^uR^v$, wherein each $R^u$ and $R^v$ is independently selected from hydrogen, $C_{1-8}$ alkyl, and $C_{1-8}$ haloalkyl. In some embodiments, m is 1 and $R^{6b}$ is F.

In some embodiments,

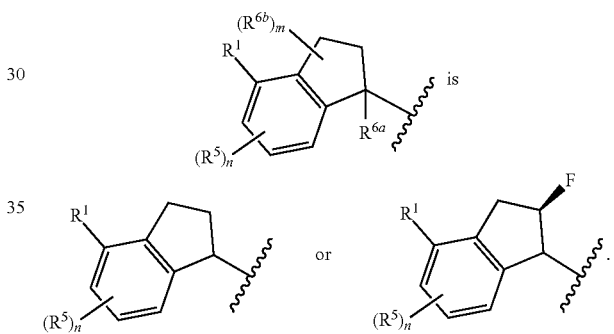

In some embodiments,

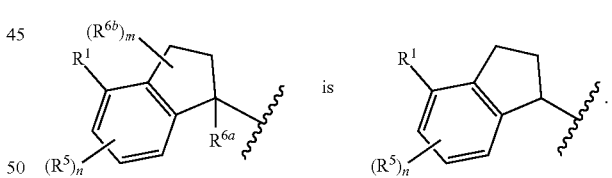

In some embodiments, $R^4$ is selected from the group consisting of O—$C_{1-4}$ alkyl, O—$C_{1-6}$ alkyl-$R^z$, $C_{6-10}$ aryl, $C_{5-10}$ heteroaryl, —O—$C_{1-4}$ alkyl-$C_{6-10}$aryl and —O—$C_{1-4}$ alkyl-$C_{5-10}$ heteroaryl, wherein the $C_{6-10}$ aryl and the $C_{5-10}$ heteroaryl are optionally substituted with 1 to 2 $R^z$, wherein each $R^z$ is independently selected from the group consisting of halogen, —CN, —$R^m$, —$CO_2R''$, —$CONR''R^p$, —C(O)R'', —OC(O)$NR''R^p$, —$NR''C(O)R^p$, —$NR''C(O)_2R^m$, —NR''—C(O)$NR''R^p$, —$NR''R^p$, —OR'', —S(O)$_2NR''R^p$, three to seven-membered carbocyclic ring and four to seven-membered heterocyclic ring wherein the three to seven-membered carbocyclic or four to seven-membered heterocyclic ring is optionally substituted with 1 to 2 $R^t$, wherein each $R^t$ is independently selected from the group consisting of $C_{1-8}$ alkyl, $C_{1-8}$haloalkyl, —$CO_2R''$, —$CONR''R^p$, —C(O)R$^n$, —OC(O)NR$^n$R$^p$, —NR$^n$C(O)R$^p$, —NR$^n$C(O)$_2$R$^m$, —NR$^n$—C(O)NR$^n$R$^p$, —NR$^n$R$^p$, —OR$^n$, and —S(O)$_2$NR$^n$R$^p$. In some embodiments, R$^4$ is selected from the group consisting of O—C$_{1-4}$ alkyl, O—C$_{1-6}$ alkyl-CN, phenyl, pyridinyl, —O—C$_{1-2}$ alkyl-pyridinyl, —O—C$_{1-2}$ alkyl-pyrimidinyl, —O—C$_{1-2}$ alkyl-pyridazinyl, and —O—C$_{1-2}$ alkyl-phenyl, wherein the pyridinyl, phenyl, pyrimidinyl and pyridazinyl is optionally substituted with 1 to 2 R$^z$, wherein each R$^z$ is independently selected from the group consisting of halogen, —CN, —CO$_2$R$^n$, —NR$^n$R$^p$, —OR$^n$, and piperidinyl optionally substituted with OH.

In some embodiments, R$^4$ is selected from the group consisting of:

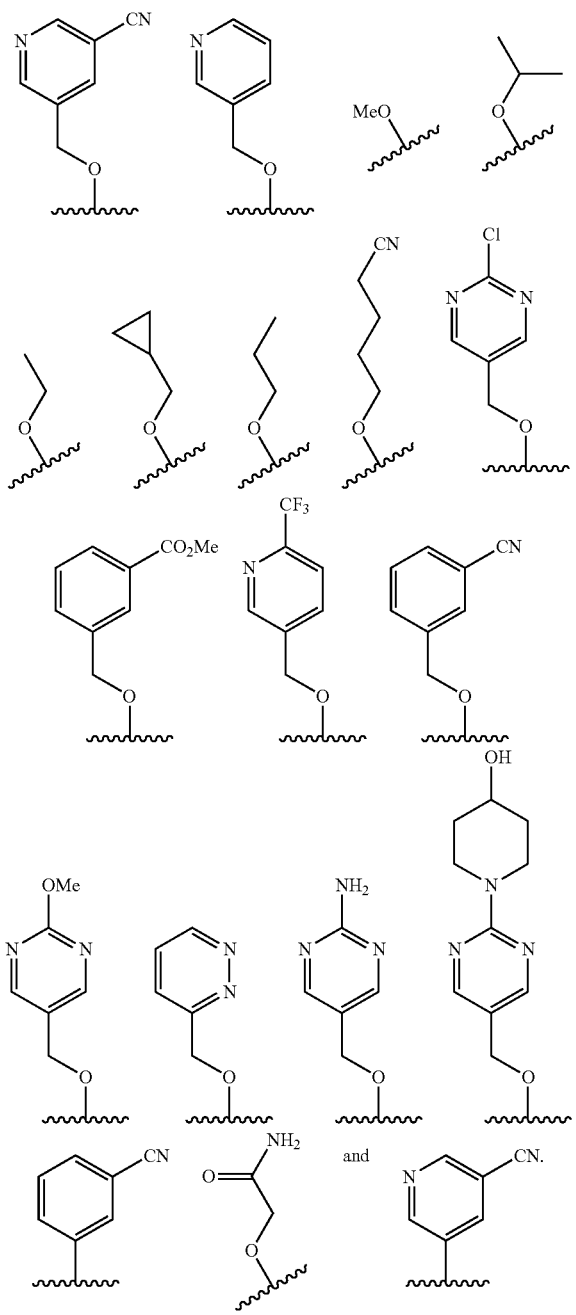

In some embodiments, R$^4$ is

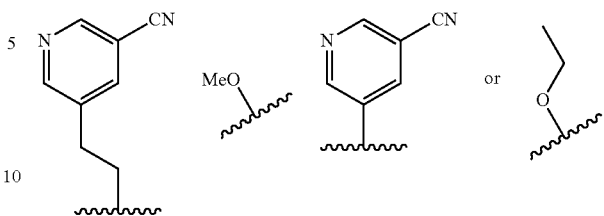

In some embodiments, R$^3$ is selected from the group consisting of NR$^g$R$^h$ and C$_{4-6}$ heterocyclyl wherein the C$_{4-6}$ heterocyclyl is optionally substituted with 1 to 3 R$^y$, wherein R$^g$ is selected from the group consisting of H, C$_{1-8}$ haloalkyl and C$_{1-8}$ alkyl, and wherein R$^h$ is —C$_{1-8}$ alkyl substituted with from 1 to 3 substituents independently selected from OH, COOH, SO$_2$NH$_2$, CONH$_2$, CONOH, COO—C$_{1-8}$ alkyl, C$_{5-6}$ heteroaryl, C$_{5-6}$ heterocyclyl and PO$_3$H$_2$, wherein the C$_{5-6}$ heteroaryl and the C$_{5-6}$ heterocyclyl are optionally substituted with 1 to 3 substituents independently selected from OH, B(OH)$_2$, COOH, SO$_2$NH$_2$, CONH$_2$, CONOH, PO$_3$H$_2$, COO—C$_{1-8}$alkyl, C$_{1-4}$alkyl, C$_{1-4}$alkyl-OH, C$_{1-4}$alkyl-SO$_2$NH$_2$, C$_{1-4}$alkyl CONH$_2$, C$_{1-4}$alkyl-CONOH, C$_{1-4}$alkyl-PO$_3$H$_2$, and C$_{1-4}$alkyl-COOH and wherein the C$_{5-6}$ heterocyclyl is additionally optionally substituted with oxo. In some embodiments, R$^3$ is selected from the group consisting of azetidinyl, pyrrolidinyl and piperidinyl, wherein the azetidinyl, pyrrolidinyl or piperidinyl is linked through the nitrogen atom and wherein the azetidinyl, pyrrolidinyl or piperidinyl is optionally substituted with 1 to 3 R$^y$, wherein each R$^y$ is independently selected from the group consisting of —CO$_2$H, CONOH, PO$_3$H$_2$, OH, SO$_2$NH$_2$, CONH$_2$, and COO—C$_{1-8}$alkyl. In some embodiments, R$^3$ is NHR$^h$, wherein R$^h$ is —C$_{1-8}$ alkyl substituted with from 1 to 2 substituents independently selected from OH, COOH, CONH$_2$, PO$_3$H$_2$, tetrazolyl, tetrazolonyl, and pyrazolyl. In some embodiments, R$^3$ is selected from the group consisting of:

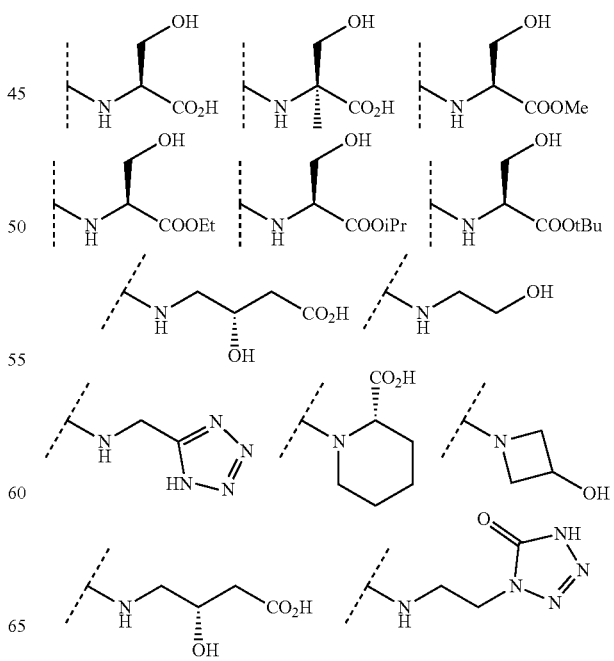

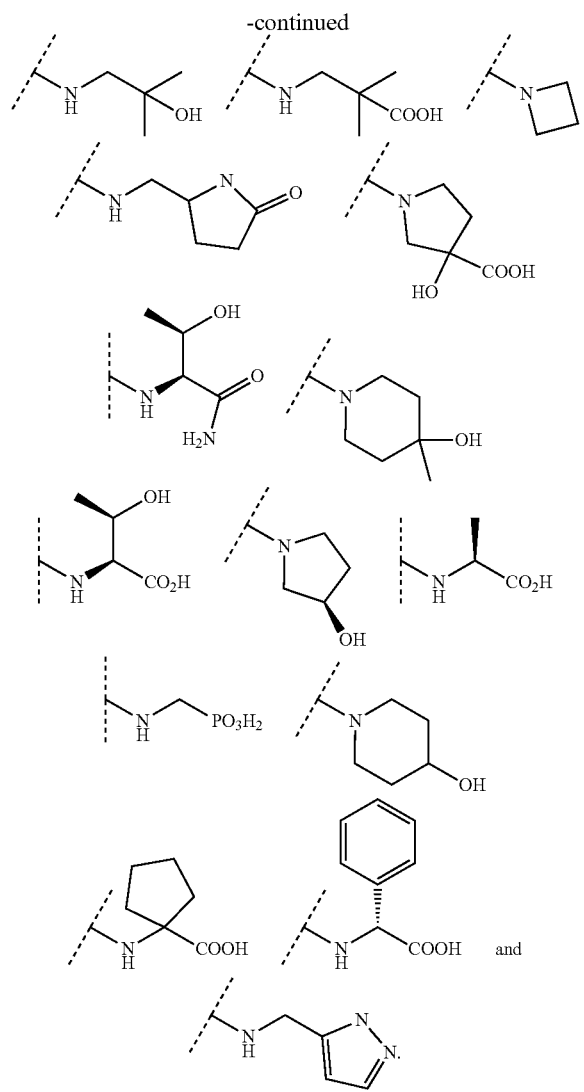

In some embodiments, $R^3$ is $-NR^gR^h$. In some embodiments, $R^h$ combined with the N to which it is attached is a mono-, di- or tri-peptide comprising 1-3 natural amino acids and 0-2 non-natural amino acids, wherein the non-natural aminoacids have an alpha carbon substituent selected from the group consisting of $C_{2-4}$ hydroxyalkyl, $C_{1-3}$ alkyl-guanidinyl, and $C_{1-4}$ alkly-heteroaryl, the alpha carbon of each natural or non-natural amino acids are optionally further substituted with a methyl group, and the terminal moiety of the mono-, di-, or tri-peptide is selected from the group consisting of C(O)OH, C(O)O—$C_{1-6}$ alkyl, and $PO_3H_2$.

In some embodiments, each natural amino acid of $R^h$ is independently selected from the group consisting of serine, alanine, glycine, lysine, arginine, threonine, phenylalanine, tyrosine, asparatate, asparagine, histidine, and leucine.

In some embodiments, $R^1$ is phenyl optionally substituted with 1 to 3 $R^x$, $R^{6a}$ is H, $R^4$ is selected from the group consisting of O—$C_{1-4}$ alkyl, O—$C_{1-6}$ alkyl-CN, phenyl, pyridinyl, —O—$C_{1-2}$ alkyl-pyridinyl, —O—$C_{1-2}$ alkyl-pyrimidinyl, —O—$C_{1-2}$ alkyl-pyridazinyl, and —O—$C_{1-2}$ alkyl-phenyl, wherein the pyridinyl, phenyl, pyrimidinyl and pyridazinyl is optionally substituted with 1 to 2 $R^z$, wherein each $R^z$ is independently selected from the group consisting of halogen, —CN, —$CO_2R^n$, —$NR^nR^p$, —$OR^n$, and piperidinyl optionally substituted with OH, and $R^3$ is selected from the group consisting of $NR^gR^h$ and $C_{4-6}$ heterocyclyl wherein the $C_{4-6}$ heterocyclyl is optionally substituted with 1 to 3 $R^y$, wherein $R^g$ is selected from the group consisting of H, $C_{1-8}$ haloalkyl and $C_{1-8}$ alkyl, and wherein $R^h$ is —$C_{1-8}$ alkyl substituted with from 1 to 3 substituents independently selected from OH, COOH, $SO_2NH_2$, $CONH_2$, CONOH, COO—$C_{1-8}$ alkyl, $C_{5-6}$ heteroaryl, $C_{5-6}$ heterocyclyl and $PO_3H_2$, wherein the $C_{5-6}$ heteroaryl and the $C_{5-6}$ heterocyclyl are optionally substituted with 1 to 3 substituents independently selected from OH, $B(OH)_2$, COOH, $SO_2NH_2$, $CONH_2$, CONOH, $PO_3H_2$, COO—$C_{1-8}$alkyl, $C_{1-4}$alkyl, $C_{1-4}$alkyl-OH, $C_{1-4}$alkyl-$SO_2NH_2$, $C_{1-4}$alkyl $CONH_2$, $C_{1-4}$alkyl-CONOH, $C_{1-4}$alkyl-$PO_3H_2$, and $C_{1-4}$alkyl-COOH and wherein the $C_{5-6}$ heterocyclyl is additionally optionally substituted with oxo.

In some embodiments, $R^1$ is phenyl optionally substituted with 1 or 2 $R^x$ wherein each $R^x$ is independently selected from halogen, $C_{1-8}$ alkyl, O—$C_{1-8}$ alkyl, O—$C_{1-8}$haloalkyl, —$NR^aR^b$, and CN, wherein $R^{2b}$ and $R^{2c}$ are both H, $R^{2a}$ is selected from the group consisting of halogen, $C_{1-4}$ alkyl, $C_{1-3}$ haloalkyl, —CN, —OMe and OEt, $R^{6a}$ is H, m is 0, n is 0, $R^4$ is

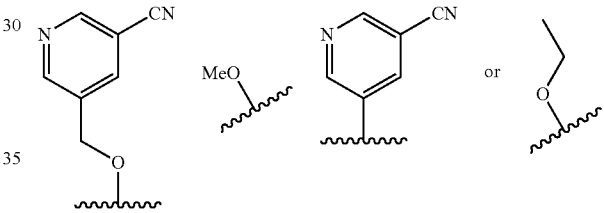

and $R^3$ is selected from the group consisting of $NHR^h$, azetidinyl, pyrrolidinyl and piperidinyl, wherein the azetidinyl, pyrrolidinyl or piperidinyl is linked through the nitrogen atom and wherein the azetidinyl, pyrrolidinyl or piperidinyl is optionally substituted with 1 to 3 $R^y$, wherein each $R^y$ is independently selected from the group consisting of $CO_2H$, CONOH, $PO_3H_2$, OH, $SO_2NH_2$, $CONH_2$, and COO—$C_{1-8}$ alkyl, and wherein $R^h$ is $C_{1-8}$ alkyl substituted with from 1 to 2 substituents independently selected from OH, COOH, $CONH_2$, $PO_3H_2$, tetrazolyl, tetrazolonyl, and pyrazolyl. In some embodiment, $R^2$ is halogen.

In some embodiments, the compound, or a pharmaceutically acceptable salt thereof, is selected from the compounds of Table 2 having an activity of ++ or +++. In some embodiments, the compound, or a pharmaceutically acceptable salt thereof, is selected from the compounds of Table 2 having an activity of +++. In some embodiments, the compound, or a pharmaceutically acceptable salt thereof, is selected from the compounds of Table 2 having an activity of ++. In some embodiments, the compound, or a pharmaceutically acceptable salt thereof, is selected from the compounds of Table 2 having an activity of +.

In some embodiments, the compound, or a pharmaceutically acceptable salt thereof, is selected from the compounds of Table 3 having an activity of ++ or +++. In some embodiments, the compound, or a pharmaceutically acceptable salt thereof, is selected from the compounds of Table 3 having an activity of +++. In some embodiments, the compound, or a pharmaceutically acceptable salt thereof, is selected from the compounds of Table 3 having an activity of ++. In some embodiments, the compound, or a pharmaceutically acceptable salt thereof, is selected from the compounds of Table 3 having an activity of +.

In one aspect, the present disclosure provides compounds having the formula (I):

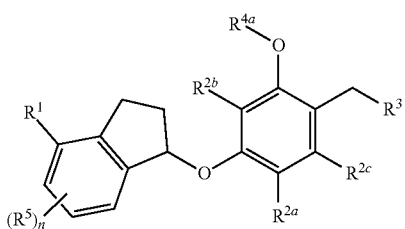

(I)

or a pharmaceutically acceptable salt thereof, wherein:

$R^1$ is selected from the group consisting of $C_{6-10}$ aryl and thienyl, wherein the $C_{6-10}$ aryl and thienyl are optionally substituted with 1 to 5 $R^x$ substituents;

each $R^x$ is independently selected from the group consisting of halogen, —CN, —$R^c$, —$CO_2R^a$, —$CONR^aR^b$, —C(O)$R^a$, —OC(O)$NR^aR^b$, —$NR^bC(O)R^a$, —$NR^bC(O)_2R^a$, —$NR^a$—C(O)$NR^aR^b$, —$NR^aR^b$, —$OR^a$, —O—$X^1$—$OR^a$, —O—$X^1$—$CO_2R^a$, —O—$X^1$—$CONR^aR^b$, —$X^1$—$OR^a$, —$X^1$—$NR^aR^b$, —$X^1$—$CO_2R^a$, —$X^1$—$CONR^aR^b$, —$SF_5$ and —$S(O)_2NR^aR^b$, wherein each $X^1$ is a $C_{1-4}$ alkylene; each $R^a$ and $R^b$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, and optionally substituted with oxo; each $R^c$ is independently selected from the group consisting of $C_{1-8}$ alkyl, $C_{2-8}$ alkenyl, and $C_{1-8}$ haloalkyl; and optionally when two $R^x$ substituents are on adjacent atoms, they are combined to form a fused five or six-membered carbocyclic or heterocyclic ring optionally substituted with oxo;

each $R^{2a}$, $R^{2b}$, and $R^{2c}$ is independently selected from the group consisting of H, halogen, —CN, —$R^d$, —$CO_2R^e$, —$CONR^eR^f$, —C(O)$R^e$, —OC(O)$NR^eR^f$, —$NR^fC(O)R^e$, —$NR^fC(O)_2R^d$, —$NR^e$—C(O)$NR^eR^f$, —$NR^eR^f$, —$OR^e$, —O—$X^2$—$OR^e$, —O—$X^2$—$NR^eR^f$, —O—$X^2$—$CO_2R^e$, —O—$X^2$—$CONR^eR^f$, —$X^2$—$OR^e$, —$X^2$—$NR^eR^f$, —$X^2$—$CO_2R^e$, —$X^2$—$CONR^eR^f$, —$SF_5$, and —$S(O)_2NR^eR^f$, wherein each $X^2$ is a $C_{1-4}$ alkylene; each $R^e$ and $R^f$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, and optionally substituted with oxo; each $R^d$ is independently selected from the group consisting of $C_{1-8}$ alkyl, $C_{2-8}$ alkenyl, and $C_{1-8}$ haloalkyl;

$R^3$ is selected from the group consisting of —$NR^gR^h$ and $C_{4-8}$ heterocyclyl wherein the $C_{4-8}$ heterocyclyl is optionally substituted with 1 to 6 $R^y$;

$R^g$ is selected from H or $C_{1-8}$ alkyl;

$R^h$ is selected from $C_{1-8}$ alkyl, $C_{1-8}$ haloalkyl, —$C_{1-8}$alkyl-$C_{4-8}$ heterocyclyl, —$C_{1-8}$alkyl-$C_{5-10}$ heteroaryl, $C_{1-8}$ alkyl-OH, and $C_{1-8}$ alkyl-COOH, wherein the $C_{1-8}$alkyl is optionally substituted with OH or COOH, wherein the $C_{5-10}$ heteroaryl is optionally substituted with 1 to 3 substituents independently selected from OH, COOH, $C_{1-4}$alkyl, $C_{1-4}$alkyl-OH, and $C_{1-4}$alkyl-COOH, and wherein the $C_{4-8}$ heterocyclyl is optionally substituted with 1 to 3 $R^w$ substituents;

each $R^w$ substituent is independently selected from $C_{1-4}$alkyl, $C_{1-4}$alkyl-OH, $C_{1-4}$alkyl-COOH and oxo;

each $R^y$ is independently selected from the group consisting of halogen, —CN, —$R^i$, —$CO_2R^j$, —$CONR^jR^k$, —$CONHC_{1-4}$alkyl-OH, —C(O)$R^j$, —OC(O)$NR^jR^k$, —$NR^jC(O)R^k$, —$NR^jC(O)_2R^k$, —$NR^j$—$C_{1-4}$alkyl-$R^jC(O)_2R^k$, —$NR^jC(O)NR^jR^k$, —$NR^jR^k$, —$OR^j$, —$S(O)_2NR^jR^k$, —O—$C_{1-4}$alkyl-$OR^j$, —O—$C_{1-4}$alkyl-$NR^jR^k$, —O—$C_{1-4}$alkyl-$CO_2R^j$, —O—$C_{1-4}$alkyl-$CONR^jR^k$, —$C_{1-4}$alkyl-$OR^j$, —$C_{1-4}$alkyl-$NR^jR^k$, —$C_{1-4}$alkyl-$CO_2R^j$, —$C_{1-4}$alkyl-$CONR^jR^k$ and $SF_5$, wherein the $C_{1-4}$alkyl is optionally substituted with OH or $CO_2H$, wherein each $R^j$ and $R^k$ is independently selected from hydrogen, $C_{1-8}$ alkyl optionally substituted with OH or $CO_2H$, and $C_{1-8}$ haloalkyl optionally substituted with OH or $CO_2H$, or when attached to the same nitrogen atom $R^j$ and $R^k$ can be combined with the nitrogen atom to form a five or six-membered ring having from 0 to 2 additional heteroatoms as ring members selected from N, O or S, and optionally substituted with oxo; each $R^i$ is independently selected from the group consisting of $C_{1-8}$ alkyl, $C_{2-8}$ alkenyl, and $C_{1-8}$ haloalkyl which may be optionally substituted with OH or $CO_2H$;

$R^{4a}$ is selected from —$C_{1-4}$alkyl-$C_{6-10}$aryl and —$C_{1-4}$alkyl-$C_{5-10}$ heteroaryl, wherein the $C_{6-10}$aryl and the $C_{5-10}$ heteroaryl are optionally substituted with 1 to 5 $R^z$;

each $R^z$ is independently selected from the group consisting of halogen, —CN, —$R^m$, —$CO_2R^n$, —$CONR''R^p$, —C(O)$R^n$, —OC(O)$NR''R^p$, —$NR''C(O)R^p$, —$NR''C(O)_2R^m$, —$NR''$—C(O)$NR''R^p$, —$NR''R^p$, —$OR^n$, —O—$X^3$—$OR^n$, —O—$X^3$—$NR''R^p$, —O—$X^3$—$CO_2R^n$, —O—$X^3$—$CONR''R^p$, —$X^3$—$OR^n$, —$X^3$—$NR''R^p$, —$X^3$—$CO_2R^n$, —$X^3$—$CONR''R^p$, —$SF_5$ and —$S(O)_2NR''R^p$, wherein each $X^3$ is a $C_{1-4}$ alkylene; each $R''$ and $R^p$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, and optionally substituted with oxo; each $R^m$ is independently selected from the group consisting of $C_{1-8}$ alkyl, $C_{2-8}$ alkenyl, and $C_{1-8}$ haloalkyl; and optionally when two $R^z$ substituents are on adjacent atoms, they are combined to form a fused five or six-membered carbocyclic or heterocyclic ring optionally substituted with oxo;

the subscript n is 0, 1, 2 or 3;

each $R^5$ is independently selected from the group consisting of halogen, —CN, —$R^q$, —$CO_2R^r$, —$CONR'R^s$, —C(O)$R^r$, —OC(O)$NR'R^s$, —$NR'C(O)R^s$, —$NR'C(O)_2R^q$, —$NR'$—C(O)$NR'R^s$, —$NR'R^s$, —$OR^r$, —O—$X^4$—$OR^r$, —O—$X^4$—$NR'R^s$, —O—$X^4$—$CO_2R^r$, —O—$X^4$—$CONR'R^s$, —$X^4$—$OR^r$, —$X^4$—$NR'R^s$, —$X^4$—$CO_2R^r$, —$X^4$—$CONR'R^s$, —$SF_5$ and —$S(O)_2NR'R^s$, wherein each $X^4$ is a $C_{1-4}$ alkylene; each $R^r$ and $R^s$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, and optionally substituted with oxo; each $R^q$ is independently selected from the group consisting of $C_{1-8}$ alkyl, and $C_{1-8}$ haloalkyl.

In some embodiments, compounds, or pharmaceutically acceptable salts thereof, are provided having the formula (Ia)

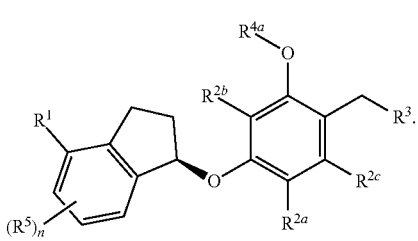

(Ia)

In some embodiments, compounds, or pharmaceutically acceptable salts thereof, are provided having the formula (Ib)

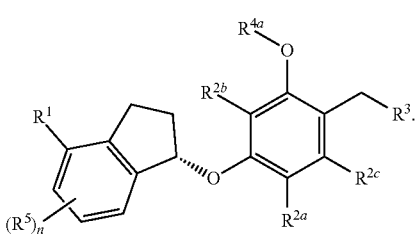

(Ib)

In some embodiments, $R^1$ is selected from the group consisting of $C_{6-10}$ aryl and thienyl, wherein the $C_{6-10}$ aryl and thienyl are optionally substituted with 1 to 5 $R^x$ substituents.

In some embodiments, $R^1$ is selected from the group consisting of phenyl and thienyl, wherein the phenyl and thienyl are optionally substituted with 1 to 5 $R^x$ substituents. In some embodiments, $R^1$ is phenyl substituted with 1 to 5 $R^x$ substituents. In some embodiments, $R^1$ is unsubstituted phenyl.

In some embodiments, each $R^{2a}$, $R^{2b}$, and $R^{2c}$ is independently selected from the group consisting of H, halogen, —CN, —$R^d$, —$NR^eR^f$, —$OR^e$, —$X^2$—$OR^e$, —$X^2$—$NR^eR^f$, wherein $X^2$ is $C_{1-4}$ alkylene; each $R^e$ and $R^f$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, and optionally substituted with oxo; each $R^d$ is independently selected from the group consisting of $C_{1-8}$ alkyl, $C_{2-8}$ alkenyl, and $C_{1-8}$ haloalkyl.

In some embodiments, each $R^{2a}$, $R^{2b}$ and $R^{2c}$ is independently selected from the group consisting of halogen, $C_{1-4}$ alkyl, $C_{2-4}$ alkenyl, $C_{1-3}$ haloalkyl, —CN, —OMe and OEt.

In some embodiments, $R^{2b}$ and $R^{2c}$ are both H and $R^{2a}$ is selected from the group consisting of halogen, $C_{1-4}$ alkyl, $C_{2-4}$ alkenyl, $C_{1-3}$ haloalkyl, —CN, —OMe and OEt.

In some embodiments, $R^{2b}$ and $R^{2c}$ are both H and $R^{2a}$ is halogen.

In some embodiments, $R^{2b}$ and $R^{2c}$ are both H and $R^{2a}$ is Cl.

In some embodiments, n is 0, 1 or 2. In some embodiments, n is 0 or 1. In some embodiments, n is 0.

In some embodiments, $R^3$ is selected from the group consisting of $NR^gR^h$ and $C_{4-8}$ heterocyclyl wherein $R^g$ is H and wherein the $C_{4-8}$ heterocyclyl is linked through a N and is optionally substituted with 1 to 6 $R^y$.

In some embodiments, $R^3$ is selected from the group consisting of $NR^gR^h$ and $C_{4-8}$ heterocyclyl wherein $R^g$ is H, $R^h$ is selected from —$C_{1-8}$alkyl-tetrazole, —$C_{1-8}$alkyl-pyrazole, —$C_{1-8}$alkyl-pyrrolidine, $C_{1-8}$ alkyl-OH, and $C_{1-8}$ alkyl-COOH, wherein the $C_{1-8}$alkyl is optionally substituted with OH or COOH, wherein the tetrazole is optionally substituted with OH, wherein the pyrrolidine is optionally substituted with oxo, wherein the $C_{4-8}$ heterocyclyl is azetidine or piperidine and is linked through the N and is optionally substituted with OH or COOH.

In some embodiments, $R^3$ is selected from the group consisting of $NR^gR^h$ and $C_{4-8}$ heterocyclyl wherein $R^g$ is H, $R^h$ is selected from —$C_{1-4}$alkyl-tetrazole, —$C_{1-4}$alkyl-pyrazole, —$C_1$-4alkyl-pyrrolidine, $C_{1-4}$ alkyl-OH, and $C_{1-4}$ alkyl-COOH, wherein the $C_{1-4}$alkyl is optionally substituted with OH or COOH, wherein the tetrazole is optionally substituted with OH, wherein the pyrrolidine is optionally substituted with oxo, wherein the $C_{4-8}$ heterocyclyl is azetidine or piperidine and is linked through the N and is optionally substituted with OH or COOH.

In some embodiments, $R^3$ is selected from the group consisting of:

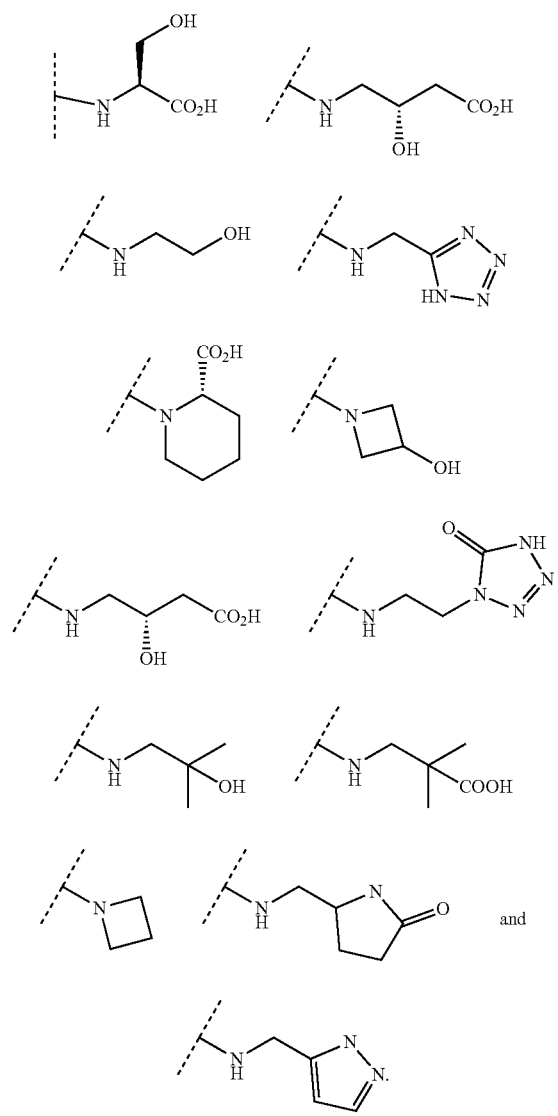

In some embodiments, $R^3$ is selected from the group consisting of:

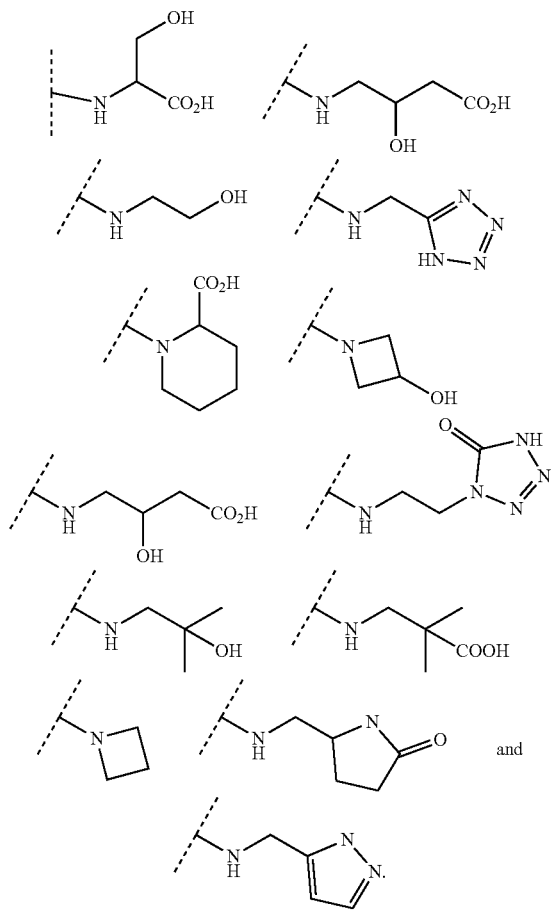

In some embodiments, $R^{4a}$ is selected from —$C_{1-2}$alkyl-$C_{6-10}$aryl and —$C_{1-2}$alkyl-$C_{5-10}$ heteroaryl, wherein the $C_{6-10}$aryl and the $C_{5-10}$ heteroaryl are optionally substituted with 1 to 5 $R^z$. In some embodiments, $R^{4a}$ is —$C_{1-2}$alkyl-$C_{5-6}$ heteroaryl, wherein the $C_{5-6}$ heteroaryl is optionally substituted with 1 to 3 $R^z$. In some embodiments, $R^{4a}$ is —$CH_2$—$C_{5-10}$ heteroaryl optionally substituted with 1 to 3 $R^z$. In some embodiments, $R^{4a}$ is —$CH_2$—$C_{5-6}$ heteroaryl optionally substituted with 1 to 3 $R^z$. In some embodiments, $R^{4a}$ is —$CH_2$-pyridinyl optionally substituted with 1 to 2 $R^z$.

In some embodiments, $R^{4a}$ is

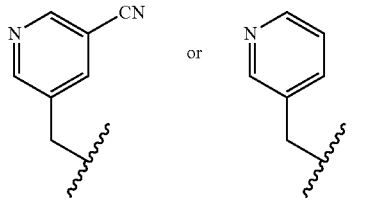

In addition to the compounds provided above, pharmaceutically acceptable salts of those compounds are also provided. In some embodiments, the pharmaceutically acceptable salts are selected from ammonium, calcium, magnesium, potassium, sodium, zinc, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, procaine, purines, theobromine, triethylamine, trimethylamine, tripropylamine, tromethamine, hydrochloric, carbonic, monohydrogencarbonic, phosphoric, monohydrogenphosphoric, dihydrogenphosphoric, acetic, propionic, isobutyric, malonic, benzoic, succinic, suberic, fumaric, mandelic, phthalic, benzenesulfonic, p-tolylsulfonic, citric, tartaric, methanesulfonic, arginate, glucuronic acid and galactunoric acids. In some embodiments, the pharmaceutically acceptable salts are selected from ammonium, calcium, magnesium, potassium, sodium, hydrochloric, carbonic, monohydrogencarbonic, phosphoric, monohydrogenphosphoric, dihydrogenphosphoric, acetic, propionic, isobutyric, malonic, benzoic, succinic, suberic, fumaric, mandelic, phthalic, benzenesulfonic, p-tolylsulfonic, citric, tartaric, methanesulfonic, arginate, glucuronic acid and galactunoric acids. In some embodiments, the pharmaceutically acceptable salts are sodium or hydrochloric.

In addition to salt forms, the present disclosure provides compounds which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

An ester may be used as a prodrug for the corresponding carboxylic acid. A $C_{1-10}$ alkyl ester or a $C_{1-10}$ haloalkyl ester may be used as a prodrug for the corresponding carboxylic acid. The following esters may be used: ter-butyl ester, methyl ester, ethyl ester, isopropyl ester. More specifically, ester prodrugs may be used as $R^3$ groups such as threonine or serine prodrug esters which are linked to the rest of the molecule through their nitrogen. More specifically, the following prodrugs may be used for $R^3$:

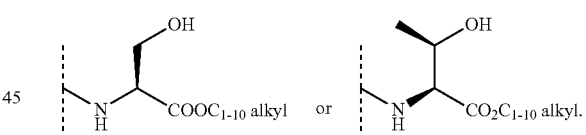

More specifically, the following prodrugs may be used for $R^3$:

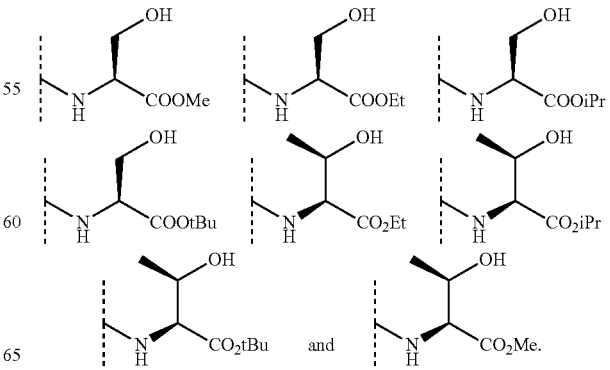

Pharmaceutical Compositions

In addition to the compounds provided herein, compositions of those compounds will typically contain a pharmaceutical carrier or diluent.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

In another embodiment, a pharmaceutical composition comprising a compound of the present disclosure including a compound of Formula (II), (IIa), (IIb), (I), (Ia), or (Ib) or a pharmaceutically acceptable salt thereof, and a pharmaceutically acceptable excipient, is provided.

In some embodiments, the pharmaceutical composition further comprises one or more additional therapeutic agents. In some embodiments, the one or more additional therapeutic agent is selected from the group consisting of an antimicrobial agent, an antiviral agent, a cytotoxic agent, a gene expression modulatory agent, a chemotherapeutic agent, an anti-cancer agent, an anti-angiogenic agent, an immunotherapeutic agent, an anti-hormonal agent, an anti-fibrotic agent, radiotherapy, a radiotherapeutic agent, an anti-neoplastic agent, and an anti-proliferation agent. In some embodiments, the one or more additional therapeutic agent is selected from the group consisting of one or more of CCX354, CCX9588, CCX140, CCX872, CCX598, CCX6239, CCX9664, CCX2553, CCX2991, CCX282, CCX025, CCX507, CCX430, CCX765, CCX224, CCX662, CCX650, CCX832, CCX168, and CCX168-M1.

The pharmaceutical compositions for the administration of the compounds of this disclosure may conveniently be presented in unit dosage form and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self-emulsifications as described in U.S. Patent Application 2002-0012680, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, polyethylene glycol (PEG) of various average sizes (e.g., PEG400, PEG4000) and certain surfactants such as cremophor or solutol, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono- or di-glycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the disclosure may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present disclosure may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present disclosure are employed. As used herein, topical application is also meant to include the use of mouth washes and gargles.

The compounds of this disclosure may also be coupled a carrier that is a suitable polymers as targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the compounds of the disclosure may be coupled to a carrier that is a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like. In one embodiment of the disclosure, the compound of the disclosure is coupled to a polymer or semipermeable polymer matrix that is formed as a stent or stent-graft device.

Methods of Treating Diseases and Disorders

The compounds of the disclosure may be used as immunomodulators. The compounds of the disclosure may be used as agonists, antagonists, partial agonists, inverse agonists, inhibitors of PD-1 and/or PD-L1 in a variety of contexts, both in vitro and in vivo. In some embodiments, the compounds of the disclosure may be used as inhibitors of the PD-1/PD-L1 protein protein interaction. In some embodiments, the compounds of the disclosure may be used as inhibitors of PD-L1. In some embodiments, the compounds of the disclosure may be used as inhibitors of the CD80/PD-L1 protein protein interaction. In some embodiments, the compounds of the disclosure may be used to inhibit the interaction between PD-1 and PD-L1 and/or PD-1 and CD80 and/or PD-1 and PD-L2 in vitro or in vivo. In some embodiments, the compounds of the disclosure may be used to inhibit VISTA and/or TIM-3. In some embodiments, the compounds of the disclosure may be inhibitors of the PD-1/PD-L1 protein protein interaction and inhibitors of VISTA and/or TIM-3. In some embodiments, in addition to being inhibitors of the PD-1/PD-L1 protein protein interaction, the compounds of the disclosure may be inhibitors of CTLA-4 and/or BTLA and/or LAG-3 and/or KLRG-1 and/or 2B4 and/or CD160 and/or HVEM and/or CD48 and/or E-cadherin and/or MHC-II and/or galectin-9 and/or CD86 and/or PD-L2 and/or VISTA and/or TIM-3 and/or CD80.

The compounds of the disclosure may be contacted with the receptor they interact with, in aqueous solution and under conditions otherwise suitable for binding of the ligand to the receptor. The receptor may be present in suspension (e.g., in an isolated membrane or cell preparation), in a cultured or isolated cell, or in a tissue or organ.

Preferably, the amount of the compounds of the disclosure contacted with the receptor should be sufficient to inhibit the PD-1/PD-L1 binding in vitro as measured, for example, using an ELISA. The receptor may be present in solution or suspension, in a cultured or isolated cell preparation or within a patient.

In some embodiments, the compounds of the present disclosure are useful for restoring and augmenting T cell activation. In some embodiments, the compounds of the present disclosure are useful for enhancing an immune response in a patient. In some embodiments, the compounds of the present disclosure are useful for treating, preventing, or slowing the progression of diseases or disorders in a variety of therapeutic areas, such as cancer and infectious diseases.

In some embodiments, the compounds of the present disclosure can be used for treating patients suffering from conditions that are responsive to PD-1/PD-L1 protein protein interaction modulation.

In some embodiments, a method of modulating an immune response mediated by the PD-1 signaling pathway in a subject, comprising administering to the subject a therapeutically effective amount of a compound of the present disclosure including a compound of Formula Formula (II), (IIa), (IIb), (I), (Ia), or (Ib), or a pharmaceutically acceptable salt thereof or a composition comprising a compound of the present disclosure including a compound of Formula (II), (IIa), (IIb), (I), (Ia), or (Ib), or a pharmaceutically acceptable salt thereof, is provided.

In some embodiments, a method of enhancing, stimulating, modulating and/or increasing the immune response in a subject in need thereof, comprising administering to the subject a therapeutically effective amount of a compound of the present disclosure including a compound of Formula (II), (IIa), (IIb), (I), (Ia), or (Ib), or a pharmaceutically acceptable salt thereof or a composition of a compound of the present disclosure including a compound of Formula (II), (IIa), (IIb), (I), (Ia), or (Ib), or a pharmaceutically acceptable salt thereof, is provided.

In some embodiments, a method of inhibiting growth, proliferation, or metastasis of cancer cells in a subject in need thereof, comprising administering to the subject a therapeutically effective amount of a compound of the present disclosure including a compound of Formula (II), (IIa), (IIb), (I), (Ia), or (Ib), or a pharmaceutically acceptable salt thereof or a composition of a compound of the present disclosure including a compound of Formula (II), (IIa), (IIb), (I), (Ia), or (Ib), or a pharmaceutically acceptable salt thereof, is provided.

In some embodiments, a method of treating a subject in need thereof, comprising administering to the subject a therapeutically effective amount of a compound of the present disclosure including a compound of Formula (II), (IIa), (IIb), (I), (Ia), or (Ib), or a pharmaceutically acceptable salt thereof or a composition of a compound of the present disclosure including a compound of Formula (II), (IIa), (IIb), (I), (Ia), or (Ib), or a pharmaceutically acceptable salt thereof, is provided.

In some embodiments, the subject suffers from a disease or disorder selected from the group consisting of an infectious disease, a bacterial infectious disease, a viral infectious disease a fungal infectious disease, a solid tumor, a hematological malignancy, an immune disorder, an inflammatory disease, and cancer. In some embodiments, the disease or disorder is selected from the group consisting of melanoma, glioblastoma, esophagus tumor, nasopharyngeal carcinoma, uveal melanoma, lymphoma, lymphocytic lymphoma, primary CNS lymphoma, T-cell lymphoma, diffuse large B-cell lymphoma, primary mediastinal large B-cell lymphoma, prostate cancer, castration-resistant prostate cancer, chronic myelocytic leukemia, Kaposi's sarcoma fibrosarcoma, liposarcoma, chondrosarcoma, osteogenic sarcoma, angiosarcoma, lymphangiosarcoma, synovioma, meningioma, leiomyosarcoma, rhabdomyosarcoma, sarcoma of soft tissue, sarcoma, sepsis, biliary tumor, basal cell carcinoma, thymus neoplasm, cancer of the thyroid gland, cancer of the parathyroid gland, uterine cancer, cancer of the adrenal gland, liver infection, Merkel cell carcinoma, nerve tumor, follicle center lymphoma, colon cancer, Hodgkin's disease, non-Hodgkin's lymphoma, leukemia, chronic or acute leukemias including acute myeloid leukemia, chronic myeloid leukemia, acute lymphoblastic leukemia, chronic lymphocytic leukemia, multiple myeloma, ovary tumor, myelodysplastic syndrome, cutaneous or intraocular malignant melanoma, renal cell carcinoma, small-cell lung cancer, lung cancer, mesothelioma, breast cancer, squamous non-small cell lung cancer (SCLC), non-squamous NSCLC, colorectal cancer, ovarian cancer, gastric cancer, hepatocellular carcinoma, pancreatic carcinoma, pancreatic cancer, Pancreatic ductal adenocarcinoma, squamous cell carcinoma of the head and neck, cancer of the head or neck, gastrointestinal tract, stomach cancer, HIV, Hepatitis A, Hepatitis B, Hepatitis C, hepatitis D, herpes viruses, papillomaviruses, influenza, bone cancer, skin cancer, rectal cancer, cancer of the anal region, testicular cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the urethra, cancer of the penis, cancer of the bladder, cancer of the kidney, cancer of the ureter, carcinoma of the renal pelvis, neoplasm of the central nervous system (CNS), tumor angiogenesis, spinal axis tumor, brain stem glioma, pituitary adenoma, epidermoid cancer, abestosis, carcinoma, adenocarcinoma, papillary carcinoma, cystadenocarcinoma, bronchogenic carcinoma, renal cell carcinoma, transitional cell carcinoma, choriocarcinoma, seminoma, embryonal carcinoma, wilm's tumor, pleomorphic adenoma, liver cell papilloma, renal tubular adenoma, cystadenoma, papilloma, adenoma, leiomyoma, rhabdomyoma, hemangioma, lymphangioma, osteoma, chondroma, lipoma and fibroma.

In some embodiments, a therapeutically effective amount of one or more additional therapeutic agents is further administered to the subject. In some embodiments, the one or more additional therapeutic agents is selected from the group consisting of an antimicrobial agent, an antiviral agent, a cytotoxic agent, a gene expression modulatory agent, a chemotherapeutic agent, an anti-cancer agent, an anti-angiogenic agent, an immunotherapeutic agent, an anti-hormonal agent, an anti-fibrotic agent, radiotherapy, a radiotherapeutic agent, an anti-neoplastic agent, and an anti-proliferation agent. In some embodiments, the one or more additional therapeutic agent is selected from the group consisting of one or more of CCX354, CCX9588, CCX140, CCX872, CCX598, CCX6239, CCX9664, CCX2553, CCX 2991, CCX282, CCX025, CCX507, CCX430, CCX765, CCX224, CCX662, CCX650, CCX832, CCX168, and CCX168-M1.

In some embodiments, the compounds of the present disclosure may be used to inhibit an infectious disease. The infectious disease includes but is not limited to HIV, Influenza, Herpes, Giardia, Malaria, *Leishmania*, the pathogenic infection by the virus Hepatitis (A, B, and C), herpes virus (e.g., VZV, HSV-I, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus, pathogenic infection by the bacteria *chlamydia*, rickettsial bacteria, mycobacteria, staphylococci, streptococci, pneumonococci, meningococci and conococci, *klebsiella, proteus, serratia, pseudomonas, E. coli, legionella*, diphtheria, *salmonella*, bacilli, cholera, tetanus, botulism, anthrax, plague, leptospirosis, and Lyme's disease bacteria, pathogenic infection by the fungi *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum*, and pathogenic infection by the parasites *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi, Nippostrongylus brasiliensis*.

In some embodiments, the compounds of the present disclosure may be used to inhibit HIV infection, delay AIDS progression, deplete HIV viral reservoir or decrease the severity of symptoms or HIV infection and AIDS.

The compounds of the present disclosure may be used for the treatment of cancers and precancerous conditions in a subject.

Treatment methods provided herein include, in general, administration to a patient an effective amount of one or more compounds provided herein. Suitable patients include those patients suffering from or susceptible to (i.e., prophylactic treatment) a disorder or disease identified herein. Typical patients for treatment as described herein include mammals, particularly primates, especially humans. Other suitable patients include domesticated companion animals such as a dog, cat, horse, and the like, or a livestock animal such as cattle, pig, sheep and the like.

In general, treatment methods provided herein comprise administering to a patient an effective amount of a compound one or more compounds provided herein. In a preferred embodiment, the compound(s) of the disclosure are preferably administered to a patient (e.g., a human) intravenously, orally or topically. The effective amount may be an amount sufficient to modulate the PD-1/PD-L1 interaction and/or an amount sufficient to reduce or alleviate the symptoms presented by the patient. Preferably, the amount administered is sufficient to yield a plasma concentration of the compound (or its active metabolite, if the compound is a pro-drug) high enough to sufficient to modulate the PD-1/PD-L1 interaction. Treatment regimens may vary depending on the compound used and the particular condition to be treated; for treatment of most disorders, a frequency of administration of 4 times daily or less is preferred. In general, a dosage regimen of 2 times daily is more preferred, with once a day dosing particularly preferred. It will be understood, however, that the specific dose level and treatment regimen for any particular patient will depend upon a variety of factors including the activity of the specific compound employed, the age, body weight, general health, sex, diet, time of administration, route of administration, rate of excretion, drug combination (i.e., other drugs being administered to the patient) and the severity of the particular disease undergoing therapy, as well as the judgment of the prescribing medical practitioner. In general, the use of the minimum dose sufficient to provide effective therapy is preferred. Patients may generally be monitored for therapeutic effectiveness using medical or veterinary criteria suitable for the condition being treated or prevented.

Combinations

A concomitant medicine comprising the compounds of the present disclosure and other drug may be administered as a combination preparation in which both components are contained in a single formulation, or administered as separate formulations. The administration by separate formulations includes simultaneous administration and administration with some time intervals. In the case of the administration with some time intervals, the compound of the present disclosure can be administered first, followed by another drug or another drug can be administered first, followed by the compound of the present disclosure. The administration method of the respective drugs may be the same or different.

The dosage of the other drug can be properly selected, based on a dosage that has been clinically used. The compounding ratio of the compound of the present disclosure and the other drug can be properly selected according to age and weight of a subject to be administered, administration method, administration time, disorder to be treated, symptom and combination thereof. For example, the other drug may be used in an amount of 0.01 to 100 parts by mass, based on 1 part by mass of the compound of the present disclosure. The other drug may be a combination of two or more kind of arbitrary drugs in a proper proportion.

The compounds described herein may be used or combined with one or more therapeutic agent such as an antimicrobial agent, an antiviral agent, a cytotoxic agent, a gene expression modulatory agent, a chemotherapeutic agent, an anti-cancer agent, an anti-angiogenic agent, an immunotherapeutic agent, an anti-hormonal agent, an anti-fibrotic agent, radiotherapy, a radiotherapeutic agent, an anti-neoplastic agent, and an anti-proliferation agent. These therapeutic agents may be in the forms of compounds, antibodies, polypeptides, or polynucleotides.

The compounds described herein may be used or combined with one or more of a therapeutic antibody, a bispecific antibody and "antibody-like" therapeutic protein (such as DARTs®, Duobodies®, Bites®, XmAbs®, TandAbs®, Fab derivatives), an antibody-drug conjugate (ADC), a virus, an oncolytic virus, gene modifiers or editors such as CRISPR (including CRISPR Cas9), zinc finger nucleases or synthetic nucleases (TALENs), a CAR (chimeric antigen receptor) T-cell immunotherapeutic agent, or any combination thereof.

Examples of chemotherapeutics include an alkylation agent, nitrosourea agent, antimetabolite, anticancer antibiotics, vegetable-origin alkaloid, topoisomerase inhibitor, hormone drug, hormone antagonist, aromatase inhibitor, P-glycoprotein inhibitor, platinum complex derivative, other immunotherapeutic drugs and other anticancer drugs.

The compounds described herein may be used or combined with a cancer treatment adjunct, such as a leucopenia (neutropenia) treatment drug, thrombocytopenia treatment drug, antiemetic and cancer pain intervention drug, concomitantly or in a mixture form.

The compounds described herein may be used or combined with a kinase inhibitor.

In one embodiment, the compounds of the present disclosure can be used with other immunomodulators and/or a potentiating agent concomitantly or in a mixture form. Examples of the immunomodulator include various cytokines, vaccines and adjuvants. Examples of these cytokines, vaccines and adjuvants that stimulates immune responses include but not limited to GM-CSF, M-CSF, G-CSF, interferon-a, beta, or gamma, IL-1, IL-2, IL-3, IL-12, Poly (I:C) and CPG. The potentiating agents include cyclophosphamide and analogs of cyclophosphamide, anti-TGF and imatinib (Gleevac), a mitosis inhibitor, such as paclitaxel, Sunitinib (Sutent) or other antiangiogenic agents, an aromatase inhibitor, such as letrozole, an A2a adenosine receptor (A2AR) antagonist, an angiogenesis inhibitor, anthracyclines, oxaliplatin, doxorubicin, TLR4 antagonists, and IL-18 antagonists.

In some embodiments, the compounds described herein may be used or combined with one or more modulator of CCR1, CCR2, CCR3, CCR4, CCR5, CCR6, CCR7, CCR8, CCR9, CCR10, CCR11, CXCR1, CXCR2, CXCR3, CXCR4, CXCR5, CXCR6, CXCR7, ChemR23, C5aR, C5a, and C5. In some embodiments, the modulator is an antagonist.

In some embodiments, the compounds described herein may be used or combined with one or more of CCX354, CCX9588, CCX140, CCX872, CCX598, CCX6239, CCX9664, CCX2553, CCX 2991, CCX282, CCX025, CCX507, CCX430, CCX765, CCX224, CCX662, CCX650, CCX832, CCX168, and CCX168-M1.

Dosage

Dosage levels of the order of from about 0.1 mg to about 140 mg per kilogram of body weight per day are useful in the treatment or preventions of conditions involving the PD-1/PD-L1 interaction (about 0.5 mg to about 7 g per human patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. For compounds administered orally, transdermally, intravaneously, or subcutaneously, it is preferred that sufficient amount of the compound be administered to achieve a serum concentration of 5 ng (nanograms)/mL-10 µg (micrograms)/mL serum, more preferably sufficient compound to achieve a serum concentration of 20 ng-1 µg/ml serum should be administered, most preferably sufficient compound to achieve a serum concentration of 50 ng/ml-200 ng/ml serum should be administered. For direct injection into the synovium (for the treatment of arthritis) sufficient compounds should be administered to achieve a local concentration of approximately 1 micromolar.

Frequency of dosage may also vary depending on the compound used and the particular disease treated. However, for treatment of most disorders, a dosage regimen of 4 times daily, three times daily, or less is preferred, with a dosage regimen of once daily or 2 times daily being particularly preferred. It will be understood, however, that the specific dose level for any particular patient will depend upon a variety of factors including the activity of the specific compound employed, the age, body weight, general health, sex, diet, time of administration, route of administration, and rate of excretion, drug combination (i.e., other drugs being administered to the patient), the severity of the particular disease undergoing therapy, and other factors, including the judgment of the prescribing medical practitioner.

In another aspect of the disclosure, the compounds of the disclosure can be used in a variety of non-pharmaceutical in vitro and in vivo application. The compounds of the disclosure may also be used as positive controls in assays for PD-1/PD-L1 interaction activity, i.e., as standards for determining the ability of a candidate agent to bind to PD-1 and/or PD-L1, or as radiotracers for positron emission tomography (PET) imaging or for single photon emission computerized tomography (SPECT).

Also within the scope of the present disclosure are kits comprising a compound of the present disclosure or pharmaceutically acceptable salts thereof and instructions for use. The kit can further contain at least one additional reagent. Kits typically include a label indicating the intended use of the contents of the kit. The term label includes any writing, or recorded material supplied on or with the kit, or which otherwise accompanies the kit.

General Synthetic Procedures

The embodiments are also directed to processes and intermediates useful for preparing the subject compounds or pharmaceutically acceptable salts thereof.

Exemplary chemical entities useful in methods of the embodiments will now be described by reference to illustrative synthetic schemes for their general preparation herein and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups.

Representative syntheses of compounds of the present disclosure are described in the scheme below, and the particular examples that follow. Schemes 1 and 2 are provided as further embodiment of the disclosure and illustrate general methods which were used to prepare compounds of the present disclosure including compounds of Formula (II), (IIa), (IIb), (I), (Ia), or (Ib), and which can be used to prepare additional compounds having the Formula (II), (IIa), (Ib), (I), (Ia), or (Ib). The methodology is compatible with a wide variety of functionalities.

Scheme 1

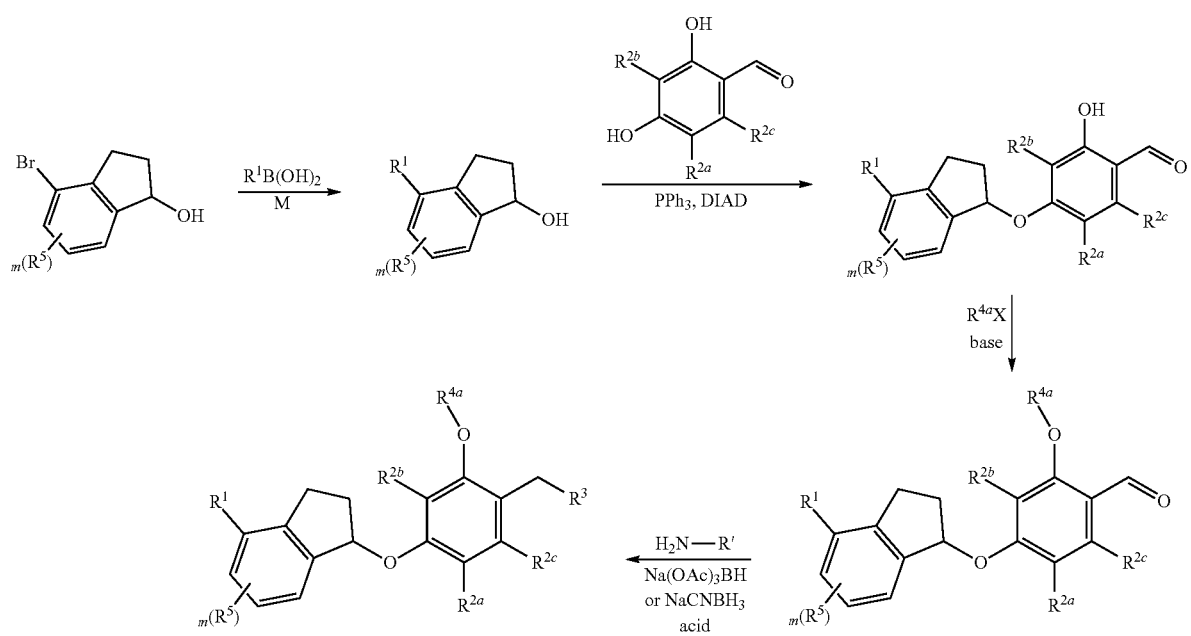

Coupling at the 4-position of the indane ring can be accomplished via transition metal mediated coupling using the appropriate 4-bromoindanol and a boronic acid or ester. In the subsequent step, the ether bond can be formed using appropriate reagents such as triphenyl phosphine and diisopropyl or diethyl azodicarboxylate. Alkylation of the phenol intermediate can be achieved using the corresponding alkyl halide or mesylate reagent. The following reductive amination can be accomplished using an appropriate primary or secondary amine (shown as $H_2N—R'$) and a reducing agent such as sodium cyanoborohydride or sodium triacetoxyborohydride in presence of a mild acid such as acetic acid. The amine group added in the reductive amination is shown as $R^3$ in the diagram above. The transformations shown in Scheme 1 may be performed in any order that is compatible with the functionality of the particular pendant groups.

reducing agent such as sodium cyanoborohydride or sodium triacetoxyborohydride in presence of a mild acid such as acetic acid. The amine group added in the reductive amination is shown as $R^3$ in the diagram above. The transformations shown in Scheme 2 may be performed in any order that is compatible with the functionality of the particular pendant groups. The indanol derivative obtained in the first step having the opposite stereocenter to the stereocenter represented in Scheme 2 can be prepared using the appropriate chiral reducing agent and the rest of the synthetic steps in the sequence can be performed without any changes to obtain final compounds with the opposite stereocenter.

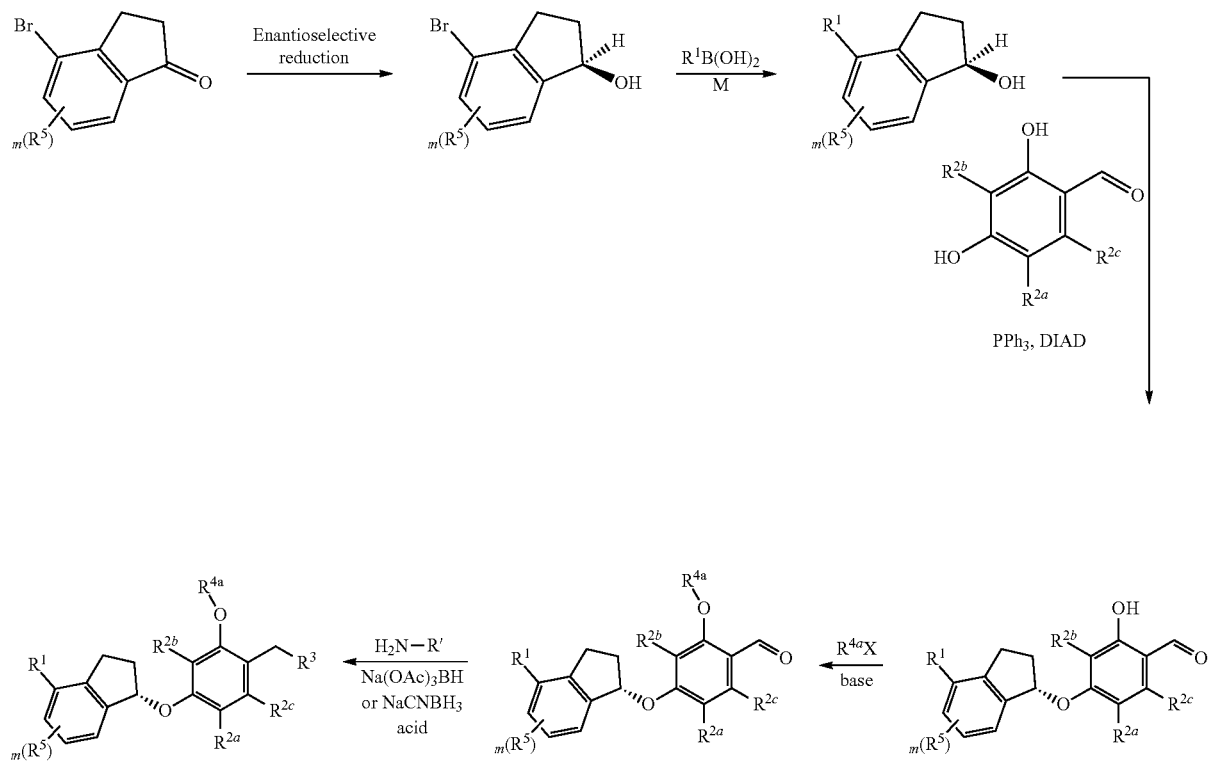

The -Bromoindanone compound can be enantioselectively reduced to its optically pure 4-bromoindanol derivative using a chiral reducing agent containing boron. Coupling at the 4-position of the indane ring can be accomplished via transition metal mediated coupling using the 4-bromoindanol and boronic acid or ester. In the subsequent step, the ether bond can be formed using reagents such as triphenyl phosphine and diisopropyl or diethyl azodicarboxylate (in this case, the reaction leads to an inversion of configuration, however, some racemization was observed). Alkylation of the phenol intermediate can be achieved using the appropriate alkyl halide or mesylate reagent. The reductive amination can be accomplished using the appropriate primary or secondary amine (shown as $H_2N—R'$) and a

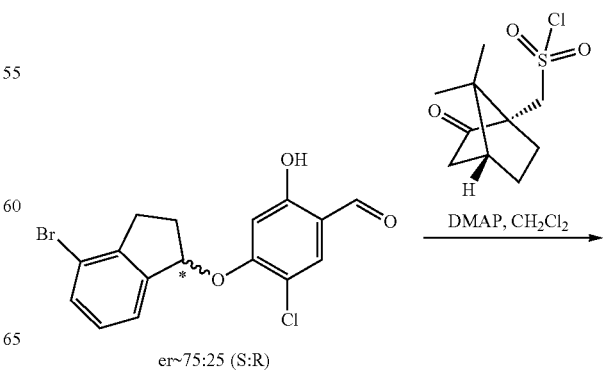

er~75:25 (S:R)

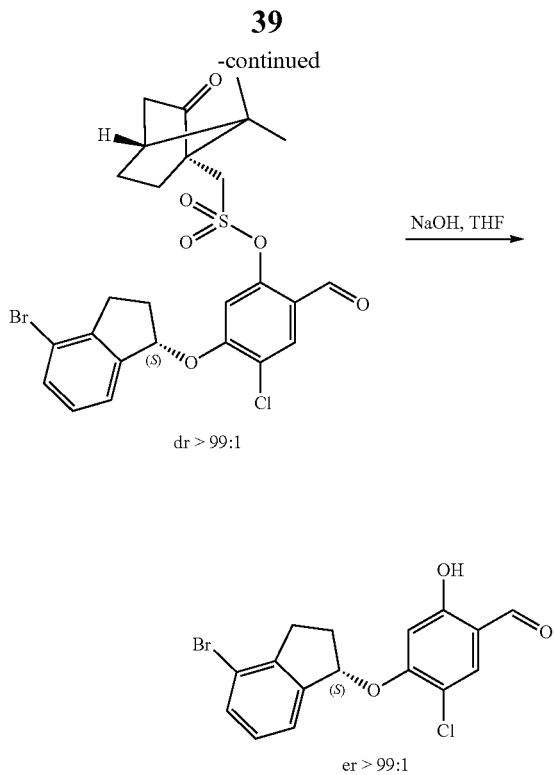

dr > 99:1 er > 99:1

As an example, enrichment of optical purity of chiral intermediates can be achieved as described in Scheme 3.

EXAMPLES

The following Examples illustrate various methods of making compounds of this disclosure including compounds of Formula (II), (IIa), (IIb), (I), (Ia), or (Ib). The following examples are offered to illustrate, but not to limit the claimed disclosure.

Reagents and solvents used below can be obtained from commercial sources such as Aldrich Chemical Co. (Milwaukee, Wis., USA). $^1$H-NMR spectra were recorded on a Varian Mercury 400 MHz NMR spectrometer. Significant peaks are provided relative to TMS and are tabulated in the order: multiplicity (s, singlet; d, doublet; t, triplet; q, quartet; m, multiplet) and number of protons. Mass spectrometry results are reported as the ratio of mass over charge. In the examples, a single m/z value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP1100 HPLC for sample delivery. Normally the analyte was dissolved in methanol or CH$_3$CN at 0.1 mg/mL and 1 microliter was infused with the delivery solvent into the mass spectrometer, which scanned from 100 to 1000 Daltons. All compounds could be analyzed in the positive or negative ESI mode, using acetonitrile/water with 1% formic acid as the delivery solvent.

The following abbreviations are used in the Examples and throughout the description of the disclosure: TLC means Thin layer chromatography.

Compounds within the scope of this disclosure can be synthesized as described below, using a variety of reactions known to the skilled artisan. One skilled in the art will also recognize that alternative methods may be employed to synthesize the target compounds of this disclosure, and that the approaches described within the body of this document are not exhaustive, but do provide broadly applicable and practical routes to compounds of interest.

Certain molecules claimed in this patent can exist in different enantiomeric and diastereomeric forms and all such variants of these compounds are claimed unless a specific enantiomer is specified.

The detailed description of the experimental procedures used to synthesize key compounds in this text lead to molecules that are described by the physical data identifying them as well as by the structural depictions associated with them.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Example 1: Synthesis of (2S)-2-[[5-chloro-2-[(5-cyano-3-pyridyl)methoxy]-4-(4-phenylindan-1-yl)oxy-phenyl]methylamino]-3-hydroxy-propanoic acid

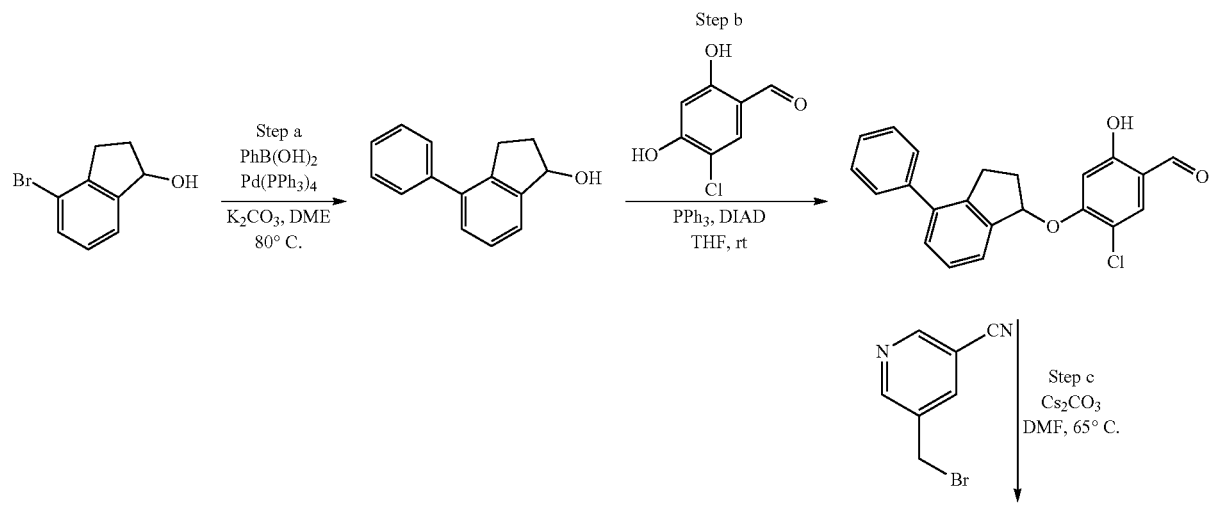

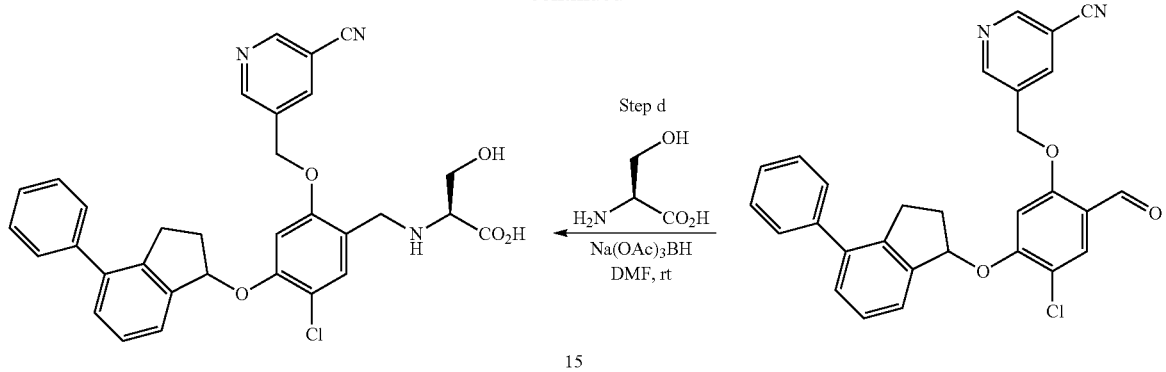

Step a: To a solution of 4-bromoindan-1-ol (500 mg, 2.34 mmol) in DME (10 mL) was added phenylboronic acid (286 mg, 2.34 mmol), $K_2CO_3$ (969 mg, 7.02 mmol) and the resulting suspension was bubbled with nitrogen gas for one minute. $Pd(PPh_3)_4$ (271 mg, 0.234 mmol) was then added and the reaction mixture was bubbled with nitrogen gas for an additional minute and stirred at 80° C. overnight. The reaction mixture was diluted with EtOAc (30 mL), washed with water (30 mL), brine (30 mL), dried ($Na_2SO_4$) and concentrated in vacuo. The crude product was purified by flash chromatography ($SiO_2$, 20% EtOAc in hexanes) to obtain 4-phenylindan-1-ol. MS: (ES) m/z calculated for $C_{15}H_{13}$ [M–OH]⁻ 193.1, found 193.1.

Step b: To a solution of 4-phenylindan-1-ol (418 mg, 1.99 mmol) in THF (5 mL) at room temperature was added 5-chloro-2,4-dihydroxy-benzaldehyde (309 mg, 1.791 mmol) and $PPh_3$ (521 mg, 1.99 mmol). The resulting solution was cooled to to 0° C. before DIAD (402 mg, 1.99 mmol) in THF (2 mL) was added slowly dropwise. The resulting solution was allowed to warm to room temperature with stirring. After 12 h at room temperature, the volatiles were evaporated in vacuo. The resulting residue was purified by flash chromatography ($SiO_2$, 50% EtOAc in hexanes) to obtain 5-chloro-2-hydroxy-4-(4-phenylindan-1-yl)oxy-benzaldehyde. MS: (ES) m/z calculated for $C_{22}H_{16}ClO_3$ [M–H]⁺ 360.1, found 360.0 (negative mode).

Step c: To a solution of 5-chloro-2-hydroxy-4-(4-phenylindan-1-yl)oxy-benzaldehyde (100 mg, 0.274 mmol) in DMF (5 mL) was added 5-(bromomethyl)pyridine-3-carbonitrile (108 mg, 0.549 mmol) followed by $Cs_2CO_3$ (178 mg, 0.549 mmol). The resulting suspension was then stirred at 65° C. for 2 h. The reaction mixture was diluted with EtOAc (20 mL), washed with water (20 mL), dried ($MgSO_4$), concentrated in vacuo. The crude residue was purified by flash chromatography ($SiO_2$, 80% EtOAc in hexanes) to obtain 5-[[4-chloro-2-formyl-5-(4-phenylindan-1-yl)oxy-phenoxy]methyl]pyridine-3-carbonitrile. MS: (ES) m/z calculated for $C_{29}H_{22}ClN_2O_3$ [M+H]⁺ 481.1, found 481.3.

Step d: To a solution of 5-[[4-chloro-2-formyl-5-(4-phenylindan-1-yl)oxy-phenoxy]methyl]pyridine-3-carbonitrile (50 mg, xx mmol) in DMF (2 mL) was added (2S)-2-amino-3-hydroxy-propanoic acid (100 mg) and $Na(OAc)_3BH$ (100 mg, xx mmol), and the resulting suspension was stirred at room temperature overnight. The reaction mixture was diluted with 2:1 $CHCl_3$/IPA (30 mL), washed with water (15 mL), dried ($MgSO_4$), and concentrated in vacuo. The crude residue was purified by reverse phase preparative HPLC ($CH_3CN$—$H_2O$ with 0.1% TFA) to obtain (2S)-2-[[5-chloro-2-[(5-cyano-3-pyridyl)methoxy]-4-(4-phenylindan-1-yl)oxy-phenyl]methylamino]-3-hydroxy-propanoic acid. MS: (ES) m/z calculated for $C_{32}H_{29}ClN_3O_5$ [M+H]⁺ 570.2, found 570.1. ¹H NMR (400 MHz, Methanol-$d_4$) δ 8.99 (d, J=2.1 Hz, 1H), 8.92 (d, J=2.0 Hz, 1H), 8.43 (t, J=2.1 Hz, 1H), 7.53 (s, 1H), 7.50-7.28 (m, 8H), 7.11 (d, J=1.6 Hz, 1H), 6.02 (dd, J=6.4, 4.2 Hz, 1H), 5.45-5.33 (m, 2H), 4.35 (q, J=13.1 Hz, 2H), 4.01 (s, 3H), 3.34-3.14 (m, 1H), 2.98 (ddd, J=16.2, 8.2, 5.3 Hz, 1H), 2.56 (dq, J=13.7, 6.7 Hz, 1H), 2.21-2.10 (m, 1H).

Example 2: Synthesis of (3S)-4-[[5-chloro-2-[(5-cyano-3-pyridyl)methoxy]-4-(4-phenylindan-1-yl)oxy-phenyl]methylamino]-3-hydroxy-butanoic acid

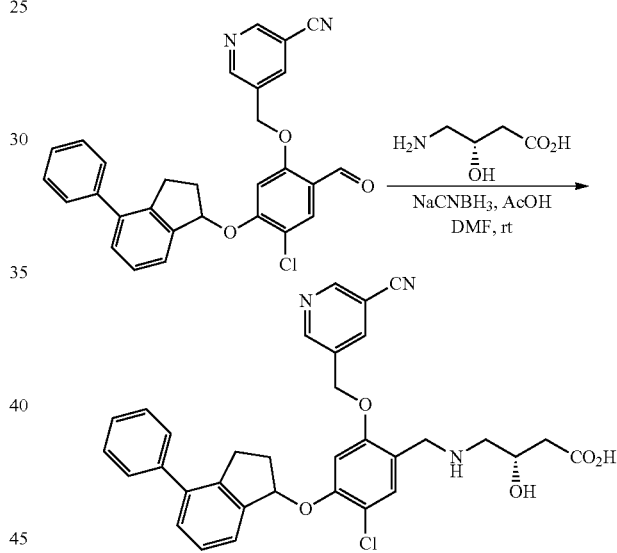

To a solution of 5-[[4-chloro-2-formyl-5-(4-phenylindan-1-yl)oxy-phenoxy]methyl]pyridine-3-carbonitrile (120 mg, 0.25 mmol) in DMF (3 mL) was added (3S)-4-amino-3-hydroxy-butanoic acid (200 mg, 1 mmol) and AcOH (100 μL), followed by $NaCNBH_3$ (100 mg, 1.58 mmol). The resulting suspension was stirred at room temperature overnight. The reaction mixture was diluted with 2:1 $CHCl_3$/IPA (30 mL), washed with water (15 mL), dried ($MgSO_4$), and concentrated in vacuo. The crude was purified by reverse phase preparative HPLC ($CH_3CN$—$H_2O$ with 0.1% TFA) to obtain (3S)-4-[[5-chloro-2-[(5-cyano-3-pyridyl)methoxy]-4-(4-phenylindan-1-yl)oxy-phenyl]methylamino]-3-hydroxy-butanoic acid. MS: (ES) m/z calculated for $C_{33}H_{31}ClN_3O_5$ [M+H]⁺ 584.2, found 584.1. ¹H NMR (400 MHz, Methanol-$d_4$) δ 8.99 (d, J=2.2 Hz, 1H), 8.93 (d, J=2.0 Hz, 1H), 8.44-8.34 (m, 1H), 7.57-7.28 (m, 9H), 7.11 (d, J=1.0 Hz, 1H), 6.01 (dd, J=6.4, 4.2 Hz, 1H), 5.51-5.34 (m, 2H), 4.83-4.68 (m, 1H), 4.32-4.17 (m, 2H), 3.27-3.14 (m, 2H), 3.05-2.92 (m, 2H), 2.58-2.48 (m, 3H), 2.19-2.11 (m, 1H).

Example 3: Synthesis of (3S)-4-[[5-chloro-2-[(5-cyano-3-pyridyl)methoxy]-4-[(1S)-4-phenylindan-1-yl]oxy-phenyl]methylamino]-3-hydroxy-butanoic acid

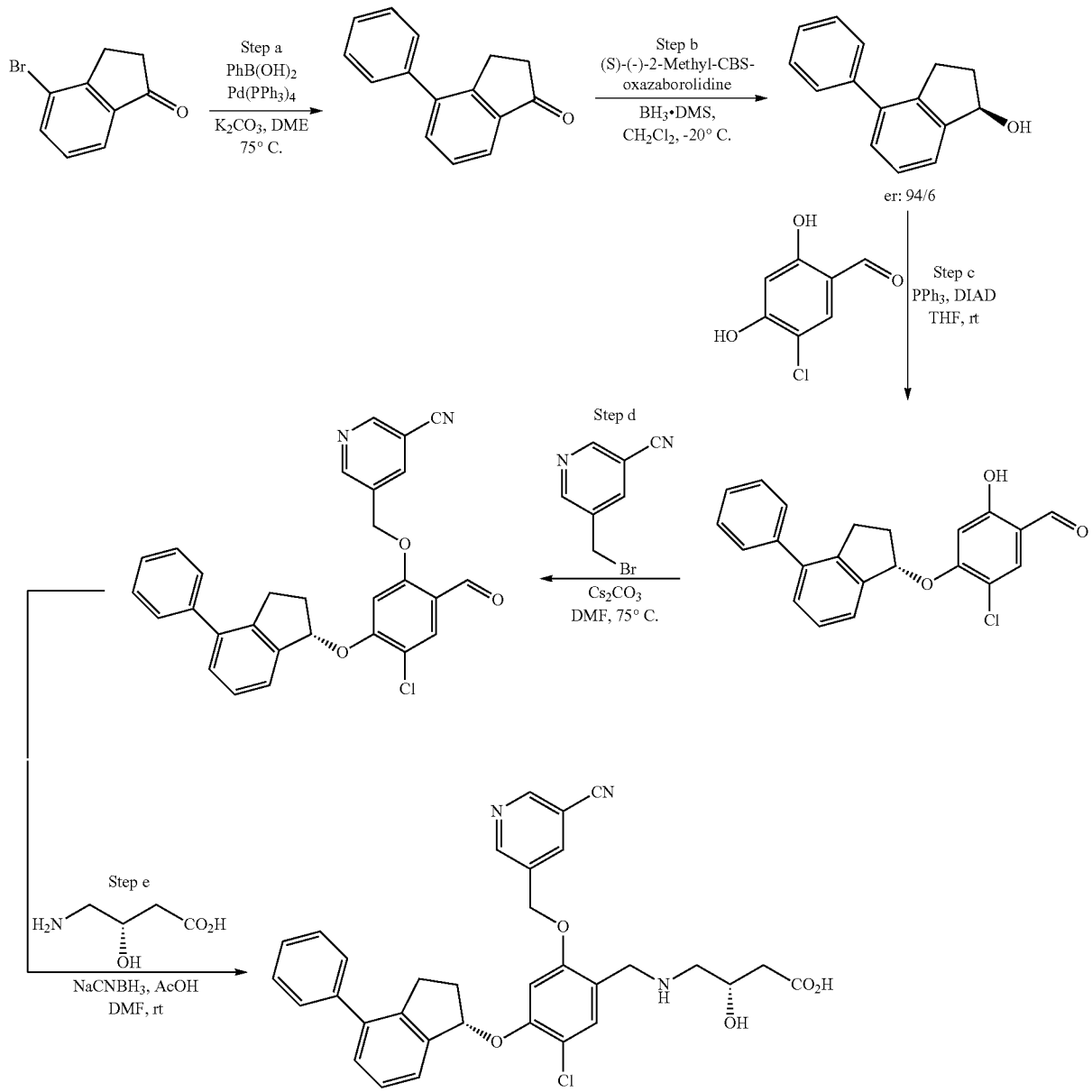

Step a: To a solution of 4-bromoindan-1-one (3 g, 2.34 mmol) in DME (15 mL) was added phenylboronic acid (1.73 g, 14.2 mmol) and K$_2$CO$_3$ (5.9 g, 42.6 mmol). The resulting suspension was bubbled with nitrogen gas for one minute before Pd(PPh$_3$)$_4$ (1.64 g, 1.42 mmol) was added. The reaction mixture was bubbled with nitrogen gas for an additional minute and subsequently stirred at 75° C. overnight. The mixture was diluted with EtOAc (100 mL), washed with water (50 mL), brine (50 mL), dried (MgSO$_4$), and concentrated in vacuo. The crude product was purified by flash chromatography (SiO$_2$, 50% EtOAc in hexanes) to obtain 4-phenylindan-1-one. MS: (ES) m/z calculated for C$_{15}$H$_{13}$O [M+H]$^+$ 209.1, found 209.3.

Step b: To (S)-(−)-2-Methyl-CBS (Corey-Bakshi-Shibata)-oxazaborolidine (900 μL, 0.887 mmol, 1 M in THF) was added BH$_3$.DMS (443 μL, 0.887 mmol, 2 M solution in THF) under nitrogen atmosphere and the reaction mixture was stirred at room temperature for 10 minutes. The reaction was diluted with CH$_2$Cl$_2$ (5 mL). followed by the addition of BH$_3$.DMS (16.3 mL, 32.52 mmol, 2 M solution in THF). The mixture was cooled to −20° C. before 4-phenylindan-1-one (1.23 g, 5.913 mmol) in CH$_2$Cl$_2$ (5 mL) was added dropwise. After stirring for 2 h at −20° C., the reaction was carefully quenched by the addition of MeOH (10 mL). The volatiles were removed in vacuo and the crude product was purified by flash chromatography (SiO$_2$, 50% EtOAc in hexanes) to obtain (1R)-4-phenylindan-1-ol (er: 94/6). The enantiomeric ratio was determined by $^{19}$F NMR analysis of the corresponding (S)-Mosher's ester. MS: (ES) m/z calculated for $C_{15}H_{13}$ [M-OH]$^-$ 193.1, found 193.1.

Step c: To a solution of (1R)-4-phenylindan-1-ol (840 mg, 4.0 mmol) in THF (10 mL) at room temperature was added 5-chloro-2,4-dihydroxy-benzaldehyde (690 mg, 4.0 mmol), followed by PPh$_3$ (1.05 g, 4 mmol), and the resulting solution was cooled to 0° C. DIAD (808 mg, 4.0 mmol) in THF (3 mL) was added slowly dropwise and the resulting solution was allowed to warm to room temperature with stirring. After 12 h at room temperature, the volatiles were evaporated in vacuo, The crude was purified by flash chromatography (SiO$_2$, 50% EtOAc in hexanes) to obtain 5-chloro-2-hydroxy-4-[(1S)-4-phenylindan-1-yl]oxy-benzaldehyde. MS: (ES) m/z calculated for $C_{22}H_{16}ClO_3$ [M+H]$^+$ 363.1, found 363.0. Approximately 22% of racemization was observed during the reaction and the enantiomeric ratio (er) of the obtained product was ~3.5:1. All the final compounds described in examples 10, 12, 13, 14 and 15 were prepared using this intermediate with er: 3.5:1.

Step d: To a solution of 5-chloro-2-hydroxy-4-[(1S)-4-phenylindan-1-yl]oxy-benzaldehyde (178 mg, 0.489 mmol) in DMF (5 mL) was added 5-(bromomethyl)pyridine-3-carbonitrile (192 mg, 0.978 mmol) and Cs$_2$CO$_3$ (318 mg, 0.978 mmol) and the resulting suspension was then stirred at 75° C. for 2 h. The reaction mixture was diluted with EtOAc (30 mL), washed with water (20 mL), dried (MgSO$_4$), and concentrated in vacuo. The crude was purified by flash chromatography (SiO$_2$, 80% EtOAc in hexanes) to obtain 5-[[4-chloro-2-formyl-5-[(1S)-4-phenylindan-1-yl]oxy-phenoxy]methyl]pyridine-3-carbonitrile, er: ~3.5:1. MS: (ES) m/z calculated for $C_{29}H_{22}ClN_2O_3$ [M+H]$^+$ 481.1, found 481.1.

Step e: To a solution of 5-[[4-chloro-2-formyl-5-[(1S)-4-phenylindan-1-yl]oxy-phenoxy]methyl]pyridine-3-carbonitrile (66 mg, 0.1375 mmol) in DMF (4 mL) was added (2S)-2-amino-3-hydroxy-propanoic acid (33 mg, 0.275 mmol), AcOH (20 µL, 0.1375 mmol), followed by NaCNBH$_3$ (20 mg, 0.206 mmol). The resulting mixture was stirred at room temperature overnight before it was diluted with 2:1 CHCl$_3$/IPA (30 mL), washed with water (15 mL), dried (MgSO$_4$), and concentrated in vacuo. The crude was purified by reverse phase preparative HPLC (CH$_3$CN—H$_2$O with 0.1% TFA) to obtain (3S)-4-[[5-chloro-2-[(5-cyano-3-pyridyl)methoxy]-4-[(1S)-4-phenylindan-1-yl]oxy-phenyl]methylamino]-3-hydroxy-butanoic acid, dr (diastereomeric ratio): 3.5:1. MS: (ES) m/z calculated for $C_{33}H_{31}ClN_3O_5$ [M+H]$^+$ 584.2, found 584.1. $^1$H NMR (400 MHz, Methanol-d$_4$) δ 8.99 (d, J=2.2 Hz, 1H), 8.93 (d, J=2.0 Hz, 1H), 8.44-8.34 (m, 1H), 7.57-7.28 (m, 9H), 7.11 (d, J=1.0 Hz, 1H), 6.01 (dd, J=6.4, 4.2 Hz, 1H), 5.51-5.34 (m, 2H), 4.83-4.68 (m, 1H), 4.32-4.17 (m, 2H), 3.27-3.14 (m, 2H), 3.05-2.92 (m, 2H), 2.58-2.48 (m, 3H), 2.19-2.11 (m, 1H).

Example 4: Synthesis of (3S)-4-[[5-chloro-2-[(5-cyano-3-pyridyl)methoxy]-4-[(1R)-4-phenylindan-1-yl]oxy-phenyl]methylamino]-3-hydroxy-butanoic acid

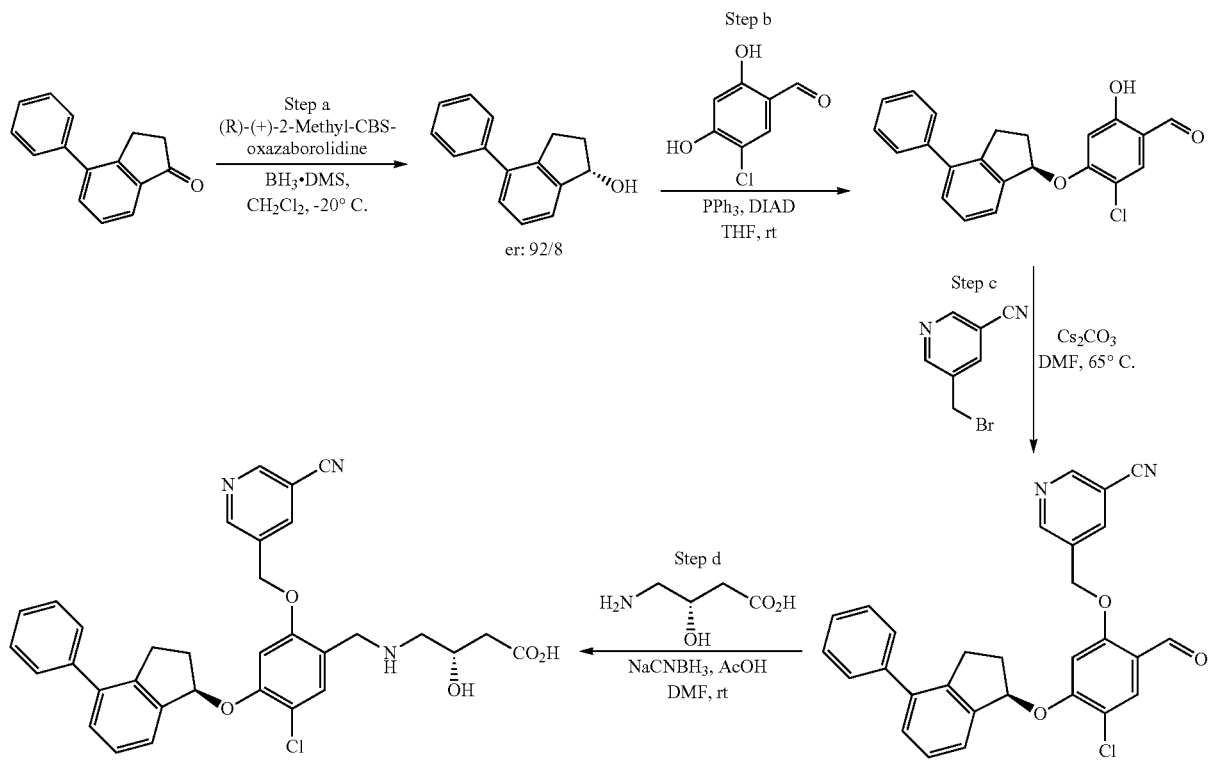

Step a: To (R)-(+)-2-methyl-CBS (Corey-Bakshi-Shibata)-oxazaborolidine (900 µL, 0.887 mmol, 1 M solution in THF) under nitrogen atmosphere was added BH$_3$-DMS (443 µL, 0.887 mmol, 2 M solution in THF) at room temperature and stirred for 10 minutes. The reaction mixture was diluted with CH$_2$Cl$_2$ (5 mL) and BH$_3$.DMS (16.3 mL, 32.52 mmol, 2 M solution in THF) was added before cooling to –20° C. 4-Phenylindan-1-one (1.23 g, 5.913 mmol) in CH$_2$Cl$_2$ (5 mL) was then added drop wise and the mixture was stirred for 2 h at –20° C. The reaction was quenched by the careful addition of MeOH (10 mL). The volatiles were removed in vacuo and the resulting crude was purified by flash chromatography (SiO$_2$, 50% EtOAc in hexanes) to obtain (1S)-4-phenylindan-1-ol (er 92/8). The enantiomeric ratio was determined by $^{19}$F NMR analysis of the corresponding (S)-Mosher's ester. MS: (ES) m/z calculated for C$_{15}$H$_{13}$ [M-OH]$^-$ 193.1, found 193.1.

Step b: To a solution of (1S)-4-phenylindan-1-ol (840 mg, 4 mmol) in THF (10 mL) at room temperature was added 5-chloro-2,4-dihydroxy-benzaldehyde (690 mg, 4 mmol) followed by PPh$_3$ (1.05 g, 4 mmol). The resulting solution was cooled to 0° C. before DIAD (808 mg, 4 mmol) in THF (3 mL) was added slowly dropwise. The solution was allowed warm to room temperature and stirred for 12 h. The volatiles were removed in vacuo and the crude was purified by flash chromatography (SiO$_2$, 50% EtOAc in hexanes) to obtain 5-chloro-2-hydroxy-4-[(1R)-4-phenylindan-1-yl]oxy-benzaldehyde. MS: (ES) m/z calculated for C$_{22}$H$_{16}$ClO$_3$ [M–H]$^-$ 363.1, found 363.0 Approximately 17% of racemization was observed during the reaction and the enantiomeric ratio of the obtained product was ~5:1.

Step c: To a solution of 5-chloro-2-hydroxy-4-[(1R)-4-phenylindan-1-yl]oxy-benzaldehyde (340 mg, 0.934 mmol) in DMF (5 mL) was added 5-(bromomethyl)pyridine-3-carbonitrile (366 mg, 1.868 mmol), followed by Cs$_2$CO$_3$ (607 mg, 1.868 mmol). The resulting suspension was then stirred at 75° C. for 2 h. Reaction mixture was diluted with EtOAc (30 mL), washed with water (20 mL), dried (MgSO$_4$), and concentrated in vacuo. The crude was purified by flash chromatography (SiO$_2$, 80% EtOAc in hexanes) to obtain 5-[[4-chloro-2-formyl-5-[(1R)-4-phenylindan-1-yl]oxy-phenoxy]methyl]pyridine-3-carbonitrile, er ~5:1. MS: (ES) m/z calculated for C$_{29}$H$_{22}$ClN$_2$O$_3$ [M+H]$^+$ 481.1, found 481.0.

Step d: To a solution of 5-[[4-chloro-2-formyl-5-[(1R)-4-phenylindan-1-yl]oxy-phenoxy]methyl]pyridine-3-carbonitrile (304 mg, 0.633 mmol) in DMF (5 mL) was added (2S)-2-amino-3-hydroxy-propanoic acid (301 mg, 2.53 mmol) and AcOH (152 µL, 2.53 mmol), followed by NaCNBH$_3$ (159 mg, 2.53 mmol), and the resulting suspension was stirred at room temperature overnight. The reaction mixture was diluted with 2:1 CHCl$_3$/IPA (30 mL), washed with water (15 mL), dried (MgSO$_4$), and concentrated in vacuo. The crude was purified by reverse phase preparative HPLC (CH$_3$CN—H$_2$O with 0.1% TFA) to obtain (3S)-4-[[5-chloro-2-[(5-cyano-3-pyridyl)methoxy]-4-[(1R)-4-phenylindan-1-yl]oxy-phenyl]methylamino]-3-hydroxy-butanoic acid, dr ~5:1. MS: (ES) m/z calculated for C$_{33}$H$_{31}$ClN$_3$O$_5$ [M+H]$^+$ 584.2, found 584.2. $^1$H NMR (400 MHz, Methanol-d$_4$) δ 8.99 (d, J=2.2 Hz, 1H), 8.93 (d, J=2.0 Hz, 1H), 8.44-8.34 (m, 1H), 7.57-7.28 (m, 9H), 7.11 (d, J=1.0 Hz, 1H), 6.01 (dd, J=6.4, 4.2 Hz, 1H), 5.51-5.34 (m, 2H), 4.83-4.68 (m, 1H), 4.32-4.17 (m, 2H), 3.27-3.14 (m, 2H), 3.05-2.92 (m, 2H), 2.58-2.48 (m, 3H), 2.19-2.11 (m, 1H).

Example 5: Synthesis of 5-[[4-chloro-5-(4-phenylindan-1-yl)oxy-2-[(1H-tetrazol-5-ylmethylamino)methyl]phenoxy]methyl]pyridine-3-carbonitrile

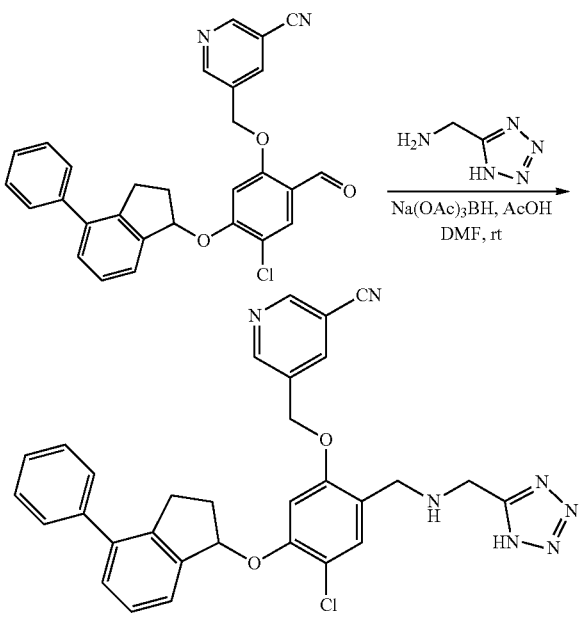

To a solution of 5-[[4-chloro-2-formyl-5-(4-phenylindan-1-yl)oxy-phenoxy]methyl]pyridine-3-carbonitrile (50 mg, 0.104 mmol) in DMF (2 mL) was added 1H-tetrazol-5-ylmethanamine (100 mg, 0.99 mmol), AcOH (100 µL, 1.66 mmol) followed by Na(OAc)$_3$BH (100 mg, 0.47 mmol) and the resulting suspension was stirred at room temperature overnight. The reaction mixture was diluted with 2:1 CHCl$_3$/IPA (30 mL) and washed with water (15 mL), dried (MgSO$_4$), concentrated in vacuo and purified by reverse phase preparative HPLC (CH$_3$CN—H$_2$O with 0.1% TFA) to obtain 5-[[4-chloro-5-(4-phenylindan-1-yl)oxy-2-[(1H-tetrazol-5-ylmethylamino)methyl]phenoxy]methyl]pyridine-3-carbonitrile. MS: (ES) m/z calculated for C$_{31}$H$_{27}$ClN$_7$O$_2$ [M+H]$^+$ 564.2, found 564.2. $^1$H NMR (400 MHz, Methanol-d$_4$) δ 8.94 (dd, J=2.9, 2.1 Hz, 2H), 8.38 (t, J=2.1 Hz, 1H), 7.53 (s, 1H), 7.50-7.26 (m, 8H), 7.11 (s, 1H), 6.01 (dd, J=6.5, 4.3 Hz, 1H), 5.38 (d, J=1.8 Hz, 2H), 4.64-4.55 (m, 2H), 4.40 (s, 2H), 3.43-3.14 (m, 1H), 2.98 (ddd, J=16.2, 8.2, 5.3 Hz, 1H), 2.55 (ddt, J=14.2, 8.2, 6.1 Hz, 1H), 2.14 (ddt, J=13.3, 8.2, 4.8 Hz, 1H).

Example 6: Synthesis of 5-[[4-chloro-2-[(2-hydroxyethylamino)methyl]-5-(4-phenylindan-1-yl)oxy-phenoxy]methyl]pyridine-3-carbonitrile

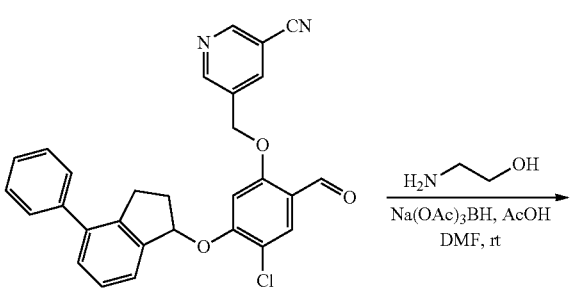

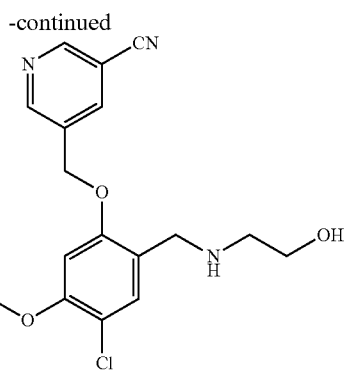

To a solution of 5-[[4-chloro-2-formyl-5-(4-phenylindan-1-yl)oxy-phenoxy]methyl]pyridine-3-carbonitrile (50 mg, 0.104 mmol) in DMF (2 mL) was added 2-aminoethanol (100 µL, 1.64 mmol) followed by Na(OAc)$_3$BH (100 mg, 0.47 mmol) and the resulting suspension was stirred at room temperature overnight. The reaction mixture was diluted with 2:1 CHCl$_3$/IPA (30 mL) and washed with water (15 mL), dried (MgSO$_4$), concentrated in vacuo and purified by reverse phase preparative HPLC (CH$_3$CN—H$_2$O with 0.1% TFA) to obtain 5-[[4-chloro-2-[(2-hydroxyethylamino)methyl]-5-(4-phenylindan-1-yl)oxy-phenoxy]methyl]pyridine-3-carbonitrile. MS: (ES) m/z calculated for C$_{31}$H$_{29}$ClN$_3$O$_3$ [M+H]$^+$ 526.2, found 526.2.

Example 7: Synthesis of (2S)-1-[[5-chloro-2-[(5-cyano-3-pyridyl)methoxy]-4-(4-phenylindan-1-yl)oxy-phenyl]methyl]piperidine-2-carboxylic acid

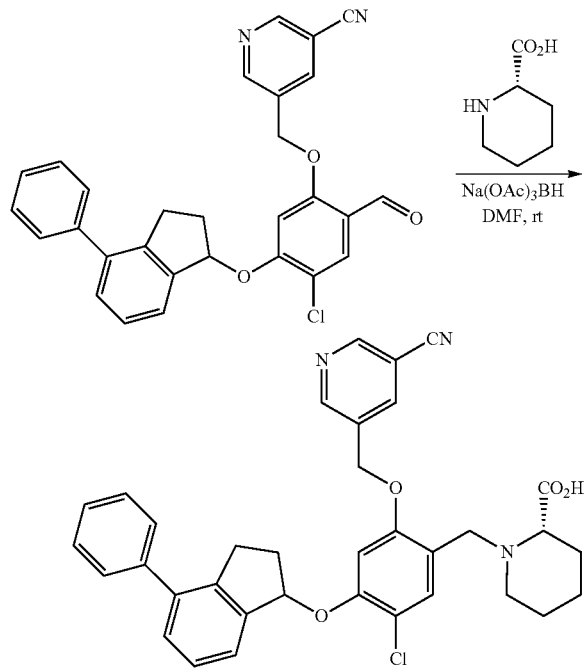

To a solution of 5-[[4-chloro-2-formyl-5-(4-phenylindan-1-yl)oxy-phenoxy]methyl]pyridine-3-carbonitrile (50 mg, 0.104 mmol) in DMF (2 mL) was added (2S)-piperidine-2-carboxylic acid (100 mg, 0.775 mmol) followed by Na(OAc)$_3$BH (100 mg, 0.47 mmol) and the resulting suspension was stirred at room temperature overnight. The reaction mixture was diluted with 2:1 CHCl$_3$/IPA (30 mL) and washed with water (15 mL), dried (MgSO$_4$), concentrated in vacuo and purified by reverse phase preparative HPLC (CH$_3$CN—H$_2$O with 0.1% TFA) to (2S)-1-[[5-chloro-2-[(5-cyano-3-pyridyl)methoxy]-4-(4-phenylindan-1-yl)oxy-phenyl]methyl]piperidine-2-carboxylic acid. MS: (ES) m/z calculated for C$_{35}$H$_{33}$ClN$_3$O$_4$ [M+H]$^+$ 594.2, found 594.1. $^1$H NMR (400 MHz, Methanol-d$_4$) δ 9.00-8.91 (m, 2H), 8.42 (d, J=1.9 Hz, 1H), 7.57 (s, 1H), 7.51-7.29 (m, 9H), 7.13 (d, J=3.5 Hz, 1H), 6.03 (dd, J=6.4, 4.3 Hz, 1H), 5.40 (d, J=2.9 Hz, 2H), 4.89-4.68 (m, 1H), 4.46 (d, J=13.6 Hz, 1H), 4.38 (s, 1H), 3.99 (s, 1H), 3.31-3.13 (m, 1H), 3.07-2.92 (m, 2H), 2.57 (dt, J=13.8, 7.5 Hz, 1H), 2.31 (s, 1H), 2.14 (tt, J=8.8, 4.6 Hz, 1H), 1.86 (s, 2H), 1.61 (s, 2H).

Example 8: Synthesis of 5-[[2-(azetidin-1-ylmethyl)-4-chloro-5-(4-phenylindan-1-yl)oxy-phenoxy]methyl]pyridine-3-carbonitrile

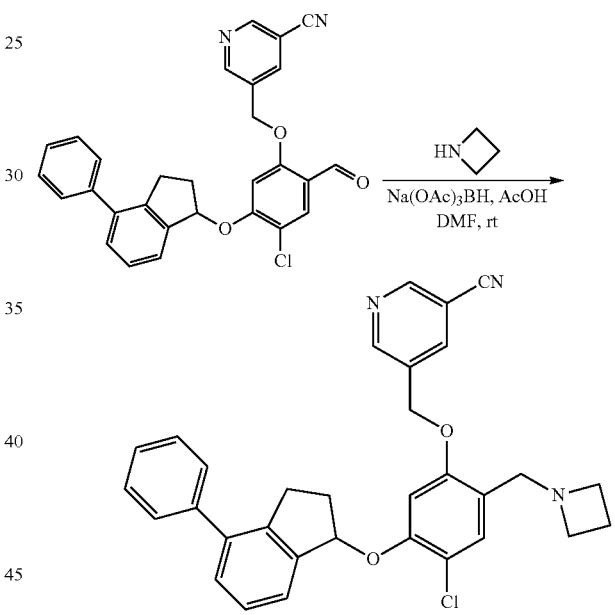

To a solution of 5-[[4-chloro-2-formyl-5-(4-phenylindan-1-yl)oxy-phenoxy]methyl]pyridine-3-carbonitrile (50 mg, 0.104 mmol) in DMF (2 mL) was added azetidine (100 µL, 1.49 mmol), AcOH (100 µL, 1.64 mmol) followed by Na(OAc)$_3$BH (100 mg, 0.47 mmol) and the resulting suspension was stirred at room temperature overnight. The reaction mixture was diluted with 2:1 CHCl$_3$/IPA (30 mL) and washed with water (15 mL), dried (MgSO$_4$), concentrated in vacuo and purified by reverse phase preparative HPLC (CH$_3$CN—H$_2$O with 0.1% TFA) to obtain 5-[[2-(azetidin-1-ylmethyl)-4-chloro-5-(4-phenylindan-1-yl)oxy-phenoxy]methyl]pyridine-3-carbonitrile. MS: (ES) m/z calculated for C$_{32}$H$_{29}$ClN$_3$O$_2$ [M+H]$^+$ 522.2, found 522.1. $^1$H NMR (400 MHz, Methanol-d$_4$) δ 8.96 (dd, J=15.9, 2.1 Hz, 2H), 8.40 (td, J=2.0, 0.6 Hz, 1H), 7.53-7.26 (m, 9H), 7.10 (s, 1H), 6.00 (dd, J=6.5, 4.2 Hz, 1H), 5.41 (s, 2H), 4.37 (s, 2H), 4.25-4.04 (m, 4H), 3.36-3.13 (m, 1H), 2.97 (ddd, J=16.2, 8.2, 5.3 Hz, 1H), 2.60-2.47 (m, 2H), 2.41 (dt, J=12.0, 5.8 Hz, 1H), 2.19-2.06 (m, 1H).

Example 9: Synthesis of 5-[[4-chloro-2-[(3-hydroxyazetidin-1-yl)methyl]-5-(4-phenylindan-1-yl)oxy-phenoxy]methyl]pyridine-3-carbonitrile

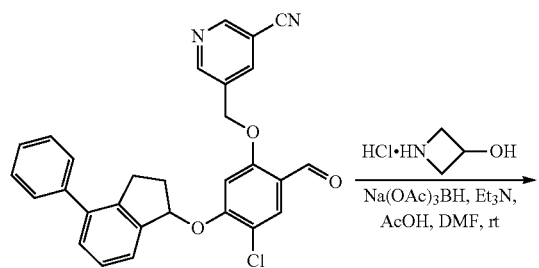

purified by reverse phase preparative HPLC (CH₃CN—H₂O with 0.1% TFA) to obtain 5-[[4-chloro-2-[(3-hydroxyazetidin-1-yl)methyl]-5-(4-phenylindan-1-yl)oxy-phenoxy]methyl]pyridine-3-carbonitrile. MS: (ES) m/z calculated for $C_{32}H_{29}ClN_3O_3$ [M+H]⁺ 538.2, found 538.1. ¹H NMR (400 MHz, Methanol-d₄) δ 8.96 (dd, J=19.5, 2.0 Hz, 2H), 8.41 (d, J=10.4 Hz, 1H), 7.54-7.28 (m, 9H), 7.11 (d, J=7.4 Hz, 1H), 6.01 (t, J=5.4 Hz, 1H), 5.41 (s, 2H), 4.67 (s, 1H), 4.57 (t, J=6.6 Hz, 1H), 4.46-4.29 (m, 4H), 4.02-3.90 (m, 2H), 3.34-3.13 (m, 1H), 2.98 (ddd, J=16.2, 8.2, 5.4 Hz, 1H), 2.58-2.50 (m, 1H), 2.18-2.08 (m, 1H).

Example 10: Synthesis of 5-[[4-chloro-2-[[2-(5-oxo-1H-tetrazol-4-yl)ethylamino]methyl]-5-[(1S)-4-phenylindan-1-yl]oxy-phenoxy]methyl]pyridine-3-carbonitrile

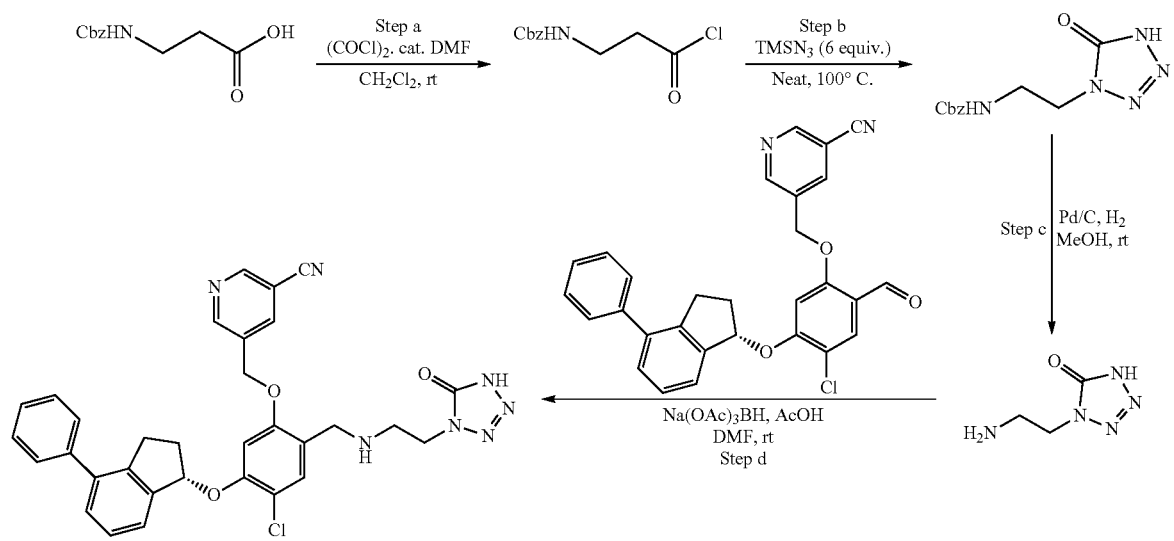

-continued

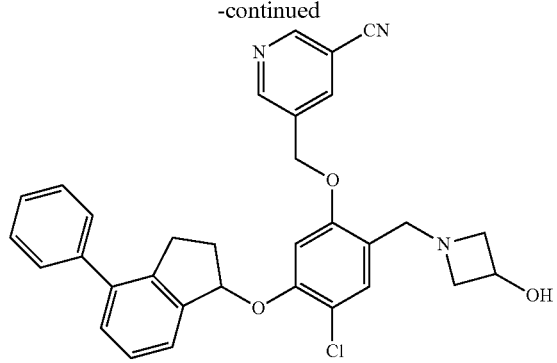

To a solution of 5-[[4-chloro-2-formyl-5-(4-phenylindan-1-yl)oxy-phenoxy]methyl]pyridine-3-carbonitrile (140 mg, 0.292 mmol) in DMF (3 mL) was added azetidin-3-ol hydrochloride (127 mg, 1.2 mmol), Et₃N (406 µL, 2.92 mmol), AcOH (200 µL, 2.92 mmol) followed by Na(OAc)₃BH (186 mg, 0.876 mmol) and the resulting suspension was stirred at room temperature overnight. The reaction mixture was diluted with 2:1 CHCl₃/IPA (30 mL) and washed with water (15 mL), dried (MgSO₄), concentrated in vacuo and Step a: Oxalyl chloride (5.7 mL, 67.26 mmol) was slowly added to 3-(benzyloxycarbonylamino)propanoic acid (5 g, 22.42 mmol) dissolved in CH₂Cl₂ (75 mL) at room temperature followed by few drops of DMF to catalyze the reaction (gas evolution was observed immediately). After 2 h, the reaction mixture was concentrated in vacuo. Additional CH₂Cl₂ (50 mL) was added and concentrated in vacuo followed by drying on high vacuum pump to obtain benzyl N-(3-chloro-3-oxo-propyl)carbamate which was used as such in the next step without any further purification. MS (after quenching the acid chloride with MeOH): (ES) m/z calculated for $C_{12}H_{15}NO_4Na$[Methyl ester, M+Na]⁺ 260.1, found 260.3.

Step b: A safety notice for the procedure: Azide compounds are potentially explosive. This reaction was performed behind a blast shield. TMSN₃ (2.4 mL, 18 mmol) was slowly added to benzyl N-(3-chloro-3-oxo-propyl)carbamate (723 mg, 6 mmol) at room temperature (gas evolution was observed). The resulting reaction mixture was heated and stirred overnight at 100° C. Volatiles were removed in vacuo and the crude product was directly purified by flash chromatography (SiO₂, 80% EtOAc in hexanes) to obtain benzyl N-[2-(5-oxo-1H-tetrazol-4-yl)

ethyl]carbamate. MS: (ES) m/z calculated for $C_{11}H_{14}N_5O_3$ [M+H]$^+$ 264.1, found 264.4 (also observed significant peak for [M+Na]$^+$).

Step c: To benzyl N-[2-(5-oxo-1H-tetrazol-4-yl)ethyl]carbamate (250 mg, 0.95 mmol) in MeOH (10 mL) was added 10% Pd/C (200 mg) in a Parr shaker flask, the resulting suspension was purged twice with hydrogen gas and agitated at room temperature under hydrogen gas (60 psi) for one hour. The reaction mixture was filtered through a pad of Celite, washed with MeOH (15 mL) and concentrated in vacuo to obtain 4-(2-aminoethyl)-1H-tetrazol-5-one which was used as such in the next step without any further purification. MS: (ES) m/z calculated for $C_3H_8N_5O$ [M+H]$^+$ 130.1, found 130.3.

Step d: To a solution of 5-[[4-chloro-2-formyl-5-[(1S)-4-phenylindan-1-yl]oxy-phenoxy]methyl]pyridine-3-carbonitrile (100 mg, 0.208 mmol) in DMF (4 mL) was added 4-(2-aminoethyl)-1H-tetrazol-5-one (50 mg, 0.387 mmol), AcOH (50 µL, 0.53 mmol) followed by Na(OAc)$_3$BH (90 mg, 0.424 mmol) and the resulting suspension was stirred at room temperature overnight. The reaction mixture was diluted with 2:1 CHCl$_3$/IPA (30 mL) and washed with water (15 mL), dried (MgSO$_4$) concentrated in vacuo and purified by reverse phase preparative HPLC (CH$_3$CN—H$_2$O with 0.1% TFA) to obtain 5-[[4-chloro-2-[[2-(5-oxo-1H-tetrazol-4-yl)ethylamino]methyl]-5-[(1S)-4-phenylindan-1-yl]oxy-phenoxy]methyl]pyridine-3-carbonitrile, er: ~3.5:1. MS: (ES) m/z calculated for $C_{32}H_{29}ClN_7O_3$ [M+H]$^+$ 594.2, found 594.5. $^1$H NMR (400 MHz, Methanol-d$_4$) δ 8.96 (dd, J=27.3, 2.0 Hz, 2H), 8.47-8.38 (m, 1H), 7.57-7.39 (m, 5H), 7.41-7.25 (m, 4H), 7.10 (s, 1H), 6.00 (dd, J=6.4, 4.2 Hz, 1H), 5.45-5.40 (m, 2H), 4.39-4.30 (m, 4H), 3.58-3.47 (m, 2H), 3.24-3.13 (m, 1H), 2.98 (td, J=8.1, 5.3 Hz, 1H), 2.58-2.47 (m, 1H), 2.18-2.07 (m, 1H).

Example 11: Synthesis of (2S)-2-[[5-chloro-4-(4-phenylindan-1-yl)oxy-2-(3-pyridylmethoxy)phenyl]methylamino]-3-hydroxy-propanoic acid

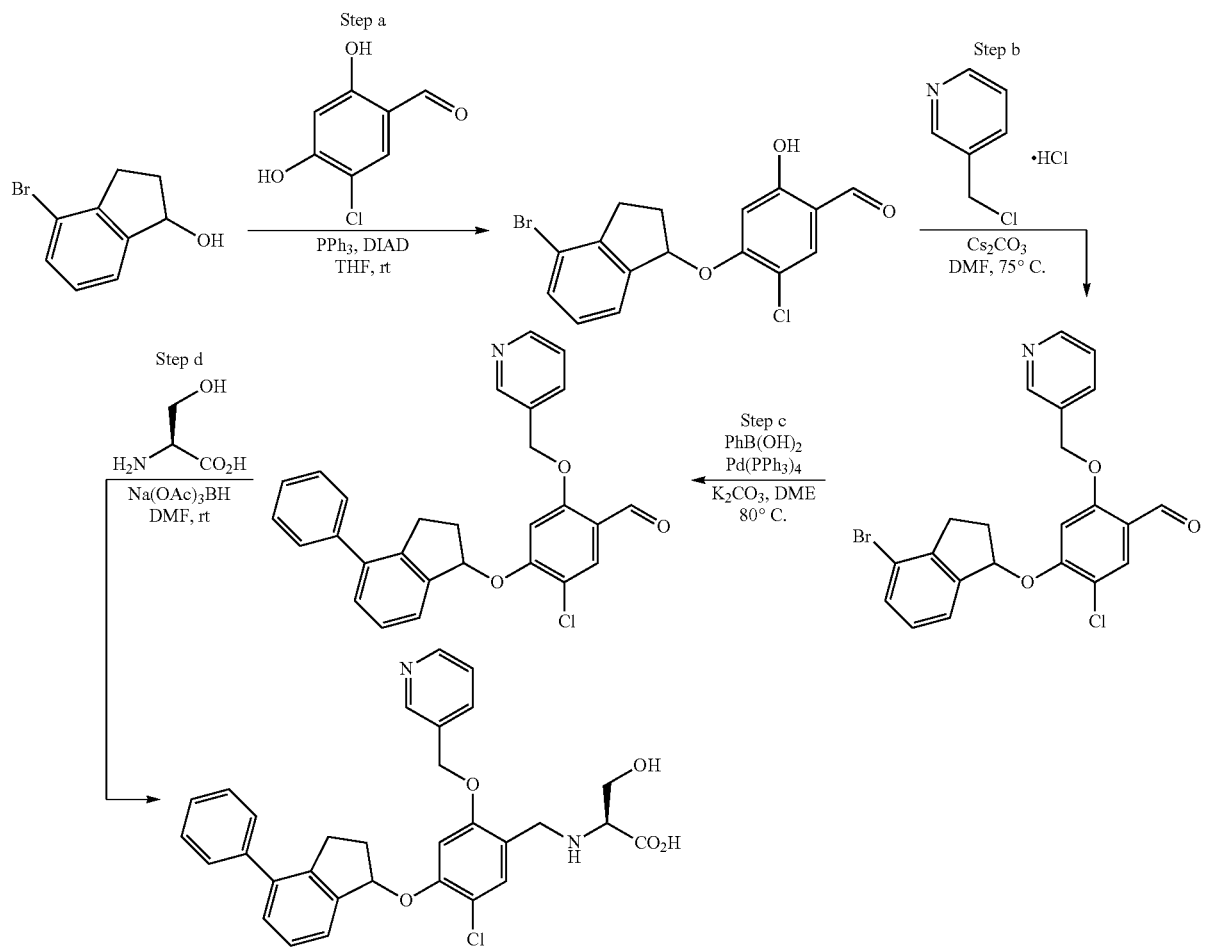

Step a: To a solution of 4-bromoindan-1-ol (5.3 g, 24.91 mmol) in THF (30 mL) at room temperature was added 5-chloro-2,4-dihydroxy-benzaldehyde (4.3 g, 24.91 mmol) followed by PPh$_3$ (6.5 g, 24.91 mmol) and the resulting solution was cooled in an ice-bath. DIAD (5.03 g, 24.91 mmol) in THF (10 mL) was added slowly dropwise at 0° C. and the resulting solution was allowed to warm to room temperature with stirring. After 12 h at room temperature, volatiles were evaporated in vacuo, the resulting residue was purified by flash chromatography (SiO$_2$, 50% EtOAc in hexanes) to obtain 4-(4-bromoindan-1-yl)oxy-5-chloro-2-hydroxy-benzaldehyde. MS: (ES) m/z calculated for $C_{16}H_{18}BrClO_3$ [M−H]$^+$ 365.0, found 364.9 (negative mode).

Step b: To a solution of 4-(4-bromoindan-1-yl)oxy-5-chloro-2-hydroxy-benzaldehyde (250 mg, 0.683 mmol) in DMF (3 mL) was added 3-(chloromethyl)pyridine hydrochloride (225 mg, 1.37 mmol) followed by Cs$_2$CO$_3$ (444 mg, 1.37 mmol). The resulting suspension was stirred at 75° C. for 2 h. The reaction mixture was diluted with EtOAc (20 mL) and washed with water (20 mL), dried (MgSO$_4$), concentrated in vacuo and purified by flash chromatography (SiO$_2$, 80% EtOAc in hexanes) to obtain 4-(4-bromoindan-1-yl)oxy-5-chloro-2-(3-pyridylmethoxy)benzaldehyde. MS: (ES) m/z calculated for C$_{22}$H$_{18}$BrClNO$_3$ [M+H]$^+$ 458.0, found 458.4.

Step c: To a solution of 4-(4-bromoindan-1-yl)oxy-5-chloro-2-(3-pyridylmethoxy)benzaldehyde (312 mg, 0.683 mmol) in DME (5 mL) was added phenylboronic acid (150 mg, 1.02 mmol), K$_2$CO$_3$ (283 mg, 2.05 mmol) and the resulting suspension was bubbled with nitrogen gas for one minute. Pd(PPh$_3$)$_4$ (80 mg, 0.0683 mmol) was then added, bubbled the reaction mixture with nitrogen gas for additional minute and stirred at 80° C. overnight. The reaction mixture was diluted with EtOAc (20 mL), washed with water (20 mL), brine (20 mL), dried (Na$_2$SO$_4$) and concentrated in vacuo. The obtained crude product was purified by flash chromatography (SiO$_2$, 80% EtOAc in hexanes) to obtain 5-chloro-4-(4-phenylindan-1-yl)oxy-2-(3-pyridylmethoxy)benzaldehyde. MS: (ES) m/z calculated for C$_{28}$H$_{23}$ClNO$_3$ [M+H]$^+$ 456.1, found 456.2.

Step d: To a solution of 5-chloro-4-(4-phenylindan-1-yl)oxy-2-(3-pyridylmethoxy)benzaldehyde (55 mg) in DMF (3 mL) was added (2S)-2-amino-3-hydroxy-propanoic acid (100 mg) followed by Na(OAc)$_3$BH (100 mg) and the resulting suspension was stirred at room temperature overnight. The reaction mixture was diluted with 2:1 CHCl$_3$/IPA (30 mL) and washed with water (15 mL), dried (MgSO$_4$) concentrated in vacuo and purified by reverse phase preparative HPLC (CH$_3$CN—H$_2$O with 0.1% TFA) to obtain (2S)-2-[[5-chloro-4-(4-phenylindan-1-yl)oxy-2-(3-pyridylmethoxy)phenyl]methylamino]-3-hydroxy-propanoic acid. MS: (ES) m/z calculated for C$_{31}$H$_{30}$ClN$_2$O$_5$ [M+H]$^+$ 545.2, found 545.4. $^1$H NMR (400 MHz, Methanol-d$_4$) δ 8.97 (d, J=2.0 Hz, 1H), 8.74 (d, J=5.3 Hz, 1H), 8.49 (d, J=8.1 Hz, 1H), 7.86 (dd, J=8.0, 5.4 Hz, 1H), 7.54 (s, 1H), 7.50-7.38 (m, 5H), 7.41-7.26 (m, 4H), 7.13 (d, J=1.4 Hz, 1H), 6.01 (dd, J=6.5, 4.3 Hz, 1H), 5.45 (t, J=1.9 Hz, 2H), 4.43-4.29 (m, 2H), 4.02 (s, 2H), 3.20 (ddd, J=16.4, 8.3, 5.8 Hz, 1H), 2.99 (td, J=8.1, 5.3 Hz, 1H), 2.61-2.50 (m, 1H), 2.21-2.10 (m, 1H).

Example 12: Synthesis of 5-[[4-chloro-2-[[(2-hydroxy-2-methyl-propyl)amino]methyl]-5-[(1S)-4-phenylindan-1-yl]oxy-phenoxy]methyl]pyridine-3-carbonitrile

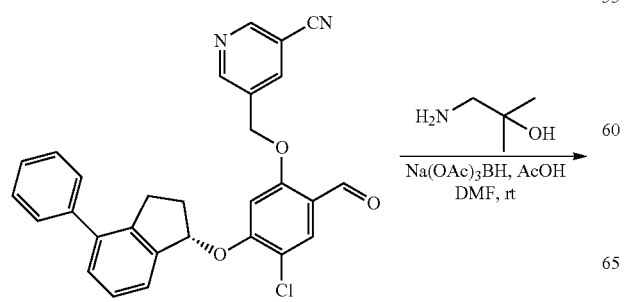

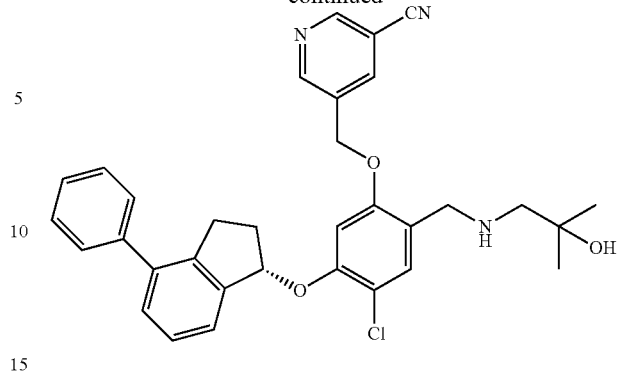

To a solution of 5-[[4-chloro-2-formyl-5-[(1S)-4-phenylindan-1-yl]oxy-phenoxy]methyl]pyridine-3-carbonitrile (50 mg, 0.104 mmol) in DMF (2 mL) was added 1-amino-2-methyl-propan-2-ol (100 mg, 0.89 mmol), AcOH (100 μL, 1.64 mmol) followed by Na(OAc)$_3$BH (100 mg, 0.47 mmol) and the resulting suspension was stirred at room temperature overnight. The reaction mixture was diluted with 2:1 CHCl$_3$/IPA (30 mL) and washed with water (15 mL), dried (MgSO$_4$), concentrated in vacuo and purified by reverse phase preparative HPLC (CH$_3$CN—H$_2$O with 0.1% TFA) to obtain 5-[[4-chloro-2-[[(2-hydroxy-2-methyl-propyl)amino]methyl]-5-[(1S)-4-phenylindan-1-yl]oxy-phenoxy]methyl]pyridine-3-carbonitrile, er: ~3.5:1. MS: (ES) m/z calculated for C$_{33}$H$_{33}$ClN$_3$O$_3$ [M+H]$^+$ 554.2, found 554.5. $^1$H NMR (400 MHz, Methanol-d$_4$) δ 8.96 (dd, J=19.1, 2.0 Hz, 2H), 8.42 (dd, J=2.4, 1.8 Hz, 1H), 7.54-7.27 (m, 9H), 7.12 (s, 1H), 6.02 (dd, J=6.4, 4.2 Hz, 1H), 5.40 (d, J=2.0 Hz, 2H), 4.26 (s, 2H), 3.27-3.14 (m, 1H), 3.04-2.89 (m, 3H), 2.63-2.49 (m, 1H), 2.15 (ddt, J=13.4, 8.8, 4.8 Hz, 1H), 1.24 (d, J=8.6 Hz, 6H).

Example 13: Synthesis of 5-[[4-chloro-2-[[(5-oxopyrrolidin-2-yl)methylamino]methyl]-5-[(1S)-4-phenylindan-1-yl]oxy-phenoxy]methyl]pyridine-3-carbonitrile

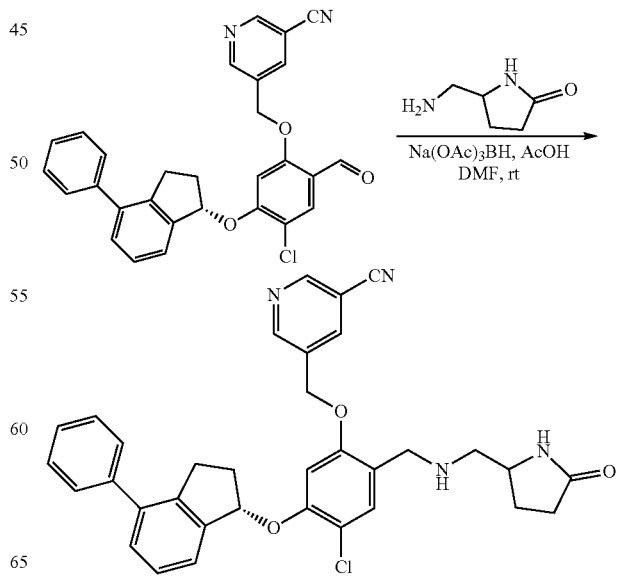

To a solution of 5-[[4-chloro-2-formyl-5-[(1S)-4-phenylindan-1-yl]oxy-phenoxy]methyl]pyridine-3-carbonitrile (50 mg, 0.104 mmol) in DMF (2 mL) was added 5-(aminomethyl)pyrrolidin-2-one (100 mg, 0.877 mmol), AcOH (100 µL, 1.66 mmol) followed by Na(OAc)₃BH (100 mg, 0.47 mmol) and the resulting suspension was stirred at room temperature overnight. The reaction mixture was diluted with 2:1 CHCl₃/IPA (30 mL) and washed with water (15 mL), dried (MgSO₄), concentrated in vacuo and purified by reverse phase preparative HPLC (CH₃CN—H₂O with 0.1% TFA) to obtain 5-[[4-chloro-2-[[(5-oxopyrrolidin-2-yl)methylamino]methyl]-5-[(1S)-4-phenylindan-1-yl]oxy-phenoxy]methyl]pyridine-3-carbonitrile, er: ~3.5:1. MS: (ES) m/z calculated for $C_{34}H_{32}ClN_4O_3$ [M+H]⁺ 579.2, found 579.5. ¹H NMR (400 MHz, Methanol-d₄) δ 8.97 (dd, J=18.3, 2.0 Hz, 2H), 8.39 (td, J=2.1, 0.7 Hz, 1H), 7.54 (d, J=0.6 Hz, 1H), 7.50-7.23 (m, 8H), 7.12 (s, 1H), 6.05-5.97 (m, 1H), 5.48-5.35 (m, 2H), 4.36-4.20 (m, 2H), 3.99 (p, J=6.3 Hz, 1H), 3.29-3.11 (m, 3H), 3.04-2.92 (m, 1H), 2.61-2.48 (m, 1H), 2.47-2.26 (m, 3H), 2.13 (ddt, J=13.2, 8.9, 4.8 Hz, 1H), 1.92-1.76 (m, 1H).

Example 14: Synthesis of 5-[[4-chloro-5-[(1S)-4-phenylindan-1-yl]oxy-2-[(1H-pyrazol-5-ylmethylamino)methyl]phenoxy]methyl]pyridine-3-carbonitrile

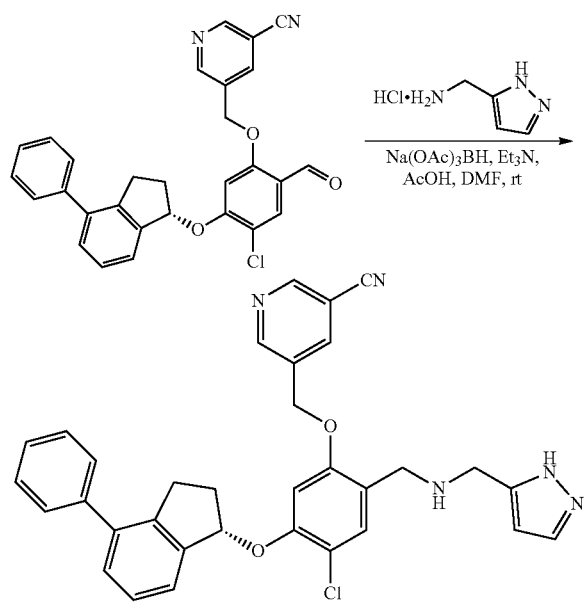

To a solution of 5-[[4-chloro-2-formyl-5-[(1S)-4-phenylindan-1-yl]oxy-phenoxy]methyl]pyridine-3-carbonitrile (50 mg, 0.104 mmol) in DMF (2 mL) was added 1H-pyrazol-5-ylmethanamine hydrochloride (100 mg, 0.75 mmol), Et₃N (100 µL, 0.723 mmol), AcOH (100 µL, 1.66 mmol) followed by Na(OAc)₃BH (100 mg, 0.47 mmol) and the resulting suspension was stirred at room temperature overnight. The reaction mixture was diluted with 2:1 CHCl₃/IPA (30 mL) and washed with water (15 mL), dried (MgSO₄), concentrated in vacuo and purified by reverse phase preparative HPLC (CH₃CN—H₂O with 0.1% TFA) to obtain 5-[[4-chloro-5-[(1S)-4-phenylindan-1-yl]oxy-2-[(1H-pyrazol-5-ylmethylamino)methyl]phenoxy]methyl]pyridine-3-carbonitrile, er: ~3.5:1. MS: (ES) m/z calculated for $C_{33}H_{29}ClN_5O_2$ [M+H]⁺ 562.2, found 562.5. ¹H NMR (400 MHz, Methanol-d₄) δ 8.93 (dd, J=8.2, 2.1 Hz, 2H), 8.33 (t, J=2.1 Hz, 1H), 7.70 (d, J=2.4 Hz, 1H), 7.52-7.26 (m, 9H), 7.10 (s, 1H), 6.41 (d, J=2.4 Hz, 1H), 6.01 (dd, J=6.5, 4.2 Hz, 1H), 5.42-5.30 (m, 2H), 4.25 (d, J=10.5 Hz, 4H), 3.34-3.14 (m, 1H), 2.98 (ddd, J=16.2, 8.2, 5.3 Hz, 1H), 2.55 (ddt, J=13.9, 8.2, 6.1 Hz, 1H), 2.14 (ddt, J=13.3, 8.5, 5.0 Hz, 1H).

Example 15: Synthesis of 3-[[5-chloro-2-[(5-cyano-3-pyridyl)methoxy]-4-[(1S)-4-phenylindan-1-yl]oxy-phenyl]methylamino]-2,2-dimethyl-propanoicacid

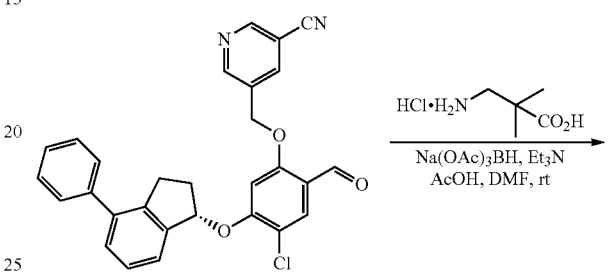

To a solution of 5-[[4-chloro-2-formyl-5-[(1S)-4-phenylindan-1-yl]oxy-phenoxy]methyl]pyridine-3-carbonitrile (50 mg, 0.104 mmol) in DMF (2 mL) was 3-amino-2,2-dimethyl-propanoic acid hydrochloride (100 mg, 0.653 mmol), Et₃N (100 µL, 0.723 mmol), AcOH (100 µL, 1.66 mmol) followed by Na(OAc)₃BH (100 mg, 0.47 mmol) and the resulting suspension was stirred at room temperature overnight. The reaction mixture was diluted with 2:1 CHCl₃/IPA (30 mL) and washed with water (15 mL), dried (MgSO₄), concentrated in vacuo and purified by reverse phase preparative HPLC (CH₃CN—H₂O with 0.1% TFA) to obtain 3-[[5-chloro-2-[(5-cyano-3-pyridyl)methoxy]-4-[(1S)-4-phenylindan-1-yl]oxy-phenyl]methylamino]-2,2-dimethyl-propanoic acid, er: ~3.5:1. MS: (ES) m/z calculated for $C_{34}H_{33}CN_3O_4$ [M+H]582.2, found 582.5. ¹H NMR (400 MHz, Methanol-d₄) δ 9.02 (d, J=2.1 Hz, 1H), 8.93 (d, J=2.0 Hz, 1H), 8.44 (s, 1H), 7.51 (s, 1H), 7.45 (d, J=2.0 Hz, 7H), 7.31 (s, 1H), 7.11 (s, 1H), 6.01 (dd, J=6.5, 4.2 Hz, 1H), 5.43 (d, J=2.2 Hz, 2H), 4.26 (s, 2H), 3.09 (d, J=15.0 Hz, 3H), 3.04-2.90 (m, 1H), 2.62-2.45 (m, 1H), 2.24-2.05 (m, 1H), 1.28 (d, J=7.9 Hz, 6H).

Example 16: Synthesis of (5-[[4-chloro-2-[(3-hydroxyazetidin-1-yl)methyl]-5-[(1S)-4-phenylindan-1-yl]oxy-phenoxy]methyl]pyridine-3-carbonitrile

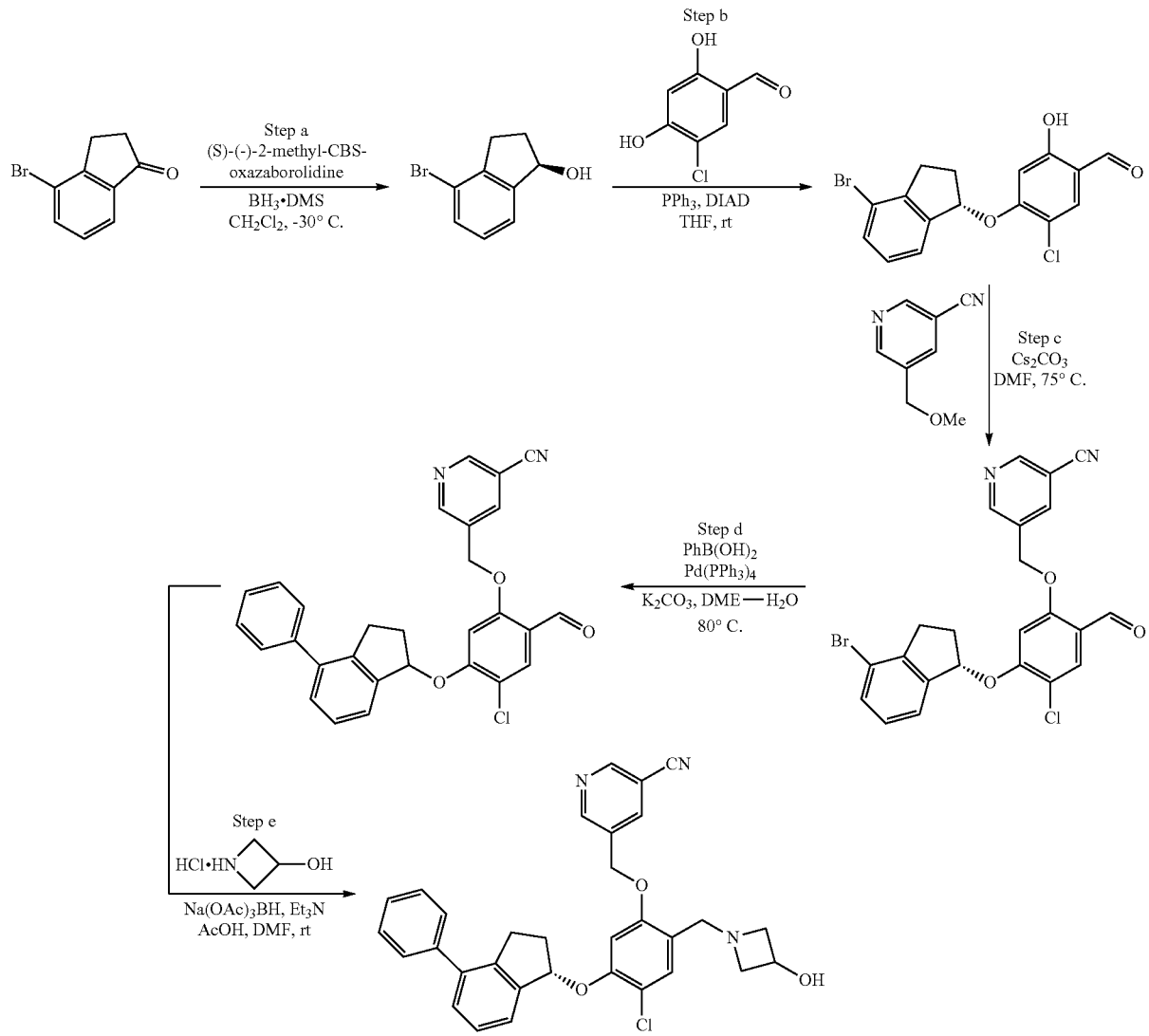

Step a: To a 500 mL three-neck round bottom flask equipped with an internal thermometer under nitrogen was added (S)-(−)-2-methyl-CBS-oxazaborolidine (7.1 mL, 7.1 mmol, 1M THF) and borane-dimethyl sulfide (3.6 mL, 7.2 mmol, 2M THF) at room temperature. The mixture was stirred for 10 min then diluted with dichloromethane (60 mL). Borane-dimethyl sulfide (130 mL, 260 mmol, 2M THF) was added at room temperature and the mixture was cooled to −30° C. A solution of 4-bromoindan-1-one (13.6 g, 64.4 mmol) in dichloromethane (40 mL) was added slowly over 25 min while maintaining the internal temperature between −30° C. and −20° C. After 1 h, the reaction was quenched carefully by the dropwise addition of methanol (50 mL). The solvent was removed in vacuo and the crude solid was purified by flash chromatography (15% EtOAc in hexane). The resulting pure (R)-4-bromoindan-1-ol was recrystallized from 1:5 EtOAc/hexane (100 mL) to give the product with 99.2% ee. Enantiomeric excess was determined by integration of peaks that were separated on a RegisCell 250×4.6 mm column at a flow rate of 1.2 mL/min and an isochratic mobile phase of 5% isopropanol in hexane. MS: (ES) m/z calculated for $C_9H_9BrO$ [M-OH]$^+$ 197.0, found 197.2. Chiral HPLC: 7(R)-4-bromoindan-1-ol was eluted using 5% IPA in hexane: $t_R$=7.63 min.

Step b: To a cooled (0° C.) solution of (R)-4-bromoindan-1-ol (11.2 g, 52.6 mmol), 5-chloro-2,4-dihydroxy-benzaldehyde (9.1 g, 52.6 mmol), and triphenylphosphine (13.8 g, 52.6 mmol) in THF (100 mL) was slowly added diisopropyl azodicarboxylate (10.3 mL, 52.6 mmol) in THF (25 mL). The mixture was allowed to gradually warm to room temperature for three days. The volatiles were removed in vacuo and the resulting crude residue was purified by flash chromatography (20% EtOAc in hexane) to afford 4-[(1S)-4-bromoindan-1-yl]oxy-5-chloro-2-hydroxy-benzaldehyde. Approximately 22% of racemization was observed during the reaction and the enantiomerica ratio of the obtained product was ~3.5:1. Enantiomeric ratio was determined by integration of peaks that were separated on a RegisCell 250×4.6 mm column at a flow rate of 1 mL/min and an isochratic mobile phase of 50% isopropanol in hexane (desired enantiomer $t_R$=6.68 min, undesired enantiomer $t_R$=5.45 min). All of the final compounds described in examples 17 to 36 were prepared using this intermediate with er: 3.5:1. MS: (ES) m/z calculated for $C_{16}H_{12}BrClO_3$ [M−H]⁻ 365.0, found 365.1.

Step c: To a solution of 4-[(1S)-4-bromoindan-1-yl]oxy-5-chloro-2-hydroxy-benzaldehyde (2.0 g, 5.4 mmol) in DMF (12 mL) was added (5-cyano-3-pyridyl)methyl methanesulfonate (1.5 g, 7.1 mmol), followed by $Cs_2CO_3$ (3.5 g, 11 mmol). The resulting suspension was stirred at 75° C. for 2 h. After cooling to room temperature, the reaction mixture was diluted with EtOAc (50 mL) and washed with water (20 mL). The aqueous layer was re-extracted with EtOAc (2×25 mL). The combined organic layers were dried ($MgSO_4$), filtered, and concentrated in vacuo. The crude was purified by flash chromatography ($SiO_2$, 50% EtOAc in hexanes) to obtain 5-[[5-[(1S)-4-bromoindan-1-yl]oxy-4-chloro-2-formyl-phenoxy]methyl]pyridine-3-carbonitrile. MS: (ES) m/z calculated for $C_{23}H_{16}BrCN_2O_3$ [M+H]⁺ 483.0, found 483.2.

Step d: To a solution of 5-[[5-[(1)-4-bromoindan-1-yl]oxy-4-chloro-2-formyl-phenoxy]methyl]pyridine-3-carbonitrile (0.83 g, 1.7 mmol) in 1,2-dimethoxyethane (10 mL) was added phenylboronic acid (0.22 g, 1.8 mmol), aqueous 2M $K_2CO_3$ (1.3 mL, 2.6 mmol) and the resulting mixture was bubbled with nitrogen gas for a few minutes. Tetrakis(triphenylphosphine)palladium(0) (0.10 g, 0.086 mmol) was then added and the reaction mixture was stirred at 80° C. overnight. After cooling to room temperature, the reaction mixture was diluted with EtOAc (30 mL) and washed with water (30 mL) and brine (30 mL). The organic layer was dried ($Na_2SO_4$), filtered, and concentrated in vacuo. The crude product was purified by flash chromatography ($SiO_2$, 30% EtOAc in hexanes) to obtain 5-[[4-chloro-2-formyl-5-[(1S)-4-phenylindan-1-yl]oxy-phenoxy]methyl]pyridine-3-carbonitrile. MS: (ES) m/z calculated for $C_{29}H_{21}CN_2O_3$ [M+H]⁺ 481.1, found 481.4.

Step e: To a solution of 5-[[4-chloro-2-formyl-5-[(1S)-4-phenylindan-1-yl]oxy-phenoxy]methyl]pyridine-3-carbonitrile (150 mg, 0.31 mmol) in DMF (3 mL) was added azetidin-3-ol hydrochloride (130 mg, 1.2 mmol), triethylamine (0.40 mL, 2.9 mmol), acetic acid (0.20 mL, 2.9 mmol), and sodium triacetoxyborohydride (190 mg, 0.88 mmol). After stirring at room temperature overnight, the reaction mixture was diluted with 2:1 $CHCl_3$/i-PrOH (30 mL) and washed with water (15 mL). The organic layer was dried ($MgSO_4$), filtered, and concentrated in vacuo. The crude residue was purified by reverse phase preparative HPLC ($CH_3CN$—$H_2O$ with 0.1% TFA) to obtain (5-[[4-chloro-2-[(3-hydroxyazetidin-1-yl)methyl]-5-[(1S)-4-phenylindan-1-yl]oxy-phenoxy]methyl]pyridine-3-carbonitrile as a di-trifluoroacetic acid salt. The diastereomeric ratio of the final compound is assumed to be ~3:1 based on the enantiomeric ration of the intermediate used in step b., er: ~3.5:1. MS: (ES) m/z calculated for $C_{32}H_{29}ClN_3O_3$ [M+H]⁺ 538.2, found 538.5. ¹H NMR (400 MHz, Methanol-d) δ 8.98 (s, 1H), 8.94 (d, J=1.9 Hz, 1H), 8.42 (s, 1H), 7.51 (s, 1H), 7.49-7.40 (m, 4H), 7.40-7.33 (m, 2H), 7.33-7.28 (m, 2H), 7.11 (d, J=8.5 Hz, 1H), 6.01 (t, J=5.4 Hz, 1H), 5.42 (s, 2H), 4.56 (m, 1H), 4.43 (s, 2H), 4.40-4.28 (m, 2H), 4.06-3.88 (m, 2H), 3.21-3.13 (m, 1H), 3.04-2.88 (m, 1H), 2.55 (m, 1H), 2.13 (m, 1H).

Example 17: Synthesis of (2S,3R)-2-[[5-chloro-4-[(1S)-4-(2-fluorophenyl)indan-1-yl]oxy-2-(pyridazin-3-ylmethoxy)phenyl]methylamino]-3-hydroxy-butanoic acid

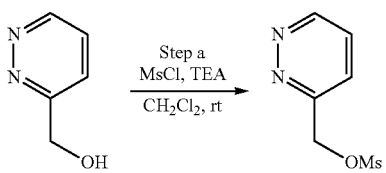

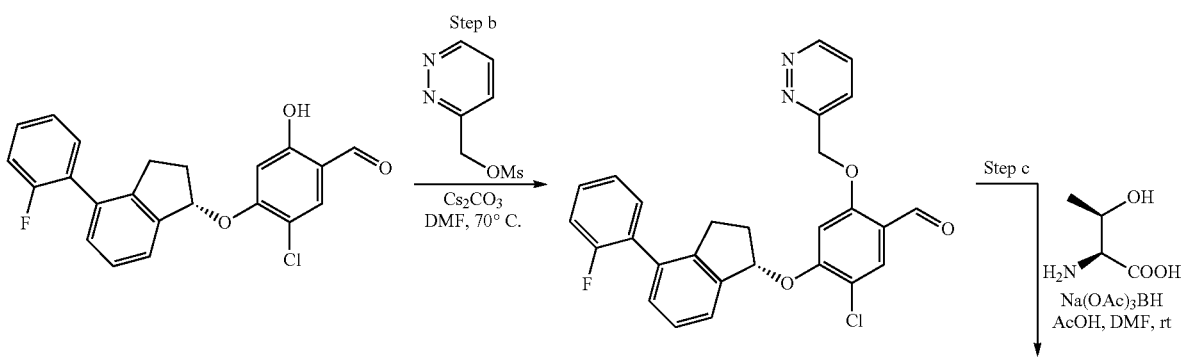

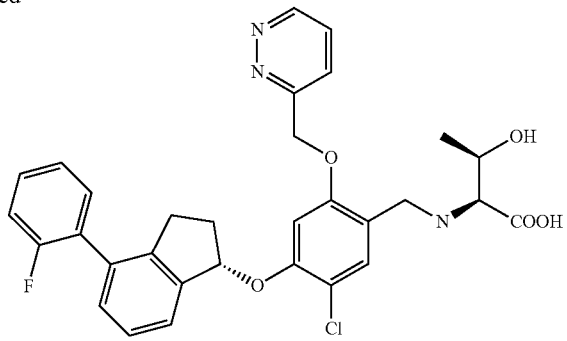

Step a: To a cold (0° C.) solution of pyridazin-3-ylmethanol (500 mg, 4.5 mmol) and triethylamine (1.26 mL, 9.1 mmol) in CH$_2$Cl$_2$ (5 mL) was added methanesulfonyl chloride (0.60 mL, 7.8 mmol) by dropwise addition. The resulting mixture was allowed to warm to room temperature and stirred for 1 h. The reaction mixture was added to water and the organic phase was separated. The aqueous phase was extracted with EtOAc, and solvent was removed from the combined organic layers in vacuo. The crude residue was purified by flash chromatography (SiO$_2$, 50% EtOAc in hexanes) to obtain (2-chloropyrimidin-5-yl)methyl methanesulfonate.

Step b: To a solution of 5-chloro-4-[(1S)-4-(2-fluorophenyl)indan-1-yl]oxy-2-hydroxy-benzaldehyde (150 mg, 0.393 mmol) and pyridazin-3-ylmethyl methanesulfonate (111 mg, 0.56 mmol) in DMF (3 mL) was added cesium carbonate (255 mg, 0.8 mmol). The mixture was stirred at 70° C. overnight. Solvent was removed in vacuo, and the crude residue was purified by flash chromatography to obtain 5-chloro-2-[(2-chloropyrimidin-5-yl)methoxy]-4-[(1S)-4-(2-fluorophenyl)indan-1-yl]oxy-benzaldehyde. MS: (ES) m/z calculated for C$_{27}$H$_{21}$ClFN$_2$O$_3$ [M+H]$^+$ 475.1, found 475.2.

Step c: To a solution of 5-chloro-4-[(1S)-4-(2-fluorophenyl)indan-1-yl]oxy-2-(pyridazin-3-ylmethoxy)benzaldehyde (50 mg, 0.1 mmol) in DMF (3 mL) was added (2S,3R)-2-amino-3-hydroxy-butanoic acid (100 mg, 0.57 mmol) Na(OAc)$_3$BH (100 mg, 0.49 mmol) and acetic acid (0.10 mL, 1.8 mmol). The resulting suspension was stirred at 45° C. for overnight. The reaction mixture was diluted with 2:1 CHCl$_3$/i-PrOH (5 mL), washed with water (1 mL), and concentrated in vacuo. The crude residue was purified by reverse phase preparative HPLC (CH$_3$CN—H$_2$O with 0.1% TFA). The fractions were combined and diluted with 2:1 CHCl$_3$/i-PrOH (30 mL). The organic layer was washed with saturated aqueous NaHCO$_3$ (15 mL), dried (MgSO$_4$), filtered, and concentrated in vacuo to obtain (2S,3R)-2-[[2-[[5-chloro-2-[(5-cyano-3-pyridyl)methoxy]-4-[(1S)-4-(2-fluorophenyl)indan-1-yl]oxy-phenyl]methylamino]acetyl]amino]-3-hydroxy-butanoic acid, dr: ~3.5:1. MS: (ES) m/z calculated for C$_{31}$H$_{30}$ClFN$_3$O$_5$ [M+H]578.2, found 578.3. $^1$H NMR (400 MHz, Methanol-d$_4$) δ. $^1$H NMR (400 MHz, Methanol-d$_4$) δ 8.87 (d, J=1.4 Hz, 1H), 8.66 (ddd, J=2.5, 1.5, 0.7 Hz, 1H), 8.59 (d, J=2.6 Hz, 1H), 7.48-7.14 (m, 8H), 7.10 (d, J=1.5 Hz, 1H), 5.94 (dd, J=6.4, 4.3 Hz, 1H), 5.60-5.45 (m, 2H), 4.24 (s, 2H), 3.99 (p, J=6.5 Hz, 1H), 3.32-3.14 (m, 1H), 3.07-2.94 (m, 1H), 2.87-2.75 (m, 1H), 2.52 (dq, J=13.8, 6.6 Hz, 1H), 2.07 (ddq, J=13.3, 8.9, 5.0, 4.6 Hz, 1H), 1.35-1.25 (m, 3H).

Example 18: Synthesis of (2S)-2-[[5-chloro-2-[(5-cyano-3-pyridyl)methoxy]-4-[(1S)-4-(2-fluorophenyl)indan-1-yl]oxy-phenyl]methylamino]-3-hydroxy-2-methyl-propanoicacid

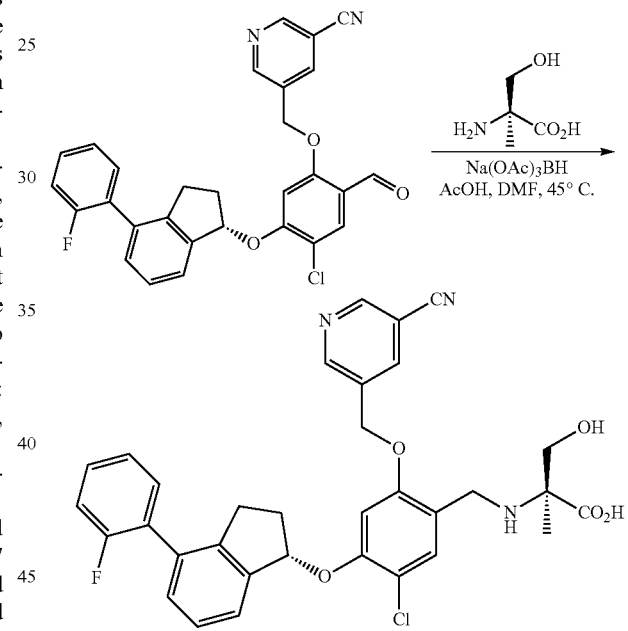

To a solution of 5-[[4-chloro-5-[(1S)-4-(2-fluorophenyl)indan-1-yl]oxy-2-formyl-phenoxy]methyl]pyridine-3-carbonitrile (50 mg, 0.1 mmol) in DMF (3 mL) was added (2S)-2-amino-3-hydroxy-2-methyl-propanoic acid (100 mg, 0.84 mmol) Na(OAc)$_3$BH (100 mg, 0.49 mmol) and acetic acid (0.10 mL, 1.8 mmol). The resulting suspension was stirred at 45° C. for overnight. The reaction mixture was diluted with 2:1 CHCl$_3$/i-PrOH (5 mL), washed with water (1 mL), and concentrated in vacuo. The crude residue was purified by reverse phase preparative HPLC (CH$_3$CN—H$_2$O with 0.1% TFA). The fractions were combined and diluted with 2:1 CHCl$_3$/i-PrOH (30 mL). The organic layer was washed with saturated aqueous NaHCO$_3$ (15 mL), dried (MgSO$_4$), filtered, and concentrated in vacuo to obtain obtain (2S)-2-[[5-chloro-2-[(5-cyano-3-pyridyl)methoxy]-4-[(1S)-4-(2-fluorophenyl)indan-1-yl]oxy-phenyl]methylamino]-3-hydroxy-2-methyl-propanoic acid, dr: ~3.5:1. MS: (ES) m/z calculated for C$_{33}$H$_{30}$ClFN$_3$O$_5$ [M+H]$^+$ 602.2, found 602.1. $^1$H NMR (400 MHz, Methanol-d$_4$) S. $^1$H NMR (400 MHz, Methanol-d$_4$) δ 8.99 (d, J=2.1 Hz, 1H), 8.89 (d, J=1.9 Hz, 1H), 8.44 (dt, J=9.6, 2.0 Hz, 1H), 7.55 (s, 1H), 7.49-7.14 (m, 7H), 7.06 (s, 1H), 6.00 (dd, J=6.6, 4.4 Hz, 1H), 5.45-5.32 (m, 2H), 4.22 (s, 2H), 3.92 (d, J=11.9 Hz, 1H), 3.73 (d, J=12.0 Hz, 1H), 3.02 (ddd, J=16.2, 8.4, 5.4 Hz, 1H), 2.82 (ddd, J=16.2, 8.2, 5.5 Hz, 1H), 2.61-2.43 (m, 1H), 2.18-2.05 (m, 1H), 1.44 (s, 3H).

Example 19: Synthesis of 1-methylethyl (2S)-2-[[5-chloro-2-[(5-cyano-3-pyridyl)methoxy]-4-[(1S)-4-(2-fluorophenyl)indan-1-yl]oxy-phenyl]methyl-amino]-3-hydroxy-propanoate

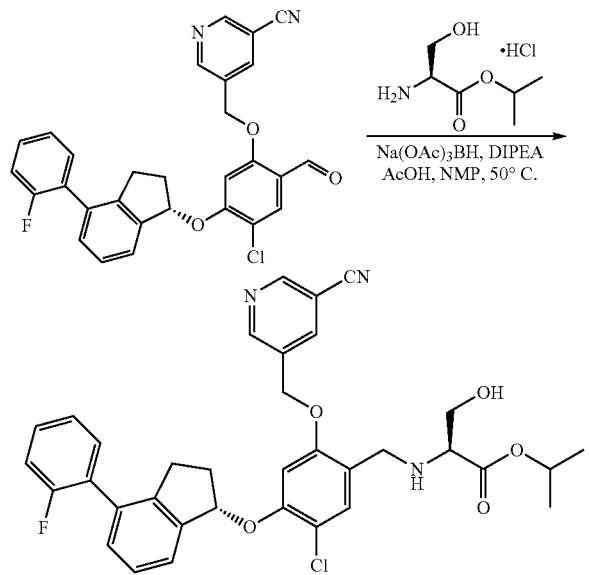

To a solution of 5-[[4-chloro-5-[(1S)-4-(2-fluorophenyl)indan-1-yl]oxy-2-formyl-phenoxy]methyl]pyridine-3-carbonitrile (67 mg, 0.13 mmol) in NMP (1 mL) was added L-serine isopropyl ester hydrochloride (110 mg, 0.59 mmol, prepared according to the procedure in *J. Med. Chem.* 53(19), 6625-6837; 2010), N-ethyl-N-(propan-2-yl))propan-2-amine (0.09 mL, 0.50 mmol), Na(OAc)$_3$BH (100 mg, 0.49 mmol) and acetic acid (0.10 mL, 1.8 mmol). The resulting suspension was stirred at 50° C. for 20 minutes. The reaction mixture was diluted with 2:1 CHCl$_3$/i-PrOH (5 mL), washed with water (1 mL), and concentrated in vacuo. The crude residue was purified by reverse phase preparative HPLC (CH$_3$CN—H$_2$O with 0.1% TFA) to obtain 1-methylethyl (2S)-2-[[5-chloro-2-[(5-cyano-3-pyridyl)methoxy]-4-[(1S)-4-(2-fluorophenyl)indan-1-yl]oxy-phenyl]methylamino]-3-hydroxy-propanoate as a trifluoroacetic acid salt. The salt was neutralized by passing the purified fractions through an Agilent Technologies PL-HCO3 MP SPE cartridge to obtain the neutral form. dr: ~3.5:1. MS: (ES) m/z calculated for C$_{35}$H$_{33}$ClFN$_3$O$_5$ [M+H]$^+$ 630.2, found 630.2. $^1$H NMR (400 MHz, Methanol-d) δ 8.97 (d, J=2.2 Hz 1H), 8.92 (d, J=2.0 Hz, 1H), 8.51 (s, 1H), 7.47 (s, 1H), 7.45-7.17 (m, 7H), 7.08 (s, 1H), 6.04-5.99 (m, 1H), 5.37 (s, 2H), 5.06 (m, 1H), 4.24-4.13 (m, 2H), 3.97-3.85 (m, 3H), 3.09-2.98 (m, 1H), 2.88-2.78 (m, 1H), 2.62-2.53 (m, 1H), 2.20-2.10 (m, 1H), 1.29-1.22 (m, 6H).

Example 20: Synthesis of (2S)-2-[[5-chloro-2-[(5-cyano-3-pyridyl)methoxy]-4-[(1R,2R)-2-fluoro-4-(2-fluorophenyl)indan-1-yl]oxy-phenyl]methylamino]-3-hydroxy-propanoic acid

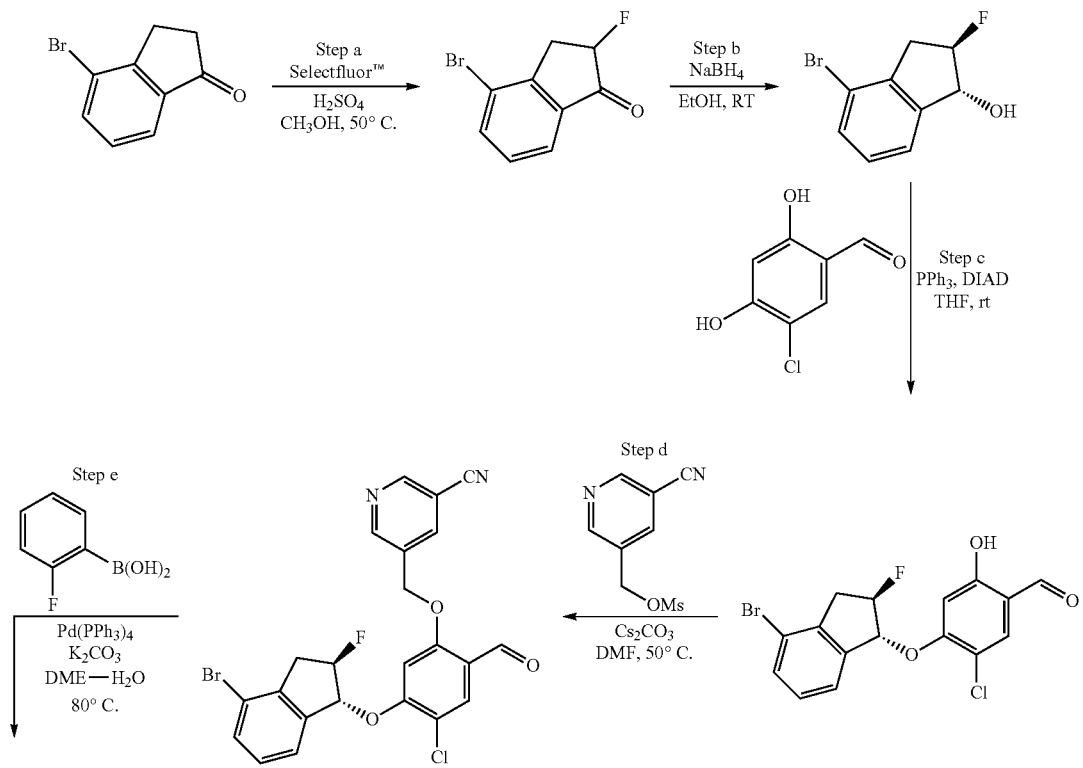

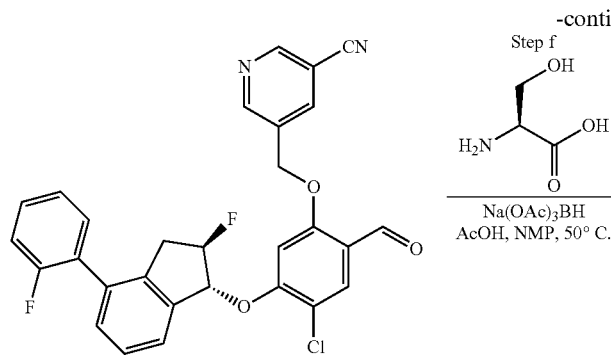 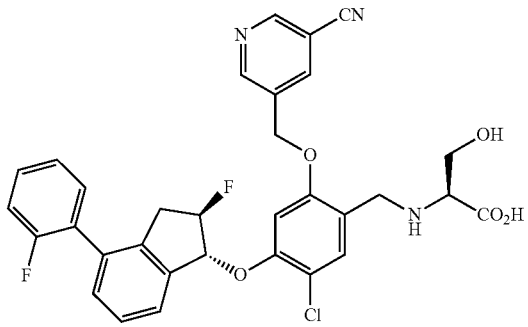

Step a: To a solution of 4-bromoindan-1-one (10 g, 47 mmol) dissolved in methanol (110 mL) was added 1-chloromethyl-4-fluoro-1,4-diazoniabicyclo[2.2.2]octane bis(tetrafluoroborate) (Selectfluor™, 25 g, 71 mmol) and 98% sulfuric acid (0.25 mL), After the mixture was stirred for 17 h at 50° C., it was filtered to remove the white solid. The solvent was removed from the filtrate in vacuo and the crude solid was purified by flash chromatography (6% MTBE in hexane) to obtain 2-fluoro-4-bromoindan-1-one. MS: (ES) m/z calculated for $C_9H_7BrFO$ $[M+H]^+$ 279.0, found 279.2.

Step b: To a solution of 4-bromo-2-fluoroindan-1-one (2.0 g, 8.7 mmol) in ethanol (40 mL) was added sodium borohydride (380 mg, 10 mmol). The mixture was stirred for 10 minutes at room temperature, then quenched with the addition of saturated aqueous sodium bicarbonate (10 mL). Ethanol was removed in vacuo, and the residue was extracted with ethyl acetate, washed with brine, dried over sodium sulfate, filtered and concentrated. The crude solid was purified by flash chromatography to obtain 4-bromo-2-fluoroindan-1-ol. MS: (ES) m/z calculated for $C_9H_7BrF$ $[M-OH]^+$ 213.0, found 213.0. The product was arbitrarily assigned the trans configuration, rel-(1R,2R)-4-bromo-2-fluoroindan-1-ol.

Step c: To a cooled (0° C.) solution of rel-(1R,2R)-4-bromo-2-fluoroindan-1-ol (1.2 g, 5.3 mmol), 5-chloro-2,4-dihydroxybenzaldehyde (0.96 g, 5.6 mmol), and triphenylphosphine (1.5 g, 5.7 mmol) in THF (40 mL) was slowly added DIAD (1.2 g, 5.6 mmol) in THF (40 mL). The mixture was allowed to warm to room temperature and stirred for 16 h. The volatiles were removed in vacuo and the resulting crude residue was purified by flash chromatography (20% EtOAc in hexane) to afford 4-[rel-(1R,2R)-4-bromo-2-fluoro-indan-1-yl]oxy-5-chloro-2-hydroxy-benzaldehyde. $^1$H NMR (400 MHz, DMSO-d) δ 11.25 (s, 1H), 10.10 (s, 1H), 7.71 (s, 1H), 7.67 (d, J=8.8 Hz), 7.49 (d, J=8.0 Hz), 7.33 (d, J=7.6 Hz), 7.00 (s, 1H), 6.20 (dd, J=16 Hz, 2.8 Hz), 5.65-5.47 (m, 1H), 3.62-3.46 (m, 1H), 3.21-3.03 (m, 1H).

Step d: To a solution of 4-[rel-(1R,2R)-4-bromo-2-fluoro-indan-1-yl]oxy-5-chloro-2-hydroxy-benzaldehyde (340 mg, 0.87 mmol) in DMF (4 mL) was added (5-cyano-3-pyridyl)methyl methanesulfonate (300 mg, 1.4 mmol), followed by $Cs_2CO_3$ (1.0 g, 3.1 mmol). The resulting suspension was stirred at 50° C. for 30 min. The reaction mixture was diluted with dichloromethane and washed with water, and the organic layer was concentrated in vacuo. The crude residue was purified by flash chromatography ($SiO_2$, 50% EtOAc in hexanes) to obtain 5-[[5-[rel-(1R,2R)-4-bromo-2-fluoro-indan-1-yl]oxy-4-chloro-2-formyl-phenoxy]methyl]pyridine-3-carbonitrile. MS: (ES) m/z calculated for $C_{23}H_{16}BrClFN_2O_3$ $[M+H]^+$ 501.0, found 501.0.

Step e: To a solution of 5-[[5-[rel-(1R,2R)-4-bromo-2-fluoro-indan-1-yl]oxy-4-chloro-2-formyl-phenoxy]methyl]pyridine-3-carbonitrile (270 mg, 0.54 mmol) in DME (5 mL) was added 2-flurophenylboronic acid (120 mg, 0.86 mmol), $K_2CO_3$ (240 mg, 1.7 mmol) and the resulting mixture was bubbled with nitrogen gas for a few minutes. $Pd(PPh_3)_4$ (110 mg, 0.096 mmol) was then added and the reaction mixture was stirred at 80° C. for 2 h. After cooling to room temperature, the reaction mixture was concentrated in vacuo and the crude product was purified by flash chromatography ($SiO_2$, 30% EtOAc in hexanes) to obtain 5-[[4-chloro-5-[rel-(1R,2R)-2-fluoro-4-(2-fluorophenyl)indan-1-yl]oxy-2-formyl-phenoxy]methyl]pyridine-3-carbonitrile. MS: (ES) m/z calculated for $C_{29}H_{20}ClF_2N_2O_3$ $[M+H]^+$ 517.1, found 517.1.

Step f: To a solution of 5-[[4-chloro-5-[rel-(1R,2R)-2-fluoro-4-(2-fluorophenyl)indan-1-yl]oxy-2-formyl-phenoxy]methyl]pyridine-3-carbonitrile (50 mg, 0.097 mmol) in DMF (2 mL) was added L-serine (100 mg, 0.95 mmol), $Na(OAc)_3BH$ (105 mg, 0.50 mmol) and acetic acid (0.10 mL, 1.8 mmol). The resulting mixture was stirred at 50° C. for 2 h. The reaction mixture was diluted with 2:1 $CHCl_3$/i-PrOH (5 mL), washed with water (1 mL), and concentrated in vacuo. The crude residue was purified by reverse phase preparative HPLC ($CH_3CN-H_2O$ with 0.1% TFA) to obtain (2S)-2-[[5-chloro-2-[(5-cyano-3-pyridyl)methoxy]-4-[rel-(1R,2R)-2-fluoro-4-(2-fluorophenyl)indan-1-yl]oxy-phenyl]methylamino]-3-hydroxy-propanoic acid. To obtain the neutral form, purified HPLC fractions were basified with sodium bicarbonate, and solvent was removed in vacuo. The residue was dissolved in 2:1 $CHCl_3$/i-PrOH, dried over $Na_2SO_4$, filtered and concentrated. The residue was finally lyophilized from water/acetonitrile to obtain a powder. MS: (ES) m/z calculated for $C_{32}H_{27}ClF_2N_3O_5$ $[M+H]^+$ 606.2, found 606.2. $^1$H NMR (400 MHz, Methanol-d) δ 8.98 (s, 1H), 8.92 (s, 1H), 8.42 (s, 1H), 7.58 (s, 1H), 7.47-7.35 (m, 5H), 7.31-7.19 (m, 3H), 6.11 (dd, J=16 Hz, 3.7 Hz, 1H), 5.50-5.30 (m, 3H), 4.44-4.29 (m, 2H), 4.02 (s, 3H), 3.45-3.33 (m, 1H), 3.17-3.02 (m, 1H).

Example 21: Synthesis of N-[2-[[5-chloro-2-[(5-cyano-3-pyridyl)methoxy]-4-[(1S)-4-(2-fluorophenyl)indan-1-yl]oxy-phenyl]methylamino]ethyl]prop-2-enamide

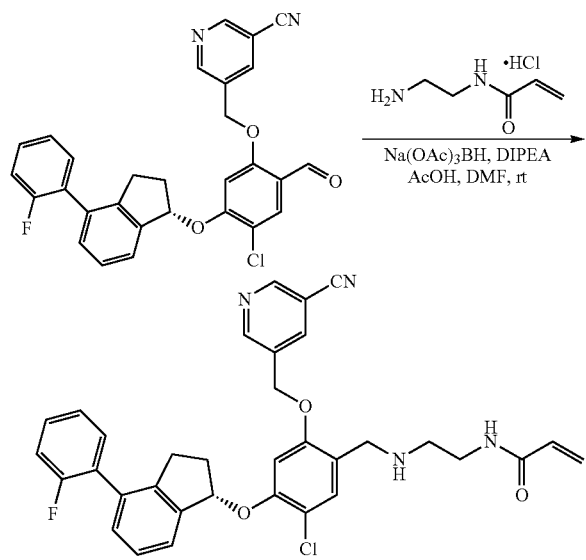

To a solution of 5-[[4-chloro-5-[(1S)-4-(2-fluorophenyl)indan-1-yl]oxy-2-formyl-phenoxy]methyl]pyridine-3-carbonitrile (54 mg, 0.11 mmol) in DMF (2 mL) was added N-(2-aminoethyl)prop-2-enamide hydrochloride (104 mg, 0.69 mmol, prepared according to the procedure in Analytical Chemistry, 86 (5), 2429-2435; 2014), N-ethyl-N-(propan-2-yl))propan-2-amine (0.12 mL, 0.69 mmol), Na(OAc)$_3$BH (96 mg, 0.45 mmol) and acetic acid (16 mg, 0.27 mmol). The resulting suspension was stirred at room temperature for 3.5 hours. The reaction mixture was diluted with 2:1 CHCl$_3$/i-PrOH (5 mL), washed with water (1 mL), and concentrated in vacuo. The crude residue was purified by reverse phase preparative HPLC (CH$_3$CN—H$_2$O with 0.1% TFA) to obtain N-[2-[[5-chloro-2-[(5-cyano-3-pyridyl)methoxy]-4-[(1S)-4-(2-fluorophenyl)indan-1-yl]oxy-phenyl]methylamino]ethyl]prop-2-enamide as a trifluoroacetic acid salt. The salt was neutralized by passing the purified fractions through an Agilent Technologies PL-HCO3 MP SPE cartridge to obtain the neutral form. er: ~3.5:1. MS: (ES) m/z calculated for C$_{34}$H$_{31}$ClFN$_4$O$_3$ [M+H]$^+$ 597.2, found 597.5. $^1$H NMR (400 MHz, Methanol-d) δ 9.00 (d, J=2.3 Hz, 1H), 8.92 (d, J=2.0 Hz, 1H), 8.42 (t, J=1.9 Hz, 1H), 7.51 (s, 1H), 7.45-7.30 (m, 5H), 7.28-7.16 (m, 2H), 7.09 (s, 1H), 6.22 (s, 1H), 6.20 (d, J=1.2 Hz, 1H), 6.02 (dd, J=6.8 Hz, 4.0 Hz), 5.71 (dd, J=6.4 Hz, 5.6 Hz, 1H), 5.42 (m, 2H), 3.52 (t, J=4.8 Hz, 2H), 3.22 (t, J=6.0 Hz, 2H), 3.08-2.98 (m, 1H), 2.88-2.78 (m, 1H), 2.60-2.50 (m, 1H), 2.17-2.07 (m, 1H).

Example 22: Synthesis of 1-[[2-[(2-aminopyrimidin-5-yl)methoxy]-5-chloro-4-[(1S)-4-(2-fluorophenyl)indan-1-yl]oxy-phenyl]methyl]piperidin-4-ol

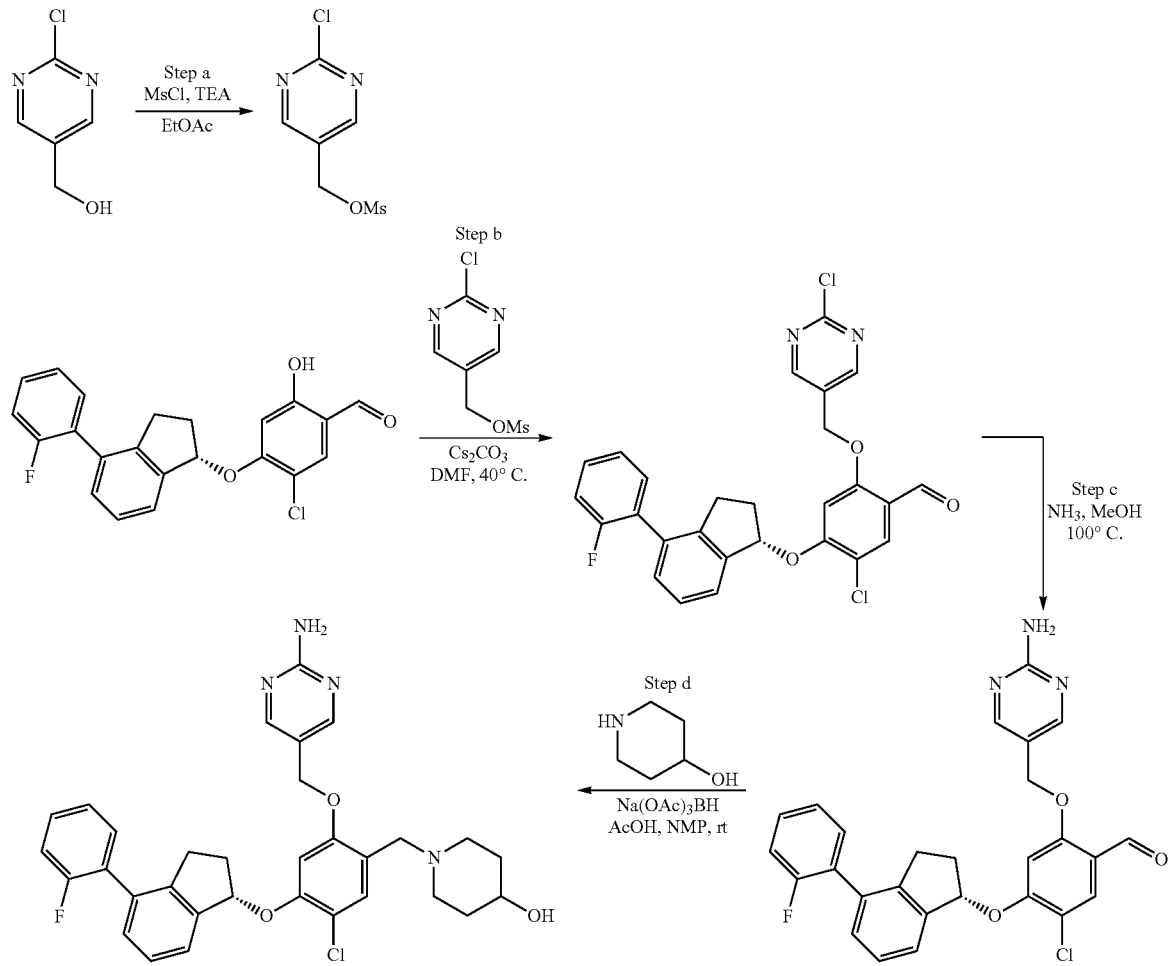

Step a: To a cold (0° C.) solution of (2-chloropyrimidin-5-yl)methanol (710 mg, 4.9 mmol) and triethylamine (1.8 mL, 13 mmol) in EtOAc (20 mL) was added methanesulfonyl chloride (0.60 mL, 7.8 mmol) by dropwise addition. The resulting mixture was allowed to warm to room temperature and stirred for 2 days. The reaction mixture was added to water and the organic phase was separated. The aqueous phase was extracted with EtOAc, and solvent was removed from the combined organic layers in vacuo. The crude residue was purified by flash chromatography (SiO$_2$, 50% EtOAc in hexanes) to obtain (2-chloropyrimidin-5-yl)methyl methanesulfonate. MS: (ES) m/z calculated for C$_6$H$_8$ClN$_2$O$_3$S [M+H]$^+$ 223.0, found 223.0.

Step b: To a solution of 5-chloro-4-[(1S)-4-(2-fluorophenyl)indan-1-yl]oxy-2-hydroxy-benzaldehyde (200 mg, 0.52 mmol) and (2-chloropyrimidin-5-yl)methyl methanesulfonate (200 mg, 0.90 mmol) in DMF (2 mL) was added cesium carbonate (400 mg, 1.2 mmol). The mixture was stirred at 40° C. overnight. Solvent was removed in vacuo, and the crude residue was purified by flash chromatography to obtain 5-chloro-2-[(2-chloropyrimidin-5-yl)methoxy]-4-[(1S)-4-(2-fluorophenyl)indan-1-yl]oxy-benzaldehyde. MS: (ES) m/z calculated for C$_{27}$H$_{20}$Cl$_2$FN$_2$O$_3$ [M+H]$^+$ 509.1, found 509.2.

Step c: To a solution of 5-chloro-2-[(2-chloropyrimidin-5-yl)methoxy]-4-[(1S)-4-(2-fluorophenyl)indan-1-yl]oxy-benzaldehyde (50 mg, 0.098 mmol) in THF (1 mL) in a 4 mL glass vial was added 7M ammonia in methanol (1.4 mL, 9.8 mmol). The vial was secured with a teflon-lined screwcap and placed in an aluminum heating block maintained at 100° C. for four hours. Solvent was removed from the reaction mixture and the crude residue of 2-[(2-aminopyrimidin-5-yl)methoxy]-5-chloro-4-[(1S)-4-(2-fluorophenyl)indan-1-yl]oxy-benzaldehyde was used without purification. MS: (ES) m/z calculated for C$_{27}$H$_{22}$ClFN$_2$O$_3$ [M+H]$^+$ 490.1, found 490.2.

Step d: To a solution of crude 2-[(2-aminopyrimidin-5-yl)methoxy]-5-chloro-4-[(1S)-4-(2-fluorophenyl)indan-1-yl]oxy-benzaldehyde (50 mg, 0.1 mmol) in NMP (1 mL) was added 4-hydroxypiperidine (113 mg, 1.1 mmol), Na(OAc)$_3$BH (125 mg, 0.59 mmol), and acetic acid (0.075 mL, 1.3 mmol). The mixture was stirred at room temperature overnight followed by an additional 6 h at 50° C. The resulting suspension was stirred at room temperature for 3.5 hours. The reaction mixture was diluted with 2:1 CHCl$_3$/i-PrOH (5 mL), washed with water (1 mL), and concentrated in vacuo. The crude residue was purified by reverse phase preparative HPLC (CH$_3$CN—H$_2$O with 0.1% TFA) to obtain 1-[[2-[(2-aminopyrimidin-5-yl)methoxy]-5-chloro-4-[(1S)-4-(2-fluorophenyl)indan-1-yl]oxy-phenyl]methyl]piperidin-4-ol as a trifluoroacetic acid salt. The salt was neutralized by passing the purified fractions through an Agilent Technologies PL-HCO3 MP SPE cartridge to obtain the neutral form. er: ~3.5:1. MS: (ES) m/z calculated for C$_{32}$H$_{33}$ClFN$_4$O$_3$ [M+H]$^+$ 575.2, found 575.4. $^1$H NMR (400 MHz, Methanol-d) δ 8.45 (d, J=2.9 Hz, 2H), 7.52 (d, J=4.8 Hz, 1H), 7.45-7.14 (m, 7H), 6.07 (dd, J=6.8 Hz, 4.8 Hz, 1H), 5.14-5.10 (m, 2H), 4.23 (d, J=5.6 Hz, 2H), 3.53-3.43 (m, 1H), 3.10-3.00 (m, 2H), 2.91-2.79 (m, 1H), 2.70-2.58 (m, 1H), 2.21-2.06 (m, 2H), 1.94-1.84 (m, 2H), 1.70-1.60 (m, 1H).

Example 23: Synthesis of 5-[[4-chloro-5-[(1S)-4-(2-fluorophenyl)indan-1-yl]oxy-2-[(4-hydroxy-1-piperidyl)methyl]phenoxy]methyl]pyridine-3-carbonitrile

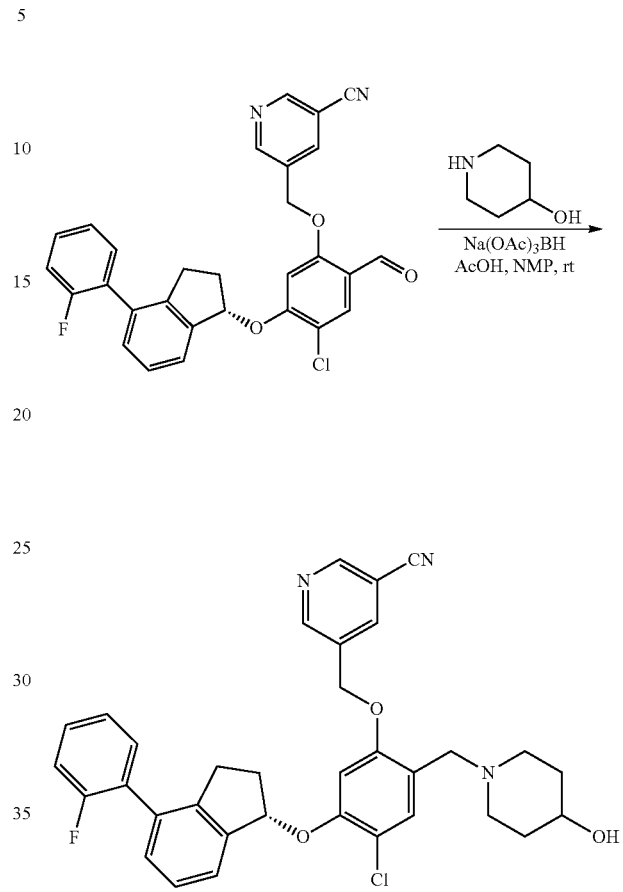

To a solution of 5-[[4-chloro-5-[(1S)-4-(2-fluorophenyl)indan-1-yl]oxy-2-formyl-phenoxy]methyl]pyridine-3-carbonitrile (170 mg, 0.34 mmol) in NMP (2 mL) was added 4-hydroxypiperidine (256 mg, 2.5 mmol), Na(OAc)$_3$BH (253 mg, 1.2 mmol) and acetic acid (0.040 mL, 0.7 mmol). The resulting suspension was stirred for 1 day at room temperature. The reaction mixture was diluted with 2:1 CHCl$_3$/i-PrOH (12 mL), washed with water (4 mL), and concentrated in vacuo. The crude residue was purified by reverse phase preparative HPLC (CH$_3$CN—H$_2$O with 0.1% TFA) to obtain 5-[[4-chloro-5-[(1S)-4-(2-fluorophenyl)indan-1-yl]oxy-2-[(4-hydroxy-1-piperidyl)methyl]phenoxy]methyl]pyridine-3-carbonitrile, er: ~3.5:1. MS: (ES) m/z calculated for C$_{34}$H$_{32}$ClFN$_3$O$_3$ [M+H]$^+$ 584.2, found 584.4. $^1$H NMR (400 MHz, Methanol-d) δ 8.90 (s, 1H), 8.87 (m, 1H), 8.31 (m, 1H), 7.43 (d, J=5.2 Hz, 1H), 7.39-7.22 (m, 5H), 7.21-7.09 (m, 2H), 7.05 (d, J=2.2 Hz, 1H), 6.00-5.96 (m, 1H), 5.32 (m, 2H), 4.23 (d, J=6.0 Hz, 2H), 3.47-3.38 (m, 1H), 3.06-2.91 (m, 2H), 2.82-2.71 (m, 1H), 2.56-2.46 (m, 1H), 2.11-1.99 (m, 2H), 1.87-1.80 (m, 2H), 1.66-1.52 (m, 1H).

Example 24: Synthesis of (2S)-2-[[5-chloro-2-[(5-cyano-3-pyridyl)methoxy]-4-[(1S)-4-(2-fluorophenyl)indan-1-yl]oxy-phenyl]methylamino]-3-hydroxy-propanoic acid

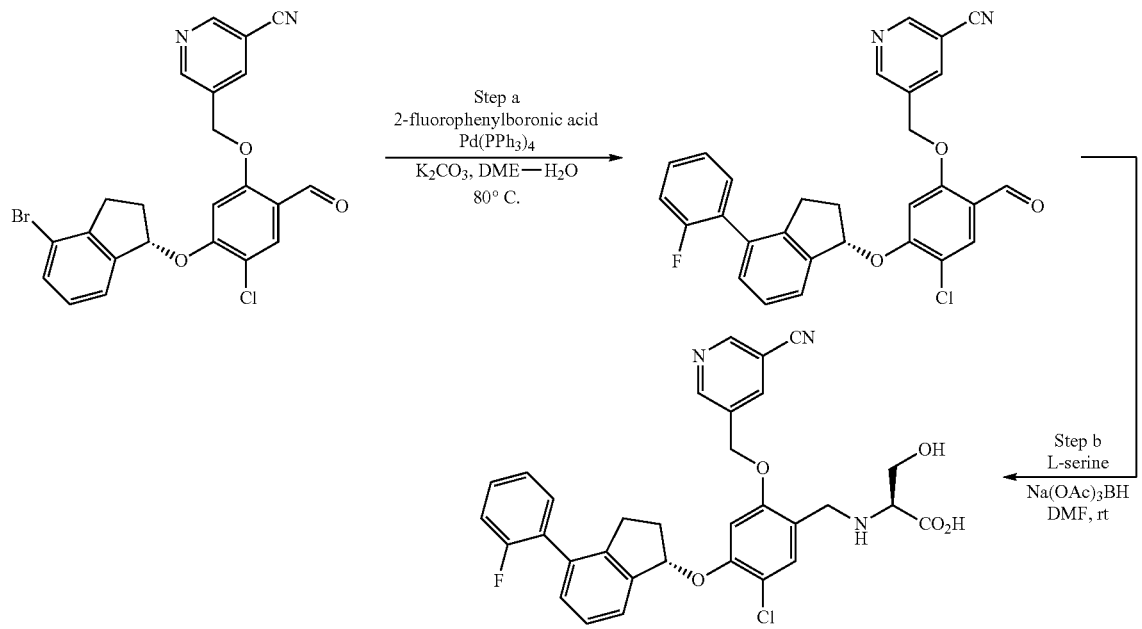

Step a: To a solution of 5-[[5-[(1S)-4-bromoindan-1-yl]oxy-4-chloro-2-formyl-phenoxy]methyl]pyridine-3-carbonitrile (570 mg, 1.2 mmol) in 1,2-dimethoxyethane (10 mL) was added 2-fluorophenylboronic acid (250 mg, 1.8 mmol), aqueous 2M $K_2CO_3$ (1.20 mL, 3.5 mmol) and the resulting mixture was bubbled with nitrogen gas for a few minutes. Tetrakis(triphenylphosphine)palladium(0) (140 mg, 0.12 mmol) was then added and the reaction mixture was stirred at 80° C. for 2 h. After cooling to room temperature, the reaction mixture was diluted with EtOAc (30 mL) and washed with water (30 mL) and brine (30 mL). The organic layer was dried ($Na_2SO_4$), filtered, and concentrated in vacuo. The crude product was purified by flash chromatography ($SiO_2$, 40% EtOAc in hexanes) to obtain 5-[[4-chloro-5-[(1S)-4-(2-fluorophenyl)indan-1-yl]oxy-2-formyl-phenoxy]methyl]pyridine-3-carbonitrile. MS: (ES) m/z calculated for $C_{29}H_{20}ClFN_2O_3$ [M+H]$^+$ 499.1, found 499.1.

Step b: To a solution of 5-[[4-chloro-5-[(1S)-4-(2-fluorophenyl)indan-1-yl]oxy-2-formyl-phenoxy]methyl]pyridine-3-carbonitrile (50 mg, 0.10 mmol) in DMF (3 mL) was added L-serine (100 mg, 0.95 mmol) and sodium triacetoxyborohydride (150 mg, 0.71 mmol). The resulting suspension was stirred at room temperature overnight. The reaction mixture was diluted with 2:1 $CHCl_3$/i-PrOH (30 mL), washed with water (15 mL), dried ($MgSO_4$), and concentrated in vacuo. The crude residue was purified by reverse phase preparative HPLC ($CH_3CN$—$H_2O$ with 0.1% TFA) to obtain (2S)-2-[[5-chloro-2-[(5-cyano-3-pyridyl)methoxy]-4-[(1S)-4-(2-fluorophenyl)indan-1-yl]oxy-phenyl]methylamino]-3-hydroxy-propanoic acid as a di-trifluoroacetic acid salt, dr: ~3.5:1. MS: (ES) m/z calculated for $C_{32}H_{27}ClFN_3O_5$ [M+H]$^+$ 588.2, found 588.4. $^1$H NMR (400 MHz, Methanol-d) δ 8.99 (d, J=2.1 Hz, 1H), 8.93 (d, J=2.0 Hz, 1H), 8.43 (s, 1H), 7.53 (s, 1H), 7.45-7.31 (m, 4H), 7.30-7.15 (m, 3H), 7.11 (s, 1H), 6.08-5.99 (m, 1H), 5.38 (s, 2H), 4.38 (d, J=13.4 Hz, 1H), 4.31 (d, J=13.1 Hz, 1H), 4.03-3.99 (m, 3H), 3.11-2.98 (m, 1H), 2.90-2.76 (m, 1H), 2.63-2.50 (m, 1H), 2.20-2.09 (m, 1H).

Example 25: Synthesis of (2S)-2-[[5-chloro-2-methoxy-4-[(1S)-4-phenylindan-1-yl]oxy-phenyl]methylamino]-3-hydroxy-propanoic acid

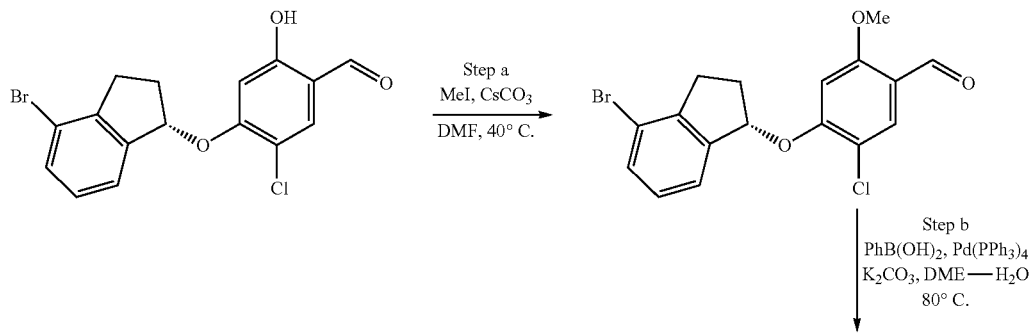

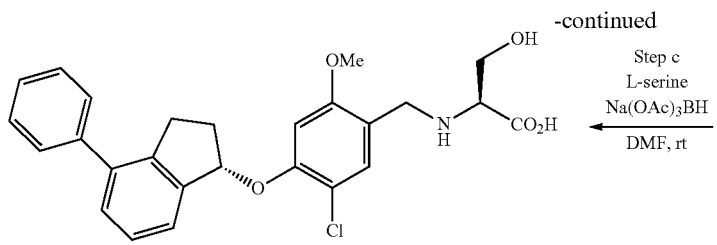 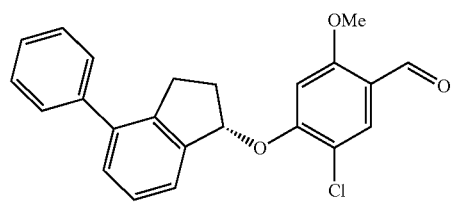

Step a: To a solution of 4-[(1S)-4-bromoindan-1-yl]oxy-5-chloro-2-hydroxy-benzaldehyde (200 mg, 0.54 mmol) in DMF (1 mL) was added iodomethane (130 μL, 2.1 mmol), followed by $Cs_2CO_3$ (360 mg, 1.1 mmol). The resulting suspension was stirred at 40° C. for 1 h. After cooling to room temperature, the reaction was diluted with dichloromethane (15 mL) and washed with water (20 mL). The aqueous layer was re-extracted with dichloromethane (2×20 mL). The combined organic layers were dried ($MgSO_4$), filtered, and concentrated in vacuo to obtain 4-[(1S)-4-bromoindan-1-yl]oxy-5-chloro-2-methoxy-benzaldehyde. MS: (ES) m/z calculated for $C_{17}H_{14}BrClO_3$ [M+Na]$^+$ 403.0, found 403.2.

Step b: To a solution of 4-[(1S)-4-bromoindan-1-yl]oxy-5-chloro-2-methoxy-benzaldehyde (210 mg, 0.54 mmol) in DME (5 mL) was added phenylboronic acid (79 mg, 0.65 mmol), aqueous 2M $K_2CO_3$ (0.41 mL, 0.81 mmol) and the resulting mixture was bubbled with nitrogen gas for a few minutes. Tetrakis(triphenylphosphine)palladium(0) (31 mg, 0.81 mmol) was then added and the reaction mixture was stirred at 80° C. overnight. After cooling to room temperature, the reaction mixture was diluted with EtOAc (10 mL) and washed with water (15 mL). The organic layer was dried ($Na_2SO_4$), filtered, and concentrated in vacuo. The crude product was purified by flash chromatography ($SiO_2$, 20% EtOAc in hexanes) to obtain 5-chloro-2-methoxy-4-[(1S)-4-phenylindan-1-yl]oxy-benzaldehyde. MS: (ES) m/z calculated for $C_{23}H_{19}ClO_3$ [M+Na]$^+$ 401.1, found 401.3.

Step c: To a solution of 5-chloro-2-methoxy-4-[(1S)-4-phenylindan-1-yl]oxy-benzaldehyde (100 mg, 0.26 mmol) in DMF (3 mL) was added L-serine (100 mg, 0.95 mmol) and sodium triacetoxyborohydride (150 mg, 0.71 mmol). The resulting suspension was stirred at room temperature overnight. The reaction mixture was diluted with 2:1 $CHCl_3$/i-PrOH (30 mL), washed with water (15 mL), dried ($MgSO_4$), filtered, and concentrated in vacuo. The crude residue was purified by reverse phase preparative HPLC ($CH_3CN$—$H_2O$ with 0.1% TFA) to obtain (2S)-2-[[5-chloro-2-methoxy-4-[(1S)-4-phenylindan-1-yl]oxy-phenyl]methylamino]-3-hydroxy-propanoic acid as a di-trifluoroacetic acid salt, dr: ~3.5:1. MS: (ES) m/z calculated for $C_{26}H_{26}ClNO_6$ [M+Na]$^+$ 490.1, found 490.3. $^1$H NMR (400 MHz, Methanol-$d_4$) δ 7.48-7.37 (m, 6H), 7.37-7.30 (m, 3H), 7.00 (s, 1H), 6.01 (dd, J=6.4, 4.2 Hz, 1H), 4.33 (d, J=13.1 Hz, 1H), 4.23 (d, J=13.2 Hz, 1H), 4.04-3.98 (m, 2H), 3.96 (s, 3H), 3.93 (t, J=4.2 Hz, 1H), 3.26-3.15 (m, 1H), 2.98 (ddd, J=16.2, 8.2, 5.4 Hz, 1H), 2.59 (ddt, J=13.9, 8.1, 6.0 Hz, 1H), 2.24-2.10 (m, 1H).

Example 26: Synthesis of (2S)-2-[[5-chloro-2-[(5-cyano-3-pyridyl)methoxy]-4-[(1S)-4-(2-fluoro-3-methoxy-phenyl)indan-1-yl]oxy-phenyl]methylamino]-3-hydroxy-propanoic acid

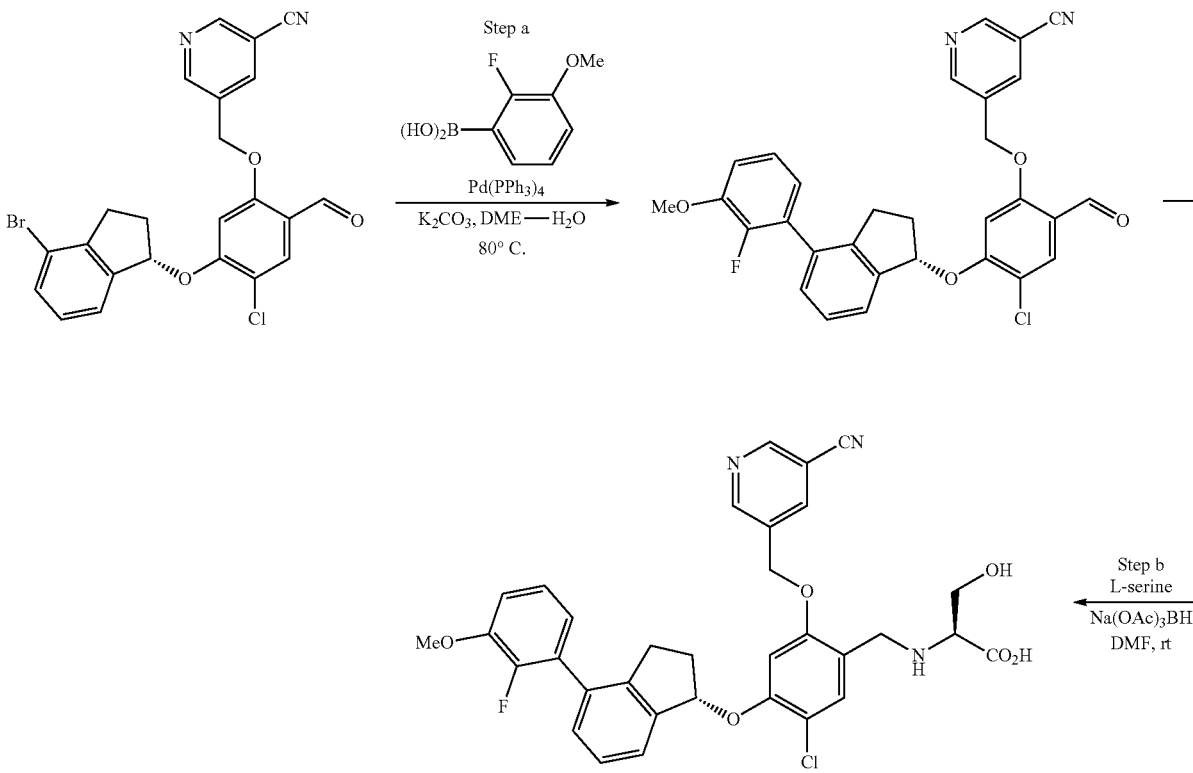

Synthesis of (2S)-2-[[5-chloro-2-[(5-cyano-3-pyridyl)methoxy]-4-[(1S)-4-(2-fluoro-3-methoxy-phenyl)indan-1-yl]oxy-phenyl]methylamino]-3-hydroxy-propanoic acid was performed in an analogous route to Example 24, substituting 2-fluoro-3-methoxyphenylboronic acid for 2-fluorophenylboronic acid in Step a. dr: ~3.5:1. MS: (ES) m/z calculated for $C_{33}H_{29}ClFN_3O_6$ [M+H]$^+$ 618.2, found 618.4. $^1$H NMR (400 MHz, Methanol-d$_4$) δ 8.99 (d, J=2.1 Hz, 1H), 8.92 (d, J=2.1 Hz, 1H), 8.43 (s, 1H), 7.53 (s, 1H), 7.35 (dd, J=19.5, 7.3 Hz, 2H), 7.30 (s, 1H), 7.23-7.04 (m, 3H), 6.89 (t, J=7.1 Hz, 1H), 6.07-5.98 (m, 1H), 5.37 (d, J=2.7 Hz, 2H), 4.38 (d, J=13.1 Hz, 1H), 4.31 (d, J=13.1 Hz, 1H), 4.01 (s, 3H), 3.91 (d, J=0.6 Hz, 2H), 3.07-2.97 (m, 1H), 2.89-2.78 (m, 1H), 2.65-2.53 (m, 1H).

Example 27: Synthesis of (2S)-2-[[5-chloro-2-ethoxy-4-[(1S)-4-(2-fluorophenyl)indan-1-yl]oxy-phenyl]methylamino]-3-hydroxy-propanoic acid

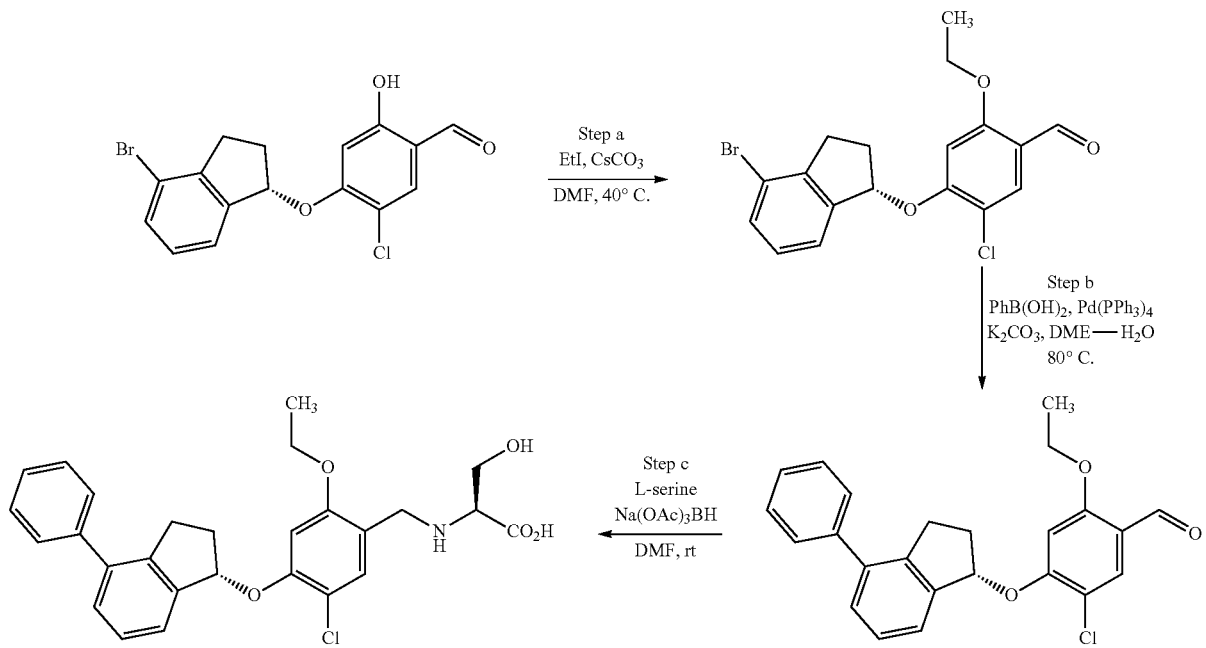

Synthesis of (2S)-2-[[5-chloro-2-ethoxy-4-[(1S)-4-(2-fluorophenyl)indan-1-yl]oxy-phenyl]methylamino]-3-hydroxy-propanoic acid was performed in an analogous route to Example 25, substituting iodoethane for iodomethane in Step a and 2-fluorophenylboronic acid for phenylboronic acid in Step b. dr: ~3.5:1. MS: (ES) m/z calculated for $C_{27}H_{27}ClFNO_5$ [M+Na]$^+$ 522.2, found 522.4. $^1$H NMR (400 MHz, DMSO-d$_6$) δ 7.51-7.39 (m, 4H), 7.36 (t, J=7.5 Hz, 1H), 7.34-7.27 (m, 3H), 7.01 (s, 1H), 6.10-6.02 (m, 1H), 4.14 (q, J=6.9 Hz, 2H), 3.94 (s, 2H), 3.72 (dd, J=11.2, 4.5 Hz, 1H), 3.62 (dd, J=11.2, 6.5 Hz, 1H), 3.31 (r s, 1H), 3.22-3.09 (m, 1H), 3.00-2.83 (m, 1H), 2.83-2.66 (m, 1H), 2.57 (dt, J=13.5, 6.6 Hz, 1H), 2.07-1.93 (m, 1H), 1.37 (t, J=6.9 Hz, 3H).

Example 28: Synthesis of (2S)-2-[[5-chloro-2-(cyclopropylmethoxy)-4-[(1S)-4-(2-fluorophenyl)indan-1-yl]oxy-phenyl]methylamino]-3-hydroxy-propanoic acid

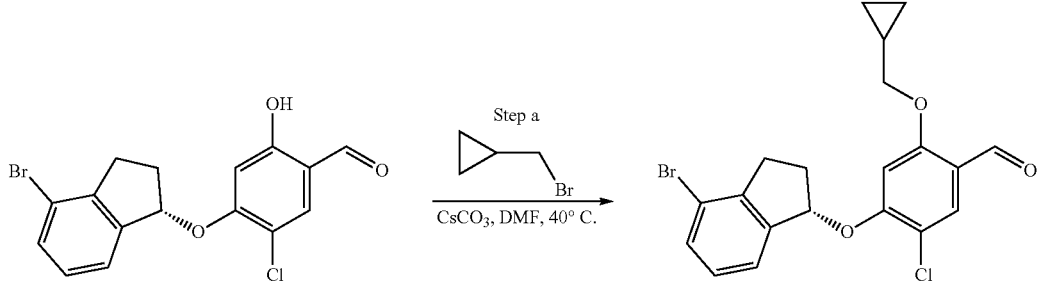

-continued

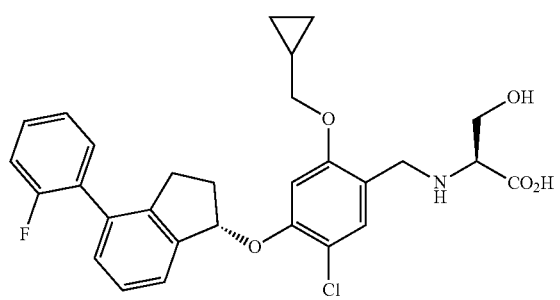

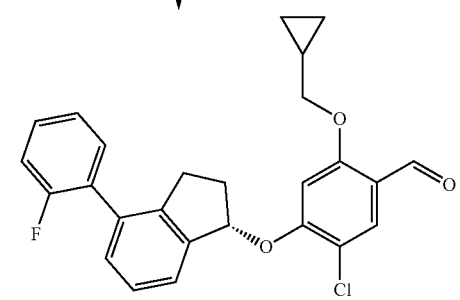

Synthesis of (2S)-2-[[5-chloro-2-(cyclopropylmethoxy)-4-[(1S)-4-(2-fluorophenyl)indan-1-yl]oxy-phenyl]methylamino]-3-hydroxy-propanoic acid was performed in an analogous route to Example 25, substituting cyclopropylmethyl bromide for iodomethane in Step a and 2-fluorophenylboronic acid for phenylboronic acid in Step b. dr: ~3.5:1. MS: (ES) m/z calculated for $C_{29}H_{29}ClFNO_5$ [M+Na]$^+$ 548.2, found 548.4. $^1$H NMR (400 MHz, Methanol-d$_4$) δ 7.45 (s, 1H), 7.44-7.37 (m, 2H), 7.37-7.32 (m, 1H), 7.32-7.25 (m, 2H), 7.21 (dd, J=17.8, 8.2 Hz, 2H), 6.96 (d, J=14.8 Hz, 1H), 6.06-5.94 (m, 1H), 4.36 (d, J=13.9 Hz, 1H), 4.31-4.25 (m, 1H), 4.08-3.88 (m, 4H), 3.08-2.99 (m, 1H), 2.87-2.75 (m, 1H), 2.67-2.50 (m, 2H), 2.24-2.11 (m, 1H), 1.39-1.26 (m, 1H), 0.75-0.60 (m, 2H), 0.45-0.40 (m, 2H).

Example 29: Synthesis of (2S)-2-[[5-chloro-4-[(1S)-4-(2-fluoro-3-methoxy-phenyl)indan-1-yl]oxy-2-methoxy-phenyl]methylamino]-3-hydroxy-propanoic acid

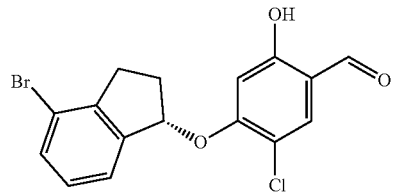

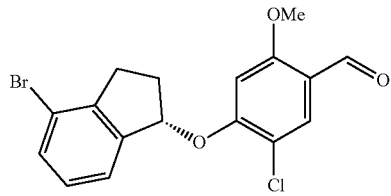

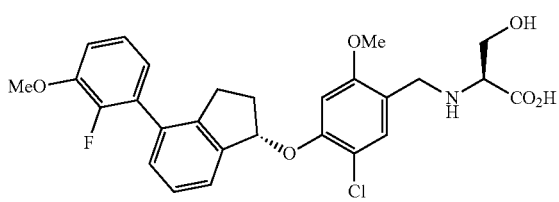

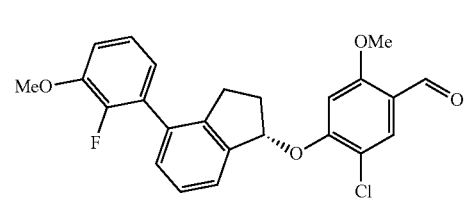

Synthesis of (2S)-2-[[5-chloro-4-[(1S)-4-(2-fluoro-3-methoxy-phenyl)indan-1-yl]oxy-2-methoxy-phenyl]methylamino]-3-hydroxy-propanoic acid was performed in an analogous route to Example 25, substituting 2-fluoro-3-methoxyphenylboronic acid for phenylboronic acid in Step b. dr: ~3.5:1. MS: (ES) m/z calculated for $C_{27}H_{27}ClFNO_6$ [M+H]$^+$ 516.2, found 516.4. $^1$H NMR (400 MHz, Methanol-$d_4$) δ 7.44 (s, 1H), 7.43 (d, J=6.9 Hz, 1H), 7.35-7.26 (m, 2H), 7.20-7.15 (m, 1H), 7.12 (td, J=8.0, 1.9 Hz, 1H), 6.98 (s, 1H), 6.89 (ddd, J=8.0, 6.3, 1.9 Hz, 1H), 6.03 (dd, J=6.5, 4.3 Hz, 1H), 4.33 (d, J=13.1 Hz, 1H), 4.23 (d, J=13.1 Hz, 1H), 4.06-3.98 (m, 2H), 3.96 (s, 3H), 3.91 (s, 3H), 3.90 (d, J=4.2 Hz, 1H), 3.09-2.97 (m, 1H), 2.89-2.77 (m, 1H), 2.61 (dq, J=13.7, 6.3 Hz, 1H), 2.17 (ddt, J=13.3, 9.1, 5.0 Hz, 1H).

Example 30: Synthesis of (2S)-2-[[5-chloro-4-[(1S)-4-(2-chloro-3-methoxy-phenyl)indan-1-yl]oxy-2-[(5-cyano-3-pyridyl)methoxy]phenyl]methylamino]-3-hydroxy-propanoic acid

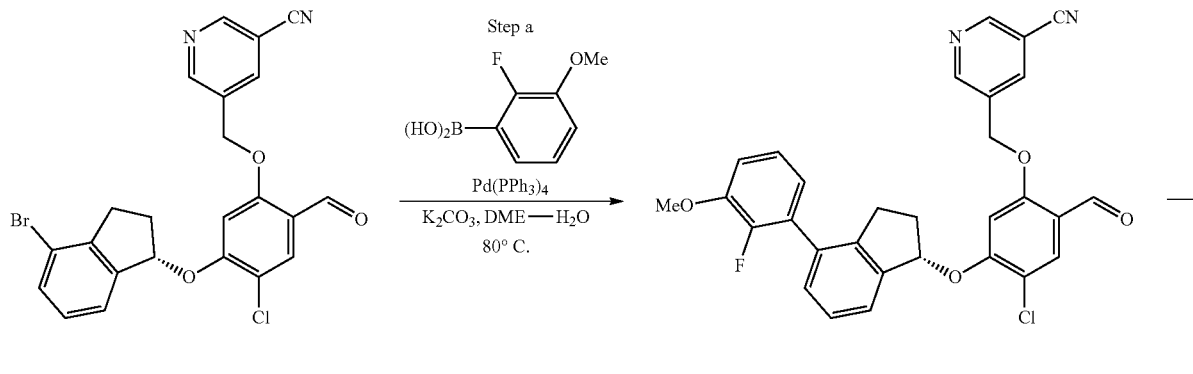

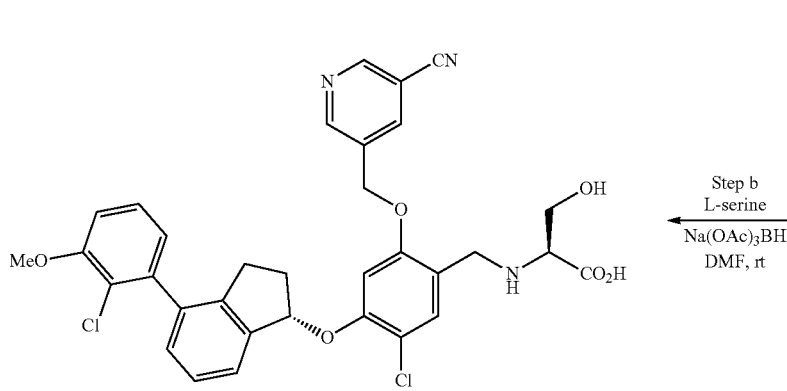

Synthesis of (2S)-2-[[5-chloro-4-[(1S)-4-(2-chloro-3-methoxy-phenyl)indan-1-yl]oxy-2-[(5-cyano-3-pyridyl)methoxy]phenyl]methylamino]-3-hydroxy-propanoic acid was performed in an analogous route to Example 24, substituting 2-chloro-3-methoxyphenylboronic acid for 2-fluorophenylboronic acid in Step a. dr: ~3.5:1. MS: (ES) m/z calculated for $C_{33}H_{29}Cl_2N_3O_6$ [M+H]$^+$ 634.2, found 634.4. $^1$H NMR (400 MHz, Methanol-$d_4$) δ 8.99 (s, 1H), 8.92 (d, J=2.0 Hz, 1H), 8.43 (s, 1H), 7.53 (s, 1H), 7.40-7.27 (m, 2H), 7.18 (d, J=7.4 Hz, 1H), 7.15-7.07 (dd, J=8.3, 1.4 Hz, 3H), 6.89 (s, 1H), 6.02 (d, J=14.3 Hz, 1H), 5.38 (s, 2H), 4.38 (d, J=13.2 Hz, 1H), 4.35-4.24 (m, 1H), 4.01 (d, J=0.9 Hz, 3H), 3.93 (s, 3H), 3.06-2.90 m, 2H), 2.90-2.76 (m, 1H), 2.68-2.49 (m, 2H), 2.19-2.02 (m, 1H).

Example 31: Synthesis of (2S)-2-[[5-chloro-2-[(5-cyano-3-pyridyl)methoxy]-4-[(1S)-4-(5-fluoro-2,3-dihydro-1,4-benzodioxin-6-yl)indan-1-yl]oxy-phenyl]methylamino]-3-hydroxy-propanoic acid
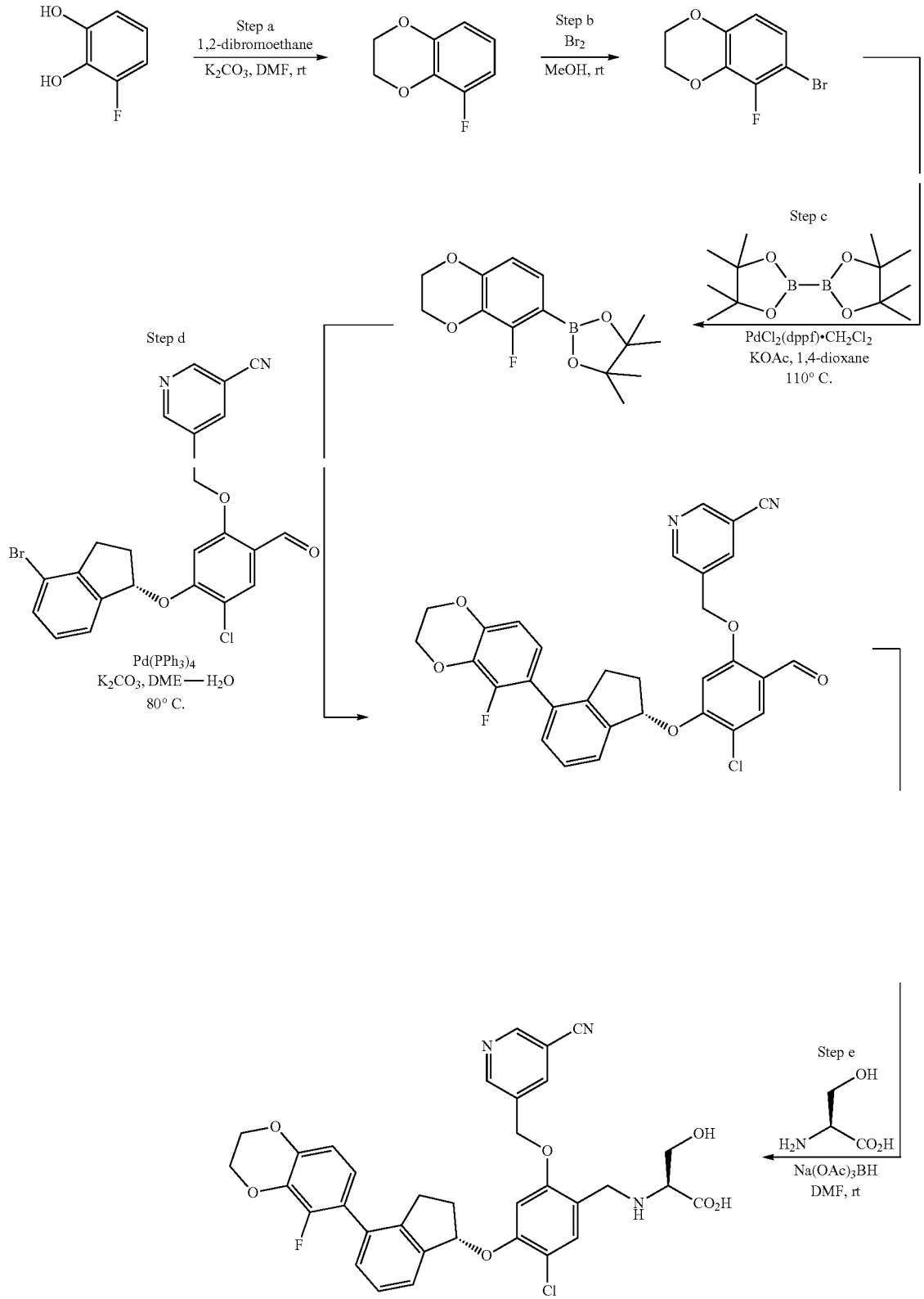

Step a: To a solution of 3-fluorocatechol (5.30 g, 41.2 mmol) and $K_2CO_3$ (17.1 g, 124 mmol) in DMF (50 mL) was added 1,2-dibromoethane (3.90 mL, 45.3 mmol) and the mixture was left to stir at room temperature for 4 days. Water (50 mL) was added and the mixture was extracted with EtOAc (3×50 mL). The combined organic layers were dried ($MgSO_4$), filtered, and concentrated in vacuo. The crude product was purified by flash chromatography ($SiO_2$, 20% EtOAc in hexanes) to obtain 5-fluoro-2,3-dihydro-1,4-benzodioxine. $^1$H NMR (400 MHz, Chloroform-d) δ 6.78-6.71 (m, 1H), 6.71-6.64 (m, 2H), 4.40-4.24 (m, 4H).

Step b: To a cooled (0° C.) solution of 5-fluoro-2,3-dihydro-1,4-benzodioxine (1.0 g, 6.5 mmol) in methanol (25 mL) was added bromine (1.2 g, 0.40 mL, 7.8 mmol), and the resulting mixture was allowed to warm to room temperature. After stirring for 24 h, saturated aqueous sodium metabisulfite (100 mL) was added and the solution was extracted with dichloromethane (3×25 mL). The combined organic layers were dried ($MgSO_4$), filtered, and concentrated in vacuo. The crude product was purified by flash chromatography ($SiO_2$, 20% EtOAc in hexanes) to obtain 6-bromo-5-fluoro-2,3-dihydro-1,4-benzodioxine. $^1$H NMR (400 MHz, Chloroform-d) δ 6.96 (ddt, J=9.0, 7.0, 0.5 Hz, 1H), 6.59 (ddt, J=9.0, 2.1, 0.5 Hz, 1H), 4.34-4.25 (m, 4H).

Step c: To a solution of 6-bromo-5-fluoro-2,3-dihydro-1,4-benzodioxine (705 mg, 3.02 mmol), bis(pinacolato)diboron (1.53 g, 6.04 mmol), and potassium acetate (890 mg, 9.06 mmol) in 1,4-dioxane (15 mL) was added [1,1'-bis(diphenylphosphino)ferrocene]dichloropalladium(II) complex with dichloromethane (244 mg, 0.299 mmol). The mixture was heated at 100° C. and stirred for 3 h. After cooling to room temperature, water (30 mL) was added and the reaction mixture was extracted with EtOAc (3×25 mL). The combined organic layers were dried ($MgSO_4$), filtered, and concentrated in vacuo. The crude product was purified by flash chromatography ($SiO_2$, 10% EtOAc in hexanes) to obtain 2-(5-fluoro-2,3-dihydro-1,4-benzodioxin-6-yl)-4,4,5,5-tetramethyl-1,3,2-dioxaborolane. $^1$H NMR (400 MHz, Methanol-$d_4$) δ 7.19-7.02 (m, 1H), 6.63 (ddd, J=8.4, 1.5, 0.6 Hz, 1H), 4.36-4.22 (m, 4H), 1.32 (d, J=0.6 Hz, 12H).

Step d: To a solution of 5-[[5-[(1S)-4-bromoindan-1-yl]oxy-4-chloro-2-formyl-phenoxy]methyl]pyridine-3-carbonitrile (100 mg, 0.20 mmol) in 1,2-dimethoxyethane (4 mL) and aqueous 2M $K_2CO_3$ (0.40 mL, 0.80 mmol) was added 2-(5-fluoro-2,3-dihydro-1,4-benzodioxin-6-yl)-4,4,5,5-tetramethyl-1,3,2-dioxaborolane (120 mg, 0.41 mmol) and the resulting mixture was bubbled with nitrogen gas for a few minutes. Tetrakis(triphenylphosphine)palladium(0) (25 mg, 0.020 mmol) was then added and the reaction mixture was stirred at 80° C. of or 1 h. After cooling to room temperature, the reaction mixture was diluted with EtOAc (30 mL) and washed with water (20 mL). The organic layer was dried ($MgSO_4$), filtered, and concentrated in vacuo. The crude product was purified by flash chromatography ($SiO_2$, 30% EtOAc in hexanes) to obtain 5-[[4-chloro-5-[(1S)-4-(5-fluoro-2,3-dihydro-1,4-benzodioxin-6-yl)indan-1-yl]oxy-2-formyl-phenoxy]methyl]pyridine-3-carbonitrile. MS: (ES) m/z calculated for $C_{31}H_{22}ClFN_2O_5$ [M+H]$^+$ 557.1, found 557.4.

Step e: To a solution of 5-[[4-chloro-5-[(1S)-4-(5-fluoro-2,3-dihydro-1,4-benzodioxin-6-yl)indan-1-yl]oxy-2-formyl-phenoxy]methyl]pyridine-3-carbonitrile (47 mg, 0.084 mmol) in DMF (3 mL) was added L-serine (70 mg, 0.67 mmol) and sodium triacetoxyborohydride (90 mg, 0.42 mmol). The resulting suspension was stirred at room temperature overnight. The reaction mixture was diluted with 2:1 $CHCl_3$/i-PrOH (30 mL), washed with water (15 mL), dried ($MgSO_4$), and concentrated in vacuo. The crude residue was purified by reverse phase preparative HPLC ($CH_3CN$—$H_2O$ with 0.1% TFA) to obtain (2S)-2-[[5-chloro-2-[(5-cyano-3-pyridyl)methoxy]-4-[(1S)-4-(5-fluoro-2,3-dihydro-1,4-benzodioxin-6-yl)indan-1-yl]oxy-phenyl]methylamino]-3-hydroxy-propanoic acid as a di-trifluoroacetic acid salt, dr: ~3.5:1. MS: (ES) m/z calculated for $C_{34}H_{29}ClFN_3O_7$ [M+H]$^+$ 646.2, found 646.4. $^1$H NMR (400 MHz, Methanol-$d_4$) δ 8.99 (s, 1H), 8.92 (d, J=2.0 Hz, 1H), 8.43 (s, 1H), 7.53 (s, 1H), 7.39-7.18 (m, 2H), 7.09 (s, 1H), 6.84-6.69 (m, 3H), 6.05-5.98 (m, 1H), 5.37 (s, 2H), 4.38 (d, J=13.1 Hz, 1H), 4.35-4.27 (m, 4H), 4.01 (s, 4H), 3.07-2.90 (m, 1H), 2.90-2.69 (m, 1H), 2.65-2.43 (m, 1H), 2.25-1.97 (m, 1H).

Example 32: Synthesis of (2S,3R)-2-[[5-chloro-2-[(5-cyano-3-pyridyl)methoxy]-4-[(1S)-4-(2-fluorophenyl)indan-1-yl]oxy-phenyl]methylamino]-3-hydroxy-butanoic acid

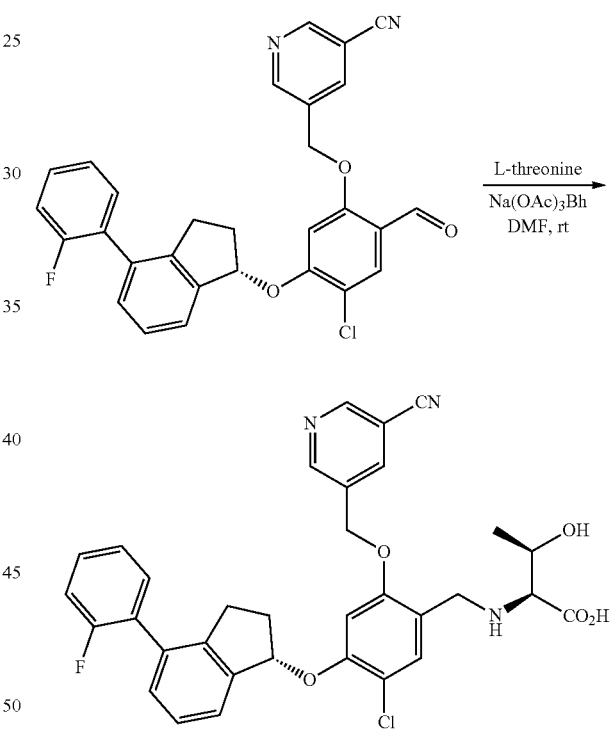

Synthesis of (2S,3R)-2-[[5-chloro-2-[(5-cyano-3-pyridyl)methoxy]-4-[(1S)-4-(2-fluorophenyl)indan-1-yl]oxy-phenyl]methylamino]-3-hydroxy-butanoic acid was performed in an analogous route to Example 24, substituting L-threonine for L-serine in Step b. dr: ~3.5:1. MS: (ES) m/z calculated for $C_{33}H_{29}ClFN_3O_5$ [M+H]$^+$ 602.2, found 602.5. $^1$H NMR (400 MHz, Methanol-$d_4$) δ 8.99 (s, 1H), 8.93 (s, 1H), 8.43 (t, J=2.0 Hz, 1H), 7.52 (s, 1H), 7.44-7.32 (m, 3H), 7.32-7.25 (m, 2H), 7.24-7.17 (m, 2H), 7.09 (s, 1H), 6.03 (dd, J=6.5, 4.3 Hz, 1H), 5.38 (s, 2H), 4.38 (d, J=13.2 Hz, 1H), 4.28 (d, J=13.2 Hz, 1H), 4.06 (q, J=6.4 Hz, 1H), 3.59 (d, J=7.1 Hz, 1H), 3.09-2.96 (m, 1H), 2.89-2.74 (m, 1H), 2.57 (dq, J=13.5, 6.3 Hz, 1H), 2.14 (ddd, J=13.4, 8.6, 4.4 Hz, 1H), 1.32 (d, J=6.3 Hz, 3H).

Example 33: Synthesis of (2S)-2-[[5-chloro-2-(5-cyano-3-pyridyl)-4-[(1S)-4-(2-fluorophenyl)indan-1-yl]oxy-phenyl]methylamino]-3-hydroxy-propanoic acid

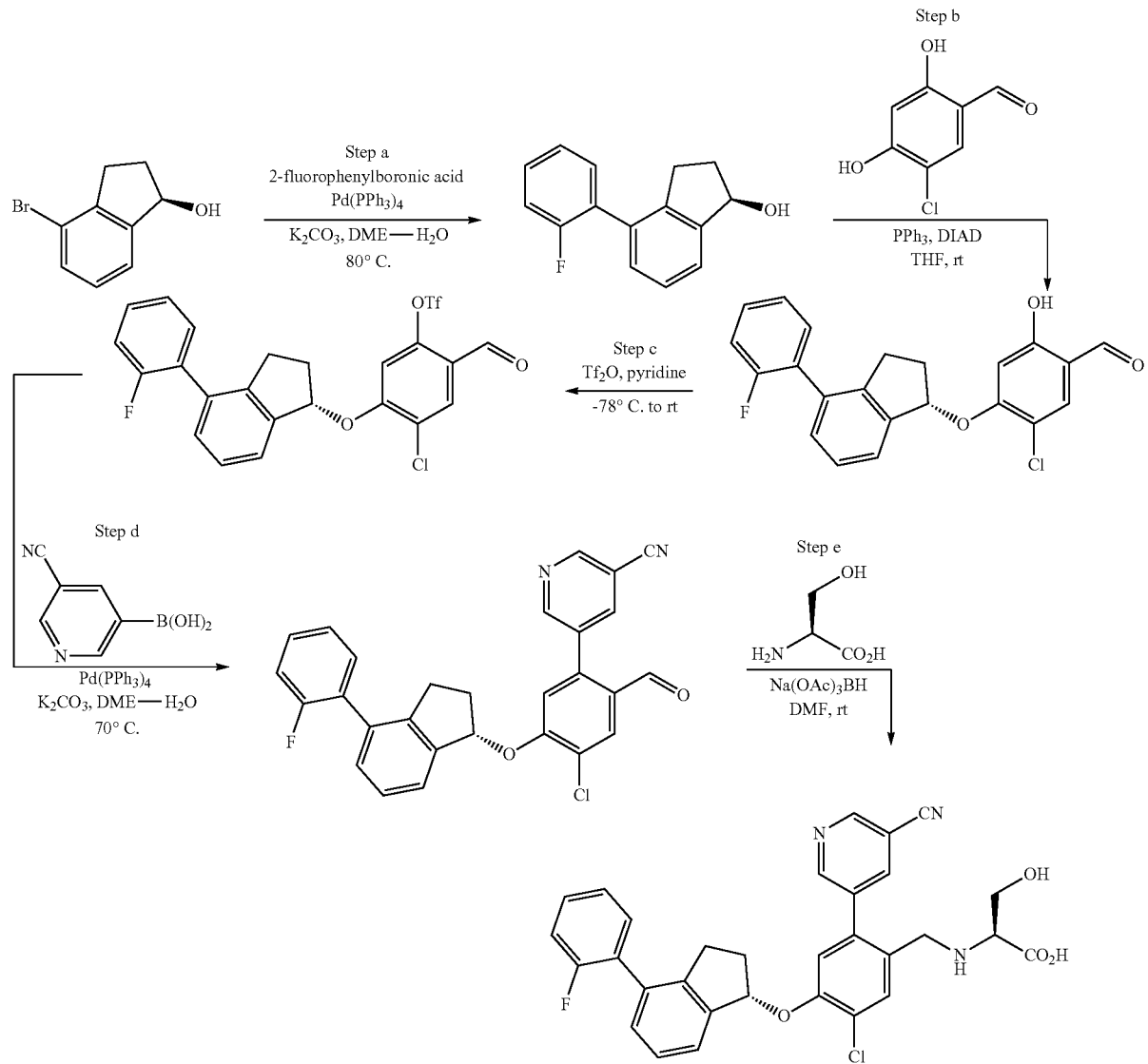

Step a: To a solution of (R)-4-bromoindan-1-ol (5.0 g, 24 mmol) in 1,2-dimethoxyethane (50 mL) and water (30 mL) was added 2-fluorophenylboronic acid (4.3, 31 mmol) and K$_2$CO$_3$ (8.1 g, 59 mmol) and the resulting mixture was bubbled with nitrogen gas for a few minutes. Tetrakis (triphenylphosphine)palladium(O) (0.81 g, 0.71 mmol) was added, and the reaction mixture was stirred at 80° C. overnight. After cooling to room temperature, the reaction mixture was diluted with EtOAc (50 mL) and washed with water (30 mL) and brine (30 mL). The organic layer was dried (Na$_2$SO$_4$), filtered, and concentrated in vacuo. The crude product was purified by flash chromatography (SiO$_2$, 30% EtOAc in hexanes) to obtain (1R)-4-(2-fluorophenyl) indan-1-ol. MS: (ES) m/z calculated for C$_{15}$H$_{13}$FO [M-OH]$^+$ 211.1, found 211.2.

Step b: To a cooled (0° C.) solution of (R)-4-(2-fluorophenyl)indan-1-ol (5.4 g, 24 mmol), 5-chloro-2,4-dihydroxy-benzaldehyde (4.1 g, 24 mmol), and triphenylphosphine (6.2 g, 24 mmol) in THF (100 mL) was slowly added diisopropyl azodicarboxylate (4.8 g, 24 mmol) in THF (10 mL). The mixture was allowed to gradually warm to room temperature for two days. The volatiles were removed in vacuo and the resulting crude residue was purified by flash chromatography (20% EtOAc in hexane) to afford 5-chloro-4-[(1S)-4-(2-fluorophenyl)indan-1-yl]oxy-2-hydroxy-benzaldehyde. Approximately 22% of racemization was observed during the reaction and the enantiomeric ratio of the obtained product was ~3.5:1. MS: (ES) m/z calculated for C$_{22}$H$_{16}$ClFO$_3$ [M+H]$^+$ 383.1, found 383.3.

Step c: To a cooled (-78° C.) solution of 5-chloro-4-[(1S)-4-(2-fluorophenyl)indan-1-yl]oxy-2-hydroxy-benzaldehyde (1.0 g, 2.6 mmol) in dichloromethane (10 mL) was sequentially added pyridine (1.0 mL, 12 mmol) and triflic anhydride (0.87 mL, 5.2 mmol). The reaction mixture was allowed to warm to room temperature. After 2 h, the reaction was quenched by the careful addition of few milliliters of saturated aqueous NaHCO$_3$. The mixture was diluted with water (30 mL) and extracted with dichloromethane (3×20 mL). The combined organic layers were dried (MgSO$_4$), filtered, and concentrated in vacuo. The crude product was purified by flash chromatography (SiO$_2$, 20% EtOAc in hexanes) to obtain [4-chloro-5-[(1S)-4-(2-fluorophenyl)indan-1-yl]oxy-2-formyl-phenyl] trifluoromethanesulfonate. MS: (ES) m/z calculated for C$_{23}$H$_{15}$ClF$_4$O$_5$S [M+Na]$^+$ 537.0, found 537.2.

Step d: To a solution of [4-chloro-5-[(1S)-4-(2-fluorophenyl)indan-1-yl]oxy-2-formyl-phenyl] trifluoromethanesulfonate (100 mg, 0.19 mmol) in 1,2-dimethoxyethane (3 mL) and 2M K$_2$CO$_3$ (0.30 mL, 0.60 mmol) was added 5-cyanopyridine-3-boronic acid (35 mg, 0.23 mmol), and the resulting mixture was bubbled with nitrogen gas for a few minutes. Tetrakis(triphenylphosphine)palladium(0) (44 mg, 0.038 mmol) was added, and the reaction mixture was stirred at 70° C. overnight. After cooling to room temperature, the reaction mixture was diluted with dichloromethane (20 mL) and washed with water (20 mL). The organic layer was dried (MgSO$_4$), filtered, and concentrated in vacuo. The crude product was purified by flash chromatography (SiO$_2$, 30% EtOAc in hexanes) to obtain (5-[4-chloro-5-[(1S)-4-(2-fluorophenyl)indan-1-yl]oxy-2-formyl-phenyl]pyridine-3-carbonitrile. MS: (ES) m/z calculated for C$_{28}$H$_{18}$ClFN$_2$O$_2$ [M+H]$^+$ 469.1, found 469.4.

Step e: To a solution of (5-[4-chloro-5-[(1S)-4-(2-fluorophenyl)indan-1-yl]oxy-2-formyl-phenyl]pyridine-3-carbonitrile (30 mg, 0.064 mmol) in DMF (2 mL) was added L-serine (60 mg, 0.57 mmol) and sodium triacetoxyborohydride (60 mg, 0.28 mmol). The resulting suspension was stirred at room temperature overnight. The reaction mixture was diluted with 2:1 CHCl$_3$/i-PrOH (30 mL), washed with water (15 mL), dried (MgSO$_4$), filtered, and concentrated in vacuo. The crude residue was purified by reverse phase preparative HPLC (CH$_3$CN—H$_2$O with 0.1% TFA) to obtain ((2S)-2-[[5-chloro-2-(5-cyano-3-pyridyl)-4-[(1S)-4-(2-fluorophenyl)indan-1-yl]oxy-phenyl]methylamino]-3-hydroxy-propanoic acid as a di-trifluoroacetic acid salt. dr: ~3.5:1. MS: (ES) m/z calculated for C$_{31}$H$_{25}$ClFN$_3$O$_4$ [M+H]$^+$ 558.2, found 558.4. $^1$H NMR (400 MHz, Methanol-d$_4$) δ 8.99 (s, 1H), 8.88 (s, 1H), 8.37 (s, 1H), 7.87 (s, 1H), 7.54-7.11 (m, 8H), 6.05 (s, 1H), 4.23 (s, 2H), 4.03-3.84 (m, 3H), 3.07-2.92 (m, 1H), 2.90-2.76 (m, 1H), 2.67-2.49 (m, 1H), 2.23-2.08 (m, 1H).

Example 34: Synthesis of (2S,3R)-2-[[5-chloro-2-[(5-cyano-3-pyridyl)methoxy]-4-[(1R)-4-(2-fluorophenyl)indan-1-yl]oxy-phenyl]methylamino]-3-hydroxy-butanoic acid

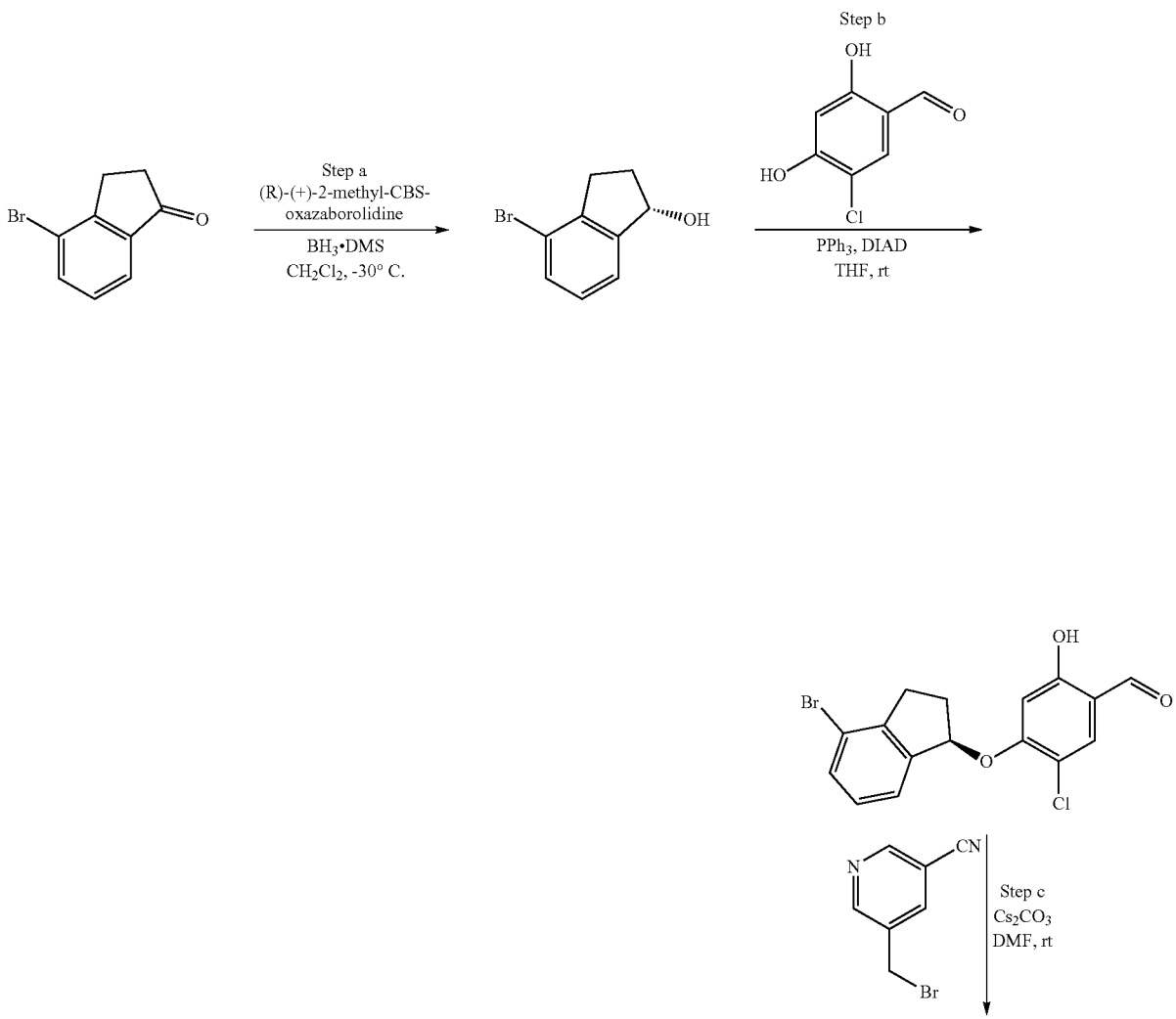

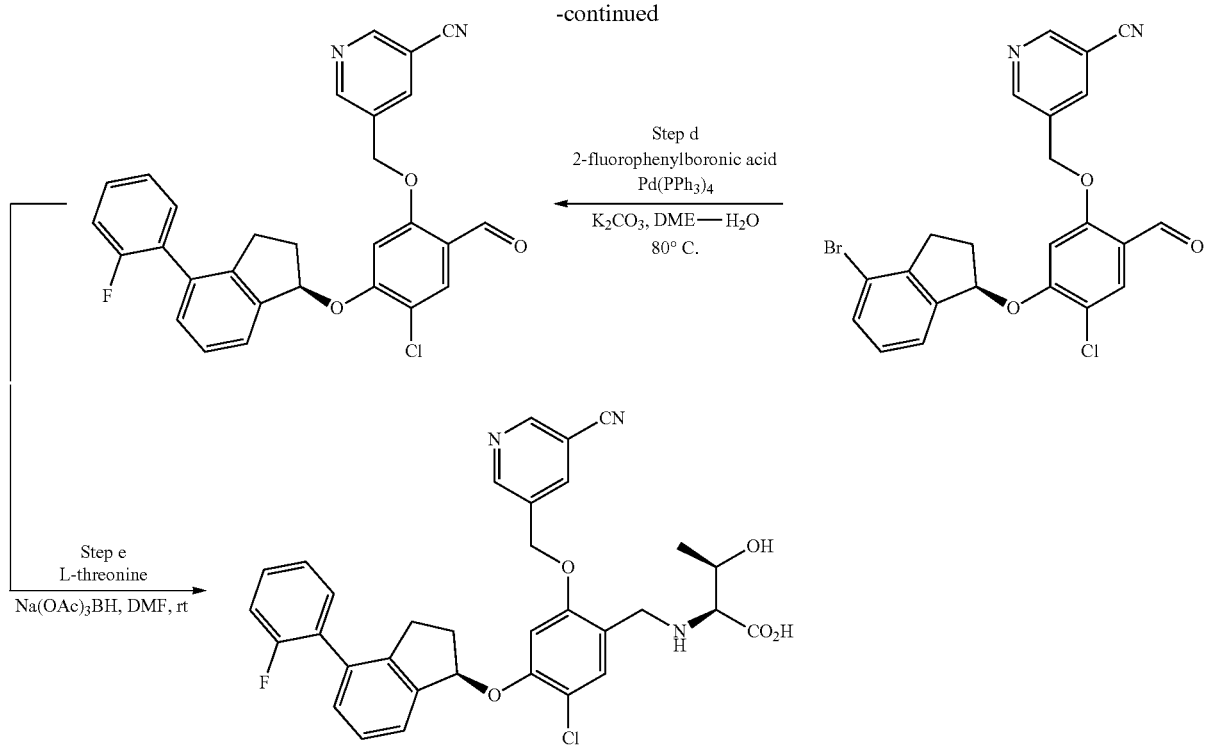

Step a: To a 1-L three-neck round bottom flask equipped with an internal thermometer under nitrogen was added (R)-(+)-2-methyl-CBS-oxazaborolidine (3.2 mL, 3.2 mmol, 1M THF) and borane-dimethyl sulfide (1.6 mL, 3.2 mmol, 2M THF) at room temperature. The mixture was stirred for 10 min then diluted with dichloromethane (100 mL). Borane-dimethyl sulfide (60 mL, 120 mmol, 2M THF) was added at room temperature and the mixture was cooled to −30° C. A solution of 4-bromoindan-1-one (5.0 g, 23.6 mmol) in dichloromethane (50 mL) was added slowly over 25 min while maintaining the internal temperature between −30° C. and −20° C. After 1 h, the reaction was quenched carefully by the dropwise addition of methanol (50 mL). The solvent was removed in vacuo and the crude solid was purified by flash chromatography (15% EtOAc in hexane). The resulting purified solid was recrystallized from 1:5 EtOAc/hexane (100 mL) to give the product with 98.2% ee. Enantiomeric excess was determined by integration of peaks that were separated on a RegisCell 250×4.6 mm column at a flow rate of 1.2 mL/min and an isochratic mobile phase of 5% isopropanol in hexane. MS: (ES) m/z calculated for $C_9H_9BrO$ [M—OH+H]$^+$ 197.0, found 197.2. Chiral HPLC: (S)-4-bromoindan-1-ol was eluted using 5% IPA in hexane: $t_R$=6.62 min.

Step b: To a cooled (0° C.) solution of (S)-4-bromoindan-1-ol (1.7 g, 7.9 mmol), 5-chloro-2,4-dihydroxy-benzaldehyde (1.3 g, 7.9 mmol), and triphenylphosphine (2.1 g, 7.9 mmol) in THF (25 mL) was slowly added diisopropyl azodicarboxylate (1.7 mL, 8.7 mmol) in THF (5 mL). The mixture was allowed to gradually warm to room temperature for three days. The volatiles were removed in vacuo and the resulting crude residue was purified by flash chromatography (20% EtOAc in hexane) to afford 4-[(1R)-4-bromoindan-1-yl]oxy-5-chloro-2-hydroxy-benzaldehyde. Approximately 17% of racemization was observed during the reaction and the enantiomeric ratio of the obtained product was ~5:1. MS: (ES) m/z calculated for $C_{16}H_{12}BrClO_3$ [M−H]$^−$ 365.0, found 365.1.

Step c: To a solution of 4-[(1R)-4-bromoindan-1-yl]oxy-5-chloro-2-hydroxy-benzaldehyde (0.84 g, 2.29 mmol) in DMF (12 mL) was added 5-(bromomethyl)nicotinonitrile (0.54 g, 2.75 mmol), followed by $Cs_2CO_3$ (1.5 g, 4.58 mmol). After stirring at room temperature overnight, the reaction mixture was diluted with 2:1 $CHCl_3$/i-PrOH (30 mL) and washed with water (20 mL). The aqueous layer was re-extracted with 2:1 $CHCl_3$/i-PrOH (2×15 mL). The combined organic layers were dried ($MgSO_4$), filtered, and concentrated in vacuo. The crude was suspended in 1:1 $CH_2Cl_2$/hexanes (10 mL) and filtered to obtain 5-[[5-[(1R)-4-bromoindan-1-yl]oxy-4-chloro-2-formyl-phenoxy]methyl]pyridine-3-carbonitrile. MS: (ES) m/z calculated for $C_{23}H_{16}BrCN_2O_3$ [M+H]$^+$ 483.0, found 483.2.

Step d: To a solution of 5-[[5-[(1R)-4-bromoindan-1-yl]oxy-4-chloro-2-formyl-phenoxy]methyl]pyridine-3-carbonitrile (282 mg, 0.58 mmol) in 1,2-dimethoxyethane (4 mL) was added 2-fluorophenylboronic acid (122 mg, 0.87 mmol), aqueous 2M $K_2CO_3$ (1.30 mL, 2.58 mmol) and the resulting mixture was bubbled with nitrogen gas for a few minutes. Tetrakis(triphenylphosphine)palladium(0) (100 mg, 0.086 mmol) was then added and the reaction mixture was stirred at 80° C. overnight. After cooling to room temperature, the reaction mixture was diluted with EtOAc (30 mL) and washed with water (30 mL) and brine (30 mL). The organic layer was dried ($Na_2SO_4$), filtered, and concentrated in vacuo. The crude product was purified by flash chromatography ($SiO_2$, 30% EtOAc in hexanes) to obtain 5-[[4-chloro-5-[(1R)-4-(2-fluorophenyl)indan-1-yl]oxy-2-formyl-phenoxy]methyl]pyridine-3-carbonitrile. MS: (ES) m/z calculated for $C_{29}H_{20}ClFN_2O_3$ [M+H]$^+$ 499.1, found 499.1.

Step e: To a solution of 5-[[4-chloro-2-formyl-5-[(1R)-4-phenylindan-1-yl]oxy-phenoxy]methyl]pyridine-3-carbonitrile (31 mg, 0.062 mmol) in DMF (2 mL) was added L-threonine (50 mg, 0.42 mmol) and sodium triacetoxyborohydride (100 mg, 0.47 mmol). After stirring at room temperature overnight, the reaction mixture was concentrated and the crude residue was purified by reverse phase preparative HPLC (CH$_3$CN—H$_2$O with 0.1% TFA). The fractions were combined and diluted with 2:1 CHCl$_3$/i-PrOH (30 mL). The organic layer was washed with saturated aqueous NaHCO$_3$ (15 mL), dried (MgSO$_4$), filtered, and concentrated in vacuo to obtain (2S,3R)-2-[[5-chloro-2-[(5-cyano-3-pyridyl)methoxy]-4-[(1R)-4-(2-fluorophenyl)indan-1-yl]oxy-phenyl]methylamino]-3-hydroxy-butanoic acid, dr: ~5:1. MS: (ES) m/z calculated for C$_{33}$H$_{29}$ClFN$_3$O$_5$ [M+H]$^+$ 602.2, found 602.5. $^1$H NMR (400 MHz, Methanol-d$_4$) 9.00 (s, 1H), 8.91 (s, 1H), 8.46 (t, J=1.9 Hz, 1H), 7.50-7.44 (m, 1H), 7.44-7.33 (m, 3H), 7.33-7.29 (m, 2H), 7.29-7.16 (m, 2H), 7.06 (s, 1H), 6.00 (dd, J=6.3, 4.4 Hz, 1H), 5.47-5.26 (m, 2H), 4.35-4.05 (m, 1H), 3.99-3.88 (m, 1H), 3.18 (d, J=6.7 Hz, 1H), 3.02 (ddd, J=16.3, 8.3, 5.5 Hz, 1H), 2.82 (ddd, J=16.3, 8.2, 5.6 Hz, 1H), 2.63-2.46 (m, 1H), 2.13 (ddt, J=13.3, 8.6, 5.3 Hz, 1H), 1.29 (d, J=8.2 Hz, 3H).

Example 35: Synthesis of (2S,3R)-2-[[5-chloro-2-[(5-cyano-3-pyridyl)methoxy]-4-[(1S)-4-(2-fluorophenyl)indan-1-yl]oxy-phenyl]methylamino]-3-hydroxy-butanamide

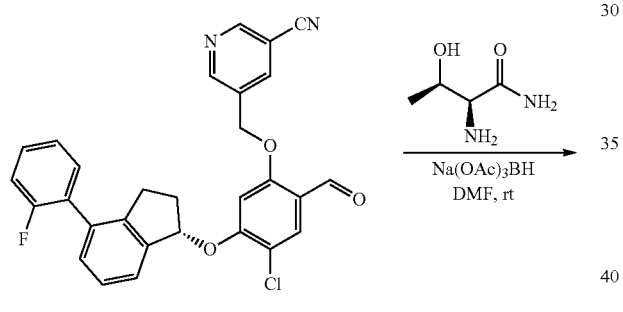

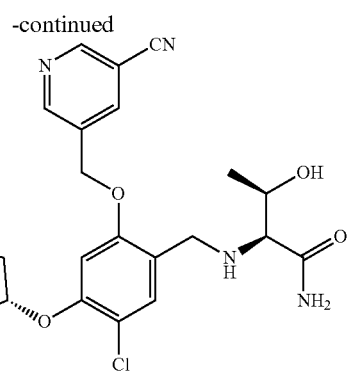

Synthesis of (2S,3R)-2-[[5-chloro-2-[(5-cyano-3-pyridyl)methoxy]-4-[(1S)-4-(2-fluorophenyl)indan-1-yl]oxy-phenyl]methylamino]-3-hydroxy-butanamide was performed in an analogous route to Example 24, substituting (2S,3R)-2-amino-3-hydroxybutanamide hydrochloride for L-serine in Step b. dr: ~3.5:1. MS: (ES) m/z calculated for C$_{33}$H$_{30}$ClFN$_4$O$_4$ [M+H]$^+$ 601.2, found 601.2. $^1$H NMR (400 MHz, Methanol-d$_4$) δ 8.96 (d, J=2.0 Hz, 1H), 8.90 (d, J=2.0 Hz, 1H), 8.38 (dd, J=2.4, 1.8 Hz, 1H), 7.44-7.32 (m, 4H), 7.32-7.25 (m, 3H), 7.25-7.16 (m, 1H), 6.96 (s, 1H), 6.01-5.85 (m, 1H), 5.29 (d, J=2.4 Hz, 2H), 3.80 (d J=13.5 Hz, 1H), 3.77 (t, J=6.4 Hz, 1H), 3.69 (d, J=13.4 Hz, 1H), 3.10-2.97 (m, 1H), 2.95 (d, J=6.7 Hz, 1H), 2.88-2.73 (m, 1H), 2.51 (m, 1H), 2.15 (m, 1H), 1.17 (d, J=6.4 Hz, 3H).

Example 36: Synthesis of (2S)-2-[[5-chloro-4-[(1S)-4-(5-chloro-2,3-dihydro-1,4-benzodioxin-6-yl)indan-1-yl]oxy-2-[(5-cyano-3-pyridyl)methoxy]phenyl]methylamino]-3-hydroxy-propanoic acid

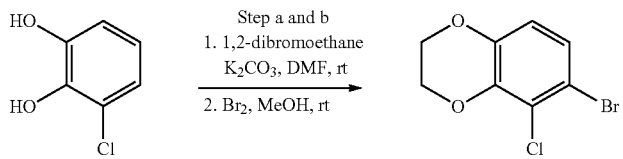

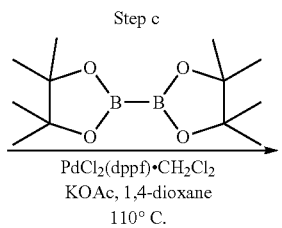

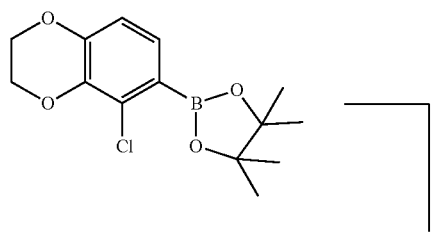

-continued
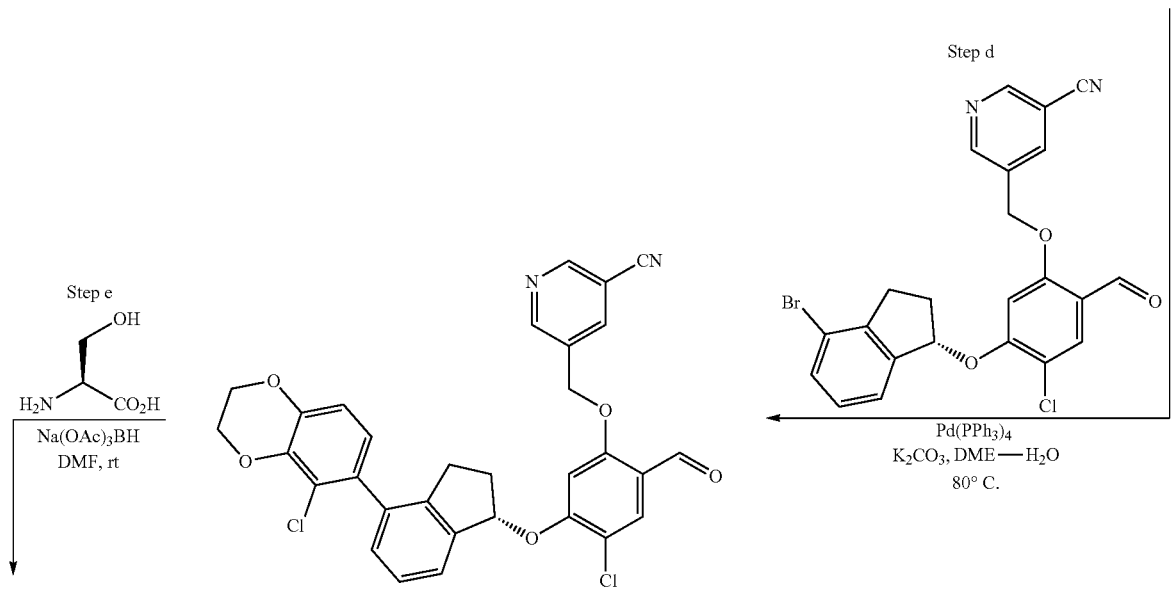
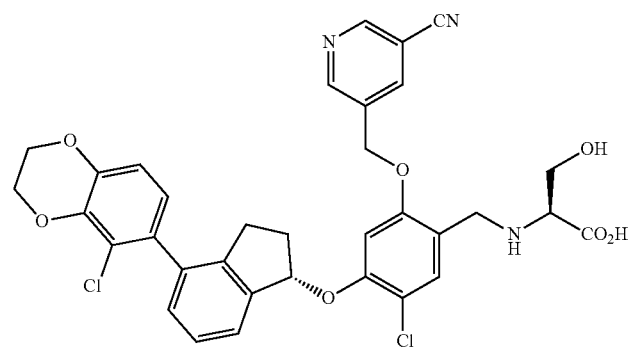

Synthesis of (2S)-2-[[5-chloro-4-[(1S)-4-(5-chloro-2,3-dihydro-1,4-benzodioxin-6-yl)indan-1-yl]oxy-2-[(5-cyano-3-pyridyl)methoxy]phenyl]methylamino]-3-hydroxy-propanoic acid was performed in an analogous route to Example 31, substituting 3-chlorocatechol for 3-fluorocatechol in Step a. dr: ~3.5:1. MS: (ES) m/z calculated for $C_{34}H_{29}C_2N_3O_7$ [M+H]$^+$ 662.2, found 662.1. $^1$H NMR (400 MHz, Methanol-d$_4$) δ 9.00 (s, 1H), 8.91 (s, 1H), 8.45 (s, 1H), 7.50 (s, 1H), 7.29 (dt, J=14.9, 7.5 Hz, 2H), 7.16 (d, J=7.5 Hz, 1H), 7.06 (s, 1H), 6.87 (d, J=8.4 Hz, 1H), 6.77 (s, 1H), 6.06-5.92 (m, 1H), 5.39 (s, 2H), 4.39-4.35 (m, 3H), 4.35-4.18 (m, 3H), 4.03-3.88 (m, 1H), 3.89-3.76 (m, 1H), 3.62-3.49 (m, 1H), 3.02-2.86 (m, 1H), 2.82-2.64 (m, 1H), 2.57-2.45 (m, 1H), 2.17-1.92 (m, 1H).

Example 37: Synthesis of (2S)-2-[[2-[[3,5-bis(methylsulfonyl)phenyl]methoxy]-5-chloro-4-[(1)-4-(2-fluorophenyl)indan-1-yl]oxy-phenyl]methylamino]-3-hydroxy-propanoicacid

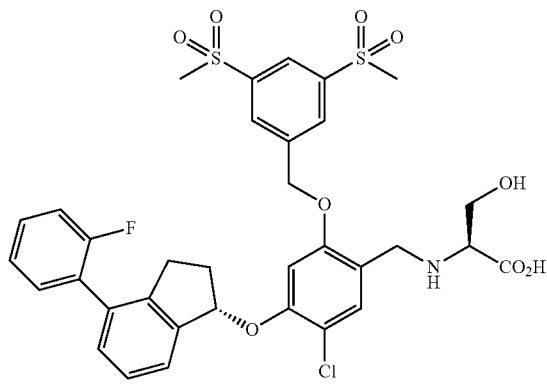 [SMILES: CS(=O)(=O)c1cc(COc2cc(O[C@H]3CCc4c(-c5ccccc5F)cccc43)c(Cl)cc2CN[C@@H](CO)C(=O)O)cc(S(C)(=O)=O)c1]

The title compound was prepared by following an analogous route to Example 11, using the optically enriched intermediate described in Scheme 3. MS: 718.1 [M+H], $^1$H NMR (400 MHz, Methanol-d$_4$) δ 8.47 (dd, J=9.4, 1.6 Hz, 3H), 7.53 (s, 1H), 7.46-7.33 (m, 2H), 7.33-7.15 (m, 5H), 7.08 (s, 1H), 6.01 (dd, J=6.6, 4.4 Hz, 1H), 5.50 (s, 2H), 4.51-4.23 (m, 2H), 4.11-3.95 (m, 3H), 3.06-2.96 (m, 1H), 2.88-2.78 (m, 1H), 2.62-2.52 (m, 1H), 2.17-2.08 (m, 1H).

Example 38: Synthesis of ((2S)-2-[[5-chloro-2-[(3,5-dicyanophenyl)methoxy]-4-[(1S)-4-(2,3-dihydro-1,4-benzodioxin-6-yl)indan-1-yl]oxy-phenyl]methylamino]-3-hydroxy-propanoic acid

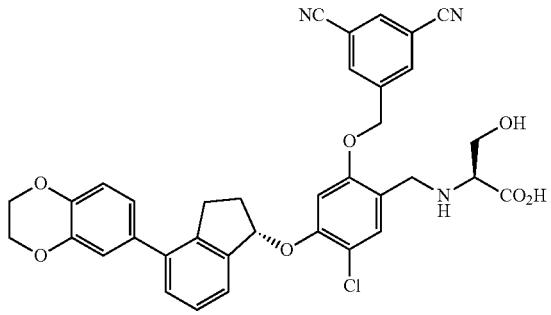 [SMILES: N#Cc1cc(C#N)cc(COc2cc(O[C@H]3CCc4c(-c5ccc6c(c5)OCCO6)cccc43)c(Cl)cc2CN[C@@H](CO)C(=O)O)c1]

The title compound was prepared by following an analogous route to Example 11, using the optically enriched intermediate described in Scheme 3. MS: 652.1 [M+H]; $^1$H NMR (400 MHz, Methanol-d$_4$) δ 8.27 (s, 2H), 8.19 (s, 1H), 7.51 (s, 1H), 7.33-7.19 (m, 3H), 6.99 (s, 1H), 6.95-6.84 (m, 3H), 5.95 (dd, J=6.4, 4.3 Hz, 1H), 5.37 (s, 2H), 4.39 (d, J=13.1 Hz, 1H), 4.27 (s, 4H), 4.00 (dd, J=11.9, 3.9 Hz, 1H), 3.86 (dd, J=11.9, 6.9 Hz, 1H), 3.59 (dd, J=6.9, 3.9 Hz, 1H), 3.39-3.11 (m, 2H), 2.96 (ddd, J=16.2, 8.2, 5.5 Hz, 1H), 2.56-2.43 (m, 1H), 2.17-2.04 (m, 1H).

Example 39: Synthesis of (2S)-2-[[5-chloro-2-[(3,5-dicyanophenyl)methoxy]-4-[(1S)-4-(2-fluoro-3-methoxy-phenyl)indan-1-yl]oxy-phenyl]methylamino]-3-hydroxy-propanoicacid

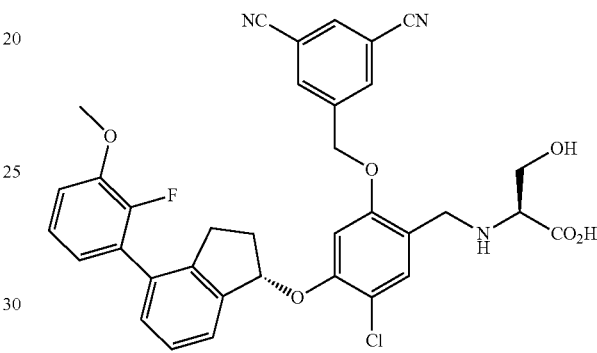

The title compound was prepared by following an analogous route to Example 11, using the optically enriched intermediate described in Scheme 3. MS: 642.1 [M+H]; $^1$H NMR (400 MHz, Methanol-d$_4$) δ 8.24 (s, 2H), 8.19 (s, 1H), 7.53 (s, 1H), 7.37-7.24 (m, 3H), 7.20-7.08 (m, 2H), 7.02 (s, 1H), 6.93-6.84 (m, 1H), 6.01 (t, J=5.5 Hz, 1H), 5.35 (s, 2H), 4.44-4.28 (m, 2H), 4.01 (s, 3H), 3.91 (d, J=2.0 Hz, 3H), 3.05-2.95 (m, 1H), 2.88-2.78 (m, 1H), 2.60-2.49 (m, 1H), 2.18-2.08 (m, 1H).

Example 40: Synthesis of (2S)-2-[[5-chloro-2-[(3,5-dicyanophenyl)methoxy]-4-[(1S)-4-(2-fluorophenyl)indan-1-yl]oxy-phenyl]methylamino]-3-hydroxy-propanoic acid

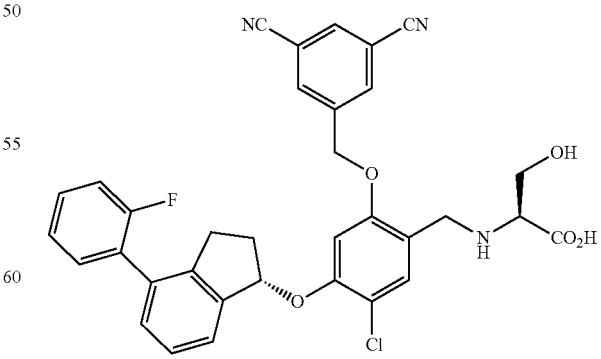

The title compound was prepared by following an analogous route to Example 11, using the optically enriched intermediate described in Scheme 3. MS: 612.1 [M+H]; $^1$H NMR (400 MHz, Methanol-d$_4$) δ 8.24 (s, 2H), 8.19 (d, J=2.1 Hz, 1H), 7.53 (s, 1H), 7.47-7.14 (m, 7H), 7.03 (s, 1H), 6.01 (t, J=5.4 Hz, 1H), 5.36 (s, 2H), 4.47-4.25 (m, 2H), 3.99 (dd, J=16.6, 4.2 Hz, 3H), 3.08-2.98 (m, 1H), 2.88-2.78 (m, 1H), 2.60-2.48 (m, 1H), 2.18-2.08 (m, 1H).

Example 41: Synthesis of (2S)-2-[[5-chloro-2-[(3,5-dicyanophenyl)methoxy]-4-[(1S)-4-(5-fluoro-2,3-dihydro-1,4-benzodioxin-6-yl)indan-1-yl]oxy-phenyl]methylamino]-3-hydroxy-2-methyl-propanoic acid

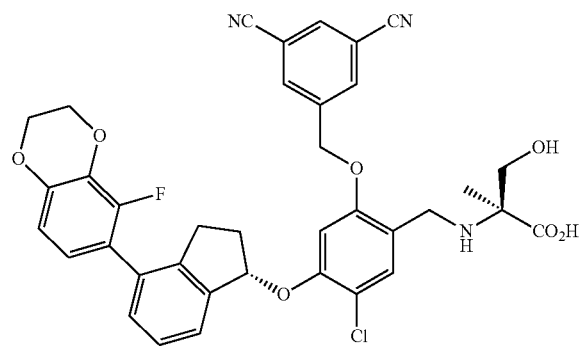 [SMILES: C[C@@](CO)(NCc1cc(Cl)c(O[C@H]2CCc3c(-c4ccc5c(c4F)OCCO5)cccc32)cc1OCc1cc(C#N)cc(C#N)c1)C(=O)O]

The title compound was prepared by following an analogous route to Example 11, using the optically enriched intermediate described in Scheme 3. MS: 684.1 [M+H]; $^1$H NMR (400 MHz, Methanol-d$_4$) δ 8.26 (s, 2H), 8.19 (s, 1H), 7.56 (s, 1H), 7.34-7.21 (m, 3H), 7.03 (s, 1H), 6.75 (d, J=6.3 Hz, 2H), 6.01 (t, J=5.3 Hz, 1H), 5.35 (d, J=3.8 Hz, 2H), 4.33 (d, J=2.0 Hz, 6H), 4.04 (d, J=12.1 Hz, 1H), 3.88-3.80 (m, 1H), 3.09-2.96 (m, 1H), 2.88-2.78 (m, 1H), 2.58-2.48 (m, 1H), 2.20-2.08 (m, 1H), 1.56 (d, J=1.7 Hz, 3H), 1.27 (d, J=7.5 Hz, 1H).

Example 42: Synthesis of (2S)-2-[[5-chloro-2-[(3,5-dicyanophenyl)methoxy]-4-[(1S)-4-(5-fluoro-2,3-dihydro-1,4-benzodioxin-6-yl)indan-1-yl]oxy-phenyl]methylamino]-3-hydroxy-propanoic acid

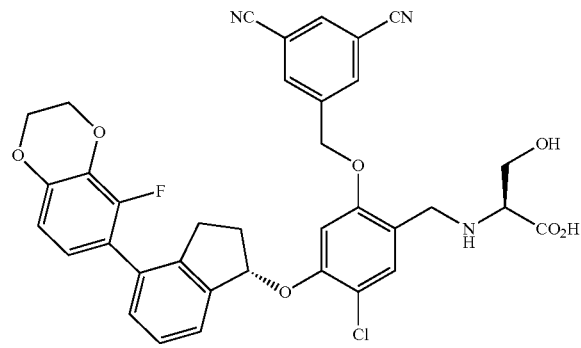 [SMILES: N#Cc1cc(C#N)cc(COc2cc(O[C@H]3CCc4c(-c5ccc6c(c5F)OCCO6)cccc43)c(Cl)cc2CN[C@@H](CO)C(=O)O)c1]

The title compound was prepared by following an analogous route to Example 11, using the optically enriched intermediate described in Scheme 3. MS: 670.0 [M+H]; $^1$H NMR (400 MHz, Methanol-d$_4$) δ 8.24 (dd, J=1.4, 0.8 Hz, 2H), 8.19 (t, J=1.5 Hz, 1H), 7.52 (s, 1H), 7.37-7.18 (m, 3H), 7.01 (s, 1H), 6.84-6.69 (m, 2H), 6.07-5.94 (m, 1H), 5.35 (s, 2H), 4.48-4.23 (m, 6H), 4.09-3.85 (m, 3H), 3.07-2.97 (m, 1H), 2.88-2.78 (m, 1H), 2.58-2.48 (m, 1H), 2.18-2.08 (m, 1H).

Example 43: Synthesis of (2S)-2-[[5-chloro-2-[(3,5-dicyanophenyl)methoxy]-4-[(1S)-4-(5-fluoro-2,3-dihydro-1,4-benzodioxin-6-yl)indan-1-yl]oxy-phenyl]methylamino]-3-hydroxy-propanoic acid

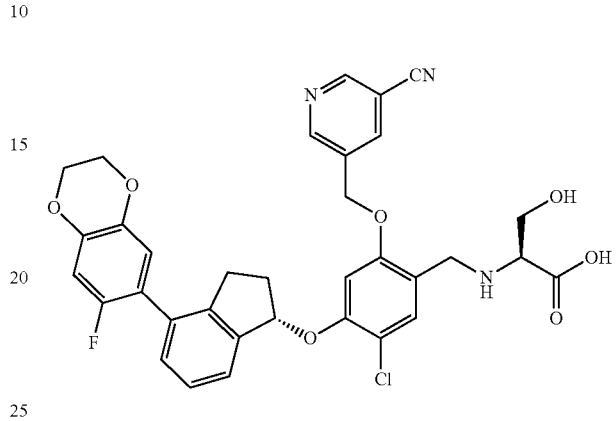

The title compound was prepared by following an analogous route to Example 11. MS: 646.2 [M+H]; $^1$H NMR (400 MHz, Methanol-d$_4$) δ 8.99 (s, 1H), 8.91 (s, 1H), 8.45 (s, 1H), 7.49 (s, 1H), 7.34-7.21 (m, 3H), 7.04 (s, 1H), 6.80 (d, J=6.8 Hz, 1H), 6.70 (d, J=10 Hz, 1H), 5.98 (br s, 1H), 5.38 (s, 2H), 4.37-4.17 (m, 6H), 4.01-3.78 (m, 2H), 3.52 (s, 1H), 3.08-2.97 (m, 1H), 2.88-2.78 (m, 1H), 2.58-2.48 (m, 1H), 2.16-2.06.

Example 44: Synthesis of (2S)-2-[[5-chloro-2-[(5-cyano-3-pyridyl)methoxy]-4-[(1S)-4-(5-fluoro-2,3-dihydro-1,4-benzodioxin-6-yl)indan-1-yl]oxy-phenyl]methylamino]-3-hydroxy-propanoic acid

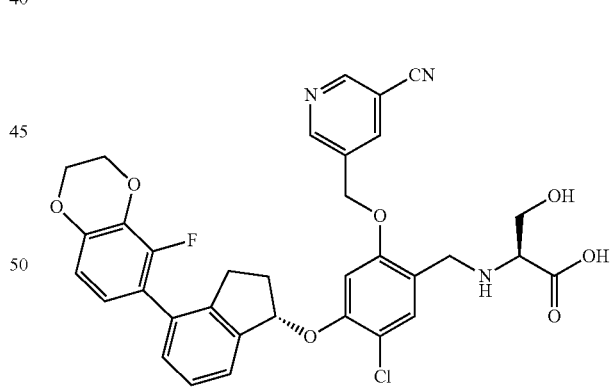

The title compound was prepared by following an analogous route to Example 11, using the optically enriched intermediate described in Scheme 3. MS: 646.2 [M+H]; $^1$H NMR (400 MHz, Methanol-d$_4$) δ 8.99 (d, J=2.1 Hz, 1H), 8.91 (d, J=2.0 Hz, 1H), 8.45 (t, J=2.1 Hz, 1H), 7.51 (d, J=0.9 Hz, 1H), 7.36-7.21 (m, 3H), 7.05 (s, 1H), 6.81-6.70 (m, 2H), 6.03-5.96 (m, 1H), 5.38 (s, 2H), 4.40-4.29 (m, 5H), 4.25 (d, J=13.1 Hz, 1H), 3.99 (dd, J=11.9, 3.9 Hz, 1H), 3.84 (dd, J=11.8, 7.1 Hz, 1H), 3.55 (dd, J=7.1, 3.9 Hz, 1H), 3.02 (dt, J=14.1, 8.0 Hz, 1H), 2.88-2.76 (m, 1H), 2.57-2.49 (m, 1H), 2.15-2.05 (m, 1H).

Example 45: Synthesis of (2S)-2-[[5-chloro-2-[(5-cyano-3-pyridyl)methoxy]-4-[(1S)-4-(5-fluoro-2,3-dihydro-1,4-benzodioxin-6-yl)indan-1-yl]oxy-phenyl]methylamino]-3-hydroxy-2-methyl-propanoic acid

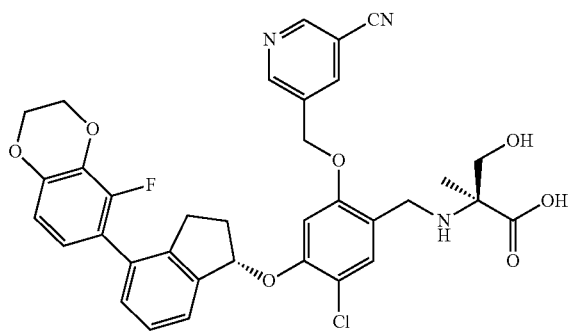 [SMILES: C[C@@](CO)(NCc1cc(Cl)c(O[C@H]2CCc3c(-c4ccc5c(c4F)OCCO5)cccc32)cc1OCc1cncc(C#N)c1)C(=O)O]

The title compound was prepared by following an analogous route to Example 11, using the optically enriched intermediate described in Scheme 3. MS: 660.1 [M+H]; $^1$H NMR (400 MHz, Methanol-$d_4$) δ 8.99 (d, J=2.1 Hz, 1H), 8.90 (d, J=2.0 Hz, 1H), 8.46 (t, J=2.2 Hz, 1H), 7.56 (s, 1H), 7.39-7.20 (m, 3H), 7.06 (s, 1H), 6.83-6.69 (m, 2H), 6.05-5.96 (m, 1H), 5.38 (d, J=3.2 Hz, 2H), 4.33 (s, 4H), 4.25 (s, 2H), 3.94 (d, J=12.1 Hz, 1H), 3.74 (d, J=12.0 Hz, 1H), 3.10-2.96 (m, 1H), 2.90-2.76 (m, 1H), 2.62-2.47 (m, 1H), 2.19-2.05 (m, 1H), 1.46 (s, 3H).

Example 46: Synthesis of (5-chloro-4-(((S)-4-(5-fluoro-2,3-dihydrobenzo[b][1,4]dioxin-6-yl)-2,3-dihydro-1H-inden-1-yl)oxy)-2-((5-(methylsulfonyl)pyridin-3-yl)methoxy)benzyl)-L-serine

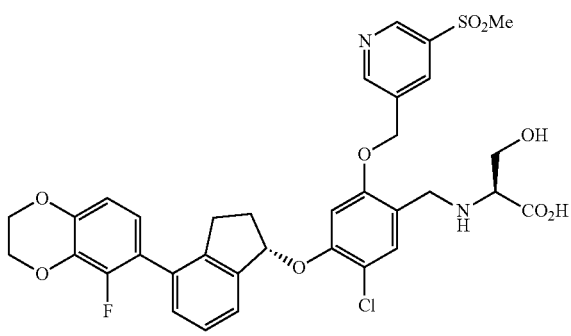 [SMILES: CS(=O)(=O)c1cncc(COc2cc(O[C@H]3CCc4c(-c5ccc6c(c5F)OCCO6)cccc43)c(Cl)cc2CN[C@@H](CO)C(=O)O)c1]

The title compound was prepared by following an analogous route to Example 3. MS: 699.0.1 [M+H]; $^1$H NMR (400 MHz, Methanol-$d_4$) δ $^1$H NMR (400 MHz, Methanol-$d_4$) δ 9.08 (dd, J=21.4, 2.1 Hz, 2H), 8.54 (t, J=2.1 Hz, 1H), 7.53 (s, 1H), 7.37-7.21 (m, 3H), 7.11 (s, 1H), 6.81-6.70 (m, 2H), 6.02 (dd, J=6.5, 4.4 Hz, 1H), 5.44 (s, 2H), 4.34 (d, J=15.1 Hz, 6H), 4.01 (s, 2H), 3.24 (s, 3H), 3.02 (ddd, J=16.2, 8.5, 5.5 Hz, 1H), 2.89-2.77 (m, 1H), 2.57 (td, J=13.6, 6.2 Hz, 1H), 2.19-2.07 (m, 1H).

Example 47: Synthesis of (2S)-2-[[5-chloro-2-[(5-cyano-3-pyridyl)methoxy]-4-[(1S)-4-(5,6-difluoro-2,3-dihydro-1,4-benzodioxin-7-yl)indan-1-yl]oxy-phenyl]methylamino]-3-hydroxy-propanoic acid

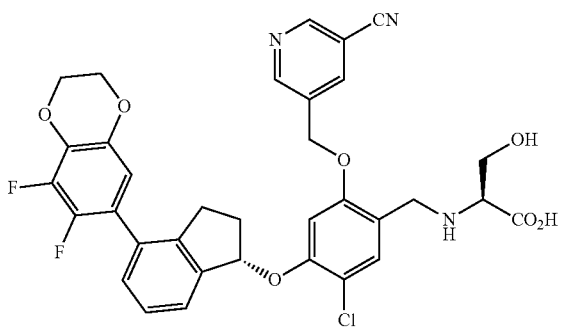 [SMILES: N#Cc1cncc(COc2cc(O[C@H]3CCc4c(-c5cc6c(c(F)c5F)OCCO6)cccc43)c(Cl)cc2CN[C@@H](CO)C(=O)O)c1]

The title compound was prepared by following an analogous route to Example 11, using the optically enriched intermediate described in Scheme 3. MS: 664.0 [M+H]; $^1$H NMR (400 MHz, Methanol-$d_4$) δ 8.99 (d, J=2.1 Hz, 1H), 8.90 (d, J=1.9 Hz, 1H), 8.45 (t, J=2.0 Hz, 1H), 7.49 (s, 1H), 7.38-7.22 (m, 3H), 7.05 (s, 1H), 6.63 (dd, J=6.6, 2.4 Hz, 1H), 5.99 (dd, J=6.5, 4.4 Hz, 1H), 5.38 (s, 2H), 4.39-4.27 (m, 5H), 4.20 (d, J=13.1 Hz, 1H), 3.96 (dd, J=11.6, 4.0 Hz, 1H), 3.82 (dd, J=11.7, 7.0 Hz, 1H), 3.51 (dd, J=6.9, 4.1 Hz, 1H), 3.09-2.97 (m, 1H), 2.89-2.77 (m, 1H), 2.61-2.48 (m, 1H), 2.23-2.06 (m, 1H).

Additional compounds prepared by methods analogous to the methods described above were made and are provided in Table 1A, Table 1B, and Table 1C.

TABLE 1A

| Compound Structure | $^1$H NMR | MS: (ES) m/z (M + H) |
|---|---|---|
| 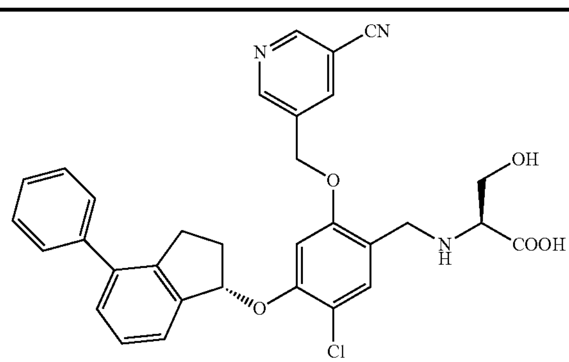 | $^1$H NMR (400 MHz, Methanol-$d_4$) δ 8.99 (d, J = 2.1 Hz, 1H), 8.92 (d, J = 2.0 Hz, 1H), 8.43 (t, J = 2.1 Hz, 1H), 7.53 (s, 1H), 7.50-7.43 (m, 4H), 7.40-7.29 (m, 4H), 7.12 (s, 1H), 6.04-5.99 (m, 1H), 5.39 (s, 2H), 4.35 (q, J = 13.1 Hz, 2H), 4.01 (s, 3H), 3.24-3.15 (m, 1H), 3.06-2.88 (m, 1H), 2.61-2.44 (m, 1H), 2.26-2.07 (m, 1H). | 570.4 |

TABLE 1A-continued

| Compound Structure | ¹H NMR | MS: (ES) m/z (M + H) |
|---|---|---|
| | ¹H NMR (400 MHz, Methanol-d₄) δ 8.99 (d, J = 2.1 Hz, 1H), 8.94 (d, J = 2.0 Hz, 1H), 8.41 (s, 1H), 7.52 (d, J = 11.5 Hz, 1H), 7.49-7.40 (m, 4H), 7.38-7.33 (m, 2H), 7.31 (d, J = 5.0 Hz, 2H), 7.16-7.08 (m, 1H), 6.07-5.94 (m, 1H), 5.42 (s, 2H), 4.43 (s, 2H), 4.38-4.22 (m, 4H), 3.65 (td, J = 8.4 Hz, 1H), 3.26-3.12 (m, 1H), 2.98 (ddd, J = 16.2, 8.2, 5.4 Hz, 1H), 2.62-2.46 (m, 1H), 2.24-2.04 (m, 1H). | 566.5 |
| | ¹H NMR (400 MHz, Methanol-d₄) δ 8.99 (d, J = 2.2 Hz, 1H), 8.93 (d, J = 2.0 Hz, 1H), 8.43 (s, 1H), 7.60-7.48 (m, 2H), 7.45-7.34 (m, 3H), 7.31 (t, J = 7.3 Hz, 2H), 7.21 (d, J = 7.4 Hz, 1H), 7.11 (s, 1H), 6.08-5.96 (m, 1H), 5.38 (s, 2H), 4.35 (q, J = 13.1 Hz, 2H), 4.05-3.98 (m, 3H), 3.02-2.84 (m, 1H), 2.83-2.66 (m, 1H), 2.66-2.48 (m, 1H), 2.19-2.06 (m, 1H). | 626.3 |
| | ¹H NMR (400 MHz, Methanol-d₄) δ 8.99 (d, J = 2.2 Hz, 1H), 8.92 (d, J = 2.0 Hz, 1H), 8.44 (t, J = 2.1 Hz, 1H), 7.69-7.62 (m, 1H), 7.56 (dd, J = 7.2, 3.3 Hz, 1H), 7.36-7.17 (m, 5H), 7.17-7.04 (m, 2H), 6.11-5.96 (m, 1H), 5.39 (s, 2H), 4.35 (q, J = 13.1 Hz, 2H), 4.07-4.00 (m, 3H), 2.95-2.72 (m, 1H), 2.72-2.60 (m, 1H), 2.60-2.47 (m, 1H), 2.17-2.05 (m, 4H). | 606.4 |
| | ¹H NMR (400 MHz, Methanol-d₄) δ 8.99 (d, J = 2.1 Hz, 1H), 8.93 (d, J = 2.0 Hz, 1H), 8.44 (d, J = 2.1 Hz, 1H), 7.53 (s, 1H), 7.50-7.44 (m, 1H), 7.43-7.32 (m, 3H), 7.29 (d, J = 7.7 Hz, 1H), 7.26-7.14 (m, 1H), 7.14-7.02 (m, 2H), 6.12-5.92 (m, 1H), 5.39 (d, J = 1.3 Hz, 2H), 4.35 (q, J = 13.1 Hz, 2H), 4.08-3.96 (m, 3H), 3.18-3.08 (m, 1H), 3.04-2.93 (m, 1H), 2.66-2.48 (m, 1H), 2.26-2.09 (m, 1H). | 588.2 |

TABLE 1A-continued

| Compound Structure | ¹H NMR | MS: (ES) m/z (M + H) |
|---|---|---|
| | ¹H NMR (400 MHz, Methanol-d₄) δ 8.99 (d, J = 2.2 Hz, 1H), 8.93 (d, J = 2.0 Hz, 1H), 8.43 (s, 1H), 7.53 (s, 1H), 7.43-7.24 (m, 4H), 7.11 (s, 1H), 7.03 (d, J = 7.6 Hz, 1H), 6.99 (s, 1H), 6.93 (d, J = 8.2 Hz, 1H), 6.05-5.97 (m, 1H), 5.39 (s, 2H), 4.35 (q, J = 13.0 Hz, 2H), 4.03-3.95 (m, 3H), 3.84 (s, 3H), 3.23-3.13 (m, 1H), 3.10-2.77 (m, 1H), 2.65-2.45 (m, 1H), 2.23-2.10 (m, 1H). | 600.3 |
| | ¹H NMR (400 MHz, Methanol-d₄) δ 8.98 (t, J = 2.2 Hz 1H), 8.94 (dd, J = 4.4 Hz, 2.1 Hz 1H), 8.42 (dt, J = 11 Hz, 0.94 Hz, 1H), 7.57 (s, 1H), 7.44-7.17 (m, 7H), 7.13 (d, J = 7.2 Hz, 1H), 6.08-6.02 (m, 1H), 5.43-5.39 (m, 2H), 4.54 (br s, 1H), 4.50 (s, 1H), 4.38 (s, 1H), 3.08-2.98 (m, 1H), 2.89-2.80 (m, 1H), 2.64-2.53 (m, 1H), 2.40-2.30 (m, 1H), 2.18-2.07 (m, 1H), 2.03-1.95 (m, 1H). | 570.3 |
| | ¹H NMR (400 MHz, Methanol-d₄) δ 8.99 (d, J = 1.8 Hz, 1H), 8.94 (d, J = 2.0 Hz, 1H), 8.41 (s, 1H), 7.58 (s, 1H), 7.45-7.17 (m, 7H), 7.13 (s, 1H), 6.05 (dd, J = 6.4 Hz, 4.4 Hz, 1H), 5.41 (s, 2H), 4.55-4.44 (m, 2H), 3.51-3.41 (m, 1H), 2.90-2.79 (m, 1H), 2.65-2.53 (m, 2H), 2.20-2.09 (m, 2H). | 614.3 |
| | ¹H NMR (400 MHz, Methanol-d₄) δ 8.99 (d, J = 2.2 Hz, 1H), 8.92 (d, J = 2.0 Hz, 1H), 8.43 (d, J = 2.2 Hz, 1H), 7.53 (s, 1H), 7.39-7.22 (m, 3H), 7.10 (s, 1H), 6.98-6.81 (m, 3H), 6.05-5.81 (m, 1H), 5.38 (s, 2H), 4.34 (q, J = 13.1 Hz, 2H), 4.28 (d, J = 0.5 Hz, 4H), 4.02-3.99 (m, 3H), 3.21-3.05 (m, 1H), 3.06-2.81 (m, 1H), 2.74-2.46 (m, 1H), 2.27-1.97 (m, 1H). | 628.4 |

TABLE 1A-continued

| Compound Structure | $^1$H NMR | MS: (ES) m/z (M + H) |
|---|---|---|
| 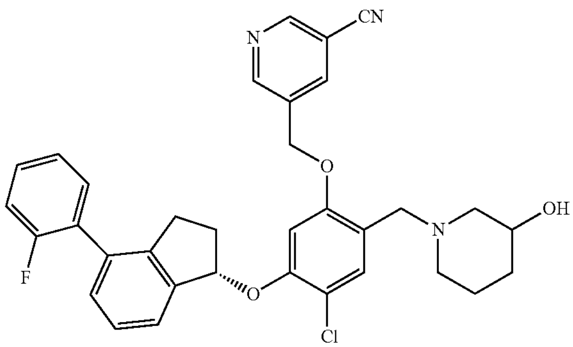 [SMILES: N#Cc1cncc(COc2cc(O[C@H]3CCc4c(-c5ccccc5F)cccc43)c(Cl)cc2CN2CCCC(O)C2)c1] | $^1$H NMR (400 MHz, Methanol-d$_4$) δ 8.98 (d, J = 1.8 Hz 1H), 8.95 (d, J = 1.8 Hz, 1H), 8.41 (s, 1H), 7.56 (s, 1H), 7.45-7.17 (m, 7H), 7.15-7.11 (m, 1H), 6.08-6.03 (m, 1H), 5.40 (s, 2H), 4.41-4.17 (m, 2H), 4.13 (s, 1H), 3.51-3.34 (m, 1H), 3.11-2.96 (m, 2H), 2.92-2.80 (m, 1H), 2.65-2.54 (m, 1H), 2.27-1.98 (m, 2H), 1.87-1.58 (m, 2H). | 584.3 |
| 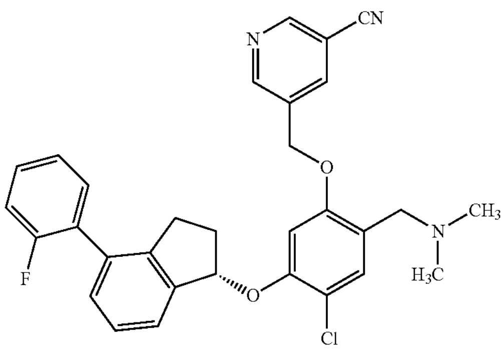 [SMILES: CN(C)Cc1cc(Cl)c(O[C@H]2CCc3c(-c4ccccc4F)cccc32)cc1OCc1cncc(C#N)c1] | $^1$H NMR (400 MHz, Methanol-d$_4$) δ 8.98 (d, J = 2.0 Hz 1H), 8.94 (d, J = 2.0 Hz, 1H), 8.40 (t, J = 2.0 Hz, 1H), 7.54 (s, 1H), 7.44-7.30 (m, 5H), 7.29-7.17 (m, 2H), 7.12 (s, 1H), 6.05 (dd, J = 6.4 Hz, 4.4 Hz, 1H), 5.43-5.40 (m, 2H), 4.32 (s, 2H), 3.08-2.98 (m, 1H), 2.89-2.80 (m, 7H), 2.62-2.52 (m, 1H), 2.17-2.08 (m, 1H). | 528.3 |
| 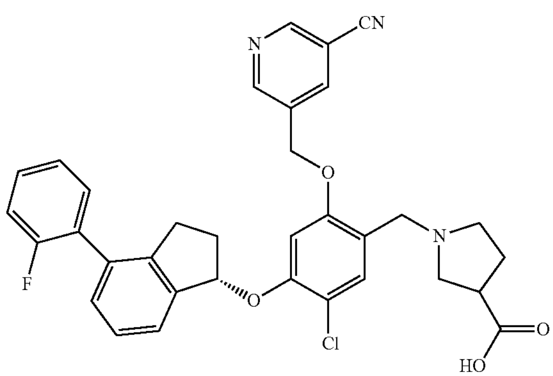 [SMILES: N#Cc1cncc(COc2cc(O[C@H]3CCc4c(-c5ccccc5F)cccc43)c(Cl)cc2CN2CCC(C(=O)O)C2)c1] | $^1$H NMR (400 MHz, Methanol-d$_4$) δ 8.99 (d, J = 2.0 Hz, 1H), 8.94 (d, J = 2.0 Hz, 1H), 8.41 (m, 1H), 7.56 (s, 1H), 7.45-7.16 (m, 7H), 7.13 (s, 1H), 6.05 (dd, J = 6.4 Hz, 4.4 Hz, 1H), 5.41 (s, 2H), 4.47-4.38 (m, 2H), 3.72-3.50 (m, 2H), 3.07-2.99 (m, 1H), 2.89-2.79 (m, 1H), 2.63-2.54 (m, 1H), 2.42-2.07 (m, 3H). | 598.3 |
| 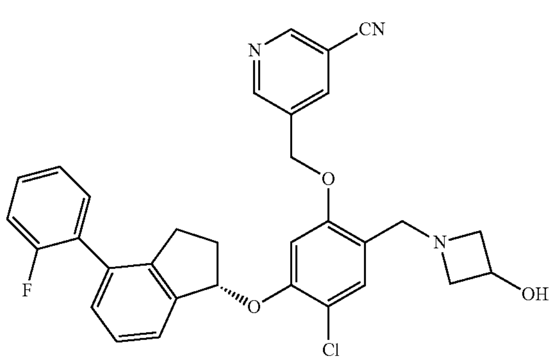 [SMILES: N#Cc1cncc(COc2cc(O[C@H]3CCc4c(-c5ccccc5F)cccc43)c(Cl)cc2CN2CC(O)C2)c1] | $^1$H NMR (400 MHz, Methanol-d$_4$) δ 8.90 (s, 1H), 8.87 (m, 1H), 8.31 (m, 1H), 7.43 (d, J = 5.2 Hz, 1H), 7.39-7.22 (m, 5H), 7.21-7.09 (m, 2H), 7.05 (d, J = 2.2 Hz, 1H), 6.00-5.96 (m, 1H), 5.40 (s, 2H), 4.70-4.53 (m, 1H), 4.43-4.29 (m, 4H), 4.02-3.89 (m, 2H), 3.22-3.19 (m, 1H), 3.01-2.93 (m, 1H), 2.59-2.48 (m, 1H), 2.17-2.07 (m, 1H). | 556.3 |

TABLE 1A-continued

| Compound Structure | ¹H NMR | MS: (ES) m/z (M + H) |
|---|---|---|
| | ¹H NMR (400 MHz, DMSO-d₆) δ 7.44 (s, 1H), 7.35 (q, J = 4.1 Hz, 1H), 7.32-7.27 (m, 2H), 7.01 (s, 1H), 6.97-6.87 (m, 3H), 6.04 (t, J = 5.5 Hz, 1H), 4.27 (s, 4H), 3.92 (s, 2H), 3.87 (s, 3H), 3.71 (dd, J = 11.2, 4.6 Hz, 1H), 3.61 (dd, J = 11.2, 6.4 Hz, 1H), 3.15 (dd, J = 6.4, 4.5 Hz, 1H), 3.09 (ddd, J = 13.7, 8.6, 4.3 Hz, 1H), 2.99-2.85 (m, 1H), 2.56 (dq, J = 13.4, 6.5, 6.0 Hz, 1H), 2.09-1.98 (m, 1H). | 548.4 |
| | ¹H NMR (400 MHz, Methanol-d₄) δ 8.99 (d, J = 2.1 Hz, 1H), 8.92 (d, J = 2.0 Hz, 1H), 8.43 (t, J = 2.0 Hz, 1H), 7.53 (s, 1H), 7.44-7.29 (m, 3H), 7.15-7.01 (m, 2H), 6.94 (dt, J = 9.0, 3.5 Hz, 1H), 6.86 (dd, J = 6.0, 3.2 Hz, 1H), 6.11-6.00 (m, 1H), 5.38 (s, 2H), 4.34 (q, J = 13.1 Hz, 2H), 4.01 (s, 3H), 3.81 (d, J = 0.7 Hz, 3H), 3.11-2.96 (m, 1H), 2.92-2.79 (m, 1H), 2.59 (dt, J = 13.0, 6.4 Hz, 1H), 2.20-2.04 (m, 1H). | 618.5 |
| | ¹H NMR (400 MHz, Methanol-d₄) δ 8.99 (d, 1H), 8.92 (d, J = 2.0 Hz, 1H), 8.43 (t, J = 2.1 Hz, 1H), 7.53 (s, 1H), 7.39-7.34 (m, 1H), 7.32 (d, J = 7.5 Hz, 1H), 7.30-7.29 (m, 1H), 7.29-7.21 (m, 2H), 7.15 (td, J = 7.4, 6.8, 4.9 Hz, 2H), 7.11 (d, J = 2.6 Hz, 1H), 6.04 (dd, J = 6.5, 4.3 Hz, 1H), 5.38 (d, J = 2.3 Hz, 2H), 4.35 (q, J = 13.1 Hz, 2H), 4.10-3.95 (m, 3H), 3.09-2.96 (m, 1H), 2.87-2.74 (m, 1H), 2.57 (dq, J = 13.7, 6.6 Hz, 1H), 2.33 (d, J = 1.9 Hz, 3H), 2.14 (td, J = 8.5, 3.7 Hz, 1H). | 602.5 |
| | ¹H NMR (400 MHz, Methanol-d₄) δ 9.04-8.95 (m, 1H), 8.92 (d, J = 2.0 Hz, 1H), 8.43 (q, J = 2.0 Hz, 1H), 7.52 (d, J = 1.0 Hz, 1H), 7.34 (dd, J = 8.4, 4.9 Hz, 1H), 7.24-7.09 (m, 3H), 7.08-6.97 (m, 1H), 6.95-6.80 (m, 1H), 6.20 (dd, J = 6.3, 1.9 Hz, 1H), 5.37 (d, J = 2.0 Hz, 2H), 4.47-4.22 (m, 2H), 4.00 (s, 3H), 3.91 (s, 3H), 3.22-2.98 (m, 1H), 2.79 (ddd, J = 16.6, 8.6, 2.9 Hz, 1H), 2.58-2.38 (m, 1H), 2.36-2.11 (m, 1H). | 636.3 |

TABLE 1A-continued

| Compound Structure | ¹H NMR | MS: (ES) m/z (M + H) |
|---|---|---|
| | ¹H NMR (400 MHz, Methanol-d₄) δ 7.45 (s, 1H), 7.42 (d, 1H), 7.32 (t, J = 7.4 Hz, 1H), 7.30-7.26 (m, 1H), 7.20-7.14 (m, 1H), 7.12 (td, J = 8.0, 1.9 Hz, 1H), 6.96 (d, J = 1.7 Hz, 1H), 6.89 (ddd, J = 7.5, 6.3, 1.8 Hz, 1H), 6.00 (dd, J = 6.5, 4.4 Hz, 1H), 4.35 (d, J = 13.1 Hz, 1H), 4.28-4.13 (m, 3H), 4.02 (dd, J = 4.3, 1.8 Hz, 2H), 3.96 (t, J = 4.2 Hz, 1H), 3.91 (s, 3H), 3.08-2.94 (m, 1H), 2.88-2.73 (m, 1H), 2.59 (dq, J = 13.7, 6.6 Hz, 1H), 2.16 (ddt, J = 13.3, 9.0, 4.9 Hz, 1H), 1.49 (t, J = 7.0 Hz, 3H). | 552.4 |
| | ¹H NMR (400 MHz, Methanol-d₄) δ 8.98 (s, 1H), 8.94 (d, J = 1.6 Hz, 1H), 8.43-8.38 (m, 1H), 7.51 (s, 1H), 7.31-7.23 (m, 3H), 7.12-7.07 (m, 1H), 6.94-6.88 (m, 3H), 6.01-5.97 (m, 1H), 5.40 (s, 2H), 4.70-4.53 (m, 1H), 4.43-4.29 (m, 4H), 4.27 (s, 4H), 4.02-3.89 (m, 2H), 3.22-3.14 (m, 1H), 3.01-2.93 (m, 1H), 2.59-2.48 (m, 1H), 2.17-2.07 (m, 1H). | 596.4 |
| | ¹H NMR (400 MHz, Methanol-d₄) δ 8.98 (d, J = 1.7 Hz, 1H), 8.94 (d, J = 1.7 Hz, 1H), 8.43-8.41 (m, 1H), 7.51 (s, 1H), 7.38-7.27 (m, 3H), 7.20-7.06 (m, 3H), 6.92-6.87 (m, 1H), 6.05-6.00 (m, 1H), 5.41-5.37 (m, 2H), 4.60-4.53 (m, 1H), 4.43 (s, 1H), 4.38-4.28 (m, 3H), 4.00-3.92 (m, 2H), 3.91 (s, 3H), 3.06-2.95 (m, 1H), 2.89-2.77 (m, 1H), 2.62-2.53 (m, 1H), 2.17-2.07 (m, 1H). | 586.3 |
| | ¹H NMR (400 MHz, Methanol-d₄) δ 7.44 (s, 1H), 7.39 (d, J = 7.3 Hz, 1H), 7.30 (t, J = 7.5 Hz, 1H), 7.25 (d, J = 7.5 Hz, 1H), 6.95 (s, 1H), 6.80-6.69 (m, 2H), 6.02-5.90 (m, 1H), 4.34-4.31 (m, 5H), 4.26-4.11 (m, 3H), 4.02 (t, J = 3.6 Hz, 2H), 3.94 (t, J = 4.2 Hz, 1H), 3.08-2.96 (m, 1H), 2.91-2.76 (m, 1H), 2.58 (s, 1H), 2.22-2.11 (m, 1H), 1.49 (t, J = 7.0 Hz, 3H). | 580.5 |

TABLE 1A-continued

| Compound Structure | ¹H NMR | MS: (ES) m/z (M + H) |
|---|---|---|
| | ¹H NMR (400 MHz, Methanol-d₄) δ 8.97 (s, 1H), 8.95 (s, 1H), 8.38 (s, 1H), 7.58-7.50 (m, 1H), 7.33 (t, J = 7.0 Hz, 1H), 7.27 (dd, J = 10.8, 7.2 Hz, 2H), 7.10 (d, J = 3.5 Hz, 1H), 6.85-6.71 (m, 2H), 6.04 (t, J = 5.5 Hz, 1H), 5.39 (d, J = 2.9 Hz, 2H), 4.35-4.32 (m, 4H), 4.31 (d, J = 6.2 Hz, 3H), 4.05 (s, 1H), 3.83 (d, J = 16.3 Hz, 1H), 3.50 (d, J = 14.4 Hz, 1H), 3.14-2.93 (m, 2H), 2.89-2.74 (m, 1H), 2.57 (d, J = 7.3 Hz, 1H), 2.22-2.10 (m, 2H), 1.90 (s, 2H), 1.66 (d, J = 12.4 Hz, 1H). | 642.5 |
| | ¹H NMR (400 MHz, Methanol-d₄) δ 9.01 (s, 1H), 8.93 (s, 1H), 8.46 (s, 1H), 7.57 (s, 1H), 7.53-7.12 (m, 7H), 7.05 (s, 1H), 6.01 (m, 1H), 5.44 (s, 2H), 4.36 (s, 2H), 3.09 (m, 2H), 3.03 (m, 1H), 2.83 (m, 1H), 2.54 (m, 1H), 2.06 (m, 1H). | 594.3 |
| | ¹H NMR (400 MHz, Methanol-d₄) δ 8.98 (s, 1H), 8.93 (d, J = 2.0 Hz, 1H), 8.41 (s, 1H), 7.58 (s, 1H), 7.40-7.28 (m, 3H), 7.21-7.08 (m, 3H), 6.93-6.87 (m, 1H), 6.08-6.03 (m, 1H), 5.40 (s, 2H), 4.71 (s, 1H), 4.53-4.37 (m, 2H), 3.91 (s, 3H), 3.07-2.97 (m, 2H), 2.8-2.79 (m, 2H), 2.65-2.53 (m, 2H), 2.20-2.09 (m, 2H). | 644.4 |
| | ¹H NMR (400 MHz, Methanol-d₄) δ 8.99 (s, 1H), 8.92 (s, 1H), 8.43 (s, 1H), 7.53 (s, 1H), 7.43-7.35 (m, 2H), 7.33-7.27 (m, 1H), 7.21 (d, J = 7.4 Hz, 1H), 7.10 (s, 1H), 6.98-6.89 (m, 1H), 6.85 (s, 1H), 6.09-5.96 (m, 1H), 5.38 (s, 2H), 4.34 (q, J = 13.2 Hz, 2H), 4.04-3.96 (m, 3H), 3.81 (s, 3H), 3.05-2.86 (m, 1H), 2.85-2.69 (m, 1H), 2.64-2.45 (m, 1H), 2.18-2.08 (m, 1H). | 634.4 |

TABLE 1A-continued

| Compound Structure | ¹H NMR | MS: (ES) m/z (M + H) |
|---|---|---|
| 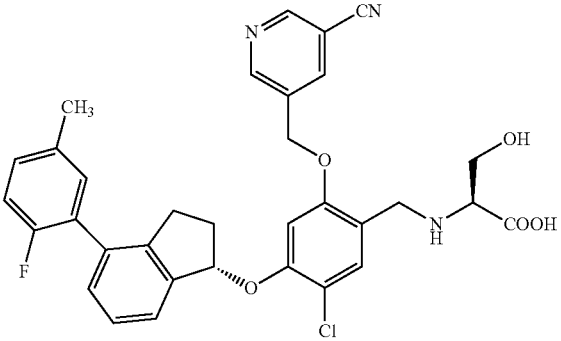 [SMILES: Cc1ccc(F)c(-c2cccc3c2CC[C@@H]3Oc2cc(OCc3cncc(C#N)c3)c(CN[C@@H](CO)C(=O)O)cc2Cl)c1] | ¹H NMR (400 MHz, Methanol-d₄) δ 8.99 (d, J = 2.2 Hz, 1H), 8.92 (d, J = 1.9 Hz, 1H), 8.43 (s, 1H), 7.53 (s, 1H), 7.37 (d, J = 7.1 Hz, 1H), 7.33 (d, J = 7.4 Hz, 1H), 7.29 (d, J = 7.4 Hz, 2H), 7.23-7.14 (m, 1H), 7.09 (d, J = 5.8 Hz, 1H), 7.05 (d, J = 8.4 Hz, 1H), 6.05-5.97 (m, 1H), 5.38 (s, 2H), 4.35 (q, J = 13.1 Hz, 2H), 4.05-3.94 (m, 3H), 3.10-2.90 (m, 1H), 2.90-2.77 (m, 1H), 2.70-2.50 (m, 1H), 2.36 (s, 3H), 2.22-2.05 (m, 1H). | 602.5 |
| 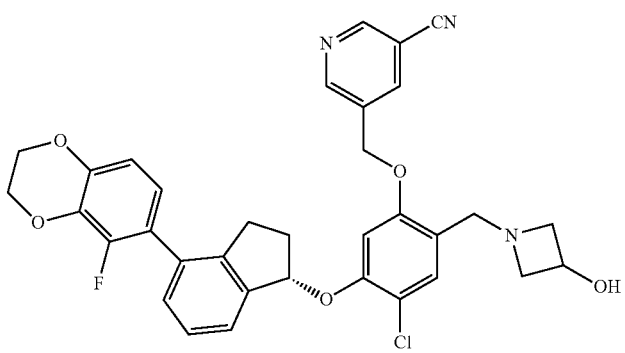 [SMILES: N#Cc1cncc(COc2cc(O[C@H]3CCc4c(-c5ccc6c(c5F)OCCO6)cccc43)c(Cl)cc2CN2CC(O)C2)c1] | ¹H NMR (400 MHz, Methanol-d₄) δ 8.98 (s, 1H), 8.94 (s, 1H), 8.40 (d, J = 12.4 Hz, 1H), 7.50 (d, J = 3.6 Hz, 1H), 7.35-7.22 (m, 3H), 7.08 (d, J = 10.2 Hz, 1H), 6.78-6.71 (m, 2H), 6.02 (s, 1H), 5.39 (s, 2H), 4.41 (d, J = 20.7 Hz, 2H), 4.38-4.24 (m, 6H), 4.04-3.82 (m, 2H), 3.71-3.55 (m, 1H), 3.07-2.96 (m, 1H), 2.93-2.65 (m, 1H), 2.60-2.48 (m, 1H), 2.18-2.06 (m, 1H). | 614.5 |
| 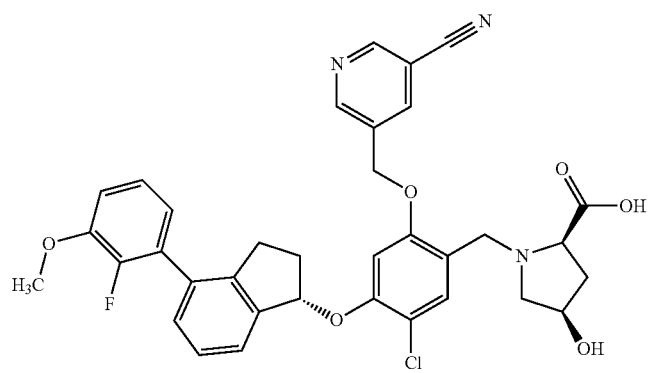 [SMILES: COc1cccc(-c2cccc3c2CC[C@@H]3Oc2cc(OCc3cncc(C#N)c3)c(CN3C[C@H](O)C[C@@H]3C(=O)O)cc2Cl)c1F] | ¹H NMR (400 MHz, Methanol-d) δ 9.00 (d, J = 1.9 Hz, 1H), 8.93 (d, J = 1.9 Hz, 1H), 8.43 (br s, 1H), 7.54 (s, 1H), 7.42-7.27 (m, 3H), 7.21-7.09 (m, 3H), 6.93-6.87 (m, 1H), 6.05 (dd, J = 6.8 Hz, 4.4 Hz, 1H), 5.46-5.34 (m, 2H), 4.56 (d, J = 13 Hz, 1H), 4.48 (br s, 1H), 4.43-4.37 (m, 2H), 3.50-3.44 (m, 1H), 3.08-2.97 (m, 1H), 2.89-2.79 (m, 1H), 2.71-2.55 (m, 2H), 2.31-2.23 (m, 1H), 2.19-2.10 (m, 1H). | 644.4 |
| 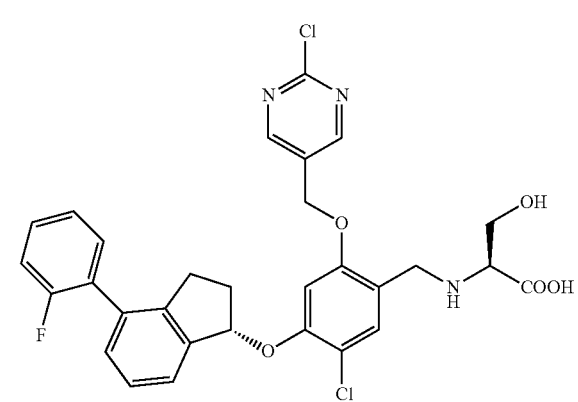 [SMILES: O=C(O)[C@H](CO)NCc1cc(Cl)c(O[C@H]2CCc3c(-c4ccccc4F)cccc32)cc1OCc1cnc(Cl)nc1] | ¹H NMR (400 MHz, Methanol-d₄) δ 8.89 (d, J = 13.8 Hz, 2H), 7.53 (s, 1H), 7.44-7.37 (m, 3H), 7.38-7.30 (m, 2H), 7.31-7.23 (m, 1H), 7.23-7.16 (m, 1H), 7.14 (s, 1H), 6.18-5.96 (m, 1H), 5.37-5.27 (m, 2H), 4.29 (dd, J = 24.0, 7.4 Hz, 2H), 4.00 (d, J = 1.2 Hz, 3H), 3.10-2.96 (m, 1H), 2.92-2.79 (m, 1H), 2.71-2.51 (m, 1H), 2.23-2.11 (m, 1H). | 598.3 |

TABLE 1A-continued

| Compound Structure | ¹H NMR | MS: (ES) m/z (M + H) |
|---|---|---|
| | ¹H NMR (400 MHz, Methanol-$d_4$) δ 9.00 (d, J = 2.2 Hz, 1H), 8.93 (d, J = 2.0 Hz, 1H), 8.44 (s, 1H), 7.53 (s, 2H), 7.48-7.14 (m, 5H), 7.10 (s, 2H), 6.15-5.93 (m, 1H), 5.39 (s, 2H), 4.32 (d, J = 12.9 Hz, 1H), 4.23 (d, 13.0 Hz, 1H), 4.10-3.83 (m, 1H), 3.14-2.92 (m, 1H), 2.94-2.75 (m, 1H), 2.64-2.45 (m, 1H), 2.24-1.89 (m, 1H), 1.56 (d, J = 7.2 Hz, 3H). | 594.4 |
| | ¹H NMR (400 MHz, Methanol-$d_4$) δ 9.00 (d, J = 2.1 Hz, 1H), 8.91 (d, J = 2.0 Hz, 1H), 8.45 (d, J = 2.4 Hz, 1H), 7.50 (s, 1H), 7.44-7.29 (m, 5H), 7.26 (td, J = 7.6, 1.2 Hz, 1H), 7.19 (dd, J = 10.3, 8.3 Hz, 1H), 7.07 (s, 1H), 6.00 (t, J = 5.4 Hz, 1H), 5.39 (d, J = 4.3 Hz, 2H), 4.39-4.29 (m, 1H), 4.24 (d, J = 13.1 Hz, 1H), 4.01-3.94 (m, 1H), 3.83 (dd, J = 11.8, 7.0 Hz, 1H), 3.54 (s, 1H), 3.02 (ddd, J = 14.5, 8.4, 5.6 Hz, 1H), 2.88-2.75 (m, 1H), 2.56 (dt, J = 14.0, 7.6 Hz, 1H), 2.12 (ddd, J = 13.2, 8.6, 4.4 Hz, 1H). | 588.4 |
| | ¹H NMR (400 MHz, Methanol-$d_4$) δ 8.95 (dd, J = 22.8, 2.0 Hz, 2H), 8.42 (t, J = 2.0 Hz, 1H), 7.52 (s, 1H), 7.44-7.24 (m, 3H), 7.24-7.03 (m, 3H), 6.89 (ddd, J = 8.0, 6.3, 1.9 Hz, 1H), 6.02 (dd, J = 6.6, 4.3 Hz, 1H), 5.37 (d, J = 2.4 Hz, 2H), 4.44-4.15 (m, 2H), 4.12-3.98 (m, 1H), 3.91 (s, 3H), 3.64 (dd, J = 7.1, 1.1 Hz, 1H), 3.08-2.92 (m, 1H), 2.90-2.71 (m, 1H), 2.67-2.45 (m, 1H), 2.14 (tt, J = 8.3, 4.6 Hz, 1H), 1.32 (d, J = 6.4 Hz, 3H). | 632.4 |
| | ¹H NMR (400 MHz, Methanol-$d_4$) δ 8.99 (d, J = 2.1 Hz, 1H), 8.92 (d, J = 2.0 Hz, 1H), 8.43 (t, J = 2.0 Hz, 1H), 7.53 (s, 1H), 7.41-7.25 (m, 3H), 7.22-7.06 (m, 3H), 6.89 (ddd, J = 7.9, 6.3, 1.9 Hz, 1H), 6.03 (dd, J = 6.5, 4.4 Hz, 1H), 5.43-5.31 (m, 2H), 4.42-4.27 (m, 2H), 4.01 (d, J = 1.1 Hz, 3H), 3.91 (s, 3H), 3.08-2.96 (m, 1H), 2.89-2.79 (m, 1H), 2.58 (dq, J = 13.5, 6.4 Hz, 1H), 2.15 (ddd, J = 13.3, 8.9, 4.3 Hz, 1H). | 618.4 |

TABLE 1A-continued

| Compound Structure | ¹H NMR | MS: (ES) m/z (M + H) |
|---|---|---|
| | ¹H NMR (400 MHz, Methanol-d₄) δ 9.00 (d, J = 2.1 Hz, 1H), 8.93 (s, 1H), 8.43 (s, 1H), 7.52 (d, J = 0.5 Hz, 1H), 7.45-7.29 (m, 4H), 7.27 (d, J = 8.2 Hz, 1H), 7.20 (t, J = 9.4 Hz, 2H), 7.10 (s, 1H), 6.03 (d, J = 5.6 Hz, 1H), 5.39 (s, 2H), 4.46-4.16 (m, 3H), 4.08 (d, J = 6.6 Hz, 1H), 3.13-2.95 (m, 1H), 2.89-2.65 (m, 1H), 2.65-2.44 (m, 4H), 2.32-2.02 (m, 1H). | 630.5 |
| | ¹H NMR (400 MHz, Methanol-d₄) δ 9.01 (s, 1H), 8.92 (d, J = 2.0 Hz, 1H), 8.47 (s, 1H), 7.50 (s, 1H), 7.42-7.35 (m, 3H), 7.33-7.29 (m, 2H), 7.27 (dd, J = 7.5, 1.2 Hz, 1H), 7.21 (dd, J = 18.2, 8.7 Hz, 1H), 7.12 (d, J = 1.8 Hz, 1H), 6.09-6.02 (m, 1H), 5.41 (d, J = 4.8 Hz, 2H), 4.43-4.25 (m, 4H), 3.07-2.96 (m, 2H), 2.84 (dd, J = 17.5, 8.3 Hz, 2H), 2.68-2.49 (m, 1H), 2.27-2.09 (m, 1H). | 615.4 |
| | ¹H NMR (400 MHz, Methanol-d₄) δ 8.99 (d, J = 2.1 Hz, 1H), 8.93 (d, J = 2.0 Hz, 1H), 8.43 (d, J = 2.2 Hz, 1H), 7.52 (s, 1H), 7.42-7.34 (m, 4H), 7.31 (s, 1H), 7.30-7.16 (m, 2H), 7.09 (d, J = 0.8 Hz, 1H), 6.08-5.89 (m, 1H), 5.39 (d, J = 3.9 Hz, 2H), 4.39 (d, J = 13.2 Hz, 1H), 4.32-4.24 (m, 1H), 4.12-3.97 (m, 1H), 3.64 (d, J = 7.1 Hz, 1H), 3.11-2.97 (m, 1H), 2.97-2.75 (m, 1H), 2.67-2.43 (m, 1H), 2.26-2.07 (m, 1H), 1.32 (d, J = 6.3 Hz, 3H). | 602.5 |
| | ¹H NMR (400 MHz, Methanol-d₄) δ 8.98 (d, J = 2.1 Hz, 1H), 8.93 (d, J = 1.8 Hz, 1H), 8.41 (s, 1H), 7.53 (d, J = 0.7 Hz, 1H), 7.45-7.30 (m, 5H), 7.30-7.22 (m, 1H), 7.23-7.15 (m, 1H), 7.10 (s, 1H), 6.10-5.98 (m, 1H), 5.37 (d, J = 3.4 Hz, 2H), 4.37 (d, J = 13.3 Hz, 1H), 4.32-4.20 (m, 2H), 3.90 (d, J = 3.6 Hz, 1H), 3.10-2.98 (m, 1H), 2.91-2.75 (m, 1H), 2.66-2.50 (m, 1H), 2.14 (d, J = 5.1 Hz, 1H), 1.23 (dd, J = 6.5, 0.7 Hz, 3H). | 602.4 |

TABLE 1A-continued

| Compound Structure | ¹H NMR | MS: (ES) m/z (M + H) |
|---|---|---|
| | ¹H NMR (400 MHz, Methanol-d₄) δ 8.98 (d, J = 2.1 Hz, 1H), 8.93 (d, J = 2.1 Hz, 1H), 8.41 (t, J = 2.1 Hz, 1H), 7.53 (s, 1H), 7.45-7.31 (m, 5H), 7.30-7.23 (m, 1H), 7.23-7.16 (m, 1H), 7.11 (s, 1H), 6.07-6.00 (m, 1H), 5.38 (d, J = 2.4 Hz, 2H), 4.37 (d, J = 13.2 Hz, 1H), 4.34-4.24 (m, 2H), 3.90 (d, J = 3.6 Hz, 1H), 3.07-2.97 (m, 1H), 2.92-2.73 (m, 1H), 2.73-2.50 (m, 1H), 2.28-2.06 (m, 1H), 1.23 (d, J = 6.7 Hz, 3H). | 602.5 |
| | ¹H NMR (400 MHz, Methanol-d₄) δ 8.99 (s, 1H), 8.90 (s, 1H), 8.45 (s, 1H), 7.50 (s, 1H), 7.42-7.38 (m, 3H), 7.35 (d, J = 8.2 Hz, 1H), 7.32-7.30 (m, 1H), 7.28-7.23 (m, 1H), 7.20 (t, J = 9.4 Hz, 1H), 7.06 (s, 1H), 6.08-5.95 (m, 1H), 5.38 (s, 2H), 4.43-4.09 (m, 2H), 3.97 (s, 1H), 3.83 (s, 1H), 3.57-3.53 (m, 1H), 3.05-2.99 (m, 1H), 2.97-2.68 (m, 1H), 2.63-2.44 (m, 1H), 2.25-2.00 (m, 1H). | 588.4 |
| | ¹H NMR (400 MHz, Methanol-d₄) δ 9.02-8.93 (m, 1H), 8.91 (d, J = 2.0 Hz, 1H), 8.48 (t, J = 2.0 Hz, 1H), 8.07-7.93 (m, 1H), 7.69-7.50 (m, 1H), 7.51-7.12 (m, 6H), 7.04 (s, 1H), 6.10-5.93 (m, 1H), 5.33 (d, J = 2.1 Hz, 2H), 4.20-3.91 (m, 2H), 3.85 (d, J = 4.4 Hz, 2H), 3.73 (d, J = 0.9 Hz, 3H), 3.40 (d, J = 1.5 Hz, 1H), 3.09-2.92 (m, 1H), 2.90-2.74 (m, 1H), 2.62-2.46 (m, 1H), 2.27-2.03 (m, 1H). | 602.3 |
| | ¹H NMR (400 MHz, Methanol-d₄) δ 8.99 (s, 1H), 8.91 (s, 1H), 8.43 (s, 1H), 7.51 (s, 1H), 7.48-7.10 (m, 7H), 7.04 (s, 1H), 5.99 (s, 1H), 5.39 (s, 2H), 4.20 (s, 2H), 3.58-3.51 (m, 1H), 3.05-2.91 (m, 1H), 2.97-2.74 (m, 1H), 2.63-2.48 (m, 1H), 2.25-2.06 (m, 1H), 1.53-1.40 (m, 3H). | 594.2 |

TABLE 1A-continued

| Compound Structure | ¹H NMR | MS: (ES) m/z (M + H) |
|---|---|---|
| | ¹H NMR (400 MHz, Methanol-d₄) δ 8.99 (d, J = 2.1 Hz, 1H), 8.89 (d, J = 2.0 Hz, 1H), 8.44 (t, J = 2.1 Hz, 1H), 7.41 (s, 1H), 7.41-7.07 (m, 7H), 6.97 (s, 1H), 5.94 (dd, J = 6.5, 4.3 Hz, 1H), 5.36 (d, J = 2.3 Hz, 2H), 4.19 (s, 2H), 3.12-2.92 (m, 1H), 2.92-2.65 (m, 1H), 2.59-2.32 (m, 1H), 2.21-1.94 (m, 1H), 1.35-1.16 (m, 2H), 1.01 (d, J = 2.7 Hz, 2H). | 606.2 |
| | ¹H NMR (400 MHz, Methanol-d₄) δ 9.00 (d, J = 2.1 Hz, 1H), 8.90 (d, J = 1.9 Hz, 1H), 8.44 (t, J = 2.0 Hz, 1H), 7.52 (s, 1H), 7.47-7.13 (m, 7H), 7.03 (s, 1H), 5.98 (dd, J = 6.5, 4.3 Hz, 1H), 5.38 (d, J = 2.8 Hz, 2H), 4.07 (s, 2H), 3.01 (ddd, J = 16.3, 8.3, 5.5 Hz, 1H), 2.81 (ddd, J = 16.2, 8.2, 5.5 Hz, 1H), 2.51 (dddd, J = 11.6, 6.4, 5.2, 2.9 Hz, 3H), 2.39-2.24 (m, 2H), 2.24-2.02 (m, 2H), 1.99-1.85 (m, 1H). | 598.2 |
| | ¹H NMR (400 MHz, Methanol-d) δ 8.97 (s, 1H), 8.92 (s, 1H), 8.41 (s, 1H), 7.57 (s, 1H), 7.48-7.35 (m, 5H), 7.32-7.19 (m, 3H), 6.10 (dd, J = 16 Hz, 3.6 Hz, 1H), 5.49-5.29 (m, 3H), 4.44-4.28 (m, 2H), 4.12-4.04 (m, 1H), 3.65 (d, J = 6.8 Hz, 1H), 3.44-3.32 (m, 1H), 3.16-3.02 (m, 2H), 1.32 (d, J = 6.4 Hz, 3H). | 620.2 |
| | ¹H NMR (400 MHz, Methanol-d₄) δ 8.97 (d, J = 2.0 Hz, 1H), 8.90 (s, 1H), 8.39 (s, 1H), 7.93 (s, 1H), 7.45-7.31 (m, 6H), 7.26 (t, J = 7.4 Hz, 1H), 7.24-7.17 (m, 1H), 6.03 (s, 1H), 4.21-3.93 (m, 2H), 3.83-3.68 (m, 1H), 3.68-3.56 (m, 1H), 3.09-2.96 (m, 1H), 2.90-2.76 (m, 1H), 2.63-2.47 (m, 1H), 2.22-2.12 (m, 1H), 1.29 (s, 3H). | 572.1 |

TABLE 1A-continued
| Compound Structure | ¹H NMR | MS: (ES) m/z (M + H) |
|---|---|---|
| 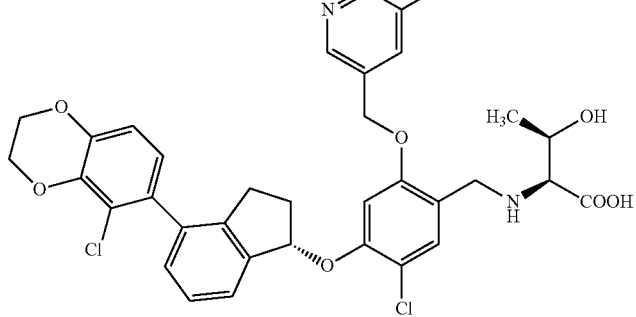 | ¹H NMR (400 MHz, Methanol-d₄) δ 9.00 (s, 1H), 8.91 (s, 1H), 8.45 (s, 1H), 7.47 (s, 1H), 7.28 (dd, J = 15.5, 8.2 Hz, 2H), 7.15 (dd, J = 7.2, 1.4 Hz, 1H), 7.05 (s, 1H), 6.86 (d, J = 8.4 Hz, 1H), 6.80-6.66 (m, 1H), 6.05-5.88 (m, 1H), 5.37 (s, 2H), 4.90-4.55 (m, 2H), 4.37 (d, J = 4.9 Hz, 2H), 4.33-4.30 (m, 2H), 4.23-4.12 (m, 1H), 4.02-3.91 (m, 1H), 3.04-2.66 (m, 2H), 2.59-2.48 (m, 1H), 2.13-2.06 (m, 1H), 1.30-1.25 (m, 3H). | 676.1 |
| 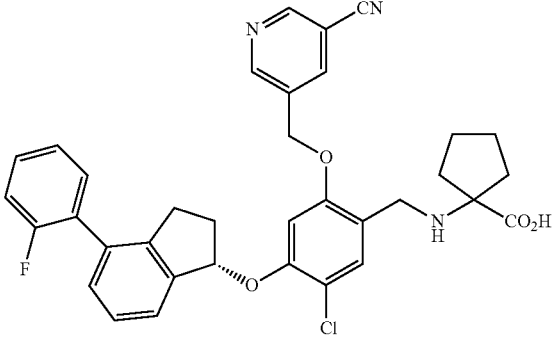 [SMILES: N#Cc1cncc(COc2cc(O[C@H]3CCc4c(-c5ccccc5F)cccc43)c(Cl)cc2CNC2(C(=O)O)CCCC2)c1] | ¹H NMR (400 MHz, Methanol-d₄) δ 9.06-8.94 (m, 1H), 8.93 (d, J = 2.0 Hz, 1H), 8.44 (td, J = 2.1, 0.7 Hz, 1H), 7.55 (d, J = 0.7 Hz, 1H), 7.46-7.11 (m, 7H), 7.05 (s, 1H), 6.00 (dd, J = 6.4, 4.4 Hz, 1H), 5.37 (d, J = 3.2 Hz, 2H), 4.17 (s, 2H), 3.10-2.90 (m, 1H), 2.82 (ddd, J = 16.2, 8.2, 5.6 Hz, 1H), 2.66-2.41 (m, 1H), 2.36-1.96 (m, 3H), 1.96-1.55 (m, 6H). | 612.1 |
TABLE 1B
| Compound Structure | MS: (ES) m/z (M + H) | RP HPLC R_t (min) |
|---|---|---|
| 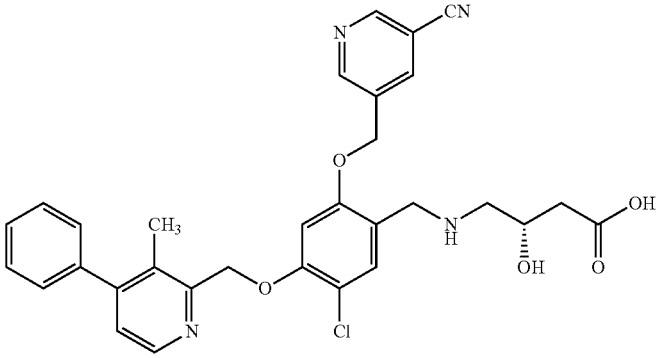 [SMILES: Cc1c(-c2ccccc2)ccnc1COc1cc(OCc2cncc(C#N)c2)c(CNC[C@@H](O)CC(=O)O)cc1Cl] | 573.1 | 2.48 |
| 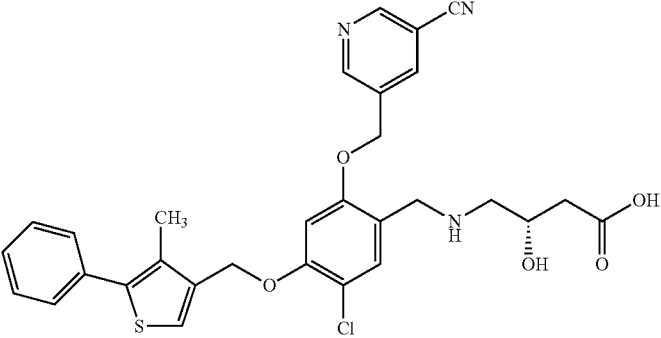 [SMILES: Cc1c(COc2cc(OCc3cncc(C#N)c3)c(CNC[C@@H](O)CC(=O)O)cc2Cl)csc1-c1ccccc1] | 578.1 | 2.49 |

TABLE 1B-continued
| Compound Structure | MS: (ES) m/z (M + H) | RP HPLC R$_t$ (min) |
|---|---|---|
| 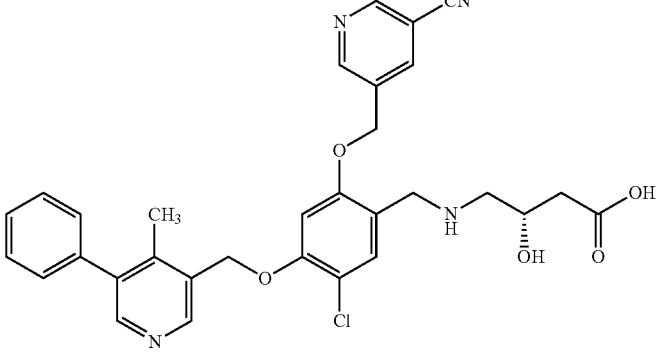 [SMILES: Cc1c(COc2cc(OCc3cncc(C#N)c3)c(CNC[C@@H](O)CC(=O)O)cc2Cl)cncc1-c1ccccc1] | 573.1 | 2.2 |
| 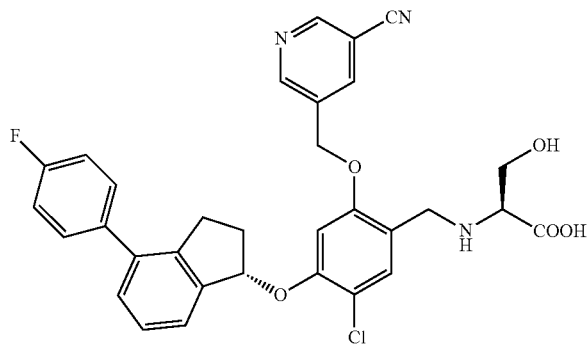 [SMILES: N#Cc1cncc(COc2cc(O[C@H]3CCc4c(-c5ccc(F)cc5)cccc43)c(Cl)cc2CN[C@@H](CO)C(=O)O)c1] | 588 | 1.71 |
| 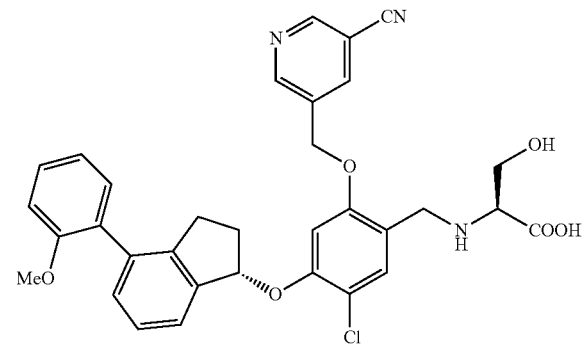 [SMILES: COc1ccccc1-c1cccc2c1CC[C@@H]2Oc1cc(OCc2cncc(C#N)c2)c(CN[C@@H](CO)C(=O)O)cc1Cl] | 600.0. | 1.58 |
| 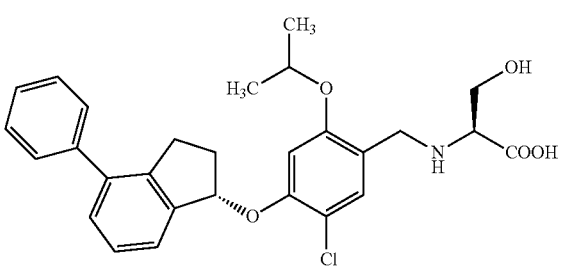 [SMILES: CC(C)Oc1cc(O[C@H]2CCc3c(-c4ccccc4)cccc32)c(Cl)cc1CN[C@@H](CO)C(=O)O] | 518.4 | 2.32 |

TABLE 1B-continued
| Compound Structure | MS: (ES) m/z (M + H) | RP HPLC $R_t$ (min) |
|---|---|---|
| 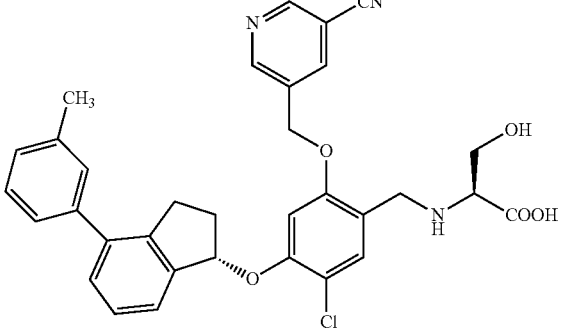 | 584 | 1.72 |
| 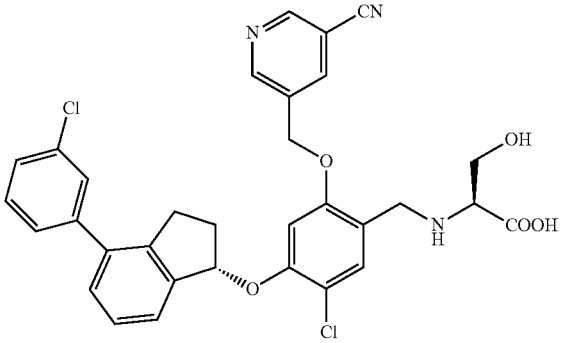 | 603.9. | 1.82 |
| 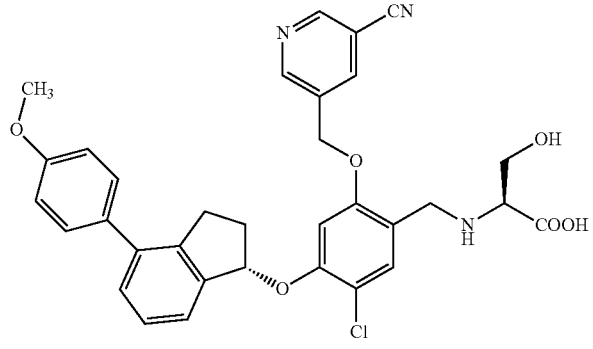 [SMILES: COc1ccc(-c2cccc3c2CC[C@@H]3Oc2cc(OCc3cncc(C#N)c3)c(CN[C@@H](CO)C(=O)O)cc2Cl)cc1] | 600.3 | 2.23 |
| 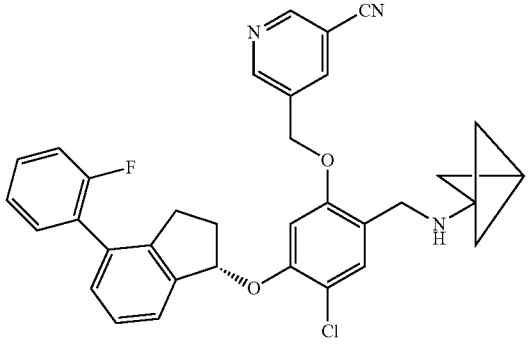 [SMILES: N#Cc1cncc(COc2cc(O[C@H]3CCc4c(-c5ccccc5F)cccc43)c(Cl)cc2CNC23CC(C2)C3)c1] | 566.4 | 2.68 |

TABLE 1B-continued
| Compound Structure | MS: (ES) m/z (M + H) | RP HPLC $R_t$ (min) |
|---|---|---|
| 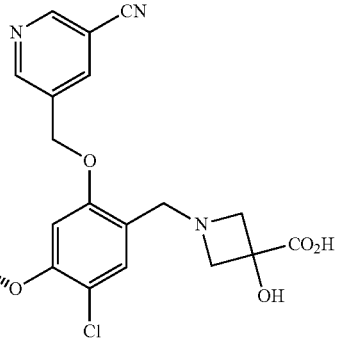 | 600.3. | 3.54* |
| 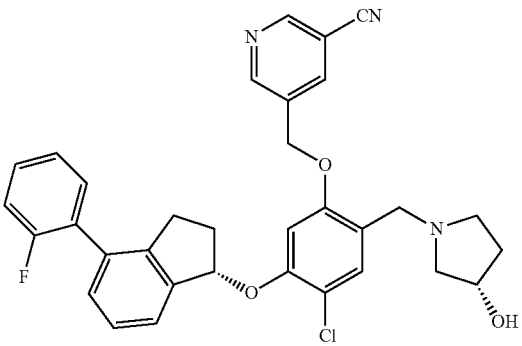 [SMILES: N#Cc1cncc(COc2cc(O[C@H]3CCc4c(-c5ccccc5F)cccc43)c(Cl)cc2CN2CC[C@H](O)C2)c1] | 570.3 | 3.42* |
| 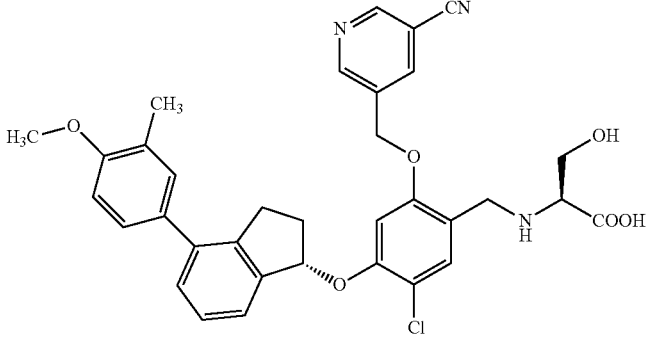 [SMILES: COc1ccc(-c2cccc3c2CC[C@@H]3Oc2cc(OCc3cncc(C#N)c3)c(CN[C@@H](CO)C(=O)O)cc2Cl)cc1C] | 636.5 | 2.13 |
| 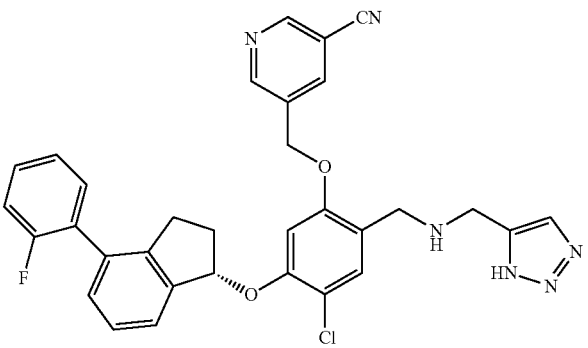 [SMILES: N#Cc1cncc(COc2cc(O[C@H]3CCc4c(-c5ccccc5F)cccc43)c(Cl)cc2CNCc2cnn[nH]2)c1] | 581.3. | 2.28 |

TABLE 1B-continued

| Compound Structure | MS: (ES) m/z (M + H) | RP HPLC R$_t$ (min) |
|---|---|---|
| (structure) | 627.5 | 1.29 |
| (structure) | 613.5 | 1.57 |
| (structure) | 612.5 | 2.4 |
| (structure) | 612.5 | 2.31 |

TABLE 1B-continued
| Compound Structure | MS: (ES) m/z (M + H) | RP HPLC $R_t$ (min) |
|---|---|---|
| 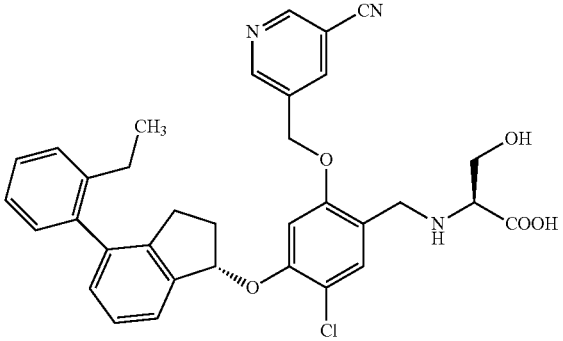 [SMILES: CCc1ccccc1-c1cccc2c1CC[C@@H]2Oc1cc(OCc2cncc(C#N)c2)c(CN[C@@H](CO)C(=O)O)cc1Cl] | 620.4 | 2.25 |
| 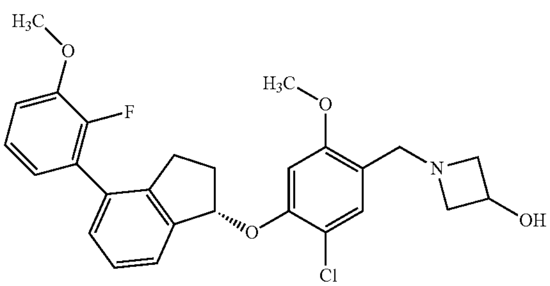 [SMILES: COc1cc(O[C@H]2CCc3c(-c4cccc(OC)c4F)cccc32)c(Cl)cc1CN1CC(O)C1] | 484.4. | 1.91 |
| 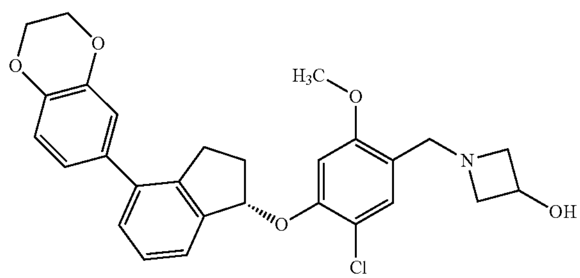 [SMILES: COc1cc(O[C@H]2CCc3c(-c4ccc5c(c4)OCCO5)cccc32)c(Cl)cc1CN1CC(O)C1] | 494.4 | 2 |
| 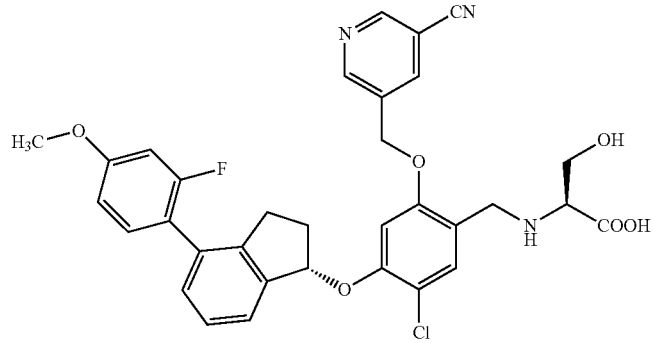 [SMILES: COc1ccc(-c2cccc3c2CC[C@@H]3Oc2cc(OCc3cncc(C#N)c3)c(CN[C@@H](CO)C(=O)O)cc2Cl)c(F)c1] | 618.5 | 2.05 |

TABLE 1B-continued

| Compound Structure | MS: (ES) m/z (M + H) | RP HPLC R$_t$ (min) |
|---|---|---|
| 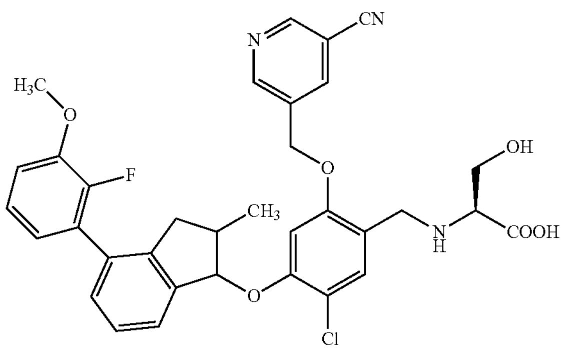 [SMILES: COc1cccc(-c2cccc3c2CC(C)C3Oc2cc(OCc3cncc(C#N)c3)c(CN[C@@H](CO)C(=O)O)cc2Cl)c1F] | 632.3. | 2.95 |
| 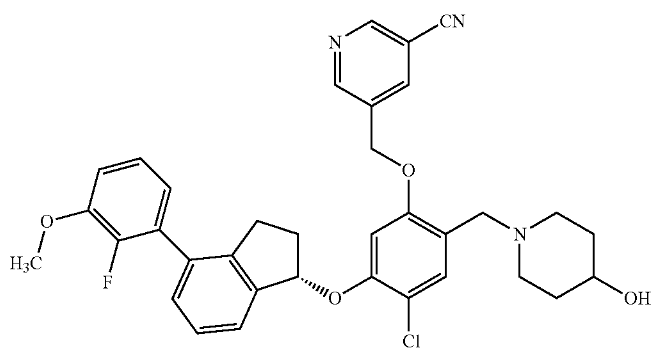 [SMILES: COc1cccc(-c2cccc3c2CC[C@@H]3Oc2cc(OCc3cncc(C#N)c3)c(CN3CCC(O)CC3)cc2Cl)c1F] | 614.2 | 3.65* |
| 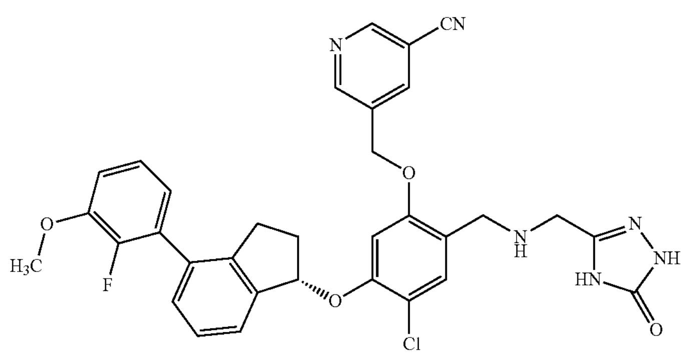 [SMILES: COc1cccc(-c2cccc3c2CC[C@@H]3Oc2cc(OCc3cncc(C#N)c3)c(CNCc3n[nH]c(=O)[nH]3)cc2Cl)c1F] | 627.4 | 3.45* |
| 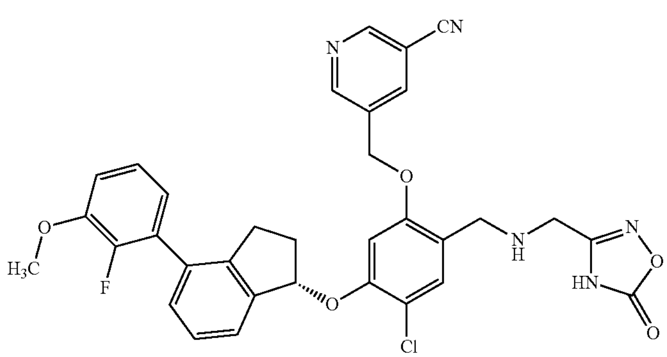 [SMILES: COc1cccc(-c2cccc3c2CC[C@@H]3Oc2cc(OCc3cncc(C#N)c3)c(CNCc3noc(=O)[nH]3)cc2Cl)c1F] | 628.4. | 3.55* |

TABLE 1B-continued

| Compound Structure | MS: (ES) m/z (M + H) | RP HPLC R$_t$ (min) |
|---|---|---|
| (structure) | 614.4 | 3.82* |
| (structure) | 554.5 | 2.16 |
| (structure) | 614.4 | 3.89* |
| (structure) | 496.3 | 4.3* |
| (structure) | 664.4 | 2.73 |

TABLE 1B-continued
| Compound Structure | MS: (ES) m/z (M + H) | RP HPLC $R_t$ (min) |
|---|---|---|
| 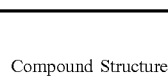 | 602.4. | 2.2 |
| 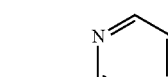 | 672.4 | 2.44 |
| 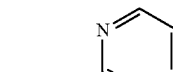 | 614.4 | 2.35 |
| 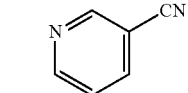 | 630.4. | 2.33 |

TABLE 1B-continued
| Compound Structure | MS: (ES) m/z (M + H) | RP HPLC R$_t$ (min) |
|---|---|---|
| 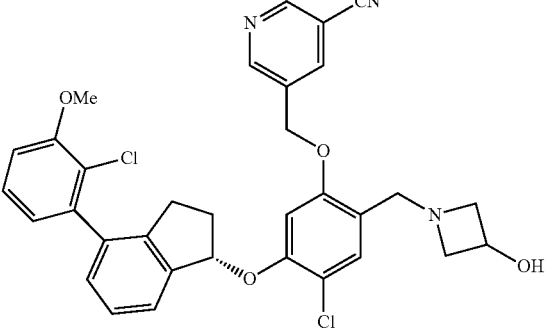 | 602.4 | 2.65 |
| 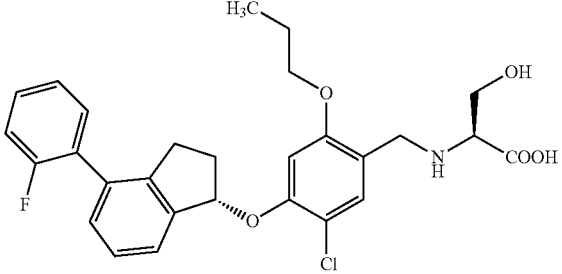 [SMILES: CCCOc1cc(O[C@H]2CCc3c(-c4ccccc4F)cccc32)c(Cl)cc1CN[C@@H](CO)C(=O)O] | 536.5 | 2.19 |
| 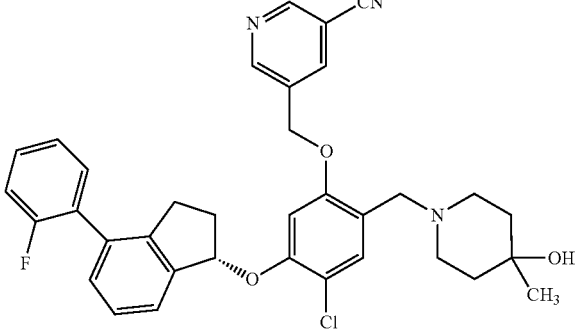 [SMILES: CC1(O)CCN(Cc2cc(Cl)c(O[C@H]3CCc4c(-c5ccccc5F)cccc43)cc2OCc2cncc(C#N)c2)CC1] | 598.4. | 3.79* |
| 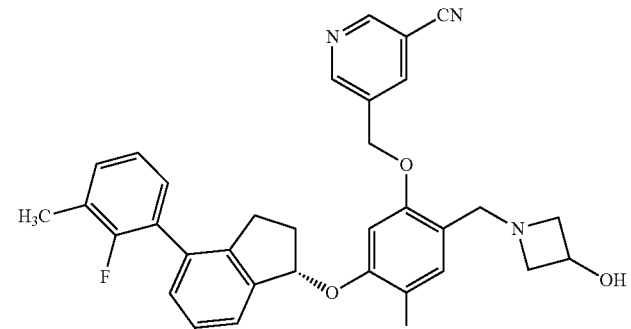 | 570.5 | 2.27 |

TABLE 1B-continued

| Compound Structure | MS: (ES) m/z (M + H) | RP HPLC R_t (min) |
|---|---|---|
| (structure) | 586.5 | 2.16 |
| (structure) | 637.3. | |
| (structure) | 614.5 | 2.36 |
| (structure) | 601.4 | 3.46* |

TABLE 1B-continued

| Compound Structure | MS: (ES) m/z (M + H) | RP HPLC R$_t$ (min) |
|---|---|---|
| 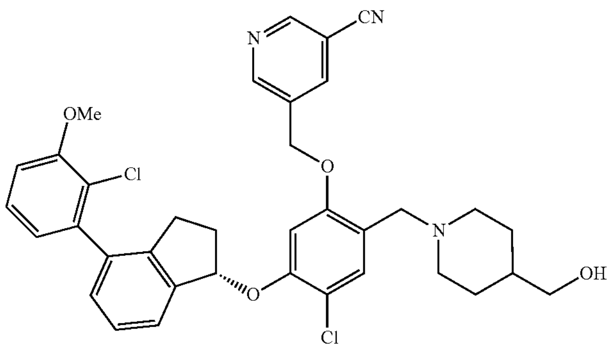 [SMILES: COc1cccc(-c2cccc3c2CC[C@@H]3Oc2cc(OCc3cncc(C#N)c3)c(CN3CCC(CO)CC3)cc2Cl)c1Cl] | 644.4. | 2.75 |
| 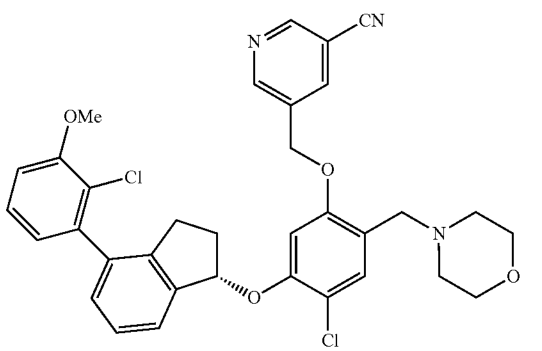 [SMILES: COc1cccc(-c2cccc3c2CC[C@@H]3Oc2cc(OCc3cncc(C#N)c3)c(CN3CCOCC3)cc2Cl)c1Cl] | 616.4 | 3.17 |
| 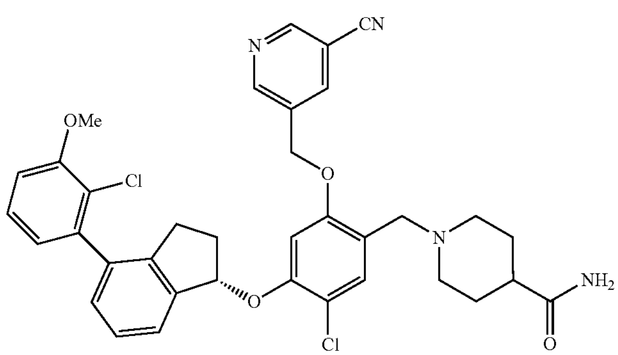 [SMILES: COc1cccc(-c2cccc3c2CC[C@@H]3Oc2cc(OCc3cncc(C#N)c3)c(CN3CCC(C(N)=O)CC3)cc2Cl)c1Cl] | 657.4 | 2.55 |
| 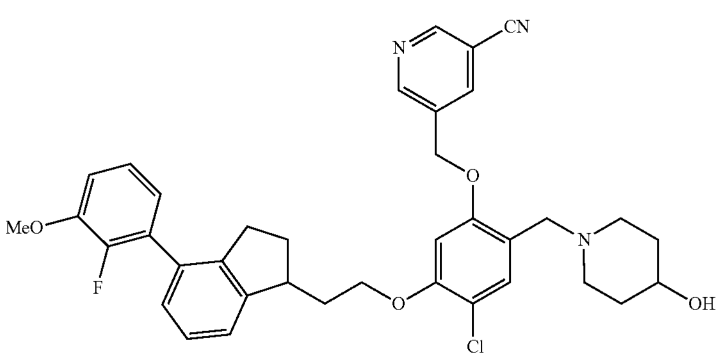 [SMILES: COc1cccc(-c2cccc3c2CCC3CCOc2cc(OCc3cncc(C#N)c3)c(CN3CCC(O)CC3)cc2Cl)c1F] | 642.5. | 2.37 |

TABLE 1B-continued
| Compound Structure | MS: (ES) m/z (M + H) | RP HPLC R_t (min) |
|---|---|---|
| 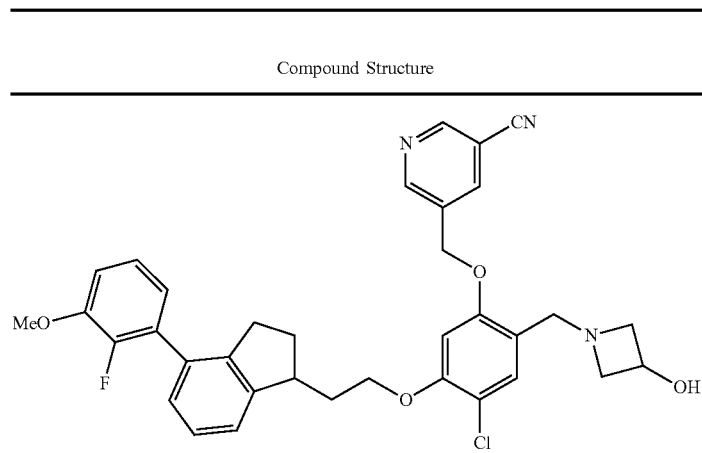 | 614.5 | 2.01 |
| 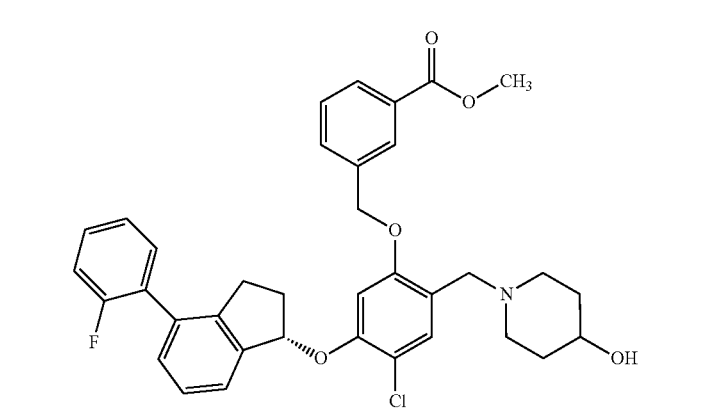 [SMILES: COC(=O)c1cccc(COc2cc(O[C@H]3CCc4c(-c5ccccc5F)cccc43)c(Cl)cc2CN2CCC(O)CC2)c1] | 616.4 | 4.05* |
| 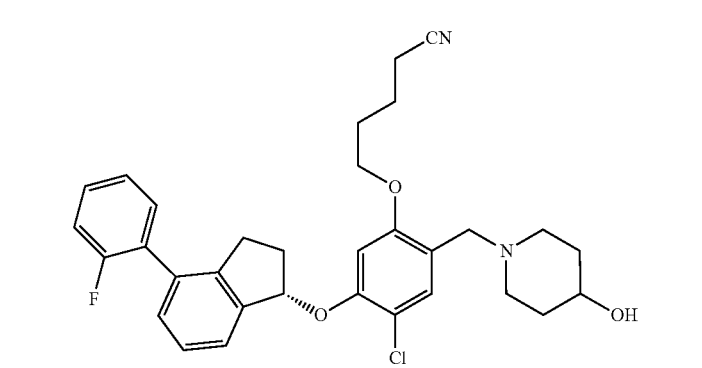 [SMILES: N#CCCCCOc1cc(O[C@H]2CCc3c(-c4ccccc4F)cccc32)c(Cl)cc1CN1CCC(O)CC1] | 549.3 | 3.75 |
| 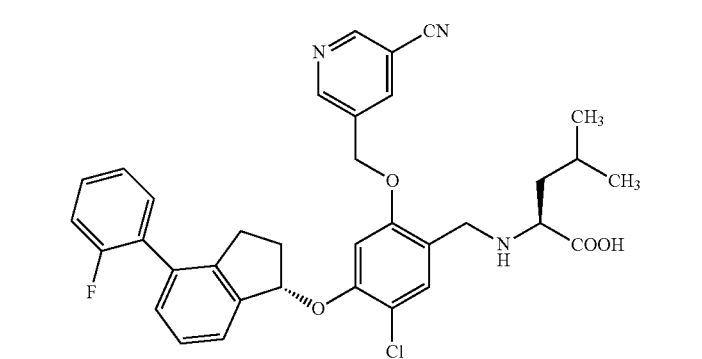 [SMILES: CC(C)C[C@H](NCc1cc(Cl)c(O[C@H]2CCc3c(-c4ccccc4F)cccc32)cc1OCc1cncc(C#N)c1)C(=O)O] | 614.5 | 2.35 |

TABLE 1B-continued
| Compound Structure | MS: (ES) m/z (M + H) | RP HPLC $R_t$ (min) |
|---|---|---|
| 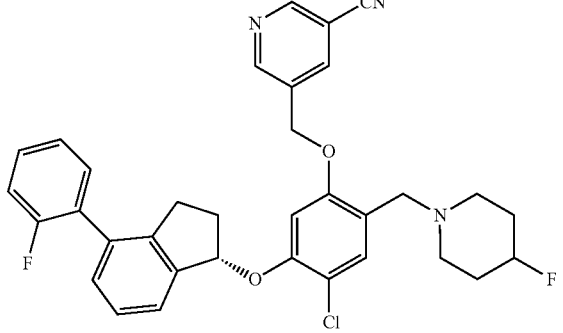 [SMILES: N#Cc1cncc(COc2cc(O[C@H]3CCc4c(-c5ccccc5F)cccc43)c(Cl)cc2CN2CCC(F)CC2)c1] | 586.4. | 2.87 |
| 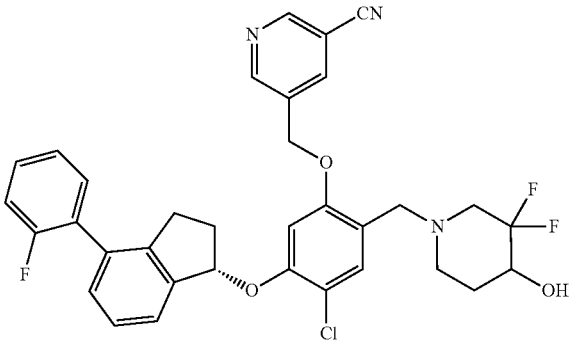 [SMILES: N#Cc1cncc(COc2cc(O[C@H]3CCc4c(-c5ccccc5F)cccc43)c(Cl)cc2CN2CCC(O)C(F)(F)C2)c1] | 620.4 | 2.73 |
| 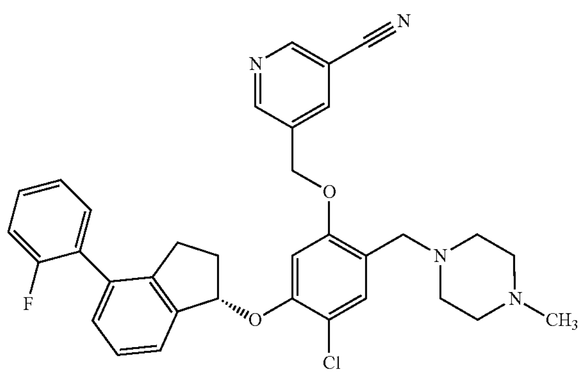 [SMILES: CN1CCN(Cc2cc(Cl)c(O[C@H]3CCc4c(-c5ccccc5F)cccc43)cc2OCc2cncc(C#N)c2)CC1] | 583.4 | 3.84* |
| 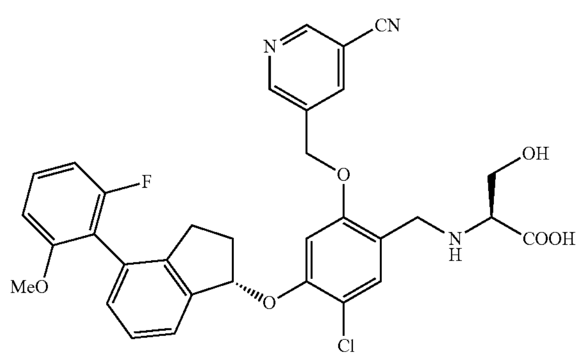 [SMILES: COc1cccc(F)c1-c1cccc2c1CC[C@@H]2Oc1cc(OCc2cncc(C#N)c2)c(CN[C@@H](CO)C(=O)O)cc1Cl] | 640.5 | 2.07 |

TABLE 1B-continued

| Compound Structure | MS: (ES) m/z (M + H) | RP HPLC R$_t$ (min) |
|---|---|---|
| 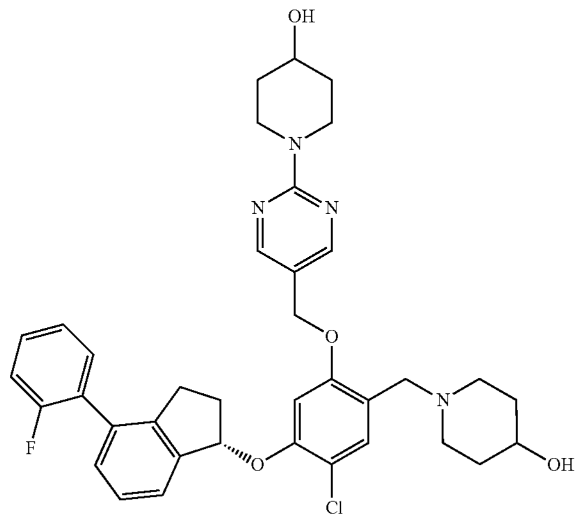 [SMILES: OC1CCN(Cc2cc(Cl)c(O[C@H]3CCc4c(-c5ccccc5F)cccc43)cc2OCc2cnc(N3CCC(O)CC3)nc2)CC1] | 659.4 | 3.57* |
| 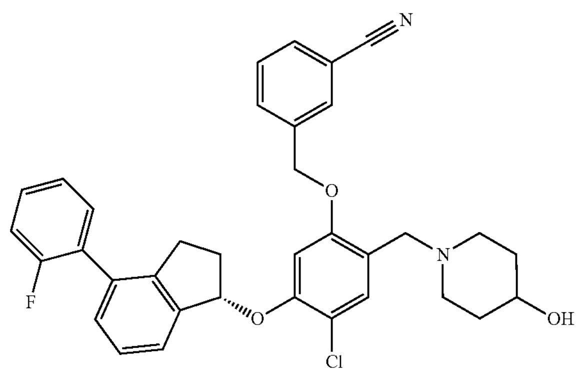 [SMILES: N#Cc1cccc(COc2cc(O[C@H]3CCc4c(-c5ccccc5F)cccc43)c(Cl)cc2CN2CCC(O)CC2)c1] | 583.2 | 3.81* |
| 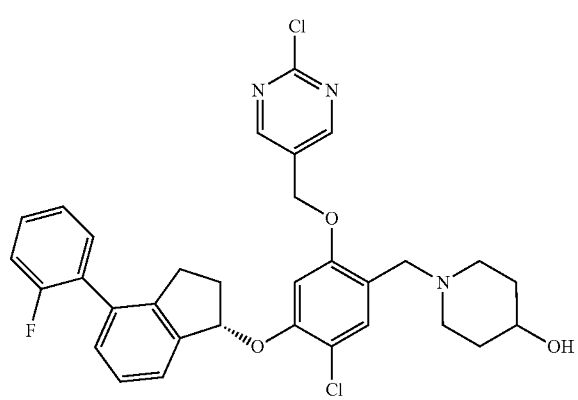 [SMILES: OC1CCN(Cc2cc(Cl)c(O[C@H]3CCc4c(-c5ccccc5F)cccc43)cc2OCc2cnc(Cl)nc2)CC1] | 594.4 | 3.92* |

TABLE 1B-continued
| Compound Structure | MS: (ES) m/z (M + H) | RP HPLC R$_t$ (min) |
|---|---|---|
| 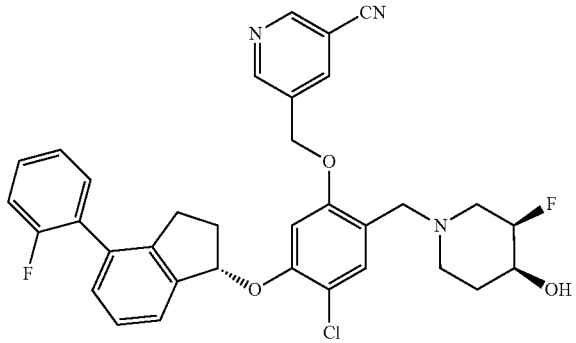 [SMILES: N#Cc1cncc(COc2cc(O[C@H]3CCc4c(-c5ccccc5F)cccc43)c(Cl)cc2CN2CC[C@H](O)[C@H](F)C2)c1] | 602.2 | 3.86* |
| 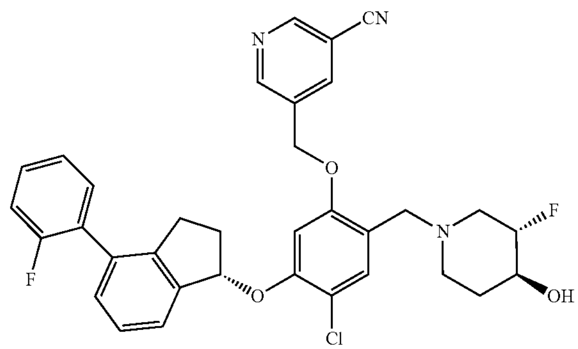 [SMILES: N#Cc1cncc(COc2cc(O[C@H]3CCc4c(-c5ccccc5F)cccc43)c(Cl)cc2CN2CC[C@H](O)[C@@H](F)C2)c1] | 602.4 | 1.76 |
| 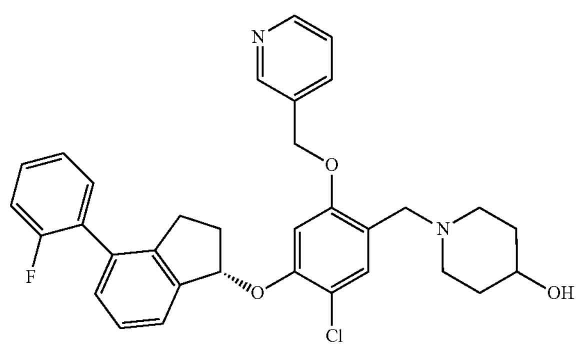 [SMILES: OC1CCN(Cc2cc(Cl)c(O[C@H]3CCc4c(-c5ccccc5F)cccc43)cc2OCc2cccnc2)CC1] | 559.4 | 3.17* |
| 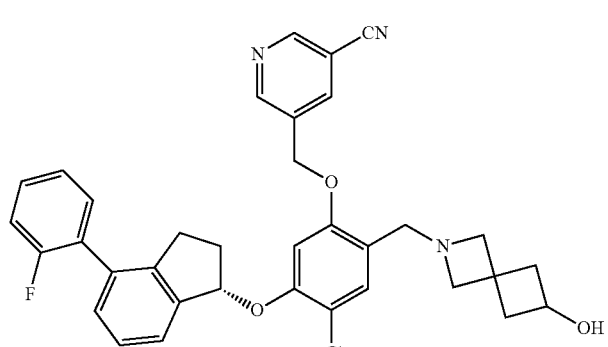 | 596.3 | 2.19 |

TABLE 1B-continued
| Compound Structure | MS: (ES) m/z (M + H) | RP HPLC R$_t$ (min) |
|---|---|---|
| 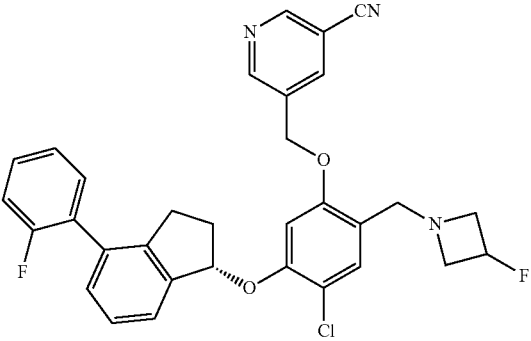 [SMILES: N#Cc1cncc(COc2cc(O[C@H]3CCc4c(-c5ccccc5F)cccc43)c(Cl)cc2CN2CC(F)C2)c1] | 558.3 | 2.47 |
| 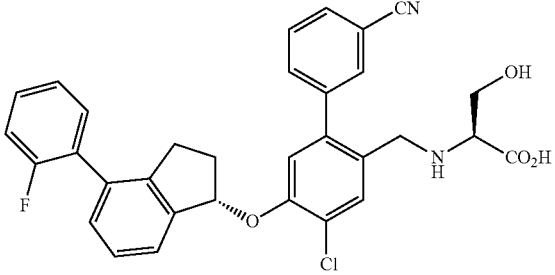 [SMILES: N#Cc1cccc(-c2cc(O[C@H]3CCc4c(-c5ccccc5F)cccc43)c(Cl)cc2CN[C@@H](CO)C(=O)O)c1] | 557.4 | 2.4 |
| 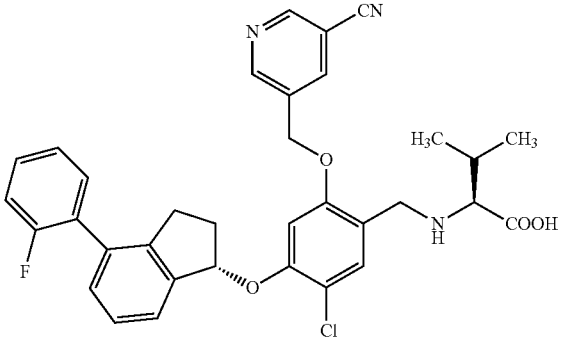 [SMILES: CC(C)[C@H](NCc1cc(Cl)c(O[C@H]2CCc3c(-c4ccccc4F)cccc32)cc1OCc1cncc(C#N)c1)C(=O)O] | 600.4 | 2.25 |
| 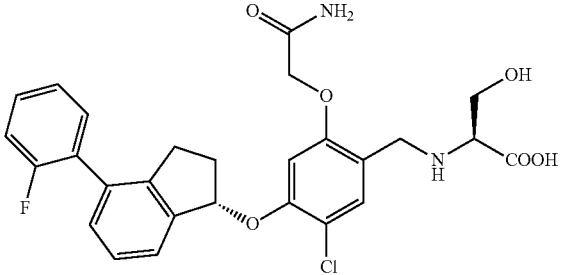 [SMILES: NC(=O)COc1cc(O[C@H]2CCc3c(-c4ccccc4F)cccc32)c(Cl)cc1CN[C@@H](CO)C(=O)O] | 529.4 | 1.81 |
| 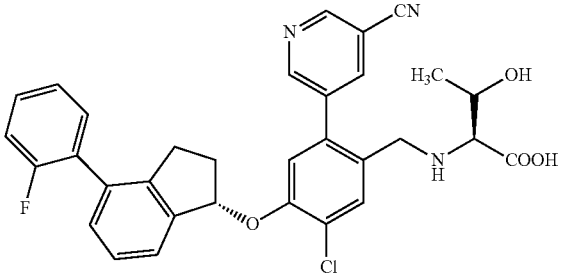 [SMILES: CC(O)[C@H](NCc1cc(Cl)c(O[C@H]2CCc3c(-c4ccccc4F)cccc32)cc1-c1cncc(C#N)c1)C(=O)O] | 572.4 | 2.09 |

TABLE 1B-continued

| Compound Structure | MS: (ES) m/z (M + H) | RP HPLC R$_t$ (min) |
|---|---|---|
| 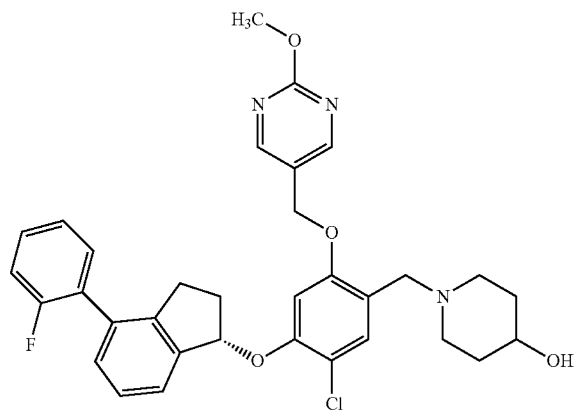 [SMILES: COc1ncc(COc2cc(O[C@H]3CCc4c(-c5ccccc5F)cccc43)c(Cl)cc2CN2CCC(O)CC2)cn1] | 590.4 | 3.57* |
| 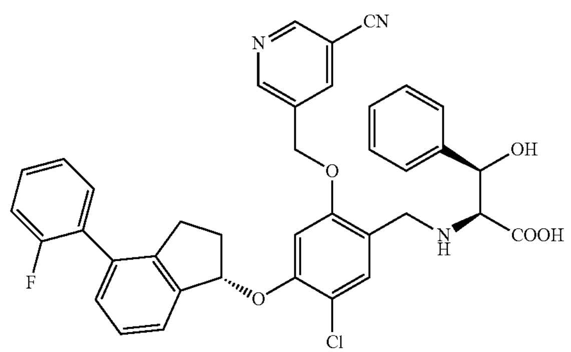 [SMILES: N#Cc1cncc(COc2cc(O[C@H]3CCc4c(-c5ccccc5F)cccc43)c(Cl)cc2CN[C@H](C(=O)O)[C@H](O)c2ccccc2)c1] | 664.4 | 2.52 |
| 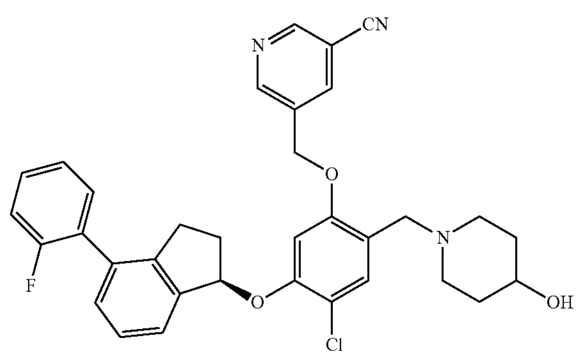 [SMILES: N#Cc1cncc(COc2cc(O[C@@H]3CCc4c(-c5ccccc5F)cccc43)c(Cl)cc2CN2CCC(O)CC2)c1] | 584.5 | 2.26 |
| 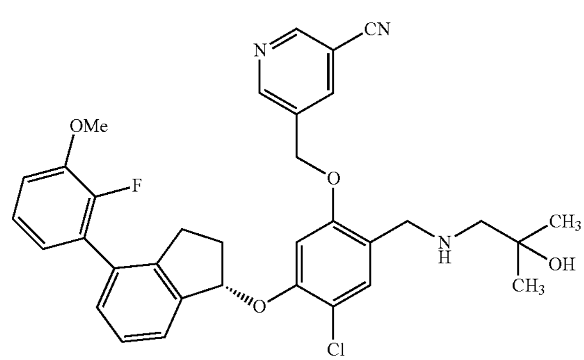 [SMILES: COc1cccc(-c2cccc3c2CC[C@@H]3Oc2cc(OCc3cncc(C#N)c3)c(CNCC(C)(C)O)cc2Cl)c1F] | 602.4 | 2.46 |

TABLE 1B-continued
| Compound Structure | MS: (ES) m/z (M + H) | RP HPLC R$_t$ (min) |
|---|---|---|
| 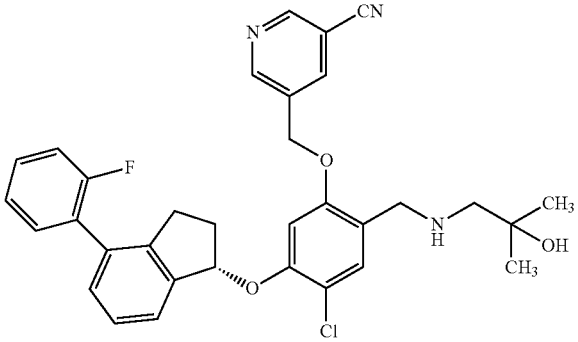 [SMILES: CC(C)(O)CNCc1cc(Cl)c(O[C@H]2CCc3c(-c4ccccc4F)cccc32)cc1OCc1cncc(C#N)c1] | 572.3 | 2.42 |
| 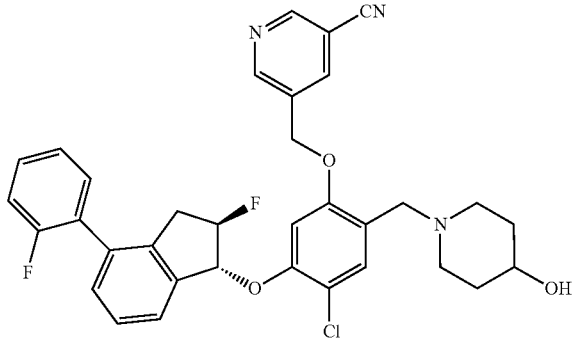 [SMILES: N#Cc1cncc(COc2cc(O[C@@H]3c4cccc(-c5ccccc5F)c4C[C@H]3F)c(Cl)cc2CN2CCC(O)CC2)c1] | 602.2 | 3.56* |
| 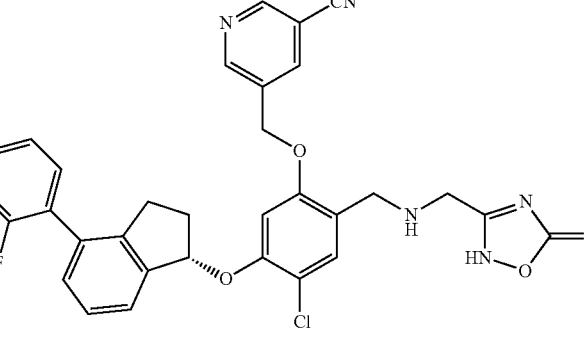 | 620.1 | 2.27 |
| 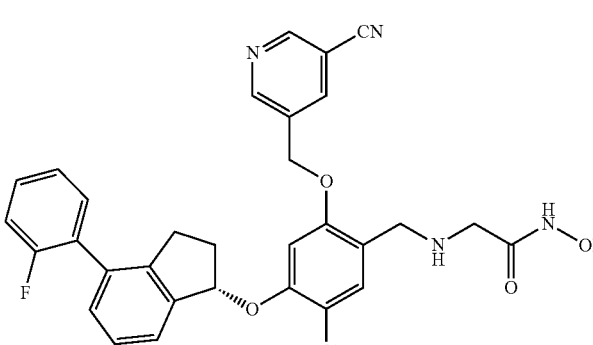 | 573.2 | 2.08 |

TABLE 1B-continued

| Compound Structure | MS: (ES) m/z (M + H) | RP HPLC R_t (min) |
|---|---|---|
| 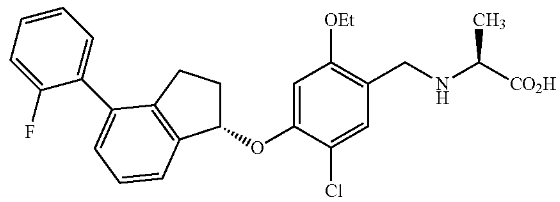 [SMILES: CCOc1cc(O[C@H]2CCc3c(-c4ccccc4F)cccc32)c(Cl)cc1CN[C@@H](C)C(=O)O] | 506.2 | 2.62 |
| 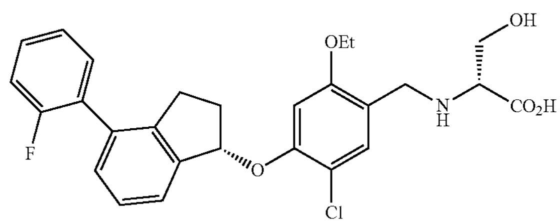 [SMILES: CCOc1cc(O[C@H]2CCc3c(-c4ccccc4F)cccc32)c(Cl)cc1CN[C@H](CO)C(=O)O] | 522 | 2.48 |
| 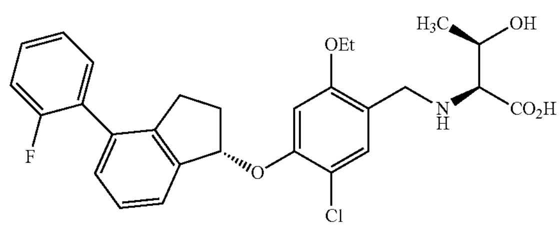 [SMILES: CCOc1cc(O[C@H]2CCc3c(-c4ccccc4F)cccc32)c(Cl)cc1CN[C@H](C(=O)O)[C@@H](C)O] | 514.1 | 2.39 |
| 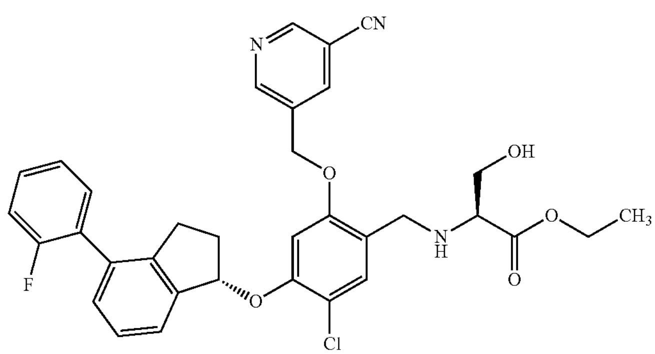 [SMILES: CCOC(=O)[C@H](CO)NCc1cc(Cl)c(O[C@H]2CCc3c(-c4ccccc4F)cccc32)cc1OCc1cncc(C#N)c1] | 616.2 | 2.45 |
| 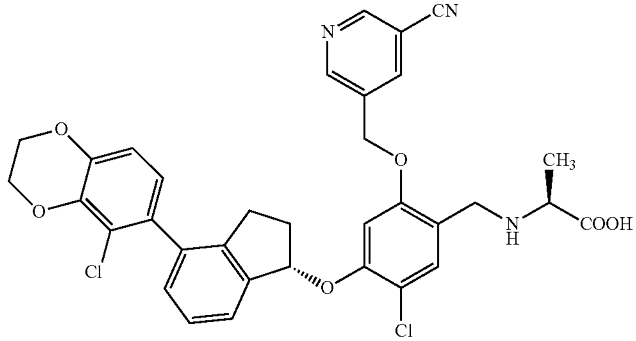 [SMILES: C[C@H](NCc1cc(Cl)c(O[C@H]2CCc3c(-c4ccc5c(c4Cl)OCCO5)cccc32)cc1OCc1cncc(C#N)c1)C(=O)O] | 668.1 | 2.5 |

TABLE 1B-continued
| Compound Structure | MS: (ES) m/z (M + H) | RP HPLC R_t (min) |
|---|---|---|
| 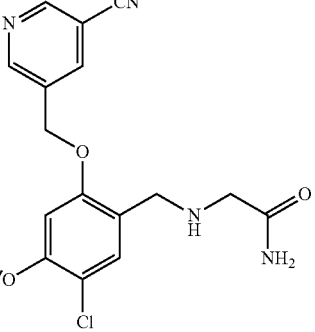 | 557.2 | 1.98 |
| 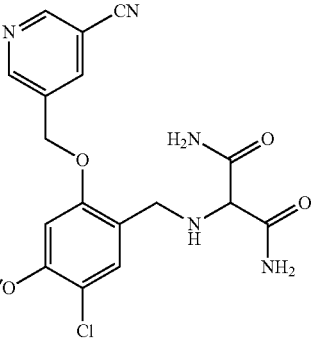 | 600.2 | 2.37 |
| 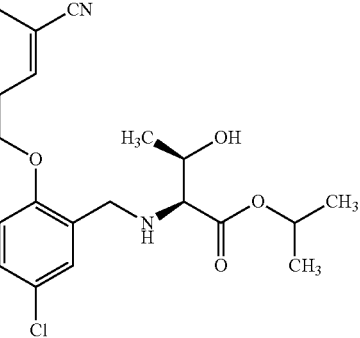 | 644.2 | 3.97* |
| 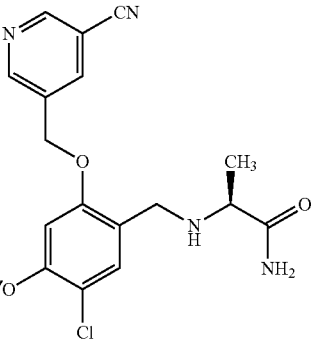 | 571.2 | 2.08 |

TABLE 1B-continued
| Compound Structure | MS: (ES) m/z (M + H) | RP HPLC R*t* (min) |
|---|---|---|
| 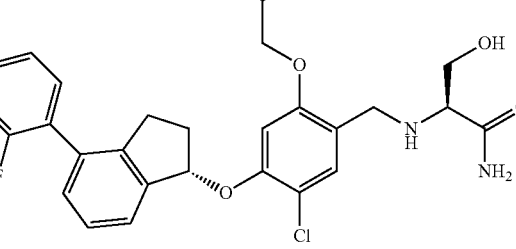 | 587.2 | 2.28 |
| 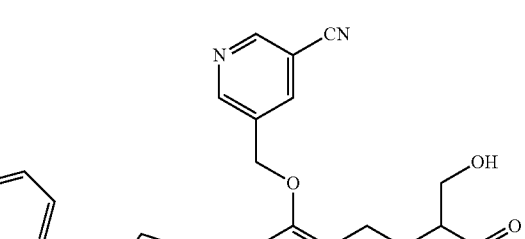 | 603.2 | 2.28 |
| 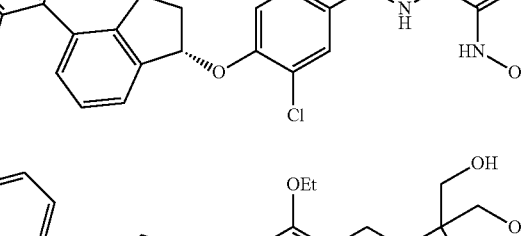 | 516.2 | 2.36 |
| 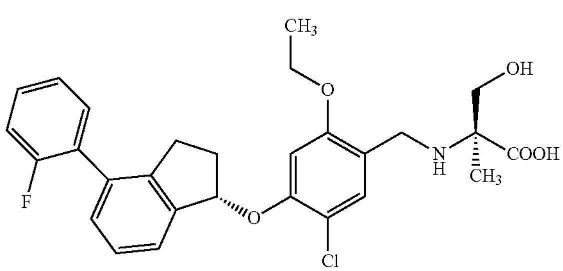 | 536.2 | 2.78 |
| 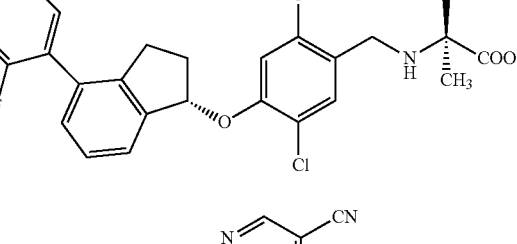 | 638.2 | 2.67 |

TABLE 1B-continued

| Compound Structure | MS: (ES) m/z (M + H) | RP HPLC R$_t$ (min) |
|---|---|---|
| 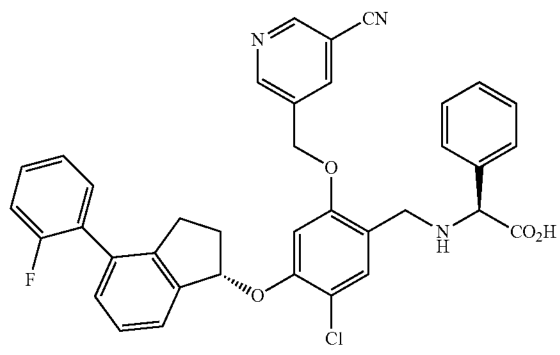 [SMILES: N#Cc1cncc(COc2cc(O[C@H]3CCc4c(-c5ccccc5F)cccc43)c(Cl)cc2CN[C@H](C(=O)O)c2ccccc2)c1] | 634.2 | 2.57 |

TABLE 1C

| Compound Structure | MS: (ES) m/z (M + H) | RP HPLC R$_t$ (min) |
|---|---|---|
| 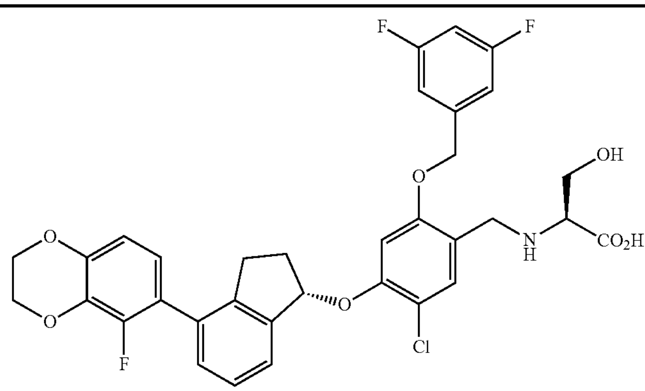 | 656.1 | 2.51 |
| 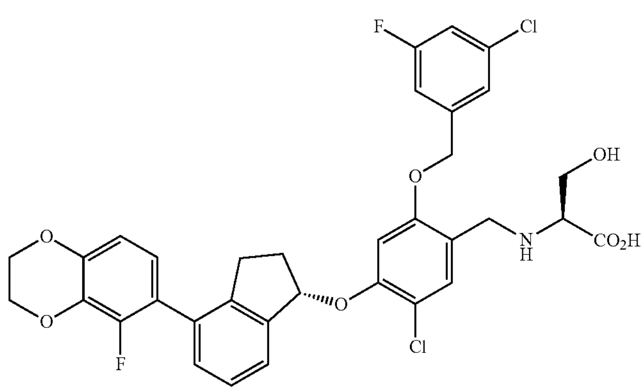 | 672 | 2.72 |

TABLE 1C-continued

| Compound Structure | MS: (ES) m/z (M + H) | RP HPLC R_t (min) |
|---|---|---|
| 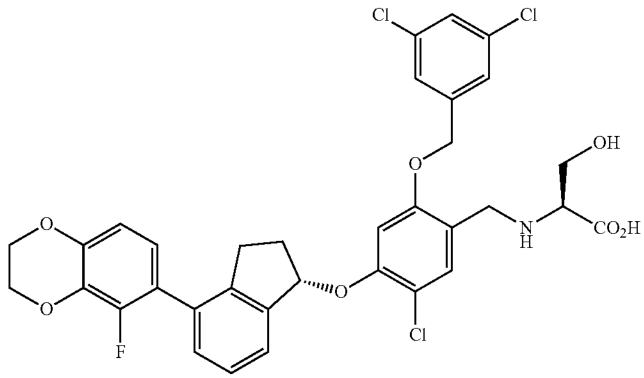 [SMILES: O=C(O)[C@H](CO)NCc1cc(Cl)c(O[C@H]2CCc3c(-c4ccc5c(c4F)OCCO5)cccc32)cc1OCc1cc(F)cc(F)c1] | 688 | 2.81 |
| 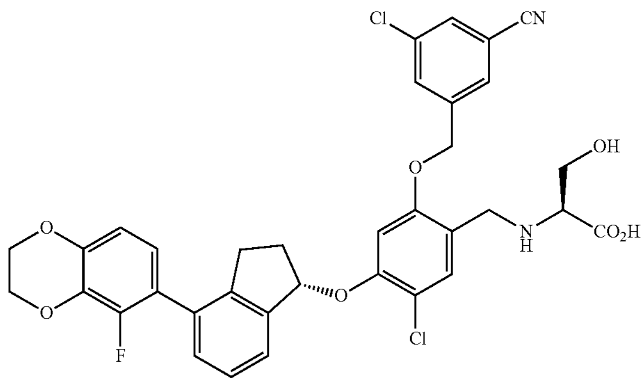 | 679 | 2.49 |
| 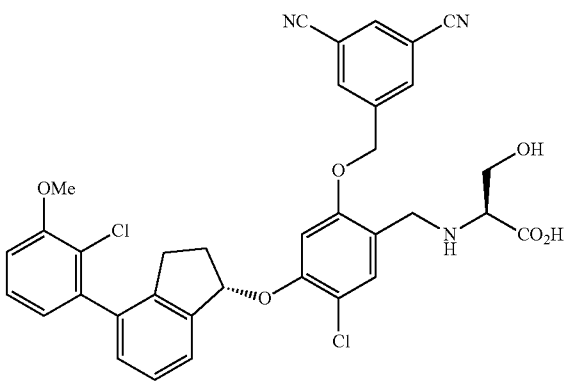 [SMILES: COc1cccc(-c2cccc3c2CC[C@@H]3Oc2cc(OCc3cc(C#N)cc(C#N)c3)c(CN[C@@H](CO)C(=O)O)cc2Cl)c1Cl] | 658 | 2.38 |
| 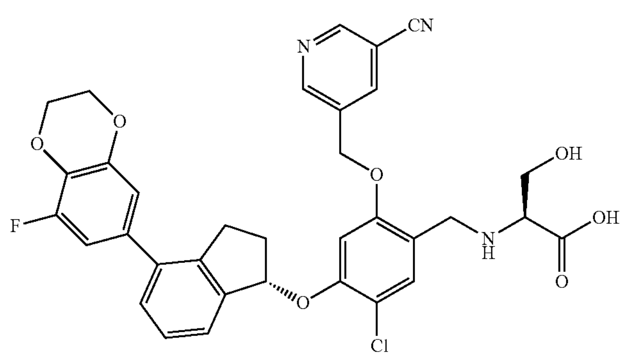 [SMILES: N#Cc1cncc(COc2cc(O[C@H]3CCc4c(-c5cc(F)c6c(c5)OCCO6)cccc43)c(Cl)cc2CN[C@@H](CO)C(=O)O)c1] | 646.1 | 3.49* |

TABLE 1C-continued

| Compound Structure | MS: (ES) m/z (M + H) | RP HPLC R$_t$ (min) |
|---|---|---|
| | 584.1 | 2.42 |
| | 584.1 | 2.99 |
| 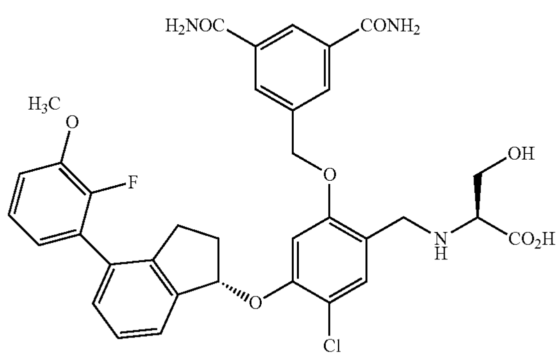 | 678.2 | 1.9 |
| 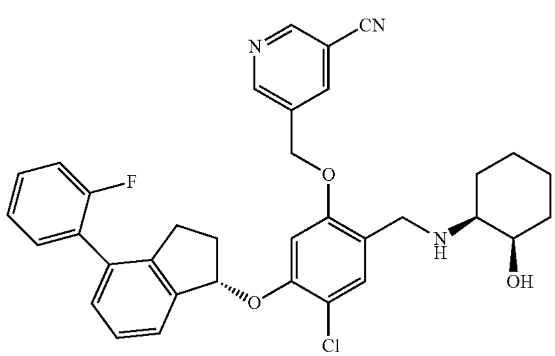 [SMILES: N#Cc1cncc(COc2cc(O[C@H]3CCc4c(-c5ccccc5F)cccc43)c(Cl)cc2CN[C@H]2CCCC[C@H]2O)c1] | 598.2 | 3.18 |

TABLE 1C-continued
| Compound Structure | MS: (ES) m/z (M + H) | RP HPLC $R_t$ (min) |
|---|---|---|
| 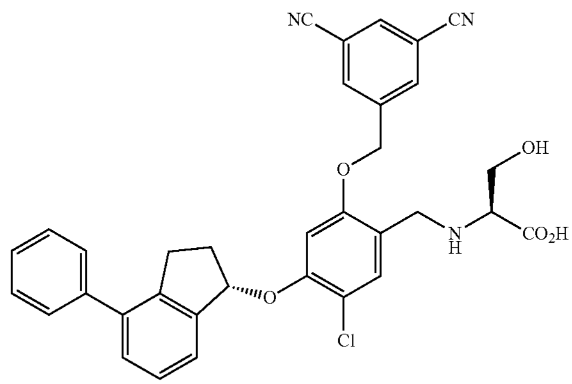 [SMILES: N#Cc1cc(C#N)cc(COc2cc(O[C@H]3CCc4c(-c5ccccc5)cccc43)c(Cl)cc2CN[C@@H](CO)C(=O)O)c1] | 594.2 | 2.57 |
| 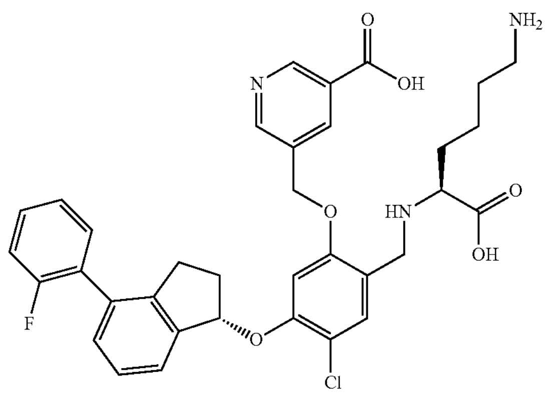 [SMILES: NCCCC[C@H](NCc1cc(Cl)c(O[C@H]2CCc3c(-c4ccccc4F)cccc32)cc1OCc1cncc(C(=O)O)c1)C(=O)O] | 648.2 | 2.05 |
| 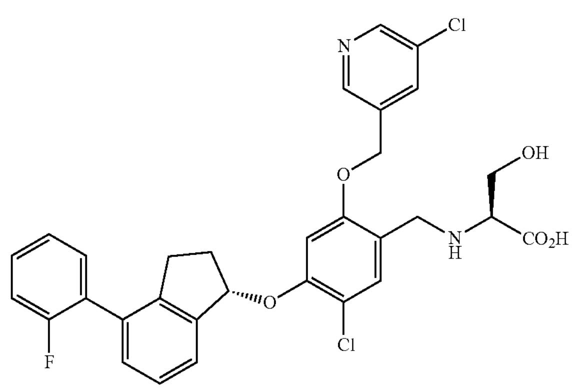 [SMILES: O=C(O)[C@H](CO)NCc1cc(Cl)c(O[C@H]2CCc3c(-c4ccccc4F)cccc32)cc1OCc1cncc(Cl)c1] | 597 | 2.53 |
| 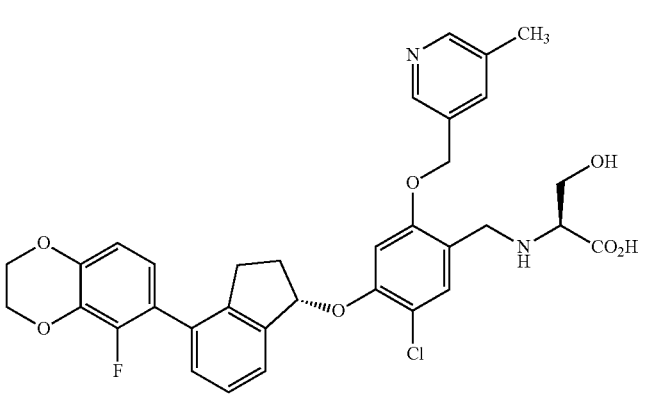 | 635 | 1.93 |

TABLE 1C-continued

| Compound Structure | MS: (ES) m/z (M + H) | RP HPLC R<sub>t</sub> (min) |
| --- | --- | --- |
| 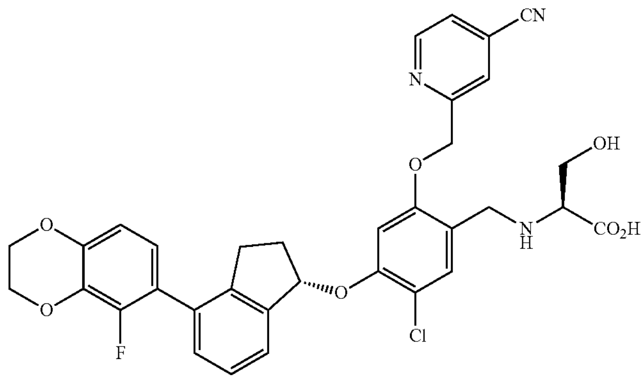 [SMILES: N#Cc1ccnc(COc2cc(O[C@H]3CCc4c(-c5ccc6c(c5F)OCCO6)cccc43)c(Cl)cc2CN[C@@H](CO)C(=O)O)c1] | 646.2 | 2.45 |
| 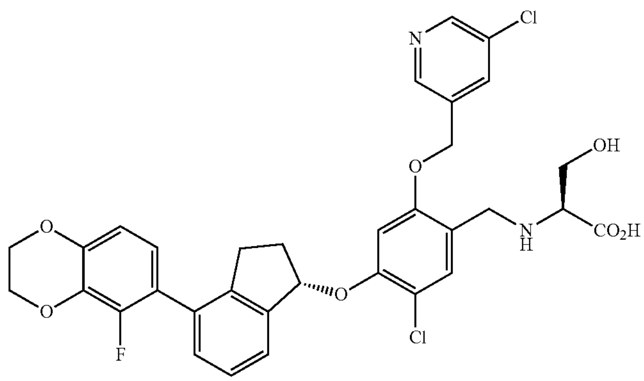 [SMILES: O=C(O)[C@H](CO)NCc1cc(Cl)c(O[C@H]2CCc3c(-c4ccc5c(c4F)OCCO5)cccc32)cc1OCc1cncc(Cl)c1] | 655 | 2.49 |
| 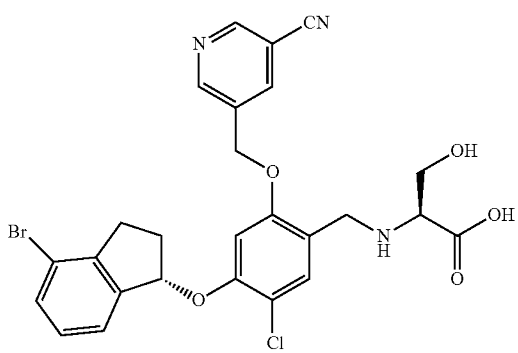 [SMILES: N#Cc1cncc(COc2cc(O[C@H]3CCc4c(Br)cccc43)c(Cl)cc2CN[C@@H](CO)C(=O)O)c1] | 572 | 3.46* |
| 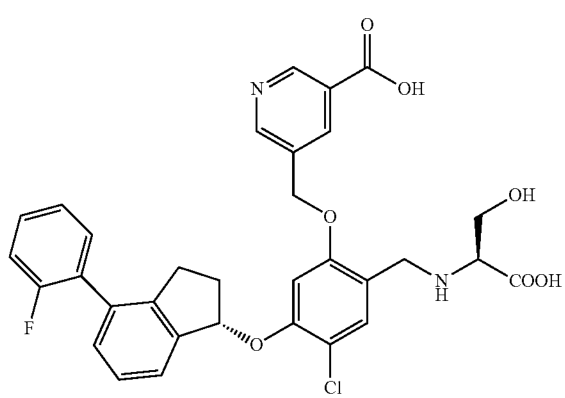 [SMILES: O=C(O)c1cncc(COc2cc(O[C@H]3CCc4c(-c5ccccc5F)cccc43)c(Cl)cc2CN[C@@H](CO)C(=O)O)c1] | 607.2 | 2.01 |

TABLE 1C-continued
| Compound Structure | MS: (ES) m/z (M + H) | RP HPLC R$_t$ (min) |
|---|---|---|
| 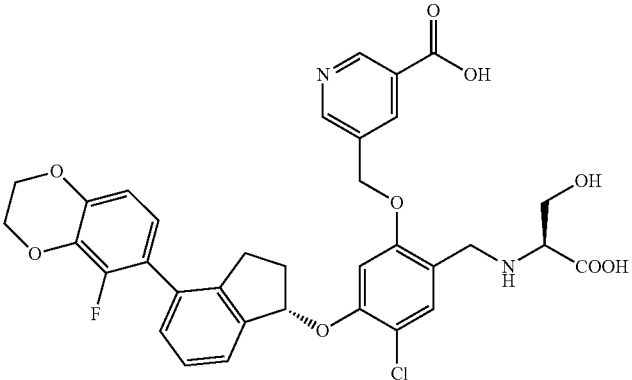 [SMILES: O=C(O)c1cncc(COc2cc(O[C@H]3CCc4c(-c5ccc6c(c5F)OCCO6)cccc43)c(Cl)cc2CN[C@@H](CO)C(=O)O)c1] | 665 | 2.23 |
| 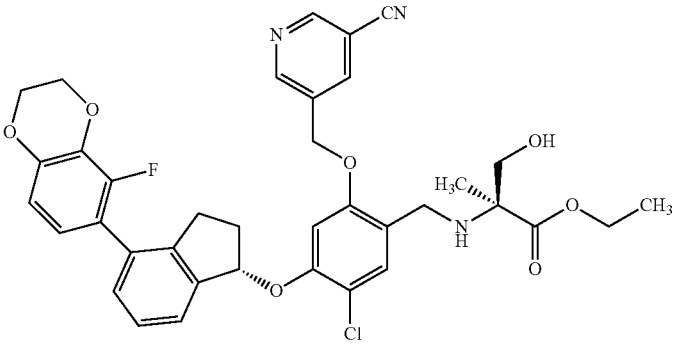 [SMILES: CCOC(=O)[C@](C)(CO)NCc1cc(Cl)c(O[C@H]2CCc3c(-c4ccc5c(c4F)OCCO5)cccc32)cc1OCc1cncc(C#N)c1] | 688.2 | 4.18* |
| 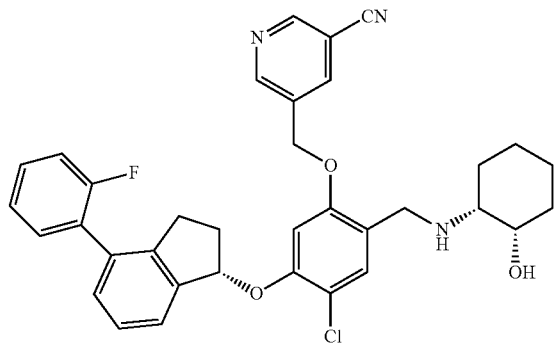 [SMILES: N#Cc1cncc(COc2cc(O[C@H]3CCc4c(-c5ccccc5F)cccc43)c(Cl)cc2CN[C@@H]2CCCC[C@@H]2O)c1] | 598.2 | 3.12 |
| 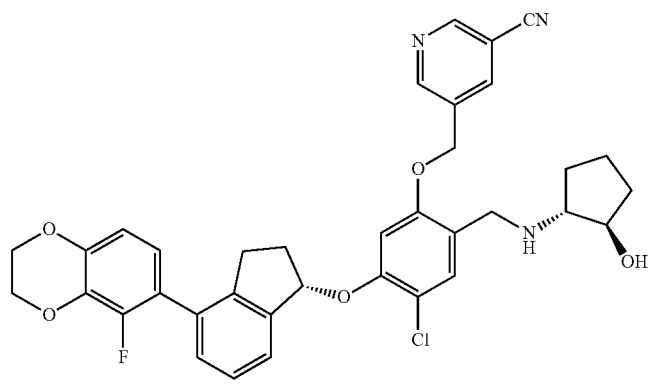 [SMILES: N#Cc1cncc(COc2cc(O[C@H]3CCc4c(-c5ccc6c(c5F)OCCO6)cccc43)c(Cl)cc2CN[C@@H]2CCC[C@H]2O)c1] | 642.1 | 2.55 |

TABLE 1C-continued

| Compound Structure | MS: (ES) m/z (M + H) | RP HPLC R$_t$ (min) |
|---|---|---|
| 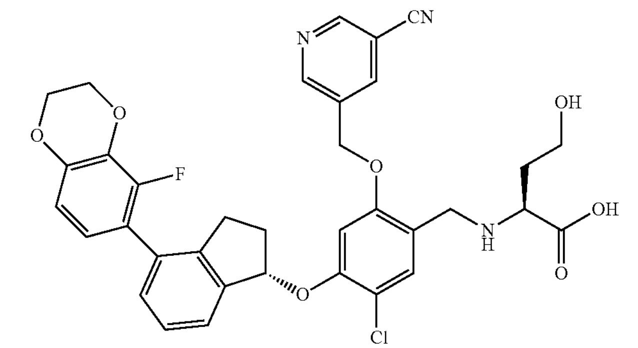 [SMILES: N#Cc1cncc(COc2cc(O[C@H]3CCc4c(-c5ccc6c(c5F)OCCO6)cccc43)c(Cl)cc2CN[C@@H](CCO)C(=O)O)c1] | 660.1 | 2.21 |
| 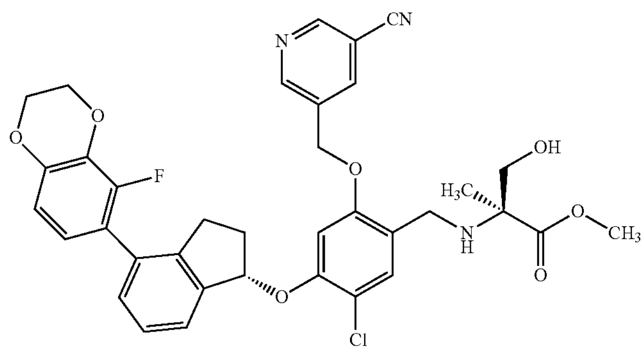 [SMILES: COC(=O)[C@](C)(CO)NCc1cc(Cl)c(O[C@H]2CCc3c(-c4ccc5c(c4F)OCCO5)cccc32)cc1OCc1cncc(C#N)c1] | 674.1 | 4.41* |
| 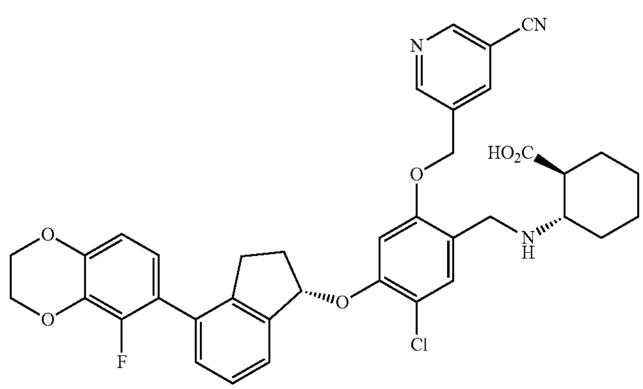 [SMILES: N#Cc1cncc(COc2cc(O[C@H]3CCc4c(-c5ccc6c(c5F)OCCO6)cccc43)c(Cl)cc2CN[C@H]2CCCC[C@@H]2C(=O)O)c1] | 684.1 | 2.767 |
| 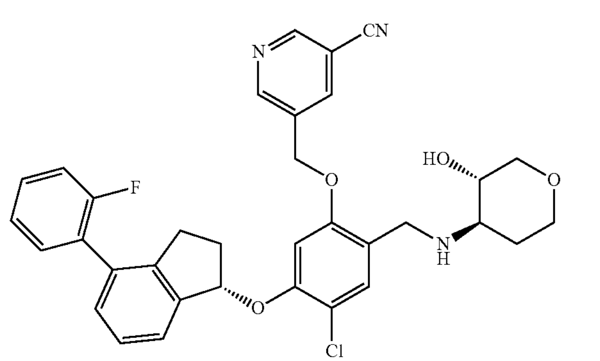 [SMILES: N#Cc1cncc(COc2cc(O[C@H]3CCc4c(-c5ccccc5F)cccc43)c(Cl)cc2CN[C@@H]2CCOC[C@H]2O)c1] | 600.1 | 2.51 |

TABLE 1C-continued

| Compound Structure | MS: (ES) m/z (M + H) | RP HPLC R<sub>t</sub> (min) |
|---|---|---|
| | 598.2 | 2.61 |
| 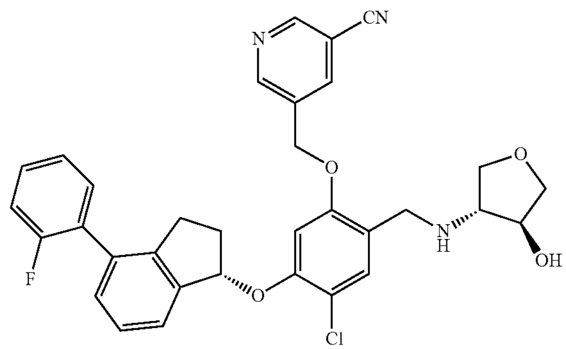 [SMILES: N#Cc1cncc(COc2cc(O[C@H]3CCc4c(-c5ccccc5F)cccc43)c(Cl)cc2CN[C@@H]2COC[C@H]2O)c1] | 586.2 | 2.43 |
| | 598.2 | |
| | 598.2 | 2.5 |

TABLE 1C-continued

| Compound Structure | MS: (ES) m/z (M + H) | RP HPLC R_t (min) |
|---|---|---|
| (structure) | 643.2 | 2.49 |
| (structure) | 702.2 | 2.2 |
| (structure) | 645.1 | 2.22 |
| (structure) | 702.1 | 4.11* |

TABLE 1C-continued

| Compound Structure | MS: (ES) m/z (M + H) | RP HPLC R$_t$ (min) |
|---|---|---|
| 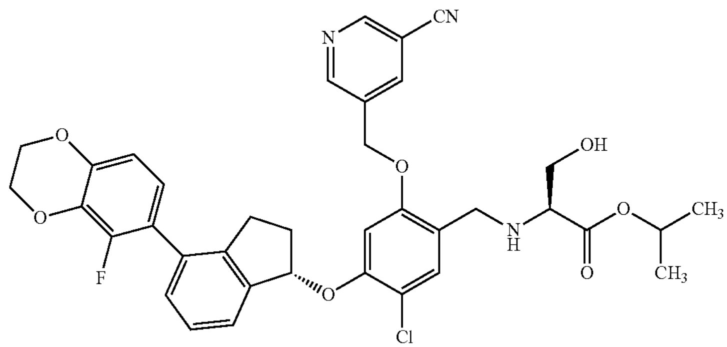 [SMILES: CC(C)OC(=O)[C@H](CO)NCc1cc(Cl)c(O[C@H]2CCc3c(-c4ccc5c(c4F)OCCO5)cccc32)cc1OCc1cncc(C#N)c1] | 688.2 | 2.63 |
| | 659.2 | 2.13 |
| 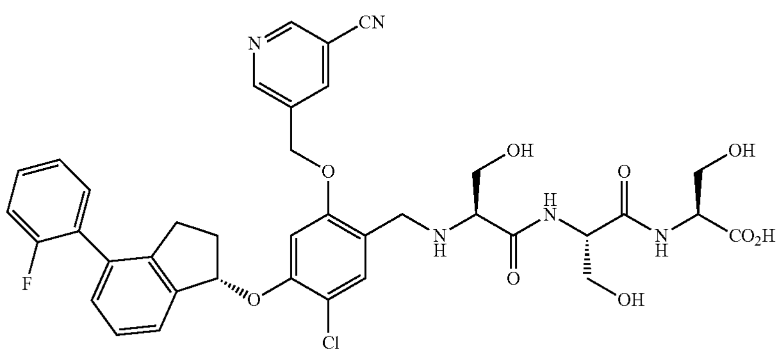 [SMILES: N#Cc1cncc(COc2cc(O[C@H]3CCc4c(-c5ccccc5F)cccc43)c(Cl)cc2CN[C@@H](CO)C(=O)N[C@@H](CO)C(=O)N[C@@H](CO)C(=O)O)c1] | 762.2 | 2.23 |
| | 659.2 | 2.17 |

TABLE 1C-continued

| Compound Structure | MS: (ES) m/z (M + H) | RP HPLC R_t (min) |
|---|---|---|
| 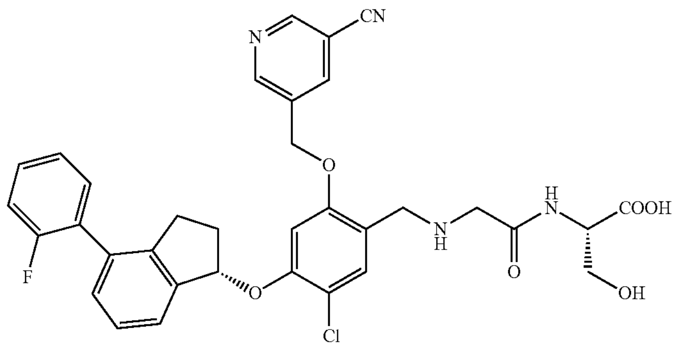 [SMILES: N#Cc1cncc(COc2cc(O[C@H]3CCc4c(-c5ccccc5F)cccc43)c(Cl)cc2CNCC(=O)N[C@@H](CO)C(=O)O)c1] | 645.1 | 2.22 |
| 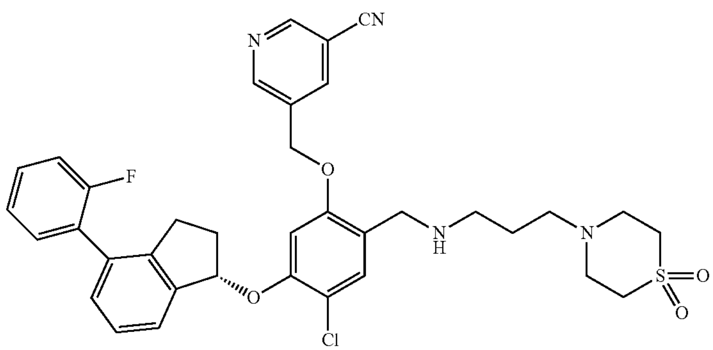 [SMILES: N#Cc1cncc(COc2cc(O[C@H]3CCc4c(-c5ccccc5F)cccc43)c(Cl)cc2CNCCCN2CCS(=O)(=O)CC2)c1] | 675.1 | 2.39 |
| 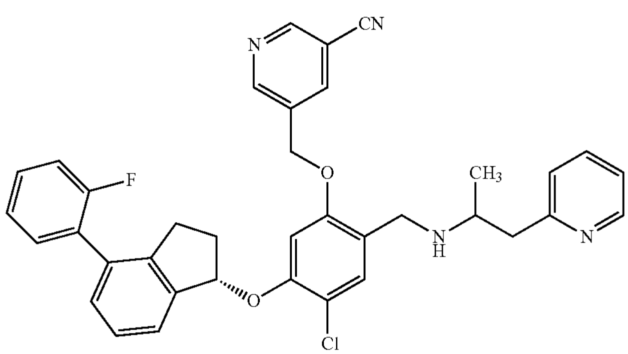 [SMILES: CC(Cc1ccccn1)NCc1cc(Cl)c(O[C@H]2CCc3c(-c4ccccc4F)cccc32)cc1OCc1cncc(C#N)c1] | 619.2 | 2.67 |
| 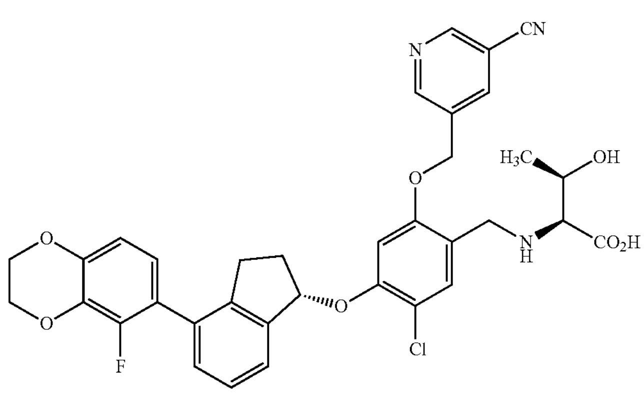 [SMILES: C[C@@H](O)[C@H](NCc1cc(Cl)c(O[C@H]2CCc3c(-c4ccc5c(c4F)OCCO5)cccc32)cc1OCc1cncc(C#N)c1)C(=O)O] | 660 | 2.26 |

TABLE 1C-continued

| Compound Structure | MS: (ES) m/z (M + H) | RP HPLC R$_t$ (min) |
|---|---|---|
| 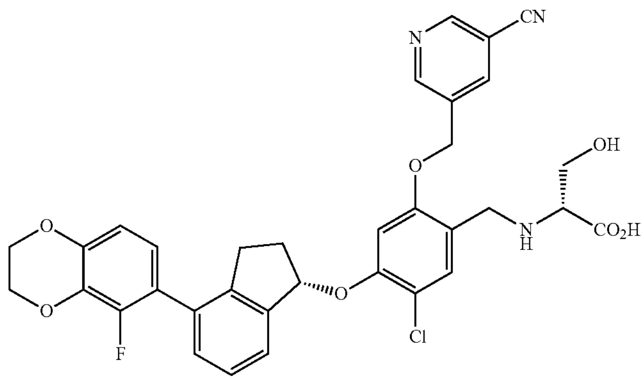 [SMILES: N#Cc1cncc(COc2cc(O[C@H]3CCc4c(-c5ccc6c(c5F)OCCO6)cccc43)c(Cl)cc2CN[C@H](CO)C(=O)O)c1] | 646.2 | 2.38 |
| 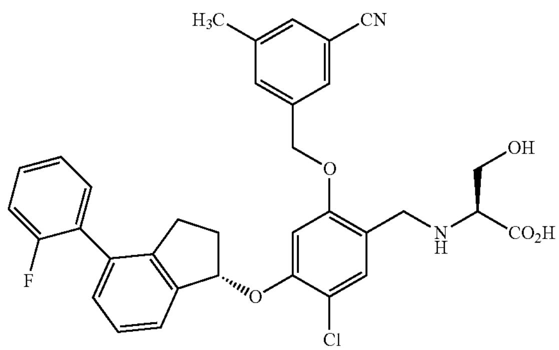 [SMILES: Cc1cc(C#N)cc(COc2cc(O[C@H]3CCc4c(-c5ccccc5F)cccc43)c(Cl)cc2CN[C@@H](CO)C(=O)O)c1] | 601.2 | 2.7 |
| 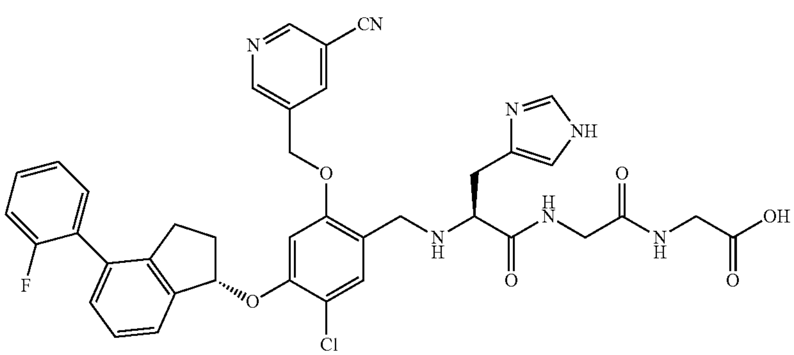 [SMILES: N#Cc1cncc(COc2cc(O[C@H]3CCc4c(-c5ccccc5F)cccc43)c(Cl)cc2CN[C@@H](Cc2c[nH]cn2)C(=O)NCC(=O)NCC(=O)O)c1] | 752.2 | 2.48 |
| 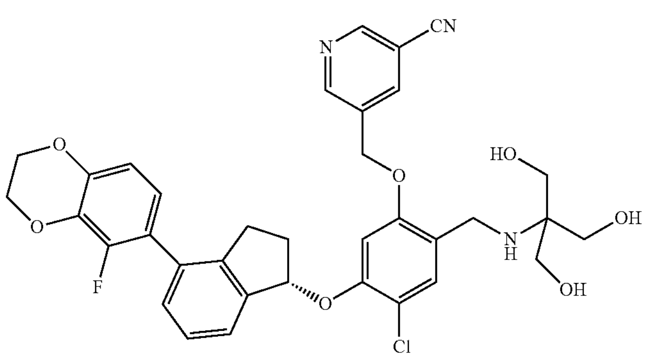 [SMILES: N#Cc1cncc(COc2cc(O[C@H]3CCc4c(-c5ccc6c(c5F)OCCO6)cccc43)c(Cl)cc2CNC(CO)(CO)CO)c1] | 662.2 | 2.31 |

TABLE 1C-continued
| Compound Structure | MS: (ES) m/z (M + H) | RP HPLC R_t (min) |
|---|---|---|
| 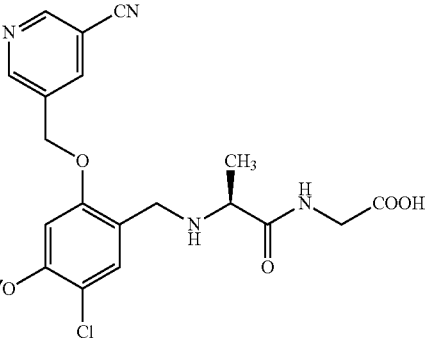 | 629.2 | 2.62 |
| 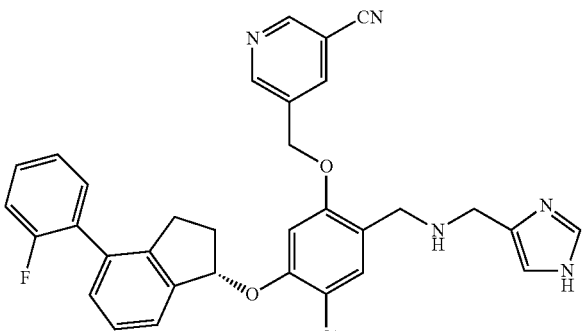 | 580.1 | 2.11 |
| 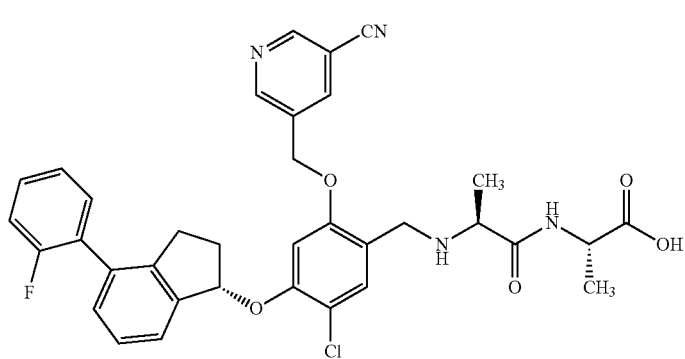 [SMILES: C[C@H](NC(=O)[C@H](C)NCc1cc(Cl)c(O[C@H]2CCc3c(-c4ccccc4F)cccc32)cc1OCc1cncc(C#N)c1)C(=O)O] | 643.2 | 2.53 |
| 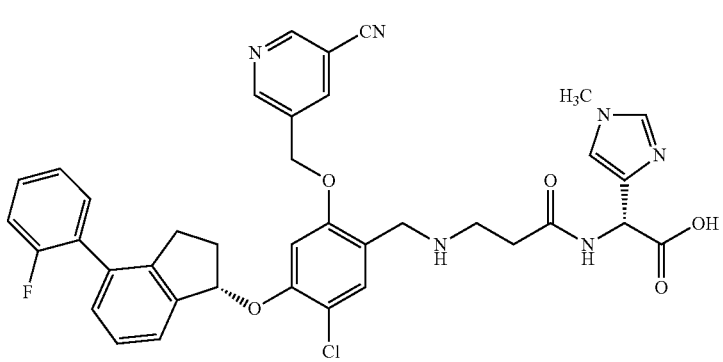 | [M + Na]733.2 | 2.34 |

TABLE 1C-continued

| Compound Structure | MS: (ES) m/z (M + H) | RP HPLC $R_t$ (min) |
|---|---|---|
| 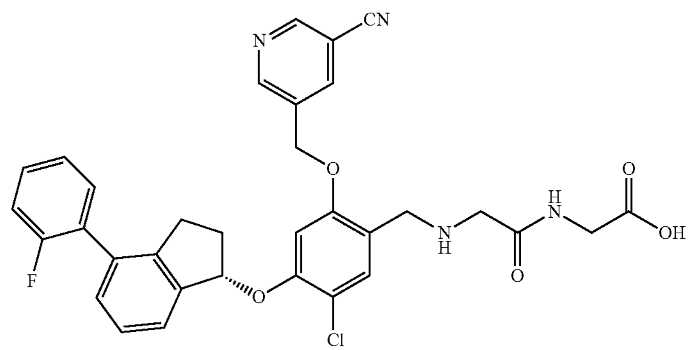 [SMILES: N#Cc1cncc(COc2cc(O[C@H]3CCc4c(-c5ccccc5F)cccc43)c(Cl)cc2CNCC(=O)NCC(=O)O)c1] | 615.1 | 2.45 |
| 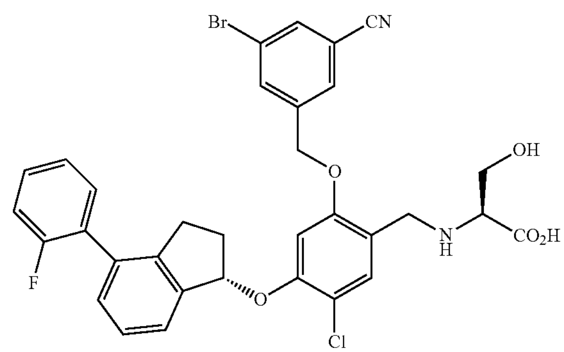 [SMILES: N#Cc1cc(Br)cc(COc2cc(O[C@H]3CCc4c(-c5ccccc5F)cccc43)c(Cl)cc2CN[C@@H](CO)C(=O)O)c1] | 667 | 2.68 |
| 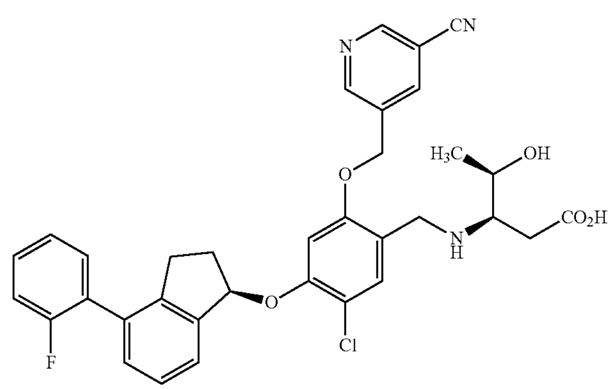 [SMILES: C[C@@H](O)[C@@H](CC(=O)O)NCc1cc(Cl)c(O[C@@H]2CCc3c(-c4ccccc4F)cccc32)cc1OCc1cncc(C#N)c1] | 597 (M − 19) | 2.72 |
| 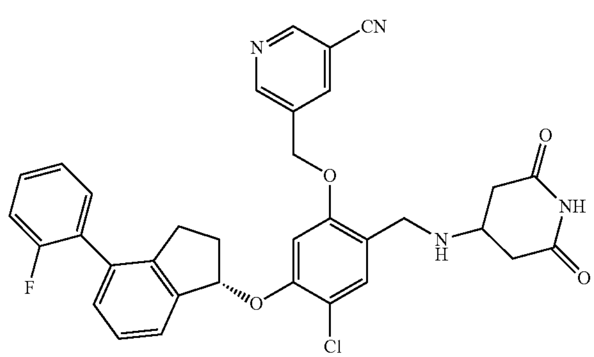 [SMILES: N#Cc1cncc(COc2cc(O[C@H]3CCc4c(-c5ccccc5F)cccc43)c(Cl)cc2CNC2CC(=O)NC(=O)C2)c1] | [M + Na] 633.1 | 2.49 |

TABLE 1C-continued
| Compound Structure | MS: (ES) m/z (M + H) | RP HPLC R_t (min) |
|---|---|---|
| 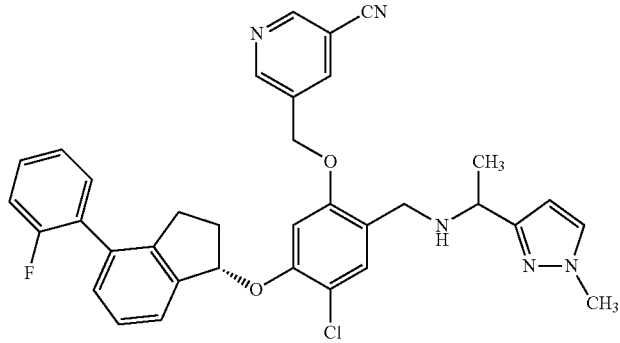 [SMILES: CC(NCc1cc(Cl)c(O[C@H]2CCc3c(-c4ccccc4F)cccc32)cc1OCc1cncc(C#N)c1)c1ccn(C)n1] | 608.2 | 2.85 |
| 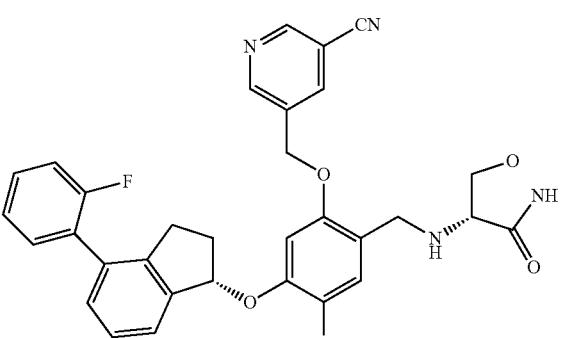 | 585.1 | 2.52 |
| 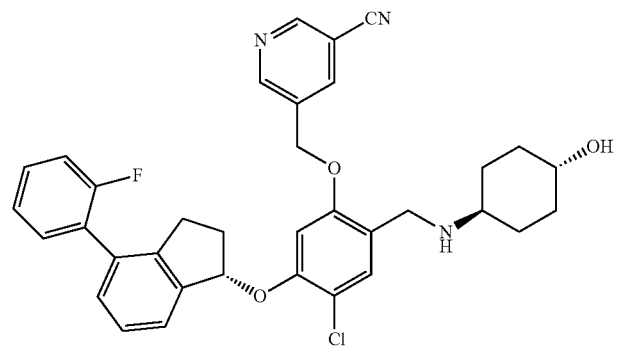 [SMILES: N#Cc1cncc(COc2cc(O[C@H]3CCc4c(-c5ccccc5F)cccc43)c(Cl)cc2CN[C@H]2CC[C@H](O)CC2)c1] | 598.2 | 2.52 |
| 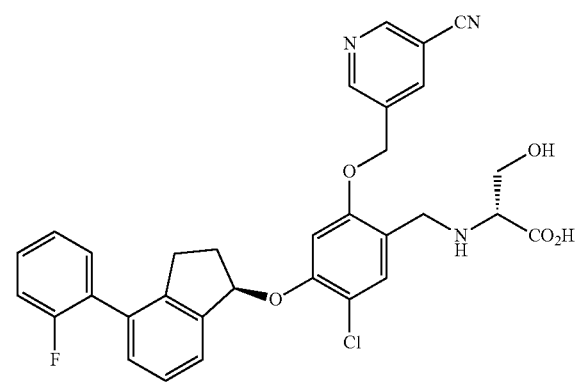 [SMILES: N#Cc1cncc(COc2cc(O[C@@H]3CCc4c(-c5ccccc5F)cccc43)c(Cl)cc2CN[C@H](CO)C(=O)O)c1] | 589 | 2.4 |

TABLE 1C-continued

| Compound Structure | MS: (ES) m/z (M + H) | RP HPLC R$_t$ (min) |
|---|---|---|
| 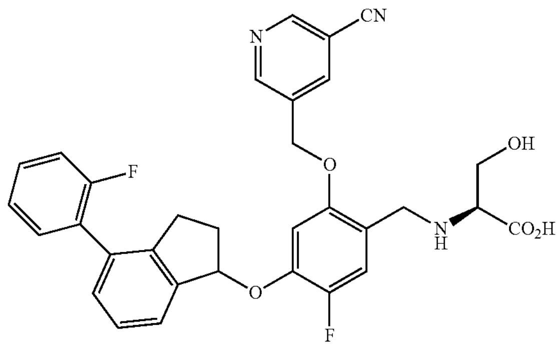 [SMILES: N#Cc1cncc(COc2cc(OC3CCc4c(-c5ccccc5F)cccc43)c(F)cc2CN[C@@H](CO)C(=O)O)c1] | 572.1 | 2.27 |
| 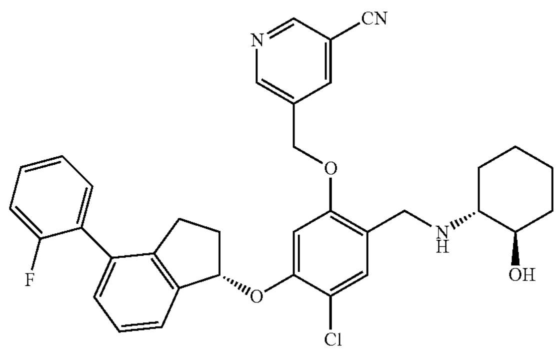 [SMILES: N#Cc1cncc(COc2cc(O[C@H]3CCc4c(-c5ccccc5F)cccc43)c(Cl)cc2CN[C@@H]2CCCC[C@H]2O)c1] | 598.2 | 2.6 |
| 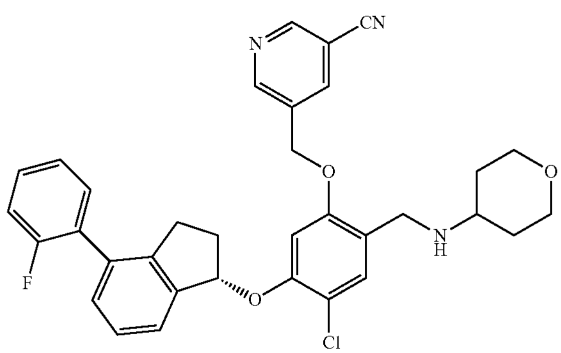 [SMILES: N#Cc1cncc(COc2cc(O[C@H]3CCc4c(-c5ccccc5F)cccc43)c(Cl)cc2CNC2CCOCC2)c1] | 584.2 | 2.29 |
| 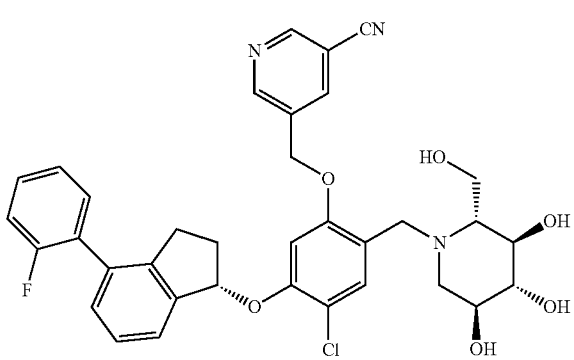 [SMILES: N#Cc1cncc(COc2cc(O[C@H]3CCc4c(-c5ccccc5F)cccc43)c(Cl)cc2CN2C[C@H](O)[C@@H](O)[C@H](O)[C@H]2CO)c1] | 646.2 | 2.14 |

TABLE 1C-continued
| Compound Structure | MS: (ES) m/z (M + H) | RP HPLC R$_t$ (min) |
|---|---|---|
| 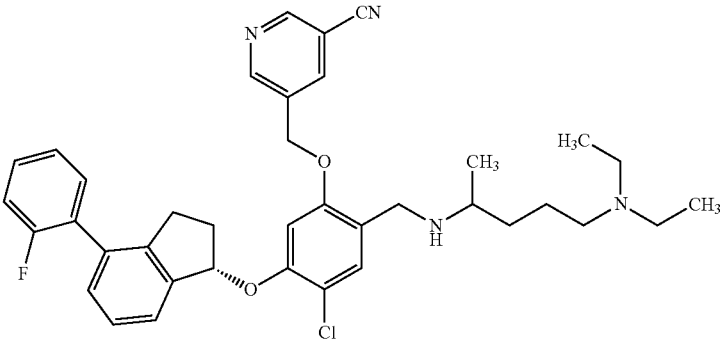 [SMILES: CCN(CC)CCCC(C)NCc1cc(Cl)c(O[C@H]2CCc3c(-c4ccccc4F)cccc32)cc1OCc1cncc(C#N)c1] | 641.3 | 2.2 |
| 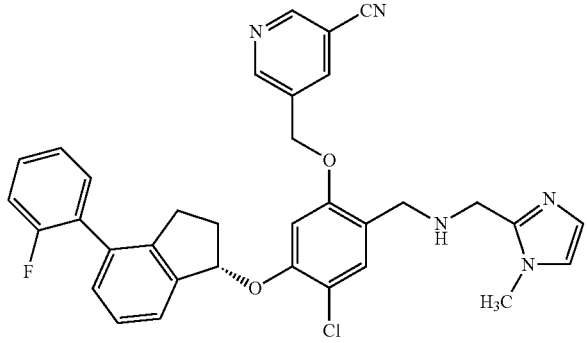 [SMILES: Cn1ccnc1CNCc1cc(Cl)c(O[C@H]2CCc3c(-c4ccccc4F)cccc32)cc1OCc1cncc(C#N)c1] | 594.1 | 2.46 |
| 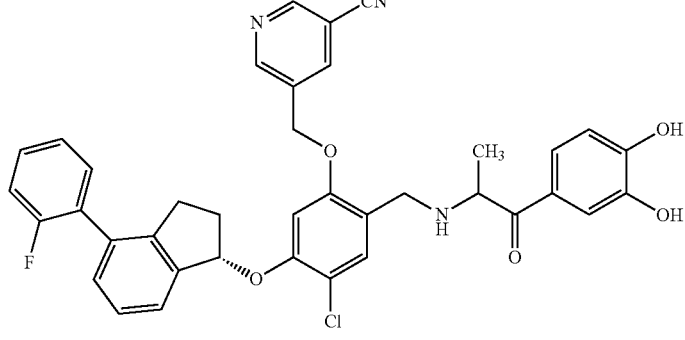 | 664.2 | 2.34 |
| 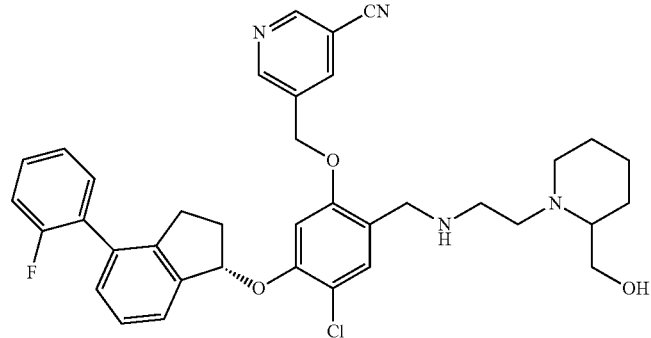 [SMILES: N#Cc1cncc(COc2cc(O[C@H]3CCc4c(-c5ccccc5F)cccc43)c(Cl)cc2CNCCN2CCCCC2CO)c1] | 641.2 | 2.04 |

TABLE 1C-continued

| Compound Structure | MS: (ES) m/z (M + H) | RP HPLC R$_t$ (min) |
|---|---|---|
| 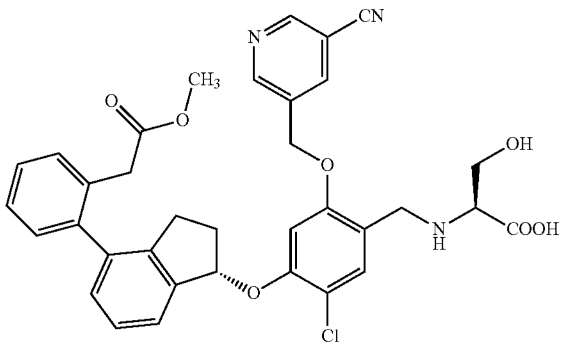 [SMILES: COC(=O)Cc1ccccc1-c1cccc2c1CC[C@@H]2Oc1cc(OCc2cncc(C#N)c2)c(CN[C@@H](CO)C(=O)O)cc1Cl] | 642.2 | 2.28 |
| 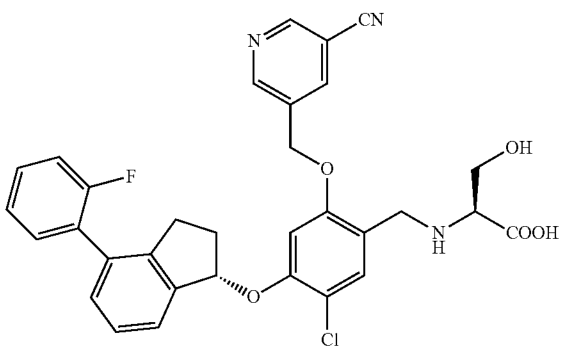 [SMILES: N#Cc1cncc(COc2cc(O[C@H]3CCc4c(-c5ccccc5F)cccc43)c(Cl)cc2CN[C@@H](CO)C(=O)O)c1] | 586.1 | 2.02 |
| 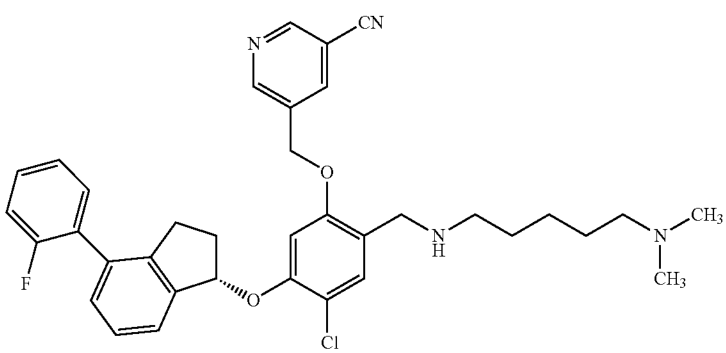 [SMILES: CN(C)CCCCCNCc1cc(Cl)c(O[C@H]2CCc3c(-c4ccccc4F)cccc32)cc1OCc1cncc(C#N)c1] | 613.2 | 1.99 |
| 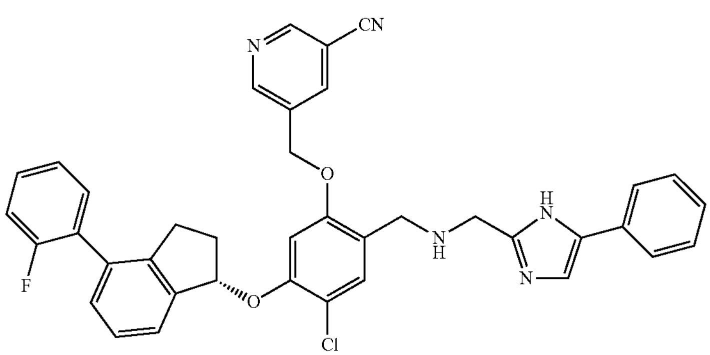 [SMILES: N#Cc1cncc(COc2cc(O[C@H]3CCc4c(-c5ccccc5F)cccc43)c(Cl)cc2CNCc2ncc(-c3ccccc3)[nH]2)c1] | 656.2 | 2.62 |

TABLE 1C-continued

| Compound Structure | MS: (ES) m/z (M + H) | RP HPLC R$_t$ (min) |
|---|---|---|
| 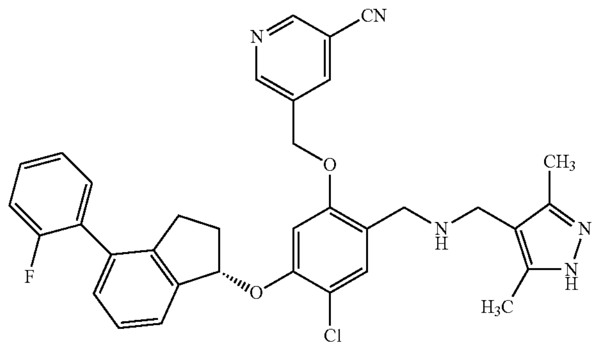 [SMILES: Cc1n[nH]c(C)c1CNCc1cc(Cl)c(O[C@H]2CCc3c(-c4ccccc4F)cccc32)cc1OCc1cncc(C#N)c1] | 608.2 | 2.77 |
| 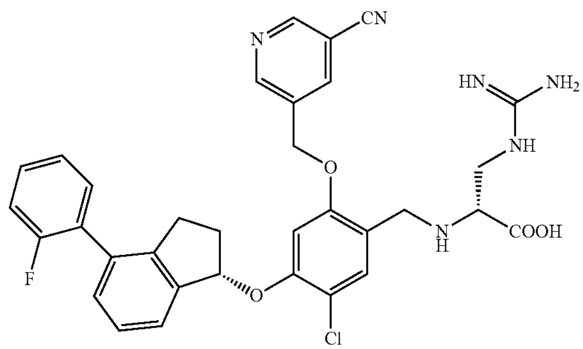 [SMILES: N#Cc1cncc(COc2cc(O[C@H]3CCc4c(-c5ccccc5F)cccc43)c(Cl)cc2CN[C@H](CNC(=N)N)C(=O)O)c1] | 629.2. | 1.94 |
| 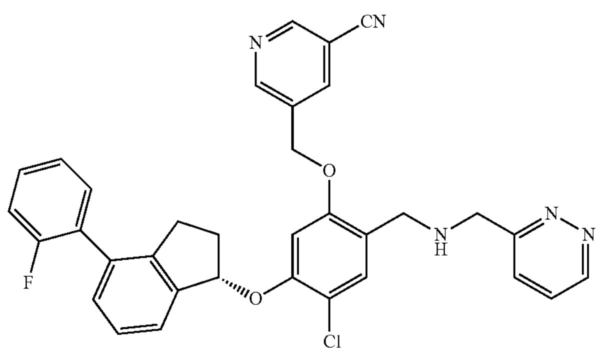 [SMILES: N#Cc1cncc(COc2cc(O[C@H]3CCc4c(-c5ccccc5F)cccc43)c(Cl)cc2CNCc2cccnn2)c1] | 592.2. | 2.46 |
| 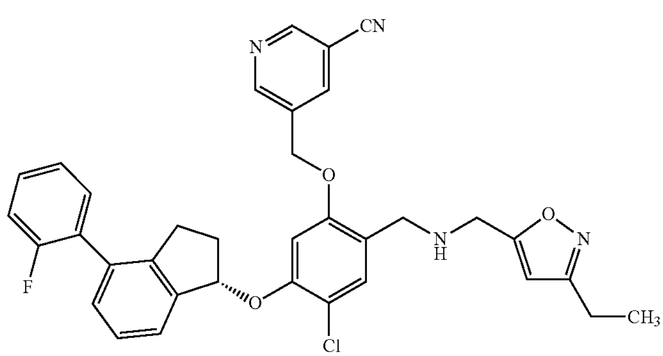 [SMILES: CCc1cc(CNCc2cc(Cl)c(O[C@H]3CCc4c(-c5ccccc5F)cccc43)cc2OCc2cncc(C#N)c2)on1] | 631.2. | 2.57 |

TABLE 1C-continued
| Compound Structure | MS: (ES) m/z (M + H) | RP HPLC R$_t$ (min) |
|---|---|---|
| 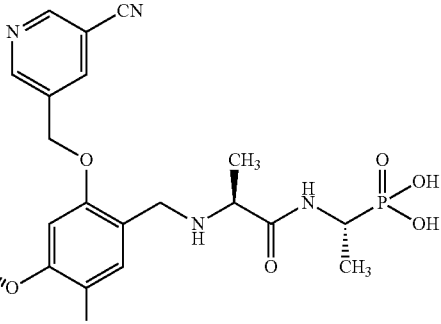 | 679.2. | 2.04 |
| 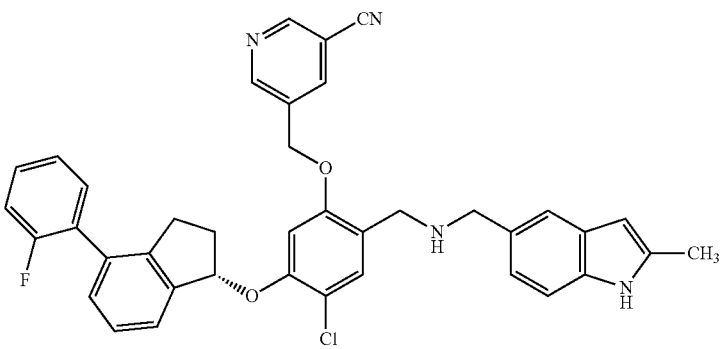 [SMILES: Cc1cc2cc(CNCc3cc(Cl)c(O[C@H]4CCc5c(-c6ccccc6F)cccc54)cc3OCc3cncc(C#N)c3)ccc2[nH]1] | 643.2 | 3.35 |
| 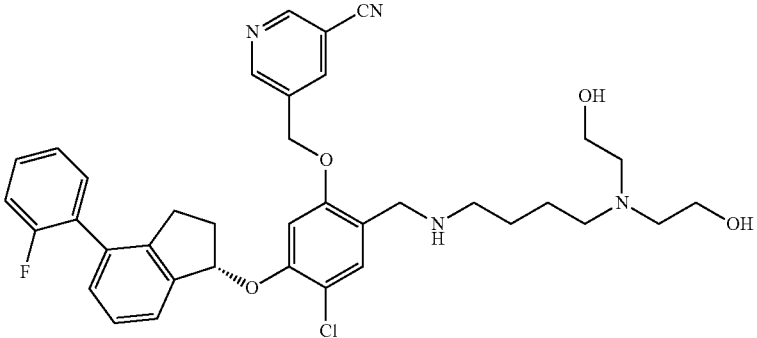 [SMILES: N#Cc1cncc(COc2cc(O[C@H]3CCc4c(-c5ccccc5F)cccc43)c(Cl)cc2CNCCCCN(CCO)CCO)c1] | 659.2. | 1.86 |
| 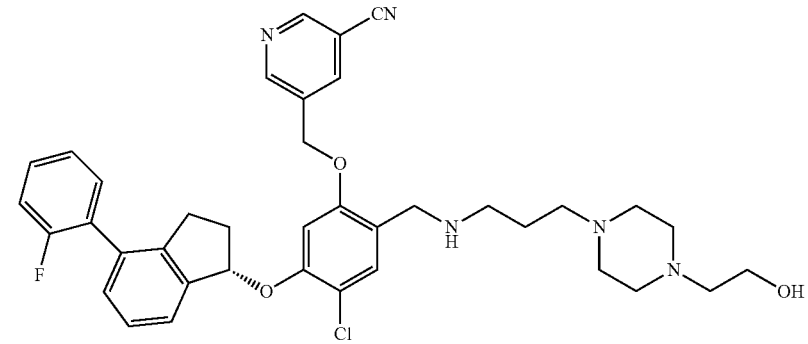 [SMILES: N#Cc1cncc(COc2cc(O[C@H]3CCc4c(-c5ccccc5F)cccc43)c(Cl)cc2CNCCCN2CCN(CCO)CC2)c1] | 670.3. | 1.59 |

TABLE 1C-continued
| Compound Structure | MS: (ES) m/z (M + H) | RP HPLC $R_t$ (min) |
|---|---|---|
| 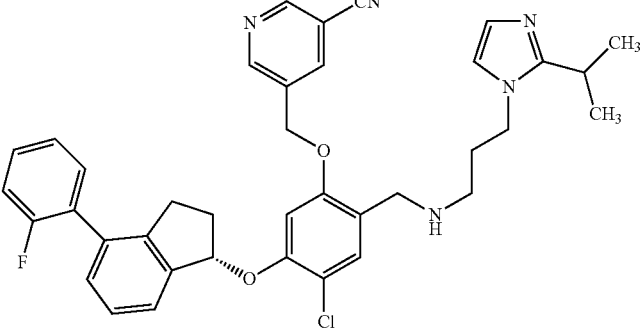 | 650.2. | 1.59 |
| 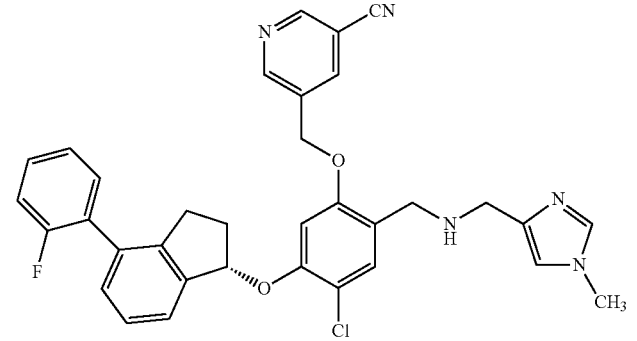 [SMILES: Cn1cnc(CNCc2cc(Cl)c(O[C@H]3CCc4c(-c5ccccc5F)cccc43)cc2OCc2cncc(C#N)c2)c1] | 594.1. | 1.8 |
| 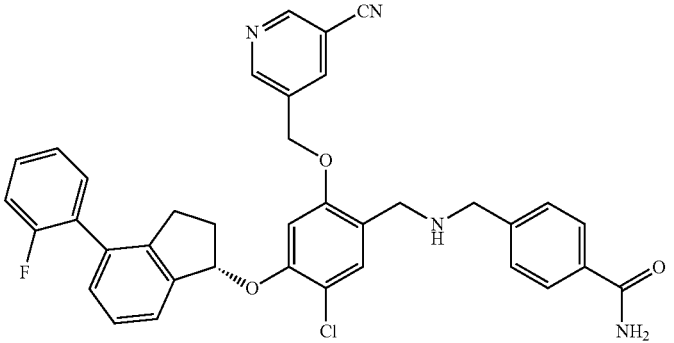 [SMILES: N#Cc1cncc(COc2cc(O[C@H]3CCc4c(-c5ccccc5F)cccc43)c(Cl)cc2CNCc2ccc(C(N)=O)cc2)c1] | 646.2. | 2.13 |
| 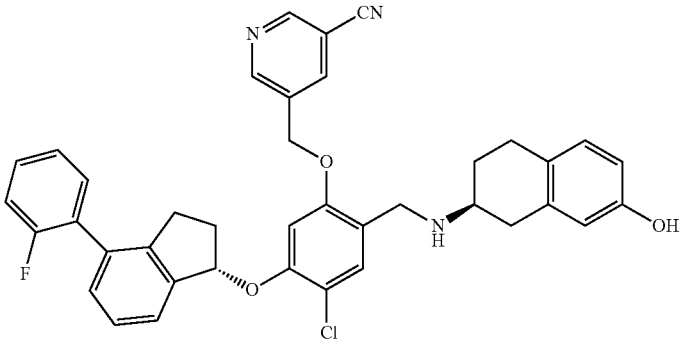 [SMILES: N#Cc1cncc(COc2cc(O[C@H]3CCc4c(-c5ccccc5F)cccc43)c(Cl)cc2CN[C@H]2CCc3ccc(O)cc3C2)c1] | 649.2. | 2.52 |

TABLE 1C-continued

| Compound Structure | MS: (ES) m/z (M + H) | RP HPLC R_t (min) |
|---|---|---|
| | 659.2. | 2.12 |
| | 659.2. | 2.12 |
| 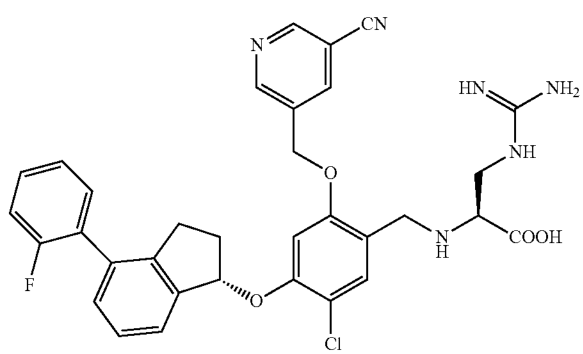 [SMILES: N#Cc1cncc(COc2cc(O[C@H]3CCc4c(-c5ccccc5F)cccc43)c(Cl)cc2CN[C@@H](CNC(=N)N)C(=O)O)c1] | 629.1. | 2.16 |
| 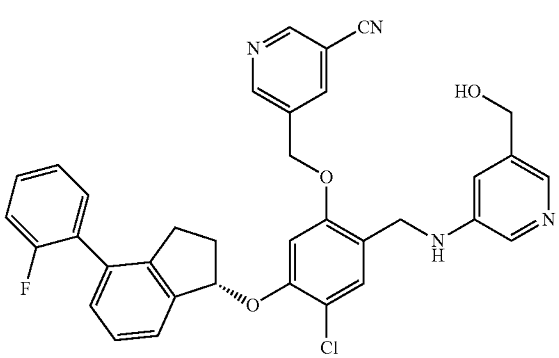 [SMILES: N#Cc1cncc(COc2cc(O[C@H]3CCc4c(-c5ccccc5F)cccc43)c(Cl)cc2CNc2cncc(CO)c2)c1] | 607.2. | 2.52 |

TABLE 1C-continued
| Compound Structure | MS: (ES) m/z (M + H) | RP HPLC R_t (min) |
|---|---|---|
| 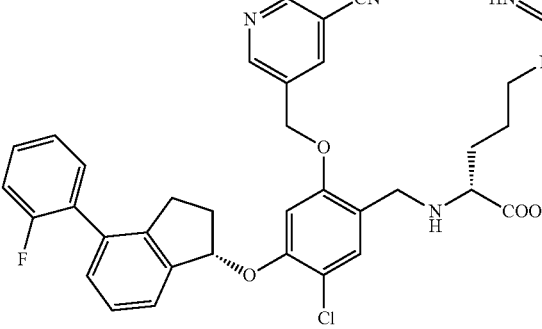 | 657.2. | 1.64 |
| 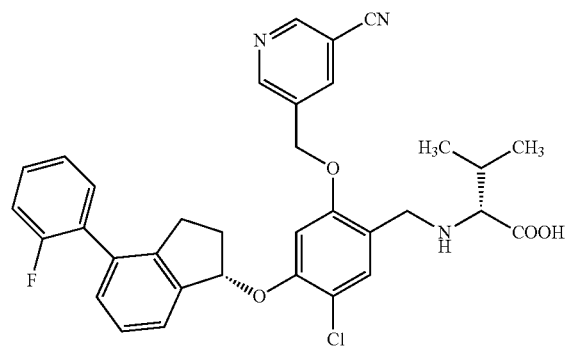 | 600.1. | 2.54 |
| 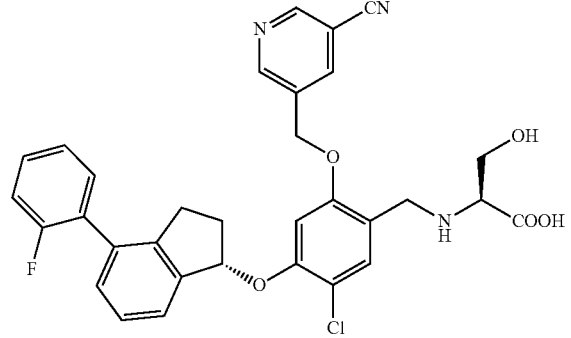 | 641.0. | 2.42 |
| 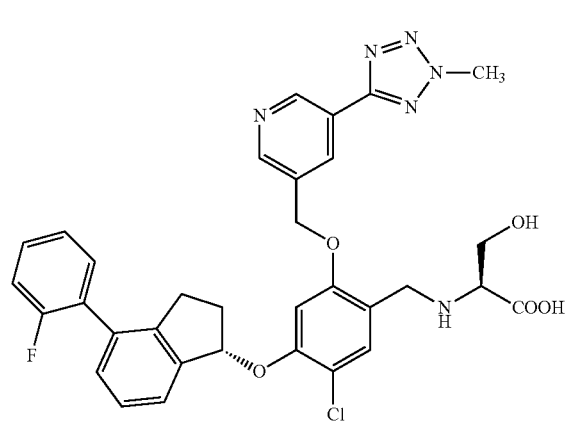 [SMILES: Cn1nnc(-c2cncc(COc3cc(O[C@H]4CCc5c(-c6ccccc6F)cccc54)c(Cl)cc3CN[C@@H](CO)C(=O)O)c2)n1] | 645.1. | 2.36 |

TABLE 1C-continued

| Compound Structure | MS: (ES) m/z (M + H) | RP HPLC R<sub>t</sub> (min) |
|---|---|---|
| 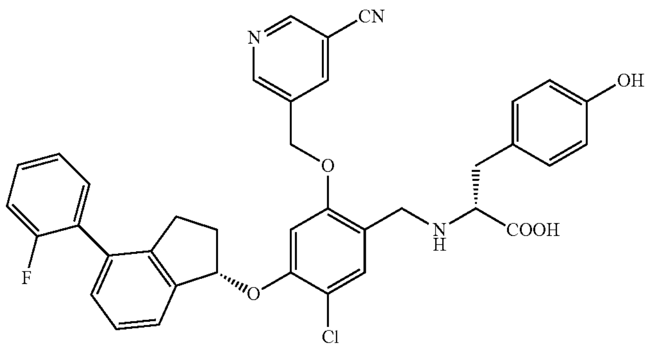 [SMILES: N#Cc1cncc(COc2cc(O[C@H]3CCc4c(-c5ccccc5F)cccc43)c(Cl)cc2CN[C@H](Cc2ccc(O)cc2)C(=O)O)c1] | 664.2. | 2.34 |
| 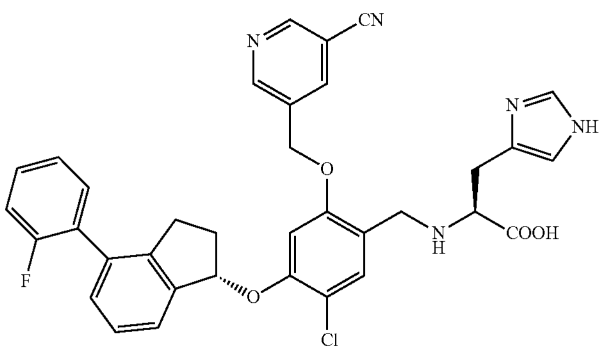 [SMILES: N#Cc1cncc(COc2cc(O[C@H]3CCc4c(-c5ccccc5F)cccc43)c(Cl)cc2CN[C@@H](Cc2c[nH]cn2)C(=O)O)c1] | 638.2. | 2.02 |
| 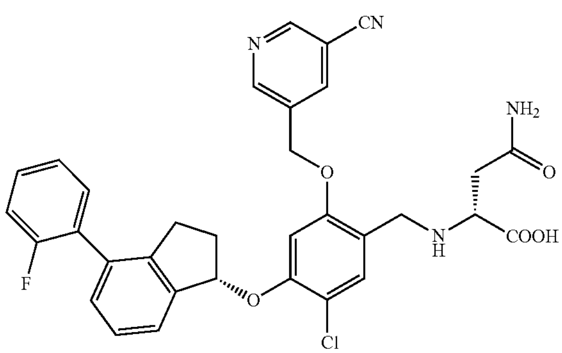 [SMILES: N#Cc1cncc(COc2cc(O[C@H]3CCc4c(-c5ccccc5F)cccc43)c(Cl)cc2CN[C@H](CC(N)=O)C(=O)O)c1] | 615.1. | 2.37 |
| 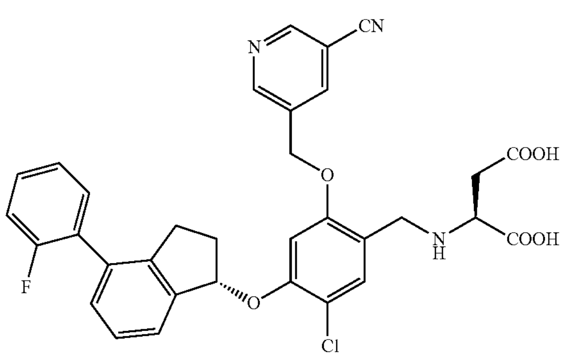 [SMILES: N#Cc1cncc(COc2cc(O[C@H]3CCc4c(-c5ccccc5F)cccc43)c(Cl)cc2CN[C@@H](CC(=O)O)C(=O)O)c1] | 616.1. | 2.23 |

TABLE 1C-continued
| Compound Structure | MS: (ES) m/z (M + H) | RP HPLC R_t (min) |
|---|---|---|
| 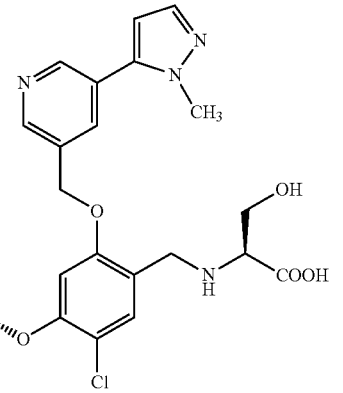 | 643.2. | 2.35 |
| 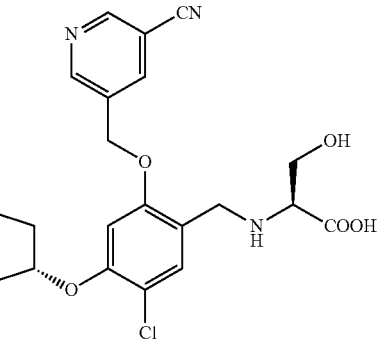 | 650.1 | 2.66 |
| 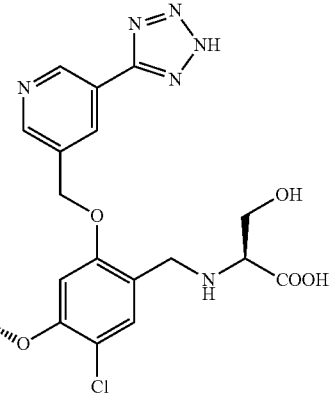 | 631.2. | 2.13 |
| 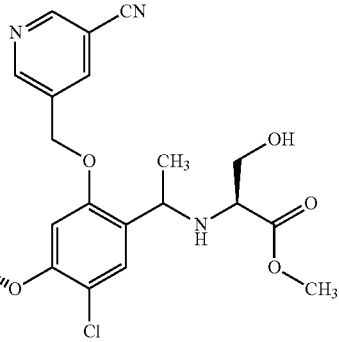 | 638.1. | 2.41 |

TABLE 1C-continued

| Compound Structure | MS: (ES) m/z (M + H) | RP HPLC $R_t$ (min) |
|---|---|---|
| 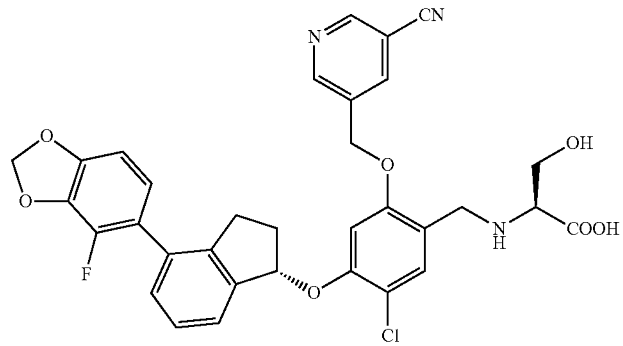 [SMILES: N#Cc1cncc(COc2cc(O[C@H]3CCc4c(-c5ccc6c(c5F)OCO6)cccc43)c(Cl)cc2CN[C@@H](CO)C(=O)O)c1] | 632.1 | 2.26 |
| 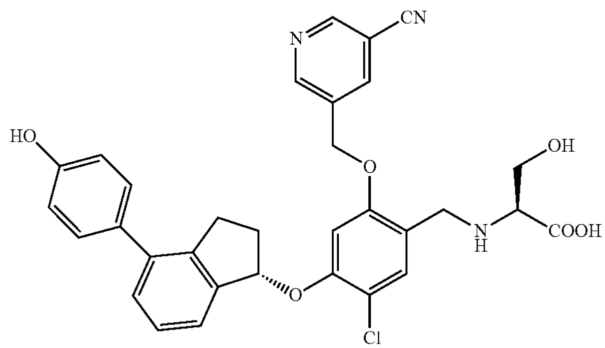 [SMILES: N#Cc1cncc(COc2cc(O[C@H]3CCc4c(-c5ccc(O)cc5)cccc43)c(Cl)cc2CN[C@@H](CO)C(=O)O)c1] | 586.0. | 1.99 |
| 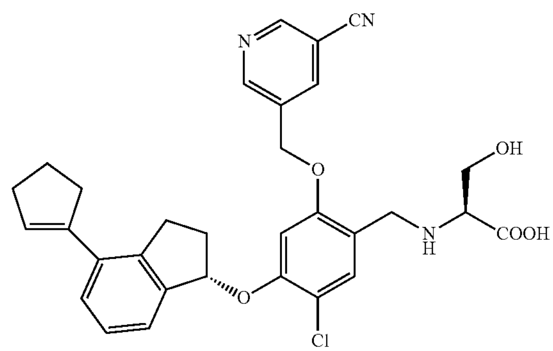 [SMILES: N#Cc1cncc(COc2cc(O[C@H]3CCc4c(C5=CCCC5)cccc43)c(Cl)cc2CN[C@@H](CO)C(=O)O)c1] | 560.1. | 2.53 |
| 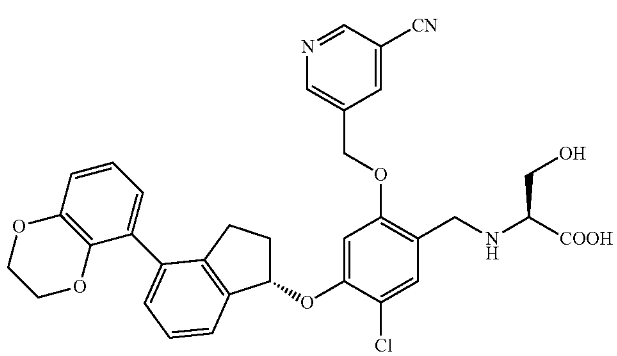 [SMILES: N#Cc1cncc(COc2cc(O[C@H]3CCc4c(-c5cccc6c5OCCO6)cccc43)c(Cl)cc2CN[C@@H](CO)C(=O)O)c1] | 628.2 | 2.37 |

TABLE 1C-continued

| Compound Structure | MS: (ES) m/z (M + H) | RP HPLC R$_t$ (min) |
|---|---|---|
| 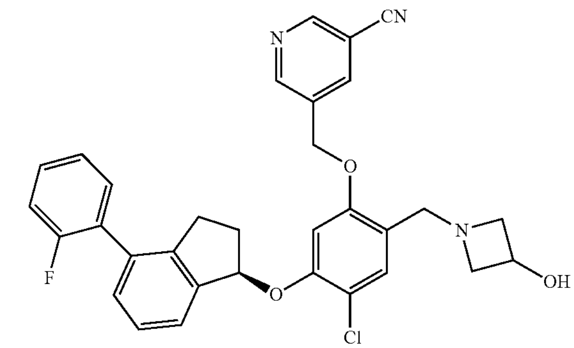 [SMILES: N#Cc1cncc(COc2cc(O[C@@H]3CCc4c(-c5ccccc5F)cccc43)c(Cl)cc2CN2CC(O)C2)c1] | 556.2 | 2.53 |
| 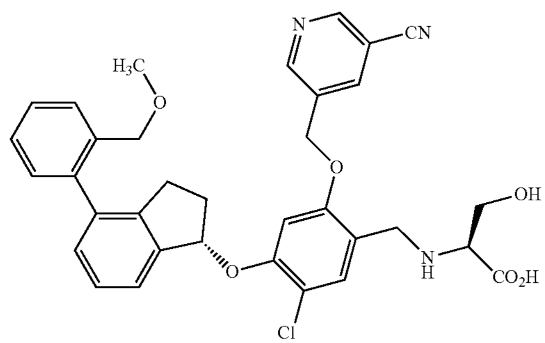 [SMILES: COCc1ccccc1-c1cccc2c1CC[C@@H]2Oc1cc(OCc2cncc(C#N)c2)c(CN[C@@H](CO)C(=O)O)cc1Cl] | 614.2 | 3.6 |
| 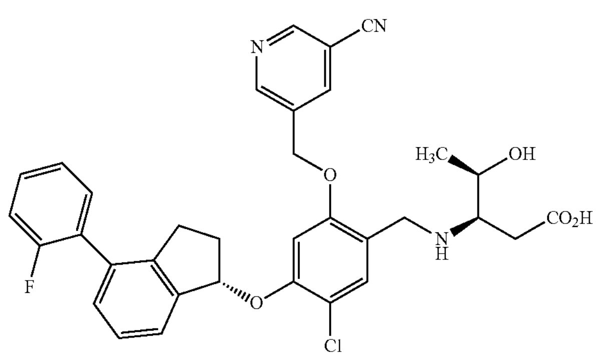 [SMILES: C[C@@H](O)[C@@H](CC(=O)O)NCc1cc(Cl)c(O[C@H]2CCc3c(-c4ccccc4F)cccc32)cc1OCc1cncc(C#N)c1] | 616.1. | 2.26 |
| 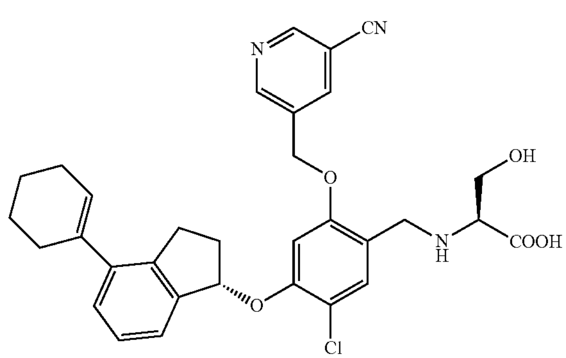 [SMILES: N#Cc1cncc(COc2cc(O[C@H]3CCc4c(C5=CCCCC5)cccc43)c(Cl)cc2CN[C@@H](CO)C(=O)O)c1] | 596.1 | 2.64 |

TABLE 1C-continued

| Compound Structure | MS: (ES) m/z (M + H) | RP HPLC R_t (min) |
|---|---|---|
| 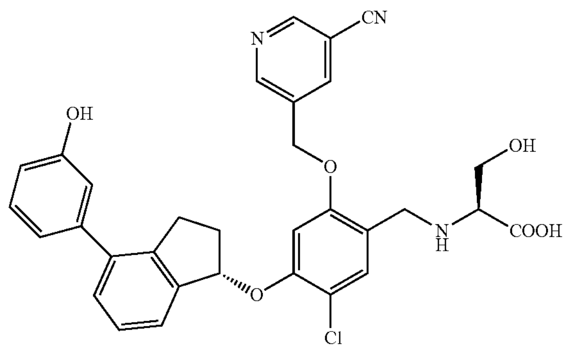 | 586.1. | 1.8 |
| 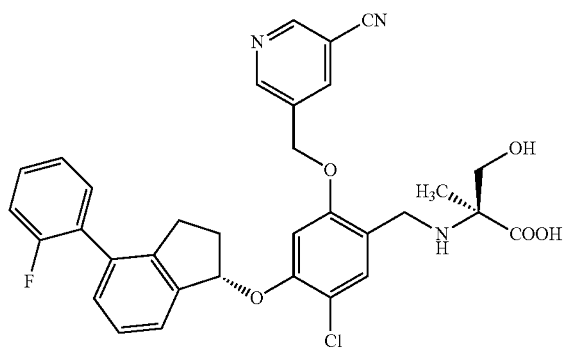 [SMILES: C[C@@](CO)(NCc1cc(Cl)c(O[C@H]2CCc3c(-c4ccccc4F)cccc32)cc1OCc1cncc(C#N)c1)C(=O)O] | 602.1. | 2.27 |
| 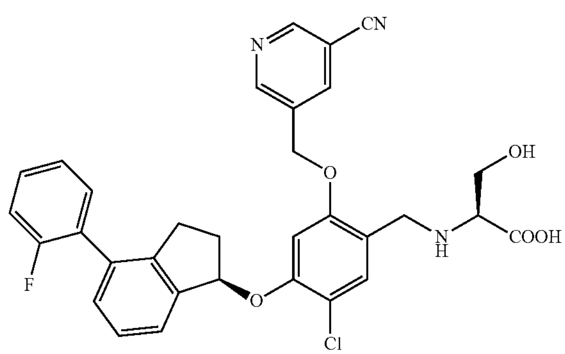 [SMILES: N#Cc1cncc(COc2cc(O[C@@H]3CCc4c(-c5ccccc5F)cccc43)c(Cl)cc2CN[C@@H](CO)C(=O)O)c1] | 588.1. | 2.41 |
| 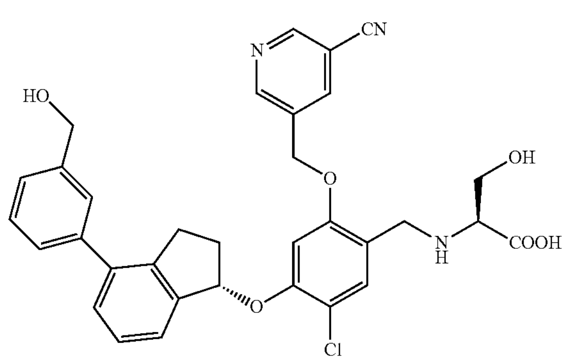 [SMILES: N#Cc1cncc(COc2cc(O[C@H]3CCc4c(-c5cccc(CO)c5)cccc43)c(Cl)cc2CN[C@@H](CO)C(=O)O)c1] | 600.1 | 2.03 |

TABLE 1C-continued
| Compound Structure | MS: (ES) m/z (M + H) | RP HPLC R$_t$ (min) |
|---|---|---|
| 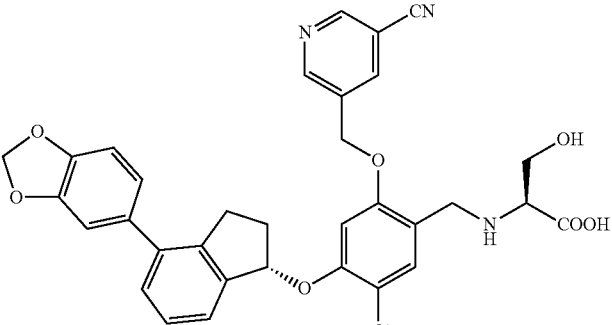 | 614.1 | 2.35 |
| 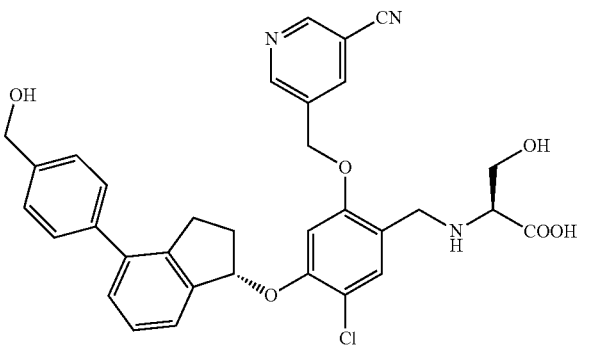 [SMILES: N#Cc1cncc(COc2cc(O[C@H]3CCc4c(-c5ccc(CO)cc5)cccc43)c(Cl)cc2CN[C@@H](CO)C(=O)O)c1] | 600.1 | 1.91 |
| 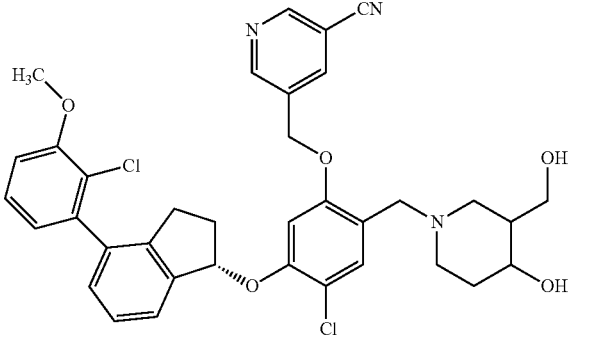 [SMILES: COc1cccc(-c2cccc3c2CC[C@@H]3Oc2cc(OCc3cncc(C#N)c3)c(CN3CCC(O)C(CO)C3)cc2Cl)c1Cl] | 660.1 | 3.62* |
| 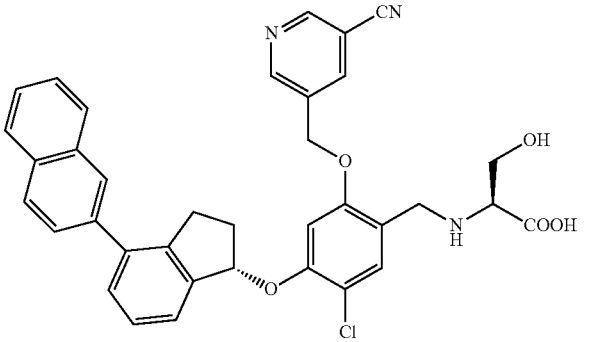 [SMILES: N#Cc1cncc(COc2cc(O[C@H]3CCc4c(-c5ccc6ccccc6c5)cccc43)c(Cl)cc2CN[C@@H](CO)C(=O)O)c1] | 620.1 | 2.79 |

TABLE 1C-continued

| Compound Structure | MS: (ES) m/z (M + H) | RP HPLC R_t (min) |
|---|---|---|
| 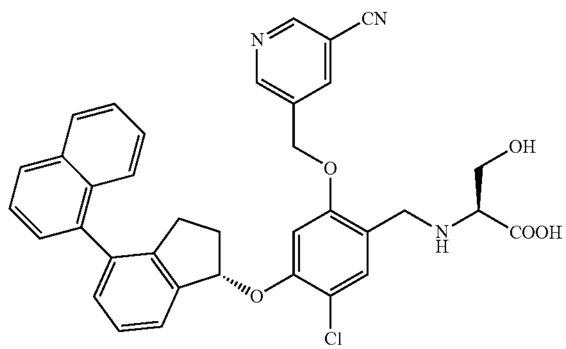 [SMILES: N#Cc1cncc(COc2cc(O[C@H]3CCc4c(-c5cccc6ccccc56)cccc43)c(Cl)cc2CN[C@@H](CO)C(=O)O)c1] | 620.1 | 2.68 |
| 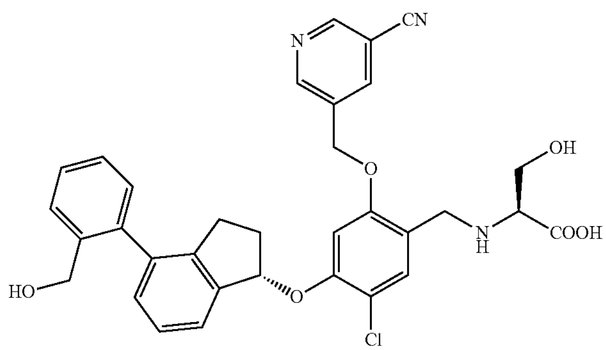 [SMILES: N#Cc1cncc(COc2cc(O[C@H]3CCc4c(-c5ccccc5CO)cccc43)c(Cl)cc2CN[C@@H](CO)C(=O)O)c1] | 600.0. | 1.74 |
| 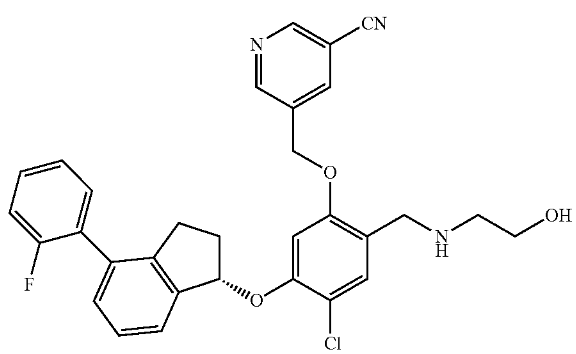 [SMILES: N#Cc1cncc(COc2cc(O[C@H]3CCc4c(-c5ccccc5F)cccc43)c(Cl)cc2CNCCO)c1] | 544.2 | 3.62 |
| 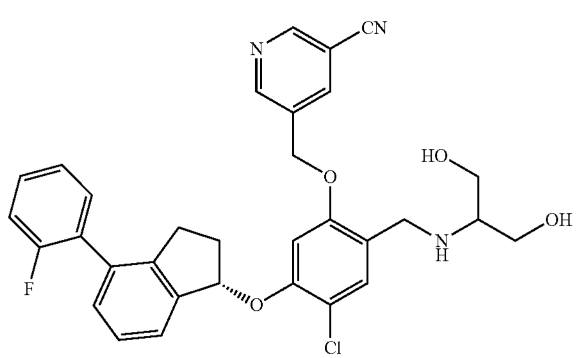 [SMILES: N#Cc1cncc(COc2cc(O[C@H]3CCc4c(-c5ccccc5F)cccc43)c(Cl)cc2CNC(CO)CO)c1] | 574.2 | 3.57 |

TABLE 1C-continued
| Compound Structure | MS: (ES) m/z (M + H) | RP HPLC R_t (min) |
|---|---|---|
| 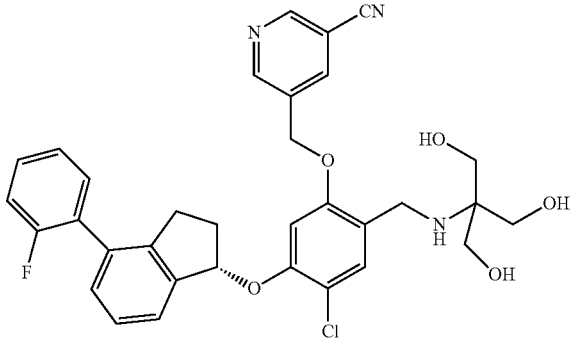 [SMILES: N#Cc1cncc(COc2cc(O[C@H]3CCc4c(-c5ccccc5F)cccc43)c(Cl)cc2CNC(CO)(CO)CO)c1] | 604.1 | 3.48 |
| 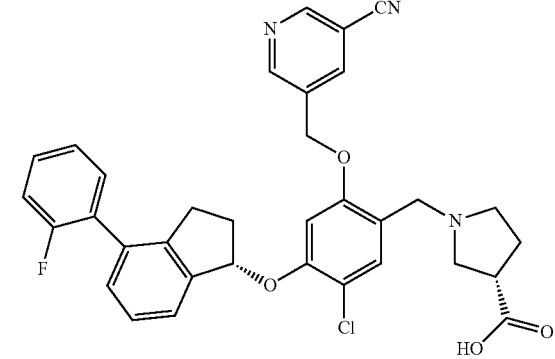 [SMILES: N#Cc1cncc(COc2cc(O[C@H]3CCc4c(-c5ccccc5F)cccc43)c(Cl)cc2CN2CC[C@H](C(=O)O)C2)c1] | 598.2. | 2.45 |
| 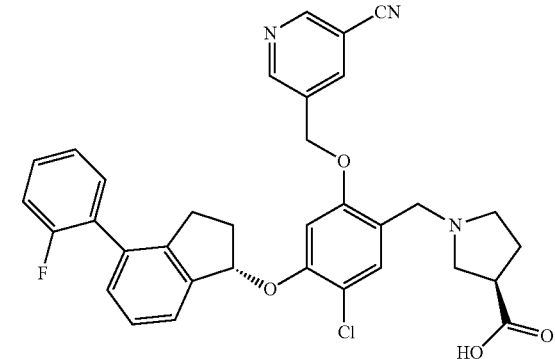 [SMILES: N#Cc1cncc(COc2cc(O[C@H]3CCc4c(-c5ccccc5F)cccc43)c(Cl)cc2CN2CC[C@@H](C(=O)O)C2)c1] | 598.2. | 2.32 |
| 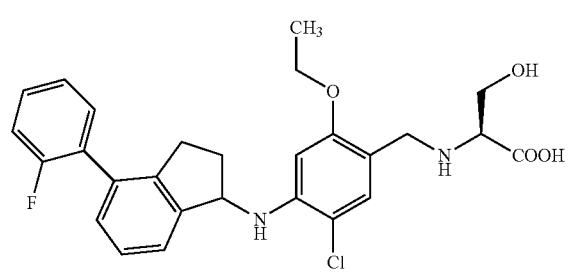 [SMILES: CCOc1cc(NC2CCc3c(-c4ccccc4F)cccc32)c(Cl)cc1CN[C@@H](CO)C(=O)O] | 394.1 | 4.49* |

TABLE 1C-continued

| Compound Structure | MS: (ES) m/z (M + H) | RP HPLC R$_t$ (min) |
|---|---|---|
| 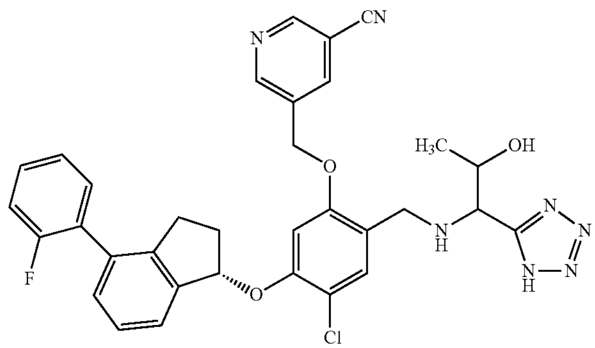 [SMILES: CC(O)C(NCc1cc(Cl)c(O[C@H]2CCc3c(-c4ccccc4F)cccc32)cc1OCc1cncc(C#N)c1)c1nnn[nH]1] | 626.2 | 2.38 |
| 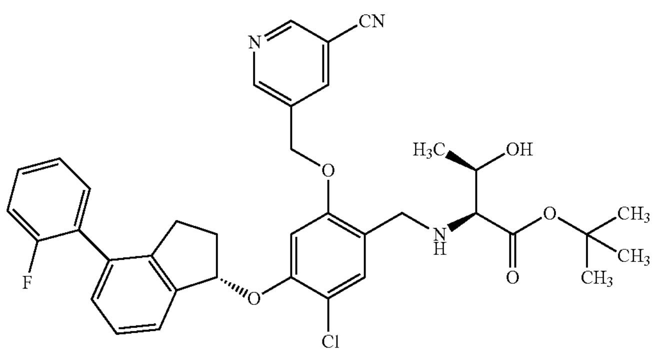 [SMILES: C[C@@H](O)[C@H](NCc1cc(Cl)c(O[C@H]2CCc3c(-c4ccccc4F)cccc32)cc1OCc1cncc(C#N)c1)C(=O)OC(C)(C)C] | 658.2 | 2.58 |
| 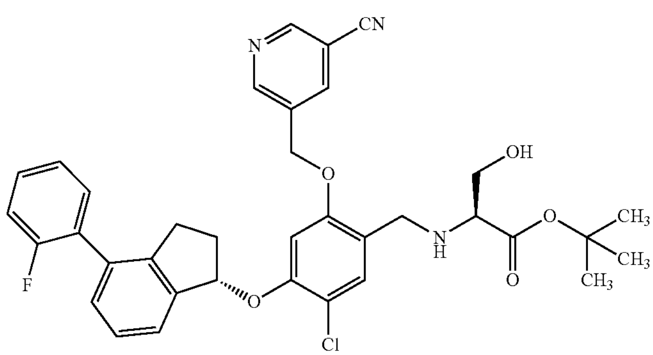 [SMILES: CC(C)(C)OC(=O)[C@H](CO)NCc1cc(Cl)c(O[C@H]2CCc3c(-c4ccccc4F)cccc32)cc1OCc1cncc(C#N)c1] | 644.2 | 2.78 |
| 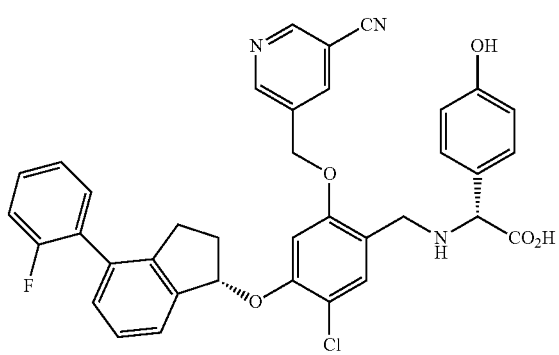 [SMILES: N#Cc1cncc(COc2cc(O[C@H]3CCc4c(-c5ccccc5F)cccc43)c(Cl)cc2CN[C@@H](C(=O)O)c2ccc(O)cc2)c1] | 650.1 | 2.4 |

TABLE 1C-continued

| Compound Structure | MS: (ES) m/z (M + H) | RP HPLC R$_t$ (min) |
|---|---|---|
| 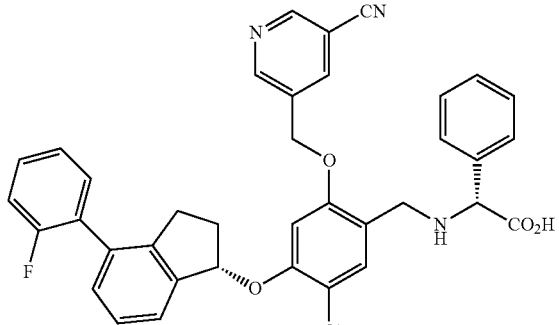 | 634.1 | 2.64 |

Reverse phase HPLC conditions used for determination of retention times in Table 1B and Table 1C:
Column: ZORBAX (SB-C18 2.1×50 mm, 5 m)
Mobile phase A: 95% H$_2$O, 5% MeCN (with 0.1% Formic Acid)
Mobile phase B: 5% H$_2$O, 95% MeCN (with 0.1% Formic Acid)
Flow rate: 1.0 mL/min
Gradient: 20 to 100% B in 3.5 min (for R$_t$ without *) or 20 to 100% B in 5.5 min (for R$_t$ with *)

Example 48: Enzyme-Linked Immunosorbent Assay—ELISA

Plates were coated with 1 μg/mL of human PD-L1 (obtained from R&D) in PBS overnight at 4° C. The wells were then blocked with PBS containing 2% BSA in PBS (W/V) with 0.05% TWEEN-20 for 1 hour at 37° C. The plates were washed 3 times with PBS/0.05% TWEEN-20 and the samples were diluted to 1:5 in dilution medium in the ELISA plates. Human PD-1 and biotin 0.3 μg/mL (ACRO Biosystems) were added and incubated for 1 hour at 37° C. then washed 3 times with PBS/0.05% TWEEN-20. A second block was added with PBS containing 2% BSA in PBS (W/V)/0.05% TWEEN-20 for 10 min at 37° C. and was washed 3 times with PBS/0.05% TWEEN-20. Streptavidin-HRP was added for 1 hour at 37° C. then washed 3 times with PBS/0.05% TWEEN-20. TMB substrate was added and reacted for 20 min at 37° C. A stop solution (2N aqueous H$_2$SO$_4$) was added. The absorbance was read at 450 nm using a micro-plate spectrophotometer. The results are shown in Tables 2 and 3.

Compounds in Table 2 and Table 3 were prepared by methods as described in the Examples, and evaluated according to the assay below. The IC$_{50}$ of the compounds are presented in Table 2 and Table 3 as follows:
+, 20000 nM≥IC$_{50}$≥500 nM;
++, 500 nM>IC$_{50}$≥100 nM;
+++, 100 nM>IC$_{50}$.

TABLE 2

| Compound Number | Compound Structure | ELISA IC$_{50}$ (nM) |
|---|---|---|
| 1.001 | 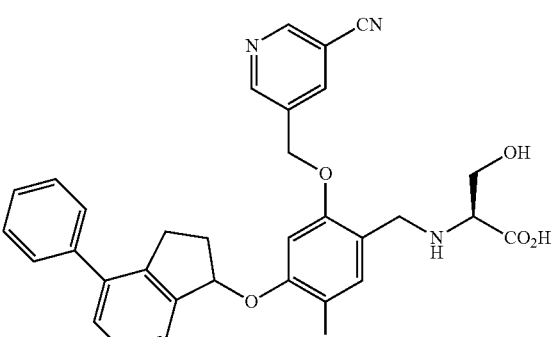 | +++ |

TABLE 2-continued

| Compound Number | Compound Structure | ELISA IC$_{50}$ (nM) |
|---|---|---|
| 1.002 | 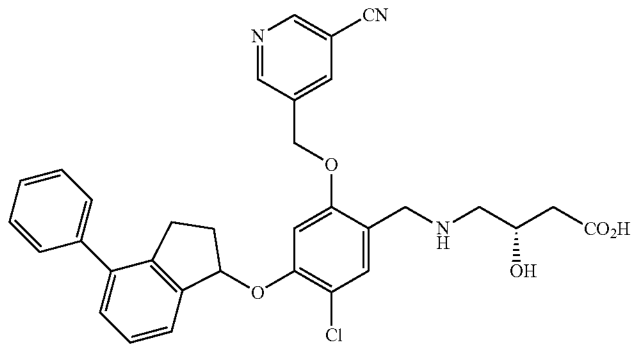 | ++ |
| 1.003 | 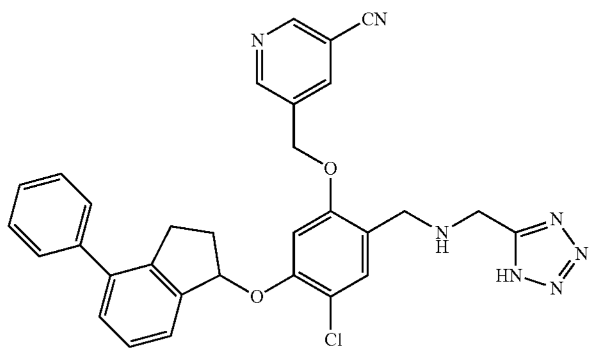 [SMILES: N#Cc1cncc(COc2cc(OC3CCc4c(-c5ccccc5)cccc43)c(Cl)cc2CNCc2nnn[nH]2)c1] | +++ |
| 1.004 | 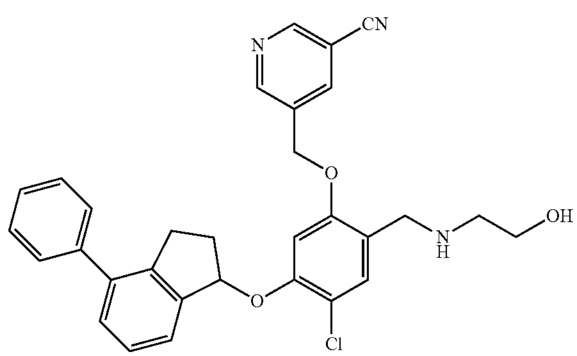 [SMILES: N#Cc1cncc(COc2cc(OC3CCc4c(-c5ccccc5)cccc43)c(Cl)cc2CNCCO)c1] | +++ |
| 1.005 | 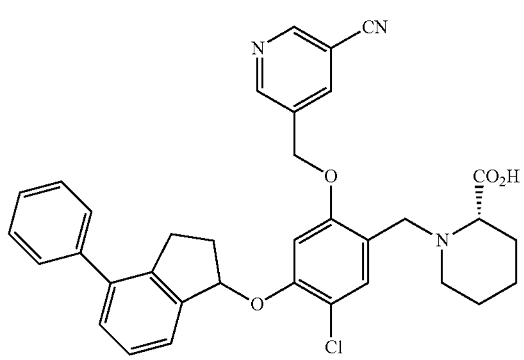 [SMILES: N#Cc1cncc(COc2cc(OC3CCc4c(-c5ccccc5)cccc43)c(Cl)cc2CN2CCCC[C@H]2C(=O)O)c1] | +++ |

TABLE 2-continued

| Compound Number | Compound Structure | ELISA IC$_{50}$ (nM) |
|---|---|---|
| 1.006 | 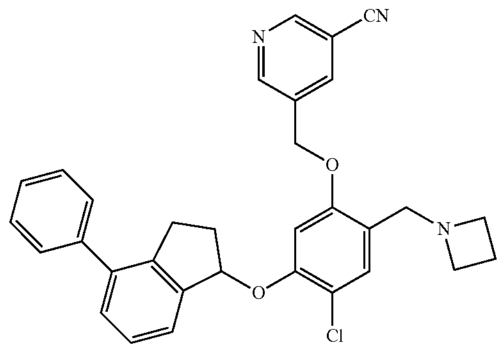 [SMILES: N#Cc1cncc(COc2cc(OC3CCc4c(-c5ccccc5)cccc43)c(Cl)cc2CN2CCC2)c1] | ++ |
| 1.007 | 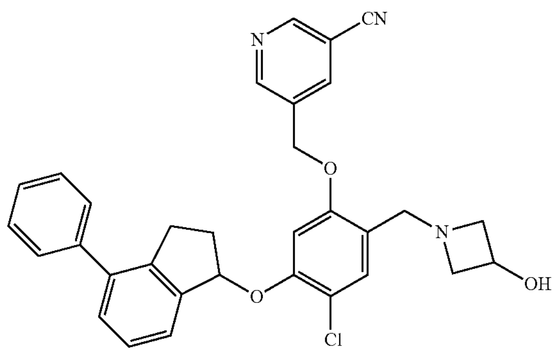 [SMILES: N#Cc1cncc(COc2cc(OC3CCc4c(-c5ccccc5)cccc43)c(Cl)cc2CN2CC(O)C2)c1] | ++ |
| 1.008 | 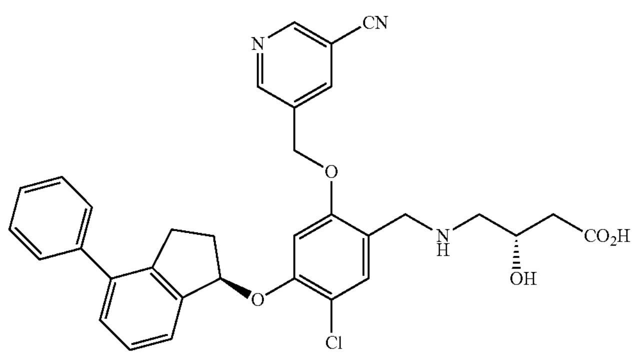 [SMILES: N#Cc1cncc(COc2cc(O[C@@H]3CCc4c(-c5ccccc5)cccc43)c(Cl)cc2CNC[C@@H](O)CC(=O)O)c1] | +++ |
| 1.009 | 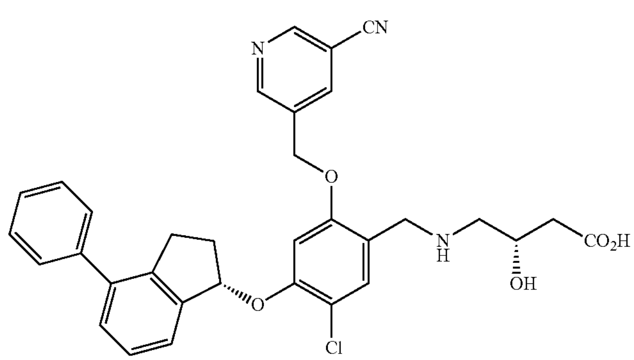 [SMILES: N#Cc1cncc(COc2cc(O[C@H]3CCc4c(-c5ccccc5)cccc43)c(Cl)cc2CNC[C@@H](O)CC(=O)O)c1] | +++ |

TABLE 2-continued

| Compound Number | Compound Structure | ELISA IC$_{50}$ (nM) |
|---|---|---|
| 1.010 | 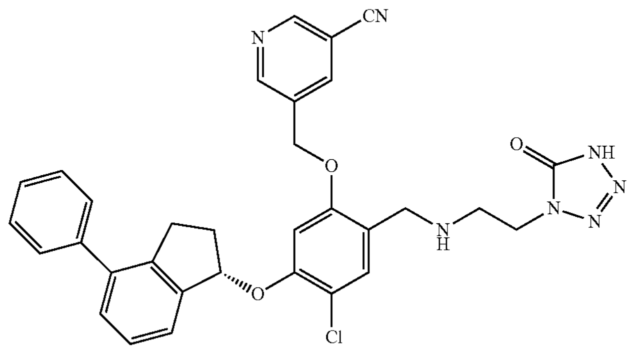 [SMILES: N#Cc1cncc(COc2cc(O[C@H]3CCc4c(-c5ccccc5)cccc43)c(Cl)cc2CNCCn2nn[nH]c2=O)c1] | ++ |
| 1.011 | 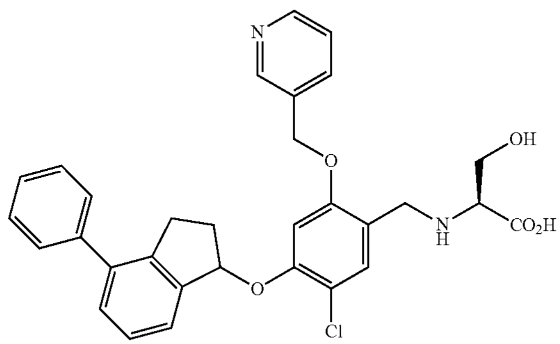 [SMILES: O=C(O)[C@H](CO)NCc1cc(Cl)c(OC2CCc3c(-c4ccccc4)cccc32)cc1OCc1cccnc1] | + |
| 1.012 | 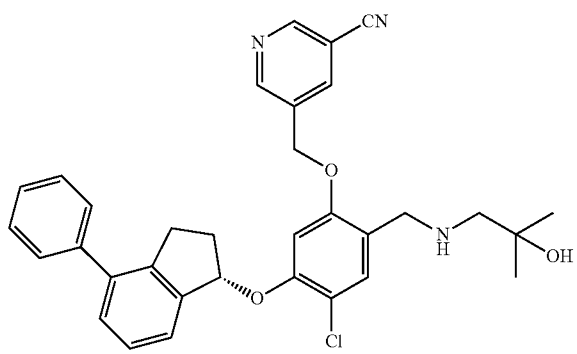 [SMILES: CC(C)(O)CNCc1cc(Cl)c(O[C@H]2CCc3c(-c4ccccc4)cccc32)cc1OCc1cncc(C#N)c1] | + |
| 1.013 | 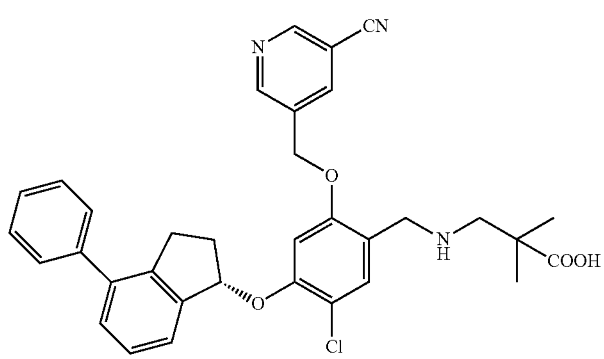 [SMILES: CC(C)(CNCc1cc(Cl)c(O[C@H]2CCc3c(-c4ccccc4)cccc32)cc1OCc1cncc(C#N)c1)C(=O)O] | + |

TABLE 2-continued

| Compound Number | Compound Structure | ELISA IC$_{50}$ (nM) |
|---|---|---|
| 1.014 | 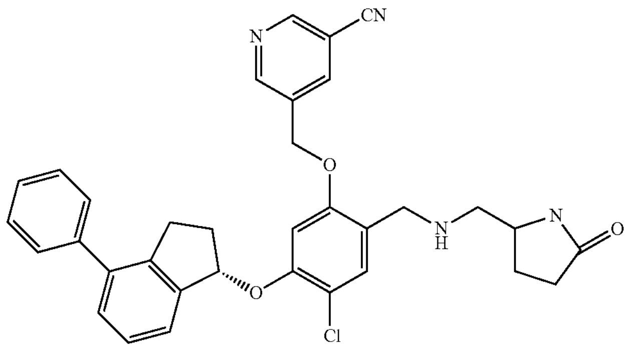 [SMILES: N#Cc1cncc(COc2cc(O[C@H]3CCc4c(-c5ccccc5)cccc43)c(Cl)cc2CNCC2CCC(=O)N2)c1] | ++ |
| 1.015 | 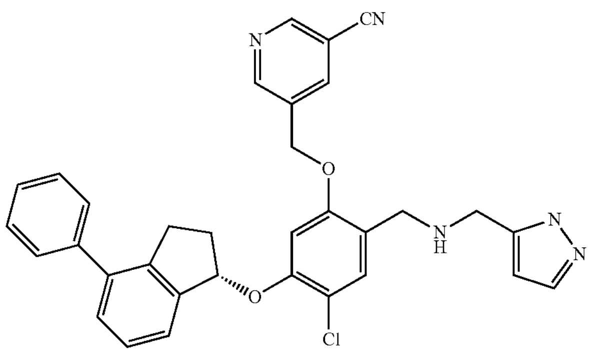 [SMILES: N#Cc1cncc(COc2cc(O[C@H]3CCc4c(-c5ccccc5)cccc43)c(Cl)cc2CNCc2ccn[nH]2)c1] | + |
| 2.001 | 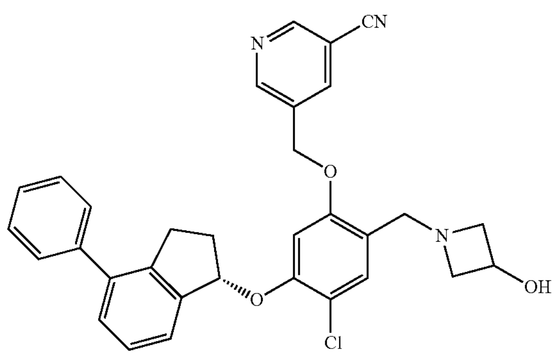 [SMILES: N#Cc1cncc(COc2cc(O[C@H]3CCc4c(-c5ccccc5)cccc43)c(Cl)cc2CN2CC(O)C2)c1] | ++ |
| 2.002 | 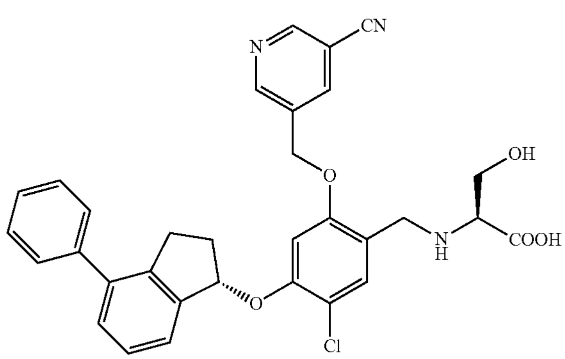 [SMILES: N#Cc1cncc(COc2cc(O[C@H]3CCc4c(-c5ccccc5)cccc43)c(Cl)cc2CN[C@@H](CO)C(=O)O)c1] | +++ |

TABLE 2-continued

| Compound Number | Compound Structure | ELISA IC$_{50}$ (nM) |
|---|---|---|
| 2.003 | 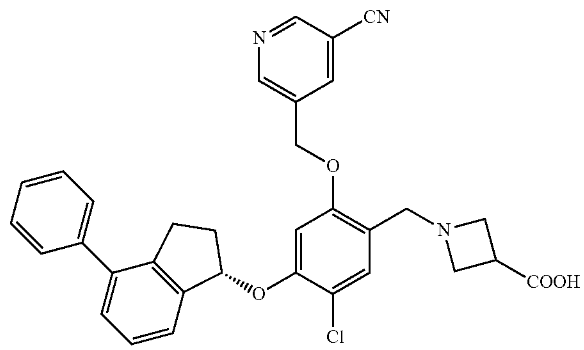 [SMILES: N#Cc1cncc(COc2cc(O[C@H]3CCc4c(-c5ccccc5)cccc43)c(Cl)cc2CN2CC(C(=O)O)C2)c1] | +++ |
| 2.004 | 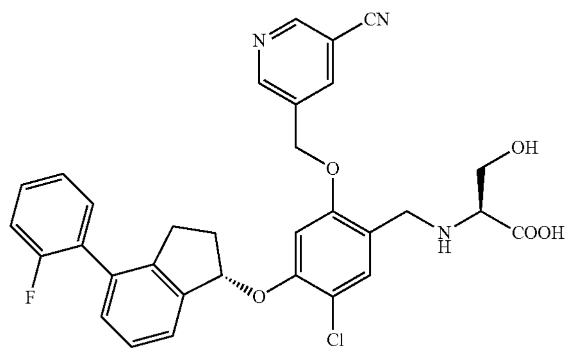 [SMILES: N#Cc1cncc(COc2cc(O[C@H]3CCc4c(-c5ccccc5F)cccc43)c(Cl)cc2CN[C@@H](CO)C(=O)O)c1] | +++ |
| 2.005 | 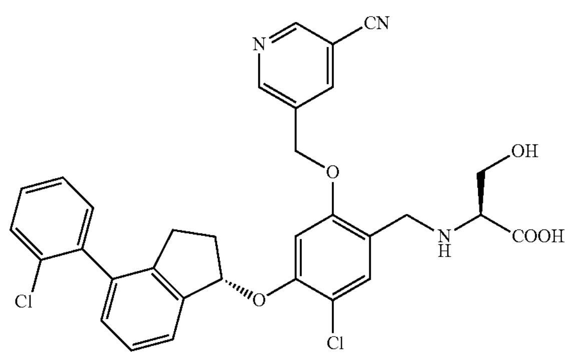 [SMILES: N#Cc1cncc(COc2cc(O[C@H]3CCc4c(-c5ccccc5Cl)cccc43)c(Cl)cc2CN[C@@H](CO)C(=O)O)c1] | +++ |
| 2.006 | 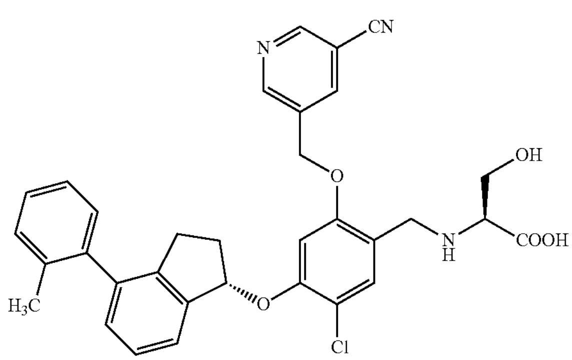 [SMILES: Cc1ccccc1-c1cccc2c1CC[C@@H]2Oc1cc(OCc2cncc(C#N)c2)c(CN[C@@H](CO)C(=O)O)cc1Cl] | +++ |

TABLE 2-continued

| Compound Number | Compound Structure | ELISA IC$_{50}$ (nM) |
|---|---|---|
| 2.007 | 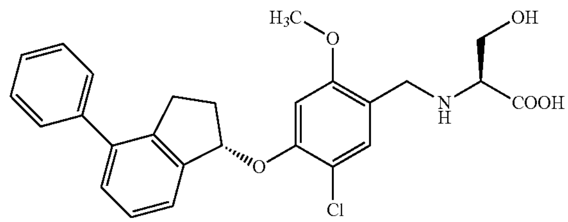 [SMILES: COc1cc(O[C@H]2CCc3c(-c4ccccc4)cccc32)c(Cl)cc1CN[C@@H](CO)C(=O)O] | ++ |
| 2.008 | 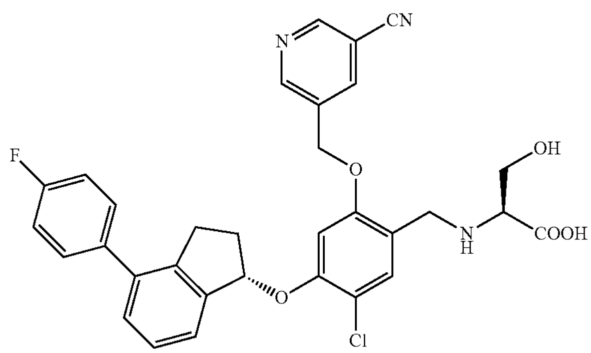 [SMILES: N#Cc1cncc(COc2cc(O[C@H]3CCc4c(-c5ccc(F)cc5)cccc43)c(Cl)cc2CN[C@@H](CO)C(=O)O)c1] | ++ |
| 2.009 | 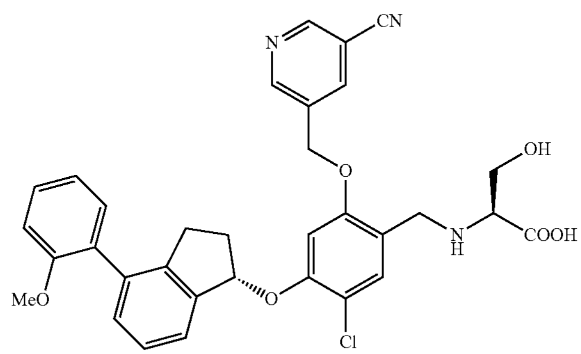 [SMILES: COc1ccccc1-c1cccc2c1CC[C@@H]2Oc1cc(OCc2cncc(C#N)c2)c(CN[C@@H](CO)C(=O)O)cc1Cl] | + |
| 2.010 | 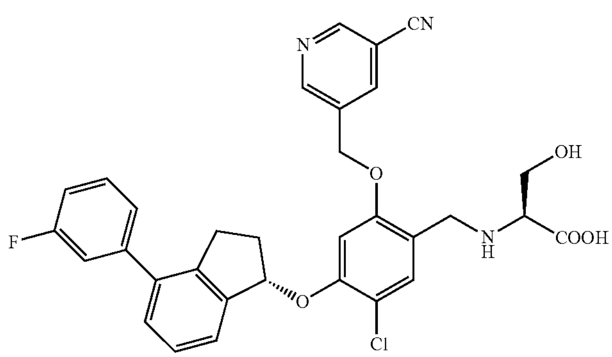 [SMILES: N#Cc1cncc(COc2cc(O[C@H]3CCc4c(-c5cccc(F)c5)cccc43)c(Cl)cc2CN[C@@H](CO)C(=O)O)c1] | +++ |
| 2.011 | 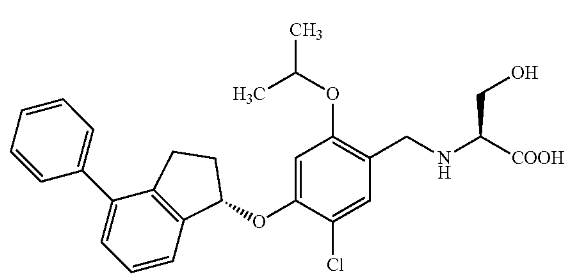 [SMILES: CC(C)Oc1cc(O[C@H]2CCc3c(-c4ccccc4)cccc32)c(Cl)cc1CN[C@@H](CO)C(=O)O] | + |

TABLE 2-continued

| Compound Number | Compound Structure | ELISA IC$_{50}$ (nM) |
|---|---|---|
| 2.012 | 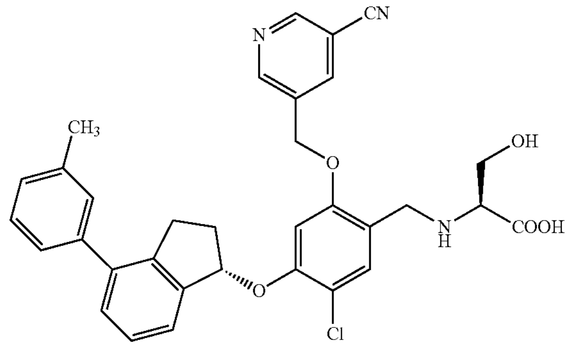 [SMILES: Cc1cccc(-c2cccc3c2CC[C@@H]3Oc2cc(OCc3cncc(C#N)c3)c(CN[C@@H](CO)C(=O)O)cc2Cl)c1] | + |
| 2.103 | 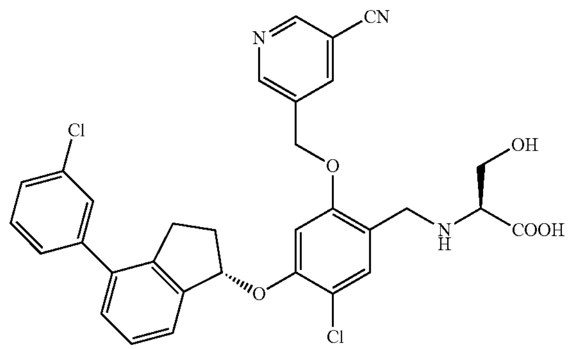 [SMILES: N#Cc1cncc(COc2cc(O[C@H]3CCc4c(-c5cccc(Cl)c5)cccc43)c(Cl)cc2CN[C@@H](CO)C(=O)O)c1] | ++ |
| 2.014 | 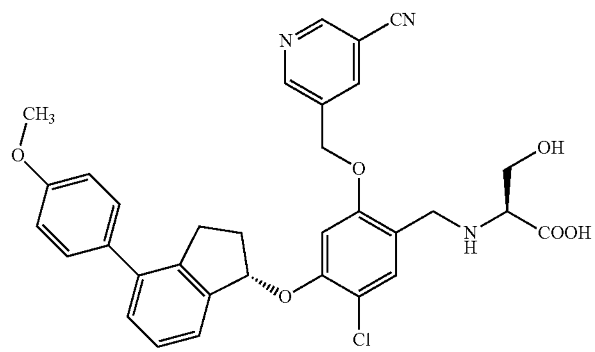 [SMILES: COc1ccc(-c2cccc3c2CC[C@@H]3Oc2cc(OCc3cncc(C#N)c3)c(CN[C@@H](CO)C(=O)O)cc2Cl)cc1] | ++ |
| 2.015 | 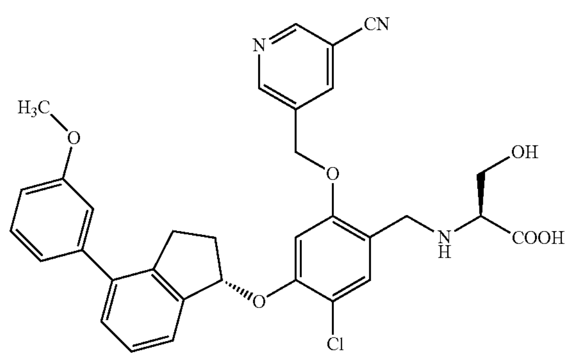 [SMILES: COc1cccc(-c2cccc3c2CC[C@@H]3Oc2cc(OCc3cncc(C#N)c3)c(CN[C@@H](CO)C(=O)O)cc2Cl)c1] | +++ |

TABLE 2-continued
| Compound Number | Compound Structure | ELISA IC$_{50}$ (nM) |
|---|---|---|
| 2.016 | 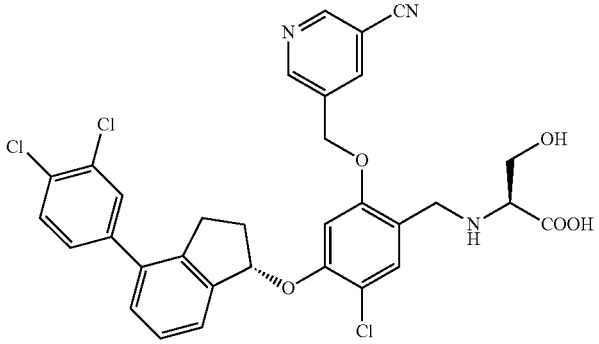 [SMILES: N#Cc1cncc(COc2cc(O[C@H]3CCc4c(-c5ccc(Cl)c(Cl)c5)cccc43)c(Cl)cc2CN[C@@H](CO)C(=O)O)c1] | + |
| 2.017 | 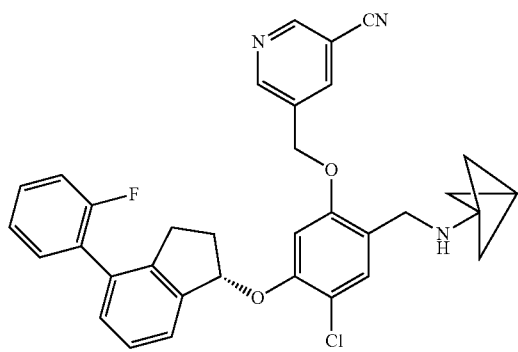 [SMILES: N#Cc1cncc(COc2cc(O[C@H]3CCc4c(-c5ccccc5F)cccc43)c(Cl)cc2CNC23CC(C2)C3)c1] | + |
| 2.018 | 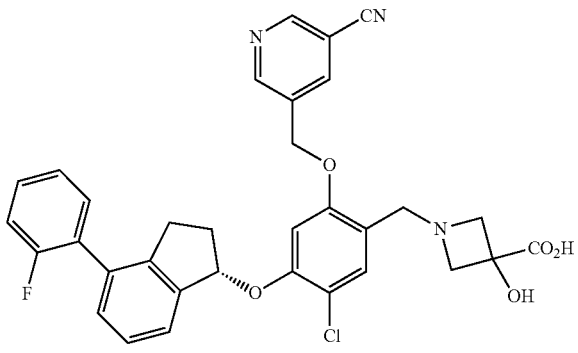 [SMILES: N#Cc1cncc(COc2cc(O[C@H]3CCc4c(-c5ccccc5F)cccc43)c(Cl)cc2CN2CC(O)(C(=O)O)C2)c1] | ++ |
| 2.019 | 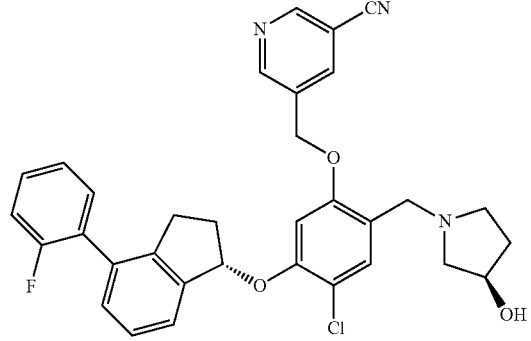 [SMILES: N#Cc1cncc(COc2cc(O[C@H]3CCc4c(-c5ccccc5F)cccc43)c(Cl)cc2CN2CC[C@@H](O)C2)c1] | +++ |

TABLE 2-continued

| Compound Number | Compound Structure | ELISA IC$_{50}$ (nM) |
|---|---|---|
| 2.020 | 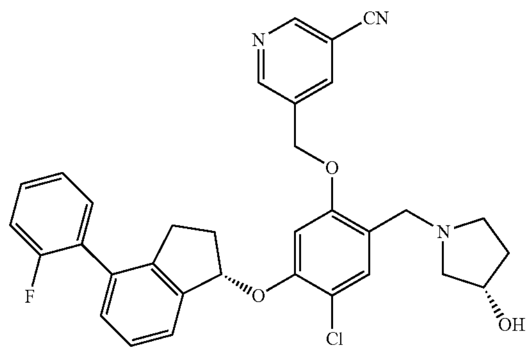 [SMILES: N#Cc1cncc(COc2cc(O[C@H]3CCc4c(-c5ccccc5F)cccc43)c(Cl)cc2CN2CC[C@H](O)C2)c1] | ++ |
| 2.021 | 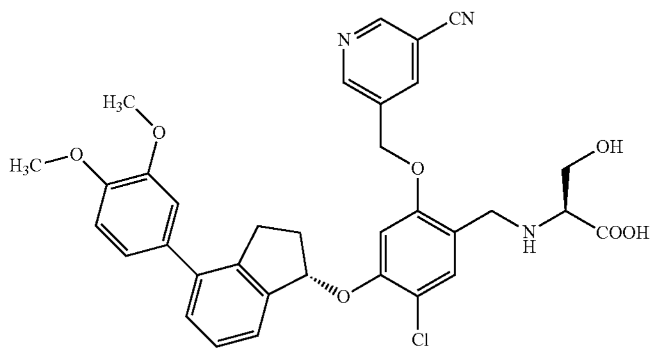 [SMILES: COc1ccc(-c2cccc3c2CC[C@@H]3Oc2cc(OCc3cncc(C#N)c3)c(CN[C@@H](CO)C(=O)O)cc2Cl)cc1OC] | + |
| 2.022 | 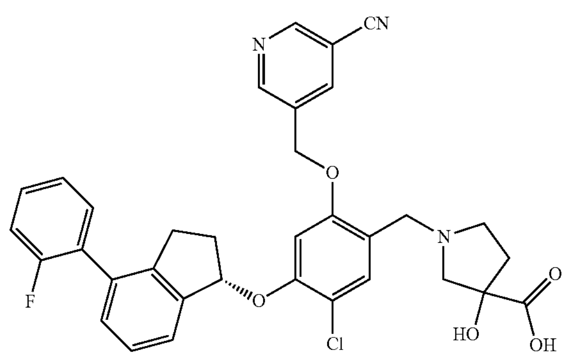 [SMILES: N#Cc1cncc(COc2cc(O[C@H]3CCc4c(-c5ccccc5F)cccc43)c(Cl)cc2CN2CCC(O)(C(=O)O)C2)c1] | +++ |
| 2.023 | 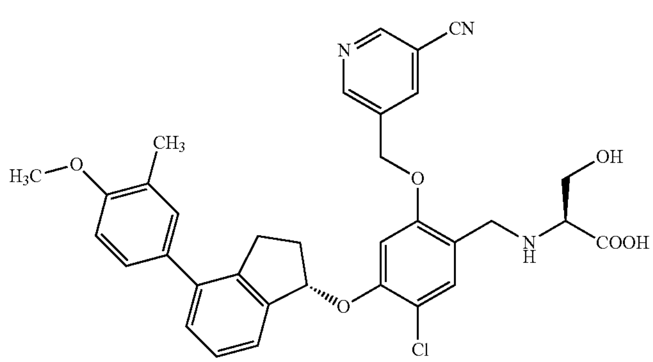 [SMILES: COc1ccc(-c2cccc3c2CC[C@@H]3Oc2cc(OCc3cncc(C#N)c3)c(CN[C@@H](CO)C(=O)O)cc2Cl)cc1C] | ++ |

TABLE 2-continued

| Compound Number | Compound Structure | ELISA IC$_{50}$ (nM) |
| --- | --- | --- |
| 2.024 | 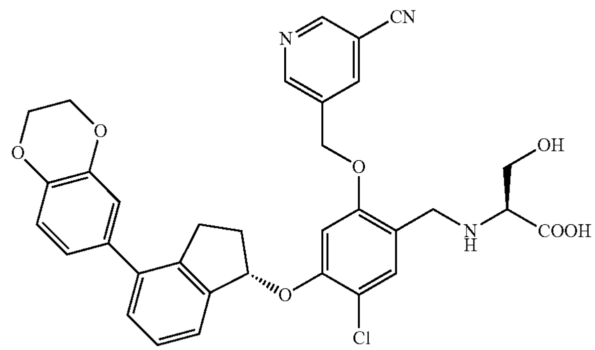 [SMILES: N#Cc1cncc(COc2cc(O[C@H]3CCc4c(-c5ccc6c(c5)OCCO6)cccc43)c(Cl)cc2CN[C@@H](CO)C(=O)O)c1] | +++ |
| 2.025 | 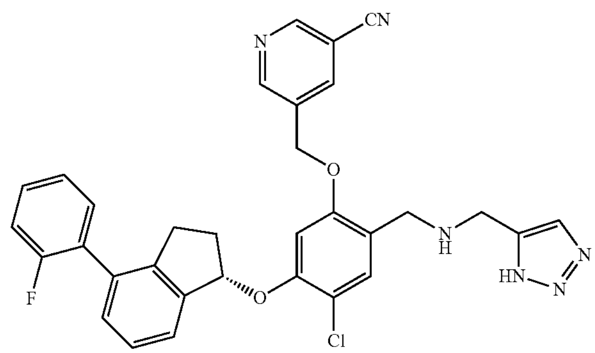 [SMILES: N#Cc1cncc(COc2cc(O[C@H]3CCc4c(-c5ccccc5F)cccc43)c(Cl)cc2CNCc2cnn[nH]2)c1] | ++ |
| 2.026 | 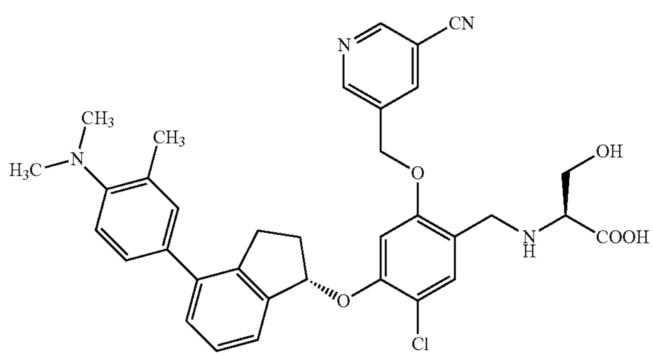 [SMILES: Cc1cc(-c2cccc3c2CC[C@@H]3Oc2cc(OCc3cncc(C#N)c3)c(CN[C@@H](CO)C(=O)O)cc2Cl)ccc1N(C)C] | + |
| 2.027 | 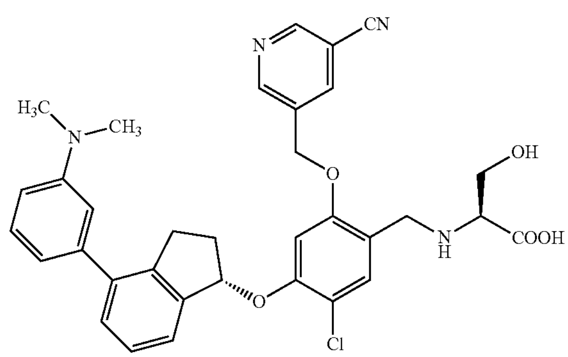 | + |

TABLE 2-continued

| Compound Number | Compound Structure | ELISA IC$_{50}$ (nM) |
|---|---|---|
| 2.028 | 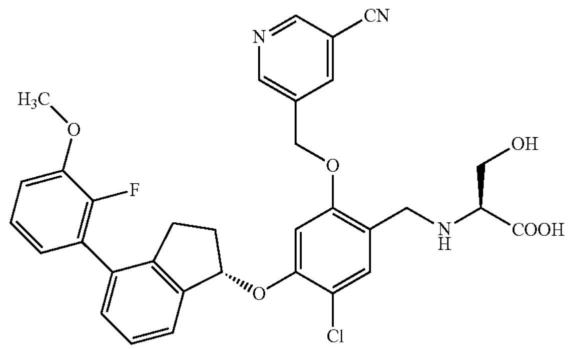 [SMILES: COc1cccc(-c2cccc3c2CC[C@@H]3Oc2cc(OCc3cncc(C#N)c3)c(CN[C@@H](CO)C(=O)O)cc2Cl)c1F] | +++ |
| 2.029 | 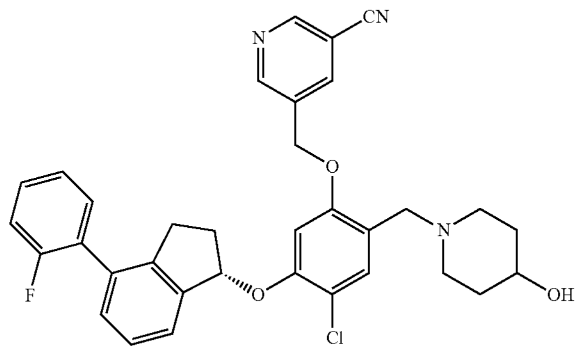 [SMILES: N#Cc1cncc(COc2cc(O[C@H]3CCc4c(-c5ccccc5F)cccc43)c(Cl)cc2CN2CCC(O)CC2)c1] | +++ |
| 2.030 | 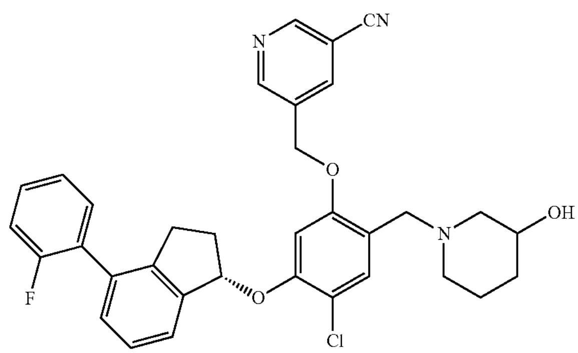 [SMILES: N#Cc1cncc(COc2cc(O[C@H]3CCc4c(-c5ccccc5F)cccc43)c(Cl)cc2CN2CCCC(O)C2)c1] | ++ |
| 2.031 | 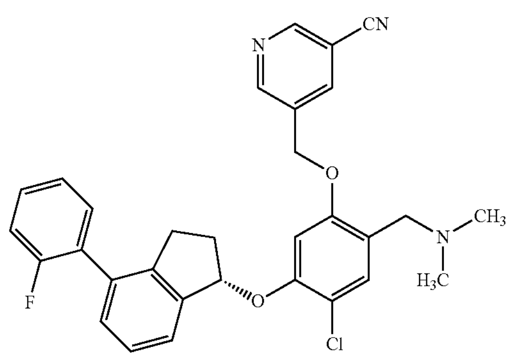 [SMILES: CN(C)Cc1cc(Cl)c(O[C@H]2CCc3c(-c4ccccc4F)cccc32)cc1OCc1cncc(C#N)c1] | +++ |

TABLE 2-continued
| Compound Number | Compound Structure | ELISA IC$_{50}$ (nM) |
|---|---|---|
| 2.032 | 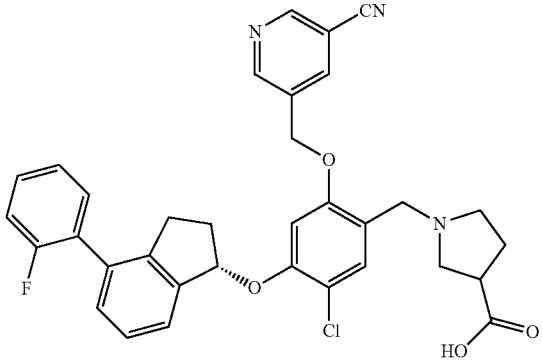 [SMILES: N#Cc1cncc(COc2cc(O[C@H]3CCc4c(-c5ccccc5F)cccc43)c(Cl)cc2CN2CCC(C(=O)O)C2)c1] | +++ |
| 2.033 | 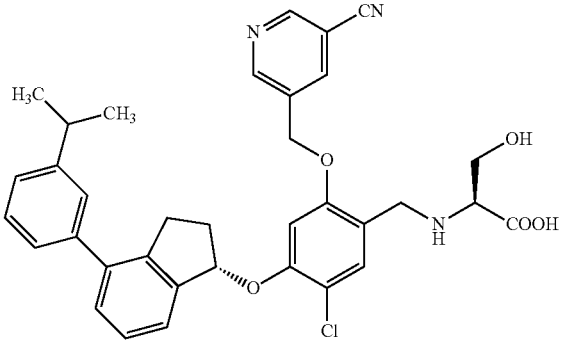 [SMILES: CC(C)c1cccc(-c2cccc3c2CC[C@@H]3Oc2cc(OCc3cncc(C#N)c3)c(CN[C@@H](CO)C(=O)O)cc2Cl)c1] | + |
| 2.034 | 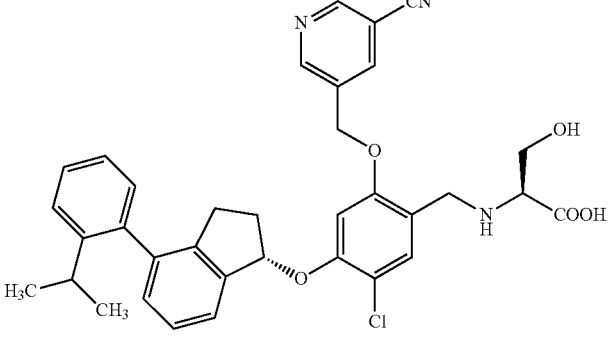 | ++ |
| 2.035 | 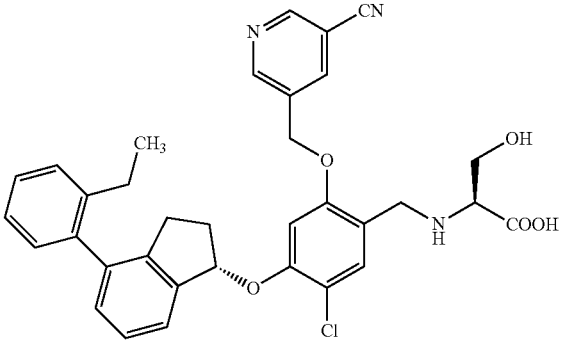 [SMILES: CCc1ccccc1-c1cccc2c1CC[C@@H]2Oc1cc(OCc2cncc(C#N)c2)c(CN[C@@H](CO)C(=O)O)cc1Cl] | ++ |

TABLE 2-continued
| Compound Number | Compound Structure | ELISA IC$_{50}$ (nM) |
|---|---|---|
| 2.036 | 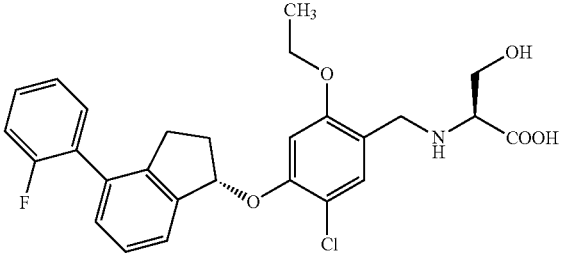 [SMILES: CCOc1cc(O[C@H]2CCc3c(-c4ccccc4F)cccc32)c(Cl)cc1CN[C@@H](CO)C(=O)O] | +++ |
| 2.037 | 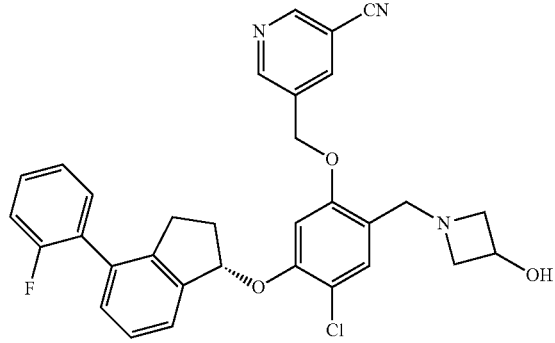 [SMILES: N#Cc1cncc(COc2cc(O[C@H]3CCc4c(-c5ccccc5F)cccc43)c(Cl)cc2CN2CC(O)C2)c1] | +++ |
| 2.038 | 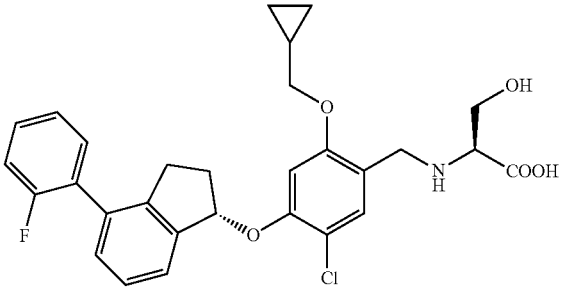 [SMILES: O=C(O)[C@H](CO)NCc1cc(Cl)c(O[C@H]2CCc3c(-c4ccccc4F)cccc32)cc1OCC1CC1] | ++ |
| 2.039 | 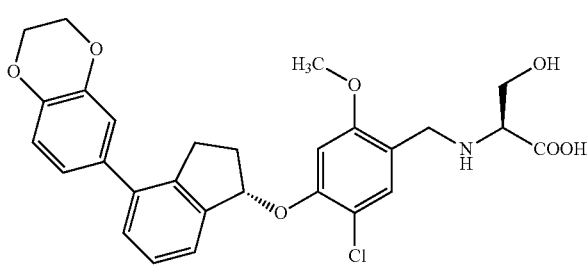 [SMILES: COc1cc(O[C@H]2CCc3c(-c4ccc5c(c4)OCCO5)cccc32)c(Cl)cc1CN[C@@H](CO)C(=O)O] | +++ |
| 2.040 | 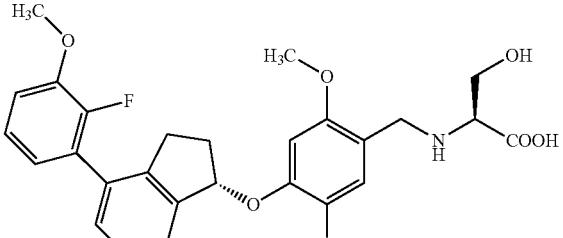 | +++ |

TABLE 2-continued

| Compound Number | Compound Structure | ELISA IC$_{50}$ (nM) |
|---|---|---|
| 2.041 | 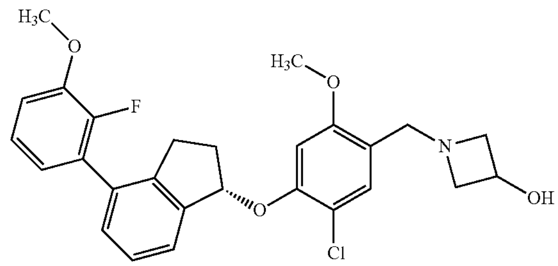 [SMILES: COc1cc(O[C@H]2CCc3c(-c4cccc(OC)c4F)cccc32)c(Cl)cc1CN1CC(O)C1] | + |
| 2.042 | 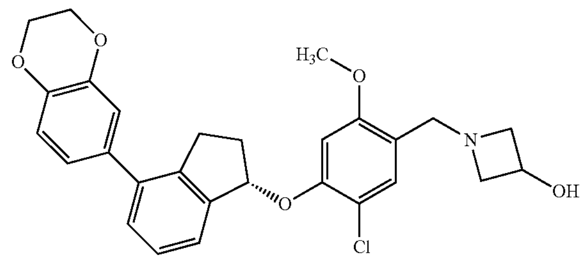 [SMILES: COc1cc(O[C@H]2CCc3c(-c4ccc5c(c4)OCCO5)cccc32)c(Cl)cc1CN1CC(O)C1] | + |
| 2.043 | 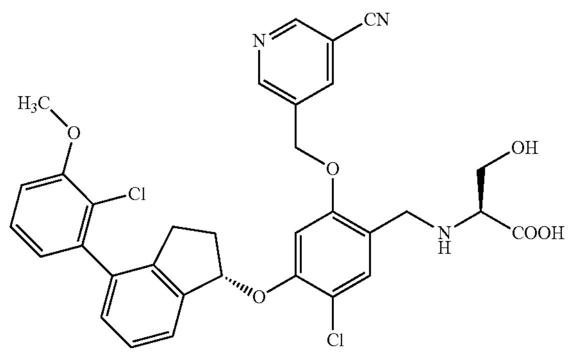 [SMILES: COc1cccc(-c2cccc3c2CC[C@@H]3Oc2cc(OCc3cncc(C#N)c3)c(CN[C@@H](CO)C(=O)O)cc2Cl)c1Cl] | +++ |
| 2.044 | 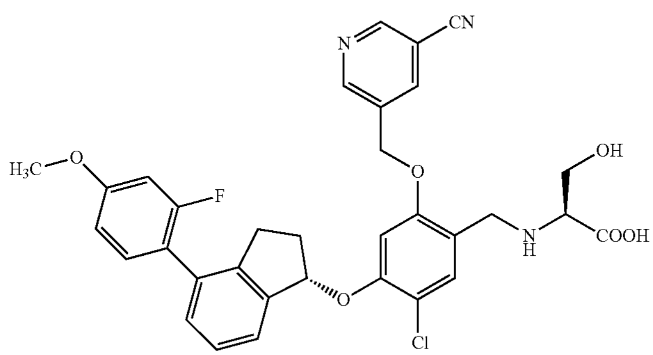 [SMILES: COc1ccc(-c2cccc3c2CC[C@@H]3Oc2cc(OCc3cncc(C#N)c3)c(CN[C@@H](CO)C(=O)O)cc2Cl)c(F)c1] | ++ |
| 2.045 | 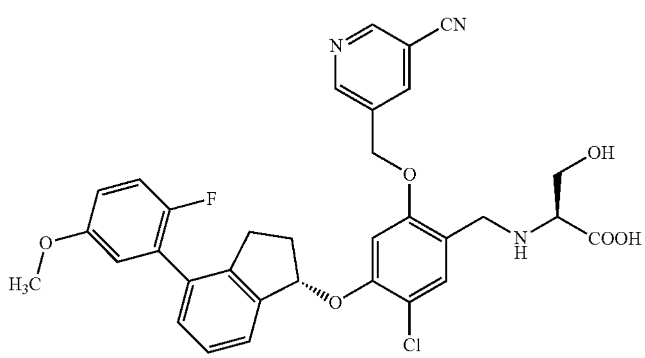 [SMILES: COc1ccc(F)c(-c2cccc3c2CC[C@@H]3Oc2cc(OCc3cncc(C#N)c3)c(CN[C@@H](CO)C(=O)O)cc2Cl)c1] | +++ |

TABLE 2-continued

| Compound Number | Compound Structure | ELISA IC$_{50}$ (nM) |
|---|---|---|
| 2.046 | 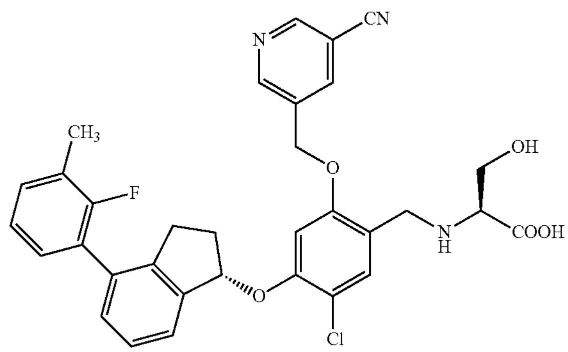 [SMILES: Cc1cccc(-c2cccc3c2CC[C@@H]3Oc2cc(OCc3cncc(C#N)c3)c(CN[C@@H](CO)C(=O)O)cc2Cl)c1F] | +++ |
| 2.047 | 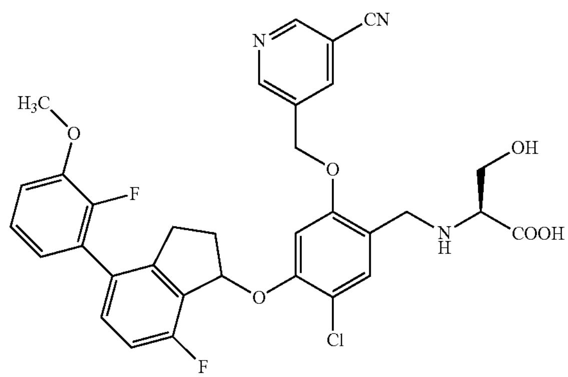 [SMILES: COc1cccc(-c2ccc(F)c3c2CCC3Oc2cc(OCc3cncc(C#N)c3)c(CN[C@@H](CO)C(=O)O)cc2Cl)c1F] | +++ |
| 2.048 | 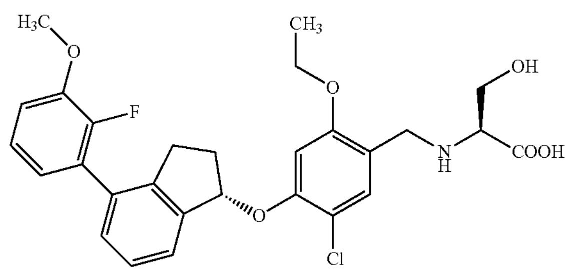 [SMILES: CCOc1cc(O[C@H]2CCc3c(-c4cccc(OC)c4F)cccc32)c(Cl)cc1CN[C@@H](CO)C(=O)O] | +++ |
| 2.049 | 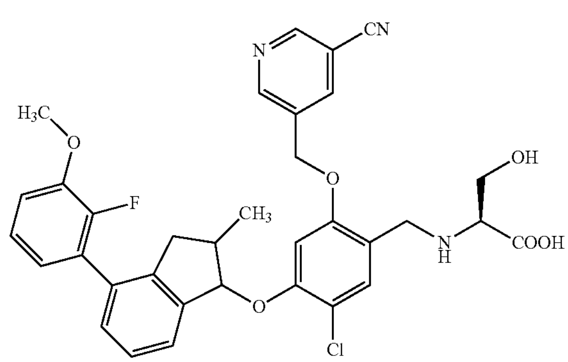 [SMILES: COc1cccc(-c2cccc3c2CC(C)C3Oc2cc(OCc3cncc(C#N)c3)c(CN[C@@H](CO)C(=O)O)cc2Cl)c1F] | + |

TABLE 2-continued
| Compound Number | Compound Structure | ELISA IC$_{50}$ (nM) |
|---|---|---|
| 2.050 | 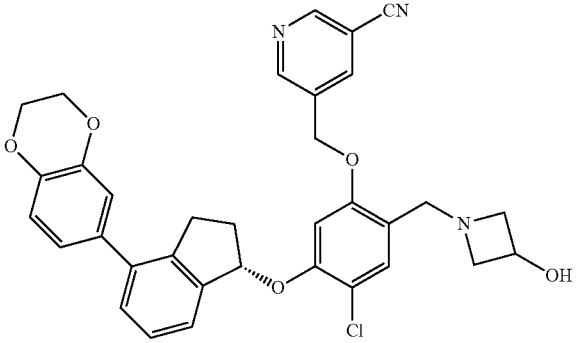 [SMILES: N#Cc1cncc(COc2cc(O[C@H]3CCc4c(-c5ccc6c(c5)OCCO6)cccc43)c(Cl)cc2CN2CC(O)C2)c1] | +++ |
| 2.051 | 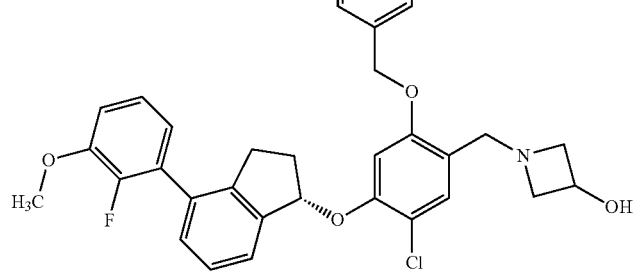 | +++ |
| 2.052 | 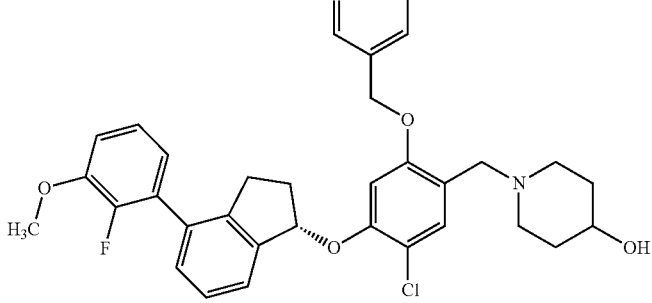 | ++ |
| 2.053 | 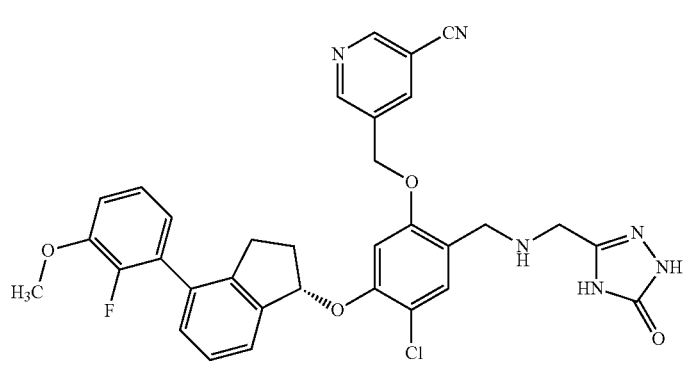 [SMILES: COc1cccc(-c2cccc3c2CC[C@@H]3Oc2cc(OCc3cncc(C#N)c3)c(CNCc3n[nH]c(=O)[nH]3)cc2Cl)c1F] | ++ |

TABLE 2-continued

| Compound Number | Compound Structure | ELISA IC$_{50}$ (nM) |
|---|---|---|
| 2.054 | 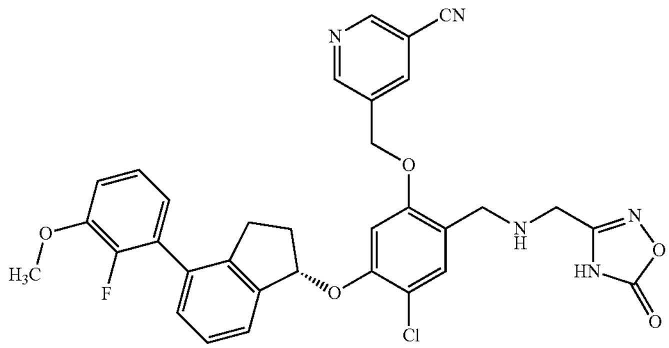 [SMILES: COc1cccc(-c2cccc3c2CC[C@@H]3Oc2cc(OCc3cncc(C#N)c3)c(CNCc3noc(=O)[nH]3)cc2Cl)c1F] | + |
| 2.055 | 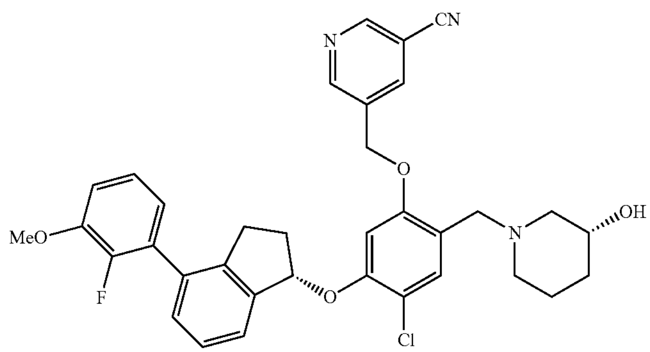 [SMILES: COc1cccc(-c2cccc3c2CC[C@@H]3Oc2cc(OCc3cncc(C#N)c3)c(CN3CCC[C@@H](O)C3)cc2Cl)c1F] | ++ |
| 2.056 | 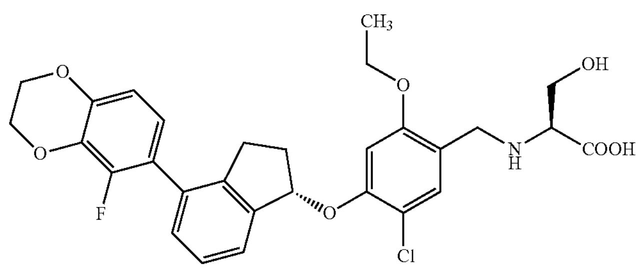 [SMILES: CCOc1cc(O[C@H]2CCc3c(-c4ccc5c(c4F)OCCO5)cccc32)c(Cl)cc1CN[C@@H](CO)C(=O)O] | +++ |
| 2.057 | 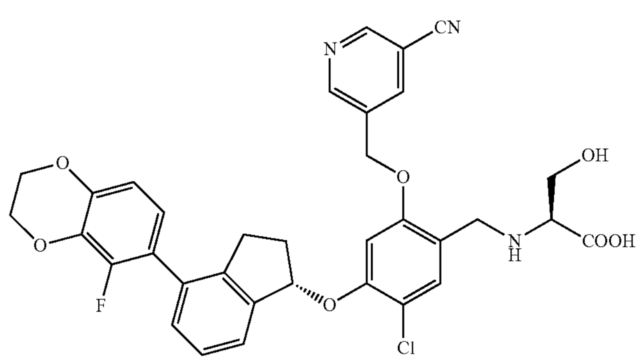 [SMILES: N#Cc1cncc(COc2cc(O[C@H]3CCc4c(-c5ccc6c(c5F)OCCO6)cccc43)c(Cl)cc2CN[C@@H](CO)C(=O)O)c1] | +++ |

TABLE 2-continued
| Compound Number | Compound Structure | ELISA IC$_{50}$ (nM) |
|---|---|---|
| 2.058 | 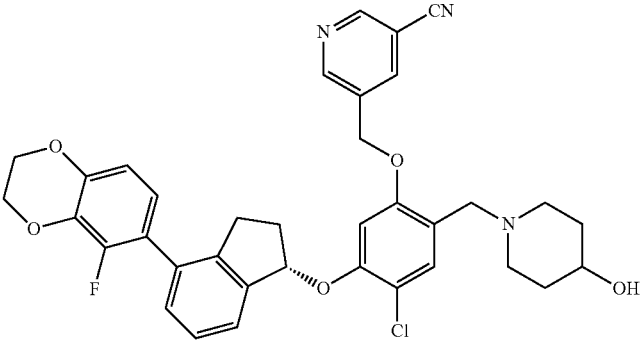 [SMILES: N#Cc1cncc(COc2cc(O[C@H]3CCc4c(-c5ccc6c(c5F)OCCO6)cccc43)c(Cl)cc2CN2CCC(O)CC2)c1] | +++ |
| 2.059 | 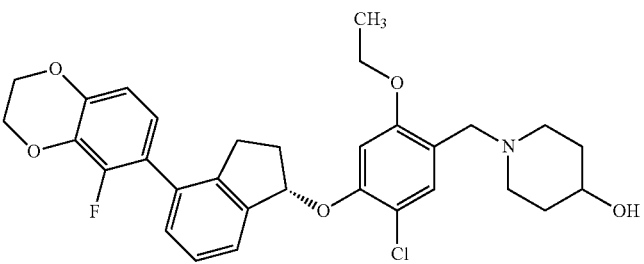 [SMILES: CCOc1cc(O[C@H]2CCc3c(-c4ccc5c(c4F)OCCO5)cccc32)c(Cl)cc1CN1CCC(O)CC1] | + |
| 2.060 | 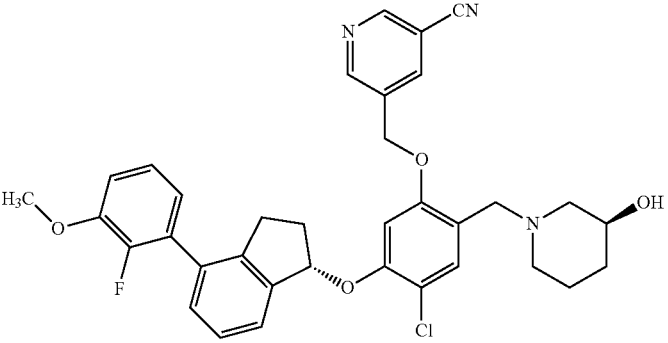 [SMILES: COc1cccc(-c2cccc3c2CC[C@@H]3Oc2cc(OCc3cncc(C#N)c3)c(CN3CCC[C@H](O)C3)cc2Cl)c1F] | ++ |
| 2.061 | 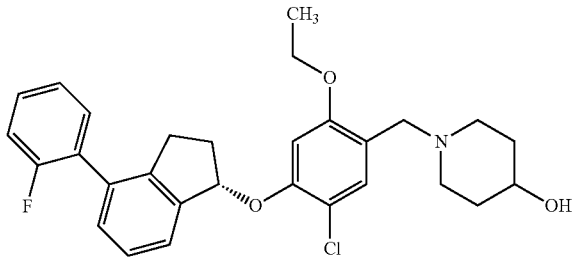 [SMILES: CCOc1cc(O[C@H]2CCc3c(-c4ccccc4F)cccc32)c(Cl)cc1CN1CCC(O)CC1] | + |
| 2.062 | 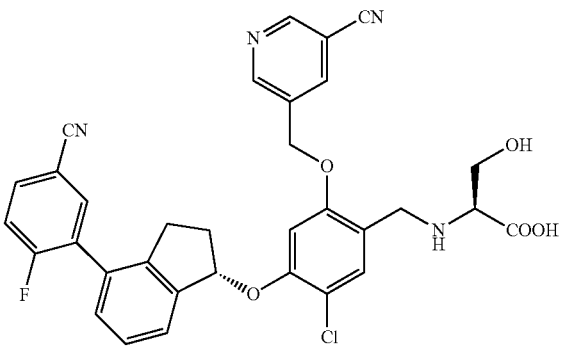 [SMILES: N#Cc1cncc(COc2cc(O[C@H]3CCc4c(-c5cc(C#N)ccc5F)cccc43)c(Cl)cc2CN[C@@H](CO)C(=O)O)c1] | + |

TABLE 2-continued

| Compound Number | Compound Structure | ELISA IC$_{50}$ (nM) |
|---|---|---|
| 2.063 | 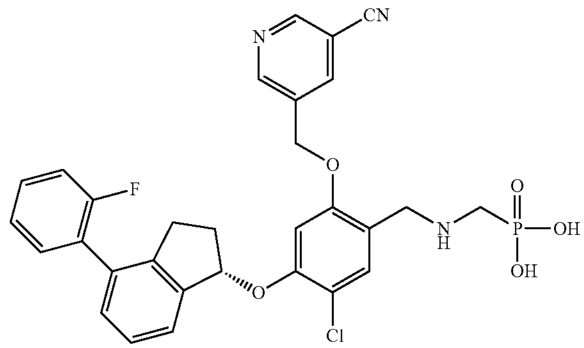 [SMILES: N#Cc1cncc(COc2cc(O[C@H]3CCc4c(-c5ccccc5F)cccc43)c(Cl)cc2CNCP(=O)(O)O)c1] | +++ |
| 2.064 | 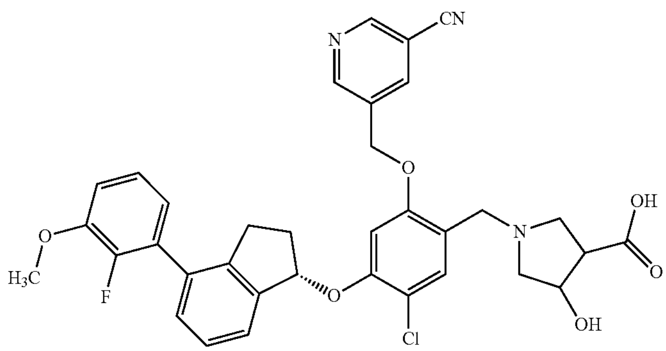 [SMILES: COc1cccc(-c2cccc3c2CC[C@@H]3Oc2cc(OCc3cncc(C#N)c3)c(CN3CC(O)C(C(=O)O)C3)cc2Cl)c1F] | +++ |
| 2.065 | 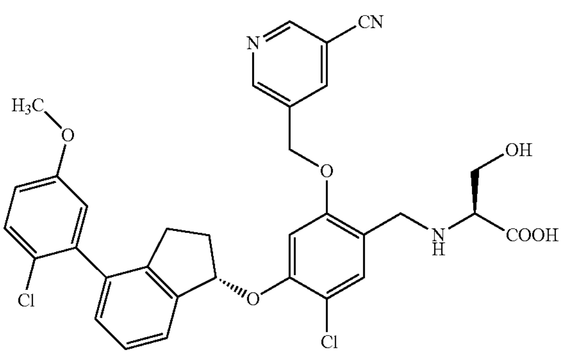 [SMILES: COc1ccc(Cl)c(-c2cccc3c2CC[C@@H]3Oc2cc(OCc3cncc(C#N)c3)c(CN[C@@H](CO)C(=O)O)cc2Cl)c1] | +++ |
| 2.066 | 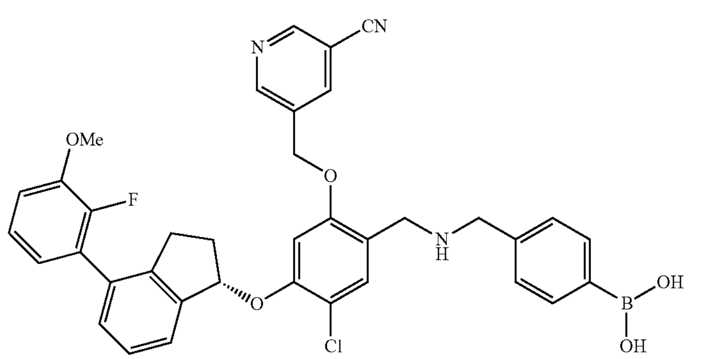 [SMILES: COc1cccc(-c2cccc3c2CC[C@@H]3Oc2cc(OCc3cncc(C#N)c3)c(CNCc3ccc(B(O)O)cc3)cc2Cl)c1F] | + |

TABLE 2-continued

| Compound Number | Compound Structure | ELISA IC$_{50}$ (nM) |
|---|---|---|
| 2.067 | 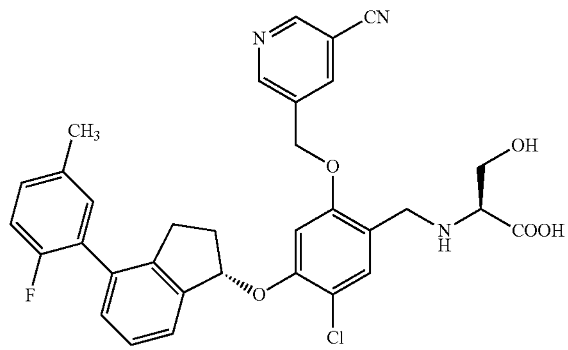 | +++ |
| 2.068 | 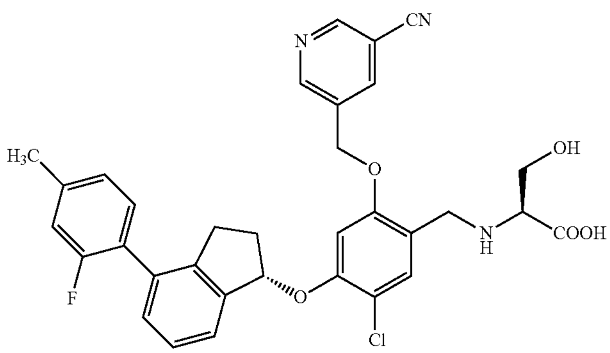 [SMILES: Cc1ccc(-c2cccc3c2CC[C@@H]3Oc2cc(OCc3cncc(C#N)c3)c(CN[C@@H](CO)C(=O)O)cc2Cl)c(F)c1] | ++ |
| 2.069 | 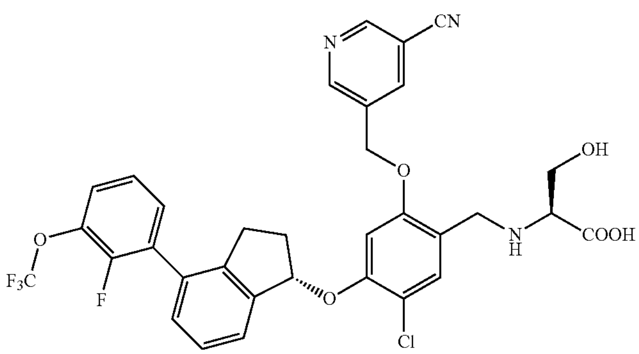 [SMILES: N#Cc1cncc(COc2cc(O[C@H]3CCc4c(-c5cccc(OC(F)(F)F)c5F)cccc43)c(Cl)cc2CN[C@@H](CO)C(=O)O)c1] | + |
| 2.070 | 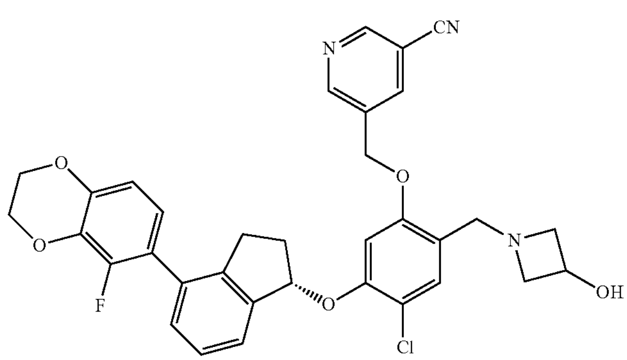 [SMILES: N#Cc1cncc(COc2cc(O[C@H]3CCc4c(-c5ccc6c(c5F)OCCO6)cccc43)c(Cl)cc2CN2CC(O)C2)c1] | +++ |

TABLE 2-continued

| Compound Number | Compound Structure | ELISA IC$_{50}$ (nM) |
|---|---|---|
| 2.071 | 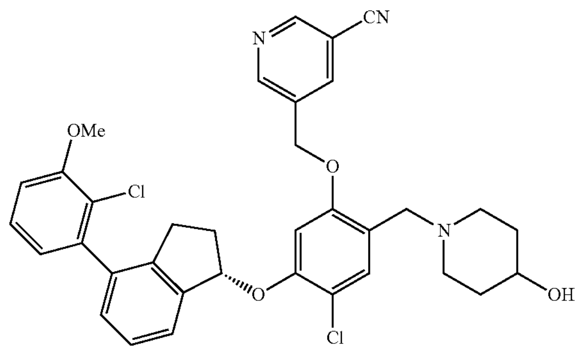 [SMILES: COc1cccc(-c2cccc3c2CC[C@@H]3Oc2cc(OCc3cncc(C#N)c3)c(CN3CCC(O)CC3)cc2Cl)c1Cl] | ++ |
| 2.072 | 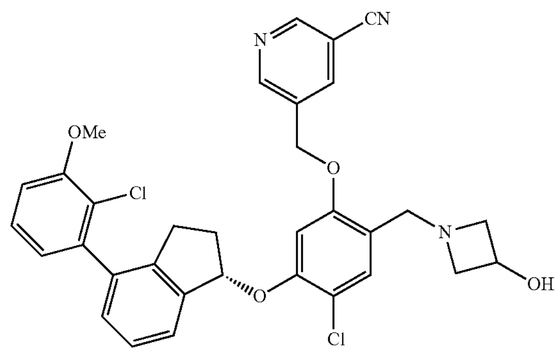 [SMILES: COc1cccc(-c2cccc3c2CC[C@@H]3Oc2cc(OCc3cncc(C#N)c3)c(CN3CC(O)C3)cc2Cl)c1Cl] | ++ |
| 2.073 | 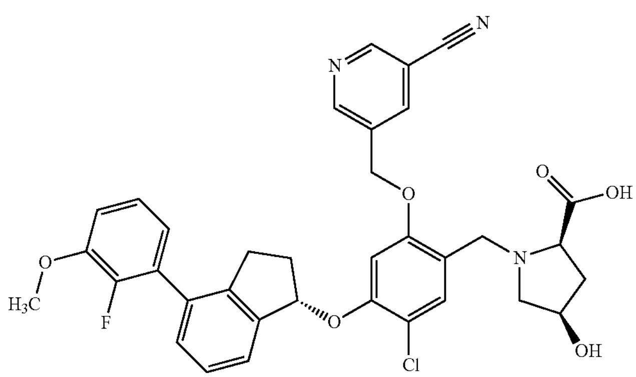 [SMILES: COc1cccc(-c2cccc3c2CC[C@@H]3Oc2cc(OCc3cncc(C#N)c3)c(CN3C[C@H](O)C[C@@H]3C(=O)O)cc2Cl)c1F] | +++ |
| 2.074 | 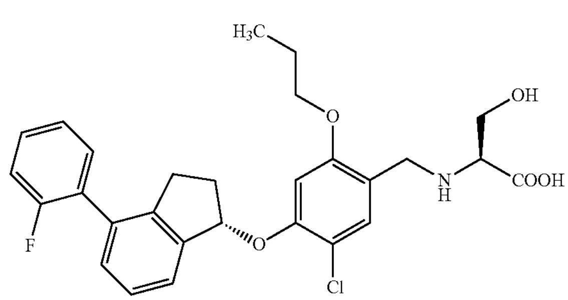 [SMILES: CCCOc1cc(O[C@H]2CCc3c(-c4ccccc4F)cccc32)c(Cl)cc1CN[C@@H](CO)C(=O)O] | ++ |

TABLE 2-continued

| Compound Number | Compound Structure | ELISA IC$_{50}$ (nM) |
|---|---|---|
| 2.075 | 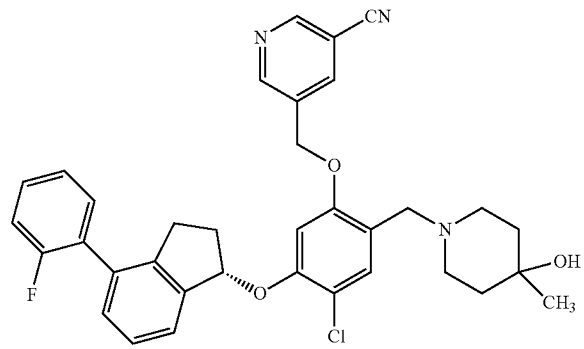 [SMILES: CC1(O)CCN(Cc2cc(Cl)c(O[C@H]3CCc4c(-c5ccccc5F)cccc43)cc2OCc2cncc(C#N)c2)CC1] | ++ |
| 2.076 | 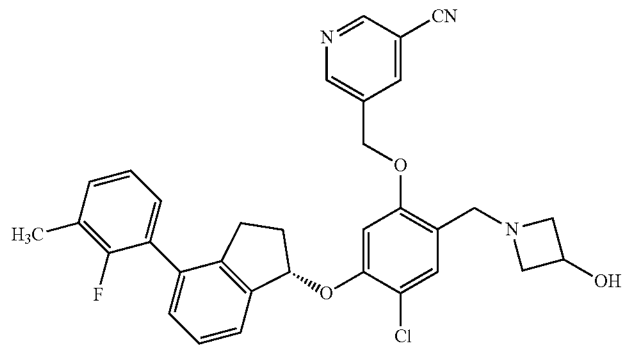 [SMILES: Cc1cccc(-c2cccc3c2CC[C@@H]3Oc2cc(OCc3cncc(C#N)c3)c(CN3CC(O)C3)cc2Cl)c1F] | ++ |
| 2.077 | 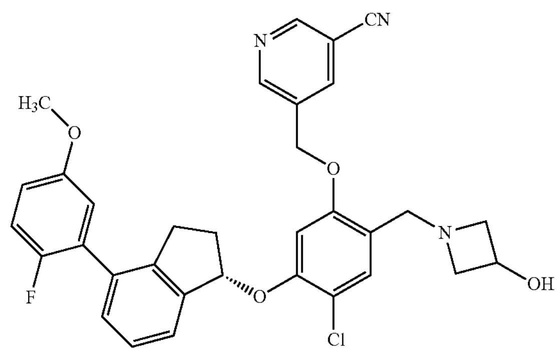 [SMILES: COc1ccc(F)c(-c2cccc3c2CC[C@@H]3Oc2cc(OCc3cncc(C#N)c3)c(CN3CC(O)C3)cc2Cl)c1] | ++ |
| 2.078 | 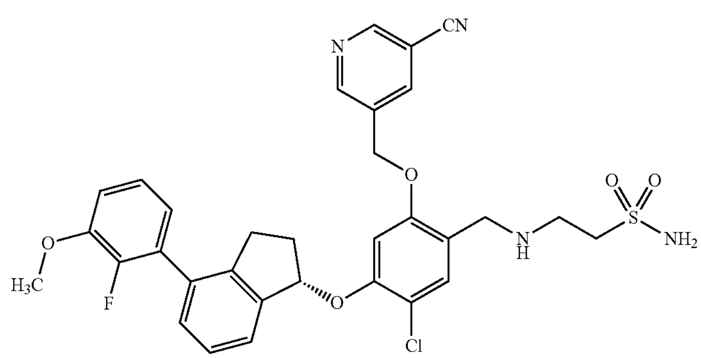 [SMILES: COc1cccc(-c2cccc3c2CC[C@@H]3Oc2cc(OCc3cncc(C#N)c3)c(CNCCS(N)(=O)=O)cc2Cl)c1F] | + |

TABLE 2-continued

| Compound Number | Compound Structure | ELISA IC$_{50}$ (nM) |
|---|---|---|
| 2.079 | 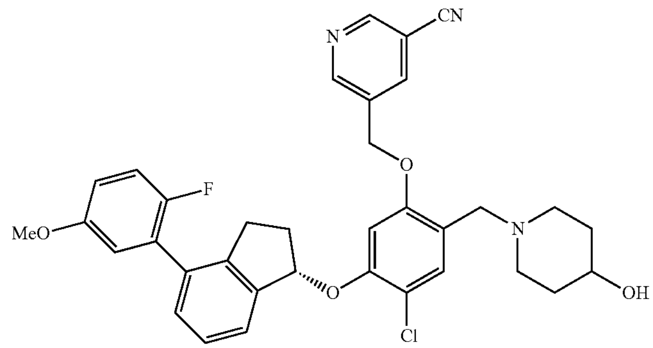 [SMILES: COc1ccc(F)c(-c2cccc3c2CC[C@@H]3Oc2cc(OCc3cncc(C#N)c3)c(CN3CCC(O)CC3)cc2Cl)c1] | ++ |
| 2.080 | 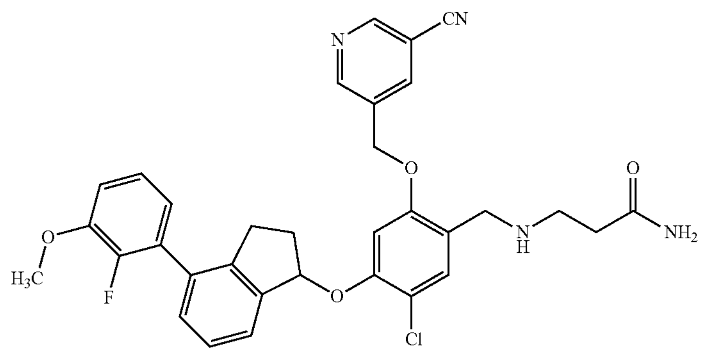 [SMILES: COc1cccc(-c2cccc3c2CCC3Oc2cc(OCc3cncc(C#N)c3)c(CNCCC(N)=O)cc2Cl)c1F] | ++ |
| 2.081 | 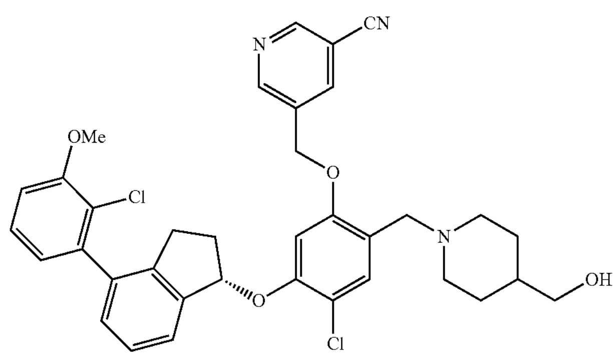 [SMILES: COc1cccc(-c2cccc3c2CC[C@@H]3Oc2cc(OCc3cncc(C#N)c3)c(CN3CCC(CO)CC3)cc2Cl)c1Cl] | ++ |
| 2.082 | 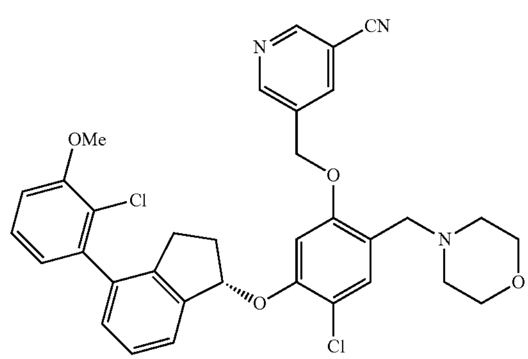 [SMILES: COc1cccc(-c2cccc3c2CC[C@@H]3Oc2cc(OCc3cncc(C#N)c3)c(CN3CCOCC3)cc2Cl)c1Cl] | + |

TABLE 2-continued
| Compound Number | Compound Structure | ELISA IC$_{50}$ (nM) |
|---|---|---|
| 2.083 | 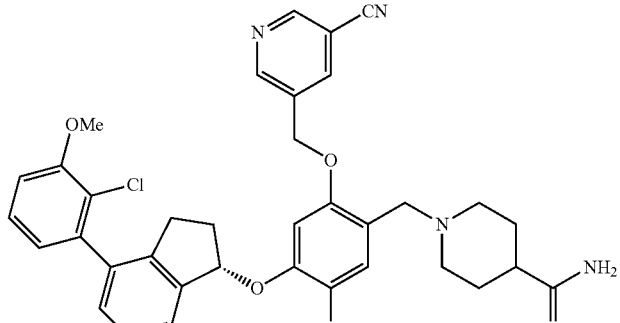 | ++ |
| 2.084 | 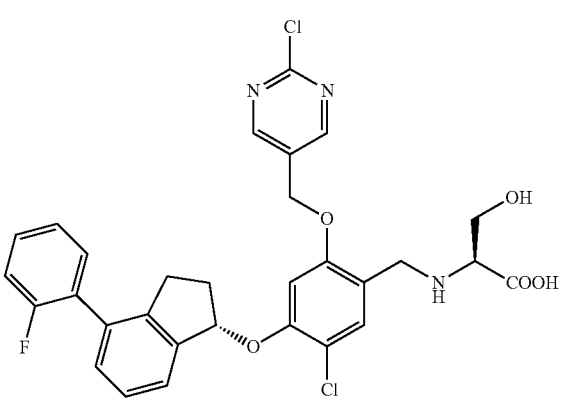 [SMILES: O=C(O)[C@H](CO)NCc1cc(Cl)c(O[C@H]2CCc3c(-c4ccccc4F)cccc32)cc1OCc1cnc(Cl)nc1] | +++ |
| 2.085 | 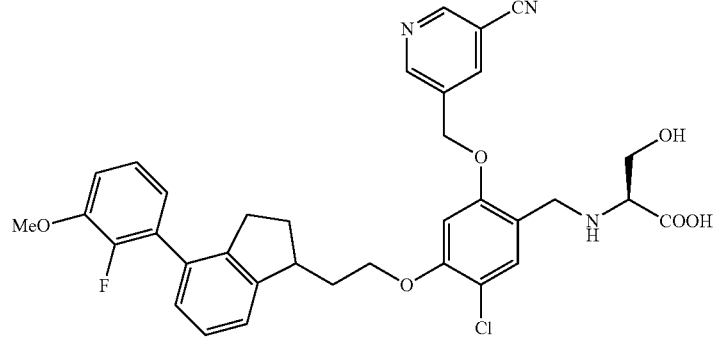 [SMILES: COc1cccc(-c2cccc3c2CCC3CCOc2cc(OCc3cncc(C#N)c3)c(CN[C@@H](CO)C(=O)O)cc2Cl)c1F] | + |
| 2.086 | 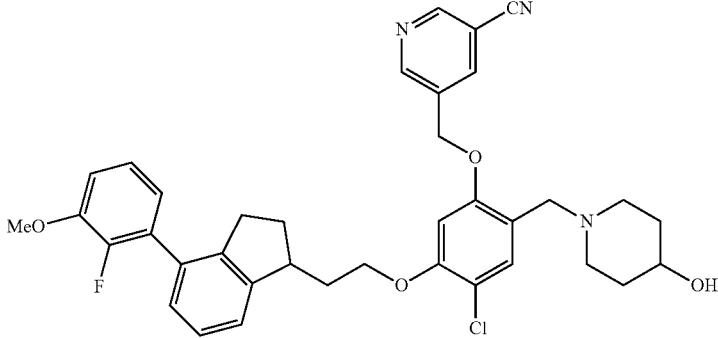 [SMILES: COc1cccc(-c2cccc3c2CCC3CCOc2cc(OCc3cncc(C#N)c3)c(CN3CCC(O)CC3)cc2Cl)c1F] | + |

TABLE 2-continued
| Compound Number | Compound Structure | ELISA IC$_{50}$ (nM) |
|---|---|---|
| 2.087 | 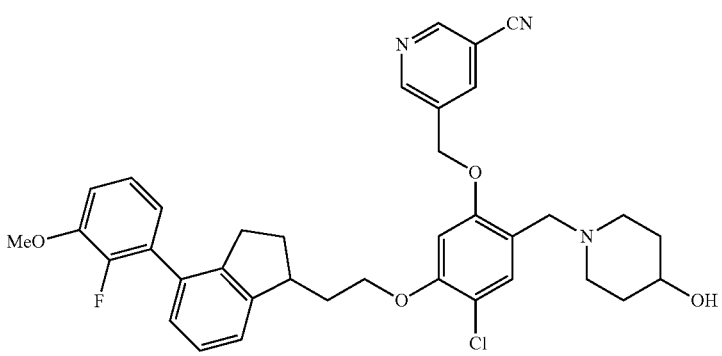 [SMILES: COc1cccc(-c2cccc3c2CCC3CCOc2cc(OCc3cncc(C#N)c3)c(CN3CCC(O)CC3)cc2Cl)c1F] | + |
| 2.088 | 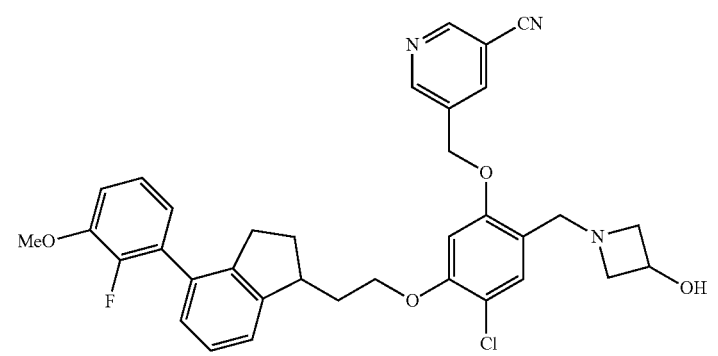 [SMILES: COc1cccc(-c2cccc3c2CCC3CCOc2cc(OCc3cncc(C#N)c3)c(CN3CC(O)C3)cc2Cl)c1F] | + |
| 2.089 | 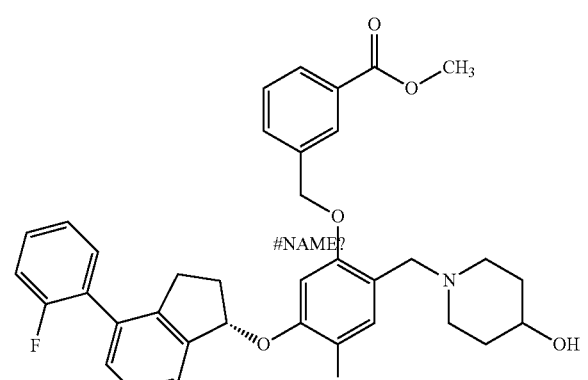 | + |
| 2.090 | 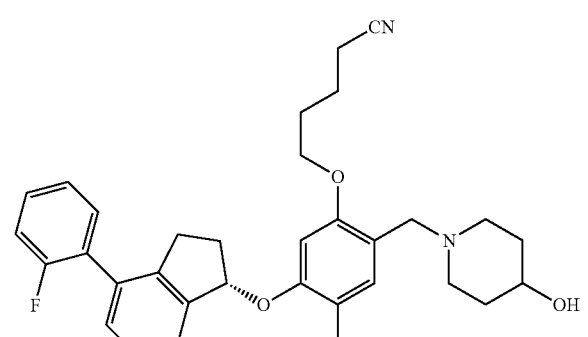 | ++ |

TABLE 2-continued
| Compound Number | Compound Structure | ELISA IC$_{50}$ (nM) |
|---|---|---|
| 2.091 | 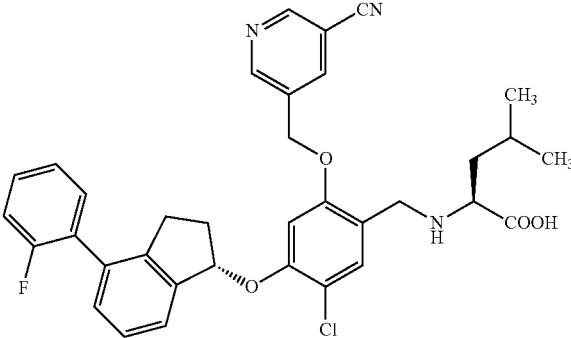 [SMILES: CC(C)C[C@H](NCc1cc(Cl)c(O[C@H]2CCc3c(-c4ccccc4F)cccc32)cc1OCc1cncc(C#N)c1)C(=O)O] | ++ |
| 2.092 | 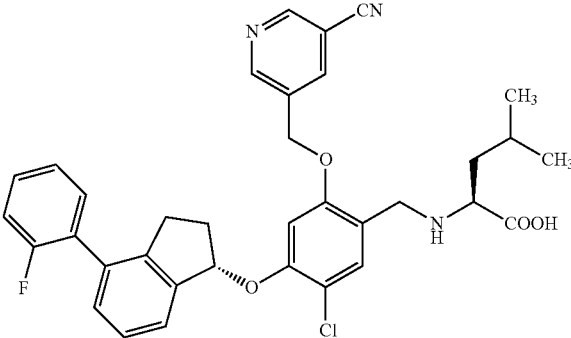 [SMILES: CC(C)C[C@H](NCc1cc(Cl)c(O[C@H]2CCc3c(-c4ccccc4F)cccc32)cc1OCc1cncc(C#N)c1)C(=O)O] | ++ |
| 2.093 | 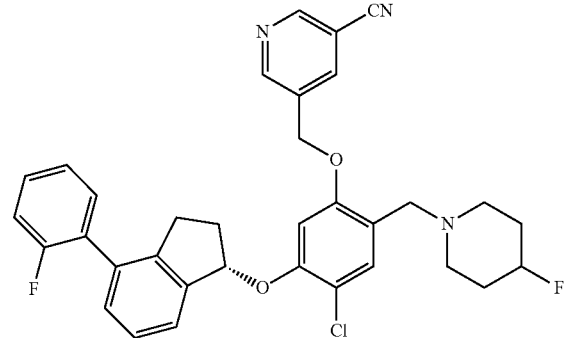 [SMILES: N#Cc1cncc(COc2cc(O[C@H]3CCc4c(-c5ccccc5F)cccc43)c(Cl)cc2CN2CCC(F)CC2)c1] | + |
| 2.094 | 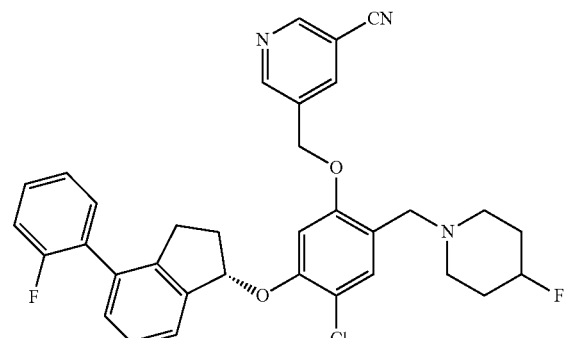 | ++ |

TABLE 2-continued
| Compound Number | Compound Structure | ELISA IC$_{50}$ (nM) |
|---|---|---|
| 2.095 | 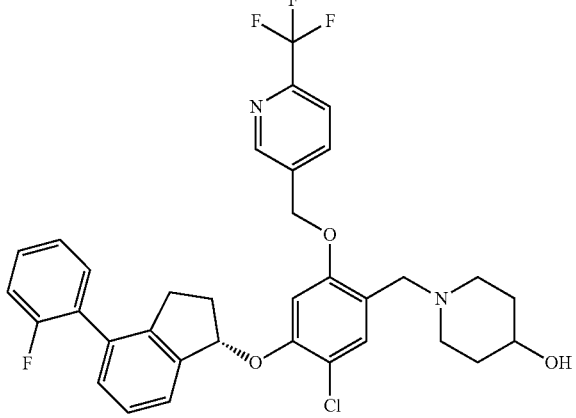 | + |
| 2.096 | 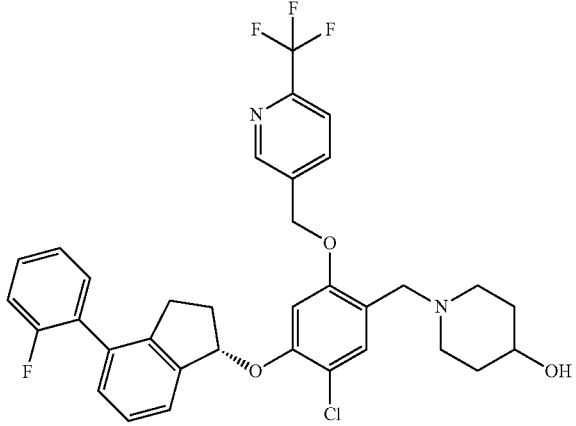 [SMILES: OC1CCN(Cc2cc(Cl)c(O[C@H]3CCc4c(-c5ccccc5F)cccc43)cc2OCc2ccc(C(F)(F)F)nc2)CC1] | + |
| 2.097 | 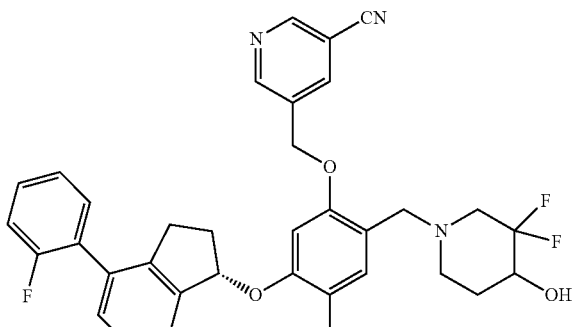 | + |
| 2.098 | 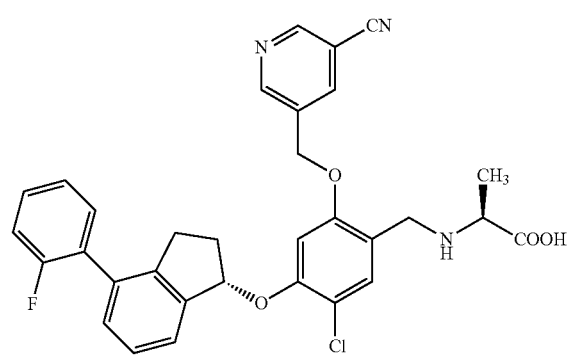 [SMILES: C[C@H](NCc1cc(Cl)c(O[C@H]2CCc3c(-c4ccccc4F)cccc32)cc1OCc1cncc(C#N)c1)C(=O)O] | +++ |

TABLE 2-continued

| Compound Number | Compound Structure | ELISA IC$_{50}$ (nM) |
|---|---|---|
| 2.099 | 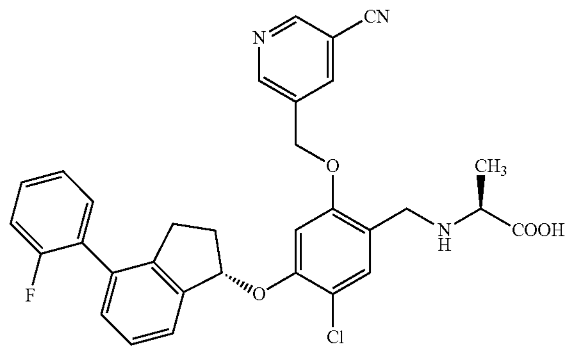 [SMILES: C[C@H](NCc1cc(Cl)c(O[C@H]2CCc3c(-c4ccccc4F)cccc32)cc1OCc1cncc(C#N)c1)C(=O)O] | +++ |
| 2.100 | 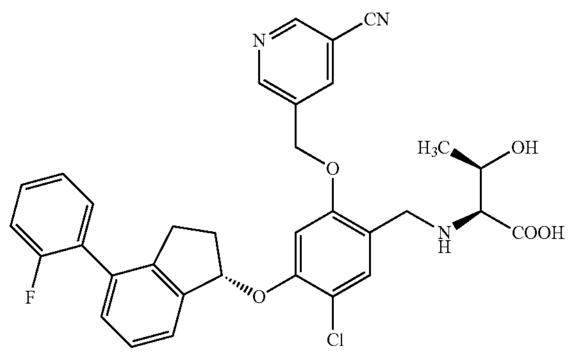 [SMILES: C[C@@H](O)[C@H](NCc1cc(Cl)c(O[C@H]2CCc3c(-c4ccccc4F)cccc32)cc1OCc1cncc(C#N)c1)C(=O)O] | +++ |
| 2.101 | 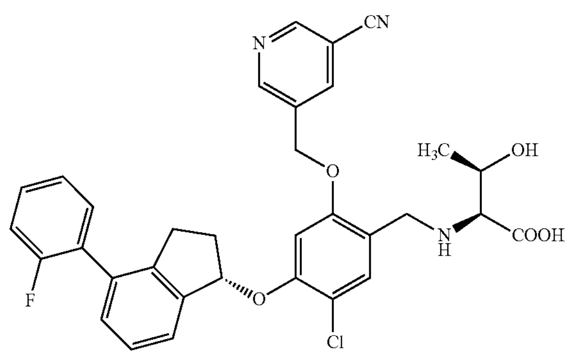 [SMILES: C[C@@H](O)[C@H](NCc1cc(Cl)c(O[C@H]2CCc3c(-c4ccccc4F)cccc32)cc1OCc1cncc(C#N)c1)C(=O)O] | +++ |
| 2.102 | 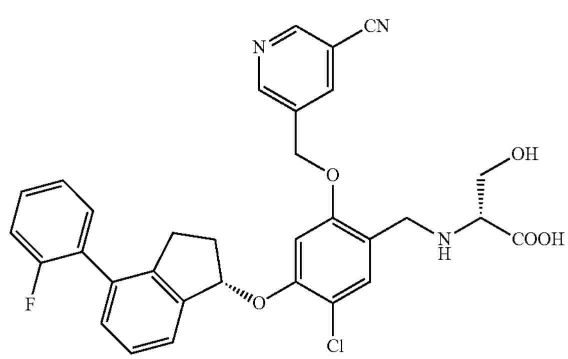 [SMILES: N#Cc1cncc(COc2cc(O[C@H]3CCc4c(-c5ccccc5F)cccc43)c(Cl)cc2CN[C@H](CO)C(=O)O)c1] | +++ |

TABLE 2-continued

| Compound Number | Compound Structure | ELISA IC$_{50}$ (nM) |
|---|---|---|
| 2.103 | 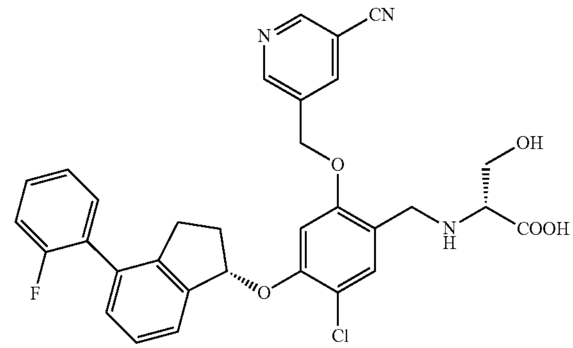 [SMILES: N#Cc1cncc(COc2cc(O[C@H]3CCc4c(-c5ccccc5F)cccc43)c(Cl)cc2CN[C@H](CO)C(=O)O)c1] | +++ |
| 2.104 | 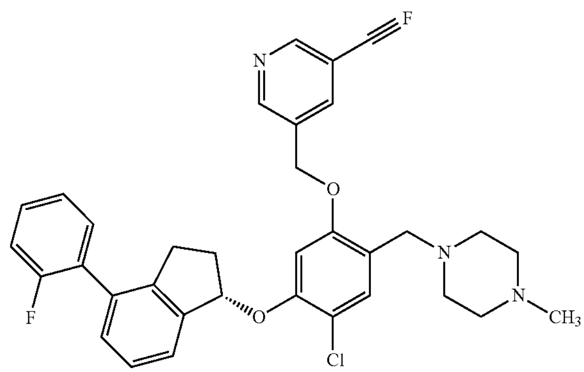 | + |
| 2.105 | 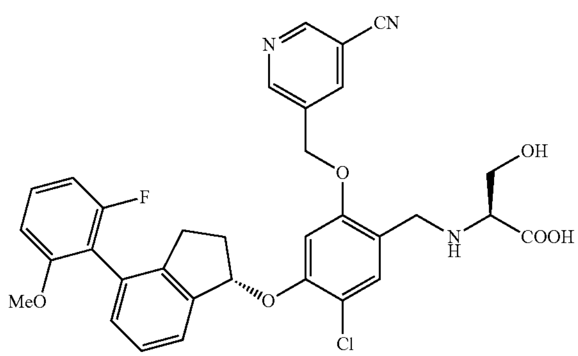 [SMILES: COc1cccc(F)c1-c1cccc2c1CC[C@@H]2Oc1cc(OCc2cncc(C#N)c2)c(CN[C@@H](CO)C(=O)O)cc1Cl] | ++ |
| 2.106 | 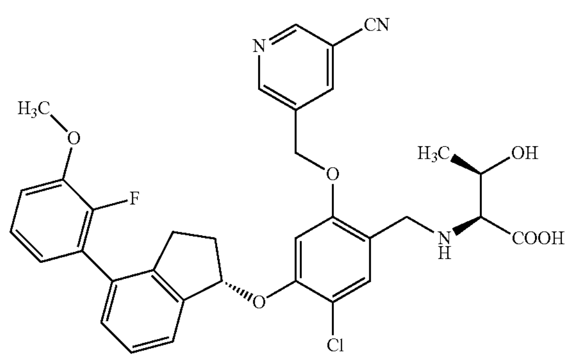 [SMILES: COc1cccc(-c2cccc3c2CC[C@@H]3Oc2cc(OCc3cncc(C#N)c3)c(CN[C@H](C(=O)O)[C@@H](C)O)cc2Cl)c1F] | +++ |

TABLE 2-continued

| Compound Number | Compound Structure | ELISA IC$_{50}$ (nM) |
|---|---|---|
| 2.107 | 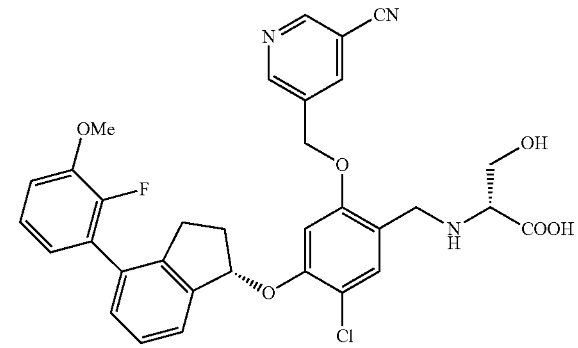 [SMILES: COc1cccc(-c2cccc3c2CC[C@@H]3Oc2cc(OCc3cncc(C#N)c3)c(CN[C@H](CO)C(=O)O)cc2Cl)c1F] | +++ |
| 2.108 | 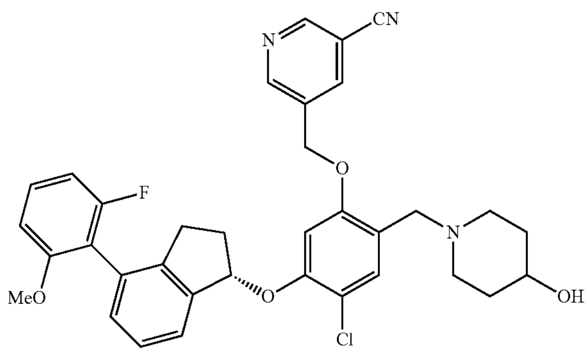 [SMILES: COc1cccc(F)c1-c1cccc2c1CC[C@@H]2Oc1cc(OCc2cncc(C#N)c2)c(CN2CCC(O)CC2)cc1Cl] | + |
| 2.109 | 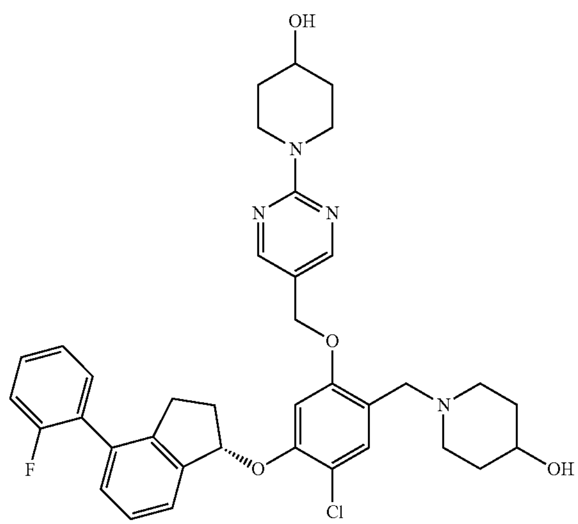 [SMILES: OC1CCN(Cc2cc(Cl)c(O[C@H]3CCc4c(-c5ccccc5F)cccc43)cc2OCc2cnc(N3CCC(O)CC3)nc2)CC1] | + |
| 2.110 | 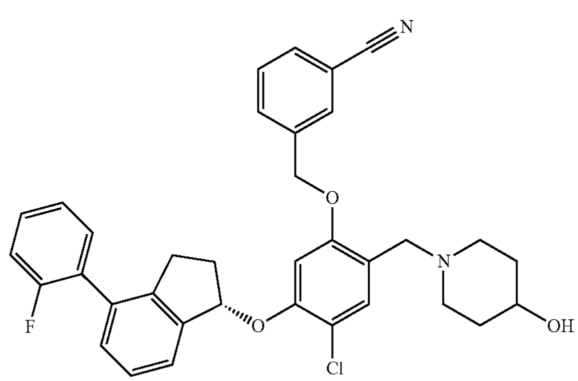 [SMILES: N#Cc1cccc(COc2cc(O[C@H]3CCc4c(-c5ccccc5F)cccc43)c(Cl)cc2CN2CCC(O)CC2)c1] | + |

TABLE 2-continued

| Compound Number | Compound Structure | ELISA IC$_{50}$ (nM) |
|---|---|---|
| 2.111 | 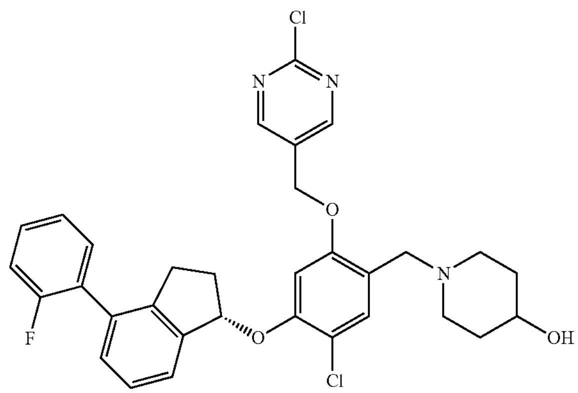 [SMILES: OC1CCN(Cc2cc(Cl)c(O[C@H]3CCc4c(-c5ccccc5F)cccc43)cc2OCc2cnc(Cl)nc2)CC1] | ++ |
| 2.112 | 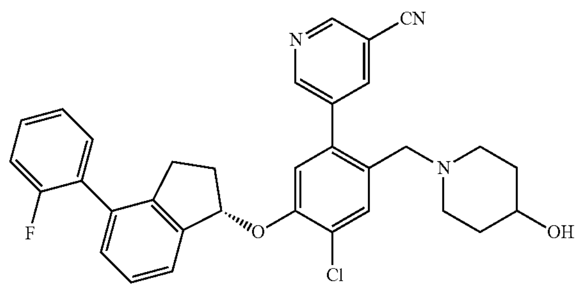 [SMILES: N#Cc1cncc(-c2cc(O[C@H]3CCc4c(-c5ccccc5F)cccc43)c(Cl)cc2CN2CCC(O)CC2)c1] | + |
| 2.113 | 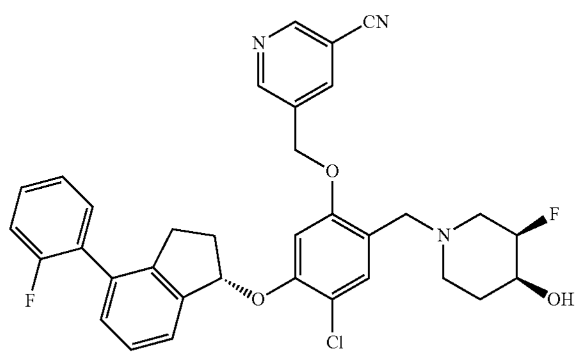 [SMILES: N#Cc1cncc(COc2cc(O[C@H]3CCc4c(-c5ccccc5F)cccc43)c(Cl)cc2CN2CC[C@H](O)[C@H](F)C2)c1] | + |
| 2.114 | 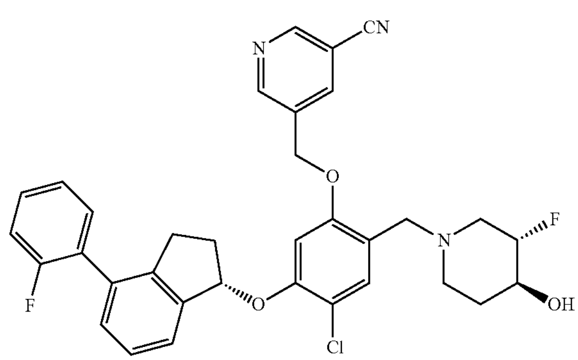 [SMILES: N#Cc1cncc(COc2cc(O[C@H]3CCc4c(-c5ccccc5F)cccc43)c(Cl)cc2CN2CC[C@H](O)[C@@H](F)C2)c1] | + |

TABLE 2-continued

| Compound Number | Compound Structure | ELISA IC$_{50}$ (nM) |
|---|---|---|
| 2.115 | 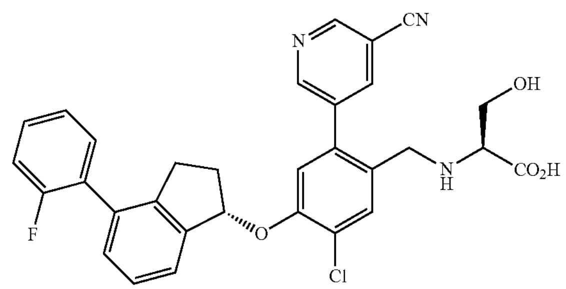 [SMILES: N#Cc1cncc(-c2cc(O[C@H]3CCc4c(-c5ccccc5F)cccc43)c(Cl)cc2CN[C@@H](CO)C(=O)O)c1] | +++ |
| 2.116 | 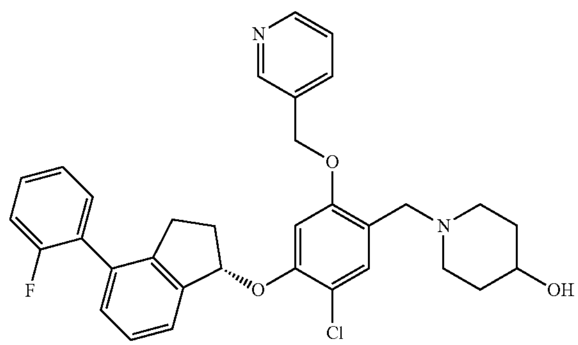 [SMILES: OC1CCN(Cc2cc(Cl)c(O[C@H]3CCc4c(-c5ccccc5F)cccc43)cc2OCc2cccnc2)CC1] | + |
| 2.117 | 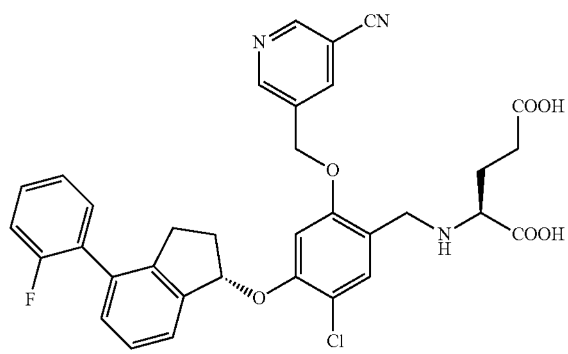 [SMILES: N#Cc1cncc(COc2cc(O[C@H]3CCc4c(-c5ccccc5F)cccc43)c(Cl)cc2CN[C@@H](CCC(=O)O)C(=O)O)c1] | +++ |
| 2.118 | 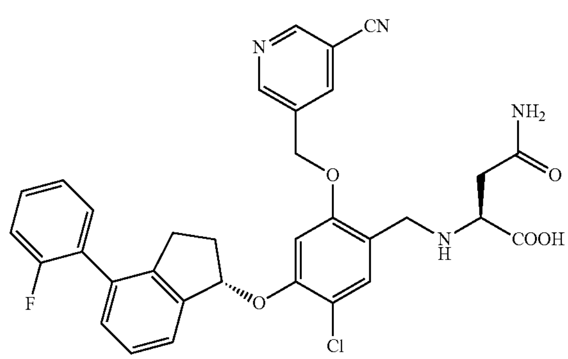 [SMILES: N#Cc1cncc(COc2cc(O[C@H]3CCc4c(-c5ccccc5F)cccc43)c(Cl)cc2CN[C@@H](CC(N)=O)C(=O)O)c1] | +++ |

TABLE 2-continued
| Compound Number | Compound Structure | ELISA IC$_{50}$ (nM) |
|---|---|---|
| 2.119 | 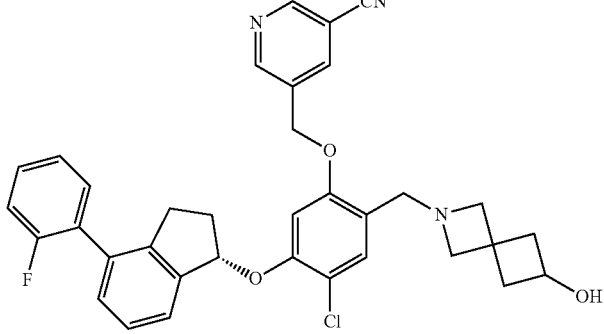 | ++ |
| 2.120 | 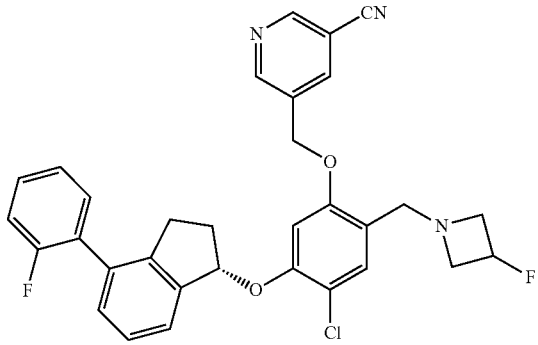 [SMILES: N#Cc1cncc(COc2cc(O[C@H]3CCc4c(-c5ccccc5F)cccc43)c(Cl)cc2CN2CC(F)C2)c1] | + |
| 2.121 | 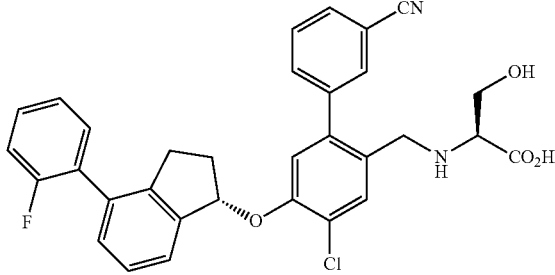 [SMILES: N#Cc1cccc(-c2cc(O[C@H]3CCc4c(-c5ccccc5F)cccc43)c(Cl)cc2CN[C@@H](CO)C(=O)O)c1] | ++ |
| 2.122 | 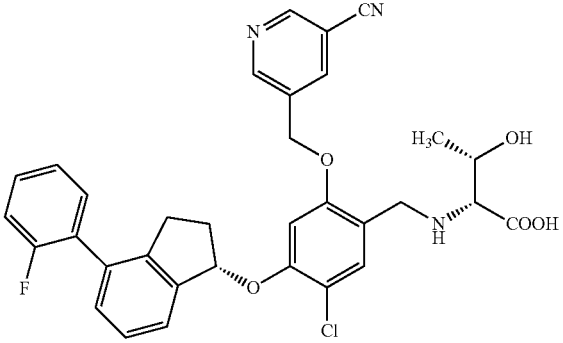 [SMILES: C[C@H](O)[C@@H](NCc1cc(Cl)c(O[C@H]2CCc3c(-c4ccccc4F)cccc32)cc1OCc1cncc(C#N)c1)C(=O)O] | +++ |

TABLE 2-continued
| Compound Number | Compound Structure | ELISA IC$_{50}$ (nM) |
|---|---|---|
| 2.123 | 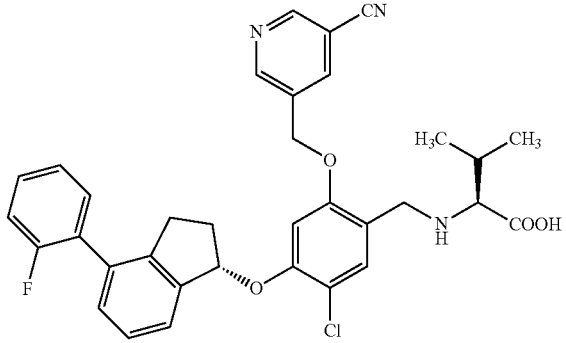 [SMILES: CC(C)[C@H](NCc1cc(Cl)c(O[C@H]2CCc3c(-c4ccccc4F)cccc32)cc1OCc1cncc(C#N)c1)C(=O)O] | ++ |
| 2.124 | 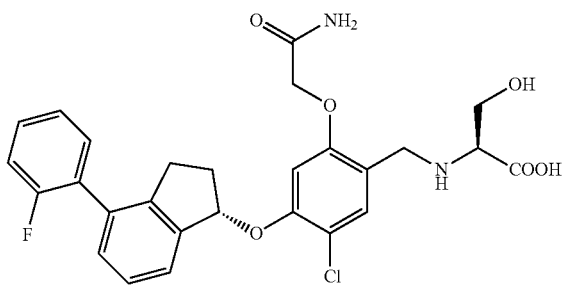 [SMILES: NC(=O)COc1cc(O[C@H]2CCc3c(-c4ccccc4F)cccc32)c(Cl)cc1CN[C@@H](CO)C(=O)O] | + |
| 2.125 | 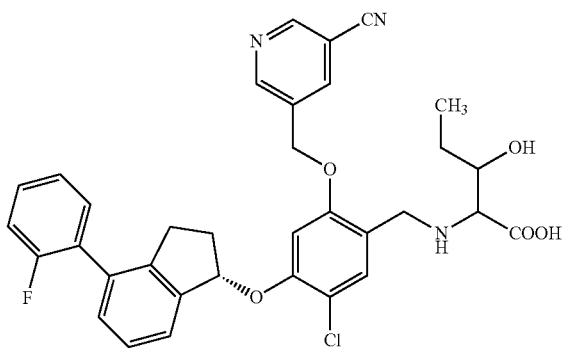 [SMILES: CCC(O)C(NCc1cc(Cl)c(O[C@H]2CCc3c(-c4ccccc4F)cccc32)cc1OCc1cncc(C#N)c1)C(=O)O] | +++ |
| 2.126 | 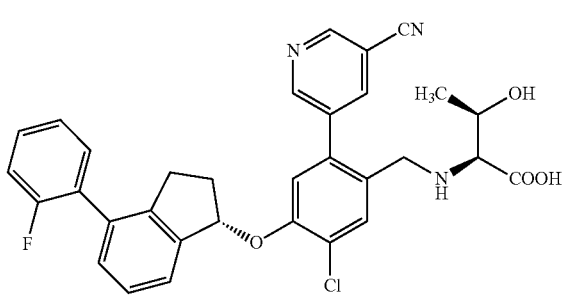 [SMILES: C[C@@H](O)[C@H](NCc1cc(Cl)c(O[C@H]2CCc3c(-c4ccccc4F)cccc32)cc1-c1cncc(C#N)c1)C(=O)O] | ++ |

TABLE 2-continued
| Compound Number | Compound Structure | ELISA IC$_{50}$ (nM) |
|---|---|---|
| 2.127 | 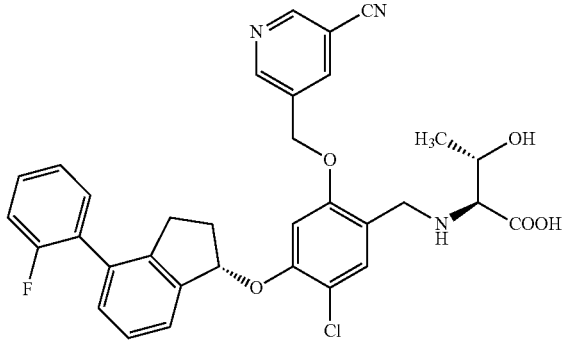 [SMILES: C[C@H](O)[C@H](NCc1cc(Cl)c(O[C@H]2CCc3c(-c4ccccc4F)cccc32)cc1OCc1cncc(C#N)c1)C(=O)O] | +++ |
| 2.128 | 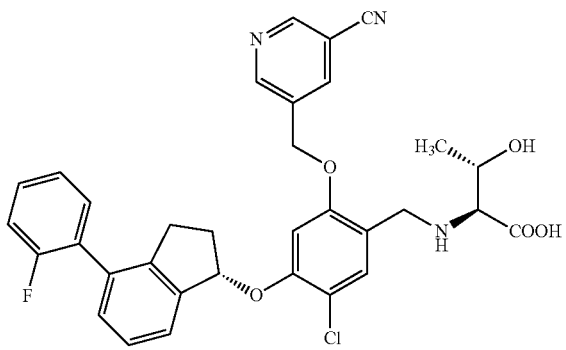 [SMILES: C[C@H](O)[C@H](NCc1cc(Cl)c(O[C@H]2CCc3c(-c4ccccc4F)cccc32)cc1OCc1cncc(C#N)c1)C(=O)O] | +++ |
| 2.129 | 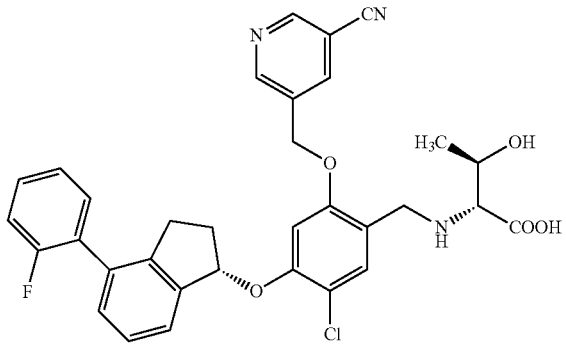 [SMILES: C[C@@H](O)[C@@H](NCc1cc(Cl)c(O[C@H]2CCc3c(-c4ccccc4F)cccc32)cc1OCc1cncc(C#N)c1)C(=O)O] | +++ |
| 2.130 | 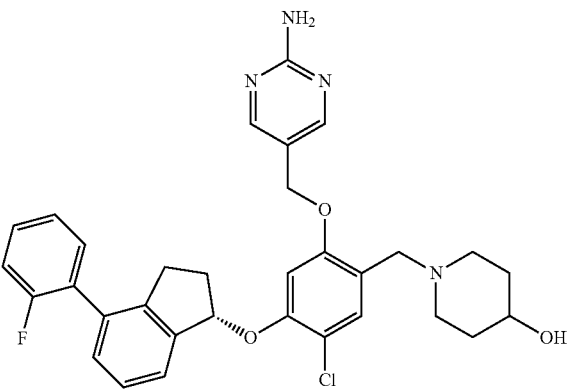 | ++ |

TABLE 2-continued

| Compound Number | Compound Structure | ELISA IC$_{50}$ (nM) |
|---|---|---|
| 2.131 | 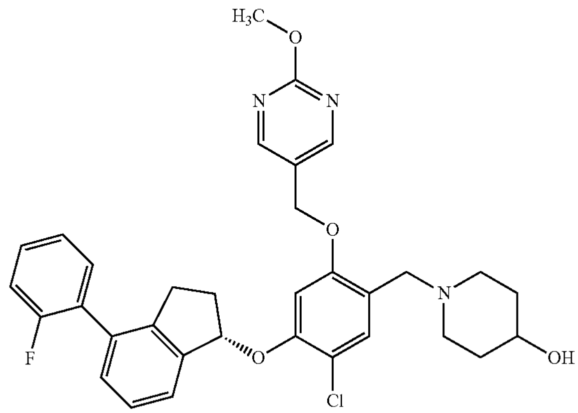 [SMILES: COc1ncc(COc2cc(O[C@H]3CCc4c(-c5ccccc5F)cccc43)c(Cl)cc2CN2CCC(O)CC2)cn1] | ++ |
| 2.132 | 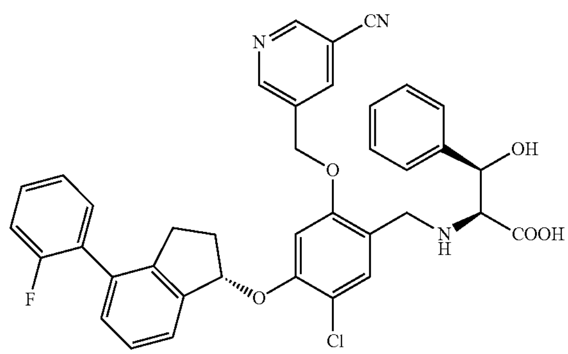 [SMILES: N#Cc1cncc(COc2cc(O[C@H]3CCc4c(-c5ccccc5F)cccc43)c(Cl)cc2CN[C@H](C(=O)O)[C@H](O)c2ccccc2)c1] | ++ |
| 2.133 | 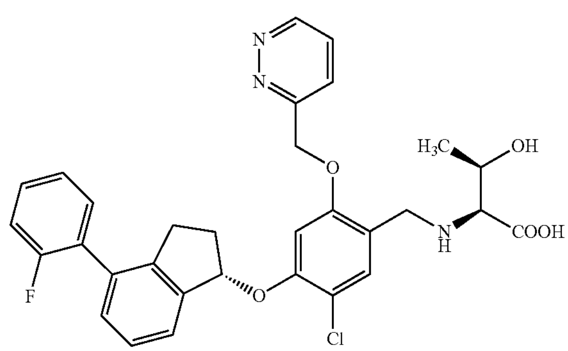 [SMILES: C[C@@H](O)[C@H](NCc1cc(Cl)c(O[C@H]2CCc3c(-c4ccccc4F)cccc32)cc1OCc1cccnn1)C(=O)O] | ++ |
| 2.134 | 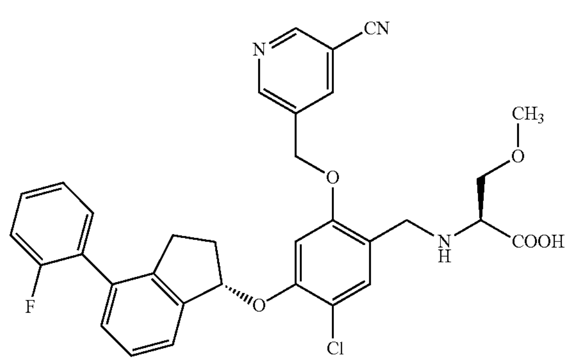 [SMILES: COC[C@H](NCc1cc(Cl)c(O[C@H]2CCc3c(-c4ccccc4F)cccc32)cc1OCc1cncc(C#N)c1)C(=O)O] | +++ |

TABLE 2-continued

| Compound Number | Compound Structure | ELISA IC$_{50}$ (nM) |
|---|---|---|
| 2.135 | 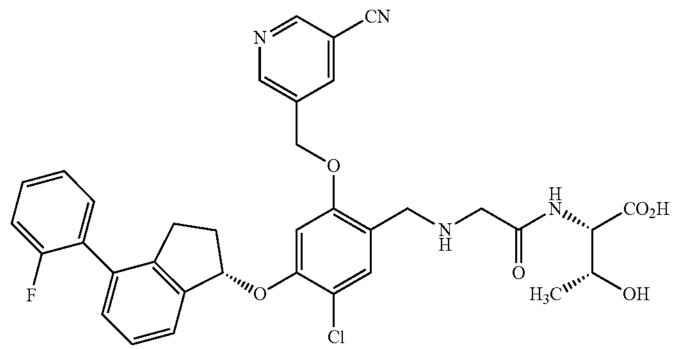 [SMILES: C[C@@H](O)[C@H](NC(=O)CNCc1cc(Cl)c(O[C@H]2CCc3c(-c4ccccc4F)cccc32)cc1OCc1cncc(C#N)c1)C(=O)O] | ++ |
| 2.136 | 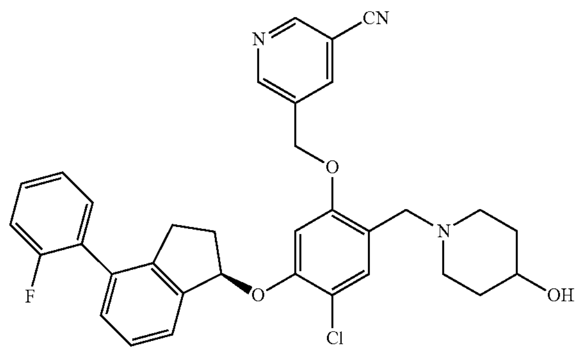 [SMILES: N#Cc1cncc(COc2cc(O[C@@H]3CCc4c(-c5ccccc5F)cccc43)c(Cl)cc2CN2CCC(O)CC2)c1] | ++ |
| 2.137 | 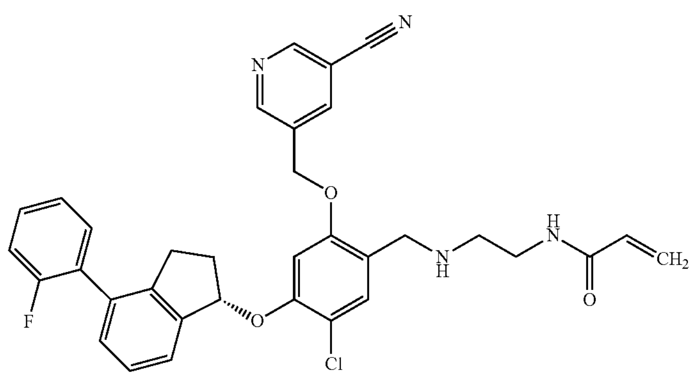 [SMILES: C=CC(=O)NCCNCc1cc(Cl)c(O[C@H]2CCc3c(-c4ccccc4F)cccc32)cc1OCc1cncc(C#N)c1] | ++ |
| 2.138 | 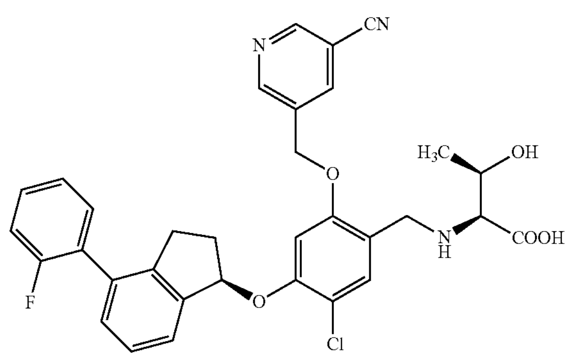 [SMILES: C[C@@H](O)[C@H](NCc1cc(Cl)c(O[C@@H]2CCc3c(-c4ccccc4F)cccc32)cc1OCc1cncc(C#N)c1)C(=O)O] | +++ |

TABLE 2-continued
| Compound Number | Compound Structure | ELISA $IC_{50}$ (nM) |
|---|---|---|
| 2.139 | 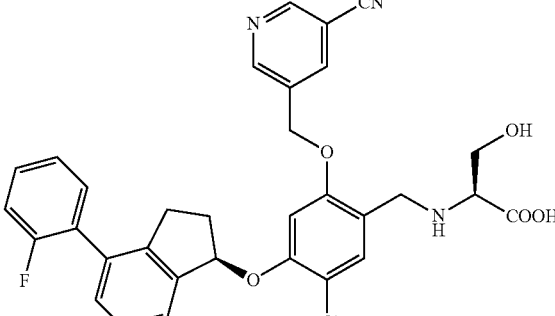 | +++ |
| 2.140 | 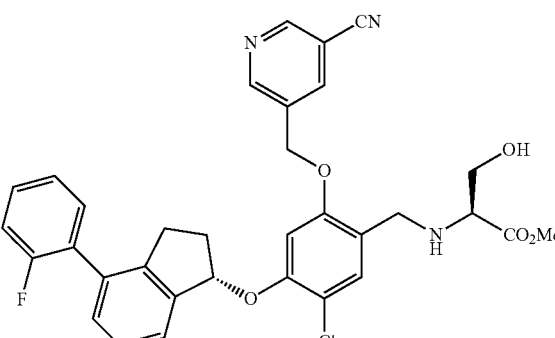 | +++ |
| 2.141 | 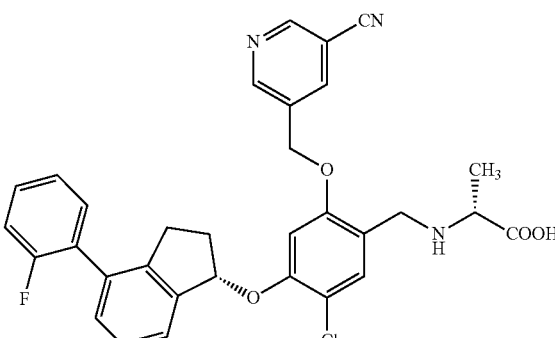 | +++ |
| 2.142 | 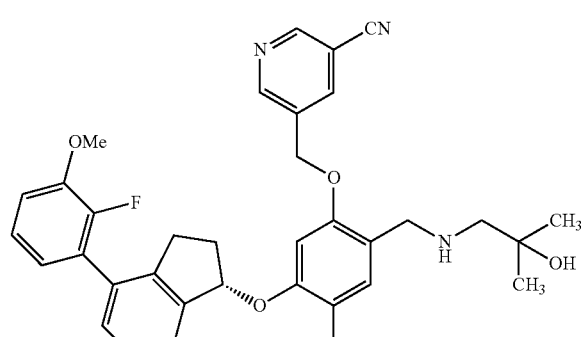 | ++ |

TABLE 2-continued
| Compound Number | Compound Structure | ELISA IC$_{50}$ (nM) |
|---|---|---|
| 2.143 | 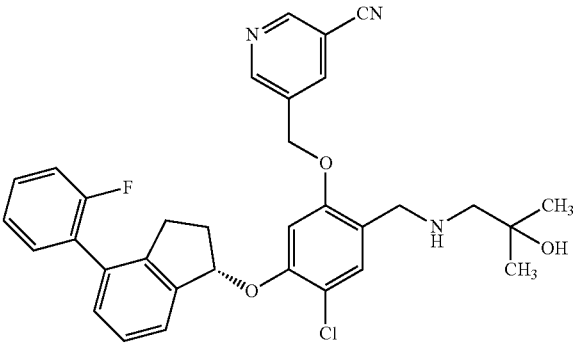 [SMILES: CC(C)(O)CNCc1cc(Cl)c(O[C@H]2CCc3c(-c4ccccc4F)cccc32)cc1OCc1cncc(C#N)c1] | ++ |
| 2.144 | 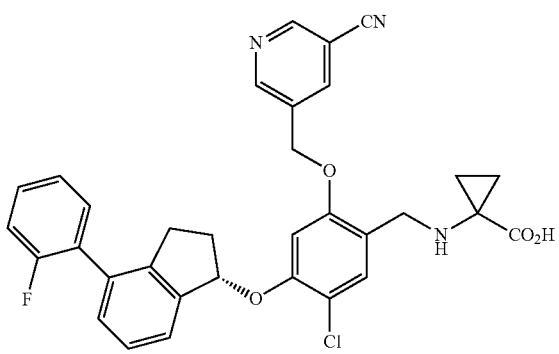 [SMILES: N#Cc1cncc(COc2cc(O[C@H]3CCc4c(-c5ccccc5F)cccc43)c(Cl)cc2CNC2(C(=O)O)CC2)c1] | +++ |
| 2.145 | 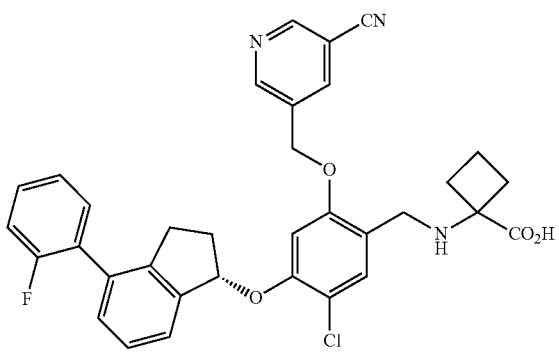 [SMILES: N#Cc1cncc(COc2cc(O[C@H]3CCc4c(-c5ccccc5F)cccc43)c(Cl)cc2CNC2(C(=O)O)CCC2)c1] | +++ |
| 2.146 | 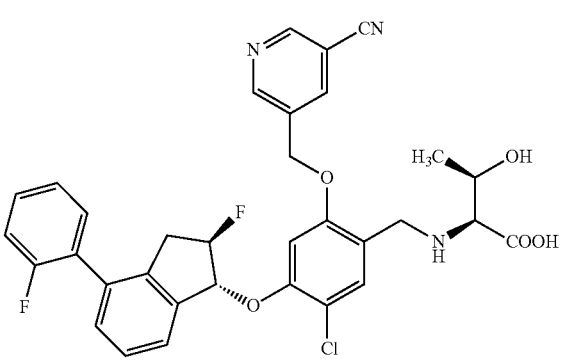 [SMILES: C[C@@H](O)[C@H](NCc1cc(Cl)c(O[C@@H]2c3cccc(-c4ccccc4F)c3C[C@H]2F)cc1OCc1cncc(C#N)c1)C(=O)O] | +++ |

TABLE 2-continued

| Compound Number | Compound Structure | ELISA IC$_{50}$ (nM) |
|---|---|---|
| 2.147 | 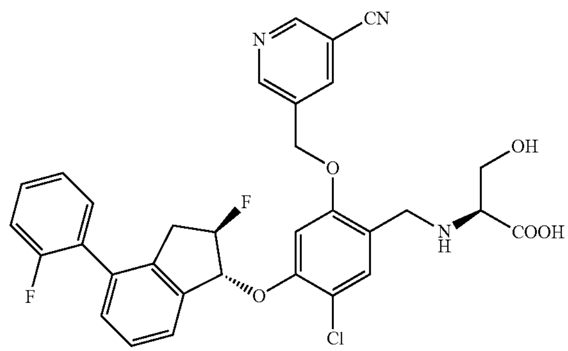 [SMILES: N#Cc1cncc(COc2cc(O[C@@H]3c4cccc(-c5ccccc5F)c4C[C@H]3F)c(Cl)cc2CN[C@@H](CO)C(=O)O)c1] | +++ |
| 2.148 | 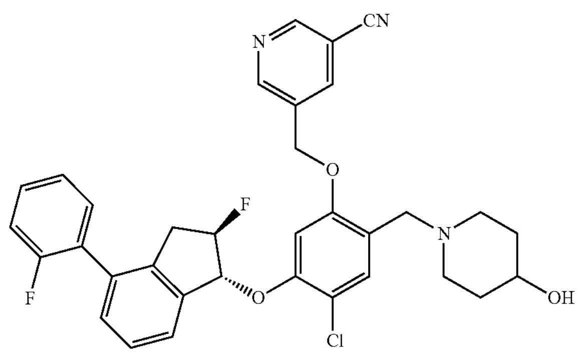 [SMILES: N#Cc1cncc(COc2cc(O[C@@H]3c4cccc(-c5ccccc5F)c4C[C@H]3F)c(Cl)cc2CN2CCC(O)CC2)c1] | + |
| 2.149 | 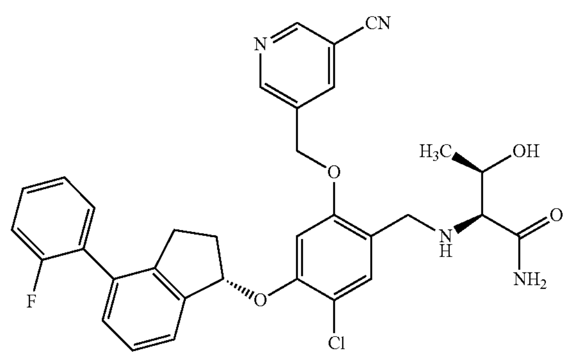 [SMILES: C[C@@H](O)[C@H](NCc1cc(Cl)c(O[C@H]2CCc3c(-c4ccccc4F)cccc32)cc1OCc1cncc(C#N)c1)C(N)=O] | ++ |
| 2.150 | 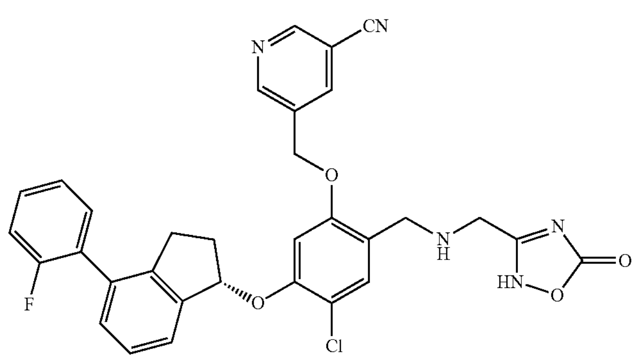 [SMILES: N#Cc1cncc(COc2cc(O[C@H]3CCc4c(-c5ccccc5F)cccc43)c(Cl)cc2CNCc2nc(=O)o[nH]2)c1] | ++ |

TABLE 2-continued

| Compound Number | Compound Structure | ELISA IC$_{50}$ (nM) |
|---|---|---|
| 2.151 | 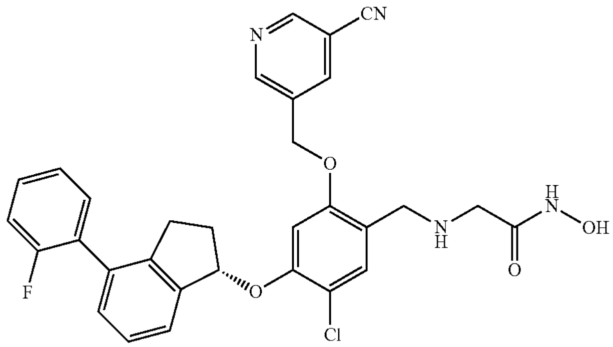 [SMILES: N#Cc1cncc(COc2cc(O[C@H]3CCc4c(-c5ccccc5F)cccc43)c(Cl)cc2CNCC(=O)NO)c1] | + |
| 2.152 | 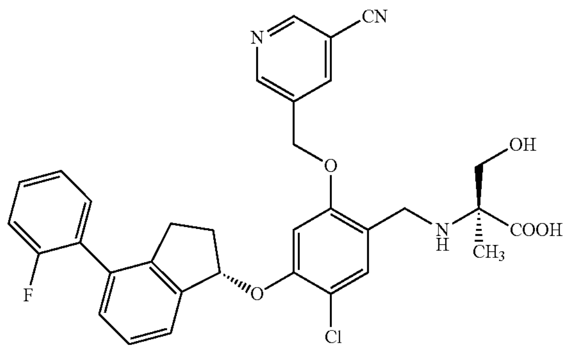 | +++ |
| 2.153 | 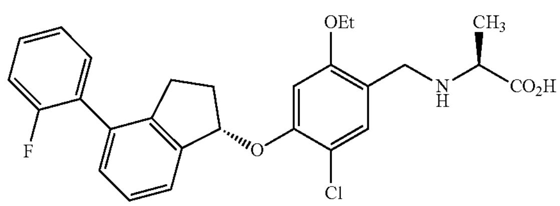 [SMILES: CCOc1cc(O[C@H]2CCc3c(-c4ccccc4F)cccc32)c(Cl)cc1CN[C@@H](C)C(=O)O] | ++ |
| 2.154 | 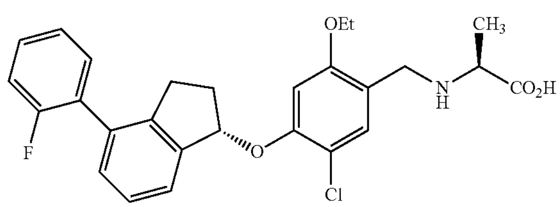 [SMILES: CCOc1cc(O[C@H]2CCc3c(-c4ccccc4F)cccc32)c(Cl)cc1CN[C@@H](C)C(=O)O] | ++ |
| 2.155 | 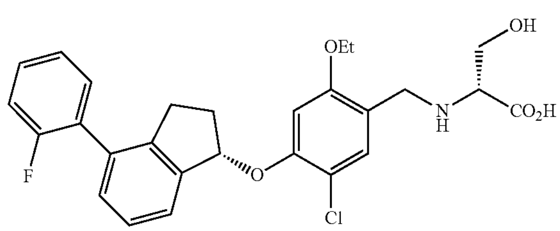 [SMILES: CCOc1cc(O[C@H]2CCc3c(-c4ccccc4F)cccc32)c(Cl)cc1CN[C@H](CO)C(=O)O] | ++ |
| 2.156 | 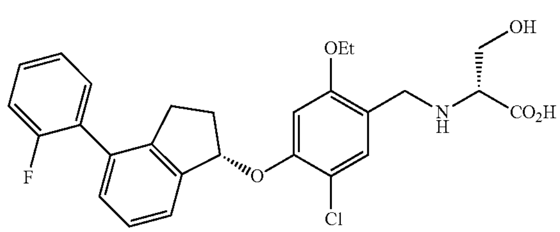 [SMILES: CCOc1cc(O[C@H]2CCc3c(-c4ccccc4F)cccc32)c(Cl)cc1CN[C@H](CO)C(=O)O] | ++ |

US 11,426,364 B2
317                                                                                       318
TABLE 2-continued
| Compound Number | Compound Structure | ELISA IC$_{50}$ (nM) |
|---|---|---|
| 2.157 | 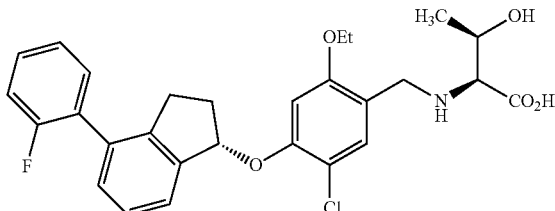 | ++ |
| 2.158 | 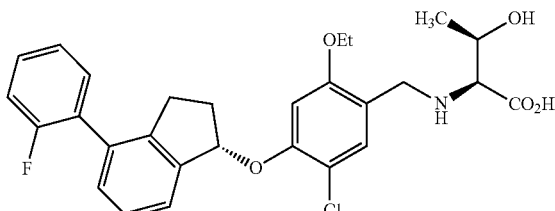 | ++ |
| 2.159 | 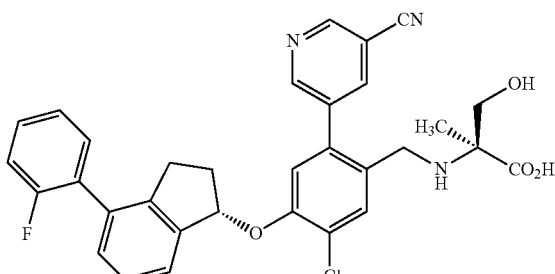 | +++ |
| 2.160 | 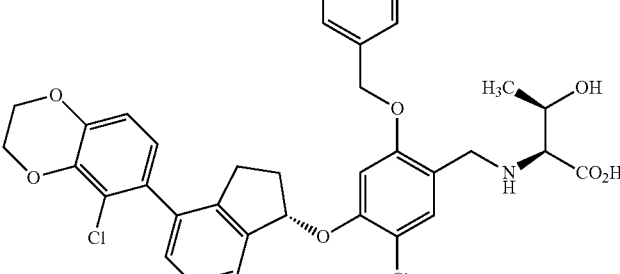 | +++ |
| 2.161 | 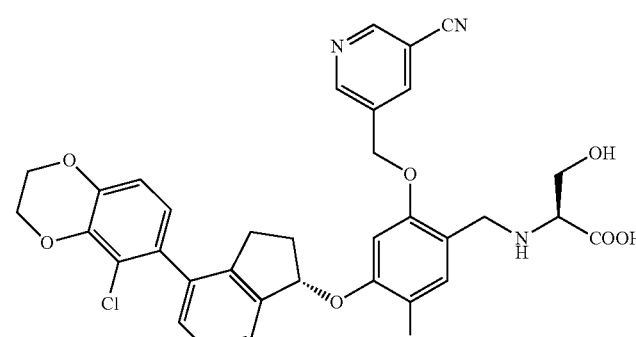 | +++ |

TABLE 2-continued
| Compound Number | Compound Structure | ELISA IC$_{50}$ (nM) |
|---|---|---|
| 2.162 | 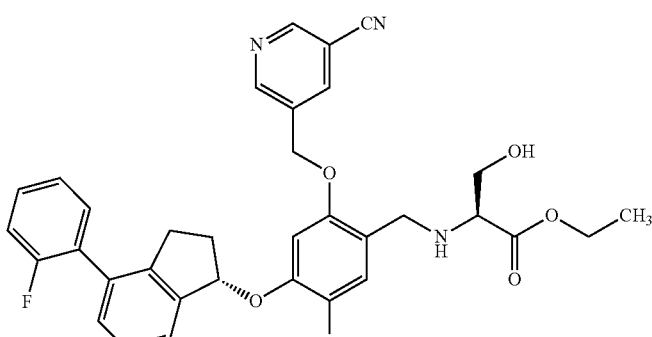 | + |
| 2.163 | 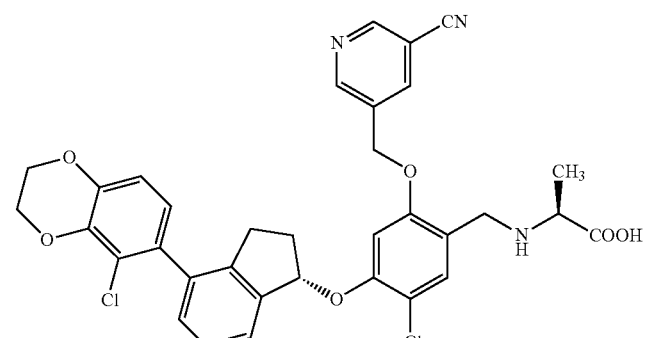 | ++ |
| 2.164 | 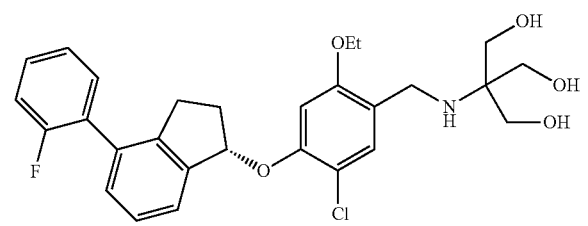 [SMILES: CCOc1cc(O[C@H]2CCc3c(-c4ccccc4F)cccc32)c(Cl)cc1CNC(CO)(CO)CO] | +++ |
| 2.165 | 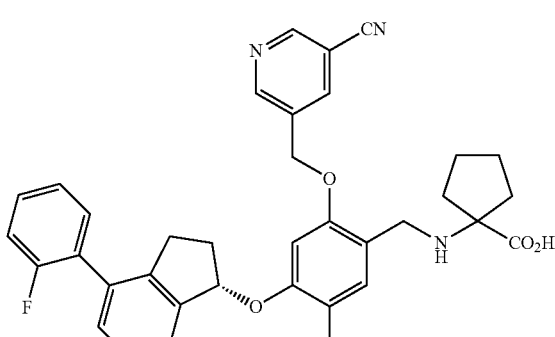 | +++ |

TABLE 2-continued

| Compound Number | Compound Structure | ELISA IC$_{50}$ (nM) |
|---|---|---|
| 2.166 | 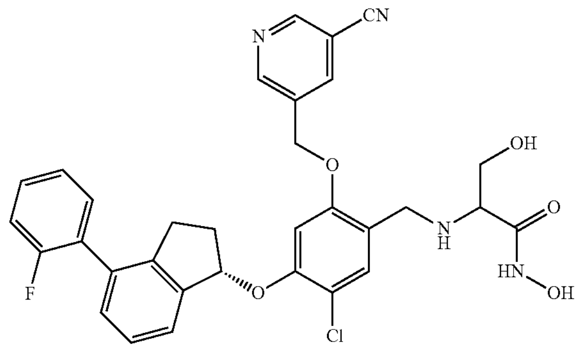 [SMILES: N#Cc1cncc(COc2cc(O[C@H]3CCc4c(-c5ccccc5F)cccc43)c(Cl)cc2CNC(CO)C(=O)NO)c1] | ++ |
| 2.167 | 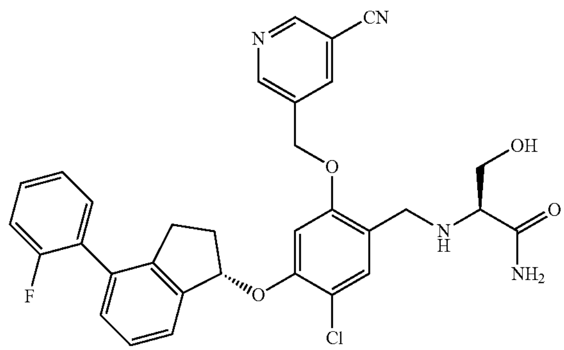 [SMILES: N#Cc1cncc(COc2cc(O[C@H]3CCc4c(-c5ccccc5F)cccc43)c(Cl)cc2CN[C@@H](CO)C(N)=O)c1] | ++ |
| 2.168 | 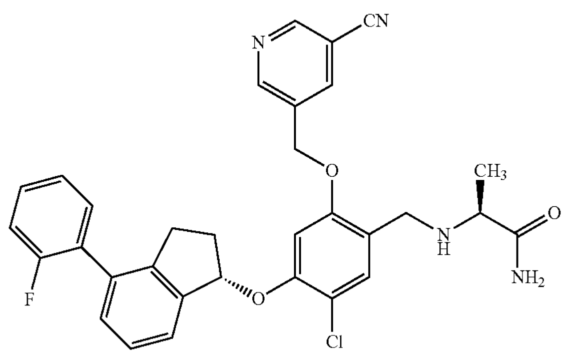 [SMILES: C[C@H](NCc1cc(Cl)c(O[C@H]2CCc3c(-c4ccccc4F)cccc32)cc1OCc1cncc(C#N)c1)C(N)=O] | ++ |
| 2.169 | 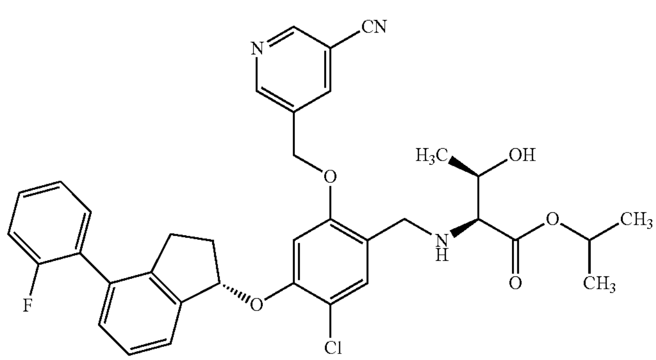 [SMILES: CC(C)OC(=O)[C@@H](NCc1cc(Cl)c(O[C@H]2CCc3c(-c4ccccc4F)cccc32)cc1OCc1cncc(C#N)c1)[C@@H](C)O] | + |

TABLE 2-continued
| Compound Number | Compound Structure | ELISA IC$_{50}$ (nM) |
|---|---|---|
| 2.170 | 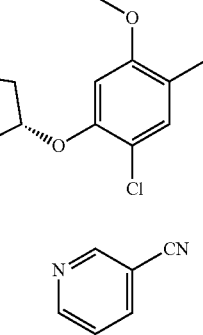 | + |
| 2.171 | 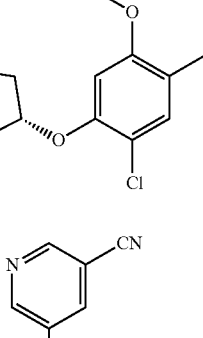 | ++ |
| 2.172 | 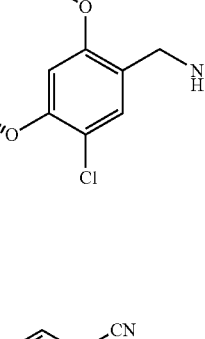 | + |
| 2.173 | 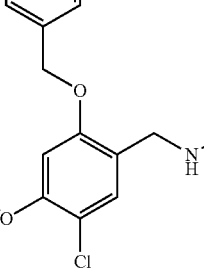 | + |

TABLE 2-continued

| Compound Number | Compound Structure | ELISA IC$_{50}$ (nM) |
|---|---|---|
| 2.174 | 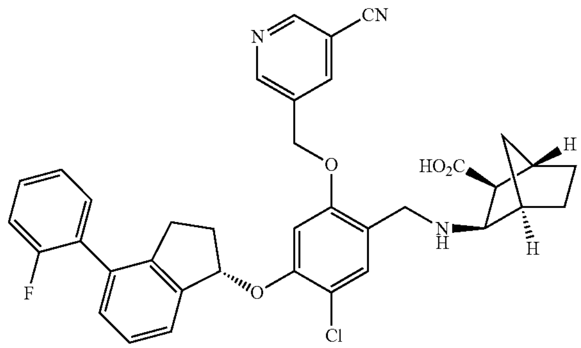 [SMILES: N#Cc1cncc(COc2cc(O[C@H]3CCc4c(-c5ccccc5F)cccc43)c(Cl)cc2CN[C@@H]2[C@@H]3CC[C@@H](C3)[C@@H]2C(=O)O)c1] | + |
| 2.175 | 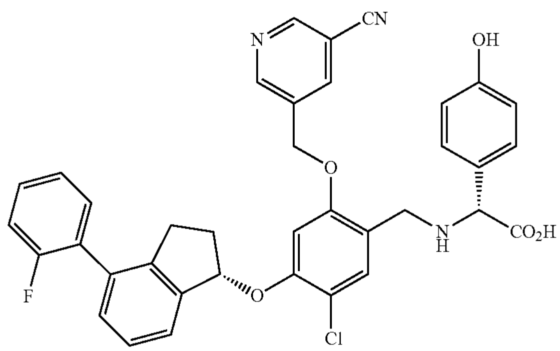 [SMILES: N#Cc1cncc(COc2cc(O[C@H]3CCc4c(-c5ccccc5F)cccc43)c(Cl)cc2CN[C@@H](C(=O)O)c2ccc(O)cc2)c1] | ++ |
| 2.176 | 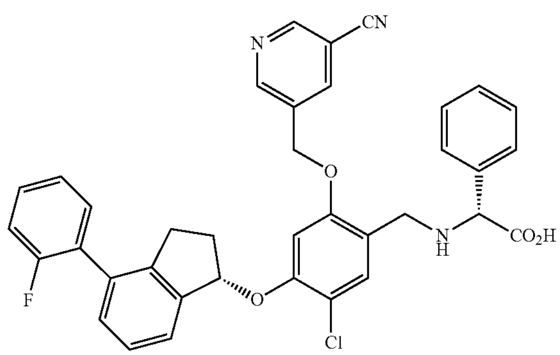 [SMILES: N#Cc1cncc(COc2cc(O[C@H]3CCc4c(-c5ccccc5F)cccc43)c(Cl)cc2CN[C@@H](C(=O)O)c2ccccc2)c1] | +++ |
| 2.177 | 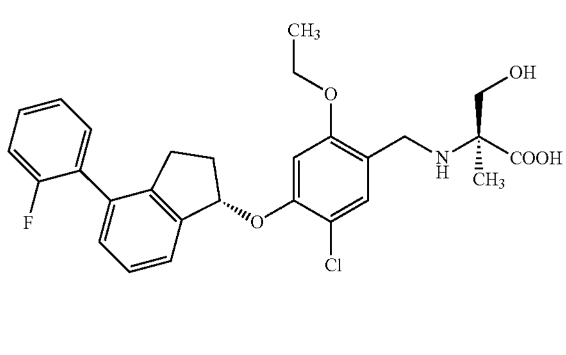 | ++ |

TABLE 2-continued
| Compound Number | Compound Structure | ELISA IC$_{50}$ (nM) |
|---|---|---|
| 2.178 | 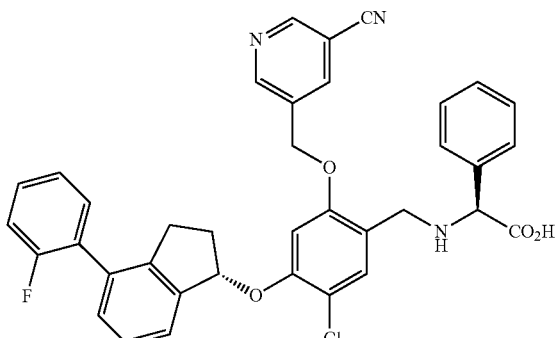 | ++ |
TABLE 3
Structures and Activity
| Compound Number | Compound Structure | ELISA IC$_{50}$ (nM) |
|---|---|---|
| 3.001 | 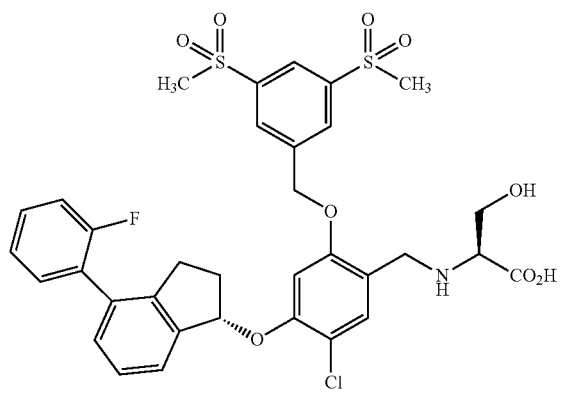 [SMILES: CS(=O)(=O)c1cc(COc2cc(O[C@H]3CCc4c(-c5ccccc5F)cccc43)c(Cl)cc2CN[C@@H](CO)C(=O)O)cc(S(C)(=O)=O)c1] | +++ |
| 3.002 | 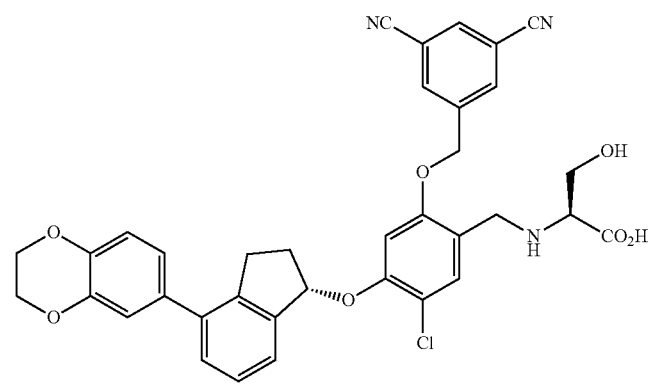 [SMILES: N#Cc1cc(C#N)cc(COc2cc(O[C@H]3CCc4c(-c5ccc6c(c5)OCCO6)cccc43)c(Cl)cc2CN[C@@H](CO)C(=O)O)c1] | +++ |

TABLE 3-continued
Structures and Activity
| Compound Number | Compound Structure | ELISA IC$_{50}$ (nM) |
|---|---|---|
| 3.003 | 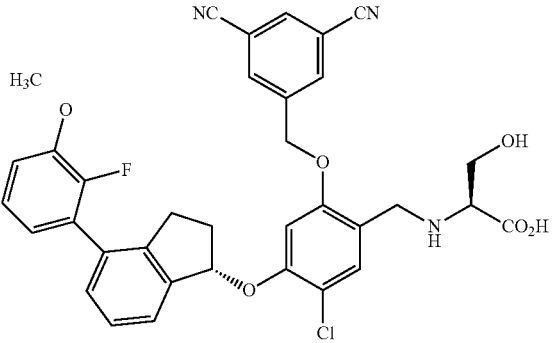 | +++ |
| 3.004 | 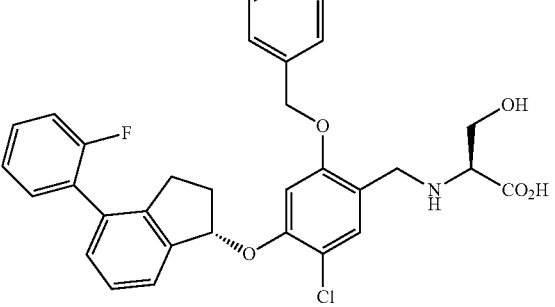 | +++ |
| 3.005 | 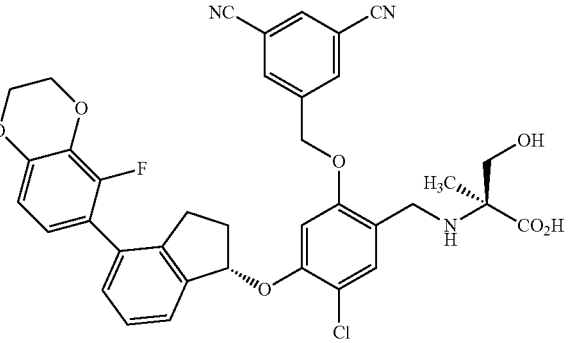 | +++ |
| 3.006 | 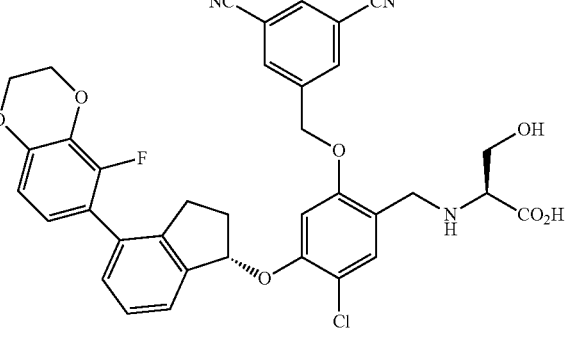 | +++ |

TABLE 3-continued
Structures and Activity
| Compound Number | Compound Structure | ELISA IC$_{50}$ (nM) |
|---|---|---|
| 3.007 | 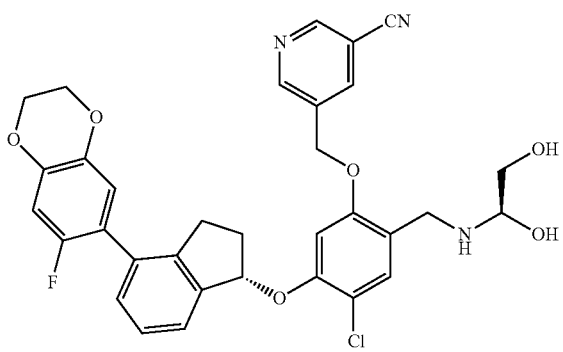 [SMILES: N#Cc1cncc(COc2cc(O[C@H]3CCc4c(-c5cc6c(cc5F)OCCO6)cccc43)c(Cl)cc2CN[C@H](O)CO)c1] | +++ |
| 3.008 | 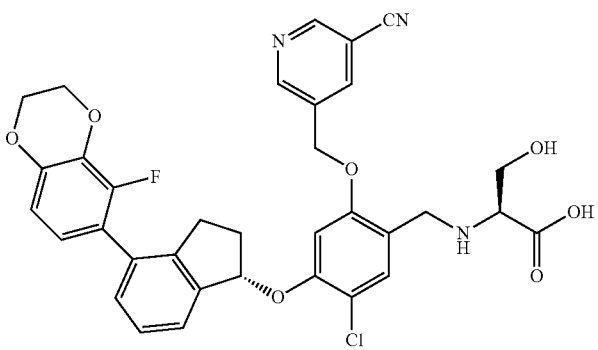 [SMILES: N#Cc1cncc(COc2cc(O[C@H]3CCc4c(-c5ccc6c(c5F)OCCO6)cccc43)c(Cl)cc2CN[C@@H](CO)C(=O)O)c1] | +++ |
| 3.009 | 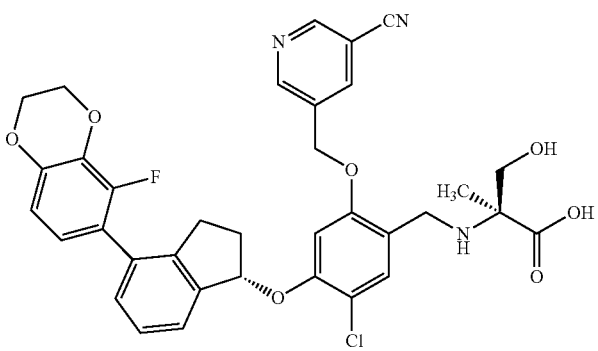 [SMILES: C[C@@](CO)(NCc1cc(Cl)c(O[C@H]2CCc3c(-c4ccc5c(c4F)OCCO5)cccc32)cc1OCc1cncc(C#N)c1)C(=O)O] | +++ |
| 3.010 | 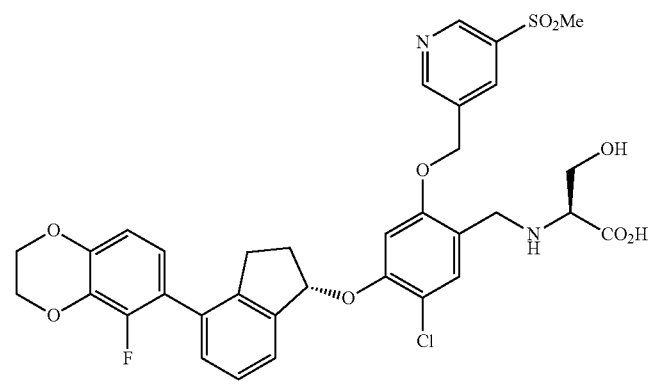 [SMILES: CS(=O)(=O)c1cncc(COc2cc(O[C@H]3CCc4c(-c5ccc6c(c5F)OCCO6)cccc43)c(Cl)cc2CN[C@@H](CO)C(=O)O)c1] | +++ |

TABLE 3-continued
Structures and Activity
| Compound Number | Compound Structure | ELISA IC$_{50}$ (nM) |
| --- | --- | --- |
| 3.011 | 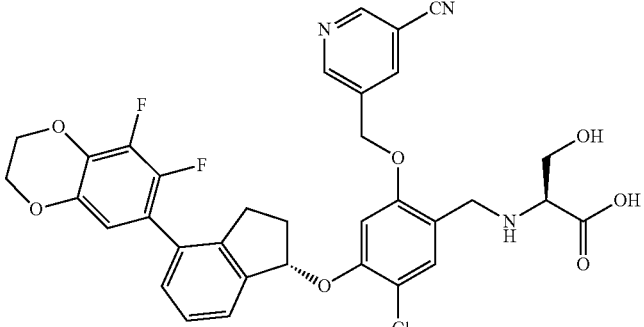 | +++ |
| 3.012 | 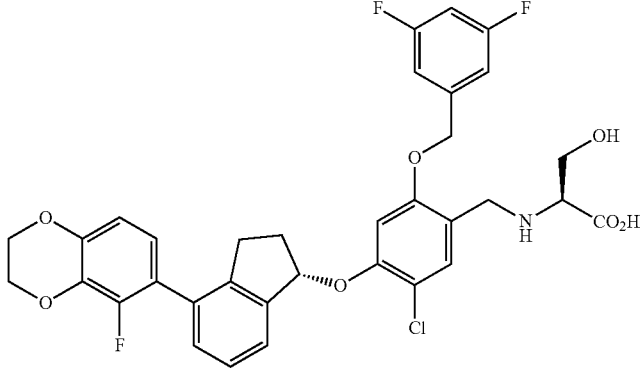 [SMILES: O=C(O)[C@H](CO)NCc1cc(Cl)c(O[C@H]2CCc3c(-c4ccc5c(c4F)OCCO5)cccc32)cc1OCc1cc(F)cc(F)c1] | + |
| 3.013 | 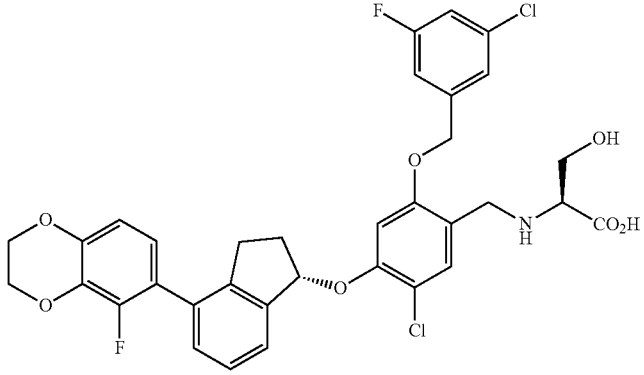 | + |
| 3.014 | 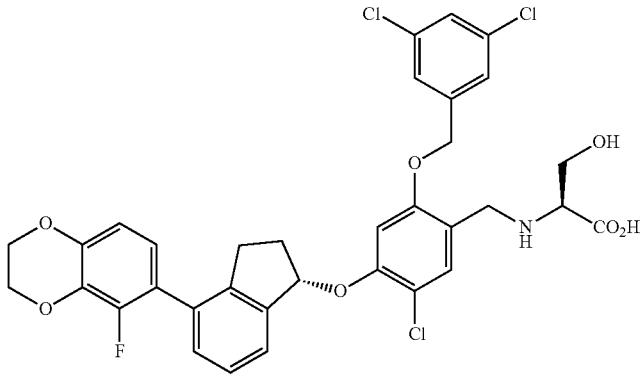 | + |

TABLE 3-continued
Structures and Activity
| Compound Number | Compound Structure | ELISA IC$_{50}$ (nM) |
|---|---|---|
| 3.015 | 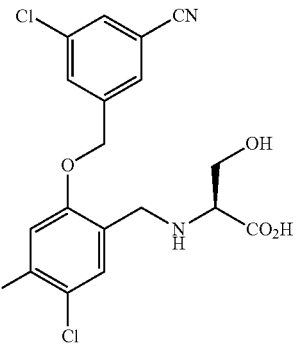 | +++ |
| 3.016 | 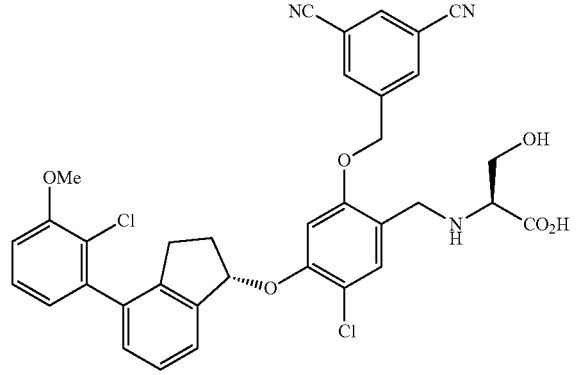 [SMILES: COc1cccc(-c2cccc3c2CC[C@@H]3Oc2cc(OCc3cc(C#N)cc(C#N)c3)c(CN[C@@H](CO)C(=O)O)cc2Cl)c1Cl] | +++ |
| 3.017 | 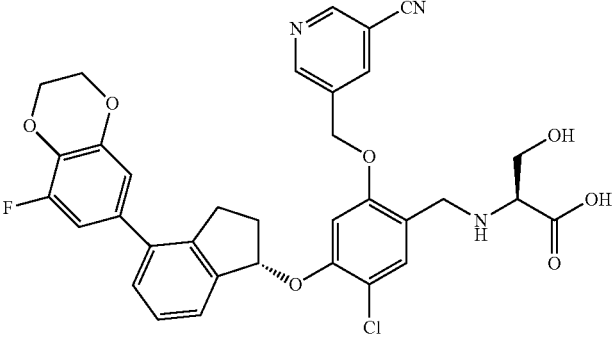 [SMILES: N#Cc1cncc(COc2cc(O[C@H]3CCc4c(-c5cc(F)c6c(c5)OCCO6)cccc43)c(Cl)cc2CN[C@@H](CO)C(=O)O)c1] | +++ |
| 3.018 | 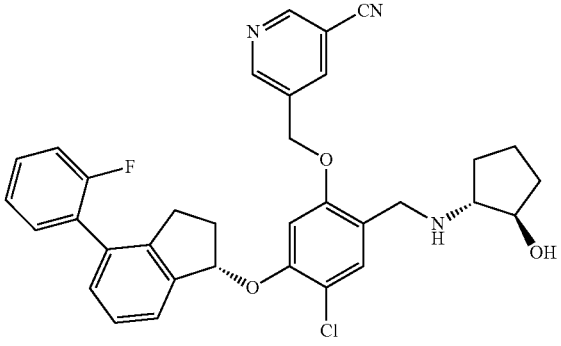 [SMILES: N#Cc1cncc(COc2cc(O[C@H]3CCc4c(-c5ccccc5F)cccc43)c(Cl)cc2CN[C@@H]2CCC[C@H]2O)c1] | +++ |

TABLE 3-continued

Structures and Activity

| Compound Number | Compound Structure | ELISA IC$_{50}$ (nM) |
| --- | --- | --- |
| 3.019 | 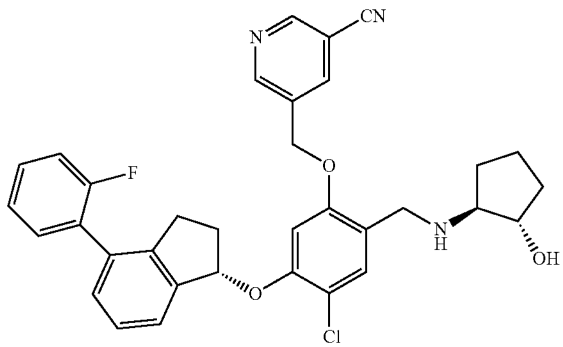 [SMILES: N#Cc1cncc(COc2cc(O[C@H]3CCc4c(-c5ccccc5F)cccc43)c(Cl)cc2CN[C@H]2CCC[C@@H]2O)c1] | +++ |
| 3.020 | 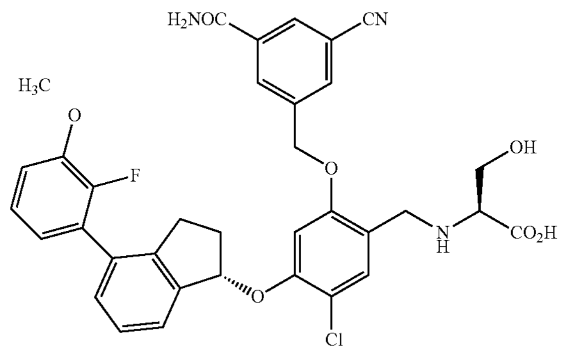 | +++ |
| 3.021 | 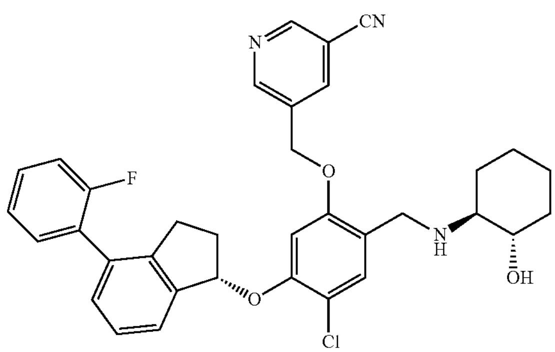 [SMILES: N#Cc1cncc(COc2cc(O[C@H]3CCc4c(-c5ccccc5F)cccc43)c(Cl)cc2CN[C@H]2CCCC[C@@H]2O)c1] | +++ |
| 3.022 | 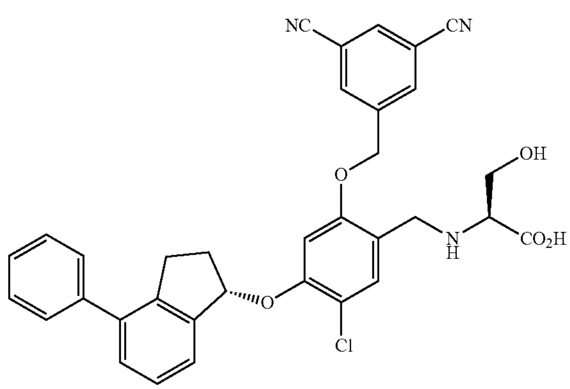 [SMILES: N#Cc1cc(C#N)cc(COc2cc(O[C@H]3CCc4c(-c5ccccc5)cccc43)c(Cl)cc2CN[C@@H](CO)C(=O)O)c1] | +++ |

TABLE 3-continued
Structures and Activity
| Compound Number | Compound Structure | ELISA IC$_{50}$ (nM) |
|---|---|---|
| 3.023 | 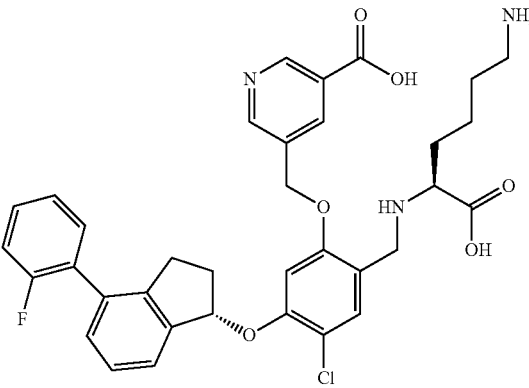 | ++ |
| 3.024 | 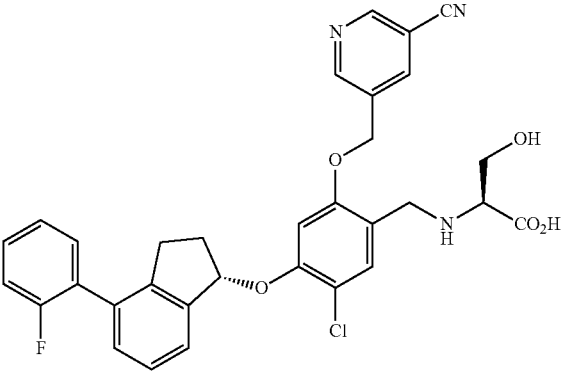 [SMILES: N#Cc1cncc(COc2cc(O[C@H]3CCc4c(-c5ccccc5F)cccc43)c(Cl)cc2CN[C@@H](CO)C(=O)O)c1] | +++ |
| 3.025 | 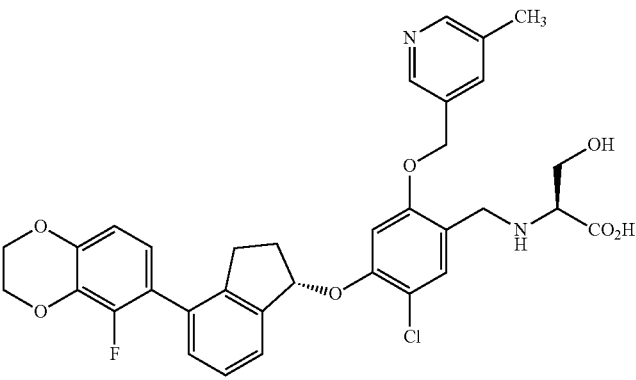 | +++ |
| 3.026 | 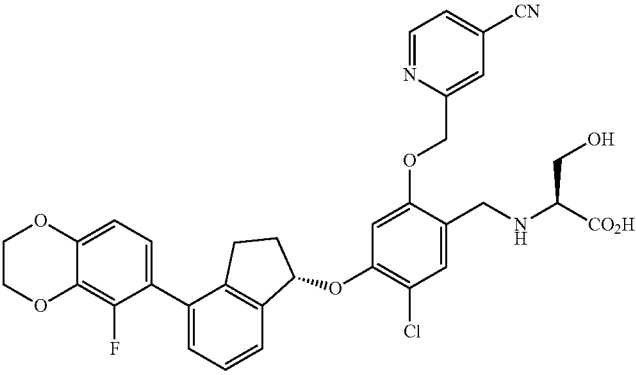 [SMILES: N#Cc1ccnc(COc2cc(O[C@H]3CCc4c(-c5ccc6c(c5F)OCCO6)cccc43)c(Cl)cc2CN[C@@H](CO)C(=O)O)c1] | +++ |

TABLE 3-continued

Structures and Activity

| Compound Number | Compound Structure | ELISA IC$_{50}$ (nM) |
|---|---|---|
| 3.027 | 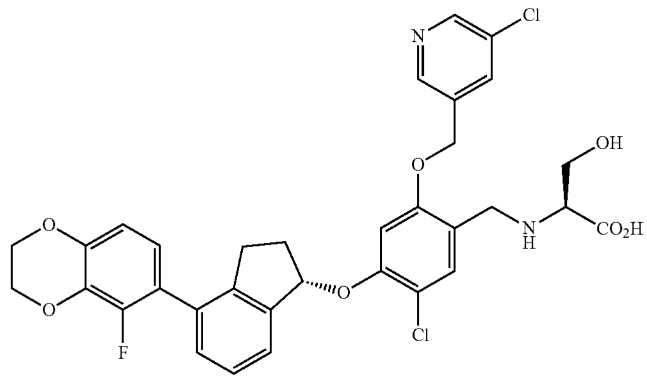 [SMILES: O=C(O)[C@H](CO)NCc1cc(Cl)c(O[C@H]2CCc3c(-c4ccc5c(c4F)OCCO5)cccc32)cc1OCc1cncc(Cl)c1] | +++ |
| 3.028 | 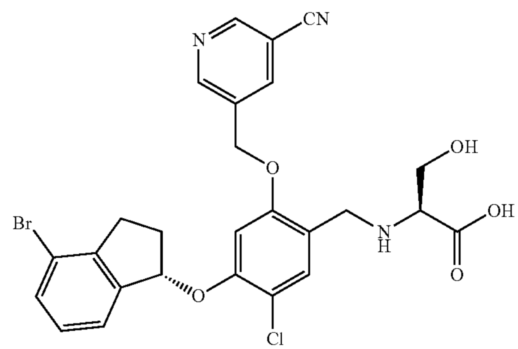 [SMILES: N#Cc1cncc(COc2cc(O[C@H]3CCc4c(Br)cccc43)c(Cl)cc2CN[C@@H](CO)C(=O)O)c1] | + |
| 3.029 | 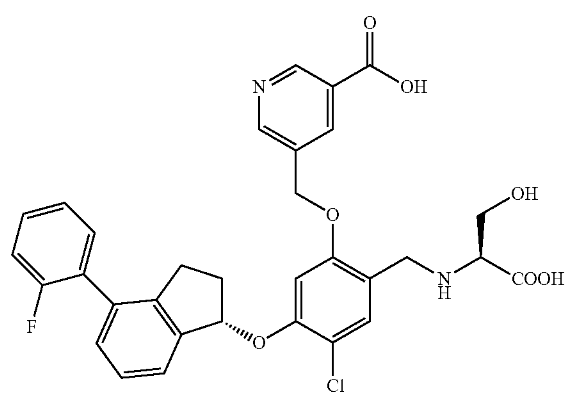 [SMILES: O=C(O)c1cncc(COc2cc(O[C@H]3CCc4c(-c5ccccc5F)cccc43)c(Cl)cc2CN[C@@H](CO)C(=O)O)c1] | ++ |
| 3.030 | 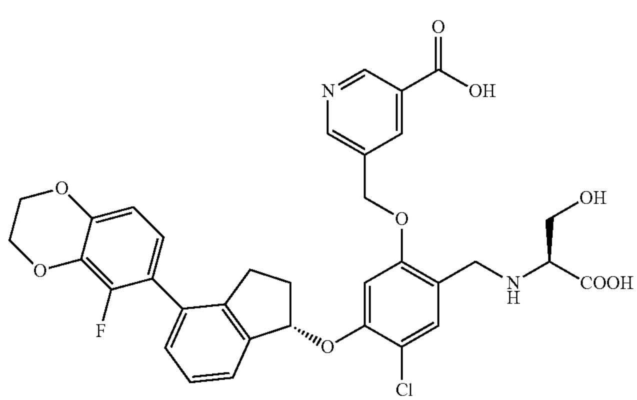 [SMILES: O=C(O)c1cncc(COc2cc(O[C@H]3CCc4c(-c5ccc6c(c5F)OCCO6)cccc43)c(Cl)cc2CN[C@@H](CO)C(=O)O)c1] | ++ |

TABLE 3-continued

Structures and Activity

| Compound Number | Compound Structure | ELISA IC$_{50}$ (nM) |
|---|---|---|
| 3.031 | 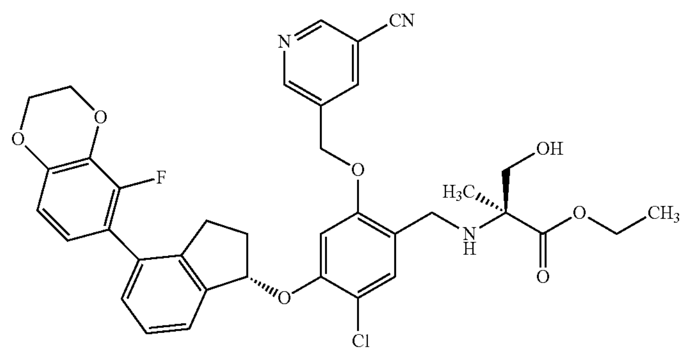 [SMILES: CCOC(=O)[C@](C)(CO)NCc1cc(Cl)c(O[C@H]2CCc3c(-c4ccc5c(c4F)OCCO5)cccc32)cc1OCc1cncc(C#N)c1] | ++ |
| 3.032 | 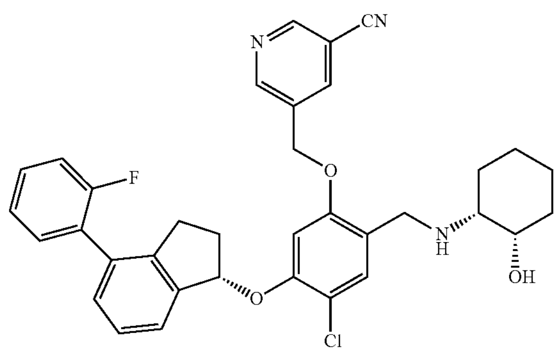 [SMILES: N#Cc1cncc(COc2cc(O[C@H]3CCc4c(-c5ccccc5F)cccc43)c(Cl)cc2CN[C@@H]2CCCC[C@@H]2O)c1] | +++ |
| 3.033 | 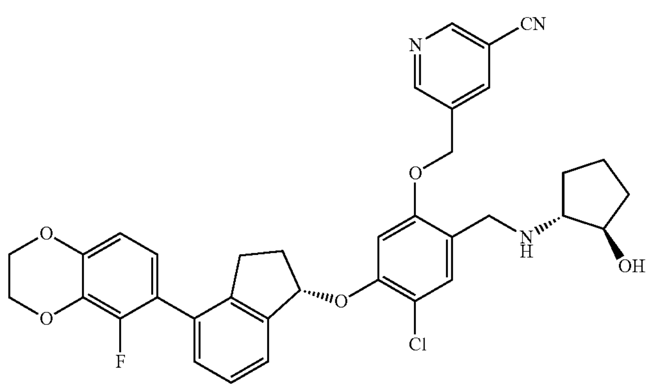 [SMILES: N#Cc1cncc(COc2cc(O[C@H]3CCc4c(-c5ccc6c(c5F)OCCO6)cccc43)c(Cl)cc2CN[C@@H]2CCC[C@H]2O)c1] | +++ |
| 3.034 | 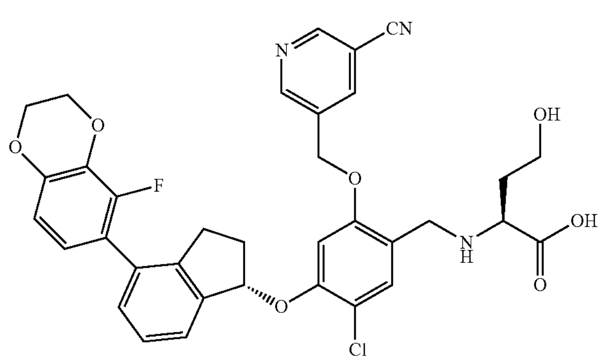 [SMILES: N#Cc1cncc(COc2cc(O[C@H]3CCc4c(-c5ccc6c(c5F)OCCO6)cccc43)c(Cl)cc2CN[C@@H](CCO)C(=O)O)c1] | +++ |

TABLE 3-continued

Structures and Activity

| Compound Number | Compound Structure | ELISA IC$_{50}$ (nM) |
|---|---|---|
| 3.035 | 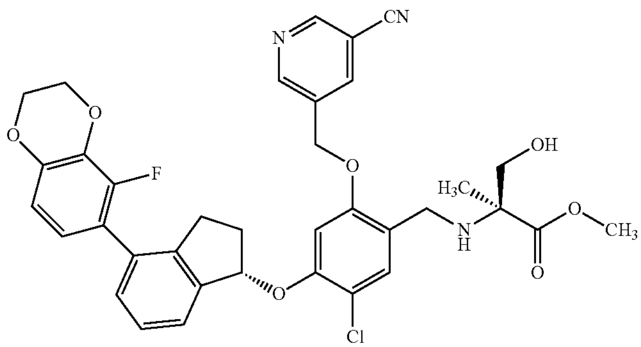 [SMILES: COC(=O)[C@](C)(CO)NCc1cc(Cl)c(O[C@H]2CCc3c(-c4ccc5c(c4F)OCCO5)cccc32)cc1OCc1cncc(C#N)c1] | ++ |
| 3.036 | 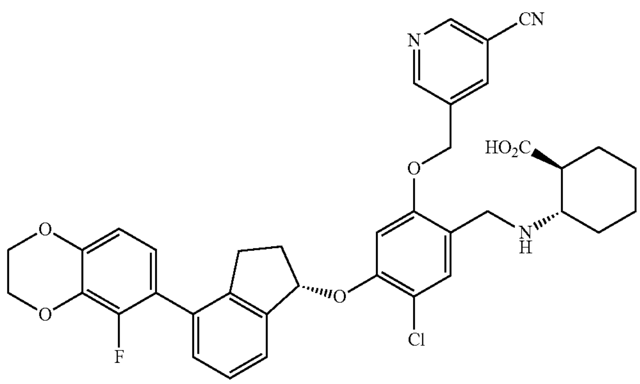 [SMILES: N#Cc1cncc(COc2cc(O[C@H]3CCc4c(-c5ccc6c(c5F)OCCO6)cccc43)c(Cl)cc2CN[C@H]2CCCC[C@@H]2C(=O)O)c1] | ++ |
| 3.037 | 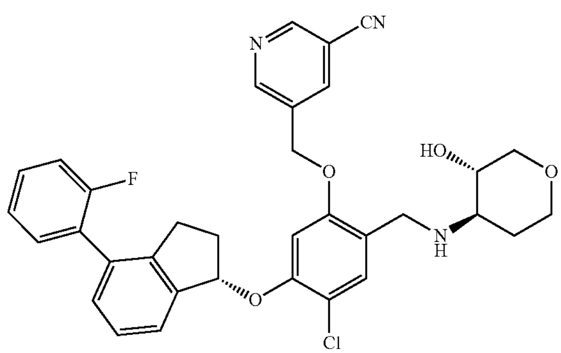 [SMILES: N#Cc1cncc(COc2cc(O[C@H]3CCc4c(-c5ccccc5F)cccc43)c(Cl)cc2CN[C@@H]2CCOC[C@H]2O)c1] | +++ |
| 3.038 | 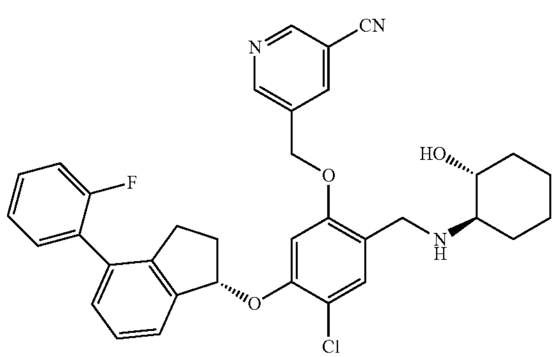 [SMILES: N#Cc1cncc(COc2cc(O[C@H]3CCc4c(-c5ccccc5F)cccc43)c(Cl)cc2CN[C@@H]2CCCC[C@H]2O)c1] | +++ |

TABLE 3-continued

Structures and Activity

| Compound Number | Compound Structure | ELISA IC$_{50}$ (nM) |
|---|---|---|
| 3.039 | 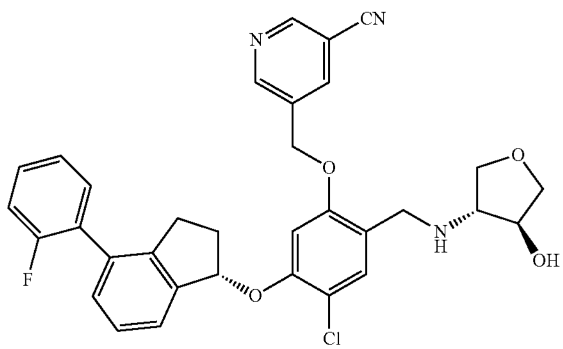 [SMILES: N#Cc1cncc(COc2cc(O[C@H]3CCc4c(-c5ccccc5F)cccc43)c(Cl)cc2CN[C@@H]2COC[C@H]2O)c1] | +++ |
| 3.040 | 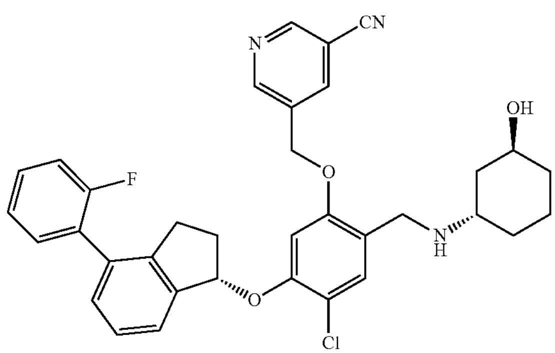 [SMILES: N#Cc1cncc(COc2cc(O[C@H]3CCc4c(-c5ccccc5F)cccc43)c(Cl)cc2CN[C@H]2CCC[C@H](O)C2)c1] | +++ |
| 3.041 | 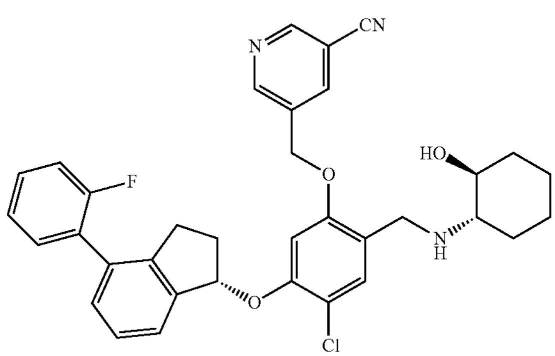 [SMILES: N#Cc1cncc(COc2cc(O[C@H]3CCc4c(-c5ccccc5F)cccc43)c(Cl)cc2CN[C@H]2CCCC[C@@H]2O)c1] | +++ |
| 3.042 | 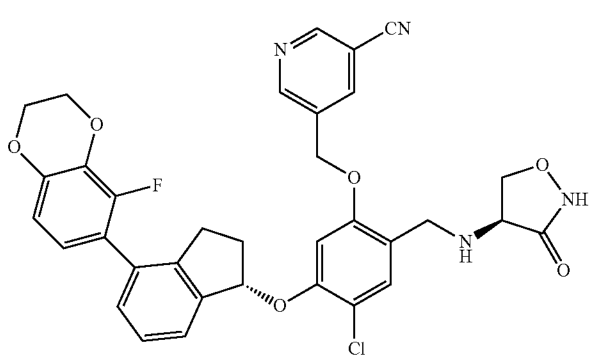 [SMILES: N#Cc1cncc(COc2cc(O[C@H]3CCc4c(-c5ccc6c(c5F)OCCO6)cccc43)c(Cl)cc2CN[C@H]2CONC2=O)c1] | + |

TABLE 3-continued

Structures and Activity

| Compound Number | Compound Structure | ELISA IC$_{50}$ (nM) |
|---|---|---|
| 3.043 | | +++ |
| 3.044 | | +++ |
| 3.045 | | + |
| 3.046 | | + |

TABLE 3-continued
Structures and Activity
| Compound Number | Compound Structure | ELISA IC$_{50}$ (nM) |
|---|---|---|
| 3.047 | 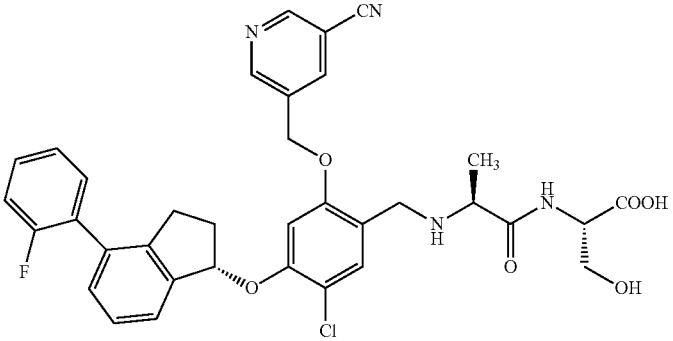 [SMILES: C[C@H](NCc1cc(Cl)c(O[C@H]2CCc3c(-c4ccccc4F)cccc32)cc1OCc1cncc(C#N)c1)C(=O)N[C@@H](CO)C(=O)O] | +++ |
| 3.048 | 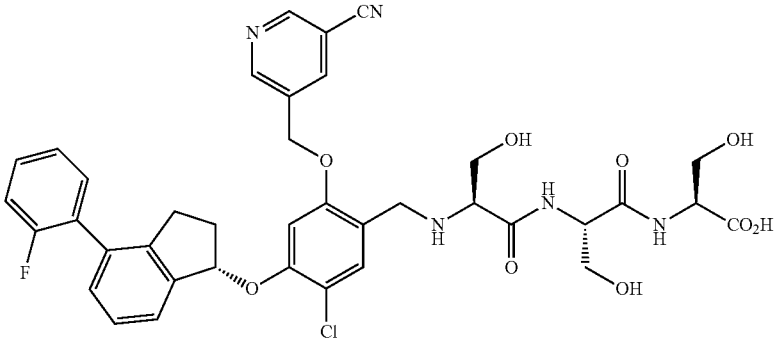 [SMILES: N#Cc1cncc(COc2cc(O[C@H]3CCc4c(-c5ccccc5F)cccc43)c(Cl)cc2CN[C@@H](CO)C(=O)N[C@@H](CO)C(=O)N[C@@H](CO)C(=O)O)c1] | +++ |
| 3.049 | 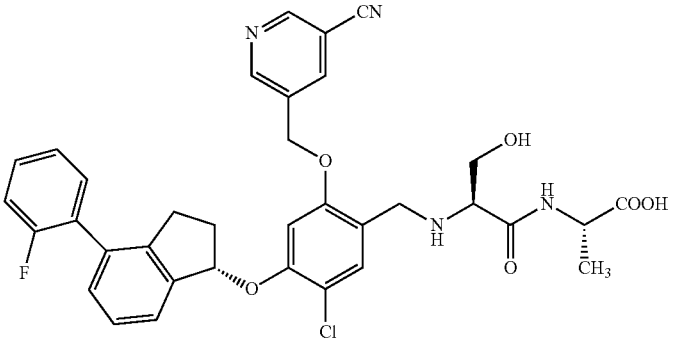 [SMILES: C[C@H](NC(=O)[C@H](CO)NCc1cc(Cl)c(O[C@H]2CCc3c(-c4ccccc4F)cccc32)cc1OCc1cncc(C#N)c1)C(=O)O] | +++ |
| 3.050 | 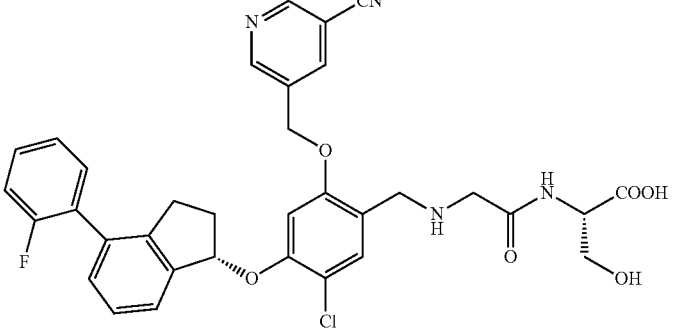 | ++ |

TABLE 3-continued

Structures and Activity

| Compound Number | Compound Structure | ELISA IC$_{50}$ (nM) |
|---|---|---|
| 3.051 | 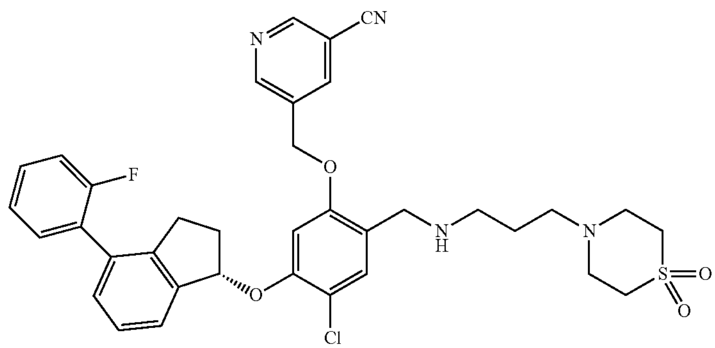 [SMILES: N#Cc1cncc(COc2cc(O[C@H]3CCc4c(-c5ccccc5F)cccc43)c(Cl)cc2CNCCCN2CCS(=O)(=O)CC2)c1] | ++ |
| 3.052 | 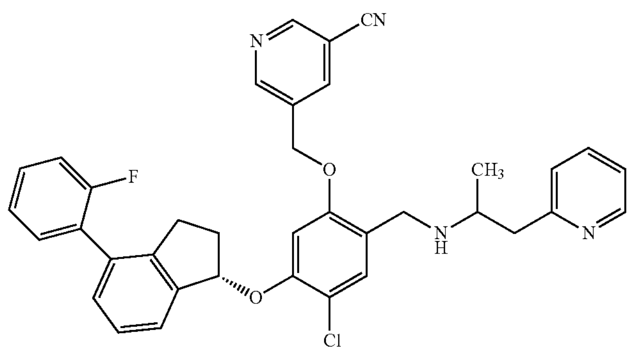 [SMILES: CC(Cc1ccccn1)NCc1cc(Cl)c(O[C@H]2CCc3c(-c4ccccc4F)cccc32)cc1OCc1cncc(C#N)c1] | ++ |
| 3.053 | 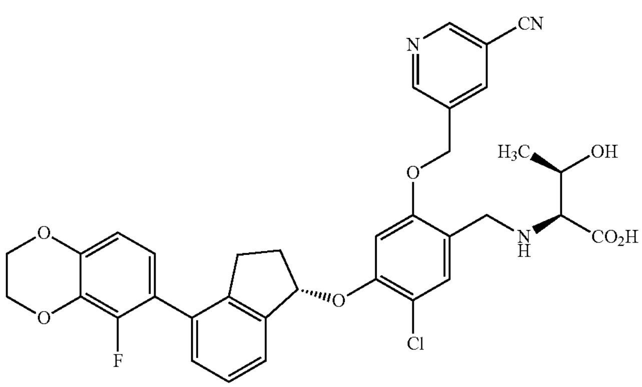 [SMILES: C[C@@H](O)[C@H](NCc1cc(Cl)c(O[C@H]2CCc3c(-c4ccc5c(c4F)OCCO5)cccc32)cc1OCc1cncc(C#N)c1)C(=O)O] | +++ |
| 3.054 | 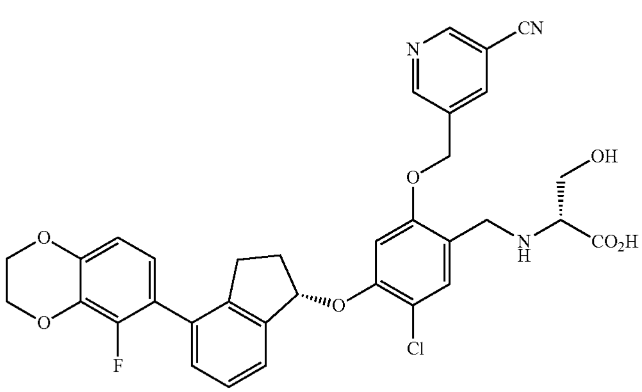 [SMILES: N#Cc1cncc(COc2cc(O[C@H]3CCc4c(-c5ccc6c(c5F)OCCO6)cccc43)c(Cl)cc2CN[C@H](CO)C(=O)O)c1] | +++ |

TABLE 3-continued
Structures and Activity
| Compound Number | Compound Structure | ELISA IC$_{50}$ (nM) |
|---|---|---|
| 3.055 | 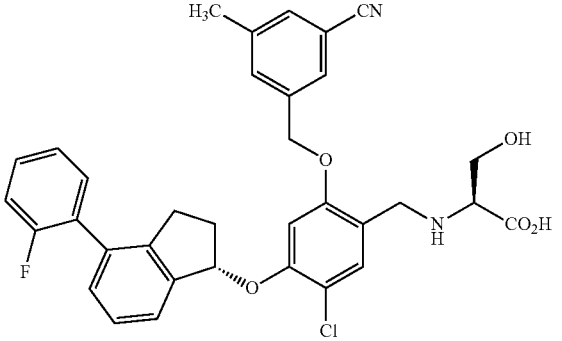 [SMILES: Cc1cc(C#N)cc(COc2cc(O[C@H]3CCc4c(-c5ccccc5F)cccc43)c(Cl)cc2CN[C@@H](CO)C(=O)O)c1] | ++ |
| 3.056 | 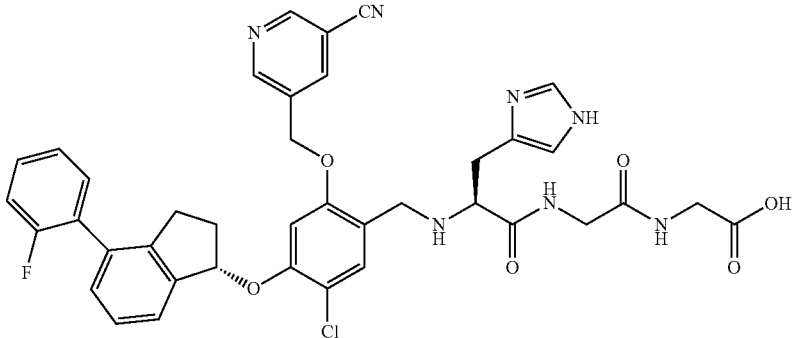 [SMILES: N#Cc1cncc(COc2cc(O[C@H]3CCc4c(-c5ccccc5F)cccc43)c(Cl)cc2CN[C@@H](Cc2c[nH]cn2)C(=O)NCC(=O)NCC(=O)O)c1] | + |
| 3.057 | 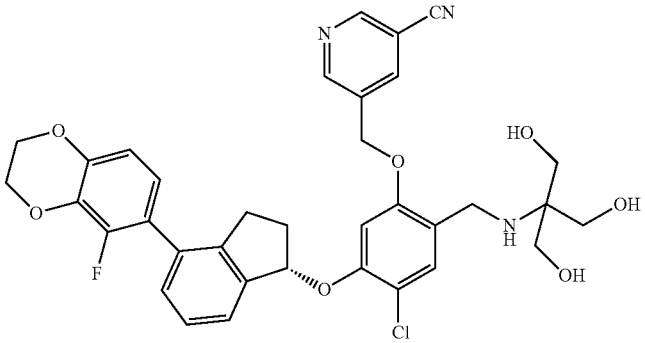 [SMILES: N#Cc1cncc(COc2cc(O[C@H]3CCc4c(-c5ccc6c(c5F)OCCO6)cccc43)c(Cl)cc2CNC(CO)(CO)CO)c1] | +++ |
| 3.058 | 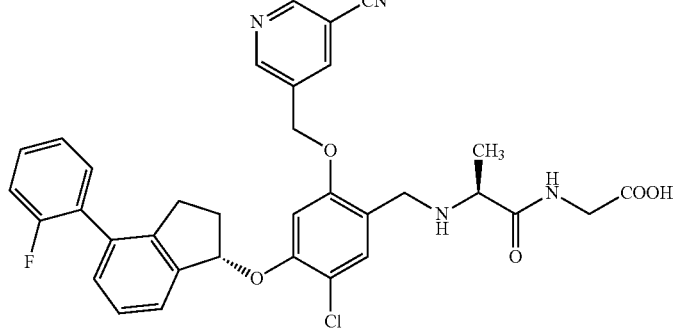 | ++ |

TABLE 3-continued

Structures and Activity

| Compound Number | Compound Structure | ELISA IC$_{50}$ (nM) |
|---|---|---|
| 3.059 | 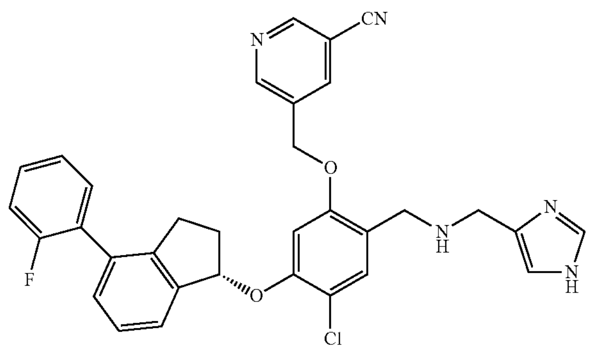 [SMILES: N#Cc1cncc(COc2cc(O[C@H]3CCc4c(-c5ccccc5F)cccc43)c(Cl)cc2CNCc2c[nH]cn2)c1] | +++ |
| 3.060 | 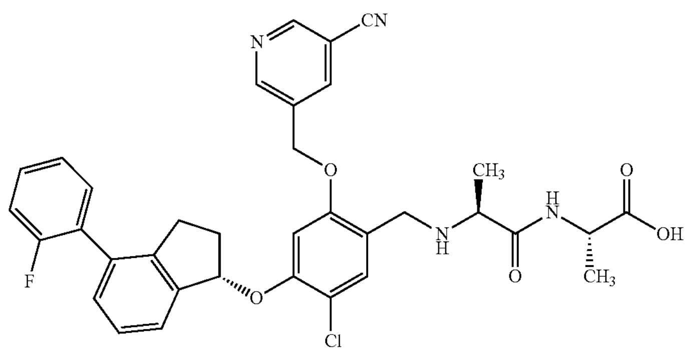 [SMILES: C[C@H](NC(=O)[C@H](C)NCc1cc(Cl)c(O[C@H]2CCc3c(-c4ccccc4F)cccc32)cc1OCc1cncc(C#N)c1)C(=O)O] | +++ |
| 3.061 | 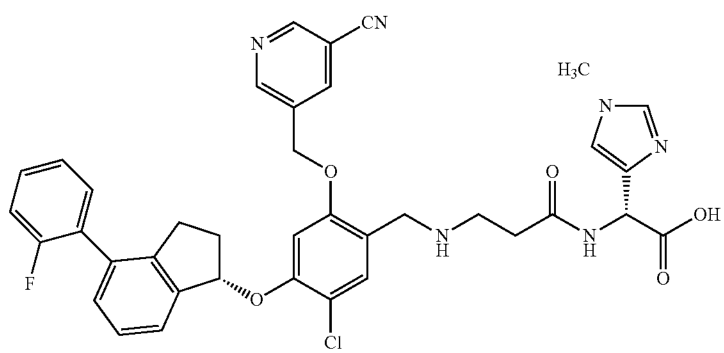 | ++ |
| 3.062 | 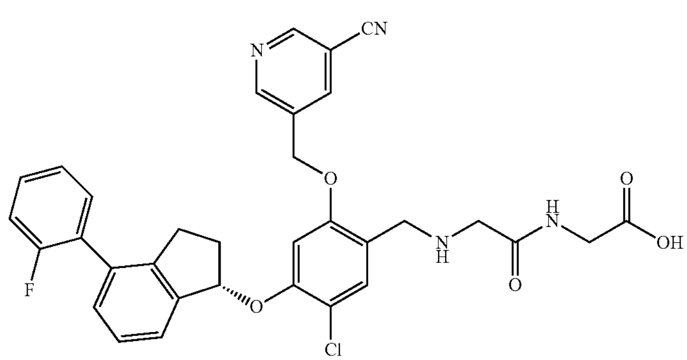 [SMILES: N#Cc1cncc(COc2cc(O[C@H]3CCc4c(-c5ccccc5F)cccc43)c(Cl)cc2CNCC(=O)NCC(=O)O)c1] | +++ |

TABLE 3-continued

Structures and Activity

| Compound Number | Compound Structure | ELISA IC$_{50}$ (nM) |
|---|---|---|
| 3.063 | 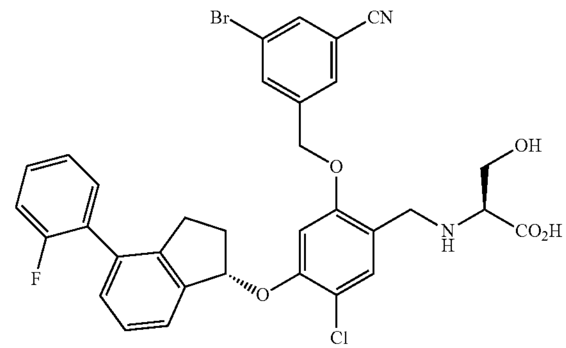 [SMILES: N#Cc1cc(Br)cc(COc2cc(O[C@H]3CCc4c(-c5ccccc5F)cccc43)c(Cl)cc2CN[C@@H](CO)C(=O)O)c1] | +++ |
| 3.064 | 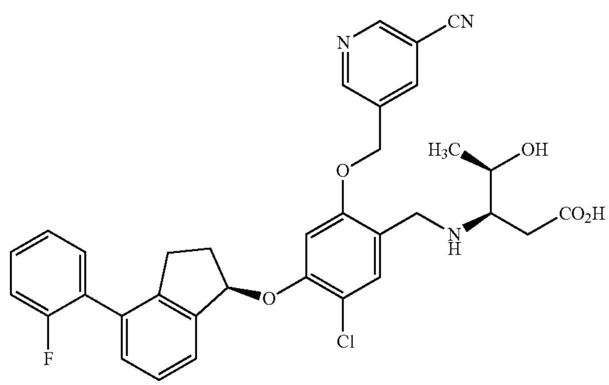 [SMILES: C[C@@H](O)[C@@H](CC(=O)O)NCc1cc(Cl)c(O[C@@H]2CCc3c(-c4ccccc4F)cccc32)cc1OCc1cncc(C#N)c1] | + |
| 3.065 | 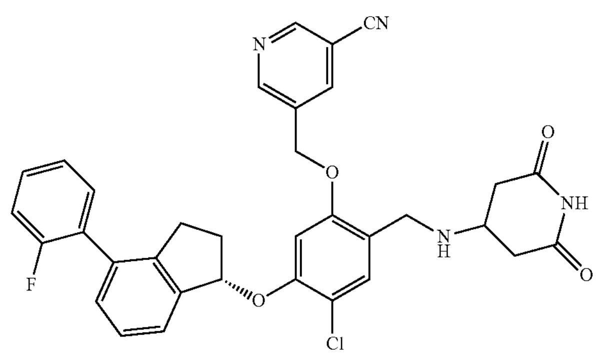 [SMILES: N#Cc1cncc(COc2cc(O[C@H]3CCc4c(-c5ccccc5F)cccc43)c(Cl)cc2CNC2CC(=O)NC(=O)C2)c1] | + |
| 3.066 | 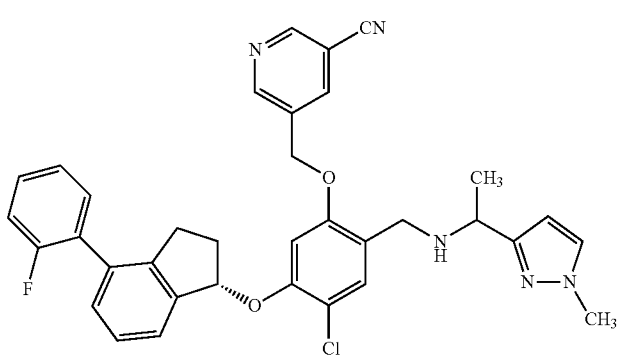 [SMILES: CC(NCc1cc(Cl)c(O[C@H]2CCc3c(-c4ccccc4F)cccc32)cc1OCc1cncc(C#N)c1)c1ccn(C)n1] | ++ |

TABLE 3-continued

Structures and Activity

| Compound Number | Compound Structure | ELISA IC$_{50}$ (nM) |
|---|---|---|
| 3.067 | 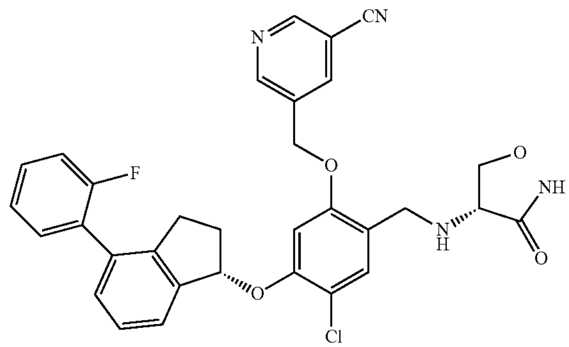 [SMILES: N#Cc1cncc(COc2cc(O[C@H]3CCc4c(-c5ccccc5F)cccc43)c(Cl)cc2CN[C@H](CO)C(N)=O)c1] | + |
| 3.068 | 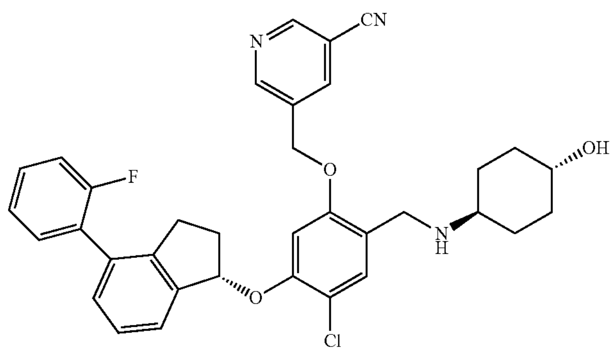 [SMILES: N#Cc1cncc(COc2cc(O[C@H]3CCc4c(-c5ccccc5F)cccc43)c(Cl)cc2CN[C@H]2CC[C@H](O)CC2)c1] | +++ |
| 3.069 | 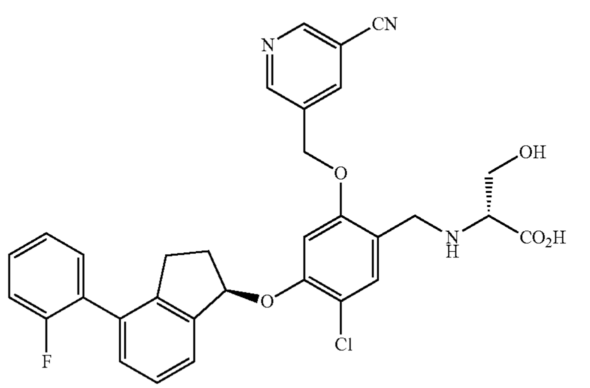 [SMILES: N#Cc1cncc(COc2cc(O[C@@H]3CCc4c(-c5ccccc5F)cccc43)c(Cl)cc2CN[C@H](CO)C(=O)O)c1] | +++ |
| 3.070 | 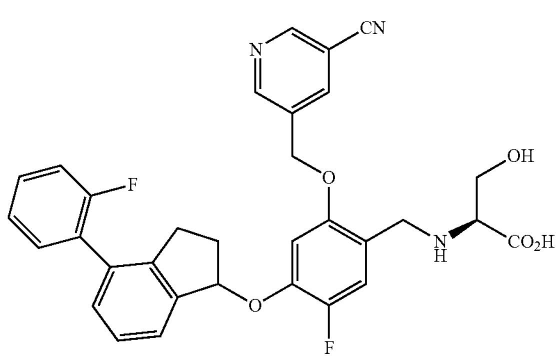 [SMILES: N#Cc1cncc(COc2cc(OC3CCc4c(-c5ccccc5F)cccc43)c(F)cc2CN[C@@H](CO)C(=O)O)c1] | +++ |

TABLE 3-continued

Structures and Activity

| Compound Number | Compound Structure | ELISA IC$_{50}$ (nM) |
|---|---|---|
| 3.071 | 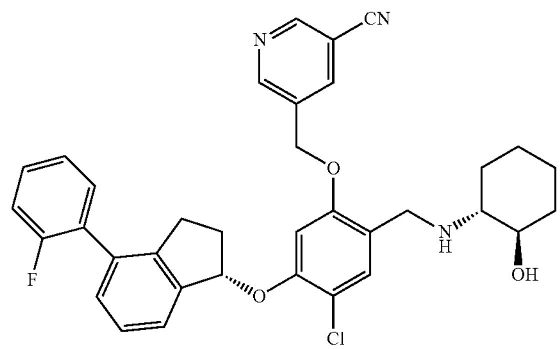 [SMILES: N#Cc1cncc(COc2cc(O[C@H]3CCc4c(-c5ccccc5F)cccc43)c(Cl)cc2CN[C@@H]2CCCC[C@H]2O)c1] | +++ |
| 3.072 | 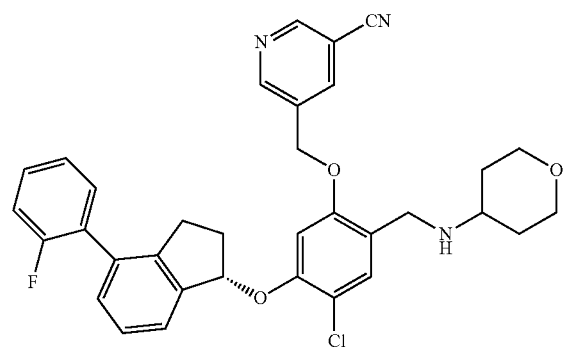 [SMILES: N#Cc1cncc(COc2cc(O[C@H]3CCc4c(-c5ccccc5F)cccc43)c(Cl)cc2CNC2CCOCC2)c1] | +++ |
| 3.073 | 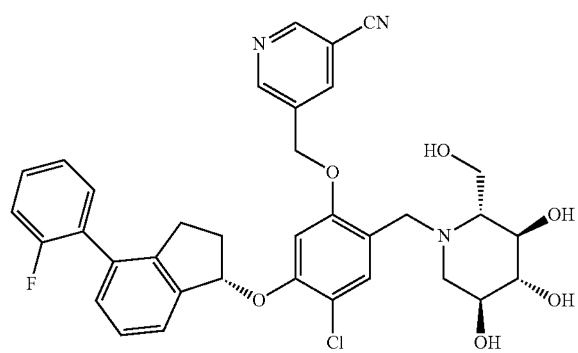 [SMILES: N#Cc1cncc(COc2cc(O[C@H]3CCc4c(-c5ccccc5F)cccc43)c(Cl)cc2CN2C[C@H](O)[C@@H](O)[C@H](O)[C@H]2CO)c1] | + |
| 3.074 | 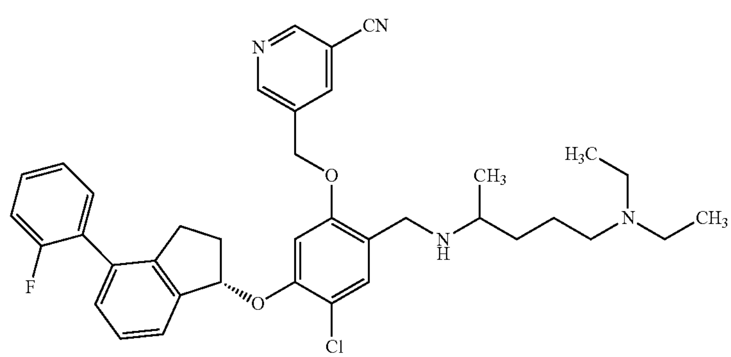 [SMILES: CCN(CC)CCCC(C)NCc1cc(Cl)c(O[C@H]2CCc3c(-c4ccccc4F)cccc32)cc1OCc1cncc(C#N)c1] | +++ |

TABLE 3-continued

Structures and Activity

| Compound Number | Compound Structure | ELISA IC$_{50}$ (nM) |
|---|---|---|
| 3.075 | 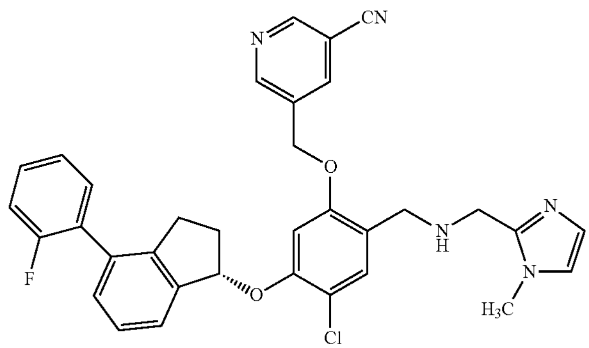 [SMILES: Cn1ccnc1CNCc1cc(Cl)c(O[C@H]2CCc3c(-c4ccccc4F)cccc32)cc1OCc1cncc(C#N)c1] | ++ |
| 3.076 | 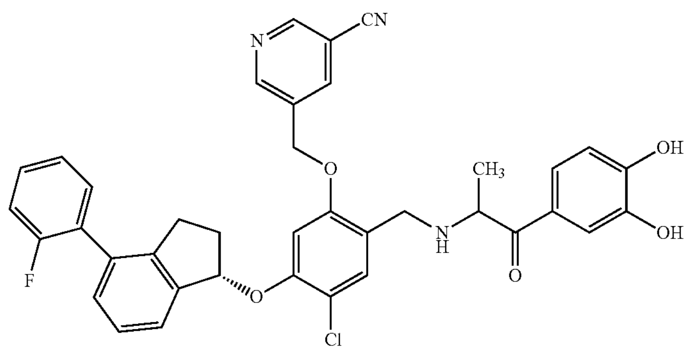 [SMILES: CC(NCc1cc(Cl)c(O[C@H]2CCc3c(-c4ccccc4F)cccc32)cc1OCc1cncc(C#N)c1)C(=O)c1ccc(O)c(O)c1] | ++ |
| 3.077 | 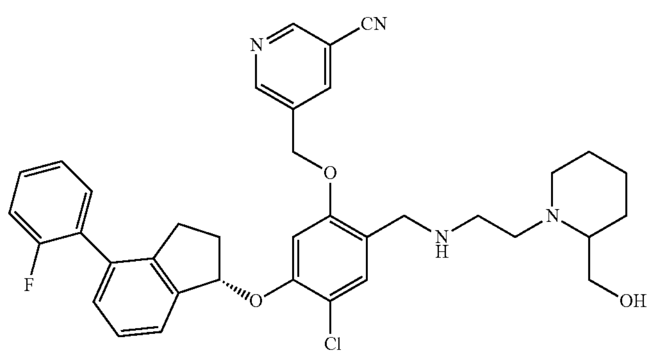 [SMILES: N#Cc1cncc(COc2cc(O[C@H]3CCc4c(-c5ccccc5F)cccc43)c(Cl)cc2CNCCN2CCCCC2CO)c1] | ++ |
| 3.078 | 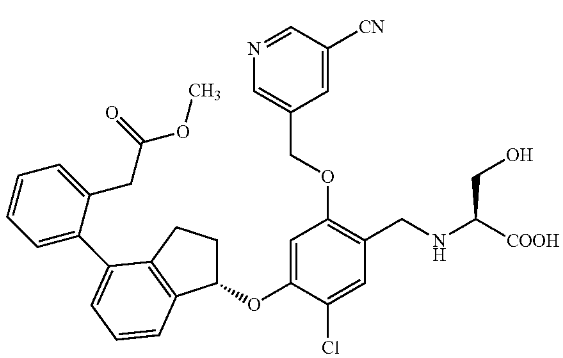 [SMILES: COC(=O)Cc1ccccc1-c1cccc2c1CC[C@@H]2Oc1cc(OCc2cncc(C#N)c2)c(CN[C@@H](CO)C(=O)O)cc1Cl] | + |

TABLE 3-continued
Structures and Activity
| Compound Number | Compound Structure | ELISA IC$_{50}$ (nM) |
|---|---|---|
| 3.079 | 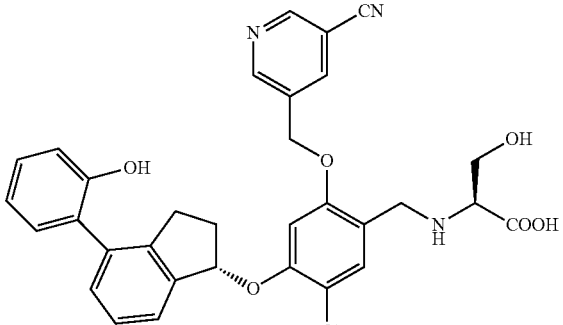 | ++ |
| 3.080 | 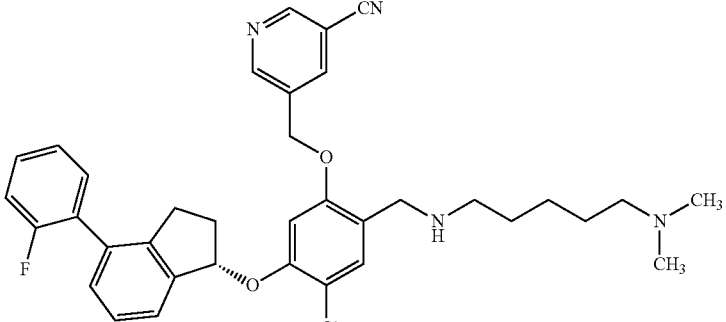 | +++ |
| 3.081 | 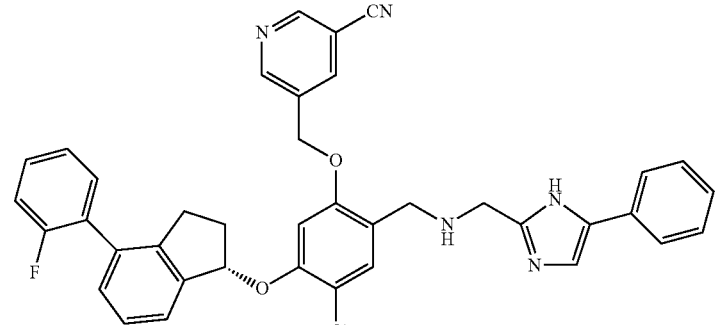 | + |
| 3.082 | 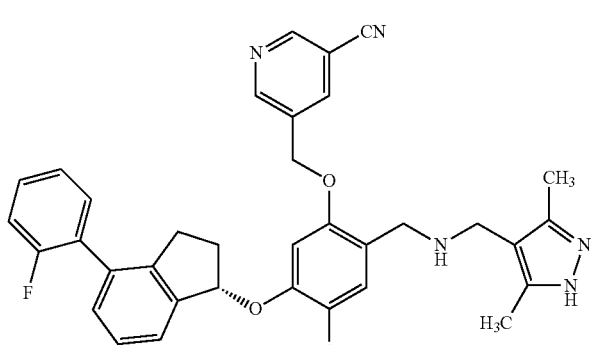 | ++ |

TABLE 3-continued
Structures and Activity
| Compound Number | Compound Structure | ELISA IC$_{50}$ (nM) |
|---|---|---|
| 3.083 | 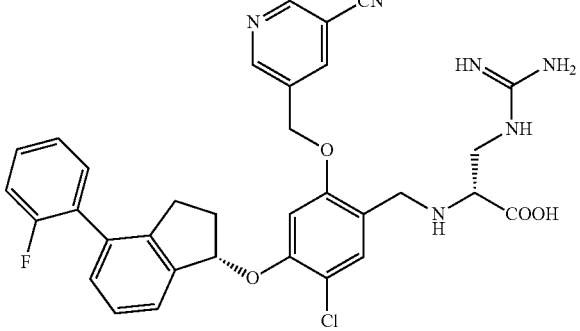 | +++ |
| 3.084 | 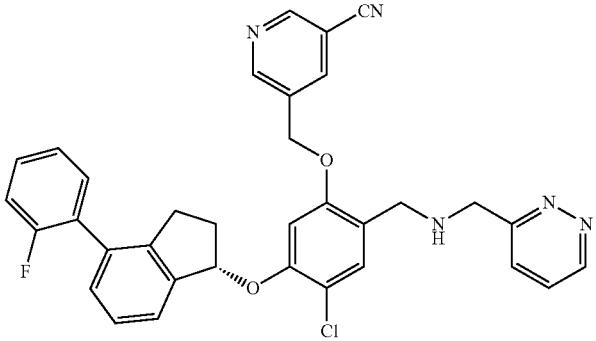 [SMILES: N#Cc1cncc(COc2cc(O[C@H]3CCc4c(-c5ccccc5F)cccc43)c(Cl)cc2CNCc2cccnn2)c1] | +++ |
| 3.085 | 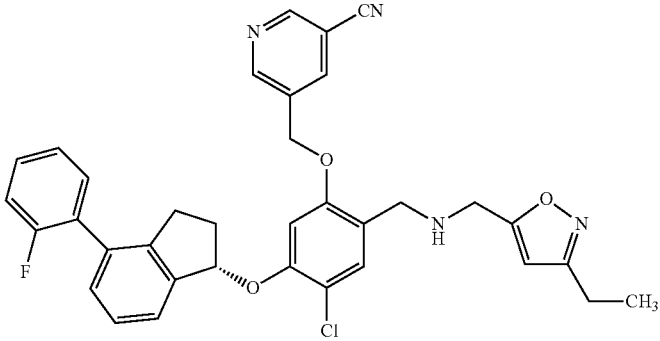 [SMILES: CCc1cc(CNCc2cc(Cl)c(O[C@H]3CCc4c(-c5ccccc5F)cccc43)cc2OCc2cncc(C#N)c2)on1] | + |
| 3.086 | 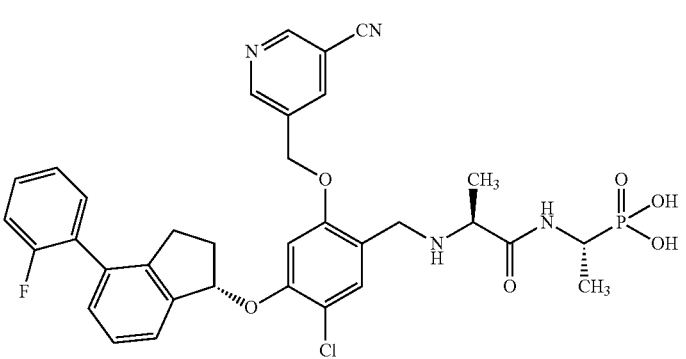 [SMILES: C[C@H](NCc1cc(Cl)c(O[C@H]2CCc3c(-c4ccccc4F)cccc32)cc1OCc1cncc(C#N)c1)C(=O)N[C@@H](C)P(=O)(O)O] | +++ |

TABLE 3-continued
Structures and Activity
| Compound Number | Compound Structure | ELISA IC$_{50}$ (nM) |
|---|---|---|
| 3.087 | 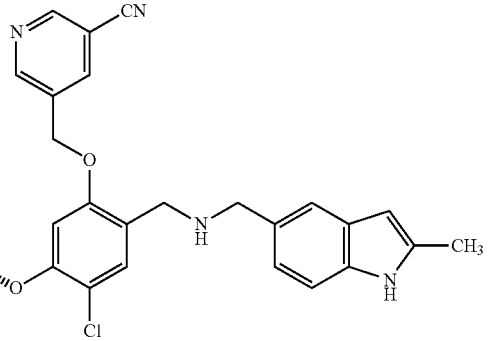 | + |
| 3.088 | 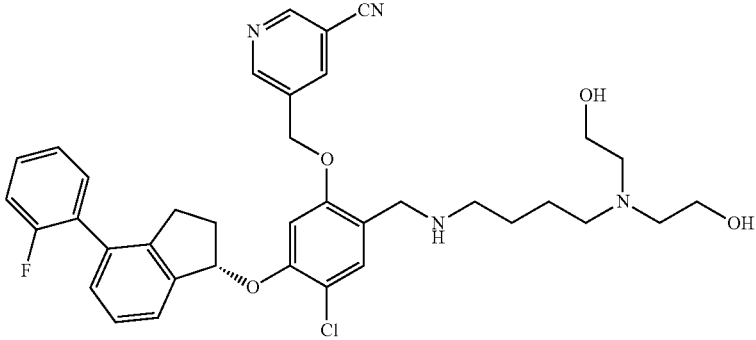 [SMILES: N#Cc1cncc(COc2cc(O[C@H]3CCc4c(-c5ccccc5F)cccc43)c(Cl)cc2CNCCCCN(CCO)CCO)c1] | ++ |
| 3.089 | 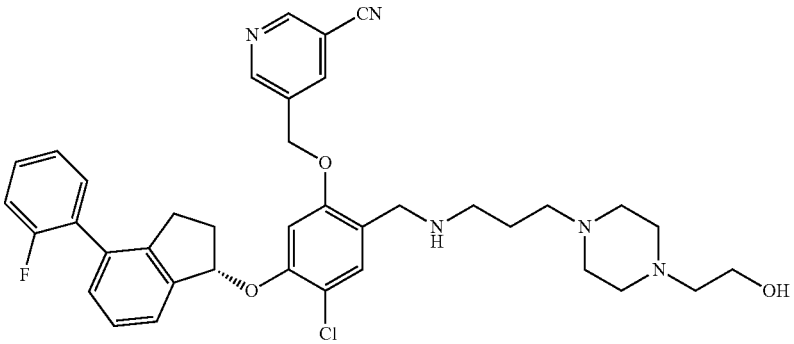 [SMILES: N#Cc1cncc(COc2cc(O[C@H]3CCc4c(-c5ccccc5F)cccc43)c(Cl)cc2CNCCCN2CCN(CCO)CC2)c1] | ++ |
| 3.090 | 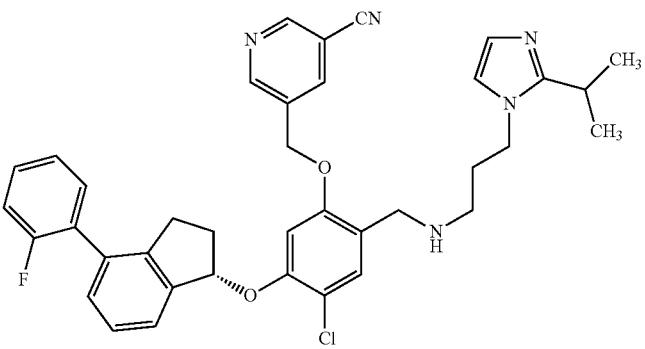 [SMILES: CC(C)c1nccn1CCCNCc1cc(Cl)c(O[C@H]2CCc3c(-c4ccccc4F)cccc32)cc1OCc1cncc(C#N)c1] | ++ |

TABLE 3-continued

Structures and Activity

| Compound Number | Compound Structure | ELISA IC$_{50}$ (nM) |
|---|---|---|
| 3.091 | 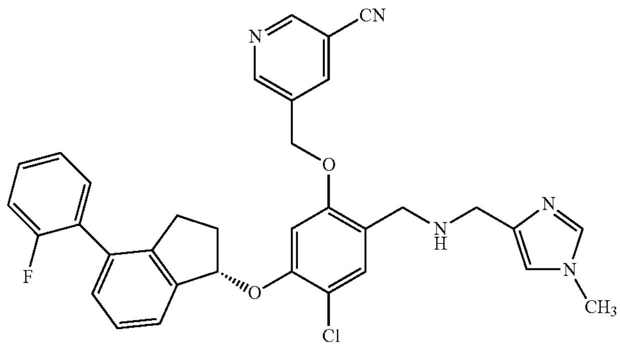 [SMILES: Cn1cnc(CNCc2cc(Cl)c(O[C@H]3CCc4c(-c5ccccc5F)cccc43)cc2OCc2cncc(C#N)c2)c1] | +++ |
| 3.092 | 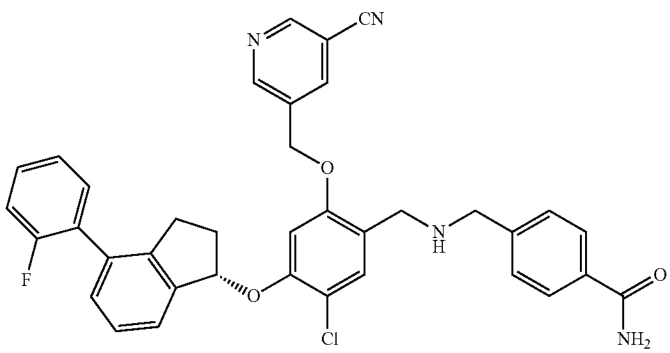 [SMILES: N#Cc1cncc(COc2cc(O[C@H]3CCc4c(-c5ccccc5F)cccc43)c(Cl)cc2CNCc2ccc(C(N)=O)cc2)c1] | ++ |
| 3.093 | 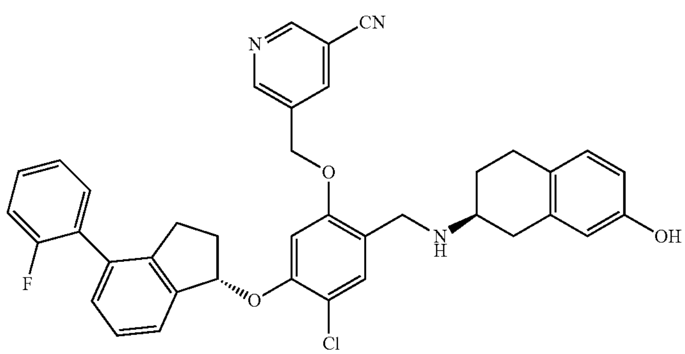 [SMILES: N#Cc1cncc(COc2cc(O[C@H]3CCc4c(-c5ccccc5F)cccc43)c(Cl)cc2CN[C@H]2CCc3ccc(O)cc3C2)c1] | ++ |
| 3.094 | 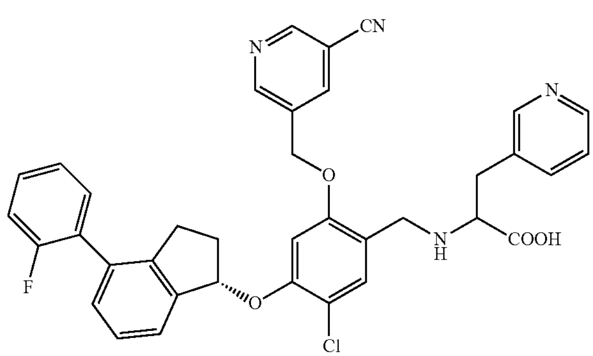 [SMILES: N#Cc1cncc(COc2cc(O[C@H]3CCc4c(-c5ccccc5F)cccc43)c(Cl)cc2CNC(Cc2cccnc2)C(=O)O)c1] | +++ |

TABLE 3-continued
Structures and Activity
| Compound Number | Compound Structure | ELISA IC$_{50}$ (nM) |
|---|---|---|
| 3.095 | 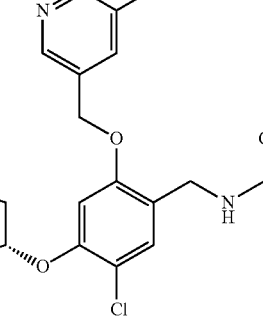 | +++ |
| 3.096 | 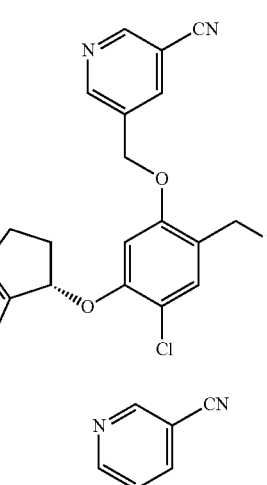 | ++ |
| 3.097 | 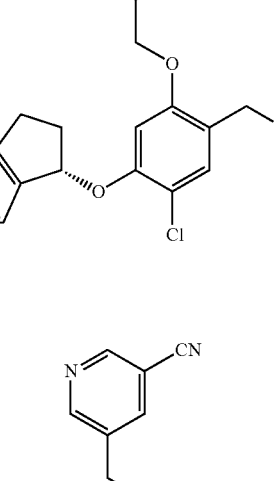 | + |
| 3.098 | 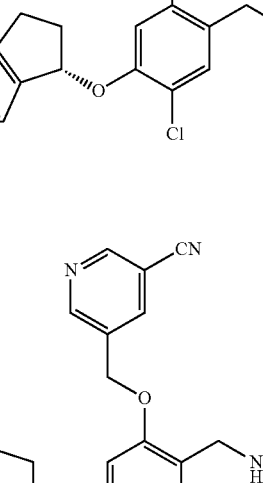 | ++ |

TABLE 3-continued
Structures and Activity
| Compound Number | Compound Structure | ELISA IC$_{50}$ (nM) |
|---|---|---|
| 3.099 | 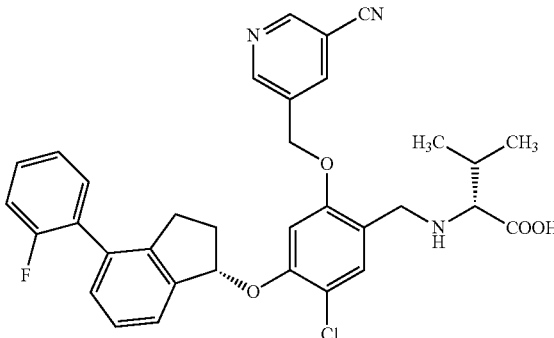 | ++ |
| 3.100 | 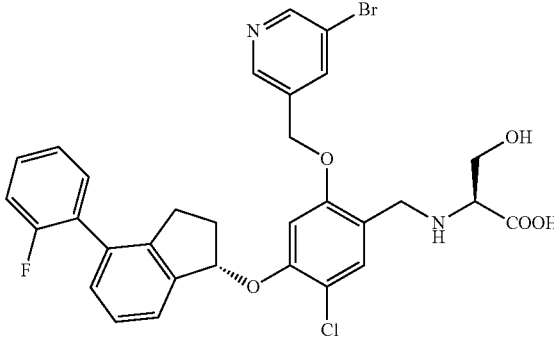 | +++ |
| 3.101 | 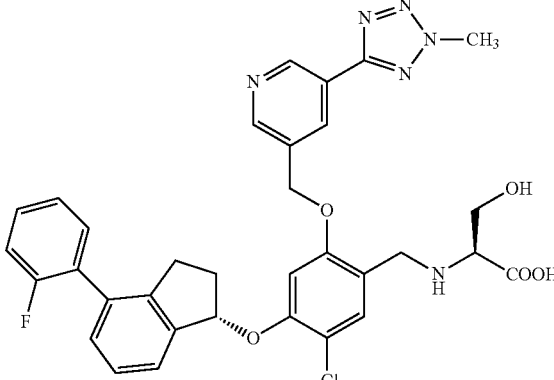 | ++ |
| 3.102 | 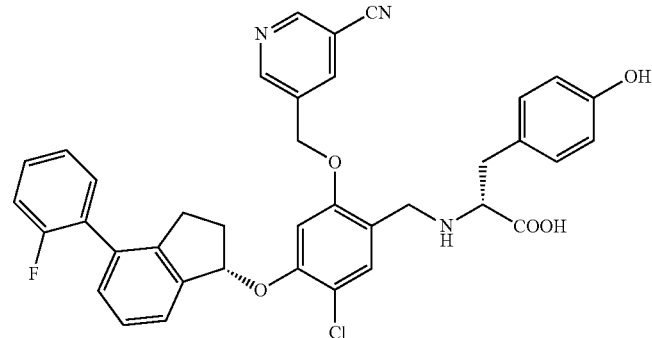 [SMILES: N#Cc1cncc(COc2cc(O[C@H]3CCc4c(-c5ccccc5F)cccc43)c(Cl)cc2CN[C@H](Cc2ccc(O)cc2)C(=O)O)c1] | + |

TABLE 3-continued

Structures and Activity

| Compound Number | Compound Structure | ELISA IC$_{50}$ (nM) |
|---|---|---|
| 3.103 | 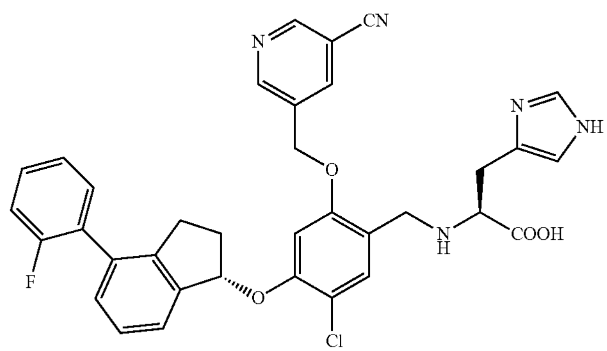 [SMILES: N#Cc1cncc(COc2cc(O[C@H]3CCc4c(-c5ccccc5F)cccc43)c(Cl)cc2CN[C@@H](Cc2c[nH]cn2)C(=O)O)c1] | ++ |
| 3.104 | 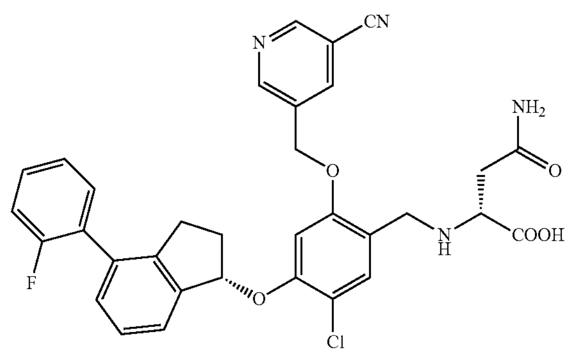 [SMILES: N#Cc1cncc(COc2cc(O[C@H]3CCc4c(-c5ccccc5F)cccc43)c(Cl)cc2CN[C@H](CC(N)=O)C(=O)O)c1] | +++ |
| 3.105 | 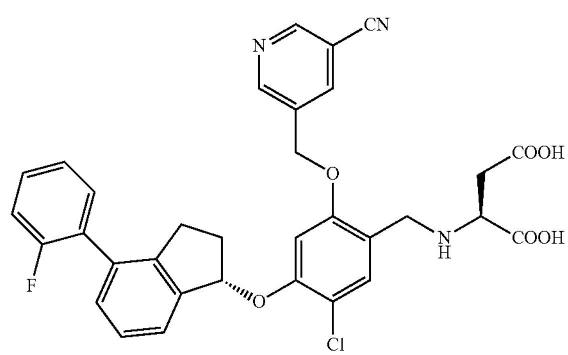 [SMILES: N#Cc1cncc(COc2cc(O[C@H]3CCc4c(-c5ccccc5F)cccc43)c(Cl)cc2CN[C@@H](CC(=O)O)C(=O)O)c1] | ++ |
| 3.106 | 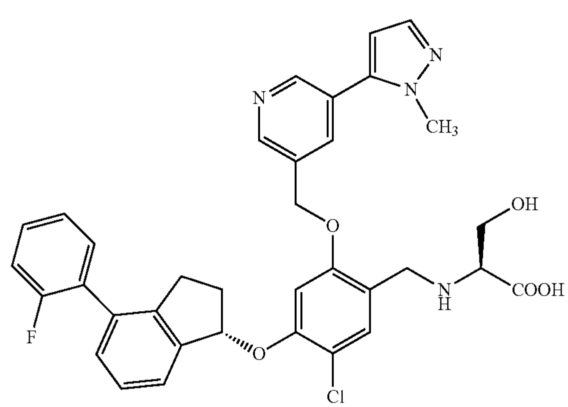 [SMILES: Cn1nccc1-c1cncc(COc2cc(O[C@H]3CCc4c(-c5ccccc5F)cccc43)c(Cl)cc2CN[C@@H](CO)C(=O)O)c1] | ++ |

TABLE 3-continued

Structures and Activity

| Compound Number | Compound Structure | ELISA IC$_{50}$ (nM) |
|---|---|---|
| 3.107 | 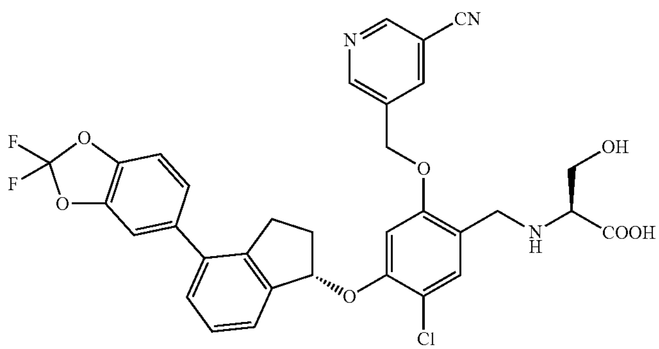 [SMILES: N#Cc1cncc(COc2cc(O[C@H]3CCc4c(-c5ccc6c(c5)OC(F)(F)O6)cccc43)c(Cl)cc2CN[C@@H](CO)C(=O)O)c1] | + |
| 3.108 | 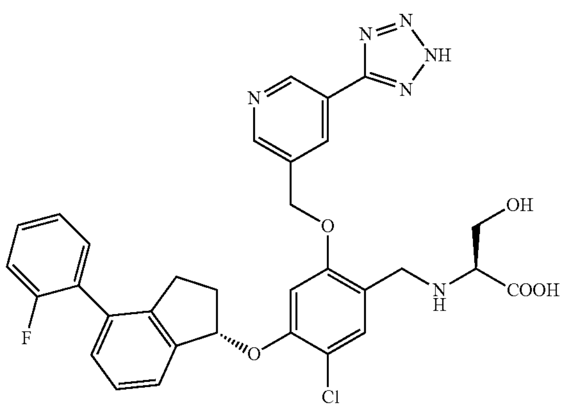 [SMILES: O=C(O)[C@H](CO)NCc1cc(Cl)c(O[C@H]2CCc3c(-c4ccccc4F)cccc32)cc1OCc1cncc(-c2nn[nH]n2)c1] | ++ |
| 3.109 | 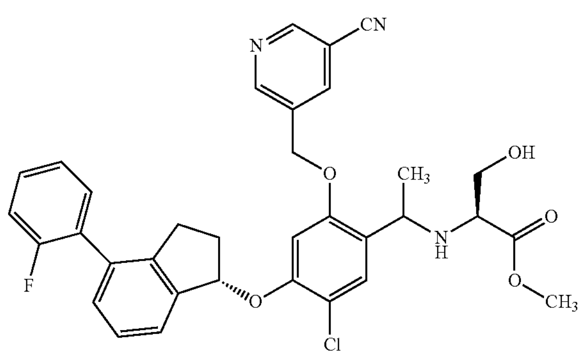 [SMILES: COC(=O)[C@H](CO)NC(C)c1cc(Cl)c(O[C@H]2CCc3c(-c4ccccc4F)cccc32)cc1OCc1cncc(C#N)c1] | + |
| 3.110 | 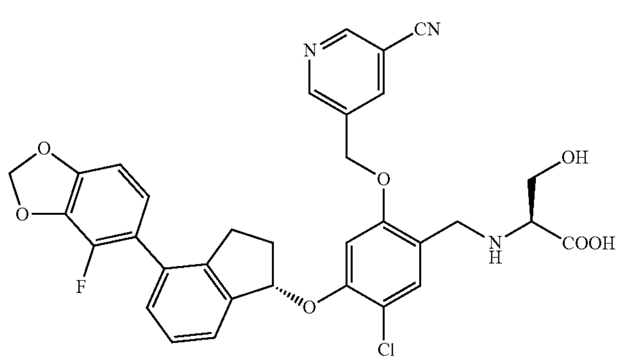 [SMILES: N#Cc1cncc(COc2cc(O[C@H]3CCc4c(-c5ccc6c(c5F)OCO6)cccc43)c(Cl)cc2CN[C@@H](CO)C(=O)O)c1] | +++ |

TABLE 3-continued

Structures and Activity

| Compound Number | Compound Structure | ELISA IC$_{50}$ (nM) |
|---|---|---|
| 3.111 | | + |
| 3.112 | | ++ |
| 3.113 | | + |
| 3.114 | | + |

TABLE 3-continued

Structures and Activity

| Compound Number | Compound Structure | ELISA IC$_{50}$ (nM) |
|---|---|---|
| 3.115 | 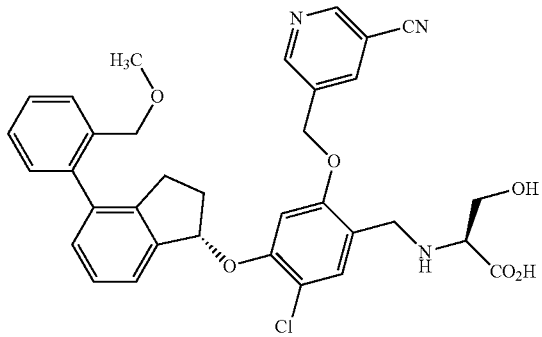 [SMILES: COCc1ccccc1-c1cccc2c1CC[C@@H]2Oc1cc(OCc2cncc(C#N)c2)c(CN[C@@H](CO)C(=O)O)cc1Cl] | + |
| 3.116 | 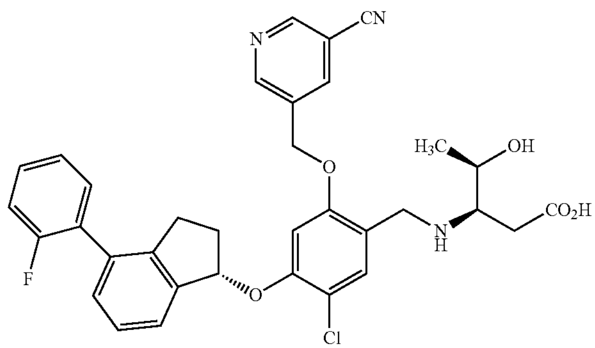 [SMILES: C[C@@H](O)[C@@H](CC(=O)O)NCc1cc(Cl)c(O[C@H]2CCc3c(-c4ccccc4F)cccc32)cc1OCc1cncc(C#N)c1] | + |
| 3.117 | 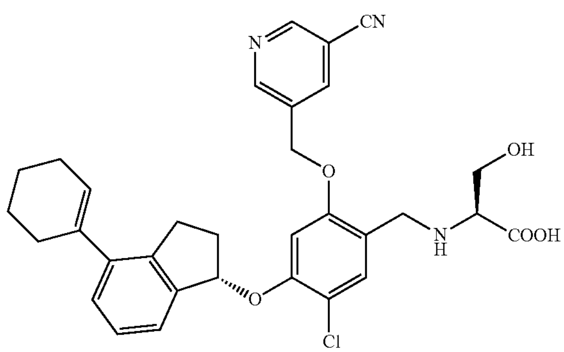 [SMILES: N#Cc1cncc(COc2cc(O[C@H]3CCc4c(C5=CCCCC5)cccc43)c(Cl)cc2CN[C@@H](CO)C(=O)O)c1] | +++ |
| 3.118 | 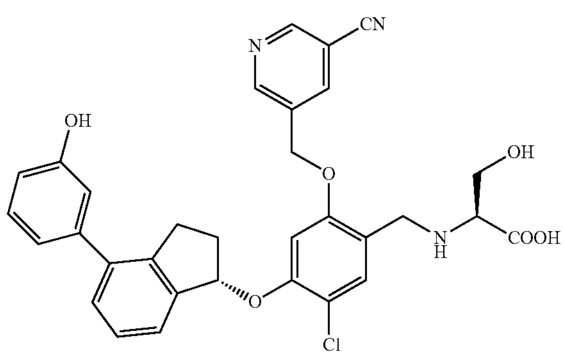 [SMILES: N#Cc1cncc(COc2cc(O[C@H]3CCc4c(-c5cccc(O)c5)cccc43)c(Cl)cc2CN[C@@H](CO)C(=O)O)c1] | +++ |

TABLE 3-continued
Structures and Activity
| Compound Number | Compound Structure | ELISA IC$_{50}$ (nM) |
|---|---|---|
| 3.119 | 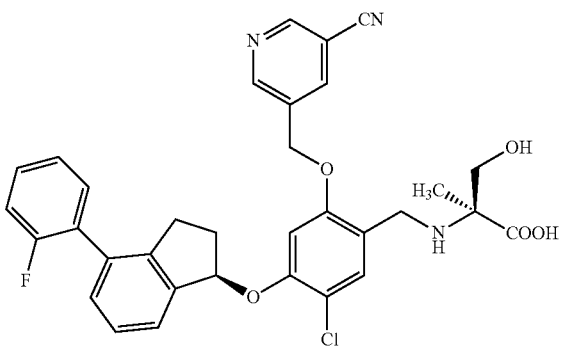 [SMILES: C[C@@](CO)(NCc1cc(Cl)c(O[C@@H]2CCc3c(-c4ccccc4F)cccc32)cc1OCc1cncc(C#N)c1)C(=O)O] | +++ |
| 3.120 | 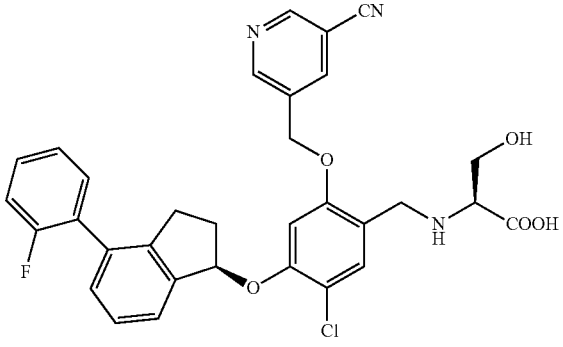 [SMILES: N#Cc1cncc(COc2cc(O[C@@H]3CCc4c(-c5ccccc5F)cccc43)c(Cl)cc2CN[C@@H](CO)C(=O)O)c1] | +++ |
| 3.121 | 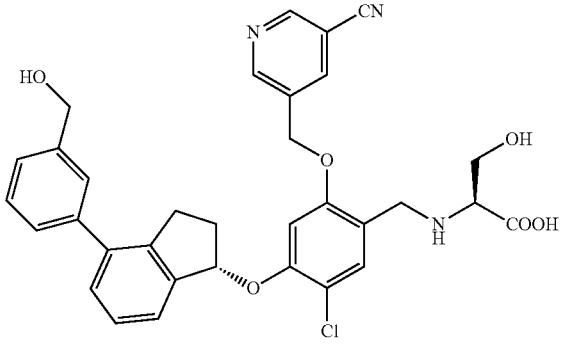 [SMILES: N#Cc1cncc(COc2cc(O[C@H]3CCc4c(-c5cccc(CO)c5)cccc43)c(Cl)cc2CN[C@@H](CO)C(=O)O)c1] | + |
| 3.122 | 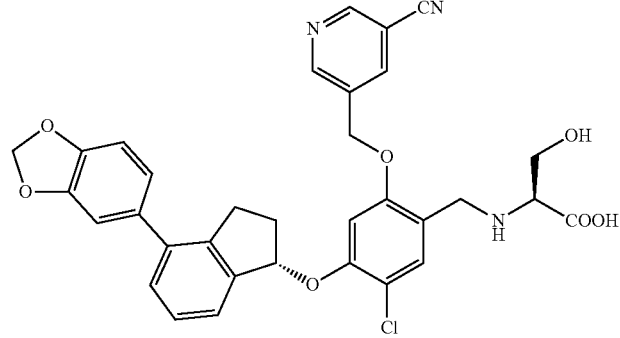 [SMILES: N#Cc1cncc(COc2cc(O[C@H]3CCc4c(-c5ccc6c(c5)OCO6)cccc43)c(Cl)cc2CN[C@@H](CO)C(=O)O)c1] | +++ |

TABLE 3-continued

Structures and Activity

| Compound Number | Compound Structure | ELISA IC$_{50}$ (nM) |
|---|---|---|
| 3.123 | 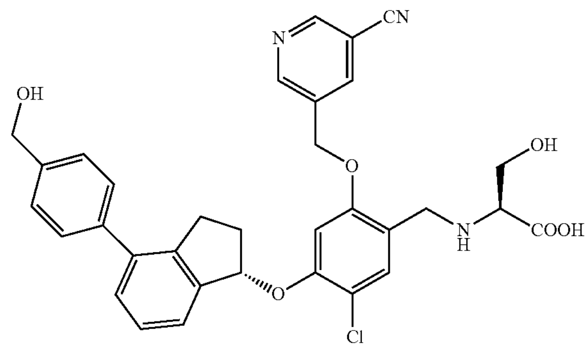 [SMILES: N#Cc1cncc(COc2cc(O[C@H]3CCc4c(-c5ccc(CO)cc5)cccc43)c(Cl)cc2CN[C@@H](CO)C(=O)O)c1] | + |
| 3.124 | 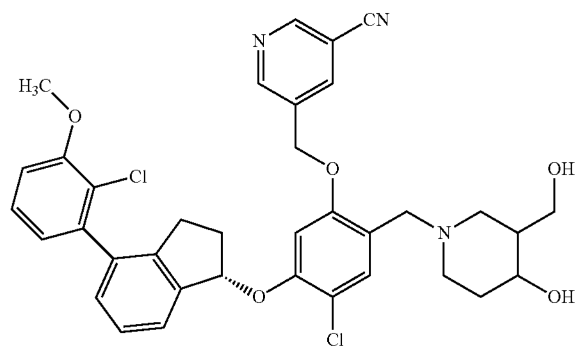 [SMILES: COc1cccc(-c2cccc3c2CC[C@@H]3Oc2cc(OCc3cncc(C#N)c3)c(CN3CCC(O)C(CO)C3)cc2Cl)c1Cl] | ++ |
| 3.125 | 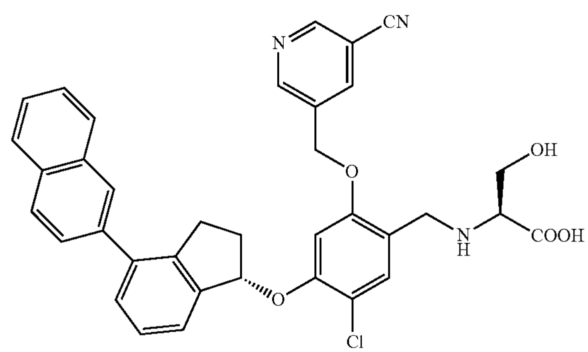 [SMILES: N#Cc1cncc(COc2cc(O[C@H]3CCc4c(-c5ccc6ccccc6c5)cccc43)c(Cl)cc2CN[C@@H](CO)C(=O)O)c1] | + |
| 3.126 | 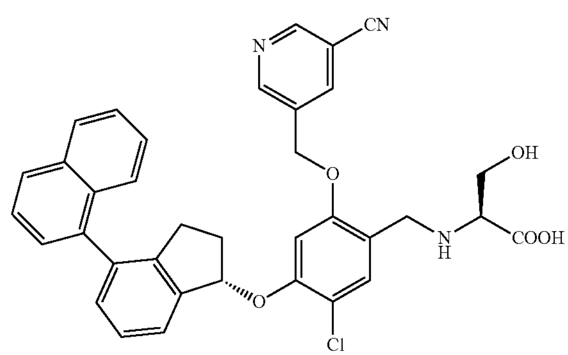 [SMILES: N#Cc1cncc(COc2cc(O[C@H]3CCc4c(-c5cccc6ccccc56)cccc43)c(Cl)cc2CN[C@@H](CO)C(=O)O)c1] | ++ |

TABLE 3-continued

Structures and Activity

| Compound Number | Compound Structure | ELISA IC$_{50}$ (nM) |
|---|---|---|
| 3.127 | 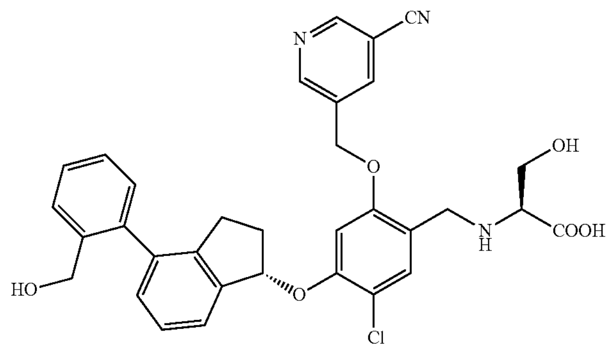 [SMILES: N#Cc1cncc(COc2cc(O[C@H]3CCc4c(-c5ccccc5CO)cccc43)c(Cl)cc2CN[C@@H](CO)C(=O)O)c1] | +++ |
| 3.128 | 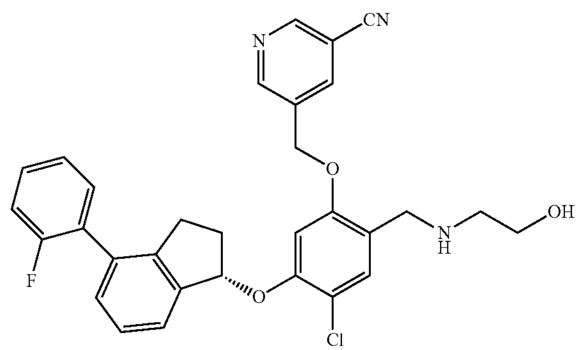 [SMILES: N#Cc1cncc(COc2cc(O[C@H]3CCc4c(-c5ccccc5F)cccc43)c(Cl)cc2CNCCO)c1] | +++ |
| 3.129 | 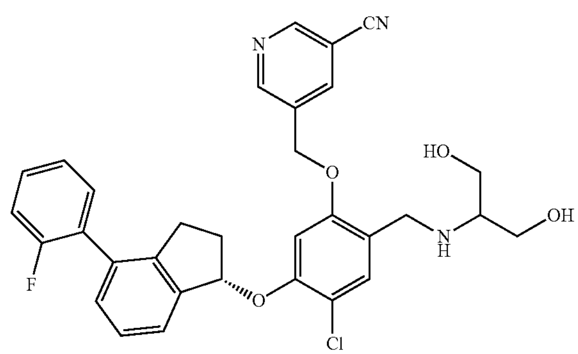 [SMILES: N#Cc1cncc(COc2cc(O[C@H]3CCc4c(-c5ccccc5F)cccc43)c(Cl)cc2CNC(CO)CO)c1] | +++ |
| 3.130 | 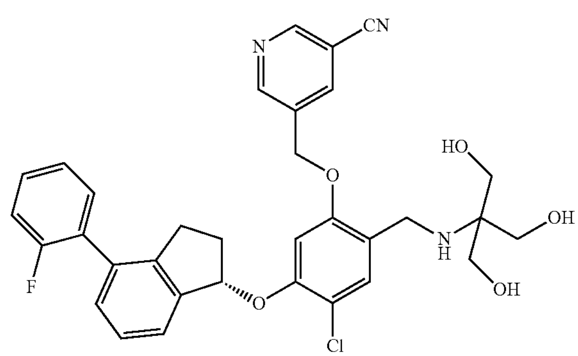 [SMILES: N#Cc1cncc(COc2cc(O[C@H]3CCc4c(-c5ccccc5F)cccc43)c(Cl)cc2CNC(CO)(CO)CO)c1] | +++ |

TABLE 3-continued

Structures and Activity

| Compound Number | Compound Structure | ELISA IC$_{50}$ (nM) |
|---|---|---|
| 3.131 | 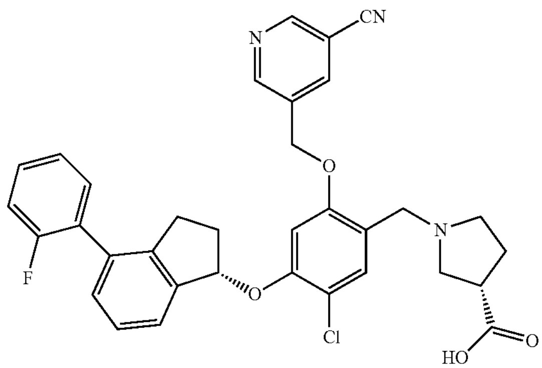 [SMILES: N#Cc1cncc(COc2cc(O[C@H]3CCc4c(-c5ccccc5F)cccc43)c(Cl)cc2CN2CC[C@H](C(=O)O)C2)c1] | +++ |
| 3.132 | 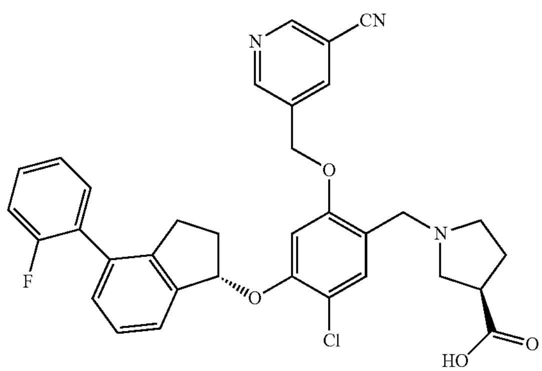 [SMILES: N#Cc1cncc(COc2cc(O[C@H]3CCc4c(-c5ccccc5F)cccc43)c(Cl)cc2CN2CC[C@@H](C(=O)O)C2)c1] | +++ |
| 3.133 | 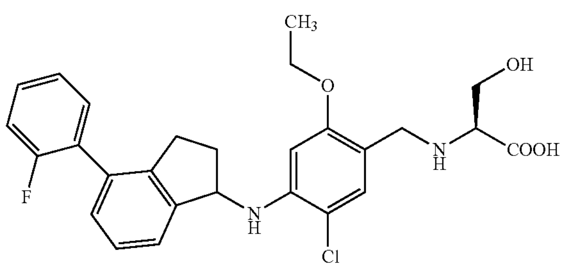 [SMILES: CCOc1cc(NC2CCc3c(-c4ccccc4F)cccc32)c(Cl)cc1CN[C@@H](CO)C(=O)O] | ++ |
| 3.134 | 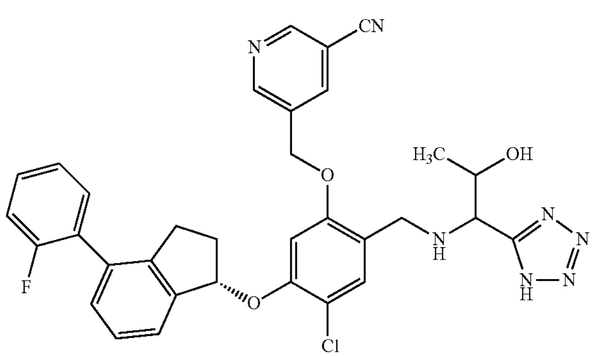 [SMILES: CC(O)C(NCc1cc(Cl)c(O[C@H]2CCc3c(-c4ccccc4F)cccc32)cc1OCc1cncc(C#N)c1)c1nnn[nH]1] | +++ |

TABLE 3-continued

Structures and Activity

| Compound Number | Compound Structure | ELISA IC$_{50}$ (nM) |
|---|---|---|
| 3.135 | 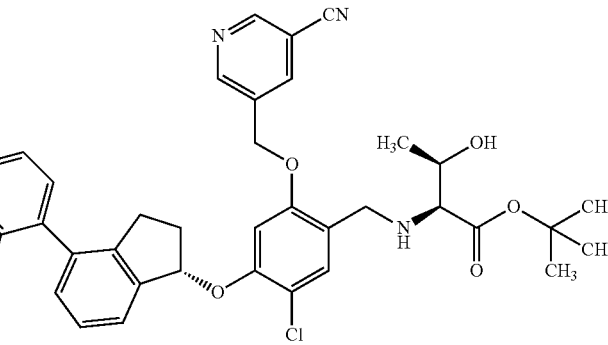 | + |
| 3.136 | 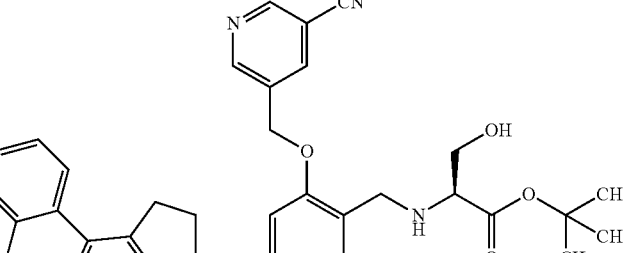 | + |

What is claimed is:

1. A method of inhibiting growth, proliferation, or metastasis of cancer cells in a subject in need thereof, wherein the cancer cells are selected from the group consisting of colorectal cancer, mesothelioma; breast cancer, colorectal cancer, carcinoma of the endometrium, cancer of the esophagus, small cell lung cancer, renal cell carcinoma, Merkel cell carcinoma, hepatocellular carcinoma, primary mediastinal large B cell lymphoma; carcinoma of the cervix, gastric cancer, cancer of the bladder, classical Hodgkin's lymphoma, head and neck squamous cell carcinoma, and non-small cell lung cancer, comprising administering to the subject a therapeutically effective amount of a compound selected from the group consisting of

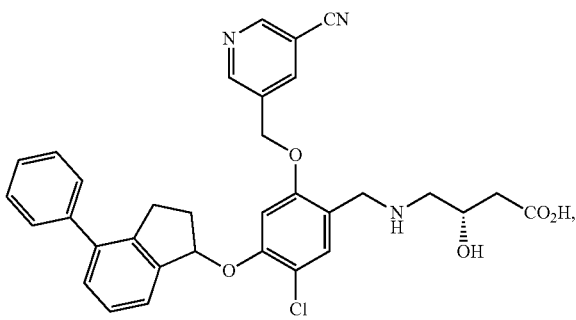

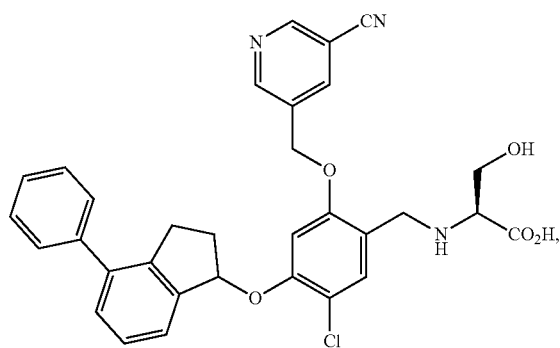

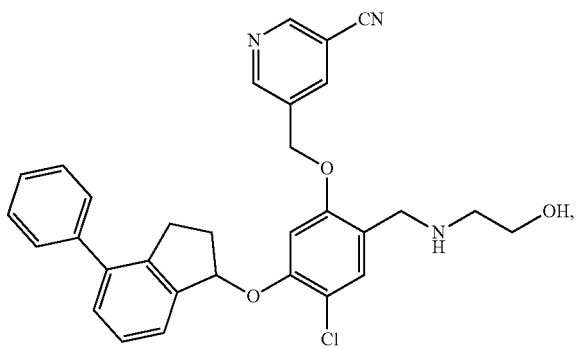

397 -continued
398 -continued
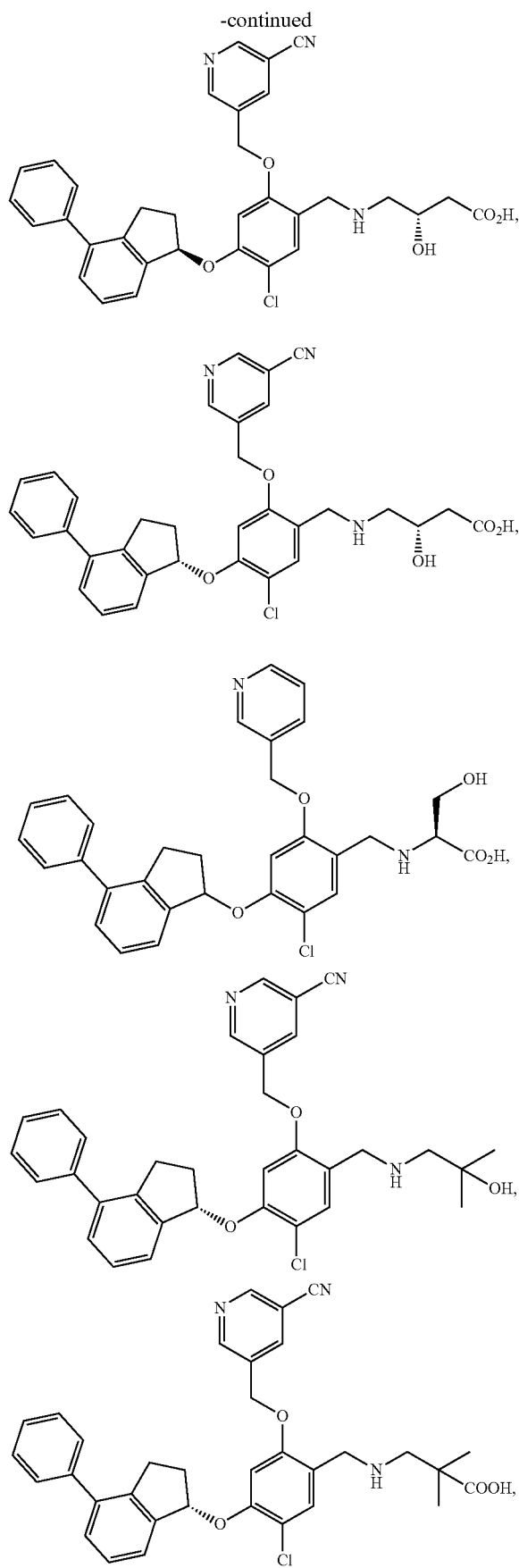
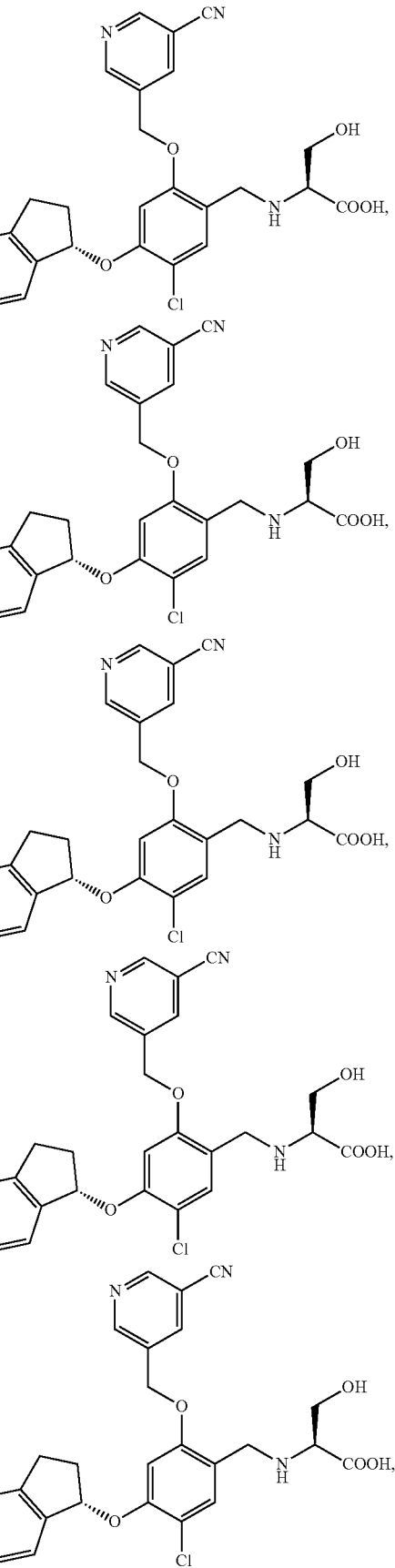

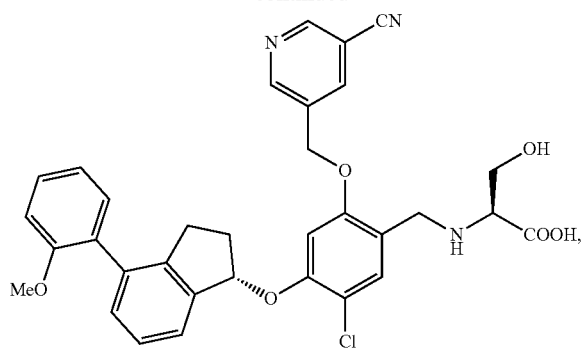
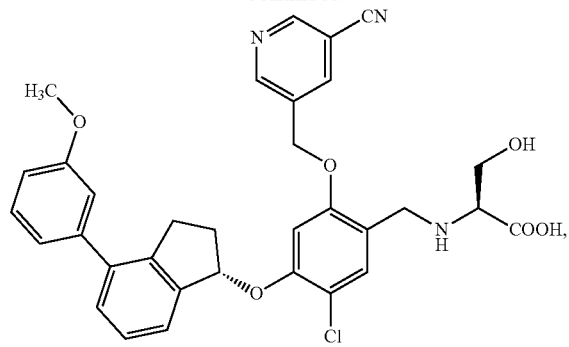
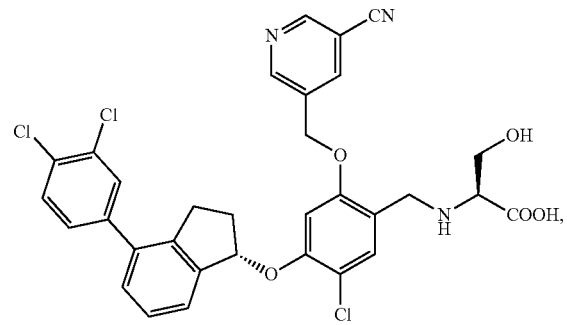
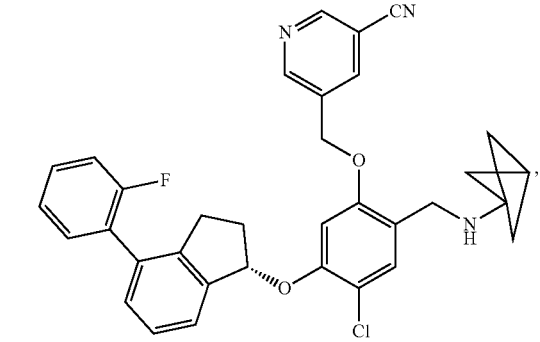
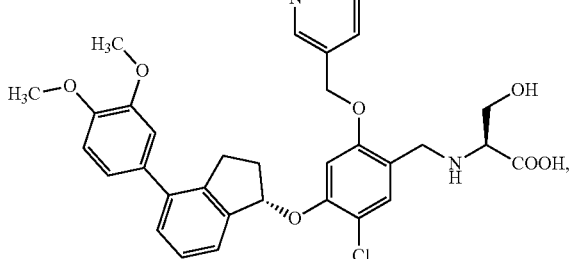
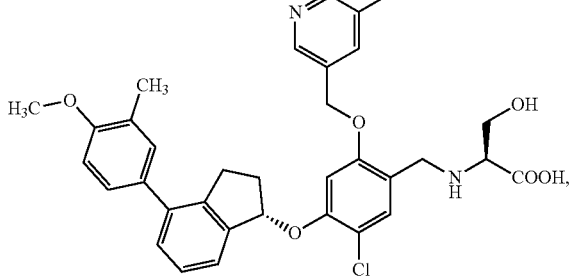

401
-continued
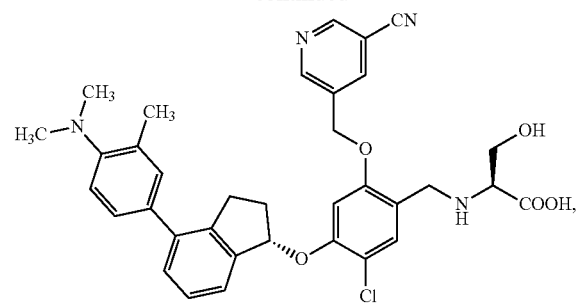
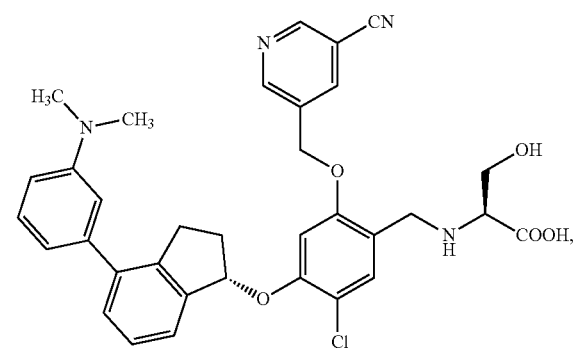
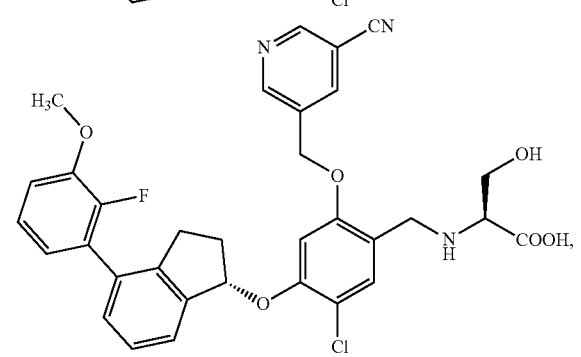
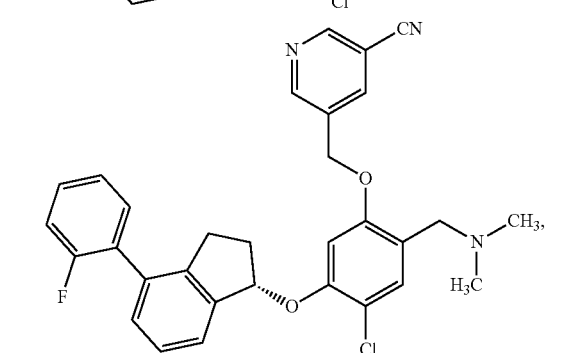
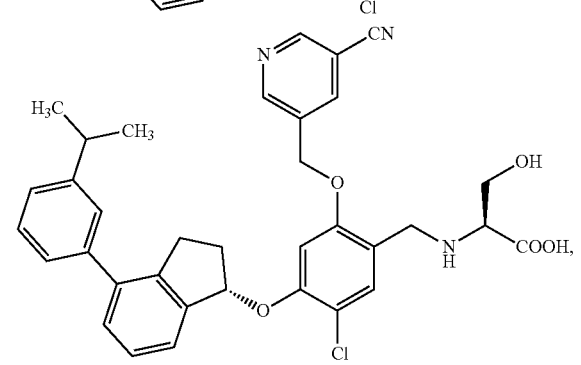
402
-continued
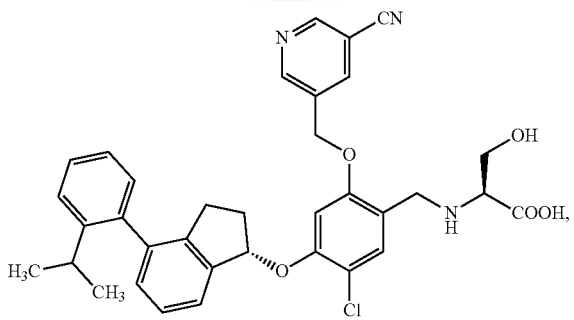
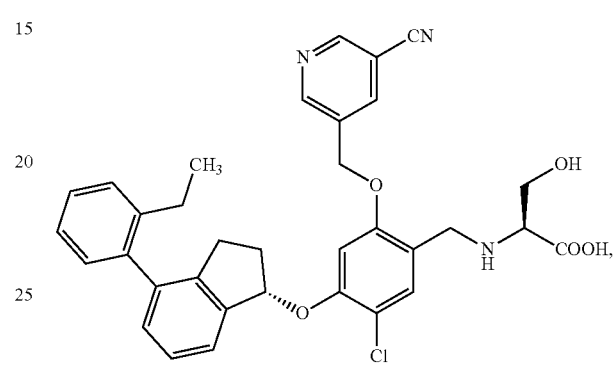
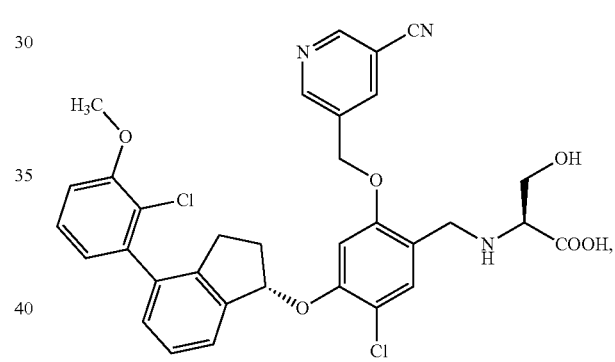
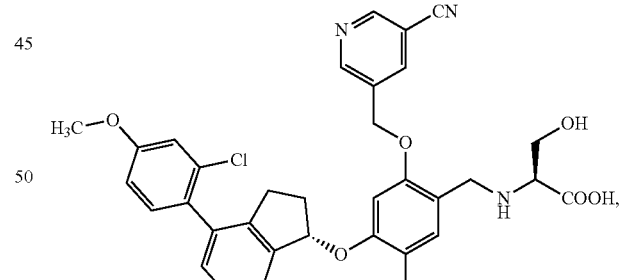
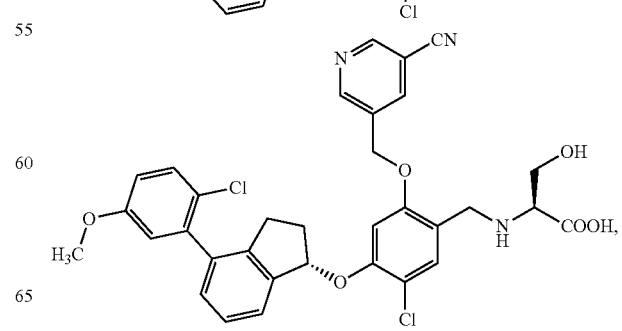

403
-continued
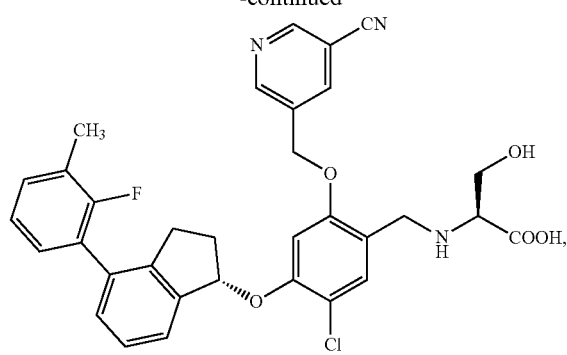
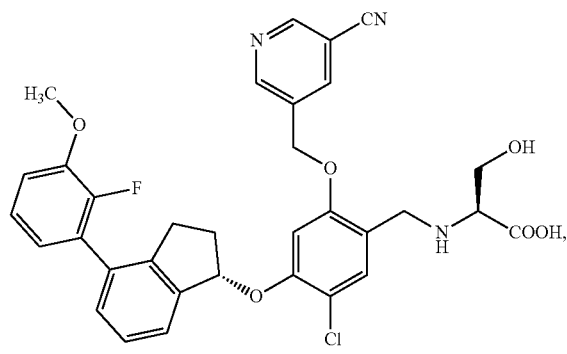
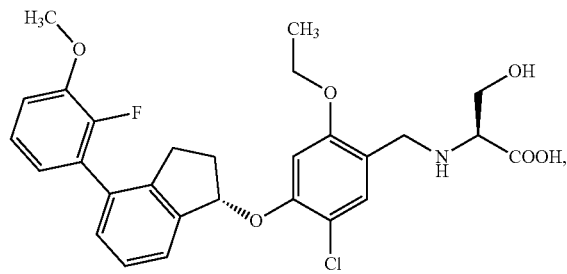
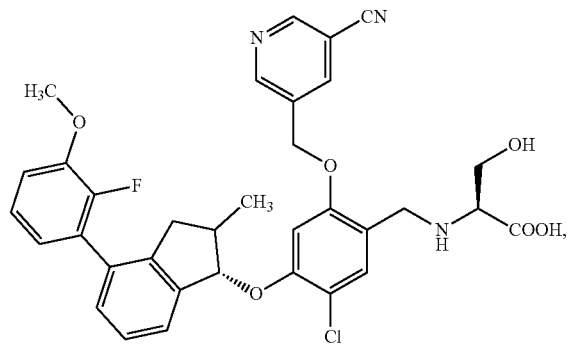
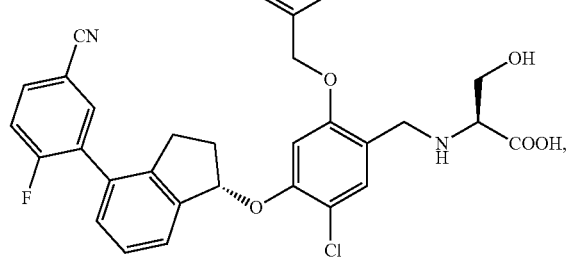
404
-continued
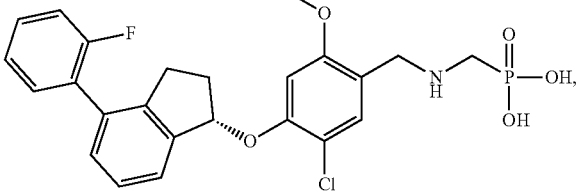
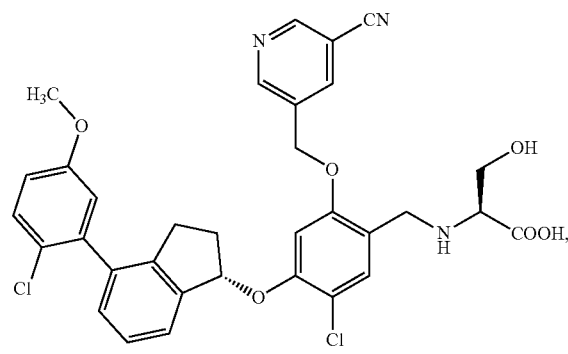
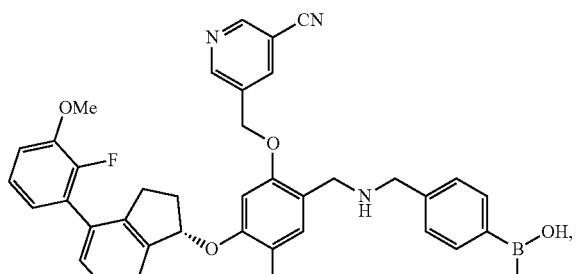
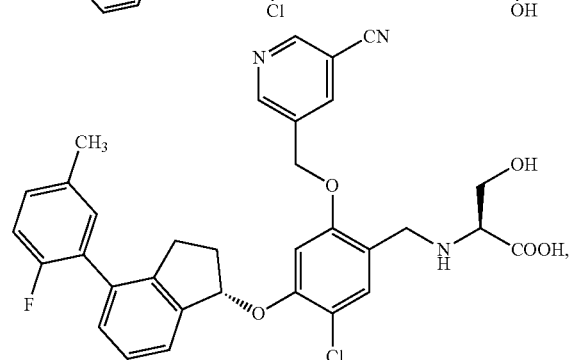

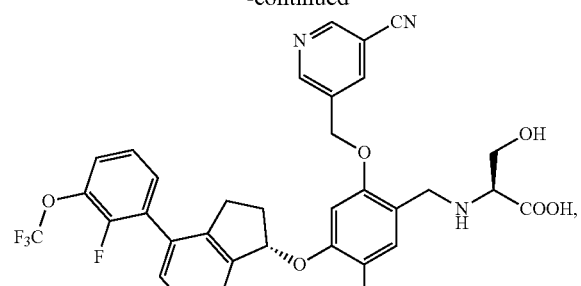
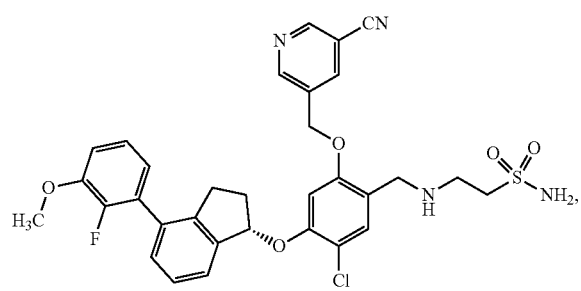
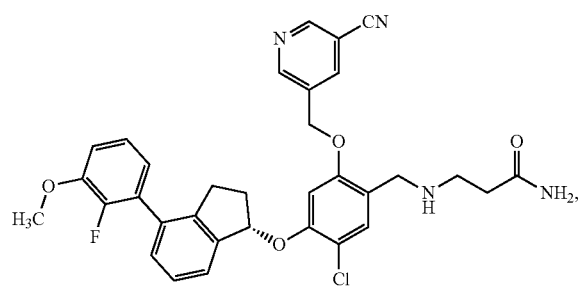
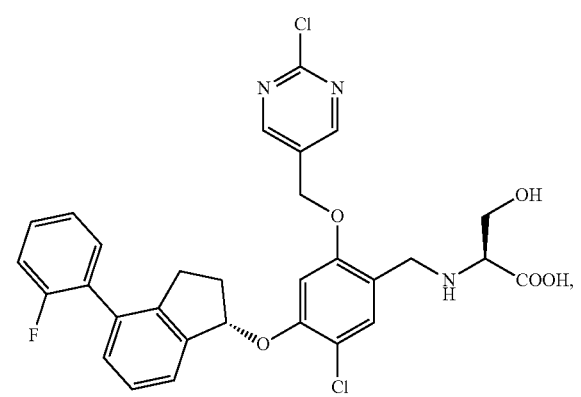
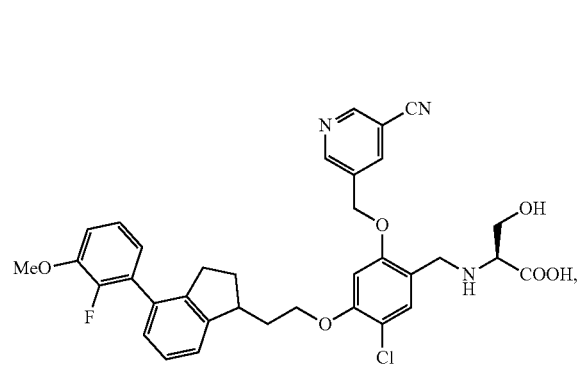
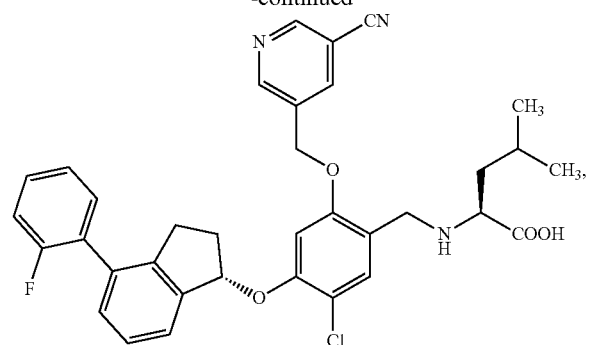
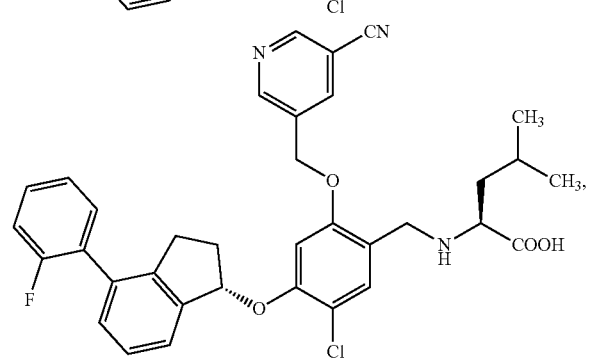
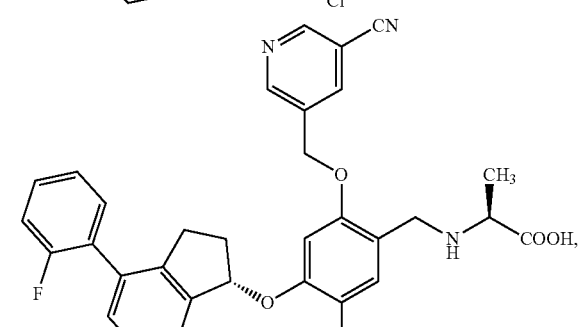
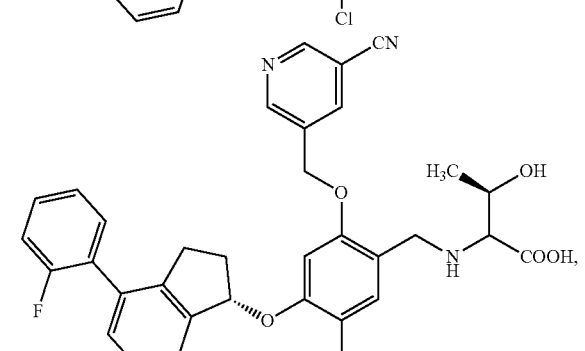
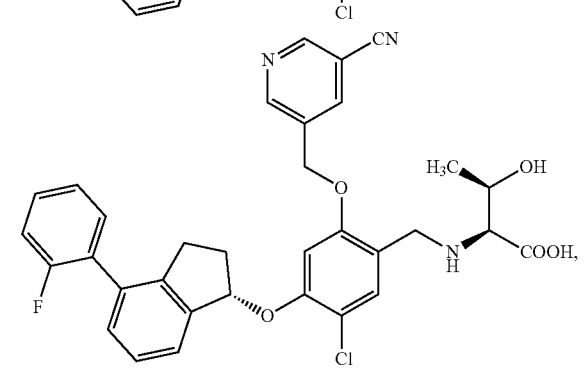

407
-continued
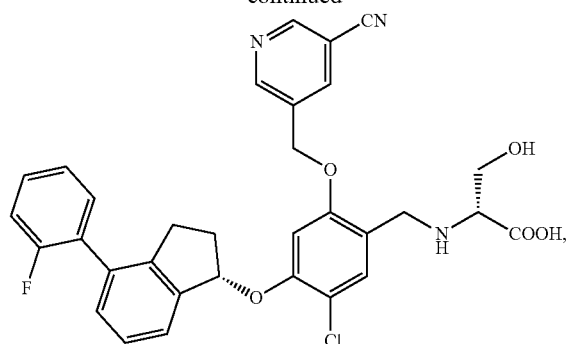
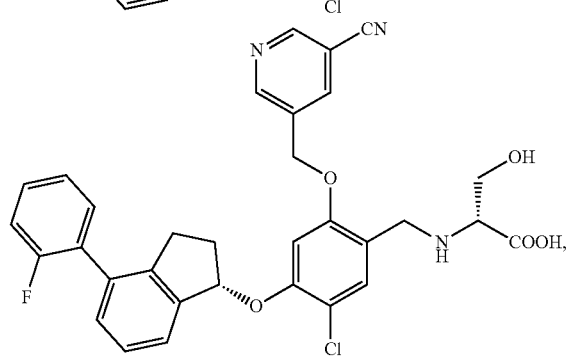
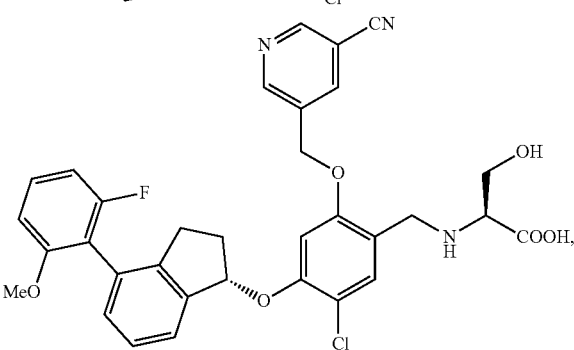
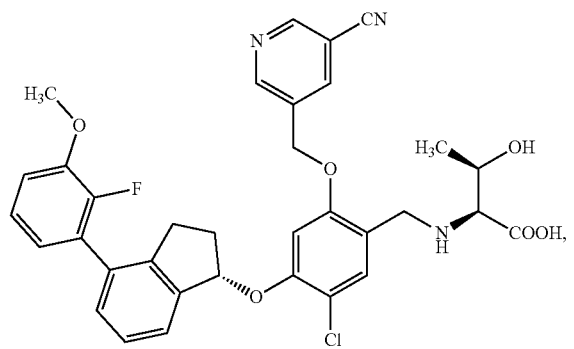
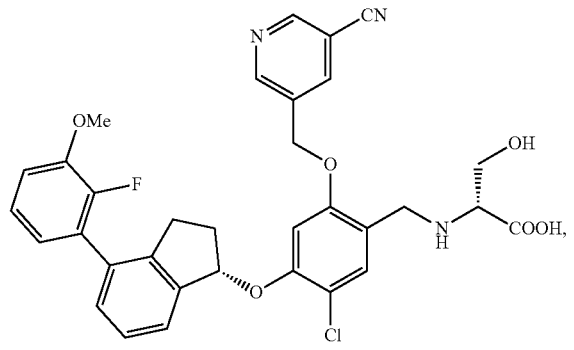
408
-continued
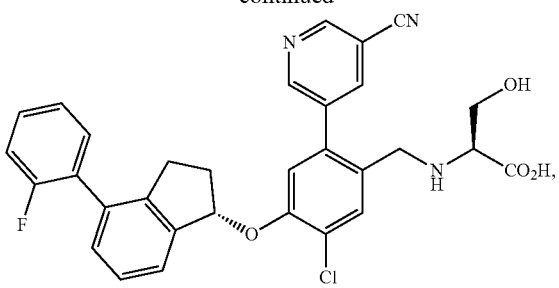
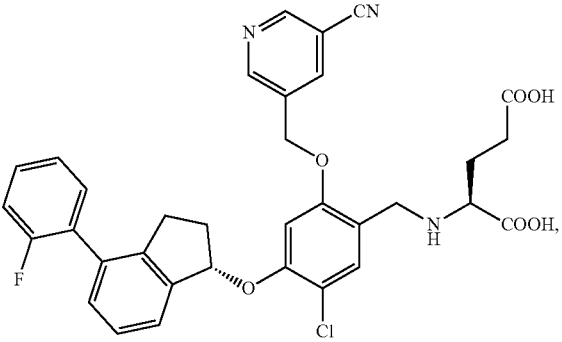
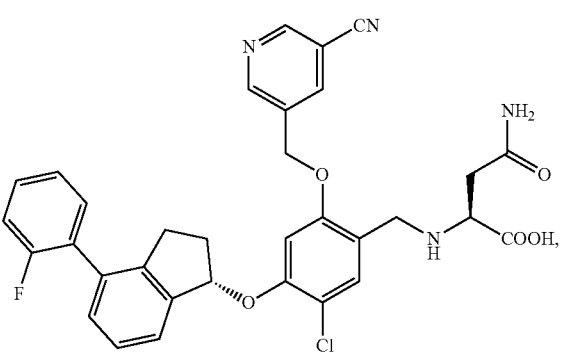
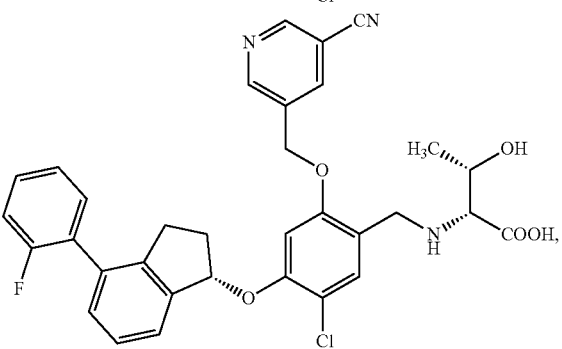
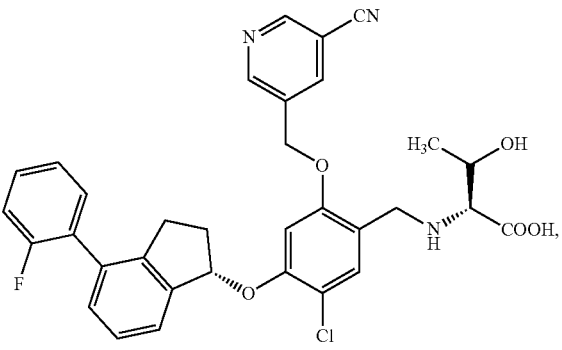

409
-continued
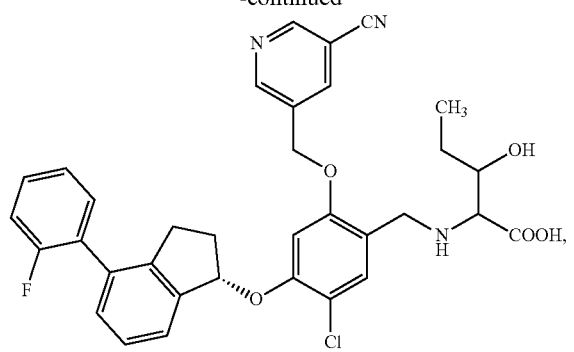
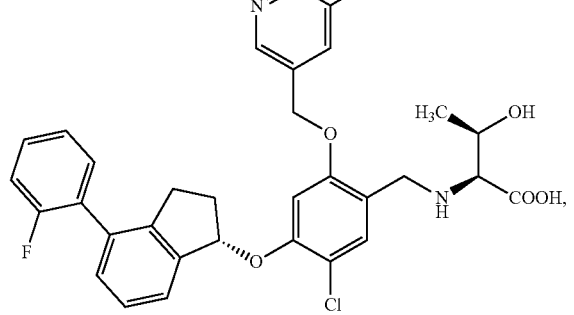
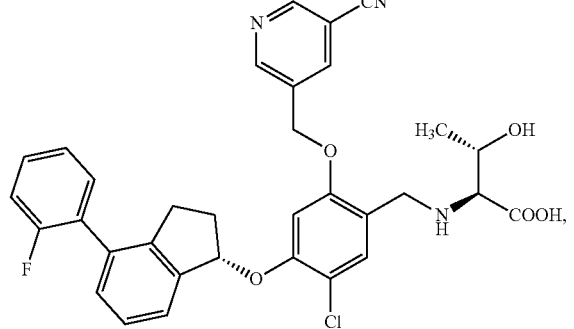
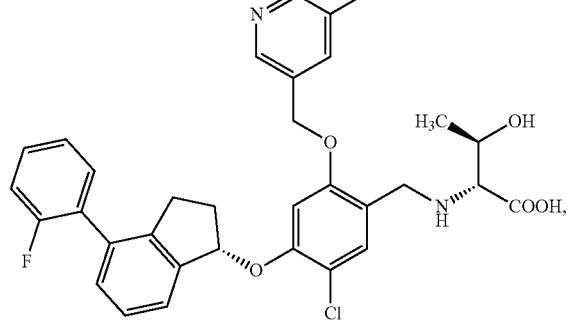
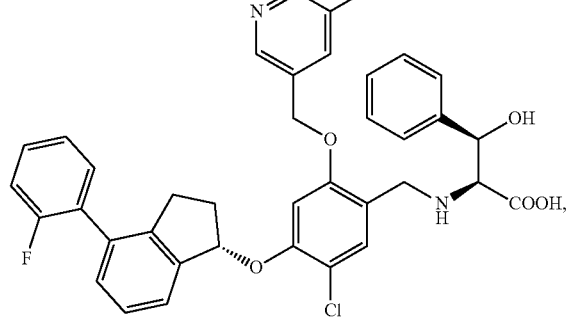
410
-continued
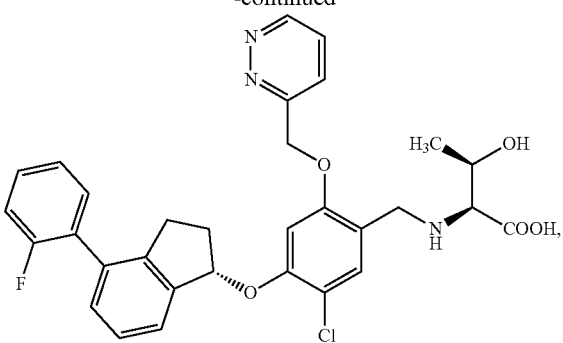
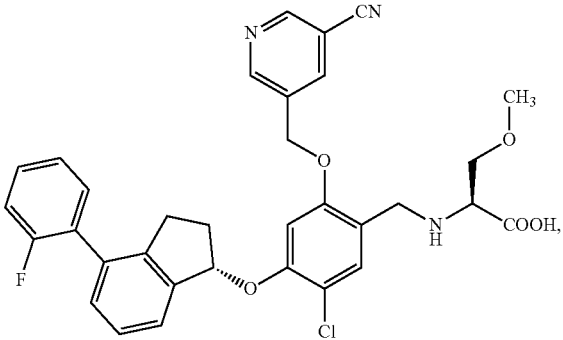
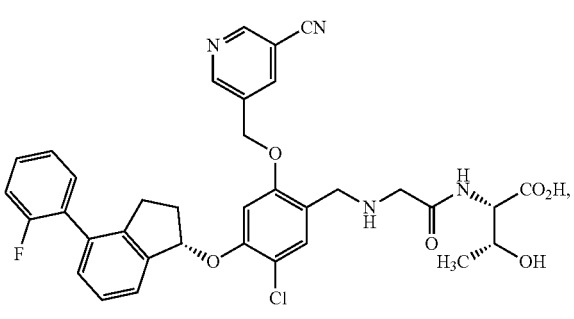
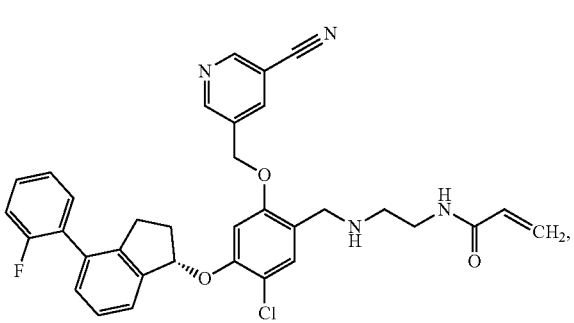
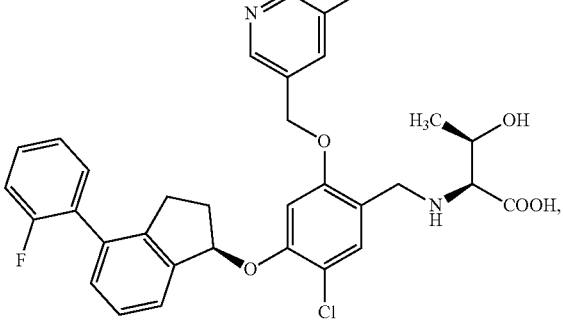

411
-continued
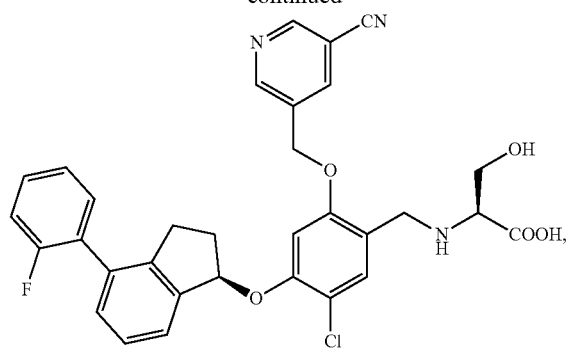
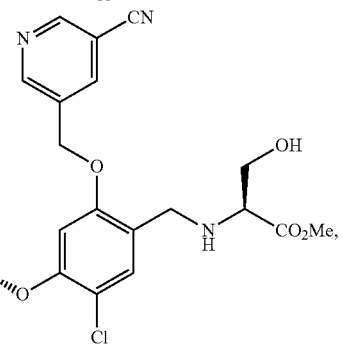
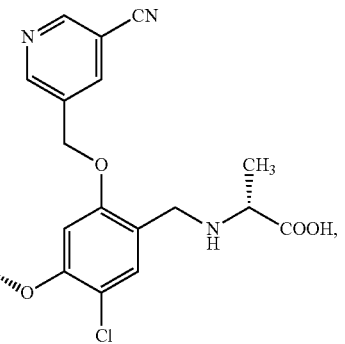
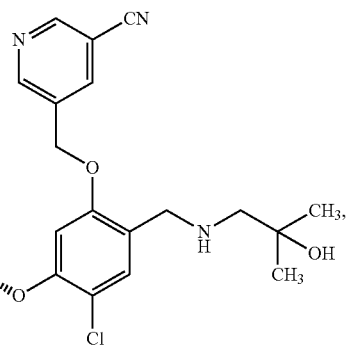
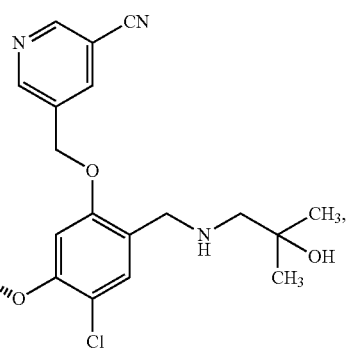
412
-continued
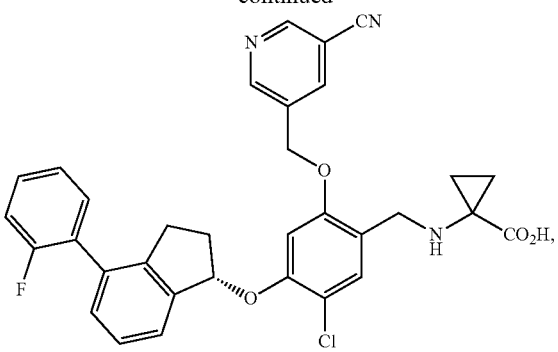
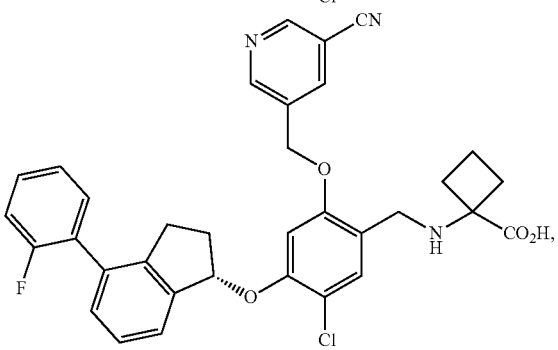
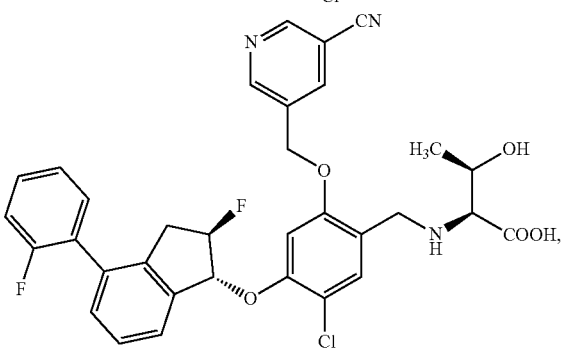
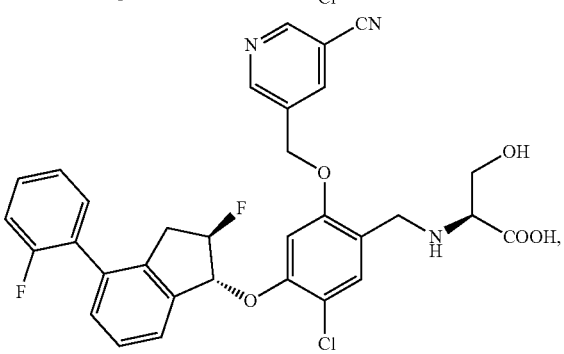
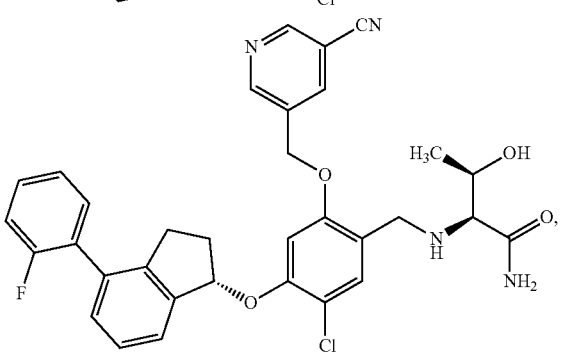

413
-continued
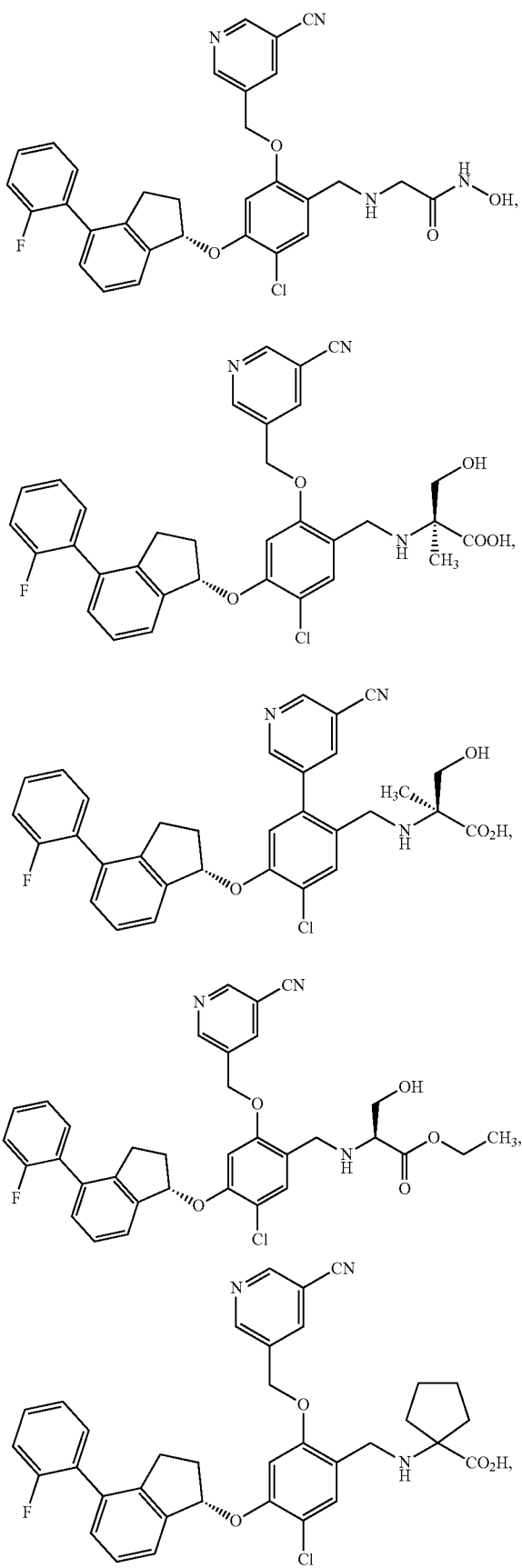
414
-continued
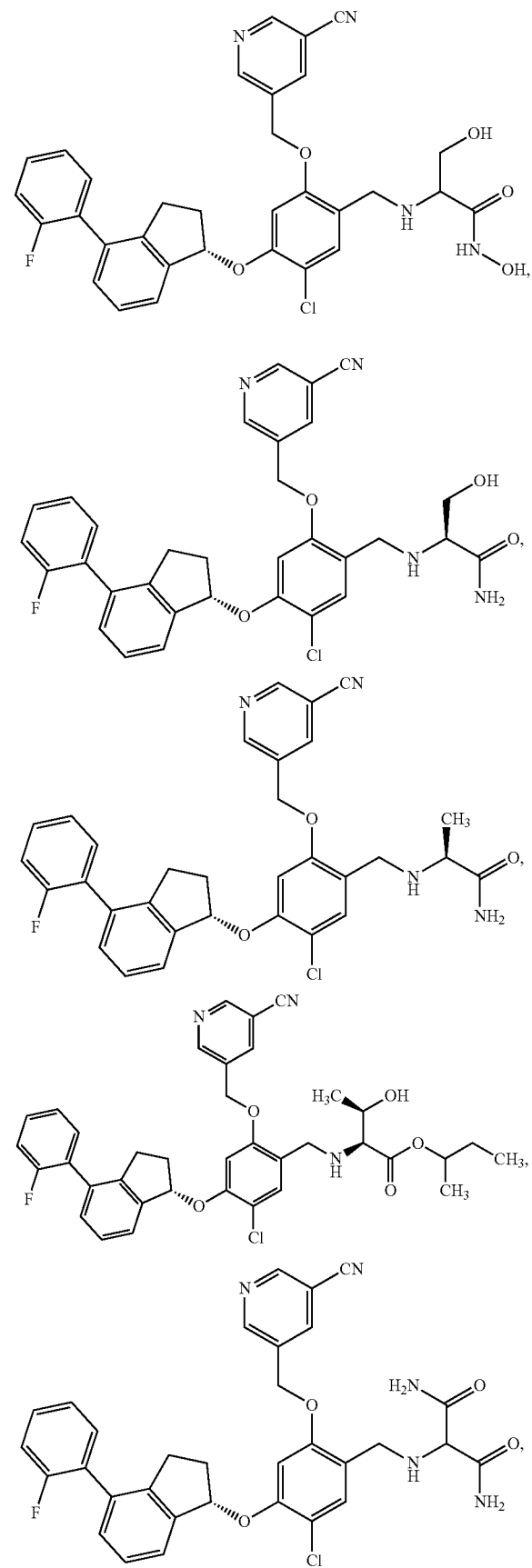

415
-continued
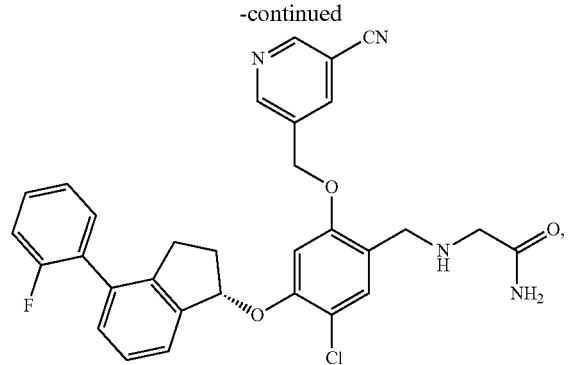
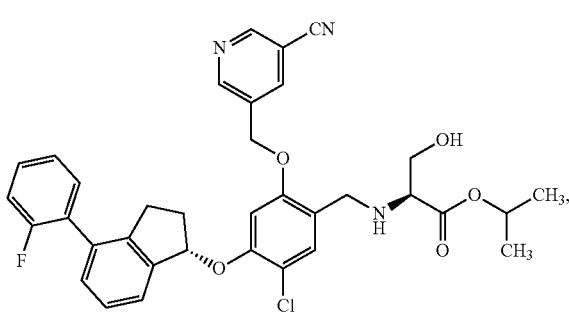
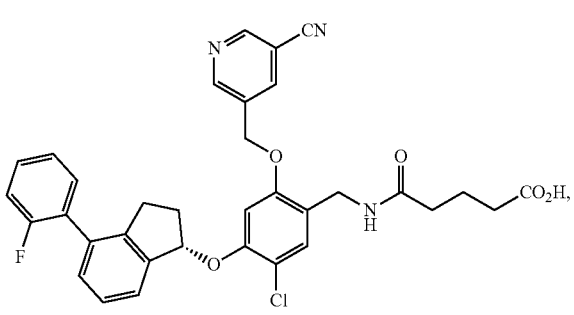
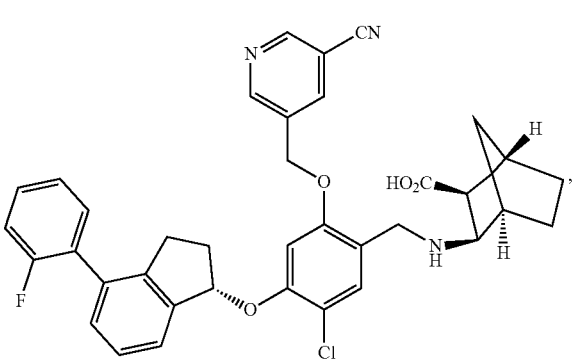
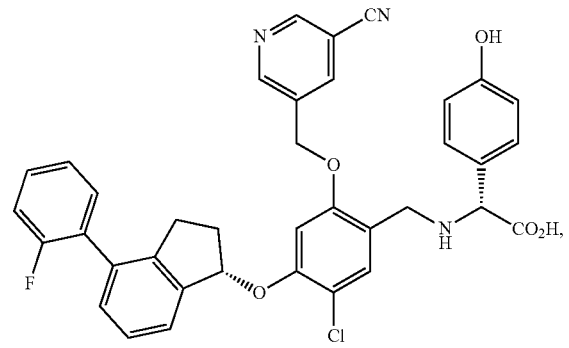
416
-continued
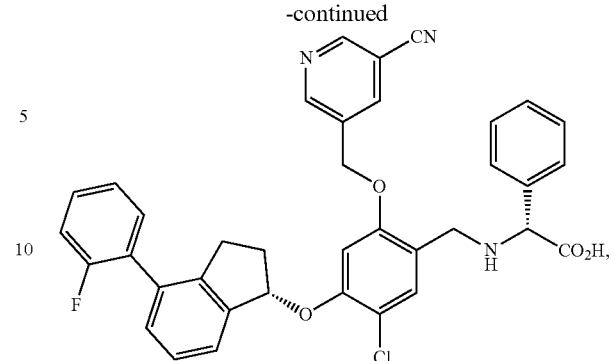
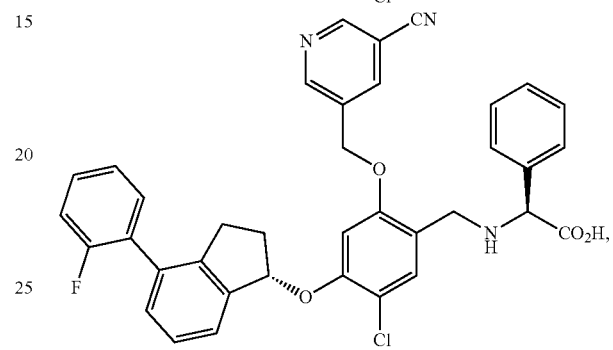
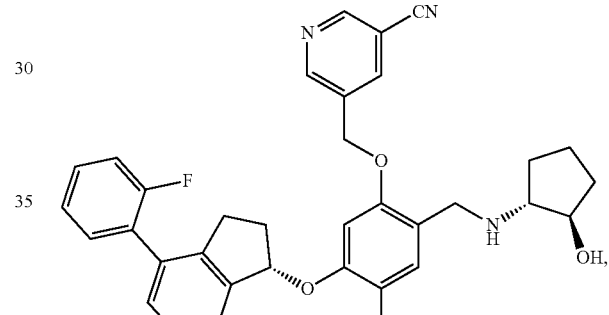
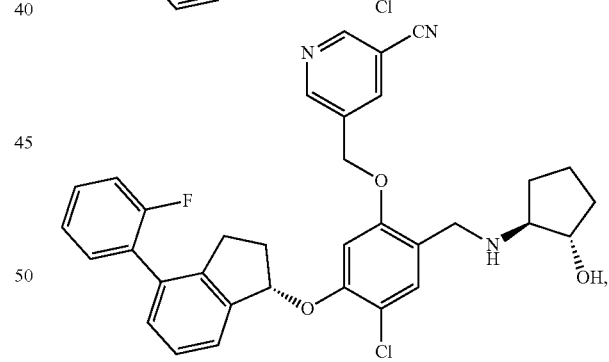
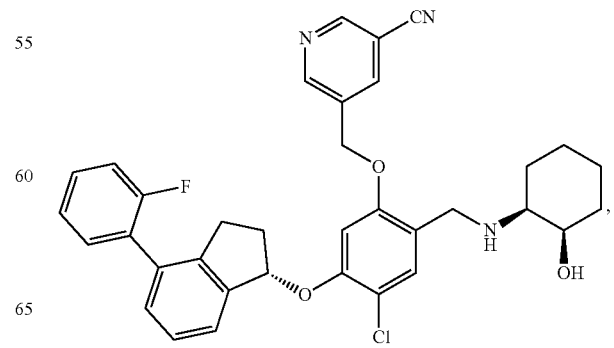

417
-continued
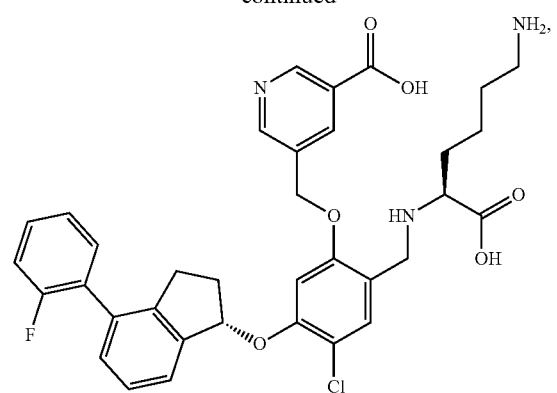
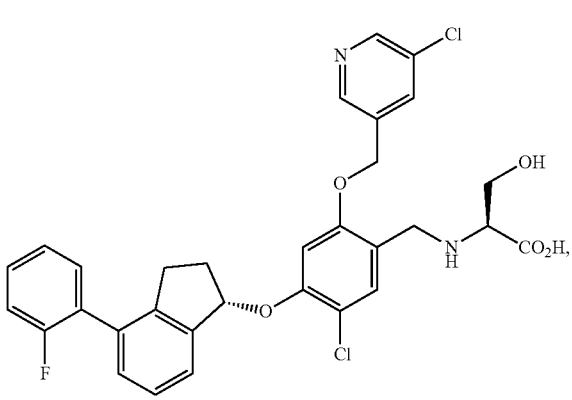
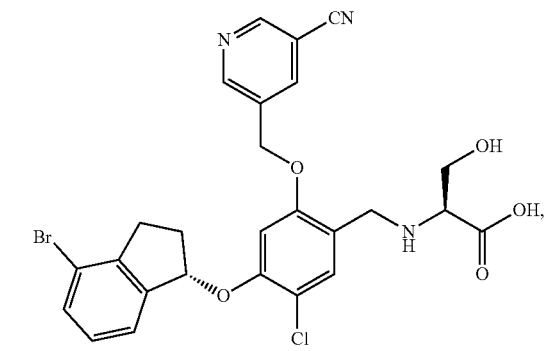
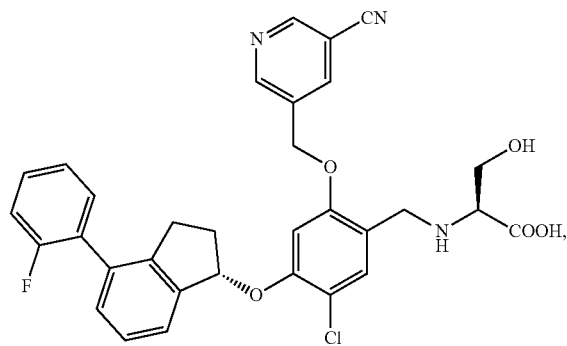
418
-continued
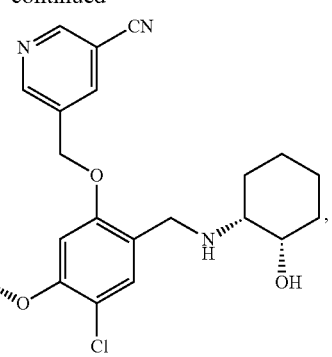
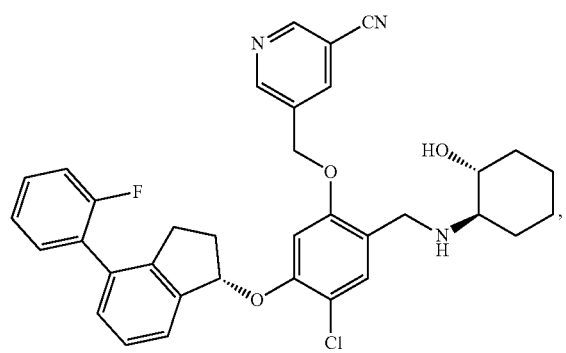
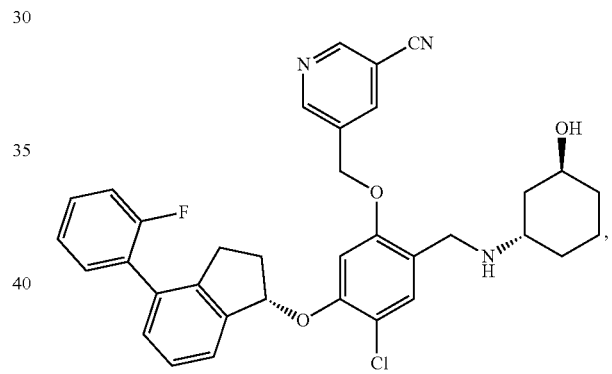
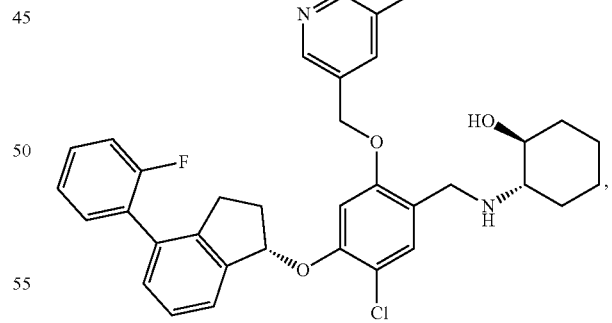
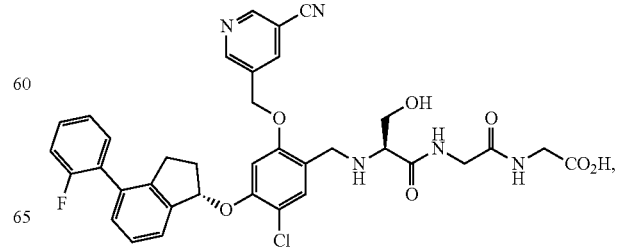

419
-continued
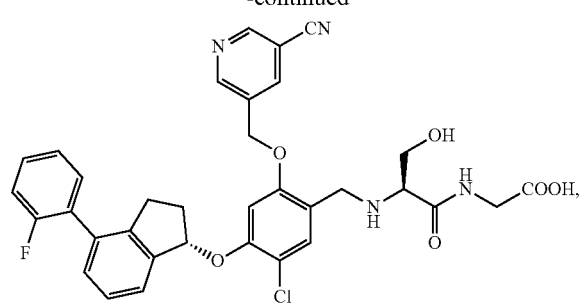
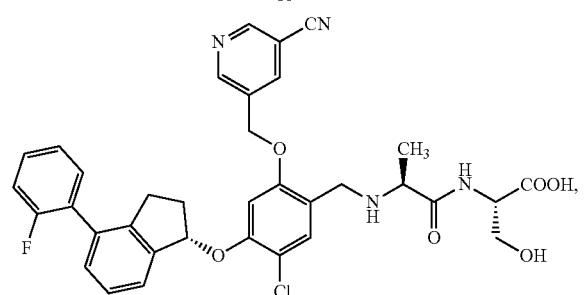
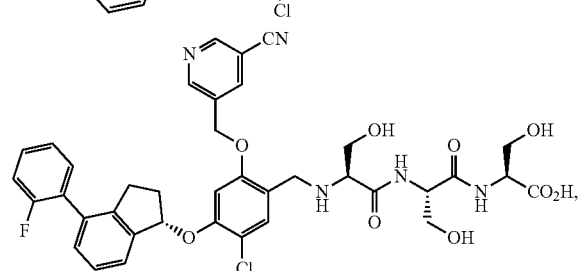
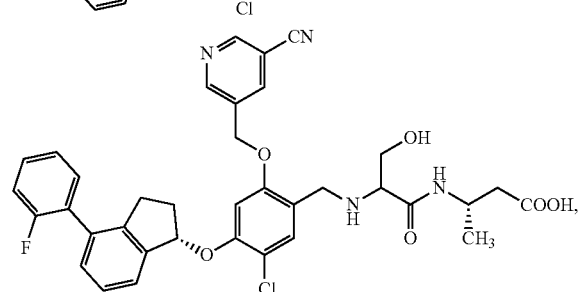
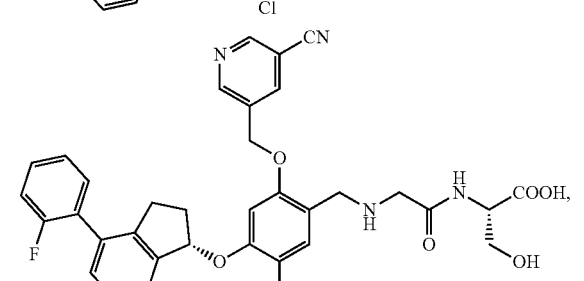
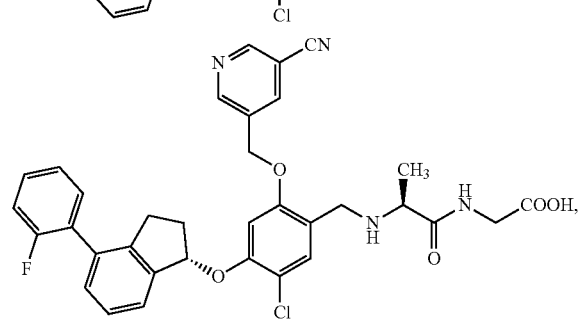
420
-continued
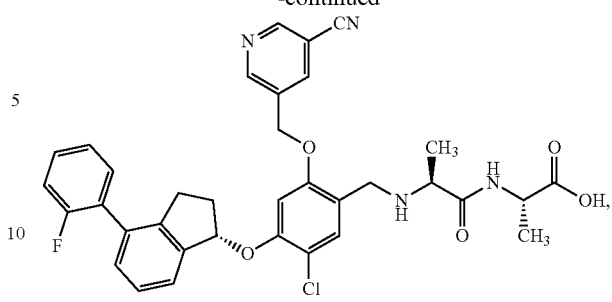
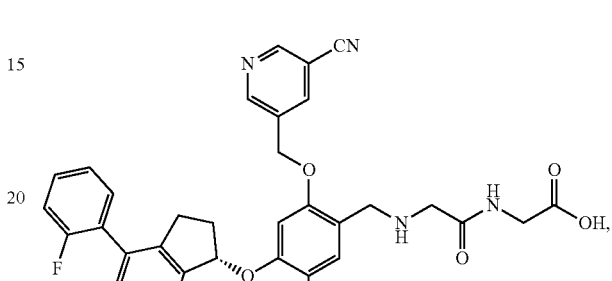
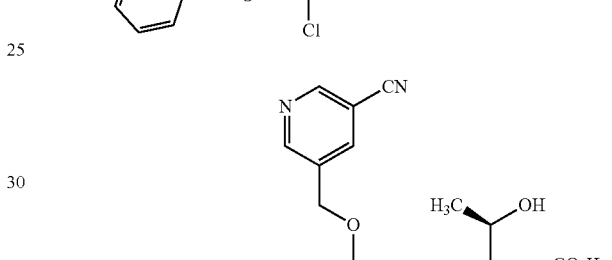
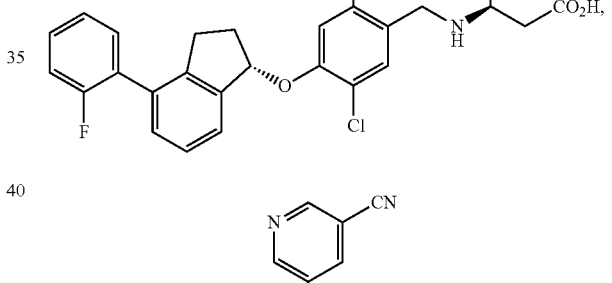
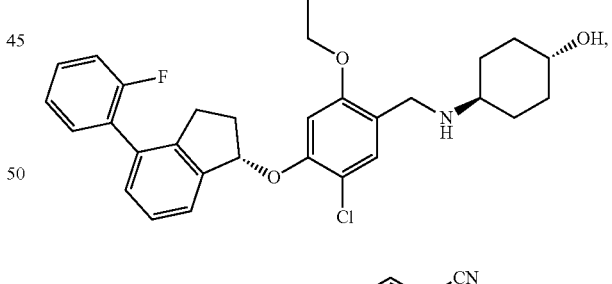
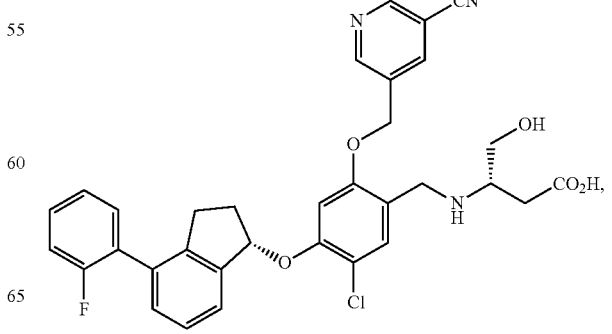

421
-continued
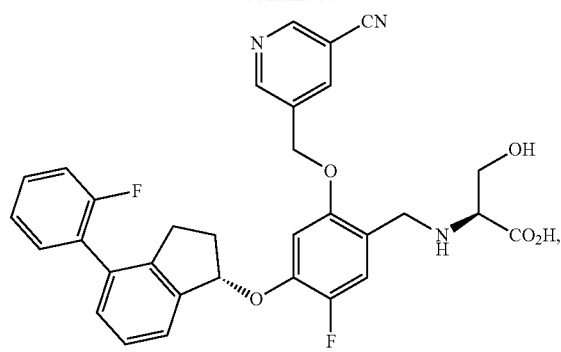
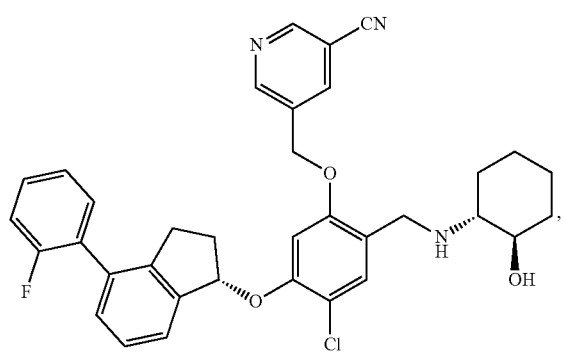
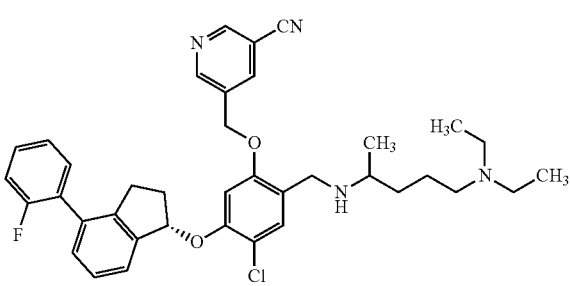
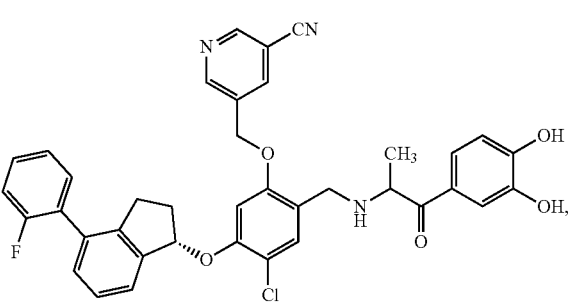
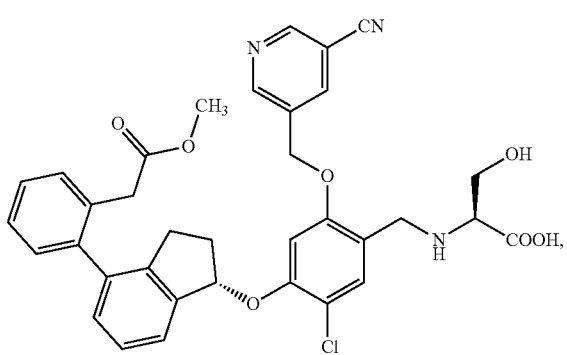
422
-continued
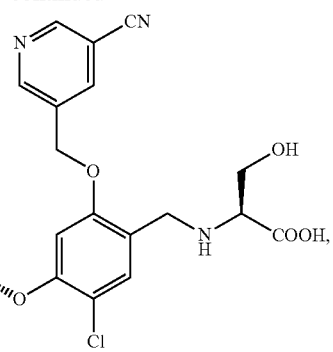
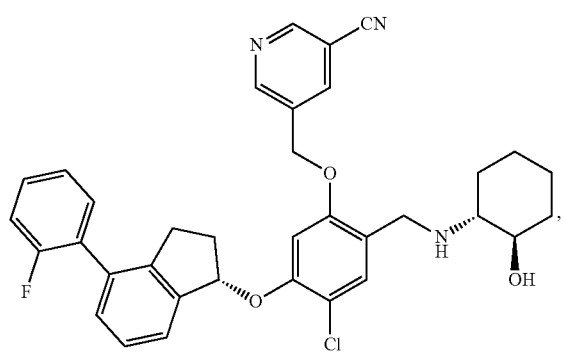
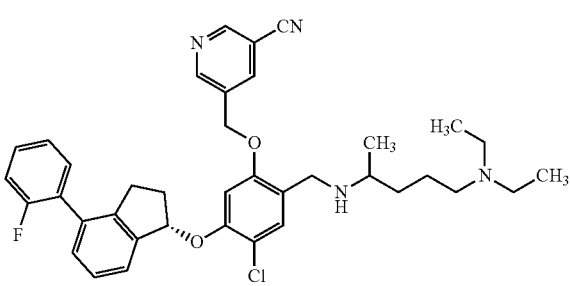
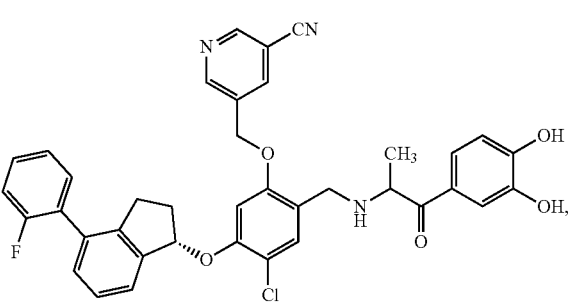
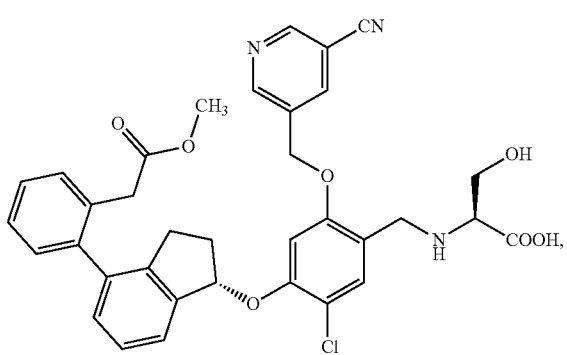

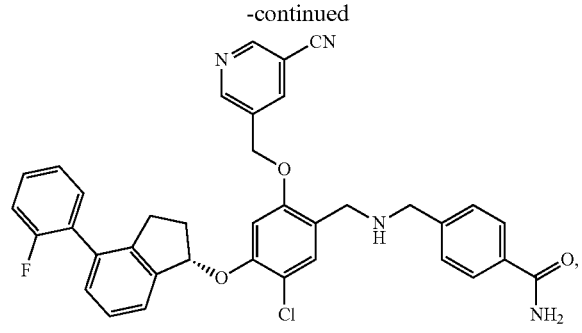
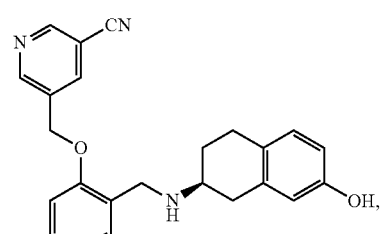
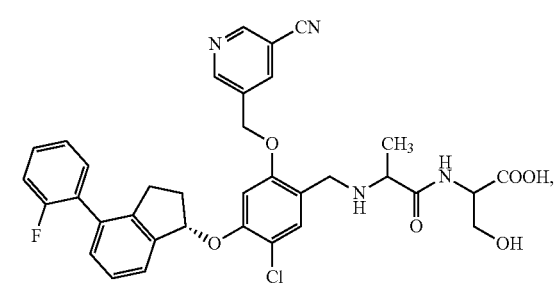
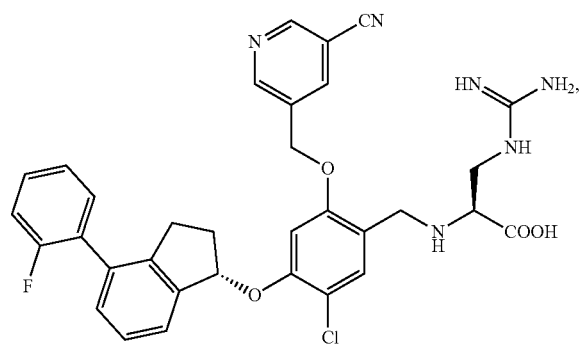
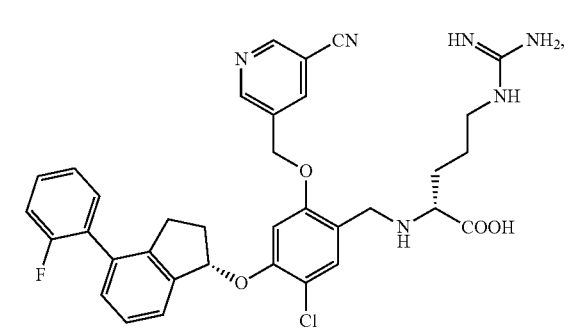
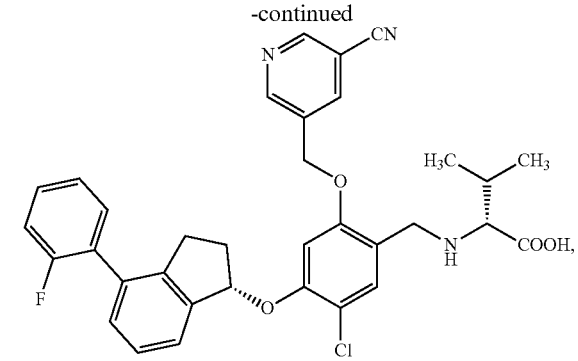
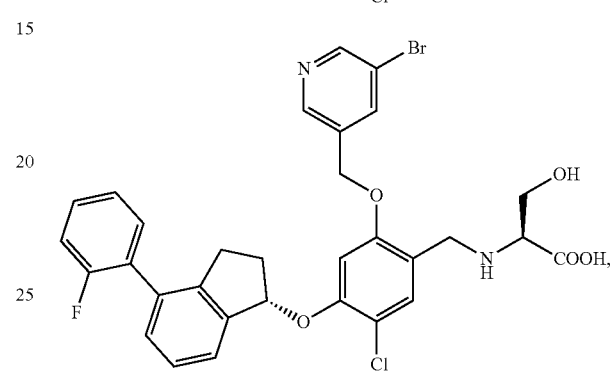
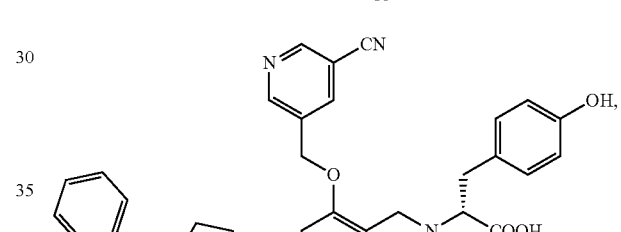
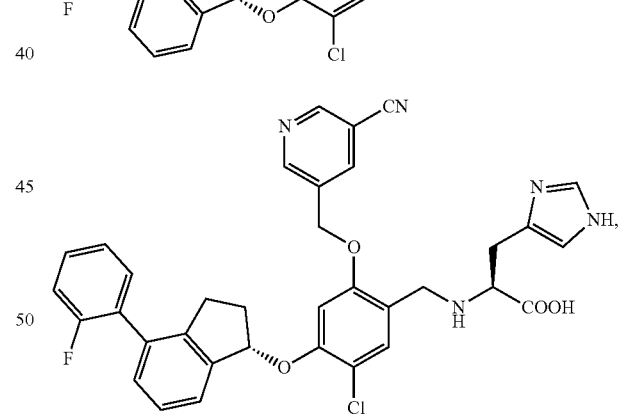
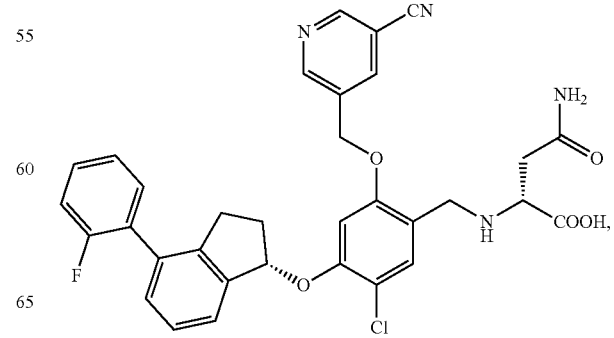

425
-continued
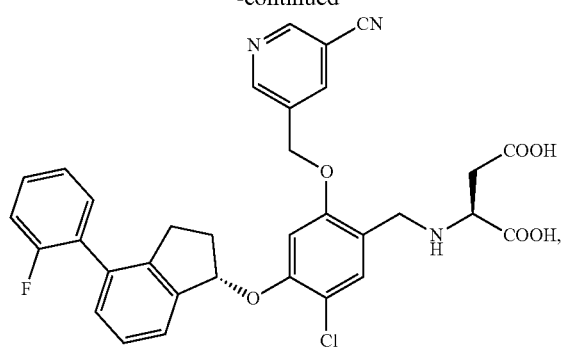
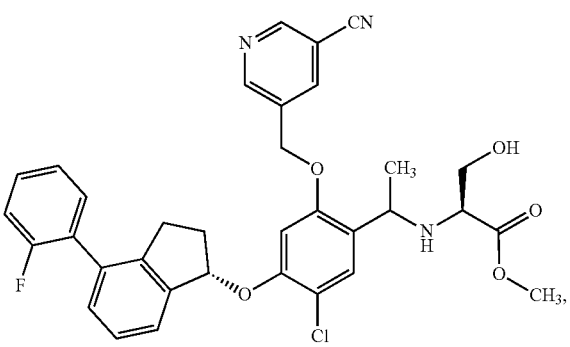
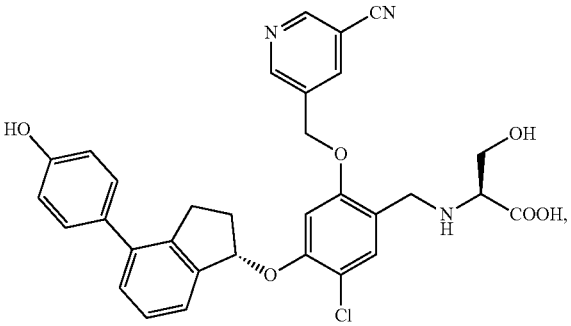
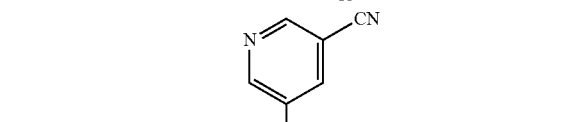
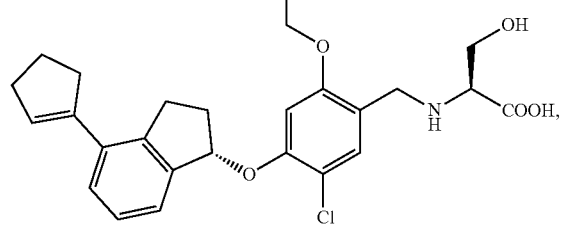
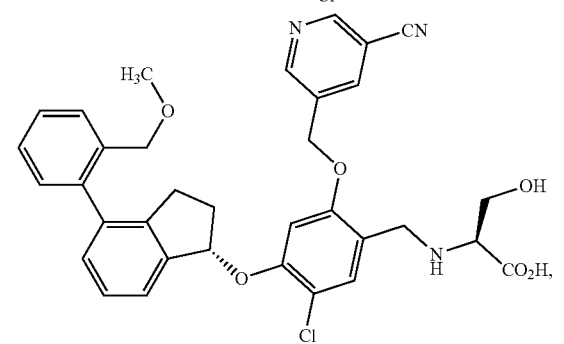
426
-continued
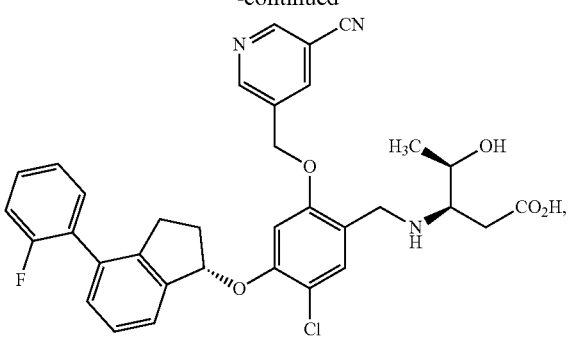
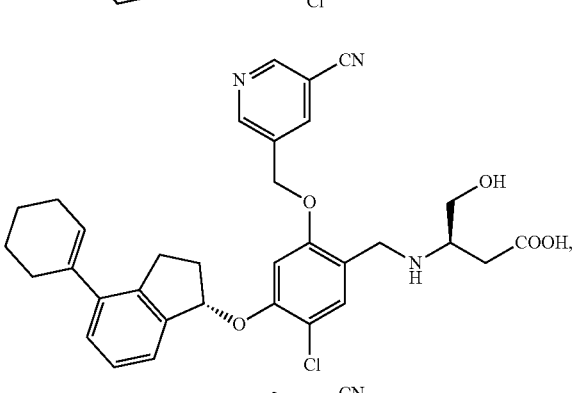
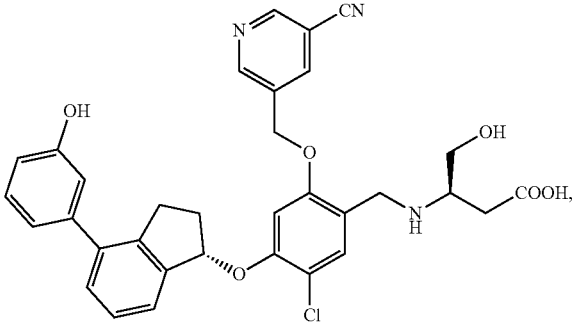
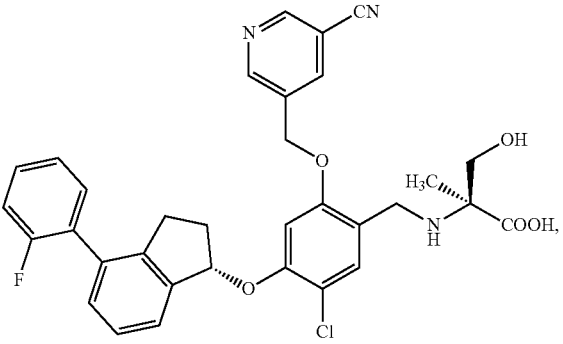
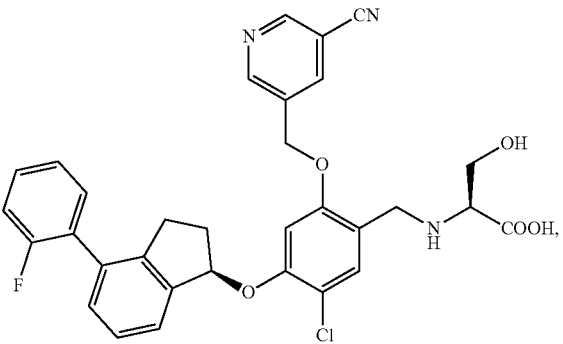

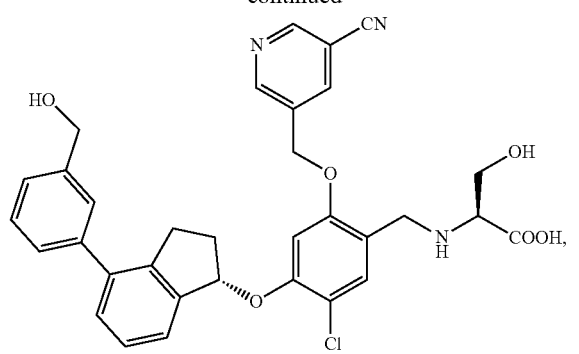
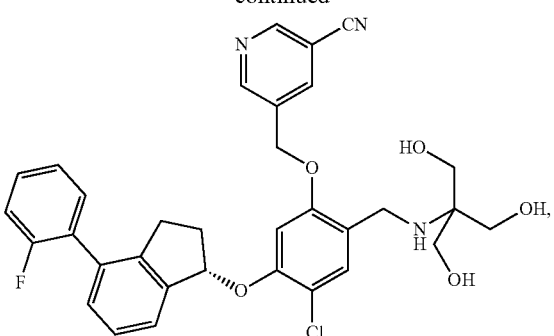
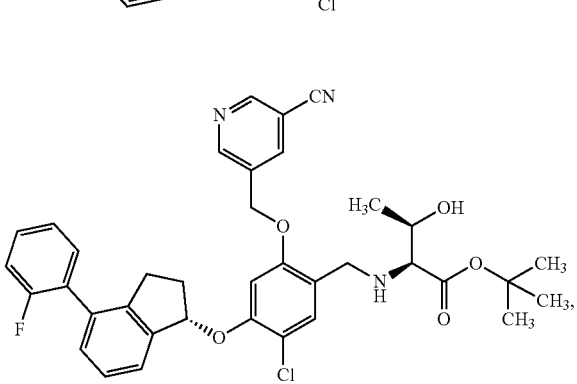
and
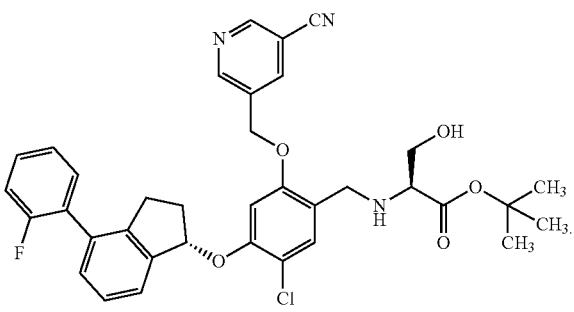
2. The method of claim 1, wherein the compound is selected from the group consisting of -continued

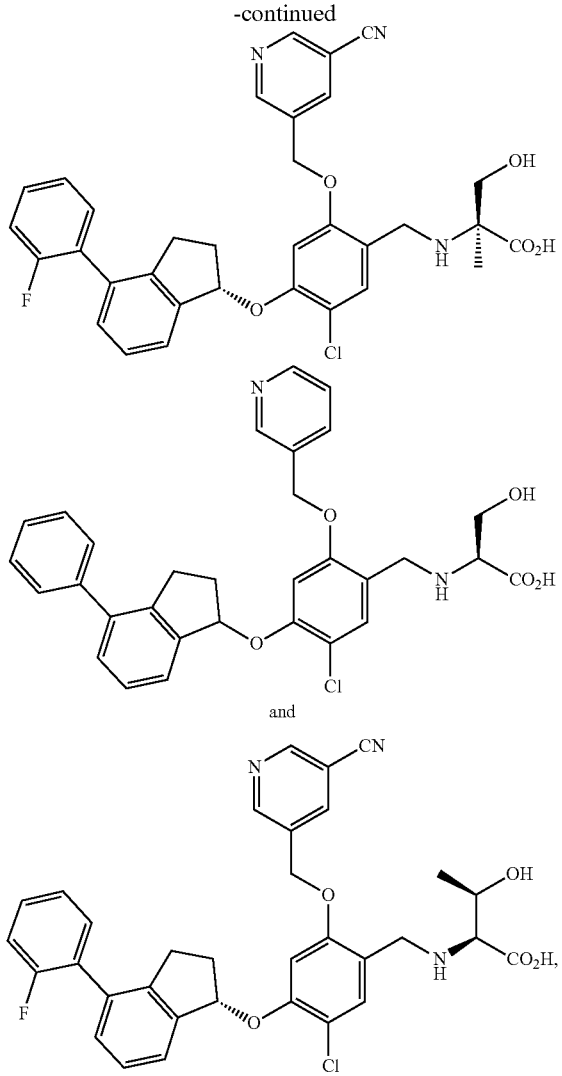

or a pharmaceutically acceptable salt thereof.

3. The method of claim 1, wherein the compound has the formula:

4. The method of claim 1, wherein the compound has the formula:

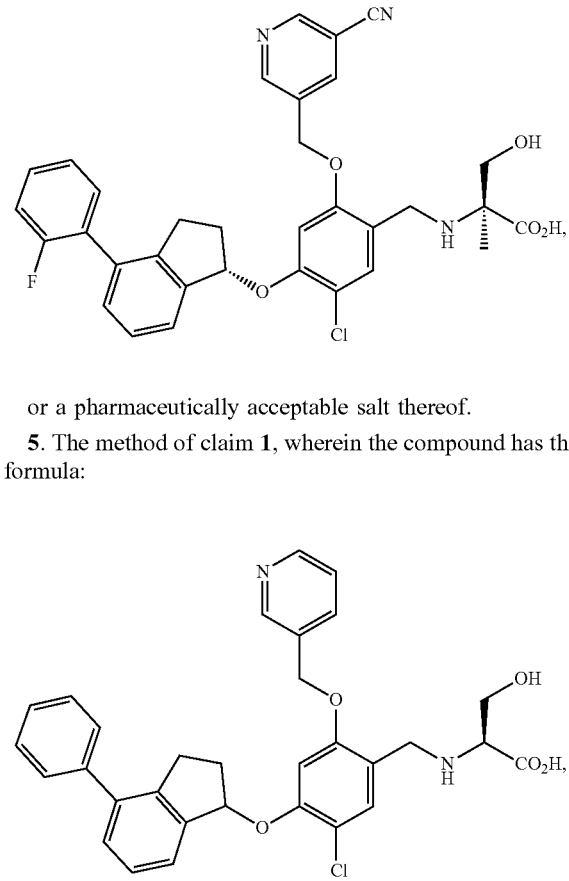

or a pharmaceutically acceptable salt thereof.

5. The method of claim 1, wherein the compound has the formula:

or a pharmaceutically acceptable salt thereof.

6. The method of claim 1, wherein the compound has the formula:

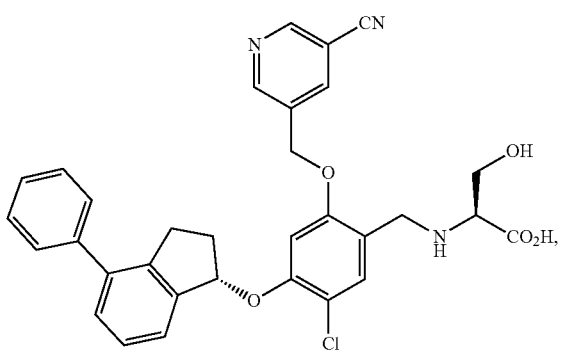 [SMILES: N#Cc1cncc(COc2cc(O[C@H]3CCc4c(-c5ccccc5)cccc43)c(Cl)cc2CN[C@@H](CO)C(=O)O)c1]

or a pharmaceutically acceptable salt thereof.

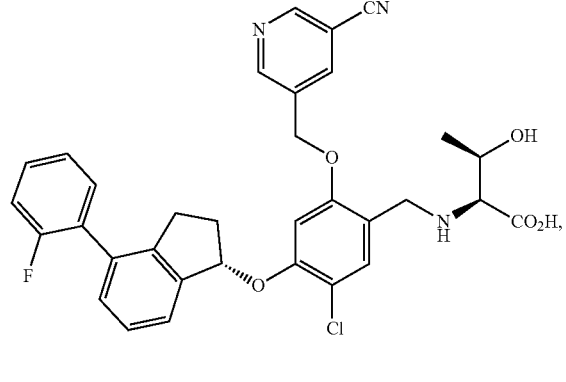 [SMILES: C[C@@H](O)[C@H](NCc1cc(Cl)c(O[C@H]2CCc3c(-c4ccccc4F)cccc32)cc1OCc1cncc(C#N)c1)C(=O)O]

or a pharmaceutically acceptable salt thereof.

* * * * *